US011602567B2

(12) United States Patent
Naryshkin et al.

(10) Patent No.: US 11,602,567 B2
(45) Date of Patent: Mar. 14, 2023

(54) METHODS FOR MODULATING RNA SPLICING

(71) Applicant: PTC Therapeutics, Inc., South Plainfield, NJ (US)

(72) Inventors: Nikolai Naryshkin, East Brunswick, NJ (US); Amal Dakka, Whitehouse Station, NJ (US)

(73) Assignee: PTC Therapeutics, Inc., South Plainfield, NJ (US)

( * ) Notice: Subject to any disclaimer, the term of this patent is extended or adjusted under 35 U.S.C. 154(b) by 0 days.

(21) Appl. No.: 16/847,330

(22) Filed: Apr. 13, 2020

(65) Prior Publication Data

US 2021/0069350 A1 Mar. 11, 2021

Related U.S. Application Data

(62) Division of application No. 15/577,584, filed as application No. PCT/US2016/034864 on May 27, 2016, now Pat. No. 10,668,171.

(60) Provisional application No. 62/168,726, filed on May 30, 2015.

(51) Int. Cl.

| | |
|---|---|
| ***A61K 48/00*** | (2006.01) |
| ***A61K 31/519*** | (2006.01) |
| ***A61K 31/711*** | (2006.01) |
| ***C07D 239/70*** | (2006.01) |
| ***C12N 15/11*** | (2006.01) |
| ***C12N 15/85*** | (2006.01) |

(52) U.S. Cl.

CPC ........ *A61K 48/0025* (2013.01); *A61K 31/519* (2013.01); *A61K 31/711* (2013.01); *C07D 239/70* (2013.01); *C12N 15/11* (2013.01); *C12N 15/85* (2013.01); *C12N 2320/33* (2013.01); *Y02A 50/30* (2018.01)

(58) Field of Classification Search

CPC ................ A61K 31/519; A61K 31/711; A61K 48/0025; C07D 239/70; C12N 15/11; C12N 15/63; C12N 2320/33

USPC ..................... 435/6.1, 91.1, 91.31, 455, 458; 514/44 A; 536/23.1

See application file for complete search history.

(56) References Cited

U.S. PATENT DOCUMENTS

| | | | |
|---|---|---|---|
| 3,558,618 | A | 1/1971 | Trepanier et al. |
| 4,122,274 | A | 10/1978 | Juby |
| 4,342,870 | A | 8/1982 | Kennis et al. |
| 5,089,633 | A | 2/1992 | Powers et al. |
| 5,599,816 | A | 2/1997 | Chu et al. |
| 6,630,488 | B1 | 10/2003 | Lamothe et al. |
| 6,977,255 | B2 | 12/2005 | Robertson et al. |
| 7,326,711 | B2 | 2/2008 | Wang et al. |
| 7,399,767 | B2 | 7/2008 | Zhang et al. |
| 7,563,601 | B1 | 7/2009 | Gaur et al. |
| 7,569,337 | B2 | 8/2009 | Auberson |
| 7,897,792 | B2 | 3/2011 | Iikura et al. |
| 8,337,941 | B2 | 12/2012 | Gubemator et al. |
| 8,633,019 | B2 | 1/2014 | Paushkin et al. |
| 8,962,842 | B2 | 2/2015 | Roussel et al. |
| 9,371,336 | B2 | 6/2016 | Lee et al. |
| 9,399,649 | B2 | 6/2016 | Chen et al. |
| 9,586,955 | B2 | 3/2017 | Qi et al. |
| 9,617,268 | B2 | 4/2017 | Woll et al. |
| 9,879,007 | B2 | 1/2018 | Qi et al. |
| 9,969,754 | B2 | 5/2018 | Ratni et al. |
| 10,195,202 | B2 | 2/2019 | Naryshkin |
| 10,208,067 | B2 | 2/2019 | Gillespie et al. |
| 2002/0110543 | A1* | 8/2002 | Chiocca ............... A61K 38/177 424/93.2 |
| 2003/0199526 | A1 | 10/2003 | Choquette et al. |
| 2005/0048549 | A1 | 3/2005 | Cao et al. |

(Continued)

FOREIGN PATENT DOCUMENTS

| | | | |
|---|---|---|---|
| CN | 104349777 | A | 2/2015 |
| EP | 1227084 | A1 | 6/1998 |

(Continued)

OTHER PUBLICATIONS

Calder et al., Nov. 2016, "Small Molecules in Development for the Treatment of Spinal Muscular Atrophy," J Med Chem. 59(22):10067-10083.

Cheung et al., Dec. 2018, "Discovery of Small Molecule Splicing Modulators of Survival Motor Neuron-2 (SMN2) for the Treatment of Spinal Muscular Atrophy (SMA)." J Med Chem. 61(24):11021-11036.

(Continued)

*Primary Examiner* — Jane J Zara
(74) *Attorney, Agent, or Firm* — Jones Day

(57) ABSTRACT

In one aspect, described herein is a recognition element for splicing modifier (REMS) that can be recognized by a compound provided herein. In another aspect, described herein are methods for modulating the amount of a product of a gene, wherein a precursor RNA transcript transcribed from the gene contains a REMS, and the methods utilizing a compound described herein. More particularly, described herein are methods for modulating the amount of an RNA transcript or protein product encoded by a gene, wherein a precursor RNA transcript transcribed from the gene comprises a REMS, and the methods utilizing a compound described herein. In another aspect, provided herein are artificial gene constructs comprising a REMS, and uses of those artificial gene constructs to modulate functional protein production. In another aspect, provided herein are methods for altering endogenous genes to comprise a REMS, and the use of a compound described herein to modulate the functional protein produced from such altered endogenous genes.

14 Claims, 7 Drawing Sheets

Specification includes a Sequence Listing.

(56) References Cited

U.S. PATENT DOCUMENTS

| | | | | |
|---|---|---|---|---|
| 2007/0087366 | A1 * | 4/2007 | Holt | C12N 15/70 435/6.18 |
| 2008/0255162 | A1 | 10/2008 | Bruendl et al. | |
| 2009/0170793 | A1 | 7/2009 | Gaur et al. | |
| 2009/0305900 | A1 | 12/2009 | Belouchi et al. | |
| 2010/0303776 | A1 | 12/2010 | Samulski et al. | |
| 2013/0245035 | A1 | 9/2013 | Roussel et al. | |
| 2014/0206661 | A1 | 7/2014 | Axford et al. | |
| 2014/0249210 | A1 | 9/2014 | Lutz et al. | |
| 2015/0005289 | A1 | 1/2015 | Qi et al. | |
| 2015/0119380 | A1 | 4/2015 | Woll et al. | |
| 2015/0080383 | A1 | 5/2015 | Yang et al. | |
| 2017/0000794 | A1 | 1/2017 | Naryshkin et al. | |
| 2017/0001995 | A1 | 1/2017 | Metzger et al. | |
| 2018/0161456 | A1 | 6/2018 | Naryshkin et al. | |
| 2019/0134045 | A1 | 5/2019 | Naryshkin | |
| 2019/0330615 | A1 | 10/2019 | Bhattacharyya et al. | |

FOREIGN PATENT DOCUMENTS

| | | | |
|---|---|---|---|
| JP | 1981-150091 | 3/1983 | |
| WO | WO 199323398 | 11/1993 | |
| WO | WO 1996039407 A1 | 12/1996 | |
| WO | WO 1998025930 | 6/1998 | |
| WO | WO 2002087589 A1 | 11/2002 | |
| WO | WO 2004009558 | 1/2004 | |
| WO | WO 2004113335 A2 | 12/2004 | |
| WO | WO 2004113335 A3 | 12/2004 | |
| WO | WO 2005105801 A1 | 11/2005 | |
| WO | WO 2008077188 A1 | 7/2008 | |
| WO | WO 2009151546 | 5/2009 | |
| WO | WO 201019236 | 8/2009 | |
| WO | WO 2007109211 | 9/2009 | |
| WO | WO 2009156861 | 12/2009 | |
| WO | WO 2010000032 A1 | 1/2010 | |
| WO | WO 2011050245 | 4/2011 | |
| WO | WO 201162853 | 5/2011 | |
| WO | WO 201185990 | 7/2011 | |
| WO | WO 2013059606 | 4/2013 | |
| WO | WO 2013101974 | 7/2013 | |
| WO | WO 2013112788 | 8/2013 | |
| WO | WO 2013119916 | 8/2013 | |
| WO | WO-2013119916 A2 * | 8/2013 | A61K 31/519 |
| WO | WO 2013119916 A2 | 8/2013 | |
| WO | WO 2013130689 | 9/2013 | |
| WO | WO 2013142236 | 9/2013 | |
| WO | WO 2014012050 A2 | 1/2014 | |
| WO | WO-2015024876 A2 * | 2/2015 | A61K 31/519 |
| WO | WO 2015024876 A2 | 2/2015 | |
| WO | WO 2015095446 | 6/2015 | |
| WO | WO 2015095449 | 6/2015 | |
| WO | WO 2015105657 | 7/2015 | |
| WO | WO-2015105657 A1 * | 7/2015 | A61K 31/519 |
| WO | WO 2015173181 | 11/2015 | |
| WO | WO 2016042015 | 3/2016 | |
| WO | WO 2016/128343 A1 | 8/2016 | |
| WO | WO 2016196386 | 12/2016 | |
| WO | WO 2018098446 | 5/2018 | |
| WO | WO 2018232039 | 12/2018 | |

OTHER PUBLICATIONS

Supplementary European Search Report dated Feb. 4, 2021 in European Application No. 18817883 (with communication) (9 pages).

Response to Communication pursuant to Rules 70(2) and 70a(2) filed Sep. 3, 2021 in EP Application No. 18817883 (8 pages).

Coady et al., 2010, "Trans-splicing-mediated improvement in a severe mouse model of spinal muscular atrophy," J Neurosci., 30(1):126-130.

European Patent Office, a Communication pursuant to Article 94(3) EPC, Application No. 14877918.4, dated Mar. 23, 2018.

Extended European Search Report dated Nov. 2, 2018 of European Application No. 16804178.

Falaleeva et al., "Dual function of C/D box small RNAs in rRNA modification and alternative pre-mRNA splicing" PNAS, Mar. 8, 2016, 113(12):E1625-E1634.

Greene et al., 1991, Protective Groups in Organic Synthesis, Wiley, New York.

Hernández-Imaz et al., 2015, "Functional Analysis of Mutations in Exon 9 of NF1 Reveals the Presence of Several Elements Regulating Splicing," Plos One,10(10):e0141735.

Higuchi et al., 1987, "Pro-drugs as Novel Delivery Systems," vol. 14 of the A.C.S. Symposium Series, and in Bioreversible Carriers in Drug Design, ed. Edward B. Roche, American Pharmaceutical Association and Pergamon Press.

Hua et al., 2012, "Peripheral SMN restoration is essential for long-term rescue of a severe SMA mouse model," Nature, 478(7367):123-126.

Human SMN2 luciferase vector, SEQ 9, retrieved from EBI accession No. GSN:88883507, Database accession No. BBB83507 (Mar. 13, 2014) (3 pages).

International Preliminary Report dated Aug. 12, 2014 in connection with International Patent Application No. PCT/US2013/025292 (7 pages).

International Search Report dated Aug. 30, 2013 in connection with International Patent Application No. PCT/US2013/025292 (6 pages).

International Search Report dated Nov. 15, 2016 in connection with International Patent Application No. PCT/US2016/034864 (6 pages).

Jarecki et al., 2005, "Diverse small-molecule modulators of SMN expression found by high throughput compound screening: early leads towards a therapeutic for spinal muscular atrophy," Human Molecular Genetics, 14(14):2003-2018.

Knight et al., 2004, "Isoform-specific phosphoinositide 3-kinase inhibitors from an arylmorpholine scaffold," Bioorganic & Medicinal Chemistry, 12:4749-4759.

Kocar et al., 2002, "Transformations of 3-aminopyridazines. Synthesis of 4-oxo-4H-pyrimido[1,2-b]pyridazine and 1-(substituted pyridazin-3-yi)-1H-1,2,3-triazole derivatives,"ARKIVOC 2002 (viii) 143-156.

Le et al., 2005, "SMND7, the major product of the centromeric survival motor neuron (SMN2) gene, extends survival in mice with spinal muscular atrophy and associates with full-length SMN," Human Molecular Genetics, 14(6): 845-857.

Liu et al., 1996, "A novel nuclear structure containing the survival of motor neurons protein," EMBO J., 15(14):3555-3565.

Makhortova, et al. 2011, "A Screen for Regulators of Survival of Motor Neuron Protein Levels," Nat Chern Bioi, 7(8):544-552.

Naryshkin et al., 2014, "SMN2 splicing modifiers improve motor function and longevity in mice with spinal muscular atrophy," Science, 345(6197):688-693 and supplementary materials.

Palacino et al., 2015, "SMN2 splicing modifiers enhance U1-pre-mRNA association and rescue SMA mice," Nature Chemical Biology, 11(7):511-517, Supplementary Materials only.

Palacino, et al., 2015, "SMN2 splice modulators enhance U1-pre-mRNA association and rescue SMA mice," Nature chemical biology, 11(7):511-517 and supplementary materials.

Passini et al., 2001, "Antisense Oligonucleotides Delivered to the Mouse CNS Ameliorate Symptoms of Severe Spinal Muscular Atrophy," Sci Transl Med., 3(72):72ra18.

Peng et al., 2011, "Identification of pyrido [1, 2-$\alpha$] pyrimidine-4-ones as new molecules improving the transcriptional functions of estrogen-related receptor $\alpha$," J Med Chem., 54(21):7729-7733.

Pinard et al., 2017, "Discovery of a Novel Class of Survival Motor Neuron 2 Splicing Modifiers for the Treatment of Spinal Muscular Atrophy," J Med Chem., 60(10):4444-4457.

PubChem compound CID 377422. Mar. 26, 2005. [Retrieved from the Internet Oct. 27, 2014: <http://pubchem.ncbi.nlm.nih.gov//compound/377422?from=summary>) (13 pages).

Ratni et al., 2016, "Specific Correction of Alternative Survival Motor Neuron 2 Splicing by Small Molecules: Discovery of a Potential Novel Medicine to Treat Spinal Muscular Atrophy," J Med Chem., 59(13):6086-6100.

Singh et al., 2007, "Modulating role of RNA structure in alternative splicing of a critical exon in the spinal muscular atrophy genes", Nucleic Acids Research, 35(2):371-389.

(56) References Cited

OTHER PUBLICATIONS

Sivaramakrishnan et al., 2017, "Binding to SMN2 pre-mRNA-protein complex elicits specificity for small molecule splicing modifiers", Nature Communications, 8(1476): 1-13 and supplementary material.
Written Opinion of the International Searching Authority and International Search Report for International Patent Application No. PCT/US2017/063323, dated Apr. 13, 2018.
Written Opinion of the International Searching Authority and International Search Report for International Patent Application No. PCT/US2018/037412, dated Sep. 17, 2018.
Written Opinion of the International Searching Authority dated Aug. 30, 2013 in connection with International Patent Application No. PCT/US2013/025292 (6 pages).
Written Opinion of the International Searching Authority dated Nov. 15, 2016 in connection with International Patent Application No. PCT/US2016/034864 (9 pages).
Zhao et al., 2016, "Pharmacokinetics, pharmacodynamics, and efficacy of a small-molecule SMN2 splicing modifier in mouse models of spinal muscular atrophy," Hum Mol Genet., 25(10):1885-1899.
Restriction/Election Requirement dated Feb. 4, 2019 in U.S. Appl. No. 15/577,584 (9 pages).
Response to Restriction/Election Requirement filed May 6, 2019 in U.S. Appl. No. 15/577,584 (8 pages).
Non-final Office Action with a Notice of References Cited dated Jun. 5, 2019 in U.S. Appl. No. 15/577,584 (9 pages).
Response to Non-final Office Action filed Sep. 3, 2019 in U.S. Appl. No. 15/577,584 (11 pages).
Final Office Action dated Sep. 24, 2019 in U.S. Appl. No. 15/577,584 (12 pages).
Response to Final Office Action filed Dec. 20, 2019 in U.S. Appl. No. 15/577,584 (7 pages).
Notice of Allowance dated Jan. 15, 2020 in U.S. Appl. No. 15/577,584 (5 pages).
Supplementary Partial European Search Report and Provisional Opinion Accompanying the Partial Search Result dated Jun. 25, 2020 in European Patent Application No. 17873550.2 (21 pages).
Response to Communication pursuant to Rule 94(3) EPC filed on Jun. 29, 2020 in connection with European Patent Application No. 16804178.8 (9 pages).
Mercer et al., 2015, "Genome-wide discovery of human splicing branchpoints," Genome Res., 25(2):290-303.
International Preliminary Report on Patentability Chapter I dated May 28, 2019 in PCT/US2017/063323 (10 pages).
International Preliminary Report on Patentability Chapter II dated Nov. 27, 2017 in PCT/US2016/034864 (94 pages).
International Preliminary Report on Patentability Chapter I dated Aug. 12, 2014 in PCT/US2013/025292 (6 pages).
Yuo et al., 2008, "5-(N-ethyl-N-isopropyl)-amiloride enhances SMN2 exon 7 inclusion and protein expression in spinal muscular atrophy cells," Ann. Neurol., 63(1):26-34.
Shao et al., 2012, "Synthesis and structure-activity relationship (SAR) study of 4-azabenzoxazole analogues as H3 antagonists," Bioorg. Med. Chem. Lett., 22(5):2075-2078.

* cited by examiner

-4 -1 +1 +6
AGGAguaagu

Fig. 7A SMN2 (exon7)
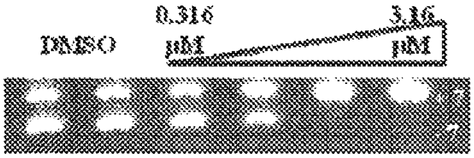
Fig. 7B FOXM1 (exon 7A exon 7A dC)
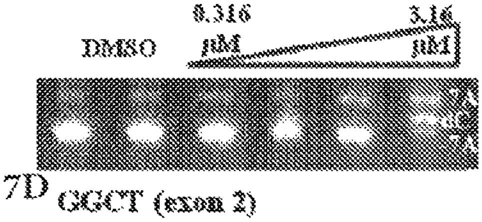
Fig. 7C APLP2 (exon 7)
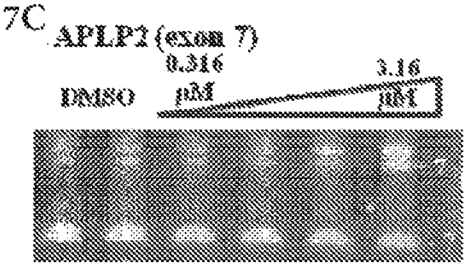
Fig. 7D GGCT (exon 2)
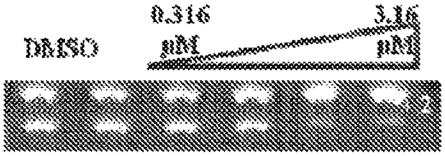
Fig. 7E ABHD10 (exon 5)
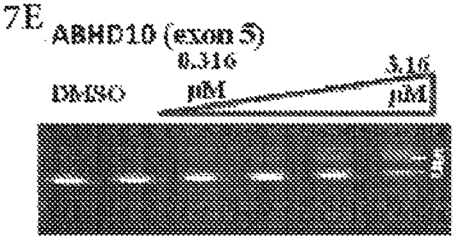
Fig. 7F STRN3 (exon 8)
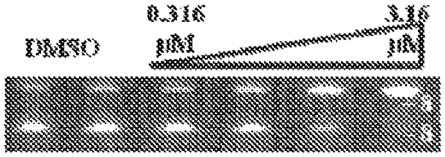
Fig. 7G VPS29 (exon 2)
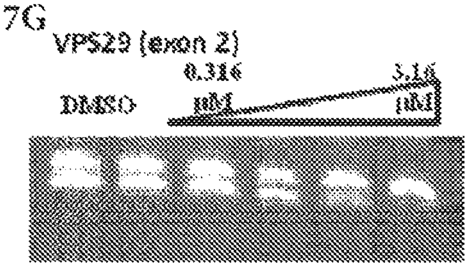
Fig. 7H ERGIC3 (exon 8)
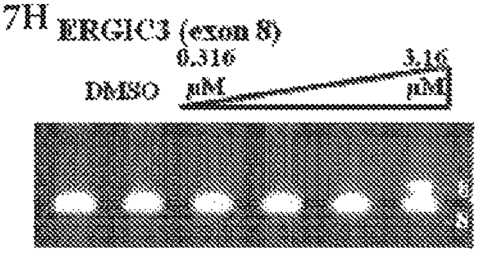
Fig. 7I MADD (exon 21)
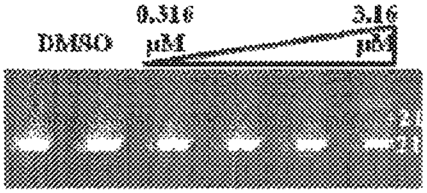
Fig. 7J LARP7 (UTR)
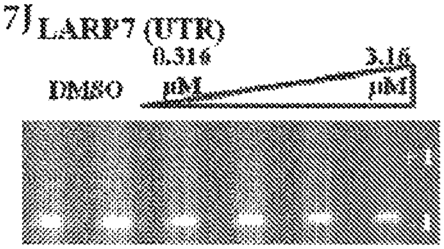
Fig. 7K LARP7 (exon 2)
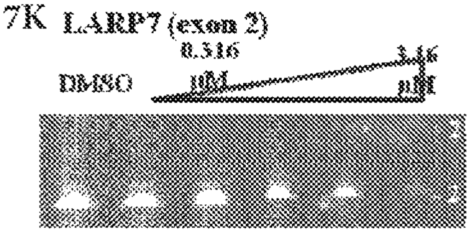
Fig. 7L COL1A1 (exon 30)
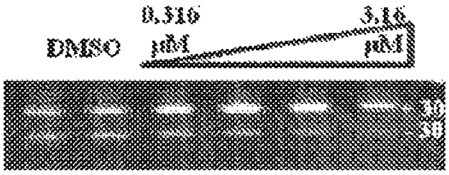

METHODS FOR MODULATING RNA SPLICING

CROSS-REFERENCE TO RELATED APPLICATIONS

This application is a divisional of U.S. patent application Ser. No. 15/577,584 (now U.S. Pat. No. 10,668,171 B2), which is a U.S. National Stage Application of International Patent Application No. PCT/US2016/034864, filed May 27, 2016, which claims the benefit of U.S. Provisional Application No. 62/168,726, filed on May 30, 2015, the content of each of which is incorporated by reference herein in its entirety.

This application incorporates by reference in its entirety the Computer Readable Form ("CRF") of a Sequence Listing in ASCII text format submitted via EFS-Web. The Sequence Listing text file submitted via EFS-Web is entitled "10589-300-999_SEQ_LISTING.txt," was created on Apr. 5, 2020 and is 29,856 bytes in size.

INTRODUCTION

In one aspect, described herein is a recognition element for splicing modifier (REMS) that can be recognized by a compound provided herein. In another aspect, described herein are methods for modulating the amount of a product of a gene, wherein a precursor RNA transcript transcribed from the gene contains a REMS, and the methods utilize a compound described herein. More particularly, described herein are methods for modulating the amount of an RNA transcript or protein product encoded by a gene, wherein a precursor RNA transcript transcribed from the gene comprises a REMS, and the methods utilize a compound described herein. In another aspect, provided herein are artificial gene constructs comprising a REMS, and uses of those artificial gene constructs to modulate functional protein production. In another aspect, provided herein are methods for altering endogenous genes to comprise a REMS, and the use of a compound described herein to modulate the functional protein produced from such altered endogenous genes.

BACKGROUND

A number of diseases are associated with aberrant expression of a gene product (e.g., an RNA transcript or protein) of a gene. The resulting aberrant amounts of RNA transcripts may lead to disease due to corresponding changes in protein expression. Changes in the amount of a particular RNA transcript may be the result of several factors. First, changes in the amount of RNA transcripts may be due to an aberrant level of transcription of a particular gene, such as by the perturbation of a transcription factor or a portion of the transcription process, resulting in a change in the expression level of a particular RNA transcript. Second, changes in the splicing of particular RNA transcripts, such as by perturbation of a particular splicing process or mutations in the gene that lead to modified splicing can change the levels of a particular RNA transcript. Changes to the stability of a particular RNA transcript or to components that maintain RNA transcript stability, such as the process of poly-A tail incorporation or an effect on certain factors or proteins that bind to and stabilize RNA transcripts, may lead to changes in the levels of a particular RNA transcript. Also, the level of translation of particular RNA transcripts can affect the amount of those transcripts, affecting or upregulating RNA transcript decay processes. Finally, aberrant RNA transport or RNA sequestration may also lead to changes in functional levels of RNA transcripts, and may have an effect on the stability, further processing, or translation of the RNA transcripts.

Often, diseases associated with changes to RNA transcript amount are treated with a focus on the aberrant protein expression. However, if the processes responsible for the aberrant changes in RNA levels, such as components of the splicing process or associated transcription factors or associated stability factors, could be targeted by treatment with a small molecule, it would be possible to restore protein expression levels such that the unwanted effects of the expression of aberrant levels of RNA transcripts or associated proteins. Therefore, there is a need for methods of modulating the amount of RNA transcripts encoded by certain genes as a way to prevent or treat diseases associated with aberrant expression of the RNA transcripts or associated proteins.

SUMMARY

In one aspect, provided herein is a recognition element for splicing modifier (otherwise referred to as "REMS") that plays a role in the recognition of a compound described herein. In a specific embodiment, the REMS has the nucleotide sequence GAgurngn (SEQ ID NO: 1) at the RNA level, wherein r is A or G (i.e., a purine nucleotide) and n is any nucleotide. In another specific embodiment, the REMS has the nucleotide sequence GAguragu (SEQ ID NO: 2) at the RNA level, wherein r is A or G. In another specific embodiment, the REMS has the nucleotide sequence ANGAgurngn (SEQ ID NO: 3) at the RNA level, wherein r is A or G (i.e., a purine nucleotide) and n or N is any nucleotide. In a preferred embodiment, the REMS has the nucleotide sequence ANGAguragu (SEQ ID NO: 4) at the RNA level, wherein r is A or G and N is any nucleotide. In a specific embodiment, the REMS is located in the 5' splice site. In certain embodiments, the REMS is located within an exon, such as in FoxM1 exon 7a. Without being bound by any theory or mechanism, it is believed that compounds described herein increase the affinity of the interaction between U1 snRNP and the nucleotides ANGA (SEQ ID NO: 9) of the REMS. This belief is based, in part, on the recognition that REMS comprises the U1 snRNP binding site.

In FIG. 1D, the REMS is located in the 5' splice site of a precursor RNA (e.g., precursor mRNA). In the presence of a compound described herein, the nucleotides between the REMS in the 5' splice site and a downstream 3' splice site of a precursor RNA (except the nucleotides of the exon) are removed and the exons of the precursor RNA are spliced together. In FIG. 1B, the REMS is located within an exon in a precursor RNA. In the presence of a compound described herein, the nucleotides between the REMS and a downstream 3' splice site of a precursor RNA (except nucleotides GA or ANGA of REMS) are removed and the remaining portions of the precursor RNA are spliced together, which may result in an RNA transcript with a truncated open reading frame due to a frameshift or internal deletions within the open reading frame.

Accordingly, in one aspect, provided herein are methods for modulating the amount of RNA transcript produced from precursor RNA containing a REMS. In another aspect, provided herein are artificial gene constructs comprising a REMS, which may be used in the context of, e.g., gene therapy or reporter assays. In another aspect, provided herein are methods for altering endogenous genes so that they contain a REMS or an additional REMS.

In another aspect, provided herein are methods for modulating the amount of one or more RNA transcripts (e.g., mRNA transcripts) or proteins thereof expressed as the product of one or more genes, wherein precursor RNA transcripts transcribed by the one or more genes comprise a REMS, the methods comprising contacting a cell with a compound of Formula (I)

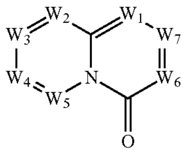

(I)

or a form thereof, wherein $w_1$, $w_2$, $w_3$, $w_4$, $w_5$, $w_6$ and $w_7$ are as defined herein. In one embodiment, provided herein is a method for modulating the amount of an RNA transcript produced from precursor RNA containing a recognition element for splicing modifier (REMS), the method comprising contacting a cell containing the precursor RNA with a compound of Formula (I) or a form thereof, wherein the REMS comprises the sequence GAgurngn (SEQ ID NO: 1), wherein r is A or G and n is any nucleotide, wherein the precursor RNA is not a gene in Table 6. In another embodiment, provided herein is a method for modulating the amount of an RNA transcript produced from precursor RNA containing a recognition element for splicing modifier (REMS), the method comprising contacting the precursor RNA with a compound of Formula (I) or a form thereof, wherein the REMS comprises the sequence GAgurngn (SEQ ID NO: 1), wherein r is A or G and n is any nucleotide, wherein the precursor RNA is not a gene in Table 6. In some embodiments, the REMS comprises the sequence GAguragu (SEQ ID NO: 2) at the RNA level, wherein r is A or G. In certain embodiments, the REMS comprises the sequence ANGAgurngn (SEQ ID NO: 3), wherein r is A or G and n or N is any nucleotide. In some embodiments, the REMS comprises the sequence ANGAguragu (SEQ ID NO: 4) at the RNA level, wherein r is A or G, and N is any nucleotide.

In another embodiment, provided herein is a method for modulating the amount of an RNA transcript produced from precursor RNA encoded by the gene ERGIC3, the method comprising contacting a cell containing the precursor RNA with a compound of Formula (I) or a form thereof. In another embodiment, provided herein is a method for modulating the amount of an RNA transcript produced from precursor RNA encoded by the gene ERGIC3, the method comprising contacting the precursor RNA with a compound of Formula (I) or a form thereof. In some embodiments, the REMS comprises the sequence GAguragu (SEQ ID NO: 2) at the RNA level, wherein r is A or G. In certain embodiments, the REMS comprises the sequence ANGAgurngn (SEQ ID NO: 3), wherein r is A or G and n or N is any nucleotide. In some embodiments, the REMS comprises the sequence ANGAguragu (SEQ ID NO: 4) at the RNA level, wherein r is A or G, and N is any nucleotide.

In one embodiment, provided herein are methods for modulating the amount of one, two, three or more RNA transcripts of a gene, by way of nonlimiting example, disclosed in Table 6, infra, the method comprising contacting a cell with a compound of Formula (I) or a form thereof. In another embodiment, provided herein are methods for modulating the amount of one, two, three or more RNA transcripts of a gene, not disclosed in Tables 1-4, infra, wherein the precursor transcript transcribed from the gene comprises a REMS, the method comprising contacting a cell with a compound of Formula (I) or a form thereof. In another embodiment, provided herein are methods for modulating the amount of one, two, three or more RNA transcripts of a gene, not disclosed in International Patent Application No. PCT/US2014/071252 (International Publication No. WO 2015/105657 A1), wherein the precursor transcript transcribed from the gene comprises a REMS, the method comprising contacting a cell with a compound of Formula (I) or a form thereof.

In another embodiment, provided herein are methods for modulating the amount of one, two, three or more RNA transcripts of a gene, not disclosed in Table 6, infra, wherein the precursor transcript transcribed from the gene comprises a REMS, the method comprising contacting a cell with a compound of Formula (I) or a form thereof. In another embodiment, provided herein are methods for modulating the amount of one, two, three or more RNA transcripts of ERGIC3, comprising contacting a cell with a compound of Formula (I) or a form thereof. See the example section for additional information regarding the genes in Table 6. In certain embodiments, the cell is contacted with the compound of Formula (I) or a form thereof in a cell culture. In other embodiments, the cell is contacted with the compound of Formula (I) or a form thereof in a subject (e.g., a non-human animal subject or a human subject). In certain embodiments, a compound of Formula (I) is a compound of Formula (II), Formula (III), Formula (IV), Formula (V), Formula (VI), Formula (VII), Formula (VIII), Formula (IX), Formula (X), Formula (XI), Formula (XII), Formula (XIII), or Formula (XIV) described infra. In some embodiments, a compound of Formula (I) is a compound selected from a compound described herein.

In another aspect, provided herein are methods for modulating the amount of one, two, three or more RNA transcripts of a gene, wherein the precursor RNA transcript transcribed from the gene comprises a REMS, the methods comprising administering to a patient in need thereof a compound of Formula (I) or a form thereof, or a pharmaceutical composition comprising a compound of Formula (I) or a form thereof and a pharmaceutically acceptable carrier, excipient or diluent. In one embodiment, provided herein are methods for modulating the amount of one, two, three or more RNA transcripts of a gene, by way of nonlimiting example, disclosed in Table 6, infra, the methods comprising administering to a patient in need thereof a compound of Formula (I) or a form thereof, or a pharmaceutical composition comprising a compound of Formula (I) or a form thereof and a pharmaceutically acceptable carrier, excipient or diluent.

In another embodiment, provided herein are methods for modulating the amount of one, two, three or more RNA transcripts of a gene, not disclosed in Tables 1-4, infra, wherein the precursor RNA transcript transcribed from the gene comprises a REMS, the methods comprising administering to a patient in need thereof a compound of Formula (I) or a form thereof, or a pharmaceutical composition comprising a compound of Formula (I) or a form thereof and a pharmaceutically acceptable carrier, excipient or diluent.

In another embodiment, provided herein are methods for modulating the amount of one, two, three or more RNA transcripts of a gene, not disclosed in International Patent Application No. PCT/US2014/071252 (International Publication No. WO 2015/105657 A1), wherein the precursor RNA transcript transcribed from the gene comprises a REMS, the methods comprising administering to a patient in need thereof a compound of Formula (I) or a form thereof, or a pharmaceutical composition comprising a compound of Formula (I) or a form thereof and a pharmaceutically acceptable carrier, excipient or diluent. In another embodiment, provided herein are methods for modulating the amount of one, two, three or more RNA transcripts of a gene, not disclosed in Table 6, infra, wherein the precursor RNA transcript transcribed from the gene comprises a REMS, the methods comprising administering to a patient in need thereof a compound of Formula (I) or a form thereof, or a pharmaceutical composition comprising a compound of Formula (I) or a form thereof and a pharmaceutically acceptable carrier, excipient or diluent.

In another embodiment, provided herein are methods for modulating the amount of one, two, three or more RNA transcripts of ERGIC3, comprising administering to a patient in need thereof a compound of Formula (I) or a form thereof, or a pharmaceutical composition comprising a compound of Formula (I) or a form thereof and a pharmaceutically acceptable carrier, excipient or diluent. See the example section for additional information regarding the genes in Table 6. In certain embodiments, a compound of Formula (I) is a compound of Formula (II), Formula (III), Formula (IV), Formula (V), Formula (VI), Formula (VII), Formula (VIII), Formula (IX), Formula (X), Formula (XI), Formula (XII), Formula (XIII), or Formula (XIV) described infra. In some embodiments, a compound of Formula (I) is a compound selected from a compound described herein.

In another aspect, provided herein are methods for preventing and/or treating a disease associated with the aberrant expression of a product of a gene (e.g., an mRNA transcript or protein), wherein the precursor RNA transcript transcribed from the gene comprises a REMS, the methods comprising administering to a patient in need thereof a compound of Formula (I) or a form thereof, or a pharmaceutical composition comprising a compound of Formula (I) or a form thereof and a pharmaceutically acceptable carrier, excipient or diluent. In one embodiment, provided herein are methods for preventing and/or treating a disease associated with aberrant expression of a product of a gene (e.g., an mRNA, RNA transcript or protein), by way of nonlimiting example, disclosed in Table 6, infra, the methods comprising administering to a patient in need thereof a compound of Formula (I) or a form thereof, or a pharmaceutical composition comprising a compound of Formula (I) or a form thereof and a pharmaceutically acceptable carrier, excipient or diluent. In another embodiment, provided herein are methods for preventing and/or treating a disease associated with aberrant expression of a product of a gene (e.g., an mRNA, RNA transcript or protein), not disclosed in Tables 1-4, infra, wherein the precursor RNA transcript transcribed from the gene comprises a REMS, the methods comprising administering to a patient in need thereof a compound of Formula (I) or a form thereof, or a pharmaceutical composition comprising a compound of Formula (I) or a form thereof and a pharmaceutically acceptable carrier, excipient or diluent. In another embodiment, provided herein are methods for preventing and/or treating a disease associated with aberrant expression of a product of a gene (e.g., an mRNA, RNA transcript or protein), by way of nonlimiting example, not disclosed in International Patent Application No. PCT/US2014/071252 (International Publication No. WO 2015/105657 A1), wherein the precursor RNA transcript transcribed from the gene comprises a REMS, the methods comprising administering to a patient in need thereof a compound of Formula (I) or a form thereof, or a pharmaceutical composition comprising a compound of Formula (I) or a form thereof and a pharmaceutically acceptable carrier, excipient or diluent. In another embodiment, provided herein are methods for preventing and/or treating a disease associated with aberrant expression of a product of a gene (e.g., an mRNA, RNA transcript or protein), not disclosed in Table 6, infra, wherein the precursor RNA transcript transcribed from the gene comprises a REMS, the methods comprising administering to a patient in need thereof a compound of Formula (I) or a form thereof, or a pharmaceutical composition comprising a compound of Formula (I) or a form thereof and a pharmaceutically acceptable carrier, excipient or diluent. In another embodiment, provided herein are methods for preventing and/or treating a disease associated with aberrant expression of a product of ERGIC3 (e.g., an mRNA, RNA transcript or protein), comprising administering to a patient in need thereof a compound of Formula (I) or a form thereof, or a pharmaceutical composition comprising a compound of Formula (I) or a form thereof and a pharmaceutically acceptable carrier, excipient or diluent. See the example section for additional information regarding the genes in Table 6. In certain embodiments, a compound of Formula (I) is a compound of Formula (II), Formula (III), Formula (IV), Formula (V), Formula (VI), Formula (VII), Formula (VIII), Formula (IX), Formula (X), Formula (XI), Formula (XII), Formula (XIII), or Formula (XIV) described infra. In some embodiments, a compound of Formula (I) is a compound selected from a compound described herein.

In another aspect, provided herein are methods for preventing and/or treating a disease in which a change in the level of expression of one, two, three or more RNA isoforms encoded by a gene is beneficial to the prevention and/or treatment of the disease, wherein the precursor RNA transcript transcribed from the gene comprises a REMS, the methods comprising administering to a patient in need thereof a compound of Formula (I) or a form thereof, or a pharmaceutical composition comprising a compound of Formula (I) or a form thereof and a pharmaceutically acceptable carrier, excipient or diluent. In one embodiment, provided herein are methods for preventing and/or treating a disease in which the alteration (e.g., increase or decrease) in the expression one, two, three or more RNA isoforms encoded by a gene, by way of nonlimiting example, disclosed in Table 6, infra, is beneficial to the prevention and/or treatment of the disease, the methods comprising administering to a patient in need thereof a compound of Formula (I) or a form thereof, or a pharmaceutical composition comprising a compound of Formula (I) or a form thereof and a pharmaceutically acceptable carrier, excipient or diluent.

In another embodiment, provided herein are methods for preventing and/or treating a disease in which the alteration (e.g., increase or decrease) in the expression one, two, three or more RNA isoforms encoded by a gene, not disclosed in Tables 1-4, infra, is beneficial to the prevention and/or treatment of the disease, wherein the precursor RNA transcript transcribed from the gene comprises a REMS, the methods comprising administering to a patient in need thereof a compound of Formula (I) or a form thereof, or a pharmaceutical composition comprising a compound of Formula (I) or a form thereof and a pharmaceutically acceptable carrier, excipient or diluent.

In another embodiment, provided herein are methods for preventing and/or treating a disease in which the alteration (e.g., increase or decrease) in the expression one, two, three or more RNA isoforms encoded by a gene, not disclosed in International Patent Application No. PCT/US2014/071252

(International Publication No. WO 2015/105657 A1), is beneficial to the prevention and/or treatment of the disease, wherein the precursor RNA transcript transcribed from the gene comprises a REMS, the methods comprising administering to a patient in need thereof a compound of Formula (I) or a form thereof, or a pharmaceutical composition comprising a compound of Formula (I) or a form thereof and a pharmaceutically acceptable carrier, excipient or diluent. In another embodiment, provided herein are methods for preventing and/or treating a disease in which the alteration (e.g., increase or decrease) in the expression one, two, three or more RNA isoforms encoded by a gene, not disclosed in Table 6, infra, is beneficial to the prevention and/or treatment of the disease, wherein the precursor RNA transcript transcribed from the gene comprises a REMS, the methods comprising administering to a patient in need thereof a compound of Formula (I) or a form thereof, or a pharmaceutical composition comprising a compound of Formula (I) or a form thereof and a pharmaceutically acceptable carrier, excipient or diluent.

In another embodiment, provided herein are methods for preventing and/or treating a disease in which the alteration (e.g., increase or decrease) in the expression one, two, three or more RNA isoforms encoded by ERGIC3, is beneficial to the prevention and/or treatment of the disease, the methods comprising administering to a patient in need thereof a compound of Formula (I) or a form thereof, or a pharmaceutical composition comprising a compound of Formula (I) or a form thereof and a pharmaceutically acceptable carrier, excipient or diluent. In a specific embodiment, one, two, three or more RNA isoforms encoded by ERGIC3 are decreased following administration of a compound of Formula (I) or a form thereof and a pharmaceutically acceptable carrier, excipient or diluent. See the example section for additional information regarding the genes in Table 6.
In certain embodiments, a compound of Formula (I) is a compound of Formula (II), Formula (III), Formula (IV), Formula (V), Formula (VI), Formula (VII), Formula (VIII), Formula (IX), Formula (X), Formula (XI), Formula (XII), Formula (XIII), or Formula (XIV) described infra. In some embodiments, a compound of Formula (I) is a compound selected from a compound described herein.

In another aspect, provided herein are methods for preventing and/or treating a disease in which a change in the level of expression of one, two, three or more protein isoforms encoded by a gene is beneficial to the prevention and/or treatment of the disease, wherein the precursor RNA transcript transcribed from the gene comprises a REMS, the methods comprising administering to a patient in need thereof a compound of Formula (I) or a form thereof, or a pharmaceutical composition comprising a compound of Formula (I) or a form thereof and a pharmaceutically acceptable carrier, excipient or diluent. In one embodiment, provided herein are methods for preventing and/or treating a disease in which the alteration (e.g., increase or decrease) in the expression one, two, three or more protein isoforms encoded by a gene, by way of nonlimiting example, disclosed in Table 6, infra, is beneficial to the prevention and/or treatment of the disease, the methods comprising administering to a patient in need thereof a compound of Formula (I) or a form thereof, or a pharmaceutical composition comprising a compound of Formula (I) or a form thereof and a pharmaceutically acceptable carrier, excipient or diluent.

In another embodiment, provided herein are methods for preventing and/or treating a disease in which the alteration (e.g., increase or decrease) in the expression one, two, three or more protein isoforms encoded by a gene, not disclosed in Tables 1-4, infra, is beneficial to the prevention and/or treatment of the disease, wherein the precursor RNA transcript transcribed from the gene comprises a REMS, the methods comprising administering to a patient in need thereof a compound of Formula (I) or a form thereof, or a pharmaceutical composition comprising a compound of Formula (I) or a form thereof and a pharmaceutically acceptable carrier, excipient or diluent. In another embodiment, provided herein are methods for preventing and/or treating a disease in which the alteration (e.g., increase or decrease) in the expression one, two, three or more protein isoforms encoded by a gene, not disclosed in International Patent Application No. PCT/US2014/071252 (International Publication No. WO 2015/105657 A1), is beneficial to the prevention and/or treatment of the disease, wherein the precursor RNA transcript transcribed from the gene comprises a REMS, the methods comprising administering to a patient in need thereof a compound of Formula (I) or a form thereof, or a pharmaceutical composition comprising a compound of Formula (I) or a form thereof and a pharmaceutically acceptable carrier, excipient or diluent. In another embodiment, provided herein are methods for preventing and/or treating a disease in which the alteration (e.g., increase or decrease) in the expression one, two, three or more protein isoforms encoded by a gene, not disclosed in Table 6, infra, is beneficial to the prevention and/or treatment of the disease, wherein the precursor RNA transcript transcribed from the gene comprises a REMS, the methods comprising administering to a patient in need thereof a compound of Formula (I) or a form thereof, or a pharmaceutical composition comprising a compound of Formula (I) or a form thereof and a pharmaceutically acceptable carrier, excipient or diluent.

In another embodiment, provided herein are methods for preventing and/or treating a disease in which the alteration (e.g., increase or decrease) in the expression one, two, three or more protein isoforms encoded by ERGIC3, is beneficial to the prevention and/or treatment of the disease, the methods comprising administering to a patient in need thereof a compound of Formula (I) or a form thereof, or a pharmaceutical composition comprising a compound of Formula (I) or a form thereof and a pharmaceutically acceptable carrier, excipient or diluent. In a specific embodiment, one, two, three or more RNA isoforms encoded by ERGIC3 are decreased following administration of a compound of Formula (I) or a form thereof and a pharmaceutically acceptable carrier, excipient or diluent. See the example section for additional information regarding the genes in Table 6. In certain embodiments, a compound of Formula (I) is a compound of Formula (II), Formula (III), Formula (IV), Formula (V), Formula (VI), Formula (VII), Formula (VIII), Formula (IX), Formula (X), Formula (XI), Formula (XII), Formula (XIII), or Formula (XIV) described infra. In some embodiments, a compound of Formula (I) is a compound selected from a compound described herein.

In another aspect, provided herein are artificial gene constructs. In one embodiment, provided herein is an artificial gene construct comprising DNA encoding exons, a 3' splice site(s) and a branch point(s), wherein a nucleotide sequence encoding an exon, which is upstream of a nucleotide sequence encoding a branch point and a nucleotide sequence encoding a 3' splice site, is modified to introduce a nucleotide sequence encoding a REMS. In another embodiment, provided herein is an artificial gene construct comprising DNA encoding exons and one, two or more introns, wherein a nucleotide sequence encoding a 5' splice site, which is upstream of a nucleotide sequence encoding a branch point and a nucleotide sequence encoding a 3' splice site, is modified to introduce a nucleotide sequence encoding a REMS. In another embodiment, provided herein is an artificial gene construct comprising DNA encoding exons, a 5' splice site(s), a 3' splice site(s) and a branch point(s), wherein a nucleotide sequence encoding a 5' splice site, which is upstream of a nucleotide sequence encoding a 3' splice site, is modified to introduce a nucleotide sequence encoding a REMS. In certain embodiments, the artificial gene construct encodes a therapeutic protein. In some embodiments, the artificial gene construct encodes a detectable reporter protein. In a specific embodiment, the nucleotide sequence of the REMS introduced into the nucleotide sequence of the artificial gene construct comprises the sequence GAgtrngn (SEQ ID NO: 5), wherein r is A or G and n is any nucleotide. In a specific embodiment, the nucleotide sequence encoding the REMS comprises the sequence ANGAgtrngn (SEQ ID NO: 7), wherein r is A or G and n or N is any nucleotide. In a further specific embodiment, the nucleotide sequence encoding the REMS comprises the sequence ANGAgtragt (SEQ ID NO: 8), wherein r is A or G and N is any nucleotide. In various specific embodiments, the nucleotide sequence encoding the REMS is a nucleotide sequence encoding a non-endogenous REMS, i.e., not naturally found in the DNA sequence of the artificial construct.

In certain embodiments, provided herein is a vector comprising the artificial gene construct described herein. In some embodiments, provided herein is a cell comprising an artificial gene construct described herein or a vector comprising an artificial gene construct described herein.

In another aspect, provided herein is a method of modulating the amount of a functional protein produced by a cell containing an artificial gene construct described herein. In one embodiment, provided herein is a method of modulating the amount of a functional protein produced by a cell containing an artificial gene construct described herein, the method comprising contacting the cell with a compound of Formula (I) or a form thereof. In certain embodiments, the artificial gene construct encodes a therapeutic protein. In some embodiments, the artificial gene construct encodes a detectable reporter protein.

In another aspect, provided herein is a method of modulating the amount of a functional protein produced by a subject, wherein the subject is or was administered an artificial gene construct described herein. In one embodiment, provided herein is method of regulating the amount of a functional protein produced by a subject, the method comprising: (a) administering an artificial gene construct or a vector comprising the artificial gene construct described herein to the subject; and (b) administering a compound of Formula (I) or a form thereof to the subject. In another embodiment, provided herein is a method of regulating the amount of a functional protein produced by a subject, the method comprising administering a compound of Formula (I) or a form thereof to a subject carrying a gene containing a nucleotide sequence encoding a REMS. In another embodiment, provided herein is a method of regulating the amount of a functional protein produced by a subject, the method comprising administering a compound of Formula (I) to the subject, wherein the subject was previously administered an artificial gene construct described herein. In certain embodiments, the artificial gene construct encodes a therapeutic protein. In some embodiments, the artificial gene construct encodes a detectable reporter protein. In certain embodiments, the subject is a non-human. In specific embodiments, the subject is a human.

In another aspect, provided herein is a method for modulating the amount of an RNA transcript produced from precursor RNA containing a non-endogenous recognition element for splicing modifier (REMS), the method comprising contacting the precursor RNA with a compound of Formula (I) or a form thereof, wherein the non-endogenous REMS comprises the sequence GAgurngn (SEQ ID NO: 1), wherein r is A or G and n is any nucleotide, and wherein Formula (I) is

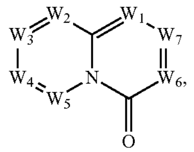

(I)

wherein:

$w_1$ and $w_5$ are independently C—$R_a$ or N;

$w_2$ is C—$R_b$ or N;

$w_3$, $w_4$ and $w_7$ are independently C—$R_1$, C—$R_2$, C—$R_a$ or N;

$w_6$ is C—$R_1$, C—$R_2$, C—$R_c$ or N;

wherein one of $w_3$, $w_4$, $w_6$ and $w_7$ is C—$R_1$ and one other of $w_3$, $w_4$, $w_6$ and $w_7$ is C—$R_2$, provided that, when $w_3$ is C—$R_1$, then $w_6$ is C—$R_2$ and $w_4$ and $w_7$ are independently C—$R_a$ or N; or, when $w_3$ is C—$R_2$, then $w_6$ is C—$R_1$ and $w_4$ and $w_7$ are independently C—$R_a$ or N; or, when $w_4$ is C—$R_1$, then $w_7$ is C—$R_2$ and $w_3$ is C—$R_a$ or N and $w_6$ is C—$R_c$ or N; or, when $w_4$ is C—$R_2$, then $w_7$ is C—$R_1$ and $w_3$ is C—$R_a$ or N and $w_6$ is C—$R_c$ or N; and, wherein any one, two or three of $w_1$, $w_2$, $w_3$, $w_4$, $w_5$, $w_6$ and $w_7$ may optionally be N;

$R_1$ is $C_{1-8}$alkyl, amino, $C_{1-8}$alkyl-amino, $(C_{1-8}$alkyl$)_2$-amino, $C_{1-8}$alkoxy-$C_{1-8}$alkyl-amino, $(C_{1-8}$alkoxy-$C_{1-8}$alkyl$)_2$-amino, $(C_{1-8}$alkoxy-$C_{1-8}$alkyl$)(C_{1-8}$alkyl$)$amino, amino-$C_{1-8}$alkyl, $C_{1-8}$alkyl-amino-$C_{1-8}$alkyl, $(C_{1-8}$alkyl$)_2$-amino-$C_{1-8}$alkyl, $C_{1-8}$alkoxy-$C_{1-8}$alkyl-amino-$C_{1-8}$alkyl, $(C_{1-8}$alkoxy-$C_{1-8}$alkyl$)_2$-amino-$C_{1-8}$alkyl, $(C_{1-8}$alkoxy-$C_{1-8}$alkyl$)(C_{1-8}$alkyl$)$amino-$C_{1-8}$alkyl, amino-$C_{1-8}$alkyl-amino, (amino-$C_{1-8}$alkyl$)_2$-amino, (amino-$C_{1-8}$alkyl$)(C_{1-8}$alkyl$)$amino, $C_{1-8}$alkyl-amino-$C_{1-8}$alkyl-amino, $(C_{1-8}$alkyl-amino-$C_{1-8}$alkyl$)_2$-amino, $(C_{1-8}$alkyl-amino-$C_{1-8}$alkyl$)(C_{1-8}$alkyl$)$amino, $(C_{1-8}$alkyl$)_2$-amino-$C_{1-8}$alkyl-amino, $[(C_{1-8}$alkyl$)_2$-amino-$C_{1-8}$alkyl$](C_{1-8}$alkyl$)$amino, amino-$C_{1-8}$alkoxy, $C_{1-8}$alkyl-amino-$C_{1-8}$alkoxy, $(C_{1-8}$alkyl$)_2$-amino-$C_{1-8}$alkoxy, $C_{1-8}$alkoxy-$C_{1-8}$alkyl-amino-$C_{1-8}$alkoxy, $C_{1-8}$alkoxy-$C_{1-8}$alkyl-amino-$C_{1-8}$alkoxy, $(C_{1-8}$alkoxy-$C_{1-8}$alkyl$)(C_{1-8}$alkyl$)$amino-$C_{1-8}$alkoxy, amino-$C_{2-8}$alkenyl, $C_{1-8}$alkyl-amino-$C_{2-8}$alkenyl, $(C_{1-8}$alkyl$)_2$-amino-$C_{2-8}$alkenyl, amino-$C_{2-8}$alkynyl, $C_{1-8}$alkyl-amino-$C_{2-8}$alkynyl, $(C_{1-8}$alkyl$)_2$-amino-$C_{2-8}$alkynyl, halo-$C_{1-8}$alkyl-amino, (halo-$C_{1-8}$alkyl$)_2$-amino, (halo-$C_{1-8}$alkyl$)(C_{1-8}$alkyl$)$amino, hydroxy-$C_{1-8}$alkyl, hydroxy-$C_{1-8}$alkoxy-$C_{1-8}$alkyl, hydroxy-$C_{1-8}$alkyl-amino, (hydroxy-$C_{1-8}$alkyl$)_2$-amino, (hydroxy-$C_{1-8}$alkyl$)(C_{1-8}$alkyl$)$amino, hydroxy-$C_{1-8}$alkyl-amino-$C_{1-8}$alkyl, (hydroxy-$C_{1-8}$alkyl$)_2$-amino-$C_{1-8}$alkyl, (hydroxy-$C_{1-8}$alkyl$)(C_{1-8}$alkyl$)$amino-$C_{1-8}$alkyl, hydroxy-$C_{1-8}$alkyl-amino-$C_{1-8}$alkoxy, (hydroxy-$C_{1-8}$alkyl$)_2$-amino-$C_{1-8}$alkoxy, (hydroxy-$C_{1-8}$alkyl$)(C_{1-8}$alkyl$)$amino-$C_{1-8}$alkoxy, hydroxy-$C_{1-8}$alkylamino-$C_{1-8}$alkyl-amino, (hydroxy-$C_{1-8}$alkyl-amino-$C_{1-8}$alkyl)$_2$-amino, (hydroxy-$C_{1-8}$alkyl)$_2$-amino-$C_{1-8}$alkyl-amino, (hydroxy-$C_{1-8}$alkyl-amino-$C_{1-8}$alkyl)($C_{1-8}$alkyl)amino, (hydroxy-$C_{1-8}$alkyl)($C_{1-8}$alkyl)amino-$C_{1-8}$alkyl-amino, [(hydroxy-$C_{1-8}$alkyl)$_2$-amino-$C_{1-8}$alkyl]($C_{1-8}$alkyl)amino, [(hydroxy-$C_{1-8}$alkyl)($C_{1-8}$alkyl)amino-$C_{1-8}$alkyl]($C_{1-8}$alkyl)amino, heterocyclyl, heterocyclyl-$C_{1-8}$alkyl, heterocyclyl-$C_{1-8}$alkoxy, heterocyclyl-amino, (heterocyclyl)($C_{1-8}$alkyl)amino, heterocyclyl-amino-$C_{1-8}$alkyl, heterocyclyl-$C_{1-8}$alkyl-amino, (heterocyclyl-$C_{1-8}$alkyl)$_2$-amino, (heterocyclyl-$C_{1-8}$alkyl)($C_{1-8}$alkyl)amino, heterocyclyl-$C_{1-8}$alkyl-amino-$C_{1-8}$alkyl, (heterocyclyl-$C_{1-8}$alkyl)$_2$-amino-$C_{1-8}$alkyl, (heterocyclyl-$C_{1-8}$alkyl)($C_{1-8}$alkyl)amino-$C_{1-8}$alkyl, heterocyclyl-oxy, heterocyclyl-carbonyl, heterocyclyl-carbonyl-oxy, $C_{3-14}$cycloalkyl, aryl-$C_{1-8}$alkyl-amino, (aryl-$C_{1-8}$alkyl)$_2$-amino, (aryl-$C_{1-8}$alkyl)($C_{1-8}$alkyl)amino, aryl-$C_{1-8}$alkyl-amino-$C_{1-8}$alkyl, (aryl-$C_{1-8}$alkyl)$_2$-amino-$C_{1-8}$alkyl, (aryl-$C_{1-8}$alkyl)($C_{1-8}$alkyl)amino-$C_{1-8}$alkyl, heteroaryl, heteroaryl-$C_{1-8}$alkyl, heteroaryl-$C_{1-8}$alkoxy, heteroaryl-amino, heteroaryl-$C_{1-8}$alkyl-amino, (heteroaryl-$C_{1-8}$alkyl)$_2$-amino, (heteroaryl-$C_{1-8}$alkyl)($C_{1-8}$alkyl)amino, heteroaryl-$C_{1-8}$alkyl-amino-$C_{1-8}$alkyl, (heteroaryl-$C_{1-8}$alkyl)$_2$-amino-$C_{1-8}$alkyl or (heteroaryl-$C_{1-8}$alkyl)($C_{1-8}$alkyl)amino-$C_{1-8}$alkyl;

wherein, each instance of heterocyclyl, $C_{3-14}$cycloalkyl, aryl and heteroaryl is optionally substituted with one, two or three $R_3$ substituents and optionally, with one additional $R_4$ substituent; or, wherein, each instance of heterocyclyl, $C_{3-14}$cycloalkyl, aryl and heteroaryl is optionally substituted with one, two, three or four $R_3$ substituents;

$R_2$ is aryl, aryl-amino, aryl-amino-carbonyl, heterocyclyl, heteroaryl or heteroaryl-amino;

wherein, each instance of aryl, heterocyclyl and heteroaryl is optionally substituted with one, two or three $R_6$ substituents and optionally, with one additional $R_7$ substituent;

$R_a$ is, in each instance, independently selected from hydrogen, halogen, $C_{1-8}$alkyl or deuterium;

$R_b$ is hydrogen, halogen, $C_{1-8}$alkyl, $C_{1-8}$alkoxy or deuterium;

$R_c$ is hydrogen, halogen, $C_{1-8}$alkyl or deuterium;

$R_3$ is, in each instance, independently selected from cyano, halogen, hydroxy, oxo, $C_{1-8}$alkyl, halo-$C_{1-8}$alkyl, $C_{1-8}$alkyl-carbonyl, $C_{1-8}$alkoxy, halo-$C_{1-8}$alkoxy, $C_{1-8}$alkoxy-$C_{1-8}$alkyl, $C_{1-8}$alkoxy-carbonyl, amino, $C_{1-8}$alkyl-amino, ($C_{1-8}$alkyl)$_2$-amino, amino-$C_{1-8}$alkyl, $C_{1-8}$alkyl-amino-$C_{1-8}$alkyl, ($C_{1-8}$alkyl)$_2$-amino-$C_{1-8}$alkyl, amino-$C_{1-8}$alkyl-amino, $C_{1-8}$alkyl-amino-$C_{1-8}$alkyl-amino, ($C_{1-8}$alkyl-amino-$C_{1-8}$alkyl)$_2$-amino, ($C_{1-8}$alkyl)$_2$-amino-$C_{1-8}$alkyl-amino, [($C_{1-8}$alkyl)$_2$-amino-$C_{1-8}$alkyl]$_2$-amino, ($C_{1-8}$alkyl-amino-$C_{1-8}$alkyl)($C_{1-8}$alkyl)amino, [($C_{1-8}$alkyl)$_2$-amino-$C_{1-8}$alkyl]($C_{1-8}$alkyl)amino, $C_{1-8}$alkoxy-$C_{1-8}$alkyl-amino, ($C_{1-8}$alkoxy-$C_{1-8}$alkyl)$_2$-amino, ($C_{1-8}$alkoxy-$C_{1-8}$alkyl)($C_{1-8}$alkyl)amino, $C_{1-8}$alkyl-carbonyl-amino, $C_{1-8}$alkoxy-carbonyl-amino, hydroxy-$C_{1-8}$alkyl, hydroxy-$C_{1-8}$alkoxy-$C_{1-8}$alkyl, hydroxy-$C_{1-8}$alkyl-amino, (hydroxy-$C_{1-8}$alkyl)$_2$-amino or (hydroxy-$C_{1-8}$alkyl)($C_{1-8}$alkyl)amino;

$R_4$ is $C_{3-14}$cycloalkyl, $C_{3-14}$cycloalkyl-$C_{1-8}$alkyl, $C_{3-14}$cycloalkyl-amino, aryl-$C_{1-8}$alkyl, aryl-$C_{1-8}$alkoxy-carbonyl, aryl-sulfonyloxy-$C_{1-8}$alkyl, heterocyclyl or heterocyclyl-$C_{1-8}$alkyl; wherein, each instance of $C_{3-14}$cycloalkyl, aryl and heterocyclyl is optionally substituted with one, two or three $R_5$ substituents;

$R_5$ is, in each instance, independently selected from halogen, hydroxy, cyano, nitro, $C_{1-8}$alkyl, halo-$C_{1-8}$alkyl, $C_{1-8}$alkoxy, halo-$C_{1-8}$alkoxy, amino, $C_{1-8}$alkyl-amino, ($C_{1-8}$alkyl)$_2$-amino or $C_{1-8}$alkyl-thio;

$R_6$ is, in each instance, independently selected from halogen, hydroxy, cyano, nitro, $C_{1-8}$alkyl, $C_{2-8}$alkenyl, halo-$C_{1-8}$alkyl, hydroxy-$C_{1-8}$alkyl, $C_{1-8}$alkoxy, halo-$C_{1-8}$alkoxy, $C_{1-8}$alkoxy-$C_{1-8}$alkyl, amino, $C_{1-8}$alkyl-amino, ($C_{1-8}$alkyl)$_2$-amino or $C_{1-8}$alkyl-thio; and, $R_7$ is $C_{3-14}$cycloalkyl, $C_{3-14}$cycloalkyl-oxy, aryl, heterocyclyl or heteroaryl.

In another aspect, provided herein is a method of regulating the amount of a functional protein produced by a gene comprising a nucleotide sequence encoding a non-endogenous REMS in a subject, wherein the nucleotide sequence encoding a non-endogenous REMS comprises the sequence GAgtrngn (SEQ ID NO: 5), wherein r is A or G and n is any nucleotide, the method comprising administering a compound of Formula (I) to the subject, wherein Formula (I) is

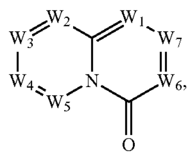

(I)

wherein:

$w_1$ and $w_5$ are independently C—$R_a$ or N;

$w_2$ is C—$R_b$ or N;

$w_3$, $w_4$ and $w_7$ are independently C—$R_1$, C—$R_2$, C—$R_a$ or N;

$w_6$ is C—$R_1$, C—$R_2$, C—$R_c$ or N;

wherein one of $w_3$, $w_4$, $w_6$ and $w_7$ is C—$R_1$ and one other of $w_3$, $w_4$, $w_6$ and $w_7$ is C—$R_2$, provided that, when $w_3$ is C—$R_1$, then $w_6$ is C—$R_2$ and $w_4$ and $w_7$ are independently C—$R_a$ or N; or, when $w_3$ is C—$R_2$, then $w_6$ is C—$R_1$ and $w_4$ and $w_7$ are independently C—$R_a$ or N; or, when $w_4$ is C—$R_1$, then $w_7$ is C—$R_2$ and $w_3$ is C—$R_a$ or N and $w_6$ is C—$R_c$ or N; or, when $w_4$ is C—$R_2$, then $w_7$ is C—$R_1$ and $w_3$ is C—$R_a$ or N and $w_6$ is C—$R_c$ or N; and, wherein any one, two or three of $w_1$, $w_2$, $w_3$, $w_4$, $w_5$, $w_6$ and $w_7$ may optionally be N;

$R_1$ is $C_{1-8}$alkyl, amino, $C_{1-8}$alkyl-amino, ($C_{1-8}$alkyl)$_2$-amino, $C_{1-8}$alkoxy-$C_{1-8}$alkyl-amino, ($C_{1-8}$alkoxy-$C_{1-8}$alkyl)$_2$-amino, ($C_{1-8}$alkoxy-$C_{1-8}$alkyl)($C_{1-8}$alkyl)amino, amino-$C_{1-8}$alkyl, $C_{1-8}$alkyl-amino-$C_{1-8}$alkyl, ($C_{1-8}$alkyl)$_2$-amino-$C_{1-8}$alkyl, $C_{1-8}$alkoxy-$C_{1-8}$alkyl-amino-$C_{1-8}$alkyl, ($C_{1-8}$alkoxy-$C_{1-8}$alkyl)$_2$-amino-$C_{1-8}$alkyl, ($C_{1-8}$alkoxy-$C_{1-8}$alkyl)($C_{1-8}$alkyl)amino-$C_{1-8}$alkyl, amino-$C_{1-8}$alkyl-amino, (amino-$C_{1-8}$alkyl)$_2$-amino, (amino-$C_{1-8}$alkyl)($C_{1-8}$alkyl)amino, $C_{1-8}$alkyl-amino-$C_{1-8}$alkyl-amino, ($C_{1-8}$alkyl-amino-$C_{1-8}$alkyl)$_2$-amino, ($C_{1-8}$alkyl-amino-$C_{1-8}$alkyl)($C_{1-8}$alkyl)amino, ($C_{1-8}$alkyl)$_2$-amino-$C_{1-8}$alkyl-amino, [($C_{1-8}$alkyl)$_2$-amino-$C_{1-8}$alkyl]($C_{1-8}$alkyl)amino, amino-$C_{1-8}$alkoxy, $C_{1-8}$alkyl-amino-$C_{1-8}$alkoxy, ($C_{1-8}$alkyl)$_2$-amino-$C_{1-8}$alkoxy, $C_{1-8}$alkoxy-$C_{1-8}$alkyl-amino-$C_{1-8}$alkoxy, $C_{1-8}$alkoxy-$C_{1-8}$alkyl-amino-$C_{1-8}$alkoxy, ($C_{1-8}$alkoxy-$C_{1-8}$alkyl)($C_{1-8}$alkyl)amino-$C_{1-8}$alkoxy, amino-$C_{2-8}$alkenyl, $C_{1-8}$alkyl-amino-$C_{2-8}$alkenyl, $(C_{1-8}alkyl)_2$-amino-$C_{2-8}$alkenyl, amino-$C_{2-8}$alkynyl, $C_{1-8}$alkyl-amino-$C_{2-8}$alkynyl, $(C_{1-8}alkyl)_2$-amino-$C_{2-8}$alkynyl, halo-$C_{1-8}$alkyl-amino, (halo-$C_{1-8}$alkyl)$_2$-amino, (halo-$C_{1-8}$alkyl)($C_{1-8}$alkyl)amino, hydroxy-$C_{1-8}$alkyl, hydroxy-$C_{1-8}$alkoxy-$C_{1-8}$alkyl, hydroxy-$C_{1-8}$alkyl-amino, (hydroxy-$C_{1-8}$alkyl)$_2$-amino, (hydroxy-$C_{1-8}$alkyl)($C_{1-8}$alkyl)amino, hydroxy-$C_{1-8}$alkyl-amino-$C_{1-8}$alkyl, (hydroxy-$C_{1-8}$alkyl)$_2$-amino-$C_{1-8}$alkyl, (hydroxy-$C_{1-8}$alkyl)($C_{1-8}$alkyl)amino-$C_{1-8}$alkyl, hydroxy-$C_{1-8}$alkyl-amino-$C_{1-8}$alkoxy, (hydroxy-$C_{1-8}$alkyl)$_2$-amino-$C_{1-8}$alkoxy, (hydroxy-$C_{1-8}$alkyl)($C_{1-8}$alkyl)amino-$C_{1-8}$alkoxy, hydroxy-$C_{1-8}$alkyl-amino-$C_{1-8}$alkyl-amino, (hydroxy-$C_{1-8}$alkyl-amino-$C_{1-8}$alkyl)$_2$-amino, (hydroxy-$C_{1-8}$alkyl)$_2$-amino-$C_{1-8}$alkyl-amino, (hydroxy-$C_{1-8}$alkyl-amino-$C_{1-8}$alkyl)($C_{1-8}$alkyl)amino, (hydroxy-$C_{1-8}$alkyl)($C_{1-8}$alkyl)amino-$C_{1-8}$alkyl-amino, [(hydroxy-$C_{1-8}$alkyl)$_2$-amino-$C_{1-8}$alkyl]($C_{1-8}$alkyl)amino, [(hydroxy-$C_{1-8}$alkyl)($C_{1-8}$alkyl)amino-$C_{1-8}$alkyl]($C_{1-8}$alkyl)amino, heterocyclyl, heterocyclyl-$C_{1-8}$alkyl, heterocyclyl-$C_{1-8}$alkoxy, heterocyclyl-amino, (heterocyclyl)($C_{1-8}$alkyl)amino, heterocyclyl-amino-$C_{1-8}$alkyl, heterocyclyl-$C_{1-8}$alkyl-amino, (heterocyclyl-$C_{1-8}$alkyl)$_2$-amino, (heterocyclyl-$C_{1-8}$alkyl)($C_{1-8}$alkyl)amino, heterocyclyl-$C_{1-8}$alkyl-amino-$C_{1-8}$alkyl, (heterocyclyl-$C_{1-8}$alkyl)$_2$-amino-$C_{1-8}$alkyl, (heterocyclyl-$C_{1-8}$alkyl)($C_{1-8}$alkyl)amino-$C_{1-8}$alkyl, heterocyclyl-oxy, heterocyclyl-carbonyl, heterocyclyl-carbonyl-oxy, $C_{3-14}$cycloalkyl, aryl-$C_{1-8}$alkyl-amino, (aryl-$C_{1-8}$alkyl)$_2$-amino, (aryl-$C_{1-8}$alkyl)($C_{1-8}$alkyl)amino, aryl-$C_{1-8}$alkyl-amino-$C_{1-8}$alkyl, (aryl-$C_{1-8}$alkyl)$_2$-amino-$C_{1-8}$alkyl, (aryl-$C_{1-8}$alkyl)($C_{1-8}$alkyl)amino-$C_{1-8}$alkyl, heteroaryl, heteroaryl-$C_{1-8}$alkyl, heteroaryl-$C_{1-8}$alkoxy, heteroaryl-amino, heteroaryl-$C_{1-8}$alkyl-amino, (heteroaryl-$C_{1-8}$alkyl)$_2$-amino, (heteroaryl-$C_{1-8}$alkyl)($C_{1-8}$alkyl)amino, heteroaryl-$C_{1-8}$alkyl-amino-$C_{1-8}$alkyl, (heteroaryl-$C_{1-8}$alkyl)$_2$-amino-$C_{1-8}$alkyl or (heteroaryl-$C_{1-8}$alkyl)($C_{1-8}$alkyl)amino-$C_{1-8}$alkyl;

wherein, each instance of heterocyclyl, $C_{3-14}$cycloalkyl, aryl and heteroaryl is optionally substituted with one, two or three $R_3$ substituents and optionally, with one additional $R_4$ substituent; or, wherein, each instance of heterocyclyl, $C_{3-14}$cycloalkyl, aryl and heteroaryl is optionally substituted with one, two, three or four $R_3$ substituents;

$R_2$ is aryl, aryl-amino, aryl-amino-carbonyl, heterocyclyl, heteroaryl or heteroaryl-amino;

wherein, each instance of aryl, heterocyclyl and heteroaryl is optionally substituted with one, two or three $R_6$ substituents and optionally, with one additional $R_7$ substituent;

$R_a$ is, in each instance, independently selected from hydrogen, halogen, $C_{1-8}$alkyl or deuterium;

$R_b$ is hydrogen, halogen, $C_{1-8}$alkyl, $C_{1-8}$alkoxy or deuterium;

$R_c$ is hydrogen, halogen, $C_{1-8}$alkyl or deuterium;

$R_3$ is, in each instance, independently selected from cyano, halogen, hydroxy, oxo, $C_{1-8}$alkyl, halo-$C_{1-8}$alkyl, $C_{1-8}$alkyl-carbonyl, $C_{1-8}$alkoxy, halo-$C_{1-8}$alkoxy, $C_{1-8}$alkoxy-$C_{1-8}$alkyl, $C_{1-8}$alkoxy-carbonyl, amino, $C_{1-8}$alkyl-amino, $(C_{1-8}alkyl)_2$-amino, amino-$C_{1-8}$alkyl, $C_{1-8}$alkyl-amino-$C_{1-8}$alkyl, $(C_{1-8}alkyl)_2$-amino-$C_{1-8}$alkyl, amino-$C_{1-8}$alkyl-amino, $C_{1-8}$alkyl-amino-$C_{1-8}$alkyl-amino, ($C_{1-8}$alkyl-amino-$C_{1-8}$alkyl)$_2$-amino, $(C_{1-8}alkyl)_2$-amino-$C_{1-8}$alkyl-amino, [$(C_{1-8}alkyl)_2$-amino-$C_{1-8}$alkyl]2-amino, ($C_{1-8}$alkyl-amino-$C_{1-8}$alkyl)($C_{1-8}$alkyl)amino, [$(C_{1-8}alkyl)_2$-amino-$C_{1-8}$alkyl]($C_{1-8}$alkyl)amino, $C_{1-8}$alkoxy-$C_{1-8}$alkyl-amino, ($C_{1-8}$alkoxy-$C_{1-8}$alkyl)$_2$-amino, ($C_{1-8}$alkoxy-$C_{1-8}$alkyl)($C_{1-8}$alkyl)amino, $C_{1-8}$alkyl-carbonyl-amino, $C_{1-8}$alkoxy-carbonyl-amino, hydroxy-$C_{1-8}$alkyl, hydroxy-$C_{1-8}$alkoxy-$C_{1-8}$alkyl, hydroxy-$C_{1-8}$alkyl-amino, (hydroxy-$C_{1-8}$alkyl)$_2$-amino or (hydroxy-$C_{1-8}$alkyl)($C_{1-8}$alkyl)amino;

$R_4$ is $C_{3-14}$cycloalkyl, $C_{3-14}$cycloalkyl-$C_{1-8}$alkyl, $C_{3-14}$cycloalkyl-amino, aryl-$C_{1-8}$alkyl, aryl-$C_{1-8}$alkoxy-carbonyl, aryl-sulfonyloxy-$C_{1-8}$alkyl, heterocyclyl or heterocyclyl-$C_{1-8}$alkyl; wherein, each instance of $C_{3-14}$cycloalkyl, aryl and heterocyclyl is optionally substituted with one, two or three $R_5$ substituents;

$R_5$ is, in each instance, independently selected from halogen, hydroxy, cyano, nitro, $C_{1-8}$alkyl, halo-$C_{1-8}$alkyl, $C_{1-8}$alkoxy, halo-$C_{1-8}$alkoxy, amino, $C_{1-8}$alkyl-amino, $(C_{1-8}alkyl)_2$-amino or $C_{1-8}$alkyl-thio;

$R_6$ is, in each instance, independently selected from halogen, hydroxy, cyano, nitro, $C_{1-8}$alkyl, $C_{2-8}$alkenyl, halo-$C_{1-8}$alkyl, hydroxy-$C_{1-8}$alkyl, $C_{1-8}$alkoxy, halo-$C_{1-8}$alkoxy, $C_{1-8}$alkoxy-$C_{1-8}$alkyl, amino, $C_{1-8}$alkyl-amino, $(C_{1-8}alkyl)_2$-amino or $C_{1-8}$alkyl-thio; and, $R_7$ is $C_{3-14}$cycloalkyl, $C_{3-14}$cycloalkyl-oxy, aryl, heterocyclyl or heteroaryl.

In specific embodiments of the foregoing aspect, the gene is ABCA1, ABCB7, ABCC1, ABHD10, ABL2, ABLIM3, ACACA, ACADVL, ACAT2, ADAM12, ADAM15, ADAM17, ADAM33, AFF2, AGK, AGPAT3, AGPS, AHCYL2, AHDC1, AHRR, AJUBA, AK021888, AK310472, AKAP1, AKAP9, AKNA, ALCAM, ALDH4A1, AMPD2, ANK2, ANKFY1, ANKHD1-EIF4EBP3, ANKRD17, ANKS6, ANP32A, ANXA11, ANXA6, AP2B1, APAF1, APLP2, APP, APPL2, APTX, ARHGAP22, ARID1A, ARID2, ARMCX3, ASAP1, ASL, ASNS, ASPH, ATAD2B, ATF7IP, ATG9A, ATMIN, ATP2C1, ATXN3, AURKA, AXIN1, B4GALT2, BACE1, BAG2, BASP1, BC033281, BCAR3, BEND6, BICD1, BIN1, BNC1, BRD2, BRPF1, BSCL2, BTBD10, BZW1, C11orf30, C11orf73, C17orf76-AS1, C4orf27, C5orf24, C6orf48, C9orf69, CAB39, CALU, CAMKK1, CAPNS1, CASC3, CASP8AP2, CAV1, CCAR1, CCDC77, CCDC88A, CCDC92, CCT6A, CD276, CD46, CDC25B, CDC40, CDC42BPA, CDCA7, CDH11, CDH13, CDK11B, CDK16, CDKAL1, CEP68, CFLAR, CHD8, CIZ1, CLIC1, CLK4, CNOT1, COG1, COL12A1, COL1A1, COL6A1, COPS7B, CPEB2, CREB5, CRLS1, CRTAP, CSDE1, CSNK1A1, CTDSP2, CTNND1, CUL2, CUL4A, CUX1, CYB5B, CYBRD1, CYP51A1, DAB2, DACT1, DARS, DAXX, DCAF10, DCAF11, DCBLD2, DCUN1D4, DDAH1, DDAH2, DDHD2, DDR1, DDX39B, DDX42, DENND1A, DENND1B, DENND5A, DGCR2, DGKA, DHCR24, DHCR7, DHFR, DHX9, DIAPH1, DIAPH3, DIS3L, DKFZp434M1735, DKK3, DLC1, DNM2, DOCK1, DPP8, DSEL, DST, DSTN, EBF1, EEA1, EEF1A1, EFCAB14, EGR1, EHMT2, EIF2B3, EIF4G1, EIF4G2, EIF4G3, ELF2, ENG, ENPP2, ENSA, EPN1, EPT1, ERC1, ERGIC3, ETV5, EXO1, EXTL2, EYA3, FADS1, FADS2, FAF, FAM111A, FAM198B, FAM219A, FAM219B, FAM3C, FAM65A, FBXO10, FBXO18, FBXO31, FBXO34, FBXO9, FDFT1, FDPS, FER, FEZ1, FGD5-AS1, FGFRL1, FHOD3, FLII, FLNB, FN1, FNBP1, FOCAD, FOS, FOSB, FOSL1, FOXK1, FOXM1, FUS, FYN, GABPB1, GALC, GALNT1, GAS7, GBA2, GCFC2, GGCT, GHDC, GIGYF2, GJC1, GMIP, GNA13, GNAS, GNL3L, GOLGA2, GOLGA4, GOLGB1, GORASP1, GPR1, GPR89A, GPSM2, GREM1, GRK6, GSE1, GTF2H2B, HAS2, HAT1, HAUS3, HAUS6, HDAC7, HEG1, HLA-A, HLA-E, HLTF, HMGA1, HMGB1, HMGCR, HMGCS1, HMOX1, HNRNPR, HNRNPUL1, HP1BP3, HRH1, HSD17B12, HSD17B4, HTT, IARS, IDH1, IDI1, IGF2BP2, IL6ST, INHBA, INSIG1, IQCE, ITGAV, ITGB5, ITM2C, ITSN1, KANSL3, KCNK2, KIAA1033, KIAA1143, KIAA1199, KIAA1522, KIAA1524, KIAA1549, KIAA1715, KIF14, KIF2A, KIF3A, KLC1, KLC2, KLF6, KLHL7, KRT18, KRT19, KRT34, KRTAP2-3, LAMA2, LAMB1, LARP4, LARP7, LATS2, LDLR, LEMD3, LGALS8, LIMS1, LINC00341, LINC00657, LMAN2L, LMO7, LONP1, LOX, LRCH4, LRIG1, LRP8, LRRC8A, LSS, LTBR, LUC7L2, LZTS2, MADD, MAGED4, MAGED4B, MAN1A2, MAP4K4, MBD1, MBOAT7, MDM2, MED1, MEDAG, MEF2D, MEIS2, MEMO1, MEPCE, MFGE8, MICAL2, MINPP1, MKL1, MKLN1, MKNK2, MLLT4, MLST8, MMAB, MMS19, MMS22L, MPPE1, MPZL1, MRPL3, MSANTD3, MSC, MSH2, MSH6, MSL3, MSMO1, MSRB3, MTAP, MTERFD1, MTHFD1L, MTMR9, MTRR, MUM1, MVD, MVK, MYADM, MYLK, MYO1D, MYO9B, MYOF, NAA35, NADK, NASP, NAV1, NAV2, NCOA1, NCOA3, NCOA4, NCSTN, NELFA, NEO1, NEURL1B, NF2, NFE2L1, NFX1, NID1, NID2, NIPA1, NKX3-1, NOL10, NOMO3, NPEPPS, NRD1, NREP, NRG1, NSUN4, NT5C2, NT5E, NTNG1, NUDT4, NUP153, NUP35, NUP50, NUPL1, NUSAP1, ODF2, OS9, OSBPL6, OSMR, P4HA1, P4HB, PABPC1, PAK4, PAPD4, PARD3, PARN, PARP14, PARP4, PARVB, PCBP2, PCBP4, PCDHGB3, PCGF3, PCM1, PCMTD2, PCNXL2, PCSK9, PDE4A, PDE7A, PDLIM7, PDXDC1, PEPD, PEX5, PFKP, PHF19, PHF8, PHRF1, PHTF2, PI4K2A, PIEZO1, PIGU, PIK3C2B, PITPNA, PITPNB, PITPNM1, PLAU, PLEC, PLEKHB2, PLSCR3, PLXNB2, PLXNC1, PMS1, POLE3, POLR3D, POSTN, POU2F1, PPAPDC1A, PPARA, PPHLN1, PPIP5K1, PPP1R12A, PPP6R1, PPP6R2, PRKACB, PRKDC, PRMT1, PRNP, PRSS23, PSMA4, PSMC1, PSMD6, PTK2B, PTPN14, PUF60, PUS7, PVR, PXN, QKI, RAB23, RAB2B, RAB34, RAD1, RAD23B, RALB, RAP1A, RAP1GDS1, RARG, RASSF8, RBCK1, RBFOX2, RBM10, RCC1, RFTN1, RFWD2, RGS10, RGS3, RIF1, RNF14, RNF19A, RNF38, RNFT1, RPL10, RPS6KC1, RRBP1, RWDD4, SAMD9, SAMD9L, SAR1A, SART3, SCAF4, SCAF8, SCD, SCLT1, SCO1, SDCBP, SEC14L1, SEC22A, SEC24B, SEC61A1, SEPT9, SERPINE2, SF1, SGOL2, SH3RF1, SKIL, SLC25A17, SLC39A3, SLC41A1, SLC4A4, SLC7A6, SLC7A8, SMARCA4, SMARCC2, SMC4, SMC6, SMCHD1, SMG1, SMN2, SMPD4, SMYD3, SMYD5, SNAP23, SNHG16, SNX14, SOCS2, SON, SOS2, SPATA20, SPATS2, SPG20, SPRED2, SQLE, SQRDL, SQSTM1, SRCAP, SREBF1, SREK1, SRSF3, STARD4, STAT1, STAT3, STAU1, STC2, STEAP2, STRIP1, STRN3, STX16, SUPT20H, SYNE1, SYNE2, SYT15, SYTL2, TACC1, TAF2, TANC2, TARBP1, TARS, TBC1D15, TBL2, TCF7L2, TENC1, TENM2, TEP1, TET3, TFCP2, TGFBI, TGFBR1, TGFBRAP1, THADA, THAP4, THRB, TIMP2, TJP2, TLE3, TLK1, TMEM154, TMEM47, TMEM63A, TNC, TNFAIP3, TNFRSF12A, TNIP1, TNKS1BP1, TNPO3, TNS1, TNS3, TOE1, TOMM40, TOMM5, TOPORS, TP53INP1, TRAF3, TRAK1, TRAPPC12, TRIB1, TRIM2, TRIM23, TRIM26, TRIM28, TRIM65, TRMT1L, TRPS1, TSC2, TSHZ1, TSPAN2, TTC7A, TUBB2C, TUBB3, TXNL1, TXNRD1, U2SURP, UBAP2L, UBE2G2, UBE2V1, UBQLN4, UCHL5, UHMK1, UHRF1BP1L, UNC5B, USP19, USP7, VANGL1, VARS2, VCL, VIPAS39, VPS13A, VPS29, VPS51, VWA8, WDR19, WDR37, WDR48, WIPF1, WNT5B, WSB1, WWTR1, XIAP, XRN2, YAP1, YES1, YPEL5, YTHDF3, Z24749, ZAK, ZBTB10, ZBTB24, ZBTB7A, ZC3H12C, ZC3H14, ZC3H18, ZCCHC11, ZEB1, ZEB2, ZFAND1, ZFAND5, ZHX3, ZMIZ1, ZMYM2, ZNF12, ZNF148, ZNF219, ZNF227, ZNF24, ZNF268, ZNF28, ZNF281, ZNF335, ZNF37A, ZNF37BP, ZNF395, ZNF583, ZNF621, ZNF652, ZNF655, ZNF674, ZNF74, ZNF764, ZNF778, ZNF780A, ZNF827, ZNF839 or ZNF91.

In another aspect, provide herein is a method of modulating the amount of a functional protein produced by a cell containing the artificial gene construct as described above, the method comprising contacting the cell with a compound of Formula (I) or a form thereof, wherein Formula (I) is (I)

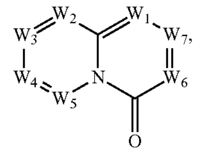

wherein:

$w_1$ and $w_5$ are independently C—$R_a$ or N;

$w_2$ is C—$R_b$ or N;

$w_3$, $w_4$ and $w_7$ are independently C—$R_1$, C—$R_2$, C—$R_a$ or N;

$w_6$ is C—$R_1$, C—$R_2$, C—$R_c$ or N;

wherein one of $w_3$, $w_4$, $w_6$ and $w_7$ is C—$R_1$ and one other of $w_3$, $w_4$, $w_6$ and $w_7$ is C—$R_2$, provided that, when $w_3$ is C—$R_1$, then $w_6$ is C—$R_2$ and $w_4$ and $w_7$ are independently C—$R_a$ or N; or, when $w_3$ is C—$R_2$, then $w_6$ is C—$R_1$ and $w_4$ and $w_7$ are independently C—$R_a$ or N; or, when $w_4$ is C—$R_1$, then $w_7$ is C—$R_2$ and $w_3$ is C—$R_a$ or N and $w_6$ is C—$R_c$ or N; or, when $w_4$ is C—$R_2$, then $w_7$ is C—$R_1$ and $w_3$ is C—$R_a$ or N and $w_6$ is C—$R_c$ or N; and, wherein any one, two or three of $w_1$, $w_2$, $w_3$, $w_4$, $w_5$, $w_6$ and $w_7$ may optionally be N;

$R_1$ is $C_{1-8}$alkyl, amino, $C_{1-8}$alkyl-amino, $(C_{1-8}alkyl)_2$-amino, $C_{1-8}$alkoxy-$C_{1-8}$alkyl-amino, $(C_{1-8}alkoxy\text{-}C_{1-8}alkyl)_2$-amino, $(C_{1-8}$alkoxy-$C_{1-8}$alkyl)$(C_{1-8}$alkyl)amino, amino-$C_{1-8}$alkyl, $C_{1-8}$alkyl-amino-$C_{1-8}$alkyl, $(C_{1-8}alkyl)_2$-amino-$C_{1-8}$alkyl, $C_{1-8}$alkoxy-$C_{1-8}$alkyl-amino-$C_{1-8}$alkyl, $(C_{1-8}alkoxy\text{-}C_{1-8}alkyl)_2$-amino-$C_{1-8}$alkyl, $(C_{1-8}$alkoxy-$C_{1-8}$alkyl)$(C_{1-8}$alkyl)amino-$C_{1-8}$alkyl, amino-$C_{1-8}$alkyl-amino, $(amino\text{-}C_{1-8}alkyl)_2$-amino, (amino-$C_{1-8}$alkyl)$(C_{1-8}$alkyl)amino, $C_{1-8}$alkyl-amino-$C_{1-8}$alkyl-amino, $(C_{1-8}alkyl\text{-}amino\text{-}C_{1-8}alkyl)_2$-amino, $(C_{1-8}$alkyl-amino-$C_{1-8}$alkyl)$(C_{1-8}$alkyl)amino, $(C_{1-8}alkyl)_2$-amino-$C_{1-8}$alkyl-amino, $[(C_{1-8}alkyl)_2$-amino-$C_{1-8}$alkyl]$(C_{1-8}$alkyl)amino, amino-$C_{1-8}$alkoxy, $C_{1-8}$alkyl-amino-$C_{1-8}$alkoxy, $(C_{1-8}alkyl)_2$-amino-$C_{1-8}$alkoxy, $C_{1-8}$alkoxy-$C_{1-8}$alkyl-amino-$C_{1-8}$alkoxy, $C_{1-8}$alkoxy-$C_{1-8}$alkyl-amino-$C_{1-8}$alkoxy, $(C_{1-8}$alkoxy-$C_{1-8}$alkyl)$(C_{1-8}$alkyl)amino-$C_{1-8}$alkoxy, amino-$C_{2-8}$alkenyl, $C_{1-8}$alkyl-amino-$C_{2-8}$alkenyl, $(C_{1-8}alkyl)_2$-amino-$C_{2-8}$alkenyl, amino-$C_{2-8}$alkynyl, $C_{1-8}$alkyl-amino-$C_{2-8}$alkynyl, $(C_{1-8}alkyl)_2$-amino-$C_{2-8}$alkynyl, halo-$C_{1-8}$alkyl-amino, $(halo\text{-}C_{1-8}alkyl)_2$-amino, (halo-$C_{1-8}$alkyl)$(C_{1-8}$alkyl)amino, hydroxy-$C_{1-8}$alkyl, hydroxy-$C_{1-8}$alkoxy-$C_{1-8}$alkyl, hydroxy-$C_{1-8}$alkyl-amino, $(hydroxy\text{-}C_{1-8}alkyl)_2$-amino, (hydroxy-$C_{1-8}$alkyl)$(C_{1-8}$alkyl)amino, hydroxy-$C_{1-8}$alkyl-amino-$C_{1-8}$alkyl, $(hydroxy\text{-}C_{1-8}alkyl)_2$-amino-$C_{1-8}$alkyl, (hydroxy-$C_{1-8}$alkyl)($C_{1-8}$alkyl)amino-$C_{1-8}$alkyl, hydroxy-$C_{1-8}$alkyl-amino-$C_{1-8}$alkoxy, (hydroxy-$C_{1-8}$alkyl)$_2$-amino-$C_{1-8}$alkoxy, (hydroxy-$C_{1-8}$alkyl)($C_{1-8}$alkyl)amino-$C_{1-8}$alkoxy, hydroxy-$C_{1-8}$alkyl-amino-$C_{1-8}$alkyl-amino, (hydroxy-$C_{1-8}$alkyl-amino-$C_{1-8}$alkyl)$_2$-amino, (hydroxy-$C_{1-8}$alkyl)$_2$-amino-$C_{1-8}$alkyl-amino, (hydroxy-$C_{1-8}$alkyl-amino-$C_{1-8}$alkyl)($C_{1-8}$alkyl)amino, (hydroxy-$C_{1-8}$alkyl)($C_{1-8}$alkyl)amino-$C_{1-8}$alkyl-amino, [(hydroxy-$C_{1-8}$alkyl)$_2$-amino-$C_{1-8}$alkyl]($C_{1-8}$alkyl)amino, [(hydroxy-$C_{1-8}$alkyl)($C_{1-8}$alkyl)amino-$C_{1-8}$alkyl]($C_{1-8}$alkyl)amino, heterocyclyl, heterocyclyl-$C_{1-8}$alkyl, heterocyclyl-$C_{1-8}$alkoxy, heterocyclyl-amino, (heterocyclyl)($C_{1-8}$alkyl)amino, heterocyclyl-amino-$C_{1-8}$alkyl, heterocyclyl-$C_{1-8}$alkyl-amino, (heterocyclyl-$C_{1-8}$alkyl)$_2$-amino, (heterocyclyl-$C_{1-8}$alkyl)($C_{1-8}$alkyl)amino, heterocyclyl-$C_{1-8}$alkyl-amino-$C_{1-8}$alkyl, (heterocyclyl-$C_{1-8}$alkyl)$_2$-amino-$C_{1-8}$alkyl, (heterocyclyl-$C_{1-8}$alkyl)($C_{1-8}$alkyl)amino-$C_{1-8}$alkyl, heterocyclyl-oxy, heterocyclyl-carbonyl, heterocyclyl-carbonyl-oxy, $C_{3-14}$cycloalkyl, aryl-$C_{1-8}$alkyl-amino, (aryl-$C_{1-8}$alkyl)$_2$-amino, (aryl-$C_{1-8}$alkyl)($C_{1-8}$alkyl)amino, aryl-$C_{1-8}$alkyl-amino-$C_{1-8}$alkyl, (aryl-$C_{1-8}$alkyl)$_2$-amino-$C_{1-8}$alkyl, (aryl-$C_{1-8}$alkyl)($C_{1-8}$alkyl)amino-$C_{1-8}$alkyl, heteroaryl, heteroaryl-$C_{1-8}$alkyl, heteroaryl-$C_{1-8}$alkoxy, heteroaryl-amino, heteroaryl-$C_{1-8}$alkyl-amino, (heteroaryl-$C_{1-8}$alkyl)$_2$-amino, (heteroaryl-$C_{1-8}$alkyl)($C_{1-8}$alkyl)amino, heteroaryl-$C_{1-8}$alkyl-amino-$C_{1-8}$alkyl, (heteroaryl-$C_{1-8}$alkyl)$_2$-amino-$C_{1-8}$alkyl or (heteroaryl-$C_{1-8}$alkyl)($C_{1-8}$alkyl)amino-$C_{1-8}$alkyl;

wherein, each instance of heterocyclyl, $C_{3-14}$cycloalkyl, aryl and heteroaryl is optionally substituted with one, two or three $R_3$ substituents and optionally, with one additional $R_4$ substituent; or, wherein, each instance of heterocyclyl, $C_{3-14}$cycloalkyl, aryl and heteroaryl is optionally substituted with one, two, three or four $R_3$ substituents;

$R_2$ is aryl, aryl-amino, aryl-amino-carbonyl, heterocyclyl, heteroaryl or heteroaryl-amino;

wherein, each instance of aryl, heterocyclyl and heteroaryl is optionally substituted with one, two or three $R_6$ substituents and optionally, with one additional $R_7$ substituent;

$R_a$ is, in each instance, independently selected from hydrogen, halogen, $C_{1-8}$alkyl or deuterium;

$R_b$ is hydrogen, halogen, $C_{1-8}$alkyl, $C_{1-8}$alkoxy or deuterium;

$R_c$ is hydrogen, halogen, $C_{1-8}$alkyl or deuterium;

$R_3$ is, in each instance, independently selected from cyano, halogen, hydroxy, oxo, $C_{1-8}$alkyl, halo-$C_{1-8}$alkyl, $C_{1-8}$alkyl-carbonyl, $C_{1-8}$alkoxy, halo-$C_{1-8}$alkoxy, $C_{1-8}$alkoxy-$C_{1-8}$alkyl, $C_{1-8}$alkoxy-carbonyl, amino, $C_{1-8}$alkyl-amino, ($C_{1-8}$alkyl)$_2$-amino, amino-$C_{1-8}$alkyl, $C_{1-8}$alkyl-amino-$C_{1-8}$alkyl, ($C_{1-8}$alkyl)$_2$-amino-$C_{1-8}$alkyl, amino-$C_{1-8}$alkyl-amino, $C_{1-8}$alkyl-amino-$C_{1-8}$alkyl-amino, ($C_{1-8}$alkyl-amino-$C_{1-8}$alkyl)$_2$-amino, ($C_{1-8}$alkyl)$_2$-amino-$C_{1-8}$alkyl-amino, [($C_{1-8}$alkyl)$_2$-amino-$C_{1-8}$alkyl]2-amino, ($C_{1-8}$alkyl-amino-$C_{1-8}$alkyl)($C_{1-8}$alkyl)amino, [($C_{1-8}$alkyl)$_2$-amino-$C_{1-8}$alkyl]($C_{1-8}$alkyl)amino, $C_{1-8}$alkoxy-$C_{1-8}$alkyl-amino, ($C_{1-8}$alkoxy-$C_{1-8}$alkyl)$_2$-amino, ($C_{1-8}$alkoxy-$C_{1-8}$alkyl)($C_{1-8}$alkyl)amino, $C_{1-8}$alkyl-carbonyl-amino, $C_{1-8}$alkoxy-carbonyl-amino, hydroxy-$C_{1-8}$alkyl, hydroxy-$C_{1-8}$alkoxy-$C_{1-8}$alkyl, hydroxy-$C_{1-8}$alkyl-amino, (hydroxy-$C_{1-8}$alkyl)$_2$-amino or (hydroxy-$C_{1-8}$alkyl)($C_{1-8}$alkyl)amino;

$R_4$ is $C_{3-14}$cycloalkyl, $C_{3-14}$cycloalkyl-$C_{1-8}$alkyl, $C_{3-14}$cycloalkyl-amino, aryl-$C_{1-8}$alkyl, aryl-$C_{1-8}$alkoxy-carbonyl, aryl-sulfonyloxy-$C_{1-8}$alkyl, heterocyclyl or heterocyclyl-$C_{1-8}$alkyl; wherein, each instance of $C_{3-14}$cycloalkyl, aryl and heterocyclyl is optionally substituted with one, two or three $R_5$ substituents;

$R_5$ is, in each instance, independently selected from halogen, hydroxy, cyano, nitro, $C_{1-8}$alkyl, halo-$C_{1-8}$alkyl, $C_{1-8}$alkoxy, halo-$C_{1-8}$alkoxy, amino, $C_{1-8}$alkyl-amino, ($C_{1-8}$alkyl)$_2$-amino or $C_{1-8}$alkyl-thio;

$R_6$ is, in each instance, independently selected from halogen, hydroxy, cyano, nitro, $C_{1-8}$alkyl, $C_{2-8}$alkenyl, halo-$C_{1-8}$alkyl, hydroxy-$C_{1-8}$alkyl, $C_{1-8}$alkoxy, halo-$C_{1-8}$alkoxy, $C_{1-8}$alkoxy-$C_{1-8}$alkyl, amino, $C_{1-8}$alkyl-amino, ($C_{1-8}$alkyl)$_2$-amino or $C_{1-8}$alkyl-thio; and, $R_7$ is $C_{3-14}$cycloalkyl, $C_{3-14}$cycloalkyl-oxy, aryl, heterocyclyl or heteroaryl.

In a specific embodiment, the nucleotide sequence encoding the REMS comprises the sequence ANGAgtrngn (SEQ ID NO: 7), wherein r is A or G and n or N is any nucleotide. In a further specific embodiment, the nucleotide sequence encoding the REMS comprises the sequence ANGAgtragt (SEQ ID NO: 8), wherein r is A or G and N is any nucleotide. In various specific embodiments, the nucleotide sequence encoding the REMS is a nucleotide sequence encoding a non-endogenous REMS, i.e., not naturally found in the DNA sequence of the artificial construct.

BRIEF DESCRIPTION OF THE DRAWINGS

FIGS. 7A-7L. Testing of alternative splicing in different genes confirmed the existence of a consensus REMS.

DETAILED DESCRIPTION

Recognition Element for Splicing Modifier (REMS)

In one aspect, provided herein is a recognition element for splicing modifier (otherwise referred to as "REMS") that plays a role in the recognition of a compound described herein. In a specific embodiment, the REMS has the nucleotide sequence GAgurngn (SEQ ID NO: 1) at the RNA level, wherein r is A or G (i.e., a purine nucleotide) and n is any nucleotide. In another specific embodiment, the REMS has the nucleotide sequence GAguragu (SEQ ID NO: 2) at the RNA level, wherein r is A or G. In another specific embodiment, the REMS has the nucleotide sequence ANGAgurngn (SEQ ID NO: 3) at the RNA level, wherein r is A or G (i.e., a purine nucleotide) and n or N is any nucleotide. In a preferred embodiment, the REMS has the nucleotide sequence ANGAguragu (SEQ ID NO: 4) at the RNA level, wherein r is A or G and N is any nucleotide.

In the context of DNA, in a specific embodiment, the nucleotide sequence encoding a REMS has the sequence GAgtrngn (SEQ ID NO: 5), wherein r is A or G (i.e., a purine nucleotide) and n is any nucleotide. In another specific embodiment, in the context of DNA, the nucleotide sequence encoding a REMS has the sequence GAgtragt (SEQ ID NO: 6), wherein r is A or G. In a specific embodiment, in the context of DNA, the nucleotide sequence encoding a REMS has the sequence ANGAgtrngn (SEQ ID NO: 7), wherein r is A or G (i.e., a purine nucleotide) and n or N is any nucleotide. In a preferred embodiment, in the context of DNA, the nucleotide sequence encoding a REMS has the sequence ANGAgtragt (SEQ ID NO: 8), wherein r is A or G and N is any nucleotide.

A REMS can be part of an endogenous RNA or can be introduced into an RNA sequence that does not naturally contain the REMS sequence (in which case, the introduced REMS is a non-endogenous REMS, i.e., a REMS not naturally present in the corresponding RNA. A nucleotide sequence encoding REMS can also be part of an endogenous DNA sequence, or a nucleotide sequence encoding a REMS can be introduced into a DNA sequence that does not naturally contain the nucleotide sequence encoding the REMS introduced.

In a specific embodiment, the REMS is located in the 5' splice site. In certain embodiments, the REMS is located within an exon, such as in FoxM1 exon 7a. Without being bound by any theory or mechanism, it is believed that compounds described herein increase the affinity of the interaction between U1 snRNP and the nucleotides ANGA (SEQ ID NO: 9) of the REMS. This belief is based, in part, on the recognition that REMS comprises the U1 snRNP binding site.

Figure 1A:
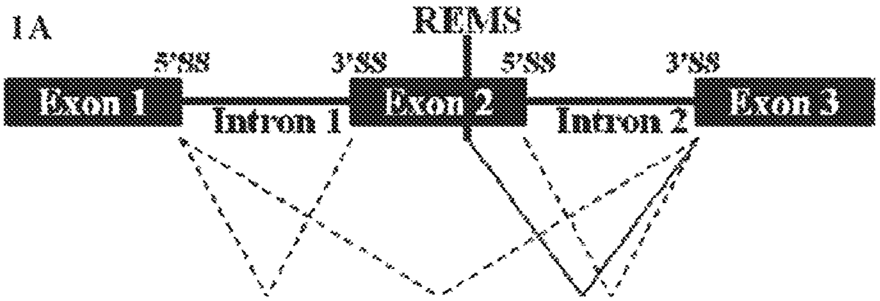
FIGS. 1A-1D. Representative schematics of splicing mediated by REMS. 5'SS is 5' splice site. 3'SS is 3' splice site. Splicing events mediated by REMS are illustrated by solid lines, splicing events not mediated by REMS are illustrated by dashed lines.
Figure 1B:
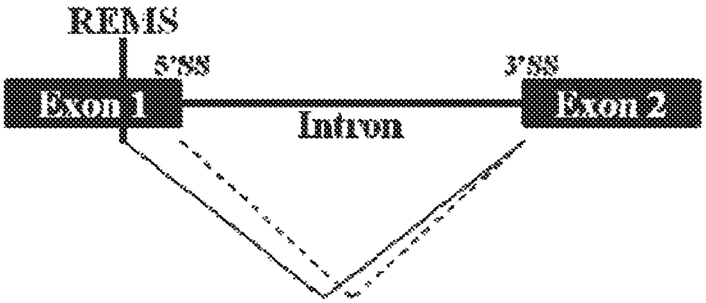
Figure 1C:
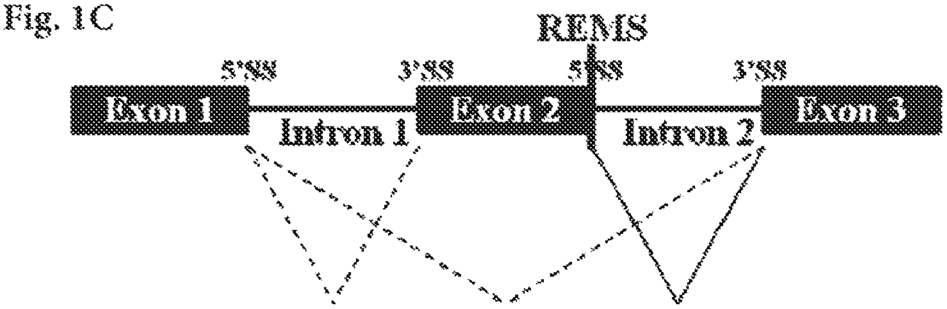
Figure 1D:
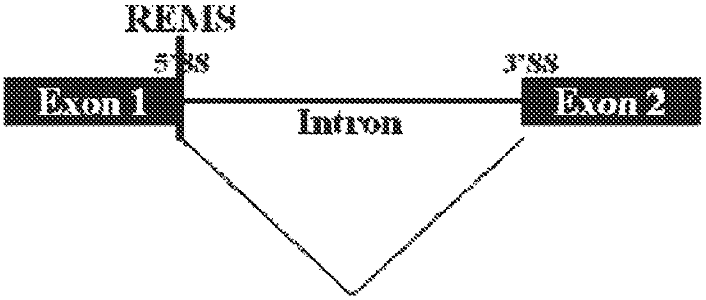

In FIG. 1D, the REMS is located in the 5' splice site of a precursor RNA. In the presence of a compound described herein, the nucleotides between the REMS in the 5' splice site and 3' splice site of a precursor RNA are (except the nucleotides of the exon) removed and the exons of the precursor RNA are spliced together. In FIG. 1B, the REMS is located within an exon in a precursor RNA. In the presence of a compound described herein, the nucleotides between the REMS and the 3' splice site of a precursor RNA (except the nucleotides GA or ANGA) are removed and the remaining portions of the precursor RNA are spliced together, which may result in an RNA transcript with a truncated open reading frame or internal deletions within the open reading frame.

In one embodiment, a precursor RNA transcript comprises three exons and two introns, wherein a REMS is present endogenously or introduced into the 5' splice site of the exon 2-intron 2 boundary of the RNA transcript. In the absence of a compound described herein, some degree of exon 2 skipping will occur and two mRNAs will be produced, e1e2e3 and e1e3. When compound is added, the balance between the two mRNAs produced is shifted so that more e1e2e3 and less e1e3 mRNA is produced. See FIGS. 1A-1D.

In another embodiment, a precursor RNA transcript comprises two exons and one intron, wherein a REMS is present endogenously or introduced into the 5'splice site of the exon 1-intron 1 boundary of the RNA transcript. In the absence of a compound described herein, some degree of inhibition of splicing altogether will occur and two RNA products will be produced—pre-mRNA e1i1e2, which is usually unstable and degraded and, thus, usually not translated so no functional protein is produced, and e1e2 mRNA. When compound is added, the balance between the two RNA products is shifted so that more e1e2 and less e1i1e2 is produced. See FIGS. 1A-1D.

In another embodiment, a precursor RNA transcript comprises a REMS inside an exon (e.g., FOXM1 exon 7a). In this situation, in the absence of a compound described herein, the splicing outcome is driven by the distal 5' splice site and the 5'splice site mediates whole exon splicing. However, when a compound described herein is present, splicing at the REMS is induced and inclusion of a shorter exon results. See FIG. 1B.

When a REMS is introduced into an RNA sequence, the splicing outcome will be governed by the presence/absence of an upstream 5' splice site(s), upstream 3' splice sites, and downstream 3' splice site(s). See FIGS. 1A and 1C.

When a REMS is introduced into an RNA sequence, the splicing outcome will be governed by the presence/absence of an upstream 5' splice site(s), upstream 3' splice sites, and downstream 3' splice site(s) and endogenous splicing control sequences.

Compounds

Provided herein are compounds of Formula (I) for use in the methods described herein:

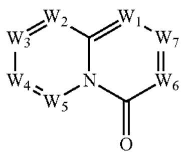

(I)

or a form thereof, wherein:

$w_1$ and $w_5$ are independently C—$R_a$ or N;

$w_2$ is C—$R_b$ or N;

$w_3$, $w_4$ and $w_7$ are independently C—$R_1$, C—$R_2$, C—$R_a$ or N;

$w_6$ is C—$R_1$, C—$R_2$, C—$R_c$ or N;

wherein one of $w_3$, $w_4$, $w_6$ and $w_7$ is C—$R_1$ and one other of $w_3$, $w_4$, $w_6$ and $w_7$ is C—$R_2$, provided that, when $w_3$ is C—$R_1$, then $w_6$ is C—$R_2$ and $w_4$ and $w_7$ are independently C—$R_a$ or N; or, when $w_3$ is C—$R_2$, then $w_6$ is C—$R_1$ and $w_4$ and $w_7$ are independently C—$R_a$ or N; or, when $w_4$ is C—$R_1$, then $w_7$ is C—$R_2$ and $w_3$ is C—$R_a$ or N and $w_6$ is C—$R_c$ or N; or, when $w_4$ is C—$R_2$, then $w_7$ is C—$R_1$ and $w_3$ is C—$R_a$ or N and $w_6$ is C—$R_c$ or N; and, wherein any one, two or three of $w_1$, $w_2$, $w_3$, $w_4$, $w_5$, $w_6$ and $w_7$ may optionally be N;

$R_1$ is $C_{1-8}$alkyl, amino, $C_{1-8}$alkyl-amino, $(C_{1-8}alkyl)_2$-amino, $C_{1-8}$alkoxy-$C_{1-8}$alkyl-amino, $(C_{1-8}alkoxy\text{-}C_{1-8}alkyl)_2$-amino, $(C_{1-8}alkoxy\text{-}C_{1-8}alkyl)(C_{1-8}alkyl)$amino, amino-$C_{1-8}$alkyl, $C_{1-8}$alkyl-amino-$C_{1-8}$alkyl, $(C_{1-8}alkyl)_2$-amino-$C_{1-8}$alkyl, $C_{1-8}$alkoxy-$C_{1-8}$alkyl-amino-$C_{1-8}$alkyl, $(C_{1-8}alkoxy\text{-}C_{1-8}alkyl)_2$-amino-$C_{1-8}$alkyl, $(C_{1-8}alkoxy\text{-}C_{1-8}alkyl)(C_{1-8}alkyl)$amino- $C_{1-8}$alkyl, amino-$C_{1-8}$alkyl-amino, (amino-$C_{1-8}$alkyl)$_2$-amino, (amino-$C_{1-8}$alkyl)($C_{1-8}$alkyl)amino, $C_{1-8}$alkyl-amino-$C_{1-8}$alkyl-amino, ($C_{1-8}$alkyl-amino-$C_{1-8}$alkyl)$_2$-amino, ($C_{1-8}$alkyl-amino-$C_{1-8}$alkyl)($C_{1-8}$alkyl)amino, ($C_{1-8}$alkyl)$_2$-amino-$C_{1-8}$alkyl-amino, [($C_{1-8}$alkyl)$_2$-amino-$C_{1-8}$alkyl]($C_{1-8}$alkyl)amino, amino-$C_{1-8}$alkoxy, $C_{1-8}$alkyl-amino-$C_{1-8}$alkoxy, ($C_{1-8}$alkyl)$_2$-amino-$C_{1-8}$alkoxy, $C_{1-8}$alkoxy-$C_{1-8}$alkyl-amino-$C_{1-8}$alkoxy, $C_{1-8}$alkoxy-$C_{1-8}$alkyl-amino-$C_{1-8}$alkoxy, ($C_{1-8}$alkoxy-$C_{1-8}$alkyl)($C_{1-8}$alkyl)amino-$C_{1-8}$alkoxy, amino-$C_{2-8}$alkenyl, $C_{1-8}$alkyl-amino-$C_{2-8}$alkenyl, ($C_{1-8}$alkyl)$_2$-amino-$C_{2-8}$alkenyl, amino-$C_{2-8}$alkynyl, $C_{1-8}$alkyl-amino-$C_{2-8}$alkynyl, ($C_{1-8}$alkyl)$_2$-amino-$C_{2-8}$alkynyl, halo-$C_{1-8}$alkyl-amino, (halo-$C_{1-8}$alkyl)$_2$-amino, (halo-$C_{1-8}$alkyl)($C_{1-8}$alkyl)amino, hydroxy-$C_{1-8}$alkyl, hydroxy-$C_{1-8}$alkoxy-$C_{1-8}$alkyl, hydroxy-$C_{1-8}$alkyl-amino, (hydroxy-$C_{1-8}$alkyl)$_2$-amino, (hydroxy-$C_{1-8}$alkyl)($C_{1-8}$alkyl)amino, hydroxy-$C_{1-8}$alkyl-amino-$C_{1-8}$alkyl, (hydroxy-$C_{1-8}$alkyl)$_2$-amino-$C_{1-8}$alkyl, (hydroxy-$C_{1-8}$alkyl)($C_{1-8}$alkyl)amino-$C_{1-8}$alkyl, hydroxy-$C_{1-8}$alkyl-amino-$C_{1-8}$alkoxy, (hydroxy-$C_{1-8}$alkyl)$_2$-amino-$C_{1-8}$alkoxy, (hydroxy-$C_{1-8}$alkyl)($C_{1-8}$alkyl)amino-$C_{1-8}$alkoxy, hydroxy-$C_{1-8}$alkyl-amino-$C_{1-8}$alkyl-amino, (hydroxy-$C_{1-8}$alkyl-amino-$C_{1-8}$alkyl)$_2$-amino, (hydroxy-$C_{1-8}$alkyl)$_2$-amino-$C_{1-8}$alkyl-amino, (hydroxy-$C_{1-8}$alkyl-amino-$C_{1-8}$alkyl)($C_{1-8}$alkyl)amino, (hydroxy-$C_{1-8}$alkyl)($C_{1-8}$alkyl)amino-$C_{1-8}$alkyl-amino, [(hydroxy-$C_{1-8}$alkyl)$_2$-amino-$C_{1-8}$alkyl]($C_{1-8}$alkyl)amino, [(hydroxy-$C_{1-8}$alkyl)($C_{1-8}$alkyl)amino-$C_{1-8}$alkyl]($C_{1-8}$alkyl)amino, heterocyclyl, heterocyclyl-$C_{1-8}$alkyl, heterocyclyl-$C_{1-8}$alkoxy, heterocyclyl-amino, (heterocyclyl)($C_{1-8}$alkyl)amino, heterocyclyl-amino-$C_{1-8}$alkyl, heterocyclyl-$C_{1-8}$alkyl-amino, (heterocyclyl-$C_{1-8}$alkyl)$_2$-amino, (heterocyclyl-$C_{1-8}$alkyl)($C_{1-8}$alkyl)amino, heterocyclyl-$C_{1-8}$alkyl-amino-$C_{1-8}$alkyl, (heterocyclyl-$C_{1-8}$alkyl)$_2$-amino-$C_{1-8}$alkyl, (heterocyclyl-$C_{1-8}$alkyl)($C_{1-8}$alkyl)amino-$C_{1-8}$alkyl, heterocyclyl-oxy, heterocyclyl-carbonyl, heterocyclyl-carbonyl-oxy, $C_{3-14}$cycloalkyl, aryl-$C_{1-8}$alkyl-amino, (aryl-$C_{1-8}$alkyl)$_2$-amino, (aryl-$C_{1-8}$alkyl)($C_{1-8}$alkyl)amino, aryl-$C_{1-8}$alkyl-amino-$C_{1-8}$alkyl, (aryl-$C_{1-8}$alkyl)$_2$-amino-$C_{1-8}$alkyl, (aryl-$C_{1-8}$alkyl)($C_{1-8}$alkyl)amino-$C_{1-8}$alkyl, heteroaryl, heteroaryl-$C_{1-8}$alkyl, heteroaryl-$C_{1-8}$alkoxy, heteroaryl-amino, heteroaryl-$C_{1-8}$alkyl-amino, (heteroaryl-$C_{1-8}$alkyl)$_2$-amino, (heteroaryl-$C_{1-8}$alkyl)($C_{1-8}$alkyl)amino, heteroaryl-$C_{1-8}$alkyl-amino-$C_{1-8}$alkyl, (heteroaryl-$C_{1-8}$alkyl)$_2$-amino-$C_{1-8}$alkyl or (heteroaryl-$C_{1-8}$alkyl)($C_{1-8}$alkyl)amino-$C_{1-8}$alkyl;

wherein, each instance of heterocyclyl, $C_{3-14}$cycloalkyl, aryl and heteroaryl is optionally substituted with one, two or three $R_3$ substituents and optionally, with one additional $R_4$ substituent; or, wherein, each instance of heterocyclyl, $C_{3-14}$cycloalkyl, aryl and heteroaryl is optionally substituted with one, two, three or four $R_3$ substituents;

$R_2$ is aryl, aryl-amino, aryl-amino-carbonyl, heterocyclyl, heteroaryl or heteroaryl-amino;

wherein, each instance of aryl, heterocyclyl and heteroaryl is optionally substituted with one, two or three $R_6$ substituents and optionally, with one additional $R_7$ substituent;

$R_a$ is, in each instance, independently selected from hydrogen, halogen, $C_{1-8}$alkyl or deuterium;

$R_b$ is hydrogen, halogen, $C_{1-8}$alkyl, $C_{1-8}$alkoxy or deuterium;

$R_c$ is hydrogen, halogen, $C_{1-8}$alkyl or deuterium;

$R_3$ is, in each instance, independently selected from cyano, halogen, hydroxy, oxo, $C_{1-8}$alkyl, halo-$C_{1-8}$alkyl, $C_{1-8}$alkyl-carbonyl, $C_{1-8}$alkoxy, halo-$C_{1-8}$alkoxy, $C_{1-8}$alkoxy-$C_{1-8}$alkyl, $C_{1-8}$alkoxy-carbonyl, amino, $C_{1-8}$alkyl-amino, ($C_{1-8}$alkyl)$_2$-amino, amino-$C_{1-8}$alkyl, $C_{1-8}$alkyl-amino-$C_{1-8}$alkyl, ($C_{1-8}$alkyl)$_2$-amino-$C_{1-8}$alkyl, amino-$C_{1-8}$alkyl-amino, $C_{1-8}$alkyl-amino-$C_{1-8}$alkyl-amino, ($C_{1-8}$alkyl-amino-$C_{1-8}$alkyl)$_2$-amino, ($C_{1-8}$alkyl)$_2$-amino-$C_{1-8}$alkyl-amino, [($C_{1-8}$alkyl)$_2$-amino-$C_{1-8}$alkyl]$_2$-amino, ($C_{1-8}$alkyl-amino-$C_{1-8}$alkyl)($C_{1-8}$alkyl)amino, [($C_{1-8}$alkyl)$_2$-amino-$C_{1-8}$alkyl]($C_{1-8}$alkyl)amino, $C_{1-8}$alkoxy-$C_{1-8}$alkyl-amino, ($C_{1-8}$alkoxy-$C_{1-8}$alkyl)$_2$-amino, ($C_{1-8}$alkoxy-$C_{1-8}$alkyl)($C_{1-8}$alkyl)amino, $C_{1-8}$alkyl-carbonyl-amino, $C_{1-8}$alkoxy-carbonyl-amino, hydroxy-$C_{1-8}$alkyl, hydroxy-$C_{1-8}$alkoxy-$C_{1-8}$alkyl, hydroxy-$C_{1-8}$alkyl-amino, (hydroxy-$C_{1-8}$alkyl)$_2$-amino or (hydroxy-$C_{1-8}$alkyl)($C_{1-8}$alkyl)amino;

$R_4$ is $C_{3-14}$cycloalkyl, $C_{3-14}$cycloalkyl-$C_{1-8}$alkyl, $C_{3-14}$cycloalkyl-amino, aryl-$C_{1-8}$alkyl, aryl-$C_{1-8}$alkoxy-carbonyl, aryl-sulfonyloxy-$C_{1-8}$alkyl, heterocyclyl or heterocyclyl-$C_{1-8}$alkyl; wherein, each instance of $C_{3-14}$cycloalkyl, aryl and heterocyclyl is optionally substituted with one, two or three $R_5$ substituents;

$R_5$ is, in each instance, independently selected from halogen, hydroxy, cyano, nitro, $C_{1-8}$alkyl, halo-$C_{1-8}$alkyl, $C_{1-8}$alkoxy, halo-$C_{1-8}$alkoxy, amino, $C_{1-8}$alkyl-amino, ($C_{1-8}$alkyl)$_2$-amino or $C_{1-8}$alkyl-thio;

$R_6$ is, in each instance, independently selected from halogen, hydroxy, cyano, nitro, $C_{1-8}$alkyl, $C_{2-8}$alkenyl, halo-$C_{1-8}$alkyl, hydroxy-$C_{1-8}$alkyl, $C_{1-8}$alkoxy, halo-$C_{1-8}$alkoxy, $C_{1-8}$alkoxy-$C_{1-8}$alkyl, amino, $C_{1-8}$alkyl-amino, ($C_{1-8}$alkyl)$_2$-amino or $C_{1-8}$alkyl-thio; and, $R_7$ is $C_{3-14}$cycloalkyl, $C_{3-14}$cycloalkyl-oxy, aryl, heterocyclyl or heteroaryl.

In one embodiment of the use of a compound of Formula (I), $w_1$ is C—$R_a$.

In another embodiment of the use of a compound of Formula (I), $w_1$ is N.

In one embodiment of the use of a compound of Formula (I), $w_2$ is C—$R_b$.

In another embodiment of the use of a compound of Formula (I), $w_2$ is N.

In one embodiment of the use of a compound of Formula (I), $w_3$ is C—$R_a$.

In another embodiment of the use of a compound of Formula (I), $w_3$ is N.

In one embodiment of the use of a compound of Formula (I), $w_4$ is C—$R_a$.

In another embodiment of the use of a compound of Formula (I), $w_4$ is N.

In one embodiment of the use of a compound of Formula (I), $w_5$ is C—$R_a$.

In another embodiment of the use of a compound of Formula (I), $w_5$ is N.

In one embodiment of the use of a compound of Formula (I), $w_6$ is C—$R_c$.

In another embodiment of the use of a compound of Formula (I), $w_6$ is N.

In one embodiment of the use of a compound of Formula (I), $w_7$ is C—$R_a$.

In another embodiment of the use of a compound of Formula (I), $w_7$ is N.

In one embodiment of the use of a compound of Formula (I), $w_3$ is C—$R_1$ and $w_6$ is C—$R_2$.

In another embodiment of the use of a compound of Formula (I), $w_3$ is C—$R_2$ and $w_6$ is C—$R_1$.

In one embodiment of the use of a compound of Formula (I), $w_4$ is C—$R_1$ and $w_7$ is C—$R_2$.

In another embodiment of the use of a compound of Formula (I), $w_4$ is C—$R_2$ and $w_7$ is C—$R_1$.

In one embodiment of the use of a compound of Formula (I), $w_3$ is C—$R_1$, $w_6$ is C—$R_2$ and $w_1$, $w_4$, $w_5$ and $w_7$ are independently C—$R_a$ or N and $w_2$ is C—$R_b$ or N.

In another embodiment of the use of a compound of Formula (I), $w_3$ is C—$R_2$, $w_6$ is C—$R_1$ and $w_1$, $w_4$, $w_5$ and $w_7$ are independently C—$R_a$ or N and $w_2$ is C—$R_b$ or N.

In one embodiment of the use of a compound of Formula (I), $w_4$ is C—$R_1$, $w_7$ is C—$R_2$, $w_1$, $w_3$ and $w_5$ are independently C—$R_a$ or N, $w_2$ is C—$R_b$ or N and $w_6$ is C—$R_c$ or N.

In another embodiment of the use of a compound of Formula (I), $w_4$ is C—$R_2$, $w_7$ is C—$R_1$, $w_1$, $w_3$ and $w_5$ are independently C—$R_a$ or N, $w_2$ is C—$R_b$ or N and $w_6$ is C—$R_c$ or N.

In one embodiment of the use of a compound of Formula (I), $w_1$ and $w_2$ are N.

In one embodiment of the use of a compound of Formula (I), $w_1$ and $w_3$ are N.

In one embodiment of the use of a compound of Formula (I), $w_1$ and $w_4$ are N.

In one embodiment of the use of a compound of Formula (I), $w_1$ and $w_5$ are N.

In one embodiment of the use of a compound of Formula (I), $w_1$ and $w_6$ are N.

In one embodiment of the use of a compound of Formula (I), $w_1$ and $w_7$ are N.

In one embodiment of the use of a compound of Formula (I), $R_1$ is $C_{1-8}$alkyl, amino, $C_{1-8}$alkyl-amino, ($C_{1-8}$alkyl)$_2$-amino, $C_{1-8}$alkoxy-$C_{1-8}$alkyl-amino, ($C_{1-8}$alkoxy-$C_{1-8}$alkyl)$_2$-amino, ($C_{1-8}$alkoxy-$C_{1-8}$alkyl)($C_{1-8}$alkyl)amino, amino-$C_{1-8}$alkyl, $C_{1-8}$alkyl-amino-$C_{1-8}$alkyl, ($C_{1-8}$alkyl)$_2$-amino-$C_{1-8}$alkyl, $C_{1-8}$alkoxy-$C_{1-8}$alkyl-amino-$C_{1-8}$alkyl, ($C_{1-8}$alkoxy-$C_{1-8}$alkyl)$_2$-amino-$C_{1-8}$alkyl, ($C_{1-8}$alkoxy-$C_{1-8}$alkyl)($C_{1-8}$alkyl)amino-$C_{1-8}$alkyl, amino-$C_{1-8}$alkyl-amino, (amino-$C_{1-8}$alkyl)$_2$-amino, (amino-$C_{1-8}$alkyl)($C_{1-8}$alkyl)amino, $C_{1-8}$alkyl-amino-$C_{1-8}$alkyl-amino, ($C_{1-8}$alkyl-amino-$C_{1-8}$alkyl)$_2$-amino, ($C_{1-8}$alkyl-amino-$C_{1-8}$alkyl)($C_{1-8}$alkyl)amino, ($C_{1-8}$alkyl)$_2$-amino-$C_{1-8}$alkyl-amino, [($C_{1-8}$alkyl)$_2$-amino-$C_{1-8}$alkyl]($C_{1-8}$alkyl)amino, amino-$C_{1-8}$alkoxy, $C_{1-8}$alkyl-amino-$C_{1-8}$alkoxy, ($C_{1-8}$alkyl)$_2$-amino-$C_{1-8}$alkoxy, $C_{1-8}$alkoxy-C-alkyl-amino-$C_{1-8}$alkoxy, ($C_{1-8}$alkoxy-$C_{1-8}$alkyl)$_2$-amino-$C_{1-8}$alkoxy, ($C_{1-8}$alkoxy-$C_{1-8}$alkyl)($C_{1-8}$alkyl)amino-$C_{1-8}$alkoxy, amino-$C_{2-8}$alkenyl, $C_{1-8}$alkyl-amino-$C_{2-8}$alkenyl, ($C_{1-8}$alkyl)$_2$-amino-$C_{2-8}$alkenyl, amino-$C_{2-8}$alkynyl, $C_{1-8}$alkyl-amino-$C_{2-8}$alkynyl, ($C_{1-8}$alkyl)$_2$-amino-$C_{2-8}$alkynyl, halo-$C_{1-8}$alkyl-amino, (halo-$C_{1-8}$alkyl)$_2$-amino, (halo-$C_{1-8}$alkyl)($C_{1-8}$alkyl)amino, hydroxy-$C_{1-8}$alkyl, hydroxy-$C_{1-8}$alkoxy-$C_{1-8}$alkyl, hydroxy-$C_{1-8}$alkyl-amino, (hydroxy-$C_{1-8}$alkyl)$_2$-amino, (hydroxy-$C_{1-8}$alkyl)($C_{1-8}$alkyl)amino, hydroxy-$C_{1-8}$alkyl-amino-$C_{1-8}$alkyl, (hydroxy-$C_{1-8}$alkyl)$_2$-amino-$C_{1-8}$alkyl, (hydroxy-$C_{1-8}$alkyl)($C_{1-8}$alkyl)amino-$C_{1-8}$alkyl, hydroxy-$C_{1-8}$alkyl-amino-$C_{1-8}$alkoxy, (hydroxy-$C_{1-8}$alkyl)$_2$-amino-$C_{1-8}$alkoxy, (hydroxy-$C_{1-8}$alkyl)($C_{1-8}$alkyl)amino-$C_{1-8}$alkoxy, hydroxy-$C_{1-8}$alkyl-amino-$C_{1-8}$alkyl-amino, (hydroxy-$C_{1-8}$alkyl-amino-$C_{1-8}$alkyl)$_2$-amino, (hydroxy-$C_{1-8}$alkyl)$_2$-amino-$C_{1-8}$alkyl-amino, (hydroxy-$C_{1-8}$alkyl-amino-$C_{1-8}$alkyl)($C_{1-8}$alkyl)amino, (hydroxy-$C_{1-8}$alkyl)($C_{1-8}$alkyl)amino-$C_{1-8}$alkyl-amino, [(hydroxy-$C_{1-8}$alkyl)$_2$-amino-$C_{1-8}$alkyl]($C_{1-8}$alkyl)amino, [(hydroxy-$C_{1-8}$alkyl)($C_{1-8}$alkyl)amino-$C_{1-8}$alkyl]($C_{1-8}$alkyl)amino, heterocyclyl, heterocyclyl-$C_{1-8}$alkyl, heterocyclyl-$C_{1-8}$alkoxy, heterocyclyl-amino, (heterocyclyl)($C_{1-8}$alkyl)amino, heterocyclyl-amino-$C_{1-8}$alkyl, heterocyclyl-$C_{1-8}$alkyl-amino, (heterocyclyl-$C_{1-8}$alkyl)$_2$-amino, (heterocyclyl-$C_{1-8}$alkyl)($C_{1-8}$alkyl)amino, heterocyclyl-$C_{1-8}$alkyl-amino-$C_{1-8}$alkyl, (heterocyclyl-$C_{1-8}$alkyl)$_2$-amino-$C_{1-8}$alkyl, (heterocyclyl-$C_{1-8}$alkyl)($C_{1-8}$alkyl)amino-$C_{1-8}$alkyl, heterocyclyl-oxy, heterocyclyl-carbonyl, heterocyclyl-carbonyl-oxy, $C_{3-14}$cycloalkyl, aryl-$C_{1-8}$alkyl-amino, (aryl-$C_{1-8}$alkyl)$_2$-amino, (aryl-$C_{1-8}$alkyl)($C_{1-8}$alkyl)amino, aryl-$C_{1-8}$alkyl-amino-$C_{1-8}$alkyl, (aryl-$C_{1-8}$alkyl)$_2$-amino-$C_{1-8}$alkyl, (aryl-$C_{1-8}$alkyl)($C_{1-8}$alkyl)amino-$C_{1-8}$alkyl, heteroaryl, heteroaryl-$C_{1-8}$alkyl, heteroaryl-$C_{1-8}$alkoxy, heteroaryl-amino, heteroaryl-$C_{1-8}$alkyl-amino, (heteroaryl-$C_{1-8}$alkyl)$_2$-amino, (heteroaryl-$C_{1-8}$alkyl)($C_{1-8}$alkyl)amino, heteroaryl-$C_{1-8}$alkyl-amino-$C_{1-8}$alkyl, (heteroaryl-$C_{1-8}$alkyl)$_2$-amino-$C_{1-8}$alkyl or (heteroaryl-$C_{1-8}$alkyl)($C_{1-8}$alkyl)amino-$C_{1-8}$alkyl; wherein, each instance of heterocyclyl, $C_{3-14}$cycloalkyl, aryl and heteroaryl is optionally substituted with $R_3$ and $R_4$ substituents.

In another embodiment of the use of a compound of Formula (I), $R_1$ is amino, ($C_{1-8}$alkyl)$_2$-amino, $C_{1-8}$alkoxy-$C_{1-8}$alkyl-amino, ($C_{1-8}$alkoxy-$C_{1-8}$alkyl)$_2$-amino, amino-$C_{1-8}$alkyl, $C_{1-8}$alkyl-amino-$C_{1-8}$alkyl, ($C_{1-8}$alkyl)$_2$-amino-$C_{1-8}$alkyl, $C_{1-8}$alkoxy-$C_{1-8}$alkyl-amino-$C_{1-8}$alkyl, ($C_{1-8}$alkoxy-$C_{1-8}$alkyl)$_2$-amino-$C_{1-8}$alkyl, ($C_{1-8}$alkoxy-$C_{1-8}$alkyl)($C_{1-8}$alkyl)amino-$C_{1-8}$alkyl, amino-$C_{1-8}$alkyl-amino, (amino-$C_{1-8}$alkyl)$_2$-amino, (amino-$C_{1-8}$alkyl)($C_{1-8}$alkyl)amino, $C_{1-8}$alkyl-amino-$C_{1-8}$alkyl-amino, ($C_{1-8}$alkyl-amino-$C_{1-8}$alkyl)$_2$-amino, ($C_{1-8}$alkyl-amino-$C_{1-8}$alkyl)($C_{1-8}$alkyl)amino, ($C_{1-8}$alkyl)$_2$-amino-$C_{1-8}$alkyl-amino, [($C_{1-8}$alkyl)$_2$-amino-$C_{1-8}$alkyl]($C_{1-8}$alkyl)amino, amino-$C_{1-8}$alkoxy, $C_{1-8}$alkyl-amino-$C_{1-8}$alkoxy, ($C_{1-8}$alkyl)$_2$-amino-$C_{1-8}$alkoxy, $C_{1-8}$alkoxy-$C_{1-8}$alkyl-amino-$C_{1-8}$alkoxy, ($C_{1-8}$alkoxy-$C_{1-8}$alkyl)$_2$-amino-$C_{1-8}$alkoxy, ($C_{1-8}$alkoxy-$C_{1-8}$alkyl)($C_{1-8}$alkyl)amino-$C_{1-8}$alkoxy, amino-$C_{2-8}$alkenyl, $C_{1-8}$alkyl-amino-$C_{2-8}$alkenyl, ($C_{1-8}$alkyl)$_2$-amino-$C_{2-8}$alkenyl, amino-$C_{2-8}$alkynyl, $C_{1-8}$alkyl-amino-$C_{2-8}$alkynyl, ($C_{1-8}$alkyl)$_2$-amino-$C_{2-8}$alkynyl, halo-$C_{1-8}$alkyl-amino, (halo-$C_{1-8}$alkyl)$_2$-amino, (halo-$C_{1-8}$alkyl)($C_{1-8}$alkyl)amino, hydroxy-$C_{1-8}$alkyl, hydroxy-$C_{1-8}$alkoxy-$C_{1-8}$alkyl, hydroxy-$C_{1-8}$alkyl-amino, (hydroxy-$C_{1-8}$alkyl)$_2$-amino, (hydroxy-$C_{1-8}$alkyl)($C_{1-8}$alkyl)amino, hydroxy-$C_{1-8}$alkyl-amino-$C_{1-8}$alkyl, (hydroxy-$C_{1-8}$alkyl)$_2$-amino-$C_{1-8}$alkyl, (hydroxy-$C_{1-8}$alkyl)($C_{1-8}$alkyl)amino-$C_{1-8}$alkyl, hydroxy-$C_{1-8}$alkyl-amino-$C_{1-8}$alkoxy, (hydroxy-$C_{1-8}$alkyl)$_2$-amino-$C_{1-8}$alkoxy, (hydroxy-$C_{1-8}$alkyl)($C_{1-8}$alkyl)amino-$C_{1-8}$alkoxy, hydroxy-$C_{1-8}$alkyl-amino-$C_{1-8}$alkyl-amino, (hydroxy-$C_{1-8}$alkyl-amino-$C_{1-8}$alkyl)$_2$-amino, (hydroxy-$C_{1-8}$alkyl)$_2$-amino-$C_{1-8}$alkyl-amino, (hydroxy-$C_{1-8}$alkyl-amino-$C_{1-8}$alkyl)($C_{1-8}$alkyl)amino, (hydroxy-$C_{1-8}$alkyl)($C_{1-8}$alkyl)amino-$C_{1-8}$alkyl-amino, [(hydroxy-$C_{1-8}$alkyl)$_2$-amino-$C_{1-8}$alkyl]($C_{1-8}$alkyl)amino, [(hydroxy-$C_{1-8}$alkyl)($C_{1-8}$alkyl)amino-$C_{1-8}$alkyl]($C_{1-8}$alkyl)amino, heterocyclyl, heterocyclyl-$C_{1-8}$alkyl, heterocyclyl-$C_{1-8}$alkoxy, heterocyclyl-amino, (heterocyclyl)($C_{1-8}$alkyl)amino, heterocyclyl-amino-$C_{1-8}$alkyl, heterocyclyl-$C_{1-8}$alkyl-amino, (heterocyclyl-$C_{1-8}$alkyl)$_2$-amino, (heterocyclyl-$C_{1-8}$alkyl)($C_{1-8}$alkyl)amino, heterocyclyl-$C_{1-8}$alkyl-amino-$C_{1-8}$alkyl, (heterocyclyl-$C_{1-8}$alkyl)$_2$-amino-$C_{1-8}$alkyl, (heterocyclyl-$C_{1-8}$alkyl)($C_{1-8}$alkyl)amino-$C_{1-8}$alkyl, heterocyclyl-oxy, heterocyclyl-carbonyl, heterocyclyl-carbonyl-oxy, $C_{3-14}$cycloalkyl, aryl-$C_{1-8}$alkyl-amino, (aryl-$C_{1-8}$alkyl)$_2$-amino, (aryl-$C_{1-8}$alkyl)($C_{1-8}$alkyl)amino, aryl-$C_{1-8}$alkyl-amino-$C_{1-8}$alkyl, (aryl-$C_{1-8}$alkyl)$_2$-amino-$C_{1-8}$alkyl, (aryl-$C_{1-8}$alkyl)($C_{1-8}$alkyl)amino-$C_{1-8}$alkyl, heteroaryl, heteroaryl- $C_{1-8}$alkyl, heteroaryl-$C_{1-8}$alkoxy, heteroaryl-$C_{1-8}$alkyl-amino, (heteroaryl-$C_{1-8}$alkyl)$_2$-amino, (heteroaryl-$C_{1-8}$alkyl)($C_{1-8}$alkyl)amino, heteroaryl-$C_{1-8}$alkyl-amino-$C_{1-8}$alkyl, (heteroaryl-$C_{1-8}$alkyl)$_2$-amino-$C_{1-8}$alkyl or (heteroaryl-$C_{1-8}$alkyl)($C_{1-8}$alkyl)amino-$C_{1-8}$alkyl; wherein, each instance of heterocyclyl, $C_{3-14}$cycloalkyl, aryl and heteroaryl is optionally substituted with $R_3$ and $R_4$ substituents.

In another embodiment of the use of a compound of Formula (I), $R_1$ is $C_{1-8}$alkyl, amino, $C_{1-8}$alkyl-amino, ($C_{1-8}$alkyl)$_2$-amino, $C_{1-8}$alkoxy-$C_{1-8}$alkyl-amino, ($C_{1-8}$alkoxy-$C_{1-8}$alkyl)$_2$-amino, ($C_{1-8}$alkoxy-$C_{1-8}$alkyl)($C_{1-8}$alkyl)amino, amino-$C_{1-8}$alkyl, $C_{1-8}$alkyl-amino-$C_{1-8}$alkyl, ($C_{1-8}$alkyl)$_2$-amino-$C_{1-8}$alkyl, $C_{1-8}$alkoxy-$C_{1-8}$alkyl-amino-$C_{1-8}$alkyl, ($C_{1-8}$alkoxy-$C_{1-8}$alkyl)$_2$-amino-$C_{1-8}$alkyl, ($C_{1-8}$alkoxy-$C_{1-8}$alkyl)($C_{1-8}$alkyl)amino-$C_{1-8}$alkyl, amino-$C_{1-8}$alkyl-amino, (amino-$C_{1-8}$alkyl)$_2$-amino, (amino-$C_{1-8}$alkyl)($C_{1-8}$alkyl)amino, $C_{1-8}$alkyl-amino-$C_{1-8}$alkyl-amino, ($C_{1-8}$alkyl-amino-$C_{1-8}$alkyl)$_2$-amino, ($C_{1-8}$alkyl-amino-$C_{1-8}$alkyl)($C_{1-8}$alkyl)amino, ($C_{1-8}$alkyl)$_2$-amino-$C_{1-8}$alkyl-amino, [($C_{1-8}$alkyl)$_2$-amino-$C_{1-8}$alkyl]($C_{1-8}$alkyl)amino, amino-$C_{1-8}$alkoxy, $C_{1-8}$alkyl-amino-$C_{1-8}$alkoxy, ($C_{1-8}$alkyl)$_2$-amino-$C_{1-8}$alkoxy, $C_{1-8}$alkoxy-$C_{1-8}$alkyl-amino-$C_{1-8}$alkoxy, ($C_{1-8}$alkoxy-$C_{1-8}$alkyl)$_2$-amino-$C_{1-8}$alkoxy, ($C_{1-8}$alkoxy-$C_{1-8}$alkyl)($C_{1-8}$alkyl)amino-$C_{1-8}$alkoxy, amino-$C_{2-8}$alkenyl, $C_{1-8}$alkyl-amino-$C_{2-8}$alkenyl, ($C_{1-8}$alkyl)$_2$-amino-$C_{2-8}$alkenyl, amino-$C_{2-8}$alkynyl, $C_{1-8}$alkyl-amino-$C_{2-8}$alkynyl, ($C_{1-8}$alkyl)$_2$-amino-$C_{2-8}$alkynyl, halo-$C_{1-8}$alkyl-amino, (halo-$C_{1-8}$alkyl)$_2$-amino, (halo-$C_{1-8}$alkyl)($C_{1-8}$alkyl)amino, hydroxy-$C_{1-8}$alkyl, hydroxy-$C_{1-8}$alkoxy-$C_{1-8}$alkyl, hydroxy-$C_{1-8}$alkyl-amino, (hydroxy-$C_{1-8}$alkyl)$_2$-amino, (hydroxy-$C_{1-8}$alkyl)($C_{1-8}$alkyl)amino, hydroxy-$C_{1-8}$alkyl-amino-$C_{1-8}$alkyl, (hydroxy-$C_{1-8}$alkyl)$_2$-amino-$C_{1-8}$alkyl, (hydroxy-$C_{1-8}$alkyl)($C_{1-8}$alkyl)amino-$C_{1-8}$alkyl, hydroxy-$C_{1-8}$alkyl-amino-$C_{1-8}$alkoxy, (hydroxy-$C_{1-8}$alkyl)$_2$-amino-$C_{1-8}$alkoxy, (hydroxy-$C_{1-8}$alkyl)($C_{1-8}$alkyl)amino-$C_{1-8}$alkoxy, hydroxy-$C_{1-8}$alkyl-amino-$C_{1-8}$alkyl-amino, (hydroxy-$C_{1-8}$alkyl-amino-$C_{1-8}$alkyl)$_2$-amino, (hydroxy-$C_{1-8}$alkyl)$_2$-amino-$C_{1-8}$alkyl-amino, (hydroxy-$C_{1-8}$alkyl-amino-$C_{1-8}$alkyl)($C_{1-8}$alkyl)amino, (hydroxy-$C_{1-8}$alkyl)($C_{1-8}$alkyl)amino-$C_{1-8}$alkyl-amino, [(hydroxy-$C_{1-8}$alkyl)$_2$-amino-$C_{1-8}$alkyl]($C_{1-8}$alkyl)amino or [(hydroxy-$C_{1-8}$alkyl)($C_{1-8}$alkyl)amino-$C_{1-8}$alkyl]($C_{1-8}$alkyl)amino.

In another embodiment of the use of a compound of Formula (I), $R_1$ is heterocyclyl, heterocyclyl-$C_{1-8}$alkyl, heterocyclyl-$C_{1-8}$alkoxy, heterocyclyl-amino, (heterocyclyl)($C_{1-8}$alkyl)amino, heterocyclyl-amino-$C_{1-8}$alkyl, heterocyclyl-$C_{1-8}$alkyl-amino, (heterocyclyl-$C_{1-8}$alkyl)$_2$-amino, (heterocyclyl-$C_{1-8}$alkyl)($C_{1-8}$alkyl)amino, heterocyclyl-$C_{1-8}$alkyl-amino-$C_{1-8}$alkyl, (heterocyclyl-$C_{1-8}$alkyl)$_2$-amino-$C_{1-8}$alkyl, (heterocyclyl-$C_{1-8}$alkyl)($C_{1-8}$alkyl)amino-$C_{1-8}$alkyl, heterocyclyl-oxy, heterocyclyl-carbonyl, heterocyclyl-carbonyl-oxy, $C_{3-14}$cycloalkyl, aryl-$C_{1-8}$alkyl-amino, (aryl-$C_{1-8}$alkyl)$_2$-amino, (aryl-$C_{1-8}$alkyl)($C_{1-8}$alkyl)amino, aryl-$C_{1-8}$alkyl-amino-$C_{1-8}$alkyl, (aryl-$C_{1-8}$alkyl)$_2$-amino-$C_{1-8}$alkyl, (aryl-$C_{1-8}$alkyl)($C_{1-8}$alkyl)amino-$C_{1-8}$alkyl, heteroaryl, heteroaryl-$C_{1-8}$alkyl, heteroaryl-$C_{1-8}$alkoxy, heteroaryl-amino, heteroaryl-$C_{1-8}$alkyl-amino, (heteroaryl-$C_{1-8}$alkyl)$_2$-amino, (heteroaryl-$C_{1-8}$alkyl)($C_{1-8}$alkyl)amino, heteroaryl-$C_{1-8}$alkyl-amino-$C_{1-8}$alkyl, (heteroaryl-$C_{1-8}$alkyl)$_2$-amino-$C_{1-8}$alkyl or (heteroaryl-$C_{1-8}$alkyl)($C_{1-8}$alkyl)amino-$C_{1-8}$alkyl; wherein, each instance of heterocyclyl, $C_{3-14}$cycloalkyl, aryl and heteroaryl is optionally substituted with $R_3$ and $R_4$ substituents.

In another embodiment of the use of a compound of Formula (I), $R_1$ is heterocyclyl, heterocyclyl-$C_{1-8}$alkyl, heterocyclyl-$C_{1-8}$alkoxy, heterocyclyl-amino, (heterocyclyl)($C_{1-8}$alkyl)amino, heterocyclyl-amino-$C_{1-8}$alkyl, heterocyclyl-$C_{1-8}$alkyl-amino, (heterocyclyl-$C_{1-8}$alkyl)$_2$-amino, (heterocyclyl-$C_{1-8}$alkyl)($C_{1-8}$alkyl)amino, heterocyclyl-$C_{1-8}$alkyl-amino-$C_{1-8}$alkyl, (heterocyclyl-$C_{1-8}$alkyl)$_2$-amino-$C_{1-8}$alkyl, (heterocyclyl-$C_{1-8}$alkyl)($C_{1-8}$alkyl)amino-$C_{1-8}$alkyl, heterocyclyl-oxy, heterocyclyl-carbonyl or heterocyclyl-carbonyl-oxy; wherein, each instance of heterocyclyl is optionally substituted with $R_3$ and $R_4$ substituents.

In another embodiment of the use of a compound of Formula (I), $R_1$ is heterocyclyl optionally substituted with $R_3$ and $R_4$ substituents.

In another embodiment of the use of a compound of Formula (I), $R_1$ is $C_{3-14}$cycloalkyl optionally substituted with $R_3$ and $R_4$ substituents.

In another embodiment of the use of a compound of Formula (I), $R_1$ is aryl-$C_{1-8}$alkyl-amino, (aryl-$C_{1-8}$alkyl)$_2$-amino, (aryl-$C_{1-8}$alkyl)($C_{1-8}$alkyl)amino, aryl-$C_{1-8}$alkyl-amino-$C_{1-8}$alkyl, (aryl-$C_{1-8}$alkyl)$_2$-amino-$C_{1-8}$alkyl or (aryl-$C_{1-8}$alkyl)($C_{1-8}$alkyl)amino-$C_{1-8}$alkyl; wherein, each instance of aryl is optionally substituted with $R_3$ and $R_4$ substituents.

In another embodiment of the use of a compound of Formula (I), $R_1$ is aryl-$C_{1-8}$alkyl-amino optionally substituted with $R_3$ and $R_4$ substituents.

In another embodiment of the use of a compound of Formula (I), $R_1$ is heteroaryl, heteroaryl-$C_{1-8}$alkyl, heteroaryl-$C_{1-8}$alkoxy, heteroaryl-amino, heteroaryl-$C_{1-8}$alkyl-amino, (heteroaryl-$C_{1-8}$alkyl)$_2$-amino, (heteroaryl-$C_{1-8}$alkyl)($C_{1-8}$alkyl)amino, heteroaryl-$C_{1-8}$alkyl-amino-$C_{1-8}$alkyl, (heteroaryl-$C_{1-8}$alkyl)$_2$-amino-$C_{1-8}$alkyl or (heteroaryl-$C_{1-8}$alkyl)($C_{1-8}$alkyl)amino-$C_{1-8}$alkyl; wherein, each instance of heterocyclyl, $C_{3-14}$cycloalkyl, aryl and heteroaryl is optionally substituted with $R_3$ and $R_4$ substituents.

In another embodiment of the use of a compound of Formula (I), $R_1$ is heteroaryl optionally substituted with $R_3$ and $R_4$ substituents.

In one embodiment of the use of a compound of Formula (I), $R_1$ is heterocyclyl selected from azetidinyl, tetrahydrofuranyl, pyrrolidinyl, piperidinyl, piperazinyl, 1,4-diazepanyl, 1,2,5,6-tetrahydropyridinyl, 1,2,3,6-tetrahydropyridinyl, hexahydropyrrolo[3,4-b]pyrrol-(1H)-yl, (3aS,6aS)-hexahydropyrrolo[3,4-b]pyrrol-(1H)-yl, (3aR,6aR)-hexahydropyrrolo[3,4-b]pyrrol-(1H)-yl, hexahydropyrrolo[3,4-b]pyrrol-(2H)-yl, (3aS,6aS)-hexahydropyrrolo[3,4-b]pyrrol-(2H)-yl, hexahydropyrrolo[3,4-c]pyrrol-(1H)-yl, (3aR,6aS)-hexahydropyrrolo[3,4-c]pyrrol-(1H)-yl, octahydro-5H-pyrrolo[3,2-c]pyridinyl, octahydro-6H-pyrrolo[3,4-b]pyridinyl, (4aR,7aR)-octahydro-6H-pyrrolo[3,4-b]pyridinyl, (4aS,7aS)-octahydro-6H-pyrrolo[3,4-b]pyridinyl, hexahydropyrrolo[1,2-a]pyrazin-(2H)-one, hexahydropyrrolo[1,2-a]pyrazin-(1H)-yl, (7R,8aS)-hexahydropyrrolo[1,2-a]pyrazin-(1H)-yl, (8aS)-hexahydropyrrolo[1,2-a]pyrazin-(1H)-yl, (8aR)-hexahydropyrrolo[1,2-a]pyrazin-(1H)-yl, (8aS)-octahydropyrrolo[1,2-a]pyrazin-(1H)-yl, (8aR)-octahydropyrrolo[1,2-a]pyrazin-(1H)-yl, octahydro-2H-pyrido[1,2-a]pyrazinyl, 3-azabicyclo[3.1.0]hexyl, (1R,5S)-3-azabicyclo[3.1.0]hexyl, 8-azabicyclo[3.2.1]octyl, (1R,5S)-8-azabicyclo[3.2.1]octyl, 8-azabicyclo[3.2.1]oct-2-enyl, (1R,5S)-8-azabicyclo[3.2.1]oct-2-enyl, 9-azabicyclo[3.3.1]nonyl, (1R,5S)-9-azabicyclo[3.3.1]nonyl, 2,5-diazabicyclo[2.2.1]heptyl, (1S,4S)-2,5-diazabicyclo[2.2.1]

heptyl, 2,5-diazabicyclo[2.2.2]octyl, 3,8-diazabicyclo[3.2.1]octyl, (1R,5S)-3,8-diazabicyclo[3.2.1]octyl, 1,4-diazabicyclo[3.2.2]nonyl, azaspiro[3.3]heptyl, 2,6-diazaspiro[3.3]heptyl, 2,7-diazaspiro[3.5]nonyl, 5,8-diazaspiro[3.5]nonyl, 2,7-diazaspiro[4.4]nonyl or 6,9-diazaspiro[4.5]decyl; wherein, each instance of heterocyclyl is optionally substituted with $R_3$ and $R_4$ substituents.

In another embodiment of the use of a compound of Formula (I), $R_1$ is heterocyclyl selected from azetidin-1-yl, tetrahydrofuran-3-yl, pyrrolidin-1-yl, piperidin-1-yl, piperidin-4-yl, piperazin-1-yl, 1,4-diazepan-1-yl, 1,2,5,6-tetrahydropyridin-5-yl, 1,2,3,6-tetrahydropyridin-4-yl, hexahydropyrrolo[3,4-b]pyrrol-1(2H)-yl, (3aS,6aS)-hexahydropyrrolo[3,4-b]pyrrol-1(2H)-yl, (3aS,6aS)-hexahydropyrrolo[3,4-b]pyrrol-5(1H)-yl, (3aR,6aR)-hexahydropyrrolo[3,4-b]pyrrol-5(1H)-yl, hexahydropyrrolo[3,4-c]pyrrol-2(1H)-yl, (3aR,6aS)-hexahydropyrrolo[3,4-c]pyrrol-2(1H)-yl, octahydro-5H-pyrrolo[3,2-c]pyridin-5-yl, octahydro-6H-pyrrolo[3,4-b]pyridin-6-yl, (4aR,7aR)-octahydro-6H-pyrrolo[3,4-b]pyridin-6-yl, (4aS,7aS)-octahydro-6H-pyrrolo[3,4-b]pyridin-6-yl, hexahydropyrrolo[1,2-a]pyrazin-6(2H)-one, hexahydropyrrolo[1,2-a]pyrazin-2(1H)-yl, (7R,8aS)-hexahydropyrrolo[1,2-a]pyrazin-2(1H)-yl, (8aS)-hexahydropyrrolo[1,2-a]pyrazin-2(1H)-yl, (8aR)-hexahydropyrrolo[1,2-a]pyrazin-2(1H)-yl, (8aS)-octahydropyrrolo[1,2-a]pyrazin-2(1H)-yl, (8aR)-octahydropyrrolo[1,2-a]pyrazin-2(1H)-yl, octahydro-2H-pyrido[1,2-a]pyrazin-2-yl, 3-azabicyclo[3.1.0]hex-3-yl, 8-azabicyclo[3.2.1]oct-3-yl, (1R,5S)-8-azabicyclo[3.2.1]oct-3-yl, 8-azabicyclo[3.2.1]oct-2-en-3-yl, (1R,5S)-8-azabicyclo[3.2.1]oct-2-en-3-yl, 9-azabicyclo[3.3.1]non-3-yl, (1R,5S)-9-azabicyclo[3.3.1]non-3-yl, 2,5-diazabicyclo[2.2.1]hept-2-yl, (1S,4S)-2,5-diazabicyclo[2.2.1]hept-2-yl, 2,5-diazabicyclo[2.2.2]oct-2-yl, 3,8-diazabicyclo[3.2.1]oct-3-yl, (1R,5S)-3,8-diazabicyclo[3.2.1]oct-3-yl, 1,4-diazabicyclo[3.2.2]non-4-yl, azaspiro[3.3]hept-2-yl, 2,6-diazaspiro[3.3]hept-2-yl, 2,7-diazaspiro[3.5]non-7-yl, 5,8-diazaspiro[3.5]non-8-yl, 2,7-diazaspiro[4.4]non-2-yl or 6,9-diazaspiro[4.5]dec-9-yl; wherein, each instance of heterocyclyl is optionally substituted with $R_3$ and $R_4$ substituents.

In another embodiment of the use of a compound of Formula (I), $R_1$ is substituted heterocyclyl selected from 4-methyl-1,4-diazepan-1-yl, (3aS,6aS)-1-methylhexahydropyrrolo[3,4-b]pyrrol-5(1H)-yl, (3aS,6aS)-5-methylhexahydropyrrolo[3,4-b]pyrrol-1(2H)-yl, (3aR,6aR)-1-methylhexahydropyrrolo[3,4-b]pyrrol-5(1H)-yl, (3aR,6aS)-5-methylhexahydropyrrolo[3,4-c]pyrrol-2(1H)-yl, (3aR,6aS)-5-(2-hydroxyethyl)hexahydropyrrolo[3,4-c]pyrrol-2(1H)-yl, (3aR,6aS)-5-(propan-2-yl)hexahydropyrrolo[3,4-c]pyrrol-2(1H)-yl, (3aR,6aS)-5-ethylhexahydropyrrolo[3,4-c]pyrrol-2(1H)-yl, (4aR,7aR)-1-methyloctahydro-6H-pyrrolo[3,4-b]pyridin-6-yl, (4aR,7aR)-1-ethyloctahydro-6H-pyrrolo[3,4-b]pyridin-6-yl, (4aR,7aR)-1-(2-hydroxyethyl)octahydro-6H-pyrrolo[3,4-b]pyridin-6-yl, (4aS,7aS)-1-methyloctahydro-6H-pyrrolo[3,4-b]pyridin-6-yl, (4aS,7aS)-1-(2-hydroxyethyl)octahydro-6H-pyrrolo[3,4-b]pyridin-6-yl, (7R,8aS)-7-hydroxyhexahydropyrrolo[1,2-a]pyrazin-2(1H)-yl, (8aS)-8a-methyloctahydropyrrolo[1,2-a]pyrazin-2(1H)-yl, (8aR)-8a-methyloctahydropyrrolo[1,2-a]pyrazin-2(1H)-yl, (1R,5S,6s)-6-(dimethylamino)-3-azabicyclo[3.1.0]hex-3-yl, (1R,5S)-8-methyl-8-azabicyclo[3.2.1]oct-3-yl, 9-methyl-9-azabicyclo[3.3.1]non-3-yl, (3-exo)-9-methyl-9-azabicyclo[3.3.1]non-3-yl, (1R,5S)-9-methyl-9-azabicyclo[3.3.1]non-3-yl, (1S,4S)-5-methyl-2,5-diazabicyclo[2.2.1]hept-2-yl or (1S,4S)-5-ethyl-2,5-diazabicyclo[2.2.1]hept-2-yl.

In one embodiment of the use of a compound of Formula (I), $R_1$ is heterocyclyl-$C_{1-8}$alkyl, wherein heterocyclyl is selected from morpholinyl, piperidinyl, piperazinyl, imidazolyl or pyrrolidinyl; and, wherein, each instance of heterocyclyl is optionally substituted with $R_3$ and $R_4$ substituents.

In another embodiment of the use of a compound of Formula (I), $R_1$ is heterocyclyl-$C_{1-8}$alkyl selected from morpholin-4-yl-methyl, morpholin-4-yl-ethyl, morpholin-4-yl-propyl, piperidin-1-yl-methyl, piperazin-1-yl-methyl, piperazin-1-yl-ethyl, piperazin-1-yl-propyl, piperazin-1-yl-butyl, imidazol-1-yl-methyl, imidazol-1-yl-ethyl, imidazol-1-yl-propyl, imidazol-1-yl-butyl, pyrrolidin-1-yl-methyl, pyrrolidin-1-yl-ethyl, pyrrolidin-1-yl-propyl or pyrrolidin-1-yl-butyl; wherein, each instance of heterocyclyl is optionally substituted with $R_3$ and $R_4$ substituents.

In one embodiment of the use of a compound of Formula (I), $R_1$ is heterocyclyl-$C_{1-8}$alkoxy, wherein heterocyclyl is selected from pyrrolidinyl, piperidinyl or morpholinyl; and, wherein, each instance of heterocyclyl is optionally substituted with $R_3$ and $R_4$ substituents.

In another embodiment of the use of a compound of Formula (I), $R_1$ is heterocyclyl-$C_{1-8}$alkoxy selected from pyrrolidin-2-yl-methoxy, pyrrolidin-2-yl-ethoxy, pyrrolidin-1-yl-methoxy, pyrrolidin-1-yl-ethoxy, piperidin-1-yl-methoxy, piperidin-1-yl-ethoxy, morpholin-4-yl-methoxy or morpholin-4-yl-ethoxy; wherein, each instance of heterocyclyl is optionally substituted with $R_3$ and $R_4$ substituents.

In one embodiment of the use of a compound of Formula (I), $R_1$ is heterocyclyl-amino, wherein heterocyclyl is selected from azetidinyl, pyrrolidinyl, piperidinyl, 9-azabicyclo[3.3.1]nonyl or (1R,5S)-9-azabicyclo[3.3.1]nonyl; and, wherein, each instance of heterocyclyl is optionally substituted with $R_3$ and $R_4$ substituents.

In another embodiment of the use of a compound of Formula (I), $R_1$ is heterocyclyl-amino selected from azetidin-3-yl-amino, pyrrolidin-3-yl-amino, piperidin-4-yl-amino, 9-azabicyclo[3.3.1]non-3-yl-amino, (1R,5S)-9-azabicyclo[3.3.1]non-3-yl-amino, 9-methyl-9-azabicyclo[3.3.1]non-3-yl-amino, (3-exo)-9-methyl-9-azabicyclo[3.3.1]non-3-yl-amino or (1R,5S)-9-methyl-9-azabicyclo[3.3.1]non-3-yl-amino; wherein, each instance of heterocyclyl is optionally substituted with $R_3$ and $R_4$ substituents.

In one embodiment of the use of a compound of Formula (I), $R_1$ is (heterocyclyl)($C_{1-8}$alkyl)amino, wherein heterocyclyl is selected from pyrrolidinyl or piperidinyl; and, wherein, each instance of heterocyclyl is optionally substituted with $R_3$ and $R_4$ substituents.

In another embodiment of the use of a compound of Formula (I), $R_1$ is (heterocyclyl)($C_{1-8}$alkyl)amino selected from (pyrrolidin-3-yl)(methyl)amino or (piperidin-4-yl)(methyl)amino; wherein, each instance of heterocyclyl is optionally substituted with $R_3$ and $R_4$ substituents.

In one embodiment of the use of a compound of Formula (I), $R_1$ is heterocyclyl-amino-$C_{1-8}$alkyl, wherein heterocyclyl is selected from tetrahydrofuranyl; and, wherein, each instance of heterocyclyl is optionally substituted with $R_3$ and $R_4$ substituents.

In another embodiment of the use of a compound of Formula (I), $R_1$ is heterocyclyl-amino-$C_{1-8}$alkyl, selected from 3-(tetrahydrofuran-3-yl-amino)propyl; wherein, each instance of heterocyclyl is optionally substituted with $R_3$ and $R_4$ substituents.

In one embodiment of the use of a compound of Formula (I), $R_1$ is heterocyclyl-$C_{1-8}$alkyl-amino-$C_{1-8}$alkyl, wherein heterocyclyl is selected from tetrahydrofuranyl, thienyl or pyridinyl; and, wherein, each instance of heterocyclyl is optionally substituted with $R_3$ and $R_4$ substituents.

In another embodiment of the use of a compound of Formula (I), $R_1$ is heterocyclyl-$C_{1-8}$alkyl-amino-$C_{1-8}$alkyl, selected from 3-[(tetrahydrofuran-2-ylmethyl)amino]propyl, 3-[(thienyl-3-ylmethyl)amino]propyl, 3-[(pyridin-2-ylmethyl)amino]propyl or 3-[(pyridin-4-ylmethyl)amino]propyl; wherein, each instance of heterocyclyl is optionally substituted with $R_3$ and $R_4$ substituents.

In one embodiment of the use of a compound of Formula (I), $R_1$ is heterocyclyl-oxy, wherein heterocyclyl is selected from pyrrolidinyl or piperidinyl; and, wherein, each instance of heterocyclyl is optionally substituted with $R_3$ and $R_4$ substituents.

In another embodiment of the use of a compound of Formula (I), $R_1$ is heterocyclyl-oxy selected from pyrrolidin-3-yl-oxy or piperidin-4-yl-oxy; wherein, each instance of heterocyclyl is optionally substituted with $R_3$ and $R_4$ substituents.

In one embodiment of the use of a compound of Formula (I), $R_1$ is heterocyclyl-carbonyl, wherein heterocyclyl is selected from piperazinyl; and, wherein, each instance of heterocyclyl is optionally substituted with $R_3$ and $R_4$ substituents.

In another embodiment of the use of a compound of Formula (I), $R_1$ is heterocyclyl-carbonyl selected from piperazin-1-yl-carbonyl; wherein, each instance of heterocyclyl is optionally substituted with $R_3$ and $R_4$ substituents.

In one embodiment of the use of a compound of Formula (I), $R_1$ is heterocyclyl-carbonyl-oxy, wherein heterocyclyl is selected from piperazinyl; and, wherein, each instance of heterocyclyl is optionally substituted with $R_3$ and $R_4$ substituents.

In another embodiment of the use of a compound of Formula (I), $R_1$ is heterocyclyl-carbonyl-oxy selected from piperazin-1-yl-carbonyl-oxy; wherein, each instance of heterocyclyl is optionally substituted with $R_3$ and $R_4$ substituents.

In one embodiment of the use of a compound of Formula (I), $R_1$ is $C_{3-14}$cycloalkyl selected from cyclopropyl, cyclobutyl, cyclopentyl, cyclohexyl, cyclohexenyl or cycloheptyl; wherein, each instance of $C_{3-14}$cycloalkyl is optionally substituted with $R_3$ and $R_4$ substituents.

In another embodiment of the use of a compound of Formula (I), $R_1$ is $C_{3-8}$cycloalkyl selected from cyclopropyl, cyclobutyl, cyclopentyl, cyclohexyl, cyclohexenyl or cycloheptyl; wherein, each instance of $C_{3-8}$cycloalkyl is optionally substituted with $R_3$ and $R_4$ substituents.

In one embodiment of the use of a compound of Formula (I), $R_1$ is aryl-$C_{1-8}$alkyl-amino-$C_{1-8}$alkyl, wherein aryl is selected from phenyl; and, wherein, each instance of aryl is optionally substituted with $R_3$ and $R_4$ substituents.

In another embodiment of the use of a compound of Formula (I), $R_1$ is aryl-$C_{1-8}$alkyl-amino-$C_{1-8}$alkyl selected from 3-(benzylamino)propyl; wherein, each instance of aryl is optionally substituted with $R_3$ and $R_4$ substituents.

In one embodiment of the use of a compound of Formula (I), $R_1$ is heteroaryl, wherein heteroaryl is selected from pyridinyl; and, wherein, each instance of heteroaryl is optionally substituted with $R_3$ and $R_4$ substituents.

In another embodiment of the use of a compound of Formula (I), $R_1$ is heteroaryl selected from pyridin-4-yl; wherein, each instance of heteroaryl is optionally substituted with $R_3$ and $R_4$ substituents.

In one embodiment of the use of a compound of Formula (I), $R_1$ is heteroaryl-$C_{1-8}$alkyl, wherein heteroaryl is selected from 1H-imidazolyl; and, wherein, each instance of heteroaryl is optionally substituted with $R_3$ and $R_4$ substituents.

In another embodiment of the use of a compound of Formula (I), $R_1$ is heteroaryl-$C_{1-8}$alkyl selected from 1H-imidazol-1-yl-methyl; wherein, each instance of heteroaryl is optionally substituted with $R_3$ and $R_4$ substituents.

In one embodiment of the use of a compound of Formula (I), $R_1$ is (heteroaryl-$C_{1-8}$alkyl)($C_{1-8}$alkyl)amino, wherein heteroaryl is selected from pyridinyl; and, wherein, each instance of heteroaryl is optionally substituted with $R_3$ and $R_4$ substituents.

In another embodiment of the use of a compound of Formula (I), $R_1$ is (heteroaryl-$C_{1-8}$alkyl)($C_{1-8}$alkyl)amino selected from (pyridin-3-ylmethyl)(methyl)amino; wherein, each instance of heteroaryl is optionally substituted with $R_3$ and $R_4$ substituents.

In one embodiment of the use of a compound of Formula (I), $R_1$ is heteroaryl-$C_{1-8}$alkyl-amino-$C_{1-8}$alkyl, wherein heteroaryl is selected from thienyl or pyridinyl; and, wherein, each instance of heteroaryl is optionally substituted with $R_3$ and $R_4$ substituents.

In another embodiment of the use of a compound of Formula (I), $R_1$ is heteroaryl-$C_{1-8}$alkyl-amino-$C_{1-8}$alkyl selected from thien-3-yl-methyl-amino-propyl, pyridin-2-yl-methyl-amino-propyl, pyridin-3-yl-methyl-amino-propyl or pyridin-4-yl-methyl-amino-propyl; wherein, each instance of heteroaryl is optionally substituted with $R_3$ and $R_4$ substituents.

In one embodiment of the use of a compound of Formula (I), $R_3$ is selected from cyano, halogen, hydroxy, oxo, $C_{1-8}$alkyl, halo-$C_{1-8}$alkyl, $C_{1-8}$alkyl-carbonyl, $C_{1-8}$alkoxy, halo-$C_{1-8}$alkoxy, $C_{1-8}$alkoxy-$C_{1-8}$alkyl, $C_{1-8}$alkoxy-carbonyl, amino, $C_{1-8}$alkyl-amino, ($C_{1-8}$alkyl)$_2$-amino, amino-$C_{1-8}$alkyl, $C_{1-8}$alkyl-amino-$C_{1-8}$alkyl, ($C_{1-8}$alkyl)$_2$-amino-$C_{1-8}$alkyl, amino-$C_{1-8}$alkyl-amino, $C_{1-8}$alkyl-amino-$C_{1-8}$alkyl-amino, ($C_{1-8}$alkyl)$_2$-amino-$C_{1-8}$alkyl-amino, $C_{1-8}$alkoxy-$C_{1-8}$alkyl-amino, $C_{1-8}$alkyl-carbonyl-amino, $C_{1-8}$alkoxy-carbonyl-amino, hydroxy-$C_{1-8}$alkyl, hydroxy-$C_{1-8}$alkoxy-$C_{1-8}$alkyl, hydroxy-$C_{1-8}$alkyl-amino, (hydroxy-$C_{1-8}$alkyl)$_2$-amino or (hydroxy-$C_{1-8}$alkyl)($C_{1-8}$alkyl)amino.

In another embodiment of the use of a compound of Formula (I), $R_3$ is selected from cyano, halogen, hydroxy, oxo, $C_{1-8}$alkyl, halo-$C_{1-8}$alkyl, $C_{1-8}$alkoxy, $C_{1-8}$alkoxy-$C_{1-8}$alkyl, $C_{1-8}$alkoxy-carbonyl, amino, $C_{1-8}$alkyl-amino, ($C_{1-8}$alkyl)$_2$-amino, amino-$C_{1-8}$alkyl, $C_{1-8}$alkyl-amino-$C_{1-8}$alkyl, ($C_{1-8}$alkyl)$_2$-amino-$C_{1-8}$alkyl, $C_{1-8}$alkyl-amino-$C_{1-8}$alkyl-amino, $C_{1-8}$alkoxy-$C_{1-8}$alkyl-amino, $C_{1-8}$alkoxy-carbonyl-amino, hydroxy-$C_{1-8}$alkyl, hydroxy-$C_{1-8}$alkoxy-$C_{1-8}$alkyl, hydroxy-$C_{1-8}$alkyl-amino, (hydroxy-$C_{1-8}$alkyl)$_2$-amino or (hydroxy-$C_{1-8}$alkyl)($C_{1-8}$alkyl)amino.

In one embodiment of the use of a compound of Formula (I), $R_3$ is $C_{1-8}$alkyl selected from methyl, ethyl, propyl, isopropyl or tert-butyl.

In another embodiment of the use of a compound of Formula (I), $R_3$ is $C_{1-8}$alkyl selected from ethyl, propyl, isopropyl or tert-butyl.

In one embodiment of the use of a compound of Formula (I), $R_3$ is halo-$C_{1-8}$alkyl selected from trihalo-methyl, dihalo-methyl, halo-methyl, trihalo-ethyl, dihalo-ethyl, halo-ethyl, trihalo-propyl, dihalo-propyl or halo-propyl; wherein, halo is selected from fluoro, chloro, bromo or iodo.

In another embodiment of the use of a compound of Formula (I), $R_3$ is halo-$C_{1-8}$alkyl selected from trihalo-methyl, dihalo-methyl, halo-methyl, trihalo-ethyl, dihalo-ethyl, trihalo-propyl or dihalo-propyl; wherein, halo is selected from fluoro, chloro, bromo or iodo.

In one embodiment of the use of a compound of Formula (I), $R_3$ is hydroxy-$C_{1-8}$alkyl selected from hydroxy-methyl, hydroxy-ethyl, hydroxy-propyl, dihydroxy-propyl, hydroxy-butyl or dihydroxy-butyl.

In another embodiment of the use of a compound of Formula (I), $R_3$ is hydroxy-$C_{1-8}$alkyl selected from hydroxy-methyl, dihydroxy-propyl, hydroxy-butyl or dihydroxy-butyl.

In one embodiment of the use of compound of Formula (I), $R_3$ is $C_{1-8}$alkoxy selected from methoxy, ethoxy, propoxy or isopropoxy.

In one embodiment of the use of a compound of Formula (I), $R_3$ is halo-$C_{1-8}$alkoxy selected from trihalo-methoxy, dihalo-methoxy, halo-methoxy, trihalo-ethoxy, dihalo-ethoxy, halo-ethoxy, trihalo-propoxy, dihalo-propoxy or halo-propoxy; wherein, halo is selected from fluoro, chloro, bromo or iodo.

In one embodiment of the use of a compound of Formula (I), $R_3$ is $C_{1-8}$alkoxy-carbonyl-amino selected from methoxy-carbonyl-amino, ethoxy-carbonyl-amino, propoxy-carbonyl-amino, isopropoxy-carbonyl-amino, tert-butoxy-carbonyl-amino.

In one embodiment of the use of a compound of Formula (I), $R_a$ is, in each instance, independently selected from hydrogen, halogen, $C_{1-8}$alkyl.

In one embodiment of the use of a compound of Formula (I), $R_a$ is, in each instance, optionally and independently deuterium.

In one embodiment of the use of a compound of Formula (I), $R_b$ is hydrogen, halogen, $C_{1-8}$alkyl, $C_{1-8}$alkoxy.

In one embodiment of the use of a compound of Formula (I), $R_c$ is, in each instance, independently selected from hydrogen, halogen, $C_{1-8}$alkyl.

In one embodiment of the use of a compound of Formula (I), $R_c$ is, in each instance, optionally and independently deuterium.

In one embodiment of the use of a compound of Formula (I), $R_b$ is deuterium.

In one embodiment of the use of a compound of Formula (I), $R_4$ is $C_{3-14}$cycloalkyl selected from cyclopropyl, cyclobutyl, cyclopentyl, cyclohexyl or cycloheptyl; wherein, each instance of $C_{3-14}$cycloalkyl is optionally substituted with $R_5$ substituents.

In another embodiment of the use of a compound of Formula (I), $R_4$ is $C_{3-8}$cycloalkyl selected from cyclopropyl, cyclobutyl, cyclopentyl, cyclohexyl or cycloheptyl; wherein, each instance of $C_{3-8}$cycloalkyl is optionally substituted with $R_5$ substituents.

In one embodiment of the use of a compound of Formula (I), $R_4$ is $C_{3-14}$cycloalkyl-$C_{1-8}$alkyl, wherein $C_{3-14}$cycloalkyl is selected from cyclopropyl, cyclobutyl, cyclopentyl, cyclohexyl or cycloheptyl; and, wherein, each instance of $C_{3-14}$cycloalkyl is optionally substituted with $R_5$ substituents.

In another embodiment of the use of a compound of Formula (I), $R_4$ is $C_{3-14}$cycloalkyl-$C_{1-8}$alkyl, wherein $C_{3-8}$cycloalkyl is selected from cyclopropyl, cyclobutyl, cyclopentyl, cyclohexyl or cycloheptyl; and, wherein, each instance of $C_{3-8}$cycloalkyl is optionally substituted with $R_5$ substituents.

In one embodiment of the use of a compound of Formula (I), $R_4$ is $C_{3-14}$cycloalkyl-amino, wherein $C_{3-14}$cycloalkyl is selected from cyclopropyl, cyclobutyl, cyclopentyl, cyclohexyl or cycloheptyl; and, wherein, each instance of $C_{3-14}$cycloalkyl is optionally substituted with $R_5$ substituents.

In another embodiment of the use of a compound of Formula (I), $R_4$ is $C_{3-8}$cycloalkyl-amino, wherein $C_{3-8}$cycloalkyl is selected from cyclopropyl, cyclobutyl, cyclopentyl, cyclohexyl or cycloheptyl; and, wherein, each instance of $C_{3-8}$cycloalkyl is optionally substituted with $R_5$ substituents.

In one embodiment of the use of a compound of Formula (I), $R_4$ is aryl-$C_{1-8}$alkyl, aryl-$C_{1-8}$alkoxy-carbonyl or aryl-sulfonyloxy-$C_{1-8}$alkyl, wherein aryl is selected from phenyl; and, wherein, each instance of aryl is optionally substituted with $R_5$ substituents.

In another embodiment of the use of a compound of Formula (I), $R_4$ is aryl-$C_{1-8}$alkyl or aryl-$C_{1-8}$alkoxy-carbonyl, wherein each instance of aryl is optionally substituted with $R_5$ substituents.

In one embodiment of the use of a compound of Formula (I), $R_4$ is heterocyclyl selected from oxetanyl, pyrrolidinyl, piperidinyl, piperazinyl, 1,3-dioxanyl or morpholinyl, wherein each instance of heterocyclyl is optionally substituted with $R_5$ substituents.

In another embodiment of the use of a compound of Formula (I), $R_4$ is heterocyclyl selected from oxetan-3-yl, pyrrolidin-1-yl, piperidin-1-yl, piperazin-1-yl, 1,3-dioxan-5-yl or morpholin-4-yl, wherein each instance of heterocyclyl is optionally substituted with $R_5$ substituents.

In one embodiment of the use of a compound of Formula (I), $R_4$ is heterocyclyl-$C_{1-8}$alkyl, wherein each instance of heterocyclyl is selected from pyrrolidinyl or piperidinyl; and, wherein, each instance of heterocyclyl is optionally substituted with $R_5$ substituents.

In another embodiment of the use of a compound of Formula (I), $R_4$ is heterocyclyl-$C_{1-8}$alkyl selected from pyrrolidin-1-yl-$C_{1-8}$alkyl or piperidin-1-yl-$C_{1-8}$alkyl, wherein each instance of heterocyclyl is optionally substituted with $R_5$ substituents.

In one embodiment of the use of a compound of Formula (I), $R_5$ is selected from halogen, hydroxy, cyano, nitro, halo-$C_{1-8}$alkyl, $C_{1-8}$alkoxy, halo-$C_{1-8}$alkoxy, amino, $C_{1-8}$alkyl-amino, $(C_{1-8}alkyl)_2$-amino or $C_{1-8}$alkyl-thio; wherein, halogen and halo is selected from fluoro, chloro, bromo or iodo.

In one embodiment of the use of a compound of Formula (I), $R_5$ is hydroxy.

In one embodiment of the use of a compound of Formula (I), $R_5$ is $C_{1-8}$alkyl selected from methyl, ethyl, propyl, isopropyl, n-butyl or tert-butyl.

In another embodiment of the use of a compound of Formula (I), $R_5$ is $C_{1-8}$alkyl selected from ethyl, propyl, isopropyl or tert-butyl.

In one embodiment of the use of a compound of Formula (I), $R_5$ is halo-$C_{1-8}$alkyl selected from trihalo-methyl, dihalo-methyl, halo-methyl, trihalo-ethyl, dihalo-ethyl, halo-ethyl, trihalo-propyl, dihalo-propyl or halo-propyl; wherein, halo is selected from fluoro, chloro, bromo or iodo.

In one embodiment of the use of a compound of Formula (I), $R_5$ is $C_{1-8}$alkoxy selected from methoxy, ethoxy, propoxy or isopropoxy.

In one embodiment of the use of a compound of Formula (I), $R_5$ is halo-$C_{1-8}$alkoxy selected from trihalo-methoxy, dihalo-methoxy, halo-methoxy, trihalo-ethoxy, dihalo-ethoxy, halo-ethoxy, trihalo-propoxy, dihalo-propoxy or halo-propoxy; wherein, halo is selected from fluoro, chloro, bromo or iodo.

In one embodiment of the use of a compound of Formula (I), $R_2$ is aryl selected from phenyl optionally substituted with $R_6$ and $R_7$ substituents.

In one embodiment of the use of a compound of Formula (I), $R_2$ is aryl-amino, wherein aryl is selected from phenyl; and, wherein, each instance of aryl is optionally substituted with $R_6$ and $R_7$ substituents.

In another embodiment of the use of a compound of Formula (I), $R_2$ is aryl-amino selected from phenyl-amino; wherein, each instance of aryl is optionally substituted with $R_6$ and $R_7$ substituents.

In one embodiment of the use of a compound of Formula (I), $R_2$ is aryl-amino-carbonyl, wherein aryl is selected from phenyl; and, wherein, each instance of aryl is optionally substituted with $R_6$ and $R_7$ substituents.

In another embodiment of the use of a compound of Formula (I), $R_2$ is aryl-amino-carbonyl selected from phenyl-amino-carbonyl; wherein, each instance of aryl is optionally substituted with $R_6$ and $R_7$ substituents.

In one embodiment of the use of a compound of Formula (I), $R_2$ is heterocyclyl selected from 1,2,3,6-tetrahydropyridinyl, 1,3-benzodioxolyl or 2,3-dihydro-1,4-benzodioxinyl; wherein, each instance of heterocyclyl is optionally substituted with $R_6$ and $R_7$ substituents.

In another embodiment of the use of a compound of Formula (I), $R_2$ is heterocyclyl selected from 1,2,3,6-tetrahydropyridin-4-yl, 1,3-benzodioxol-5-yl or 2,3-dihydro-1,4-benzodioxin-6-yl; wherein, each instance of heterocyclyl is optionally substituted with $R_6$ and $R_7$ substituents.

In one embodiment of the use of a compound of Formula (I), $R_2$ is heteroaryl selected from thienyl, 1H-pyrazolyl, 1H-imidazolyl, 1,3-thiazolyl, 1,2,4-oxadiazolyl, 1,3,4-oxadiazolyl, pyridinyl, pyrimidinyl, 1H-indolyl, 2H-indolyl, 1H-indazolyl, 2H-indazolyl, indolizinyl, benzofuranyl, benzothienyl, 1H-benzimidazolyl, 1,3-benzothiazolyl, 1,3-benzoxazolyl, 9H-purinyl, furo[3,2-b]pyridinyl, furo[3,2-c]pyridinyl, furo[2,3-c]pyridinyl, thieno[3,2-c]pyridinyl, thieno[2,3-d]pyrimidinyl, 1H-pyrrolo[2,3-b]pyridinyl, 1H-pyrrolo[2,3-c]pyridinyl, pyrrolo[1,2-a]pyrimidinyl, pyrrolo[1,2-a]pyrazinyl, pyrrolo[1,2-b]pyridazinyl, pyrazolo[1,5-a]pyridinyl, pyrazolo[1,5-a]pyrazinyl, imidazo[1,2-a]pyridinyl, imidazo[1,2-a]pyrimidinyl, imidazo[1,2-c]pyrimidinyl, imidazo[1,2-b]pyridazinyl, imidazo[1,2-a]pyrazinyl, imidazo[2,1-b][1,3]thiazolyl, imidazo[2,1-b][1,3,4]thiadiazolyl, [1,3]oxazolo[4,5-b]pyridinyl or quinoxalinyl; wherein, each instance of heteroaryl is optionally substituted with $R_6$ and $R_7$ substituents.

In another embodiment of the use of a compound of Formula (I), $R_2$ is heteroaryl selected from thien-2-yl, thien-3-yl, 1H-pyrazol-3-yl, 1H-pyrazol-4-yl, 1H-pyrazol-5-yl, 1H-imidazol-1-yl, 1H-imidazol-4-yl, 1,3-thiazol-2-yl, 1,2,4-oxadiazol-3-yl, 1,3,4-oxadiazol-2-yl, pyridin-2-yl, pyridin-3-yl, pyridin-4-yl, pyrimidin-4-yl, 1H-indol-3-yl, 1H-indol-4-yl, 1H-indol-5-yl, 1H-indol-6-yl, 1H-indazol-5-yl, 2H-indazol-5-yl, indolizin-2-yl, benzofuran-2-yl, benzofuran-5-yl, benzothien-2-yl, benzothien-3-yl, 1H-benzimidazol-2-yl, 1H-benzimidazol-6-yl, 1,3-benzoxazol-2-yl, 1,3-benzoxazol-5-yl, 1,3-benzoxazol-6-yl, 1,3-benzothiazol-2-yl, 1,3-benzothiazol-5-yl, 1,3-benzothiazol-6-yl, 9H-purin-8-yl, furo[3,2-b]pyridin-2-yl, furo[3,2-c]pyridin-2-yl, furo[2,3-c]pyridin-2-yl, thieno[3,2-c]pyridin-2-yl, thieno[2,3-d]pyrimidin-6-yl, 1H-pyrrolo[2,3-b]pyridin-5-yl, 1H-pyrrolo[2,3-c]pyridin-4-yl, pyrrolo[1,2-a]pyrimidin-7-yl, pyrrolo[1,2-a]pyrazin-7-yl, pyrrolo[1,2-b]pyridazin-2-yl, pyrazolo[1,5-a]pyridin-2-yl, pyrazolo[1,5-a]pyrazin-2-yl, imidazo[1,2-a]pyridin-2-yl, imidazo[1,2-a]pyridin-6-yl, imidazo[1,2-a]pyrimidin-2-yl, imidazo[1,2-a]pyrimidin-6-yl, imidazo[1,2-c]pyrimidin-2-yl, imidazo[1,2-b]pyridazin-2-yl, imidazo[1,2-a]pyrazin-2-yl, imidazo[2,1-b][1,3]thiazol-6-yl, imidazo[2,1-b][1,3,4]thiadiazol-6-yl, [1,3]oxazolo[4,5-b]pyridin-2-yl or quinoxalin-2-yl; wherein, each instance of heteroaryl is optionally substituted with $R_6$ and $R_7$ substituents.

In another embodiment of the use of a compound of Formula (I), $R_2$ is substituted heteroaryl selected from 4-methylthien-2-yl, 1-methyl-1H-pyrazol-3-yl, 4-methyl-1H-pyrazol-3-yl, 1-phenyl-1H-pyrazol-3-yl, 1-phenyl-1H-imidazol-4-yl, 2-methyl-1-(pyridin-2-yl)-1H-imidazol-4-yl, 4-methyl-1,3-thiazol-2-yl, 4-(trifluoromethyl)-1,3-thiazol-2-yl, 4-phenyl-1,3-thiazol-2-yl, 5-phenyl-1,2,4-oxadiazol-3-yl, 3-fluoropyridin-4-yl, 6-fluoropyridin-2-yl, 2-chloropyridin-4-yl, 4-chloropyridin-3-yl, 5-chloropyridin-2-yl, 6-methylpyridin-3-yl, 2-(trifluoromethyl)pyridin-3-yl, 4-(trifluoromethyl)pyridin-2-yl, 6-(trifluoromethyl)pyridin-2-yl, 2-methoxypyridin-4-yl, 4-methoxypyridin-3-yl, 6-methoxypyridin-2-yl, 2-ethoxypyridin-3-yl, 6-ethoxypyridin-2-yl, 6-(propan-2-yloxy)pyridin-2-yl, 6-(dimethylamino)pyridin-3-yl, 6-(methylsulfanyl)pyridin-2-yl, 6-(cyclobutyloxy)pyridin-2-yl, 6-(pyrrolidin-1-yl)pyridin-2-yl, 2-methylpyrimidin-4-yl, 2-(propan-2-yl)pyrimidin-4-yl, 2-cyclopropylpyrimidin-4-yl, 1-methyl-1H-indol-3-yl, 2-methyl-2H-indazol-5-yl, 2-methyl-1-benzofuran-5-yl, 1-methyl-1H-benzimidazol-2-yl, 4-methyl-1H-benzimidazol-2-yl 5-fluoro-1H-benzimidazol-2-yl, 4-fluoro-1,3-benzoxazol-2-yl, 5-fluoro-1,3-benzoxazol-2-yl, 4-chloro-1,3-benzoxazol-2-yl, 4-iodo-1,3-benzoxazol-2-yl, 2-methyl-1,3-benzoxazol-6-yl, 4-methyl-1,3-benzoxazol-2-yl, 4-(trifluoromethyl)-1,3-benzoxazol-2-yl, 7-(trifluoromethyl)-1,3-benzoxazol-2-yl, 2-methyl-1,3-benzothiazol-2-yl, 2-methyl-1,3-benzothiazol-5-yl, 2-methyl-1,3-benzothiazol-6-yl, 4-chloro-1,3-benzothiazol-2-yl, 7-chloro-1,3-benzothiazol-2-yl, 4-(trifluoromethyl)-1,3-benzothiazol-2-yl, 5-methylfuro[3,2-b]pyridin-2-yl, 4,6-dimethylfuro[3,2-c]pyridin-2-yl, 5,7-dimethylfuro[2,3-c]pyridin-2-yl, 4,6-dimethylthieno[3,2-c]pyridin-2-yl, 2,4-dimethylthieno[2,3-d]pyrimidin-6-yl, 1-methylpyrrolo[1,2-a]pyrazin-7-yl, 3-methylpyrrolo[1,2-a]pyrazin-7-yl, 1,3-dimethylpyrrolo[1,2-a]pyrazin-7-yl, 2-methylpyrrolo[1,2-b]pyridazin-2-yl, 4,6-dimethylpyrazolo[1,5-a]pyrazin-2-yl, 5-methylpyrazolo[1,5-a]pyridin-2-yl, 4,6-dimethylpyrazolo[1,5-a]pyrazin-2-yl, 2-chloroimidazo[2,1-b][1,3]thiazol-6-yl, 2-methylimidazo[2,1-b][1,3]thiazol-6-yl, 3-methylimidazo[2,1-b][1,3]thiazol-6-yl, 2-ethylimidazo[2,1-b][1,3]thiazol-6-yl, 2-methylimidazo[2,1-b][1,3,4]thiadiazol-6-yl, 6-cyanoimidazo[1,2-a]pyridin-2-yl (also referred to as 2-imidazo[1,2-a]pyridine-6-carbonitrile), 6-fluoroimidazo[1,2-a]pyridin-2-yl, 8-fluoroimidazo[1,2-a]pyridin-2-yl, 6,8-difluoroimidazo[1,2-a]pyridin-2-yl, 7-(trifluoromethyl)imidazo[1,2-a]pyridin-2-yl, 8-(trifluoromethyl)imidazo[1,2-a]pyridin-2-yl, 6-chloroimidazo[1,2-a]pyridin-2-yl, 7-chloroimidazo[1,2-a]pyridin-2-yl, 8-chloroimidazo[1,2-a]pyridin-2-yl, 8-bromoimidazo[1,2-a]pyridin-2-yl, 2-methylimidazo[1,2-a]pyridin-2-yl, 5-methylimidazo[1,2-a]pyridin-2-yl, 6-methylimidazo[1,2-a]pyridin-2-yl, 7-methylimidazo[1,2-a]pyridin-2-yl, 8-methylimidazo[1,2-a]pyridin-2-yl, 7-ethylimidazo[1,2-a]pyridin-2-yl, 8-ethylimidazo[1,2-a]pyridin-2-yl, 6,8-dimethylimidazo[1,2-a]pyridin-2-yl, 8-ethyl-6-methylimidazo[1,2-a]pyridin-2-yl, 7-methoxyimidazo[1,2-a]pyridin-2-yl, 8-methoxyimidazo[1,2-a]pyridin-2-yl, 6-fluoro-8-methylimidazo[1,2-a]pyridin-2-yl, 8-fluoro-6-methylimidazo[1,2-a]pyridin-2-yl, 8-chloro-6-methylimidazo[1,2-a]pyridin-2-yl, 6-methyl-8-nitroimidazo[1,2-a]pyridin-2-yl, 8-cyclopropylimidazo[1,2-a]pyridin-2-yl, 2-methylimidazo[1,2-a]pyridin-6-yl, 2-ethylimidazo[1,2-a]pyridin-6-yl, 2,3-dimethylimidazo[1,2-a]pyridin-6-yl, 2,8-dimethylimidazo[1,2-a]pyridin-6-yl, 2-(trifluoromethyl)imidazo[1,2-a]pyridin-6-yl, 8-chloro-2-methylimidazo[1,2-a]pyridin-6-yl, 8-fluoro-2-methylimidazo[1,2-a]pyridin-6-yl, 6-fluoroimidazo[1,2-a]pyrimidin-2-yl, 6-chloroimidazo[1,2-a]pyrimidin-2-yl, 6-methylimidazo[1,2-a]pyrimidin-2-yl, 7-methylimidazo[1,2-a]pyrimidin-2-yl, 2-methylimidazo[1,2-a]pyrimidin-6-yl, 6-methylimidazo[1,2-b]pyridazin-2-yl, 2-methyl-3-(1,2,3,6-tetrahydropyridin-4-yl)imidazo[1,2-b]pyridazin-6-yl, 6-methylimidazo[1,2-a]pyrazin-2-yl, 8-methylimidazo[1,2-a]pyrazin-2-yl, 6,8-dimethylimidazo[1,2-a]pyrazin-2-yl, 6-chloro-8-methylimidazo[1,2-a]pyrazin-2-yl, 6-methyl-8-(trifluoromethyl)imidazo[1,2-a]pyrazin-2-yl, 8-(methylsulfanyl)imidazo[1,2-a]pyrazin-2-yl, 2-methylimidazo[2,1-b][1,3]thiazol-6-yl, 3-methylimidazo[2,1-b][1,3]thiazol-6-yl or 2-methylimidazo[2,1-b][1,3,4]thiadiazol-6-yl.

In another embodiment of the use of a compound of Formula (I), $R_2$ is heteroaryl selected from thienyl, 1H-pyrazolyl, 1H-imidazolyl, 1,3-thiazolyl, 1,2,4-oxadiazolyl, 1,3,4-oxadiazolyl, pyridinyl, pyrimidinyl, 1H-indolyl, 2H-indolyl, 1H-indazolyl, 2H-indazolyl, indolizinyl, benzofuranyl, benzothienyl, 1H-benzimidazolyl, 1,3-benzothiazolyl, 1,3-benzoxazolyl, 9H-purinyl; wherein, each instance of heteroaryl is optionally substituted with $R_6$ and $R_7$ substituents.

In another embodiment of the use of a compound of Formula (I), $R_2$ is heteroaryl selected from furo[3,2-b]pyridinyl, furo[3,2-c]pyridinyl, furo[2,3-c]pyridinyl, thieno[3,2-c]pyridinyl, thieno[2,3-d]pyrimidinyl, 1H-pyrrolo[2,3-b]pyridinyl, 1H-pyrrolo[2,3-c]pyridinyl, pyrrolo[1,2-a]pyrimidinyl, pyrrolo[1,2-a]pyrazinyl, pyrrolo[1,2-b]pyridazinyl, pyrazolo[1,5-a]pyridinyl, pyrazolo[1,5-a]pyrazinyl, imidazo[1,2-a]pyridinyl, imidazo[1,2-a]pyrimidinyl, imidazo[1,2-c]pyrimidinyl, imidazo[1,2-b]pyridazinyl, imidazo[1,2-a]pyrazinyl, imidazo[2,1-b][1,3]thiazolyl, imidazo[2,1-b][1,3,4]thiadiazolyl, [1,3]oxazolo[4,5-b]pyridinyl or quinoxalinyl; wherein, each instance of heteroaryl is optionally substituted with $R_6$ and $R_7$ substituents.

In one embodiment of the use of a compound of Formula (I), $R_2$ is heteroaryl-amino, wherein heteroaryl is selected from pyridinyl or pyrimidinyl; and, wherein, each instance of heteroaryl is optionally substituted with $R_6$ and $R_7$ substituents.

In another embodiment of the use of a compound of Formula (I), $R_2$ is heteroaryl-amino selected from pyridin-2-yl-amino, pyridin-3-yl-amino or pyrimidin-2-yl-amino; wherein, each instance of heteroaryl is optionally substituted with $R_6$ and $R_7$ substituents.

In one embodiment of the use of a compound of Formula (I), $R_6$ is selected from halogen, hydroxy, cyano, nitro, $C_{1-8}$alkyl, halo-$C_{1-8}$alkyl, hydroxy-$C_{1-8}$alkyl, $C_{1-8}$alkoxy, halo-$C_{1-8}$alkoxy, $C_{1-8}$alkoxy-$C_{1-8}$alkyl, $(C_{1-8}alkyl)_2$-amino or $C_{1-8}$alkyl-thio; wherein, halogen and halo is selected from fluoro, chloro, bromo or iodo.

In one embodiment of the use of a compound of Formula (I), $R_6$ is $C_{1-8}$alkyl selected from methyl, ethyl, propyl, isopropyl or tert-butyl.

In another embodiment of the use of a compound of Formula (I), $R_6$ is $C_{1-8}$alkyl selected from ethyl, propyl, isopropyl or tert-butyl.

In one embodiment of the use of a compound of Formula (I), $R_6$ is $C_{2-8}$alkenyl selected from ethenyl, allyl or buta-1,3-dienyl.

In another embodiment of the use of a compound of Formula (I), $R_6$ is $C_{2-8}$alkenyl selected from ethenyl or allyl.

In one embodiment of the use of a compound of Formula (I), $R_6$ is halo-$C_{1-8}$alkyl selected from trihalo-methyl, dihalo-methyl, halo-methyl, trihalo-ethyl, dihalo-ethyl, halo-ethyl, trihalo-propyl, dihalo-propyl or halo-propyl; wherein, halo is selected from fluoro, chloro, bromo or iodo.

In one embodiment of the use of a compound of Formula (I), $R_6$ is hydroxy-$C_{1-8}$alkyl selected from hydroxy-methyl, hydroxy-ethyl, hydroxy-propyl, dihydroxy-propyl, hydroxy-butyl or dihydroxy-butyl.

In another embodiment of the use of a compound of Formula (I), $R_6$ is hydroxy-$C_{1-8}$alkyl selected from hydroxy-methyl, dihydroxy-propyl, hydroxy-butyl or dihydroxy-butyl.

In one embodiment of the use of a compound of Formula (I), $R_6$ is $C_{1-8}$alkoxy selected from methoxy, ethoxy, propoxy or isopropoxy.

In one embodiment of the use of a compound of Formula (I), $R_6$ is halo-$C_{1-8}$alkoxy selected from trihalo-methoxy, dihalo-methoxy, halo-methoxy, trihalo-ethoxy, dihalo-ethoxy, halo-ethoxy, trihalo-propoxy, dihalo-propoxy or halo-propoxy; wherein, halo is selected from fluoro, chloro, bromo or iodo.

In one embodiment of the use of a compound of Formula (I), $R_7$ is $C_{3-14}$cycloalkyl, $C_{3-14}$cycloalkyl-oxy, aryl, heterocyclyl or heteroaryl; wherein $C_{3-14}$cycloalkyl is selected from cyclopropyl or cyclobutoxy; wherein aryl is selected from phenyl; wherein heterocyclyl is selected from oxetanyl, pyrrolidinyl or 1,2,3,6-tetrahydropyridinyl; and, wherein heteroaryl is selected from thienyl or pyridinyl.

In another embodiment of the use of a compound of Formula (I), $R_7$ is $C_{3-14}$cycloalkyl or $C_{3-14}$cycloalkyl-oxy, wherein each instance of $C_{3-14}$cycloalkyl is selected from cyclopropyl, cyclobutyl, cyclopentyl, cyclohexyl or cycloheptyl.

In another embodiment of the use of a compound of Formula (I), $R_7$ is $C_{3-8}$cycloalkyl or $C_{3-8}$cycloalkyl-oxy, wherein each instance of $C_{3-8}$cycloalkyl is selected from cyclopropyl, cyclobutyl, cyclopentyl, cyclohexyl or cycloheptyl.

In one embodiment of the use of a compound of Formula (I), $R_7$ is aryl selected from phenyl.

In one embodiment of the use of a compound of Formula (I), $R_7$ is heterocyclyl selected from oxetanyl, pyrrolidinyl or 1,2,3,6-tetrahydropyridinyl.

In another embodiment of the use of a compound of Formula (I), $R_7$ is heterocyclyl selected from oxetan-3-yl, pyrrolidin-1-yl or 1,2,3,6-tetrahydropyridin-4-yl.

In one embodiment of the use of a compound of Formula (I), $R_7$ is heteroaryl selected from thienyl or pyridinyl.

In another embodiment of the use of a compound of Formula (I), $R_7$ is heteroaryl selected from pyridinyl.

In one embodiment of the use of a compound of Formula (I), $R_7$ is heteroaryl selected from thien-2-yl or pyridin-2-yl.

In another embodiment of the use of a compound of Formula (I), $R_7$ is heteroaryl selected from pyridin-2-yl.

In one embodiment of the use of a compound of Formula (I), $R_c$ is hydrogen or $C_{1-8}$alkyl.

In another embodiment of the use of a compound of Formula (I), $R_1$ is heterocyclyl, heterocyclyl-$C_{1-8}$alkyl, heterocyclyl-$C_{1-8}$alkoxy, heterocyclyl-amino, (heterocyclyl)($C_{1-8}$alkyl)amino, heterocyclyl-amino-$C_{1-8}$alkyl, heterocyclyl-$C_{1-8}$alkyl-amino, (heterocyclyl-$C_{1-8}$alkyl)$_2$-amino, (heterocyclyl-$C_{1-8}$alkyl)($C_{1-8}$alkyl)amino, heterocyclyl-$C_{1-8}$alkyl-amino-$C_{1-8}$alkyl, (heterocyclyl-$C_{1-8}$alkyl)$_2$-amino-$C_{1-8}$alkyl, (heterocyclyl-$C_{1-8}$alkyl)($C_{1-8}$alkyl)amino-$C_{1-8}$alkyl, heterocyclyl-oxy, heterocyclyl-carbonyl, heterocyclyl-carbonyl-oxy, $C_{3-14}$cycloalkyl, aryl-$C_{1-8}$alkyl-amino, (aryl-$C_{1-8}$alkyl)$_2$-amino, (aryl-$C_{1-8}$alkyl)($C_{1-8}$alkyl)amino, aryl-$C_{1-8}$alkyl-amino-$C_{1-8}$alkyl, (aryl-$C_{1-8}$alkyl)$_2$-amino-$C_{1-8}$alkyl, (aryl-$C_{1-8}$alkyl)($C_{1-8}$alkyl)amino-$C_{1-8}$alkyl, heteroaryl, heteroaryl-$C_{1-8}$alkyl, heteroaryl-$C_{1-8}$alkoxy, heteroaryl-amino, heteroaryl-$C_{1-8}$alkyl-amino, (heteroaryl-$C_{1-8}$alkyl)$_2$-amino, (heteroaryl-$C_{1-8}$alkyl)($C_{1-8}$alkyl)amino, heteroaryl-$C_{1-8}$alkyl-amino-$C_{1-8}$alkyl, (heteroaryl-$C_{1-8}$alkyl)$_2$-amino-$C_{1-8}$alkyl or (heteroaryl-$C_{1-8}$alkyl)($C_{1-8}$alkyl)amino-$C_{1-8}$alkyl; wherein, each instance of heterocyclyl, $C_{3-14}$cycloalkyl, aryl and heteroaryl is optionally substituted with $R_3$ and $R_4$ substituents; and, wherein, heterocyclyl is selected from azetidinyl, tetrahydrofuranyl, pyrrolidinyl, piperidinyl, piperazinyl, 1,4-diazepanyl, 1,2,5,6-tetrahydropyridinyl, 1,2,3,6-tetrahydropyridinyl, hexahydropyrrolo[3,4-b]pyrrol-(1H)-yl, (3aS,6aS)-hexahydropyrrolo[3,4-b]pyrrol-(1H)-yl, (3aR,6aR)-hexahydropyrrolo[3,4-b]pyrrol-(1H)-yl, hexahydropyrrolo[3,4-b]pyrrol-(2H)-yl, (3aS,6aS)-hexahydropyrrolo[3,4-b]pyrrol-(2H)-yl, hexahydropyrrolo[3,4-c]pyrrol-(1H)-yl, (3aR,6aS)-hexahydropyrrolo[3,4-c]pyrrol-(1H)-yl, octahydro-5H-pyrrolo[3,2-c]pyridinyl, octahydro-6H-pyrrolo[3,4-b]pyridinyl, (4aR,7aR)-octahydro-6H-pyrrolo[3,4-b]pyridinyl, (4aS,7aS)-octahydro-6H-pyrrolo[3,4-b]pyridinyl, hexahydropyrrolo[1,2-a]pyrazin-(2H)-one, hexahydropyrrolo[1,2-a]pyrazin-(1H)-yl, (7R,8aS)-hexahydropyrrolo[1,2-a]pyrazin-(1H)-yl, (8aS)-hexahydropyrrolo[1,2-a]pyrazin-(1H)-yl, (8aR)-hexahydropyrrolo[1,2-a]pyrazin-(1H)-yl, (8aS)-octahydropyrrolo[1,2-a]pyrazin-(1H)-yl, (8aR)-octahydropyrrolo[1,2-a]pyrazin-(1H)-yl, octahydro-2H-pyrido[1,2-a]pyrazinyl, 3-azabicyclo[3.1.0]hexyl, (1R,5S)-3-azabicyclo[3.1.0]hexyl, 8-azabicyclo[3.2.1]octyl, (1R,5S)-8-azabicyclo[3.2.1]octyl, 8-azabicyclo[3.2.1]oct-2-enyl, (1R,5S)-8-azabicyclo[3.2.1]oct-2-enyl, 9-azabicyclo[3.3.1]nonyl, (1R,5S)-9-azabicyclo[3.3.1]nonyl, 2,5-diazabicyclo[2.2.1]heptyl, (1S,4S)-2,5-diazabicyclo[2.2.1]heptyl, 2,5-diazabicyclo[2.2.2]octyl, 3,8-diazabicyclo[3.2.1]octyl, (1R,5S)-3,8-diazabicyclo[3.2.1]octyl, 1,4-diazabicyclo[3.2.2]nonyl, azaspiro[3.3]heptyl, 2,6-diazaspiro[3.3]heptyl, 2,7-diazaspiro[3.5]nonyl, 5,8-diazaspiro[3.5]nonyl, 2,7-diazaspiro[4.4]nonyl or 6,9-diazaspiro[4.5]decyl.

In another embodiment of the use of a compound of Formula (I), $R_2$ is aryl, aryl-amino, aryl-amino-carbonyl, heterocyclyl, heteroaryl or heteroaryl-amino;

wherein, aryl is phenyl;

wherein, heterocyclyl is selected from 1,2,3,6-tetrahydropyridinyl, 1,3-benzodioxolyl or 2,3-dihydro-1,4-benzodioxinyl;

wherein, heteroaryl is selected from thienyl, 1H-pyrazolyl, 1H-imidazolyl, 1,3-thiazolyl, 1,2,4-oxadiazolyl, 1,3,4-oxadiazolyl, pyridinyl, pyrimidinyl, 1H-indolyl, 2H-indolyl, 1H-indazolyl, 2H-indazolyl, indolizinyl, benzofuranyl, benzothienyl, 1H-benzimidazolyl, 1,3-benzothiazolyl, 1,3-benzoxazolyl, 9H-purinyl, furo[3,2-b]pyridinyl, furo[3,2-c]pyridinyl, furo[2,3-c]pyridinyl, thieno[3,2-c]pyridinyl, thieno[2,3-d]pyrimidinyl, 1H-pyrrolo[2,3-b]pyridinyl, 1H-pyrrolo[2,3-c]pyridinyl, pyrrolo[1,2-a]pyrimidinyl, pyrrolo[1,2-a]pyrazinyl, pyrrolo[1,2-b]pyridazinyl, pyrazolo[1,5-a]pyridinyl, pyrazolo[1,5-a]pyrazinyl, imidazo[1,2-a]pyridinyl, imidazo[1,2-a]pyrimidinyl, imidazo[1,2-c]pyrimidinyl, imidazo[1,2-b]pyridazinyl, imidazo[1,2-a]pyrazinyl, imidazo[2,1-b][1,3]thiazolyl, imidazo[2,1-b][1,3,4]thiadiazolyl, [1,3]oxazolo[4,5-b]pyridinyl or quinoxalinyl; and, wherein, each instance of aryl, heterocyclyl and heteroaryl is optionally substituted with $R_6$ and $R_7$ substituents.

In another embodiment of the use of a compound of Formula (I), $R_1$ is heterocyclyl, heterocyclyl-$C_{1-8}$alkyl, heterocyclyl-$C_{1-8}$alkoxy, heterocyclyl-amino, (heterocyclyl)($C_{1-8}$alkyl)amino, heterocyclyl-amino-$C_{1-8}$alkyl, heterocyclyl-$C_{1-8}$alkyl-amino, (heterocyclyl-$C_{1-8}$alkyl)$_2$-amino, (heterocyclyl-$C_{1-8}$alkyl)($C_{1-8}$alkyl)amino, heterocyclyl-$C_{1-8}$alkyl-amino-$C_{1-8}$alkyl, (heterocyclyl-$C_{1-8}$alkyl)$_2$-amino-$C_{1-8}$alkyl, (heterocyclyl-$C_{1-8}$alkyl)($C_{1-8}$alkyl)amino-$C_{1-8}$alkyl, heterocyclyl-oxy, heterocyclyl-carbonyl, heterocyclyl-carbonyl-oxy, $C_{3-14}$cycloalkyl, aryl-$C_{1-8}$alkyl-amino, (aryl-$C_{1-8}$alkyl)$_2$-amino, (aryl-$C_{1-8}$alkyl)($C_{1-8}$alkyl)amino, aryl-$C_{1-8}$alkyl-amino-$C_{1-8}$alkyl, (aryl-$C_{1-8}$alkyl)$_2$-amino-$C_{1-8}$alkyl, (aryl-$C_{1-8}$alkyl)($C_{1-8}$alkyl)amino-$C_{1-8}$alkyl, heteroaryl, heteroaryl-$C_{1-8}$alkyl, heteroaryl-$C_{1-8}$alkoxy, heteroaryl-amino, heteroaryl-$C_{1-8}$alkyl-amino, (heteroaryl-$C_{1-8}$alkyl)$_2$-amino, (heteroaryl-$C_{1-8}$alkyl)($C_{1-8}$alkyl)amino, heteroaryl-$C_{1-8}$alkyl-amino-$C_{1-8}$alkyl, (heteroaryl-$C_{1-8}$alkyl)$_2$-amino-$C_{1-8}$alkyl or (heteroaryl-$C_{1-8}$alkyl)($C_{1-8}$alkyl)amino-$C_{1-8}$alkyl;

wherein, heterocyclyl is selected from azetidinyl, tetrahydrofuranyl, pyrrolidinyl, piperidinyl, piperazinyl, 1,4-diazepanyl, 1,2,5,6-tetrahydropyridinyl, 1,2,3,6-tetrahydropyridinyl, hexahydropyrrolo[3,4-b]pyrrol-(1H)-yl, (3aS,6aS)-hexahydropyrrolo[3,4-b]pyrrol-(1H)-yl, (3aR,6aR)-hexahydropyrrolo[3,4-b]pyrrol-(1H)-yl, hexahydropyrrolo[3,4-b]pyrrol-(2H)-yl, (3aS,6aS)-hexahydropyrrolo[3,4-b]pyrrol-(2H)-yl, hexahydropyrrolo[3,4-c]pyrrol-(1H)-yl, (3aR,6aS)-hexahydropyrrolo[3,4-c]pyrrol-(1H)-yl, octahydro-5H-pyrrolo[3,2-c]pyridinyl, octahydro-6H-pyrrolo[3,4-b]pyridinyl, (4aR,7aR)-octahydro-6H-pyrrolo[3,4-b]pyridinyl, (4aS,7aS)-octahydro-6H-pyrrolo[3,4-b]pyridinyl, hexahydropyrrolo[1,2-a]pyrazin-(2H)-one, hexahydropyrrolo[1,2-a]pyrazin-(1H)-yl, (7R,8aS)-hexahydropyrrolo[1,2-a]pyrazin-(1H)-yl, (8aS)-hexahydropyrrolo[1,2-a]pyrazin-(1H)-yl, (8aR)-hexahydropyrrolo[1,2-a]pyrazin-(1H)-yl, (8aS)-octahydropyrrolo[1,2-a]pyrazin-(1H)-yl, (8aR)-octahydropyrrolo[1,2-a]pyrazin-(1H)-yl, octahydro-2H-pyrido[1,2-a]pyrazinyl, 3-azabicyclo[3.1.0]hexyl, (1R,5S)-3-azabicyclo[3.1.0]hexyl, 8-azabicyclo[3.2.1]octyl, (1R,5S)-8-azabicyclo[3.2.1]octyl, 8-azabicyclo[3.2.1]oct-2-enyl, (1R,5S)-8-azabicyclo[3.2.1]oct-2-enyl, 9-azabicyclo[3.3.1]nonyl, (1R,5S)-9-azabicyclo[3.3.1]nonyl, 2,5-diazabicyclo[2.2.1]heptyl, (1S,4S)-2,5-diazabicyclo[2.2.1]heptyl, 2,5-diazabicyclo[2.2.2]octyl, 3,8-diazabicyclo[3.2.1]octyl, (1R,5S)-3,8-diazabicyclo[3.2.1]octyl, 1,4-diazabicyclo[3.2.2]nonyl, azaspiro[3.3]heptyl, 2,6-diazaspiro[3.3]heptyl, 2,7-diazaspiro[3.5]nonyl, 5,8-diazaspiro[3.5]nonyl, 2,7-diazaspiro[4.4]nonyl or 6,9-diazaspiro[4.5]decyl; and, wherein, each instance of heterocyclyl, $C_{3-14}$cycloalkyl, aryl and heteroaryl is optionally substituted with $R_3$ and $R_4$ substituents; and $R_2$ is aryl, aryl-amino, aryl-amino-carbonyl, heterocyclyl, heteroaryl or heteroaryl-amino;

wherein, heterocyclyl is selected from 1,2,3,6-tetrahydropyridin-4-yl, 1,3-benzodioxol-5-yl or 2,3-dihydro-1,4-benzodioxin-6-yl;

wherein, heteroaryl is selected from thienyl, 1H-pyrazolyl, 1H-imidazolyl, 1,3-thiazolyl, 1,2,4-oxadiazolyl, 1,3,4-oxadiazolyl, pyridinyl, pyrimidinyl, 1H-indolyl, 2H-indolyl, 1H-indazolyl, 2H-indazolyl, indolizinyl, benzofuranyl, benzothienyl, 1H-benzimidazolyl, 1,3-benzothiazolyl, 1,3-benzoxazolyl, 9H-purinyl, furo[3,2-b]pyridinyl, furo[3,2-c]pyridinyl, furo[2,3-c]pyridinyl, thieno[3,2-c]pyridinyl, thieno[2,3-d]pyrimidinyl, 1H-pyrrolo[2,3-b]pyridinyl, 1H-pyrrolo[2,3-c]pyridinyl, pyrrolo[1,2-a]pyrimidinyl, pyrrolo[1,2-a]pyrazinyl, pyrrolo[1,2-b]pyridazinyl, pyrazolo[1,5-a]pyridinyl, pyrazolo[1,5-a]pyrazinyl, imidazo[1,2-a]pyridinyl, imidazo[1,2-a]pyrimidinyl, imidazo[1,2-c]pyrimidinyl, imidazo[1,2-b]pyridazinyl, imidazo[1,2-a]pyrazinyl, imidazo[2,1-b][1,3]thiazolyl, imidazo[2,1-b][1,3,4]thiadiazolyl, [1,3]oxazolo[4,5-b]pyridinyl or quinoxalinyl; and, wherein, each instance of heterocyclyl and heteroaryl is optionally substituted with $R_6$ and $R_7$ substituents.

In another embodiment of the use of a compound of Formula (I), $R_1$ is $C_{1-8}$alkyl, amino, $C_{1-8}$alkyl-amino, $(C_{1-8}alkyl)_2$-amino, $C_{1-8}$alkoxy-$C_{1-8}$alkyl-amino, ($C_{1-8}$alkoxy-$C_{1-8}$alkyl$)_2$-amino, ($C_{1-8}$alkoxy-$C_{1-8}$alkyl)($C_{1-8}$alkyl)amino, amino-$C_{1-8}$alkyl, $C_{1-8}$alkyl-amino-$C_{1-8}$alkyl, $(C_{1-8}alkyl)_2$-amino-$C_{1-8}$alkyl, $C_{1-8}$alkoxy-$C_{1-8}$alkyl-amino-$C_{1-8}$alkyl, ($C_{1-8}$alkoxy-$C_{1-8}$alkyl$)_2$-amino-$C_{1-8}$alkyl, ($C_{1-8}$alkoxy-$C_{1-8}$alkyl)($C_{1-8}$alkyl)amino-$C_{1-8}$alkyl, amino-$C_{1-8}$alkyl-amino, (amino-$C_{1-8}$alkyl$)_2$-amino, (amino-$C_{1-8}$alkyl)($C_{1-8}$alkyl)amino, $C_{1-8}$alkyl-amino-$C_{1-8}$alkyl-amino, ($C_{1-8}$alkyl-amino-$C_{1-8}$alkyl$)_2$-amino, ($C_{1-8}$alkyl-amino-$C_{1-8}$alkyl)($C_{1-8}$alkyl)amino, $(C_{1-8}alkyl)_2$-amino-$C_{1-8}$alkyl-amino, [$(C_{1-8}alkyl)_2$-amino-$C_{1-8}$alkyl]($C_{1-8}$alkyl)amino, amino-$C_{1-8}$alkoxy, $C_{1-8}$alkyl-amino-$C_{1-8}$alkoxy, $(C_{1-8}alkyl)_2$-amino-$C_{1-8}$alkoxy, $C_{1-8}$alkoxy-$C_{1-8}$alkyl-amino-$C_{1-8}$alkoxy, ($C_{1-8}$alkoxy-$C_{1-8}$alkyl$)_2$-amino-$C_{1-8}$alkoxy, ($C_{1-8}$alkoxy-$C_{1-8}$alkyl)($C_{1-8}$alkyl)amino-$C_{1-8}$alkoxy, amino-$C_{2-8}$alkenyl, $C_{1-8}$alkyl-amino-$C_{2-8}$alkenyl, $(C_{1-8}alkyl)_2$-amino-$C_{2-8}$alkenyl, amino-$C_{2-8}$alkynyl, $C_{1-8}$alkyl-amino-$C_{2-8}$alkynyl, $(C_{1-8}alkyl)_2$-amino-$C_{2-8}$alkynyl, halo-$C_{1-8}$alkyl-amino, (halo-$C_{1-8}$alkyl$)_2$-amino, (halo-$C_{1-8}$alkyl)($C_{1-8}$alkyl)amino, hydroxy-$C_{1-8}$alkyl, hydroxy-$C_{1-8}$alkoxy-$C_{1-8}$alkyl, hydroxy-$C_{1-8}$alkyl-amino, (hydroxy-$C_{1-8}$alkyl$)_2$-amino, (hydroxy-$C_{1-8}$alkyl)($C_{1-8}$alkyl)amino, hydroxy-$C_{1-8}$alkyl-amino-$C_{1-8}$alkyl, (hydroxy-$C_{1-8}$alkyl$)_2$-amino-$C_{1-8}$alkyl, (hydroxy-$C_{1-8}$alkyl)($C_{1-8}$alkyl)amino-$C_{1-8}$alkyl, hydroxy-$C_{1-8}$alkyl-amino-$C_{1-8}$alkoxy, (hydroxy-$C_{1-8}$alkyl$)_2$-amino-$C_{1-8}$alkoxy, (hydroxy-$C_{1-8}$alkyl)($C_{1-8}$alkyl)amino-$C_{1-8}$alkoxy, hydroxy-$C_{1-8}$alkyl-amino-$C_{1-8}$alkyl-amino, (hydroxy-$C_{1-8}$alkyl-amino-$C_{1-8}$alkyl$)_2$-amino, (hydroxy-$C_{1-8}$alkyl$)_2$-amino-$C_{1-8}$alkyl-amino, (hydroxy-$C_{1-8}$alkyl-amino-$C_{1-8}$alkyl)($C_{1-8}$alkyl)amino, (hydroxy-$C_{1-8}$alkyl)($C_{1-8}$alkyl)amino-$C_{1-8}$alkyl-amino, [(hydroxy-$C_{1-8}$alkyl$)_2$-amino-$C_{1-8}$alkyl]($C_{1-8}$alkyl)amino or [(hydroxy-$C_{1-8}$alkyl)($C_{1-8}$alkyl)amino-$C_{1-8}$alkyl]($C_{1-8}$alkyl) amino; and $R_2$ is aryl, aryl-amino, aryl-amino-carbonyl, heterocyclyl, heteroaryl or heteroaryl-amino, wherein, each instance of aryl, heterocyclyl and heteroaryl is optionally substituted with $R_6$ and $R_7$ substituents.

In another embodiment of the use of a compound of Formula (I), $R_1$ is heterocyclyl, heterocyclyl-$C_{1-8}$alkyl, heterocyclyl-$C_{1-8}$alkoxy, heterocyclyl-amino, (heterocyclyl)($C_{1-8}$alkyl) amino, heterocyclyl-amino-$C_{1-8}$alkyl, heterocyclyl-$C_{1-8}$alkyl-amino, (heterocyclyl-$C_{1-8}$alkyl$)_2$-amino, (heterocyclyl-$C_{1-8}$alkyl)($C_{1-8}$alkyl)amino, heterocyclyl-$C_{1-8}$alkyl-amino-$C_{1-8}$alkyl, (heterocyclyl-$C_{1-8}$alkyl$)_2$-amino-$C_{1-8}$alkyl, (heterocyclyl-$C_{1-8}$alkyl)($C_{1-8}$alkyl)amino-$C_{1-8}$alkyl, heterocyclyl-oxy, heterocyclyl-carbonyl, heterocyclyl-carbonyl-oxy, $C_{3-14}$cycloalkyl, aryl-$C_{1-8}$alkyl-amino, (aryl-$C_{1-8}$alkyl$)_2$-amino, (aryl-$C_{1-8}$alkyl)($C_{1-8}$alkyl)amino, aryl-$C_{1-8}$alkyl-amino-$C_{1-8}$alkyl, (aryl-$C_{1-8}$alkyl$)_2$-amino-$C_{1-8}$alkyl, (aryl-$C_{1-8}$alkyl)($C_{1-8}$alkyl)amino-$C_{1-8}$alkyl, heteroaryl, heteroaryl-$C_{1-8}$alkyl, heteroaryl-$C_{1-8}$alkoxy, heteroaryl-amino, heteroaryl-$C_{1-8}$alkyl-amino, (heteroaryl-$C_{1-8}$alkyl$)_2$-amino, (heteroaryl-$C_{1-8}$alkyl)($C_{1-8}$alkyl)amino, heteroaryl-$C_{1-8}$alkyl-amino-$C_{1-8}$alkyl, (heteroaryl-$C_{1-8}$alkyl$)_2$-amino-$C_{1-8}$alkyl or (heteroaryl-$C_{1-8}$alkyl)($C_{1-8}$alkyl) amino-$C_{1-8}$alkyl; wherein, each instance of heterocyclyl, $C_{3-14}$cycloalkyl, aryl and heteroaryl is optionally substituted with $R_3$ and $R_4$ substituents; and $R_2$ is aryl, aryl-amino, aryl-amino-carbonyl, heterocyclyl, heteroaryl or heteroaryl-amino, wherein, each instance of aryl, heterocyclyl and heteroaryl is optionally substituted with $R_6$ and $R_7$ substituents.

In another embodiment of the use of a compound of Formula (I), $R_1$ is heterocyclyl, heterocyclyl-$C_{1-8}$alkyl, heterocyclyl-$C_{1-8}$alkoxy, heterocyclyl-amino, (heterocyclyl)($C_{1-8}$alkyl) amino, heterocyclyl-amino-$C_{1-8}$alkyl, heterocyclyl-$C_{1-8}$alkyl-amino, (heterocyclyl-$C_{1-8}$alkyl$)_2$-amino, (heterocyclyl-$C_{1-8}$alkyl)($C_{1-8}$alkyl)amino, heterocyclyl-$C_{1-8}$alkyl-amino-$C_{1-8}$alkyl, (heterocyclyl-$C_{1-8}$alkyl$)_2$-amino-$C_{1-8}$alkyl, (heterocyclyl-$C_{1-8}$alkyl)($C_{1-8}$alkyl)amino-$C_{1-8}$alkyl, heterocyclyl-oxy, heterocyclyl-carbonyl or heterocyclyl-carbonyl-oxy; wherein, each instance of heterocyclyl is optionally substituted with $R_3$ and $R_4$ substituents; and $R_2$ is aryl, aryl-amino, aryl-amino-carbonyl, heterocyclyl, heteroaryl or heteroaryl-amino, wherein, each instance of aryl, heterocyclyl and heteroaryl is optionally substituted with $R_6$ and $R_7$ substituents.

In another embodiment of the use of a compound of Formula (I), $R_1$ is heterocyclyl optionally substituted with $R_3$ and $R_4$ substituents; and $R_2$ is aryl, aryl-amino, aryl-amino-carbonyl, heterocyclyl, heteroaryl or heteroaryl-amino, wherein, each instance of aryl, heterocyclyl and heteroaryl is optionally substituted with $R_6$ and $R_7$ substituents.

In another embodiment of the use of a compound of Formula (I), $R_1$ is $C_{3-14}$cycloalkyl optionally substituted with $R_3$ and $R_4$ substituents; and $R_2$ is aryl, aryl-amino, aryl-amino-carbonyl, heterocyclyl, heteroaryl or heteroaryl-amino, wherein, each instance of aryl, heterocyclyl and heteroaryl is optionally substituted with $R_6$ and $R_7$ substituents.

In another embodiment of the use of a compound of Formula (I), $R_1$ is aryl-$C_{1-8}$alkyl-amino, (aryl-$C_{1-8}$alkyl$)_2$-amino, (aryl-$C_{1-8}$alkyl)($C_{1-8}$alkyl)amino, aryl-$C_{1-8}$alkyl-amino-$C_{1-8}$alkyl, (aryl-$C_{1-8}$alkyl$)_2$-amino-$C_{1-8}$alkyl or (aryl-$C_{1-8}$alkyl)($C_{1-8}$alkyl)amino-$C_{1-8}$alkyl; wherein, each instance of aryl is optionally substituted with $R_3$ and $R_4$ substituents; and $R_2$ is aryl, aryl-amino, aryl-amino-carbonyl, heterocyclyl, heteroaryl or heteroaryl-amino, wherein, each instance of aryl, heterocyclyl and heteroaryl is optionally substituted with $R_6$ and $R_7$ substituents.

In another embodiment of the use of a compound of Formula (I), $R_1$ is aryl-$C_{1-8}$alkyl-amino optionally substituted with $R_3$ and $R_4$ substituents; and $R_2$ is aryl, aryl-amino, aryl-amino-carbonyl, heterocyclyl, heteroaryl or heteroaryl-amino, wherein, each instance of aryl, heterocyclyl and heteroaryl is optionally substituted with $R_6$ and $R_7$ substituents.

In another embodiment of the use of a compound of Formula (I), $R_1$ is heteroaryl, heteroaryl-$C_{1-8}$alkyl, heteroaryl-$C_{1-8}$alkoxy, heteroaryl-amino, heteroaryl-$C_{1-8}$alkyl-amino, (heteroaryl-$C_{1-8}$alkyl)$_2$-amino, (heteroaryl-$C_{1-8}$alkyl)($C_{1-8}$alkyl)amino, heteroaryl-$C_{1-8}$alkyl-amino-$C_{1-8}$alkyl, (heteroaryl-$C_{1-8}$alkyl)$_2$-amino-$C_{1-8}$alkyl or (heteroaryl-$C_{1-8}$alkyl)($C_{1-8}$alkyl)amino-$C_{1-8}$alkyl; wherein, each instance of heterocyclyl, $C_{3-14}$cycloalkyl, aryl and heteroaryl is optionally substituted with $R_3$ and $R_4$ substituents; and $R_2$ is aryl, aryl-amino, aryl-amino-carbonyl, heterocyclyl, heteroaryl or heteroaryl-amino, wherein, each instance of aryl, heterocyclyl and heteroaryl is optionally substituted with $R_6$ and $R_7$ substituents.

In another embodiment of the use of a compound of Formula (I), $R_1$ is heteroaryl optionally substituted with $R_3$ and $R_4$ substituents; and $R_2$ is aryl, aryl-amino, aryl-amino-carbonyl, heterocyclyl, heteroaryl or heteroaryl-amino, wherein, each instance of aryl, heterocyclyl and heteroaryl is optionally substituted with $R_6$ and $R_7$ substituents.

In one embodiment, the compound of Formula (I), used in a method disclosed herein, is a compound selected from Formula (II), Formula (III), Formula (IV), Formula (V), Formula (VI), Formula (VII), Formula (VIII), Formula (IX), Formula (X), Formula (XI), Formula (XII), Formula (XIII) or Formula (XIV):

(II)

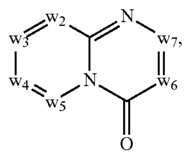

(III)

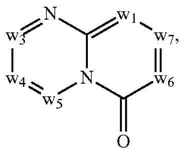

(IV)

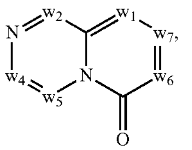

(V)

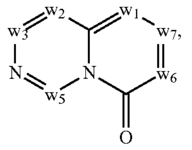

(VI)

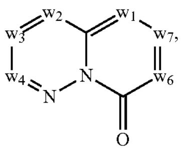

-continued (VII)

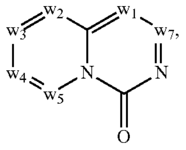

(VIII)

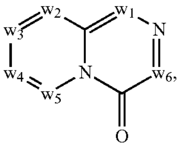

(IX)

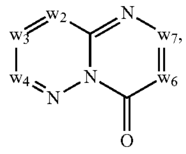

(X)

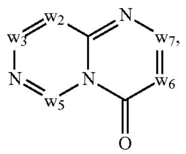

(XI)

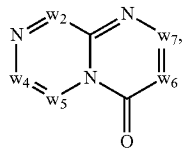

(XII)

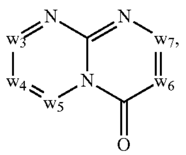

(XIII)

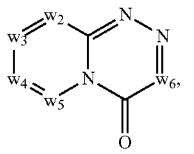

or (XIV)

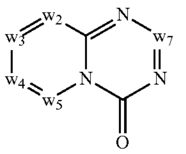

or a form thereof.

In an embodiment of the use of the compound of Formula (I), $w_3$ is C—$R_1$, $w_6$ is C—$R_2$, $w_1$, $w_4$, $w_5$ and $w_7$ are independently C—$R_a$, or N and $w_2$ is C—$R_b$ or N.

In another embodiment of the use of the compound of Formula (I), $w_3$ is C—$R_2$, $w_6$ is C—$R_1$, $w_1$, $w_4$, $w_5$ and $w_7$ are independently C—$R_a$, or N and $w_2$ is C—$R_b$ or N.

In another embodiment of the use of the compound of Formula (I), $w_4$ is C—$R_1$, $w_7$ is C—$R_2$, $w_1$, $w_3$ and $w_5$ are independently C—$R_a$ or N, $w_2$ is C—$R_b$ or N and $w_6$ is C—$R_c$ or N.

In another embodiment of the use of the compound of Formula (I), $w_4$ is C—$R_2$, $w_7$ is C—$R_1$, $w_1$, $w_3$ and $w_5$ are independently C—$R_a$ or N, $w_2$ is C—$R_b$ or N and $w_6$ is C—$R_c$ or N.

In an embodiment of the use of the compound of Formula (II), $w_3$ is C—$R_1$, $w_6$ is C—$R_2$, $w_4$, $w_5$ and $w_7$ are independently C—$R_a$ or N and $w_2$ is C—$R_b$ or N.

In another embodiment of the use of the compound of Formula (II), $w_3$ is C—$R_2$, $w_6$ is C—$R_1$, $w_4$, $w_5$ and $w_7$ are independently C—$R_a$ or N and $w_2$ is C—$R_b$ or N.

In another embodiment of the use of the compound of Formula (II), $w_4$ is C—$R_1$, $w_7$ is C—$R_2$, $w_3$ and $w_5$ are independently C—$R_a$ or N, $w_2$ is C—$R_b$ or N and $w_6$ is C—$R_c$ or N.

In another embodiment of the use of the compound of Formula (II), $w_4$ is C—$R_2$, $w_7$ is C—$R_1$, $w_3$ and $w_5$ are independently C—$R_a$ or N, $w_2$ is C—$R_b$ or N and $w_6$ is C—$R_c$ or N.

In an embodiment of the use of the compound of Formula (III), $w_3$ is C—$R_1$, $w_6$ is C—$R_2$ and $w_1$, $w_4$, $w_5$ and $w_7$ are independently C—$R_a$ or N.

In another embodiment of the use of the compound of Formula (III), $w_3$ is C—$R_2$, $w_6$ is C—$R_1$ and $w_1$, $w_4$, $w_5$ and $w_7$ are independently C—$R_a$ or N.

In another embodiment of the use of the compound of Formula (III), $w_4$ is C—$R_1$, $w_7$ is C—$R_2$, $w_1$, $w_3$ and $w_5$ are independently C—$R_a$ or N and $w_6$ is C—$R_c$ or N.

In another embodiment of the use of the compound of Formula (III), $w_4$ is C—$R_2$, $w_7$ is C—$R_1$, $w_1$, $w_3$ and $w_5$ are independently C—$R_a$ or N and $w_6$ is C—$R_c$ or N.

In an embodiment of the use of the compound of Formula (IV), $w_4$ is C—$R_1$, $w_7$ is C—$R_2$, $w_1$ and $w_5$ are independently C—$R_a$ or N, $w_2$ is C—$R_b$ or N and $w_6$ is C—$R_c$ or N.

In another embodiment of the use of the compound of Formula (IV), $w_4$ is C—$R_2$, $w_7$ is C—$R_1$, $w_1$ and $w_5$ are independently C—$R_a$ or N, $w_2$ is C—$R_b$ or N and $w_6$ is C—$R_c$ or N.

In an embodiment of the use of the compound of Formula (V), $w_3$ is C—$R_1$, $w_6$ is C—$R_2$, $w_1$, $w_5$ and $w_7$ are independently C—$R_a$ or N and $w_2$ is C—$R_b$ or N.

In another embodiment of the use of the compound of Formula (V), $w_3$ is C—$R_2$, $w_6$ is C—$R_1$, $w_1$, $w_5$ and $w_7$ are independently C—$R_a$ or N and $w_2$ is C—$R_b$ or N.

In an embodiment of the use of the compound of Formula (VI), $w_3$ is C—$R_1$, $w_6$ is C—$R_2$, $w_1$, $w_4$ and $w_7$ are independently C—$R_a$ or N and $w_2$ is C—$R_b$ or N.

In another embodiment of the use of the compound of Formula (VI), $w_3$ is C—$R_2$, $w_6$ is C—$R_1$, $w_1$, $w_4$ and $w_7$ are independently C—$R_a$ or N and $w_2$ is C—$R_b$ or N.

In another embodiment of the use of the compound of Formula (VI), $w_4$ is C—$R_1$, $w_7$ is C—$R_2$, $w_1$ and $w_3$ are independently C—$R_a$ or N, $w_2$ is C—$R_b$ or N and $w_6$ is C—R or N.

In another embodiment of the use of the compound of Formula (VI), $w_4$ is C—$R_2$, $w_7$ is C—$R_1$, $w_1$ and $w_3$ are independently C—$R_a$ or N, $w_2$ is C—$R_b$ or N and $w_6$ is C—$R_c$ or N.

In another embodiment of the use of the compound of Formula (VII), $w_4$ is C—$R_1$, $w_7$ is C—$R_2$, $w_1$, $w_3$ and $w_5$ are C—$R_a$ or N and $w_2$ is C—$R_b$ or N.

In another embodiment of the use of the compound of Formula (VII), $w_4$ is C—$R_2$, $w_7$ is C—$R_1$, $w_1$, $w_3$ and $w_5$ are C—$R_a$ or N and $w_2$ is C—$R_b$ or N.

In another embodiment of the use of the compound of Formula (VIII), $w_3$ is C—$R_1$, $w_6$ is C—$R_2$, $w_1$, $w_4$ and $w_5$ are C—$R_a$ or N and $w_2$ is C—$R_b$ or N.

In another embodiment of the use of the compound of Formula (VIII), $w_3$ is C—$R_2$, $w_6$ is C—$R_1$, $w_1$, $w_4$ and $w_5$ are C—$R_a$ or N and $w_2$ is C—$R_b$ or N.

In an embodiment of the use of the compound of Formula (IX), $w_3$ is C—$R_1$, $w_6$ is C—$R_2$, $w_4$ and $w_7$ are independently C—$R_a$ or N and $w_2$ is C—$R_b$ or N.

In another embodiment of the use of the compound of Formula (IX), $w_3$ is C—$R_2$, $w_6$ is C—$R_1$, $w_4$ and $w_7$ are independently C—$R_a$ or N and $w_2$ is C—$R_b$ or N.

In another embodiment of the use of the compound of Formula (IX), $w_4$ is C—$R_1$, $w_7$ is C—$R_2$, $w_2$ is C—$R_b$ or N, $w_3$ is C—$R_a$ or N and $w_6$ is C—$R_c$ or N.

In another embodiment of the use of the compound of Formula (IX), $w_4$ is C—$R_2$, $w_7$ is C—$R_1$, $w_2$ is C—$R_b$ or N, $w_3$ is C—$R_a$ or N and $w_6$ is C—$R_c$ or N.

In an embodiment of the use of the compound of Formula (X), $w_3$ is C—$R_1$, $w_6$ is C—$R_2$, $w_2$ is C—$R_b$ or N and $w_5$ and $w_7$ are independently C—$R_a$ or N.

In another embodiment of the use of the compound of Formula (X), $w_3$ is C—$R_2$, $w_6$ is C—$R_1$, $w_2$ is C—$R_b$ or N and $w_5$ and $w_7$ are independently C—$R_a$ or N.

In an embodiment of the use of the compound of Formula (XI), $w_4$ is C—$R_1$, $w_7$ is C—$R_2$, $w_2$ is C—$R_b$ or N, $w_5$ is C—$R_a$ or N and $w_6$ is C—$R_c$ or N.

In another embodiment of the use of the compound of Formula (XI), $w_4$ is C—$R_2$, $w_7$ is C—$R_1$, $w_2$ is C—$R_b$ or N, $w_5$ is C—$R_a$ or N and $w_6$ is C—$R_c$ or N.

In an embodiment of the use of the compound of Formula (XII), $w_3$ is C—$R_1$, $w_6$ is C—$R_2$ and $w_4$, $w_5$ and $w_7$ are independently C—$R_a$ or N.

In another embodiment of the use of the compound of Formula (XII), $w_3$ is C—$R_2$, $w_6$ is C—$R_1$ and $w_4$, $w_5$ and $w_7$ are independently C—$R_a$ or N.

In another embodiment of the use of the compound of Formula (XII), $w_4$ is C—$R_1$, $w_7$ is C—$R_2$, $w_3$ and $w_5$ are independently C—$R_a$ or N and $w_6$ is C—$R_c$ or N.

In another embodiment of the use of the compound of Formula (XII), $w_4$ is C—$R_2$, $w_7$ is C—$R_1$, $w_3$ and $w_5$ are independently C—$R_a$ or N and $w_6$ is C—$R_c$ or N.

In an embodiment of the use of the compound of Formula (XIII), $w_3$ is C—$R_1$, $w_6$ is C—$R_2$, $w_2$ is C—$R_b$ or N and $w_4$ and $w_5$ are independently C—$R_a$ or N.

In another embodiment of the use of the compound of Formula (XIII), $w_3$ is C—$R_2$, $w_6$ is C—$R_1$, $w_2$ is C—$R_b$ or N and $w_4$ and $w_5$ are independently C—$R_a$ or N.

In an embodiment of the use of the compound of Formula (XIV), $w_4$ is C—$R_1$, $w_7$ is C—$R_2$, $w_2$ is C—$R_b$ or N and $w_3$ and $w_5$ are independently C—$R_a$ or N.

In another embodiment of the use of the compound of Formula (XIV), $w_4$ is C—$R_2$, $w_7$ is C—$R_1$, $w_2$ is C—$R_b$ or N and $w_3$ and $w_5$ are independently C—$R_a$ or N.

In another embodiment, the compound of Formula (I) used in a method disclosed herein is a compound selected from Formula (II), Formula (III), Formula (IX), Formula (XI) or Formula (XII):

(II)

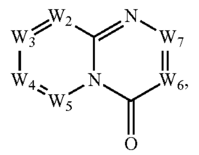

-continued (III)

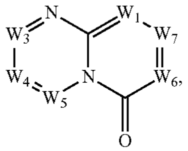

(IX)

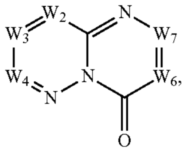

(XI)

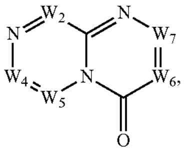

or (XII)

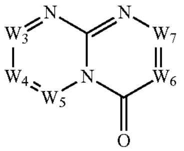

or a form thereof.

In another embodiment, the compound of Formula (I) used in a method disclosed herein is a compound of Formula (II):

(II)

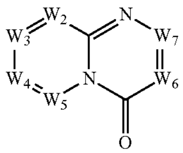

or a form thereof.

In another embodiment, the compound of Formula (I) used in a method disclosed herein is a compound of Formula (III):

(III)

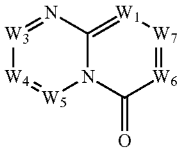

or a form thereof.

In another embodiment, the compound of Formula (I) used in a method disclosed herein is a compound of Formula (IV):

(IV)

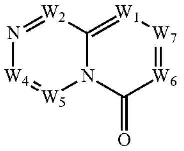

or a form thereof.

In another embodiment, the compound of Formula (I) used in a method disclosed herein is a compound of Formula (V):

(V)

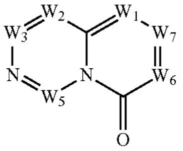

or a form thereof.

In another embodiment, the compound of Formula (I) used in a method disclosed herein is a compound of Formula (VI):

(VI)

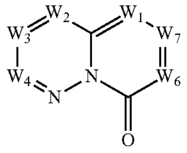

or a form thereof.

In another embodiment, the compound of Formula (I) used in a method disclosed herein is a compound of Formula (VII):

(VII)

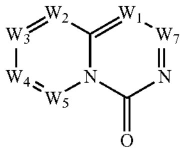

or a form thereof.

In another embodiment, the compound of Formula (I) used in a method disclosed herein is a compound of Formula (VIII):

(VIII)

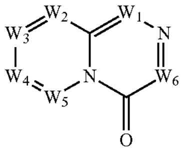

or a form thereof.

In another embodiment, the compound of Formula (I) used in a method disclosed herein is a compound of Formula (IX):

(IX)

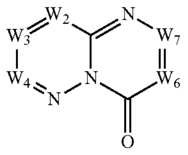

or a form thereof.

In another embodiment, the compound of Formula (I) used in a method disclosed herein is a compound of Formula (X):

(X)

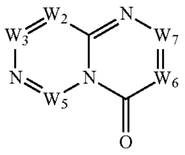

or a form thereof.

In another embodiment, the compound of Formula (I) used in a method disclosed herein is a compound of Formula (XI):

(XI)

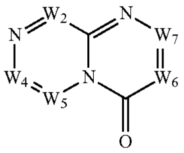

or a form thereof.

In another embodiment, the compound of Formula (I) used in a method disclosed herein is a compound of Formula (XII):

(XII)

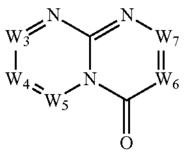

or a form thereof.

In another embodiment, the compound of Formula (I) used in a method disclosed herein is a compound of Formula (XIII):

(XIII)

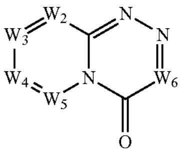

or a form thereof.

In another embodiment, the compound of Formula (I) used in a method disclosed herein is a compound of Formula (XIV):

(XIV)

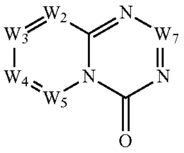

or a form thereof.

In one embodiment, the compound of Formula (I), Formula (II), Formula (III), Formula (IV), Formula (V), Formula (VI), Formula (VII), Formula (VIII), Formula (IX), Formula (X), Formula (XI), Formula (XII), Formula (XIII) or Formula (XIV) used in a method disclosed herein is a compound selected from Formula (Ia), Formula (IIa), Formula (IIIa), Formula (IVa), Formula (Va), Formula (VIa), Formula (VIIa), Formula (VIIIa), Formula (IXa), Formula (Xa), Formula (XIa), Formula (XIIa), Formula (XIIIa) or Formula (XIVa), respectively:

(Ia)

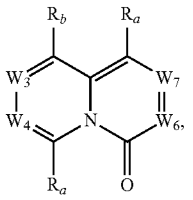

(IIa)

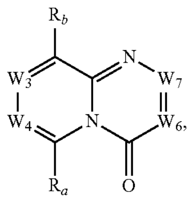

(IIIa)

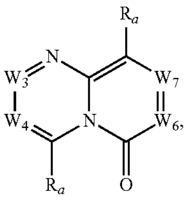

-continued (IVa)

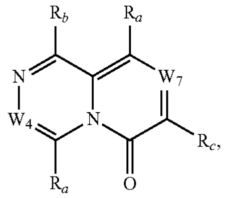

(Va)

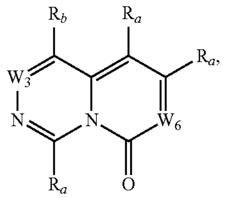

(VIa)

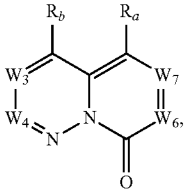

(VIIa)

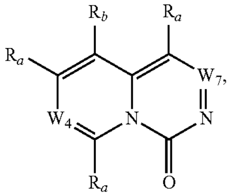

(VIIIa)

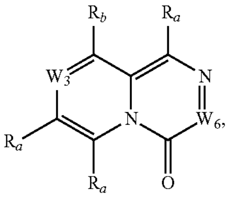

(IXa)

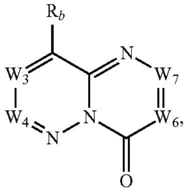

(Xa)

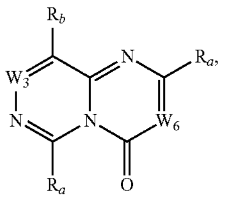

-continued (XIa)

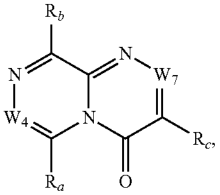

(XIIa)

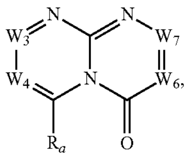

(XIIIa)

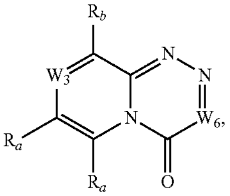

or (XIVa)

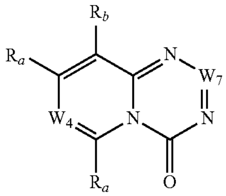

or a form thereof.

In an embodiment of the use of the compound of Formula (Ia), one of $w_3$, $w_4$, $w_6$ and $w_7$ is C—$R_1$ and one other of $w_3$, $w_4$, $w_6$ and $w_7$ is C—$R_2$, provided that, when $w_3$ is C—$R_1$, then $w_6$ is C—$R_2$ and $w_4$ and $w_7$ are independently C—$R_a$ or N; or, when $w_3$ is C—$R_2$, then $w_6$ is C—$R_1$ and $w_4$ and $w_7$ are independently C—$R_a$ or N; or, when $w_4$ is C—$R_1$, then $w_7$ is C—$R_2$ and $w_3$ is C—$R_a$ or N and $w_6$ is C—$R_c$ or N; or, when $w_4$ is C—$R_2$, then $w_7$ is C—$R_1$ and $w_3$ is C—$R_a$ or N and $w_6$ is C—$R_c$ or N.

In an embodiment of the use of the compound of Formula (IIa), one of $w_3$, $w_4$, $w_6$ and $w_7$ is C—$R_1$ and one other of $w_3$, $w_4$, $w_6$ and $w_7$ is C—$R_2$, provided that, when $w_3$ is C—$R_1$, then $w_6$ is C—$R_2$ and $w_4$ and $w_7$ are independently C—$R_a$ or N; or, when $w_3$ is C—$R_2$, then $w_6$ is C—$R_1$ and $w_4$ and $w_7$ are independently C—$R_a$ or N; or, when $w_4$ is C—$R_1$, then $w_7$ is C—$R_2$ and $w_3$ is C—$R_a$ or N and $w_6$ is C—$R_c$ or N; or, when $w_4$ is C—$R_2$, then $w_7$ is C—$R_1$ and $w_3$ is C—$R_a$ or N and $w_6$ is C—$R_c$ or N.

In an embodiment of the use of the compound of Formula (IIIa), one of $w_3$, $w_4$, $w_6$ and $w_7$ is C—$R_1$ and one other of $w_3$, $w_4$, $w_6$ and $w_7$ is C—$R_2$, provided that, when $w_3$ is C—$R_1$, then $w_6$ is C—$R_2$ and $w_4$ and $w_7$ are independently C—$R_a$ or N; or, when $w_3$ is C—$R_2$, then $w_6$ is C—$R_1$ and $w_4$ and $w_7$ are independently C—$R_a$ or N; or, when $w_4$ is C—$R_1$, then $w_7$ is C—$R_2$ and $w_3$ is C—$R_a$ or N and $w_6$ is C—$R_c$ or N; or, when $w_4$ is C—$R_2$, then $w_7$ is C—$R_1$ and $w_3$ is C—$R_a$ or N and $w_6$ is C—$R_c$ or N.

In an embodiment of the use of the compound of Formula (IVa), one of $w_4$ and $w_7$ is C—$R_1$ and the other is C—$R_2$, provided that, when $w_4$ is C—$R_1$, then $w_7$ is C—$R_2$; or, when $w_4$ is C—$R_2$, then $w_7$ is C—$R_1$.

In an embodiment of the use of the compound of Formula (Va), one of $w_3$ and $w_6$ is C—$R_1$ and the other is C—$R_2$, provided that, when $w_3$ is C—$R_1$, then $w_6$ is C—$R_2$; or, when $w_3$ is C—$R_2$, then $w_6$ is C—$R_1$.

In an embodiment of the use of the compound of Formula (VIa), one of $w_3$, $w_4$, $w_6$ and $w_7$ is C—$R_1$ and one other of $w_3$, $w_4$, $w_6$ and $w_7$ is C—$R_2$, provided that, when $w_3$ is C—$R_1$, then $w_6$ is C—$R_2$ and $w_4$ and $w_7$ are independently C—$R_a$ or N; or, when $w_3$ is C—$R_2$, then $w_6$ is C—$R_1$ and $w_4$ and $w_7$ are independently C—$R_a$ or N; or, when $w_4$ is C—$R_1$, then $w_7$ is C—$R_2$ and $w_3$ is C—$R_a$ or N and $w_6$ is C—$R_c$ or N; or, when $w_4$ is C—$R_2$, then $w_7$ is C—$R_1$ and $w_3$ is C—$R_a$ or N and $w_6$ is C—$R_c$ or N.

In an embodiment of the use of the compound of Formula (VIIa), one of $w_4$ and $w_7$ is C—$R_1$ and the other is C—$R_2$, provided that, when $w_4$ is C—$R_1$, then $w_7$ is C—$R_2$; or, when $w_4$ is C—$R_2$, then $w_7$ is C—$R_1$.

In an embodiment of the use of the compound of Formula (VIIIa), one of $w_3$ and $w_6$ is C—$R_1$ and the other is C—$R_2$, provided that, when $w_3$ is C—$R_1$, then $w_6$ is C—$R_2$; or, when $w_3$ is C—$R_2$, then $w_6$ is C—$R_1$.

In an embodiment of the use of the compound of Formula (IXa), one of $w_3$, $w_4$, $w_6$ and $w_7$ is C—$R_1$ and one other of $w_3$, $w_4$, $w_6$ and $w_7$ is C—$R_2$, provided that, when $w_3$ is C—$R_1$, then $w_6$ is C—$R_2$ and $w_4$ and $w_7$ are independently C—$R_a$ or N; or, when $w_3$ is C—$R_2$, then $w_6$ is C—$R_1$ and $w_4$ and $w_7$ are independently C—$R_a$ or N; or, when $w_4$ is C—$R_1$, then $w_7$ is C—$R_2$ and $w_3$ is C—$R_a$ or N and $w_6$ is C—$R_c$ or N; or, when $w_4$ is C—$R_2$, then $w_7$ is C—$R_1$ and $w_3$ is C—$R_a$ or N and $w_6$ is C—$R_c$ or N.

In an embodiment of the use of the compound of Formula (Xa), one of $w_3$ and $w_6$ is C—$R_1$ and the other is C—$R_2$, provided that, when $w_3$ is C—$R_1$, then $w_6$ is C—$R_2$; or, when $w_3$ is C—$R_2$, then $w_6$ is C—$R_1$.

In an embodiment of the use of the compound of Formula (XIa), one of $w_4$ and $w_7$ is C—$R_1$ and the other is C—$R_2$, provided that, when $w_4$ is C—$R_1$, then $w_7$ is C—$R_2$; or, when $w_4$ is C—$R_2$, then $w_7$ is C—$R_1$.

In an embodiment of the use of the compound of Formula (XIIa), one of $w_3$, $w_4$, $w_6$ and $w_7$ is C—$R_1$ and one other of $w_3$, $w_4$, $w_6$ and $w_7$ is C—$R_2$, provided that, when $w_3$ is C—$R_1$, then $w_6$ is C—$R_2$ and $w_4$ and $w_7$ are independently C—$R_a$ or N; or, when $w_3$ is C—$R_2$, then $w_6$ is C—$R_1$ and $w_4$ and $w_7$ are independently C—$R_a$ or N; or, when $w_4$ is C—$R_1$, then $w_7$ is C—$R_2$ and $w_3$ is C—$R_a$ or N and $w_6$ is C—$R_c$ or N; or, when $w_4$ is C—$R_2$, then $w_7$ is C—$R_1$ and $w_3$ is C—$R_a$ or N and $w_6$ is C—$R_c$ or N.

In an embodiment of the use of the compound of Formula (XIIIa), one of $w_3$ and $w_6$ is C—$R_1$ and the other is C—$R_2$, provided that, when $w_3$ is C—$R_1$, then $w_6$ is C—$R_2$; or, when $w_3$ is C—$R_2$, then $w_6$ is C—$R_1$.

In an embodiment of the use of the compound of Formula (XIVa), one of $w_4$ and $w_7$ is C—$R_1$ and the other is C—$R_2$, provided that, when $w_4$ is C—$R_1$, then $w_7$ is C—$R_2$; or, when $w_4$ is C—$R_2$, then $w_7$ is C—$R_1$.

In another embodiment, the compound of Formula (I), Formula (II), Formula (III), Formula (IX), Formula (XI) or Formula (XII), used in a method disclosed herein, is a compound selected from Formula (Ia), Formula (IIa), Formula (IIIa), Formula (IXa), Formula (XIa) or Formula (XIIa), respectively:

(Ia)

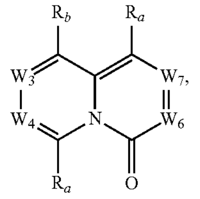

(IIa)

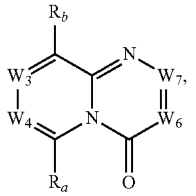

(IIIa)

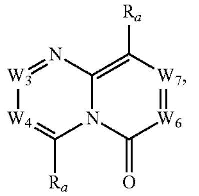

(IXa)

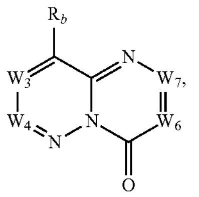

(XIa)

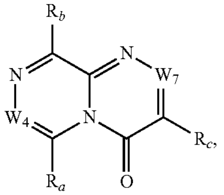

or (XIIa)

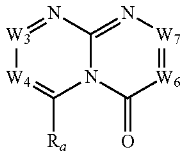

or a form thereof.

In another embodiment, the compound of Formula (I) used in a method disclosed herein is a compound of Formula (Ia):

(Ia)

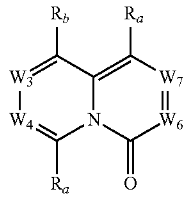

or a form thereof.

In another embodiment, the compound of Formula (II) used in a method disclosed herein is a compound of Formula (IIa):

(IIa)

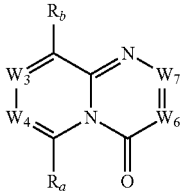

or a form thereof.

In another embodiment, the compound of Formula (III) used in a method disclosed herein is a compound of Formula (IIIa):

(IIIa)

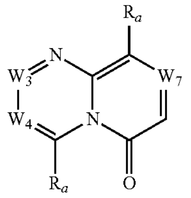

or a form thereof.

In another embodiment, the compound of Formula (IV) used in a method disclosed herein is a compound of Formula (IVa):

(IVa)

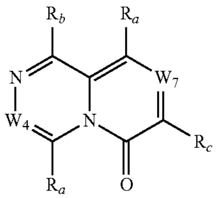

or a form thereof.

In another embodiment, the compound of Formula (V) used in a method disclosed herein is a compound of Formula (Va):

(Va)

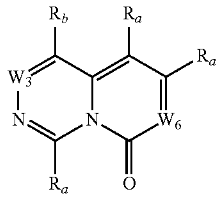

or a form thereof.

In another embodiment, the compound of Formula (VI) used in a method disclosed herein is a compound of Formula (VIa):

(VIa)

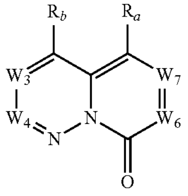

or a form thereof.

In another embodiment, the compound of Formula (VII) used in a method disclosed herein is a compound of Formula (VIIa):

(VIIa)

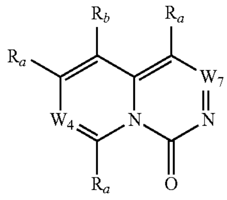

or a form thereof.

In another embodiment, the compound of Formula (VIII) used in a method disclosed herein is a compound of Formula (VIIIa):

(VIIIa)

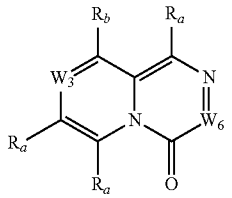

or a form thereof.

In another embodiment, the compound of Formula (IX) used in a method disclosed herein is a compound of Formula (IXa):

(IXa)

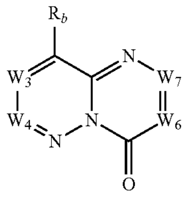

or a form thereof.

In another embodiment, the compound of Formula (X) used in a method disclosed herein is a compound of Formula (Xa):

(Xa)

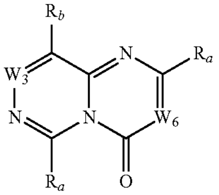

or a form thereof.

In another embodiment, the compound of Formula (XI) used in a method disclosed herein is a compound of Formula (XIa):

(XIa)

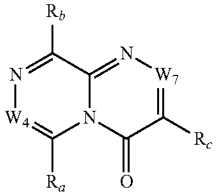

or a form thereof.

In another embodiment, the compound of Formula (XII) used in a method disclosed herein is a compound of Formula (XIIa):

(XIIa)

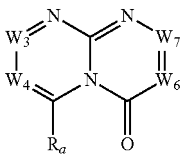

or a form thereof.

In another embodiment, the compound of Formula (XIII) used in a method disclosed herein is a compound of Formula (XIIIa):

(XIIIa)

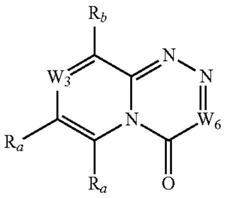

or a form thereof.

In another embodiment, the compound of Formula (XIV) used in a method disclosed herein is a compound of Formula (XIVa):

(XIVa)

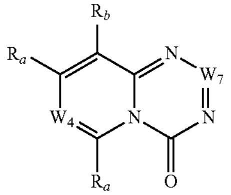

or a form thereof.

In one embodiment, the compound of Formula (Ia) used in a method disclosed herein is a compound of Formula (Ia1), Formula (Ia2), Formula (Ia3) or Formula (Ia4):

(Ia1)

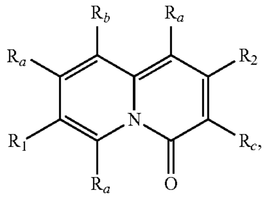

, (Ia2)

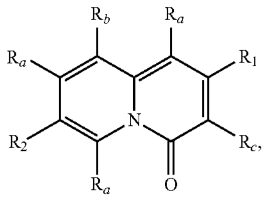

, (Ia3)

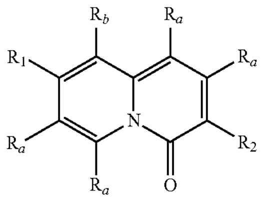

or (Ia4)

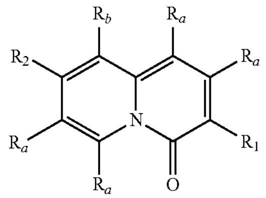

or a form thereof.

In one embodiment, the compound of Formula (IIa) used in a method disclosed herein is a compound of Formula (IIa1), Formula (IIa2), Formula (IIa3) or Formula (IIa4):

(IIa1)

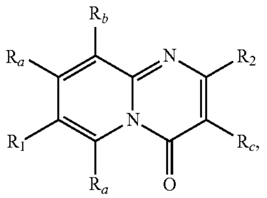

(IIa2)

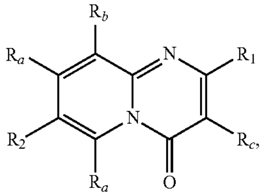

(IIa3)

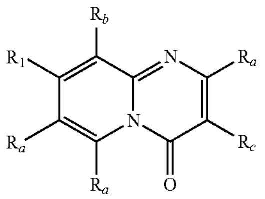

or (IIa4)

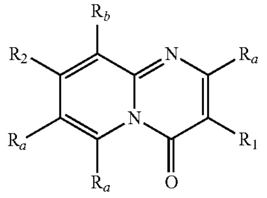

or a form thereof.

In one embodiment, the compound of Formula (IIIa) used in a method disclosed herein is a compound of Formula (IIIa1), Formula (IIIa2), Formula (IIIa3) or Formula (IIIa4):

(IIIa1)

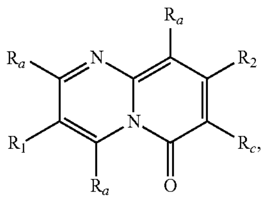

(IIIa2)

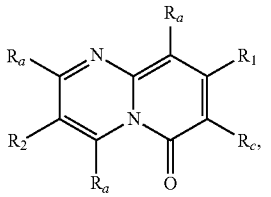

-continued (IIIa3)

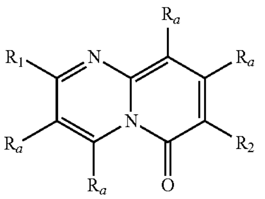

or (IIIa4)

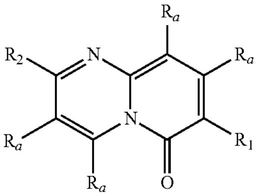

or a form thereof.

In one embodiment, the compound of Formula (IVa) used in a method disclosed herein is a compound of Formula (IVa1) or Formula (IVa2):

(IVa1)

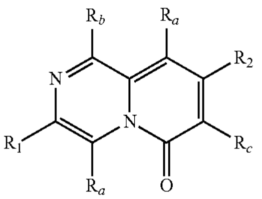

or (IVa2)

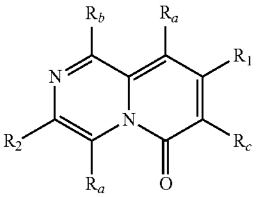

or a form thereof.

In one embodiment, the compound of Formula (Va) used in a method disclosed herein is a compound of Formula (Va1) or Formula (Va2):

(Va1)

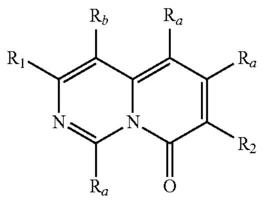

or (Va2)

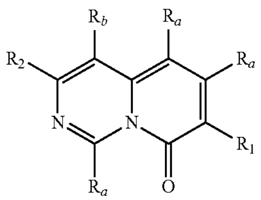

or a form thereof.

In one embodiment, the compound of Formula (VIa) used in a method disclosed herein is a compound of Formula (VIa1), Formula (VIa2), Formula (VIa3) or Formula (VIa4):

(VIa1)

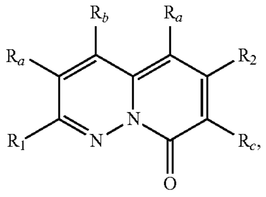

(VIa2)

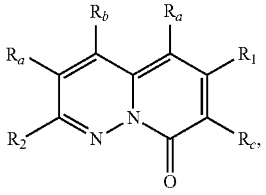

(VIa3)

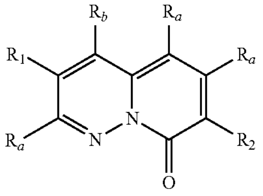

or (VIa4)

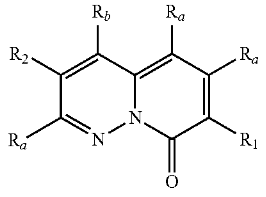

or a form thereof.

In one embodiment, the compound of Formula (VIIa) used in a method disclosed herein is a compound of Formula (VIIa1) or Formula (VIIa2):

(VIIa1)

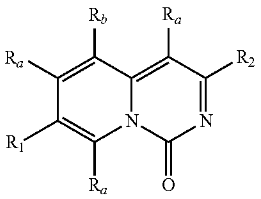

or (VIIa2)

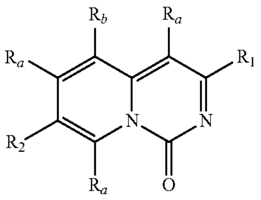

or a form thereof.

In one embodiment, the compound of Formula (VIIIa) used in a method disclosed herein is a compound of Formula (VIIIa1) or Formula (VIIIa2):

(VIIIa1)

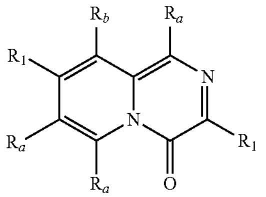

or (VIIIa2)

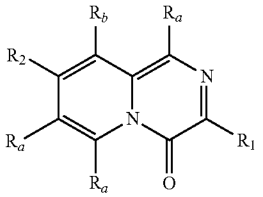

or a form thereof.

In one embodiment, the compound of Formula (IXa) used in a method disclosed herein is a compound of Formula (IXa1), Formula (IXa2), Formula (IXa3) or Formula (IXa4):

(IXa1)

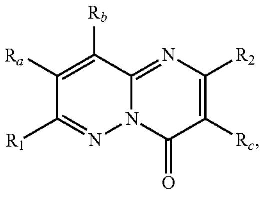

(IXa2)

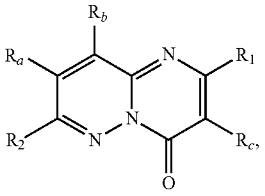

(IXa3)

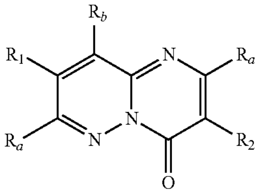

or (IXa4)

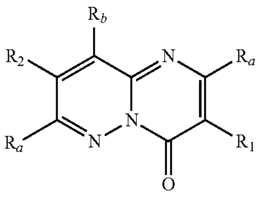

or a form thereof.

In one embodiment, the compound of Formula (Xa) used in a method disclosed herein is a compound of Formula (Xa1) or Formula (Xa2):

(Xa1)

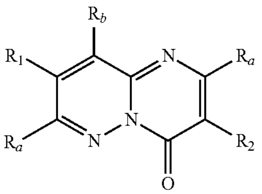

or (Xa2)

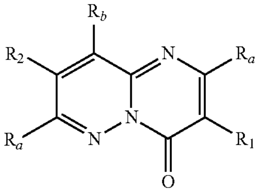

or a form thereof.

In one embodiment, the compound of Formula (XIa) used in a method disclosed herein is a compound of Formula (XIa1) or Formula (XIa2):

(XIa1)

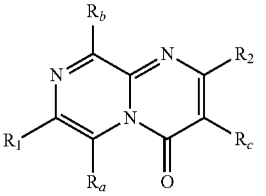

or (XIa2)

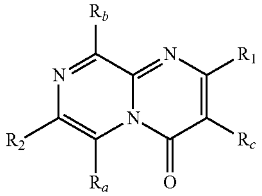

or a form thereof.

In one embodiment, the compound of Formula (XIIa) used in a method disclosed herein is a compound of Formula (XIIa1), Formula (XIIa2), Formula (XIIa3) or Formula (XIIa4):

(XIIa1)

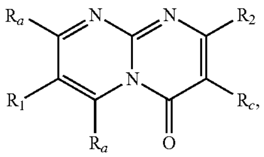

(XIIIa2)

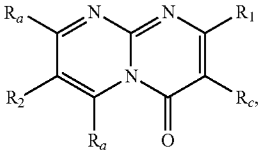

-continued (XIIa3)

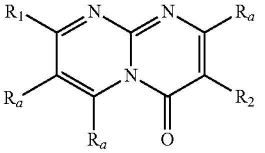

or (XIIa4)

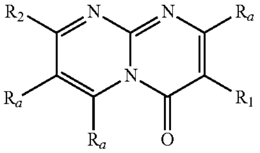

or a form thereof.

In one embodiment, the compound of Formula (XIIIa) used in a method disclosed herein is a compound of Formula (XIIIa1) or Formula (XIIIa2):

(XIIIa1)

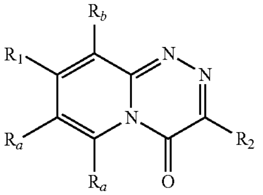

or (XIIIa2)

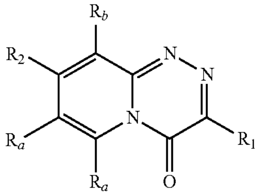

or a form thereof.

In one embodiment, the compound of Formula (XIVa) used in a method disclosed herein is a compound of Formula (XIVa1) or Formula (XIVa2):

(XIVa1)

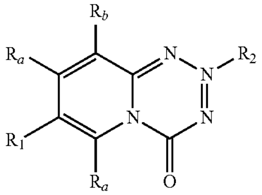

or (XIVa2)

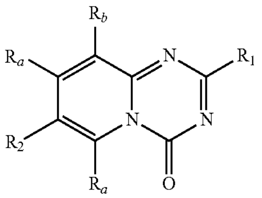

or a form thereof.

In one embodiment, the compound of Formula (Ia) used in a method disclosed herein is a compound of Formula (Ia1):

(Ia1)

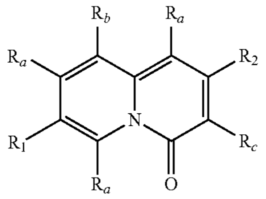

or a form thereof.

In one embodiment, the compound of Formula (Ia) used in a method disclosed herein is a compound of Formula (Ia2):

(Ia2)

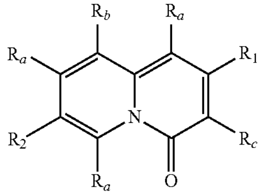

or a form thereof.

In one embodiment, the compound of Formula (Ia) used in a method disclosed herein is a compound of Formula (Ia3):

(Ia3)

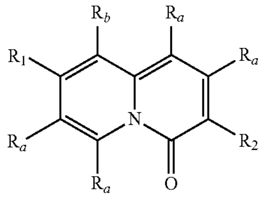

or a form thereof.

In one embodiment, the compound of Formula (Ia) used in a method disclosed herein is a compound of Formula (Ia4):

(Ia4)

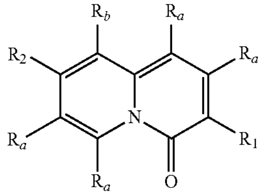

or a form thereof.

In one embodiment, the compound of Formula (IIa) used in a method disclosed herein is a compound of Formula (IIa1):

(IIa1)

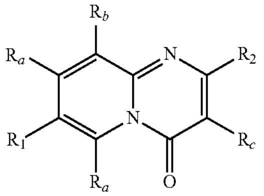

or a form thereof.

In one embodiment, the compound of Formula (IIa) used in a method disclosed herein is a compound of Formula (IIa2):

(IIa2)

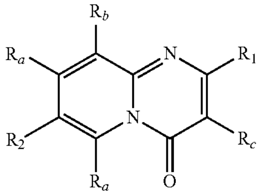

or a form thereof.

In one embodiment, the compound of Formula (IIa) used in a method disclosed herein is a compound of Formula (IIa3):

(IIa3)

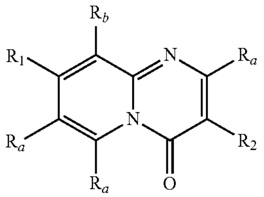

or a form thereof.

In one embodiment, the compound of Formula (IIa) used in a method disclosed herein is a compound of Formula (IIa4):

(IIa4)

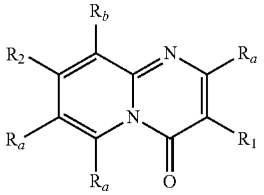

or a form thereof.

In one embodiment, the compound of Formula (IIIa) used in a method disclosed herein is a compound of Formula (IIIa1):

(IIIa1)

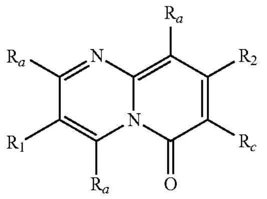

or a form thereof.

In one embodiment, the compound of Formula (IIIa) used in a method disclosed herein is a compound of Formula (IIIa2):

(IIIa2)

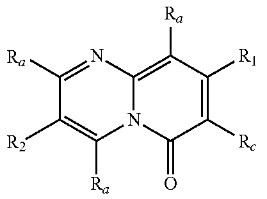

or a form thereof.

In one embodiment, the compound of Formula (IIIa) used in a method disclosed herein is a compound of Formula (IIIa3):

(IIIa3)

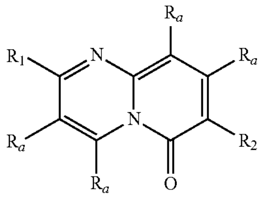

or a form thereof.

In one embodiment, the compound of Formula (IIIa) used in a method disclosed herein is a compound of Formula (IIIa4):

(IIIa4)

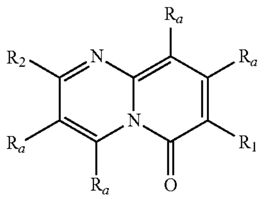

or a form thereof.

In one embodiment, the compound of Formula (IVa) used in a method disclosed herein is a compound of Formula (IVa1):

(IVa1)

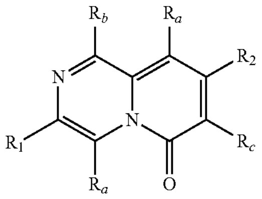

or a form thereof.

In one embodiment, the compound of Formula (IVa) used in a method disclosed herein is a compound of Formula (IVa2):

(IVa2)

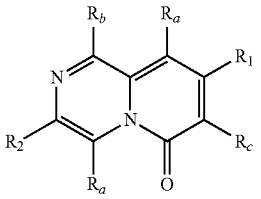

or a form thereof.

In one embodiment, the compound of Formula (Va) used in a method disclosed herein is a compound of Formula (Va1):

(Va1)

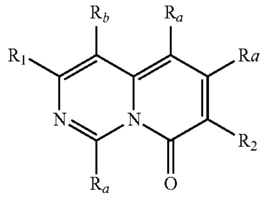

or a form thereof.

In one embodiment, the compound of Formula (Va) used in a method disclosed herein is a compound of Formula (Va2):

(Va2)

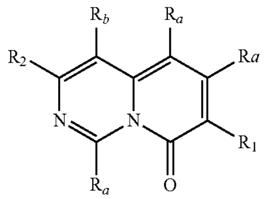

or a form thereof.

In one embodiment, the compound of Formula (VIa) used in a method disclosed herein is a compound of Formula (VIa1):

(VIa1)

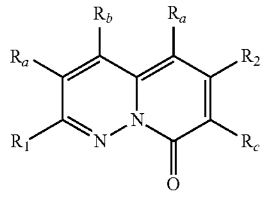

or a form thereof.

In one embodiment, the compound of Formula (VIa) used in a method disclosed herein is a compound of Formula (VIa2):

(VIa2)

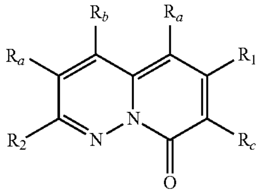

or a form thereof.

In one embodiment, the compound of Formula (VIa) used in a method disclosed herein is a compound of Formula (VIa3):

(VIa3)

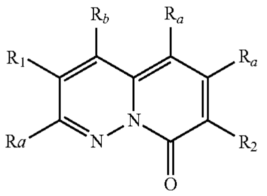

or a form thereof.

In one embodiment, the compound of Formula (VIa) used in a method disclosed herein is a compound of Formula (VIa4):

(VIa4)

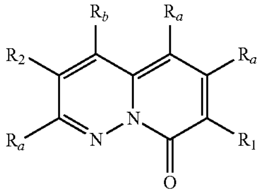

or a form thereof.

In one embodiment, the compound of Formula (VIIa) used in a method disclosed herein is a compound of Formula (VIIa1):

(VIIa1)

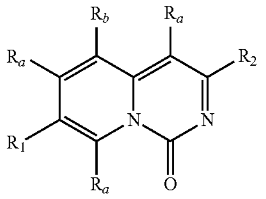

or a form thereof.

In one embodiment, the compound of Formula (VIIa) used in a method disclosed herein is a compound of Formula (VIIa2):

(VIIa2)

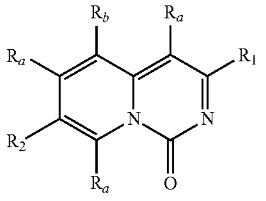

or a form thereof.

In one embodiment, the compound of Formula (VIIIa) used in a method disclosed herein is a compound of Formula (VIIIa1):

(VIIIa1)

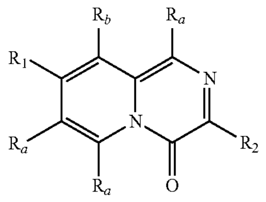

or a form thereof.

In one embodiment, the compound of Formula (VIIIa) used in a method disclosed herein is a compound of Formula (VIIIa2):

(VIIIa2)

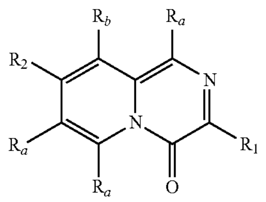

or a form thereof.

In one embodiment, the compound of Formula (IXa) used in a method disclosed herein is a compound of Formula (IXa1):

(IXa1)

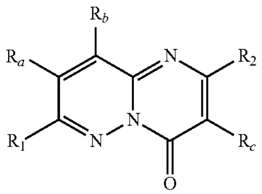

or a form thereof.

In one embodiment, the compound of Formula (IXa) used in a method disclosed herein is a compound of Formula (IXa2):

(IXa2)

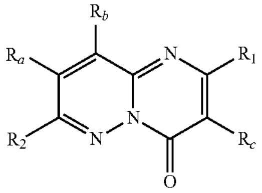

or a form thereof.

In one embodiment, the compound of Formula (IXa) used in a method disclosed herein is a compound of Formula (IXa3):

(IXa3)

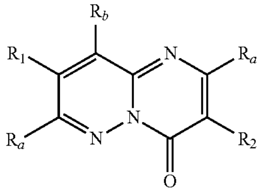

or a form thereof.

In one embodiment, the compound of Formula (IXa) used in a method disclosed herein is a compound of Formula (IXa4):

(IXa4)

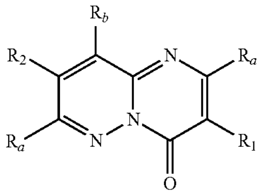

or a form thereof.

In one embodiment, the compound of Formula (Xa) used in a method disclosed herein is a compound of Formula (Xa1):

(Xa1)

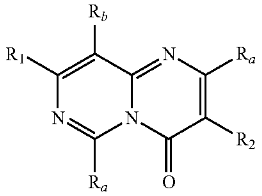

or a form thereof.

In one embodiment, the compound of Formula (Xa) used in a method disclosed herein is a compound of Formula (Xa2):

(Xa2)

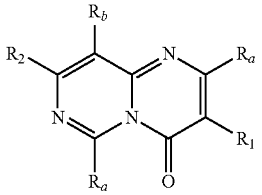

or a form thereof.

In one embodiment, the compound of Formula (XIa) used in a method disclosed herein is a compound of Formula (XIa1):

(XIa1)

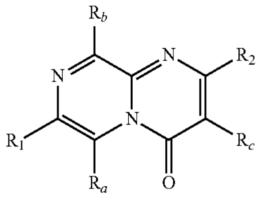

or a form thereof.

In one embodiment, the compound of Formula (XIa) used in a method disclosed herein is a compound of Formula (XIa2):

(XIa2)

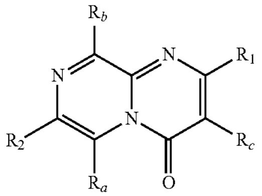

or a form thereof.

In one embodiment, the compound of Formula (XIIa) used in a method disclosed herein is a compound of Formula (XIIa1):

(XIIa1)

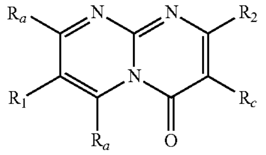

or a form thereof.

In one embodiment, the compound of Formula (XIIa) used in a method disclosed herein is a compound of Formula (XIIa2):

(XIIa2)

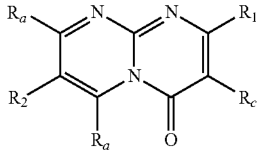

or a form thereof.

In one embodiment, the compound of Formula (XIIa) used in a method disclosed herein is a compound of Formula (XIIa3):

(XIIa3)

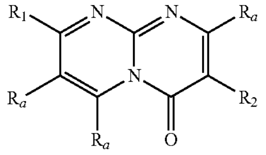

or a form thereof.

In one embodiment, the compound of Formula (XIIa) used in a method disclosed herein is a compound of Formula (XIIa4):

(XIIa4)

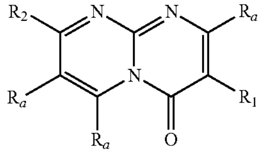

or a form thereof.

In one embodiment, the compound of Formula (XIIIa) used in a method disclosed herein is a compound of Formula (XIIIa1):

(XIIIa1)

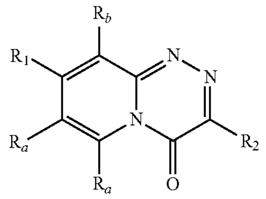

or a form thereof.

In one embodiment, the compound of Formula (XIIIa) used in a method disclosed herein is a compound of Formula (XIIIa2):

(XIIIa2)

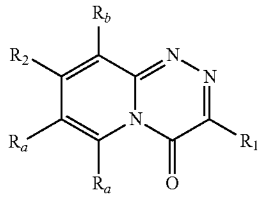

or a form thereof.

In one embodiment, the compound of Formula (XIVa) used in a method disclosed herein is a compound of Formula (XIVa1):

(XIVa1)

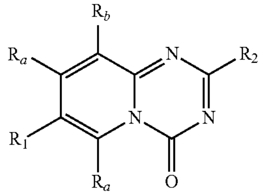

or a form thereof.

In one embodiment, the compound of Formula (XIVa) used in a method disclosed herein is a compound of Formula (XIVa2):

(XIVa2)

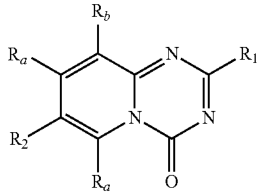

or a form thereof.

In another embodiment, the compound of Formula (I) used in a method disclosed herein is a compound selected from the group consisting of:

1

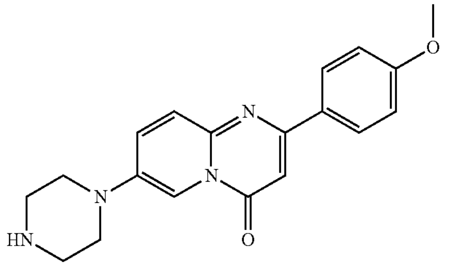

-continued
2
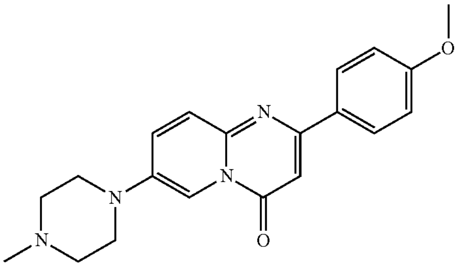
3
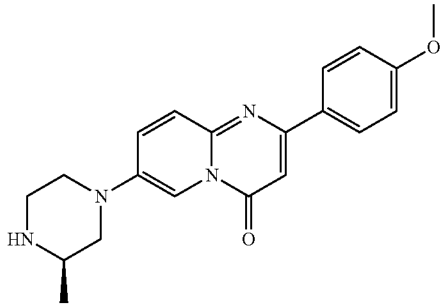
4
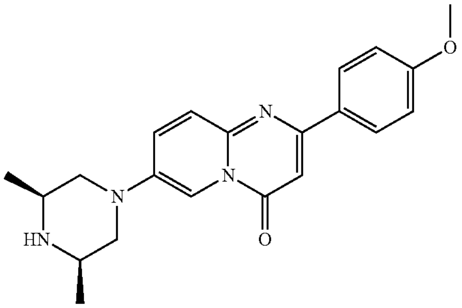
5
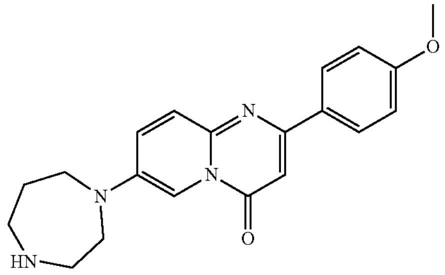
6
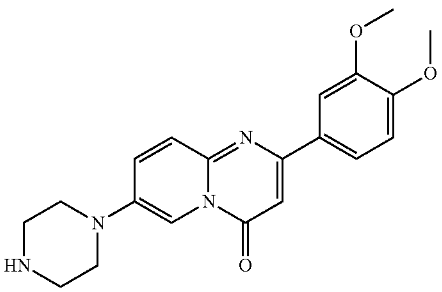
-continued
7
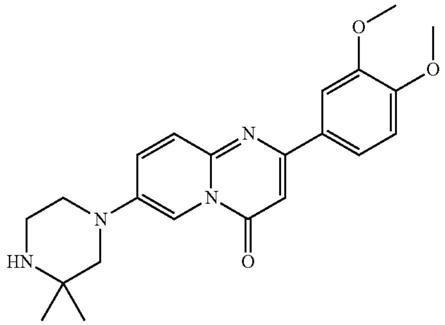
8
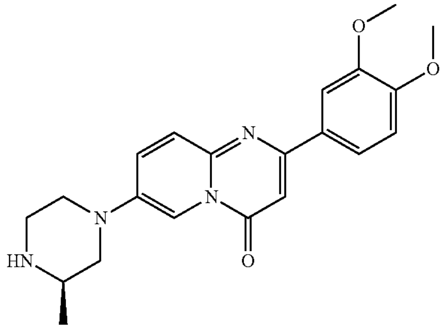
9
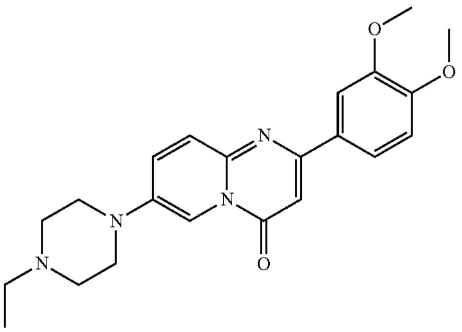
10
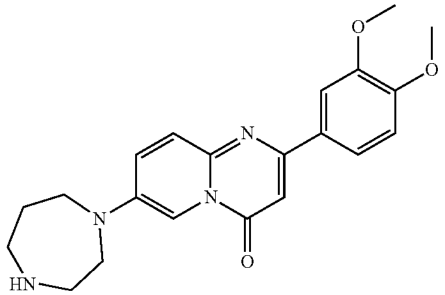
11
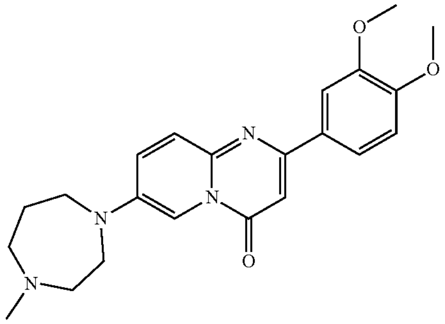

-continued
12
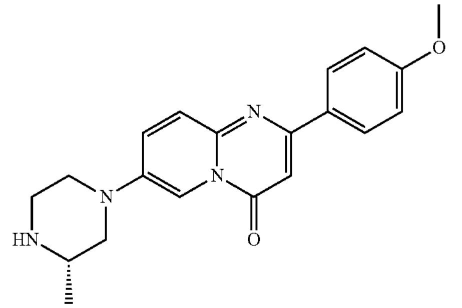
13
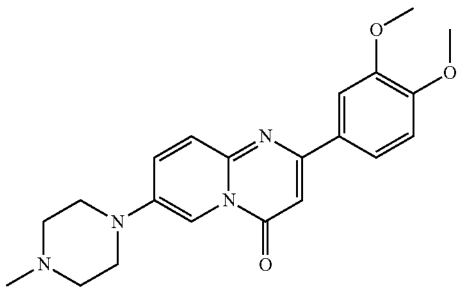
14
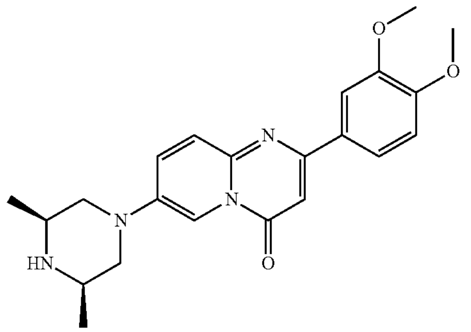
15
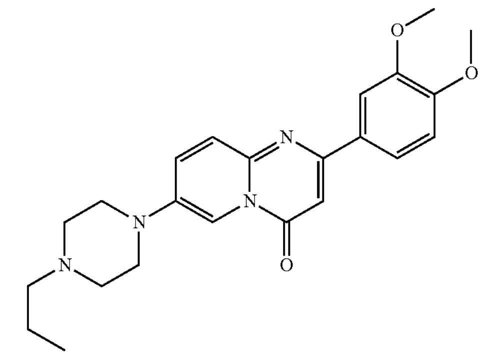
16
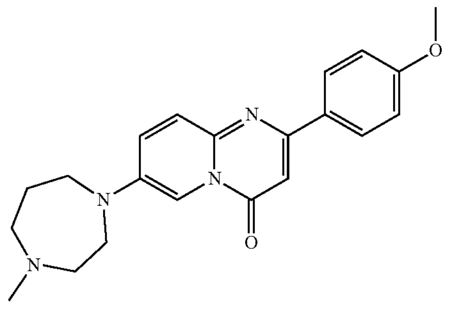
-continued
17
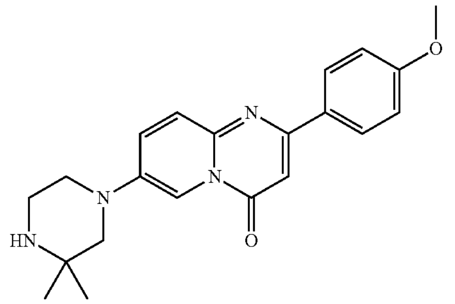
18
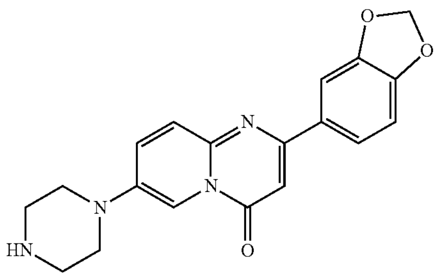
19
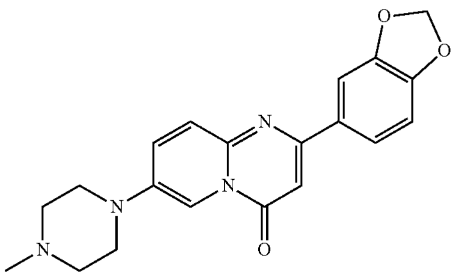
20
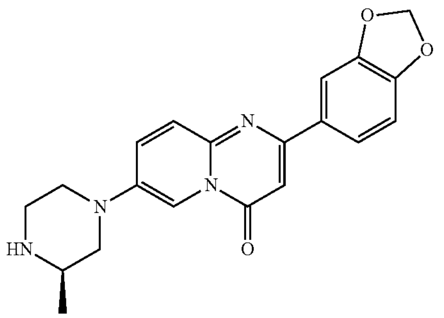
21
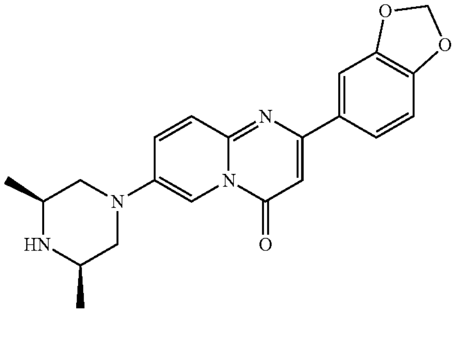

-continued
22
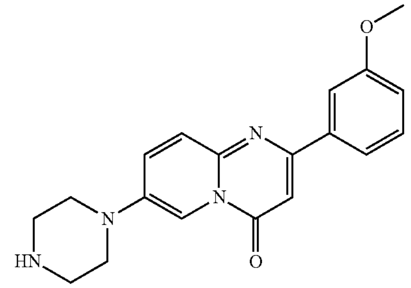
23
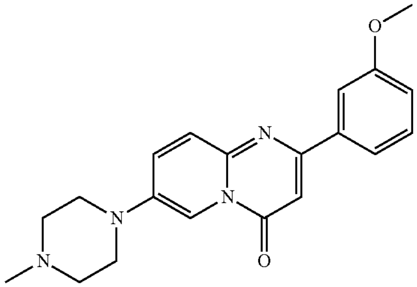
24
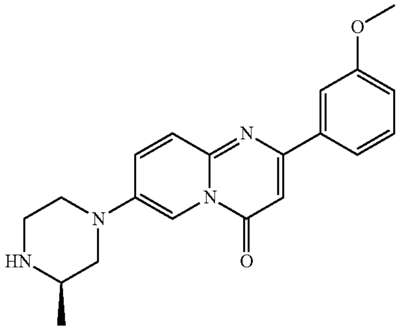
25
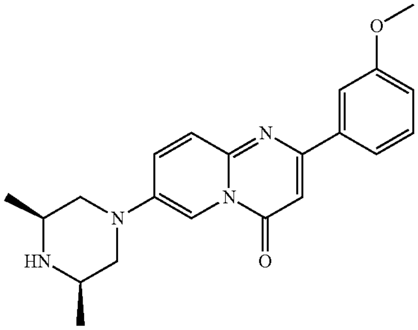
26
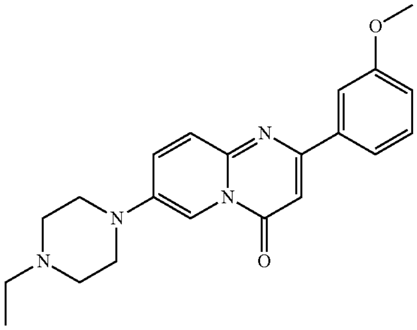
-continued
27
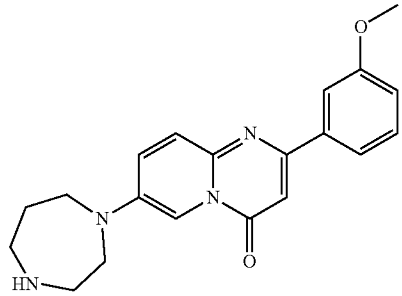
28
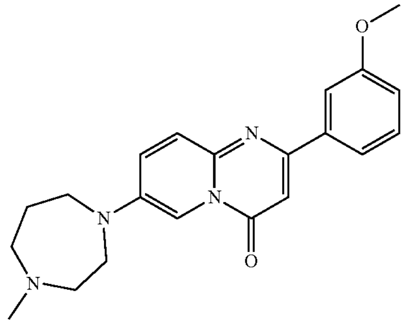
29
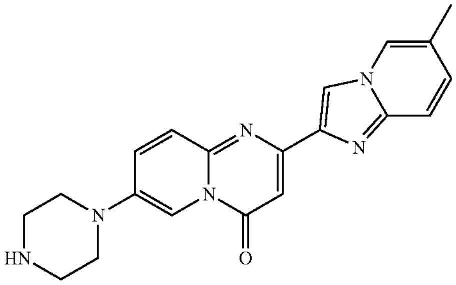
30
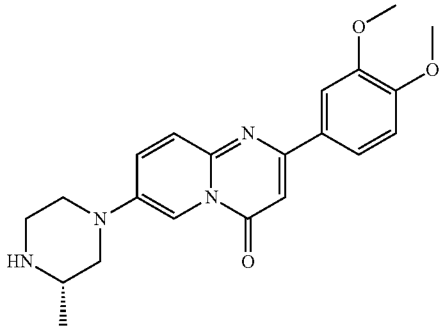
31
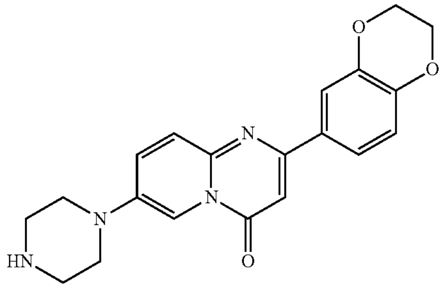

-continued
32
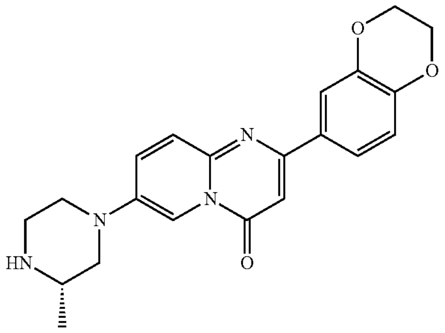
33
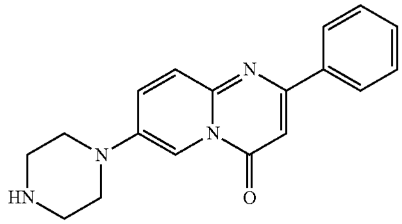
34
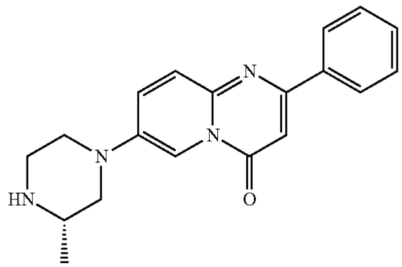
35
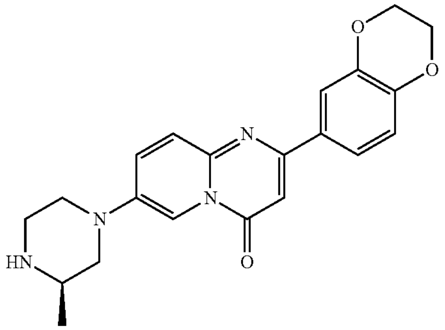
36
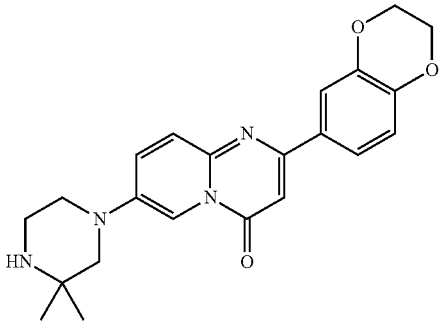
-continued
37
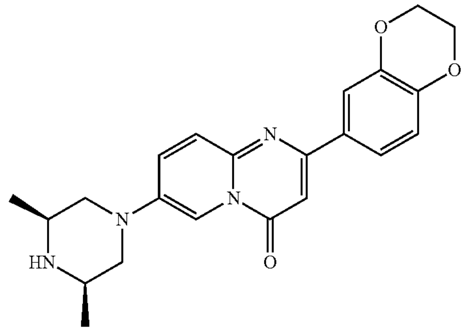
38
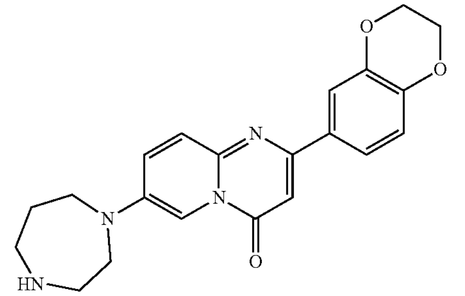
39
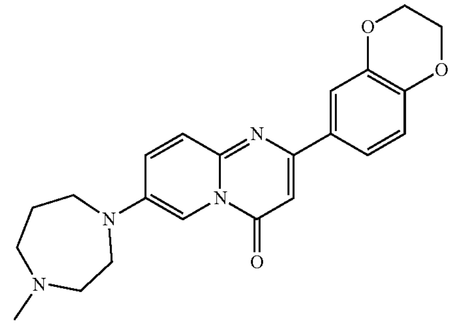
40
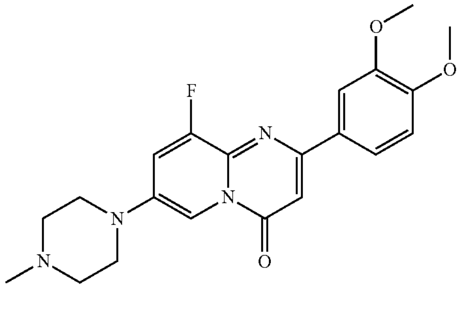
41
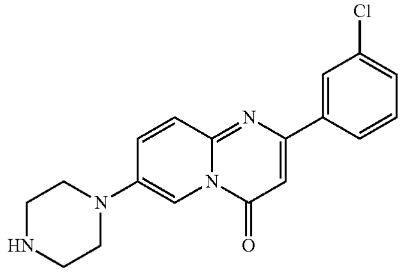

-continued
42
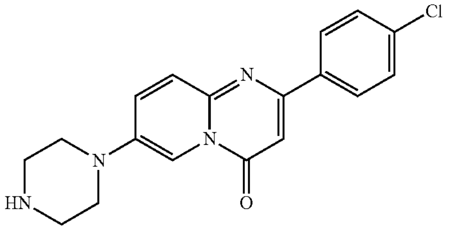
43
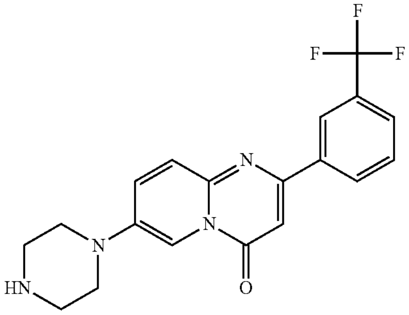
44
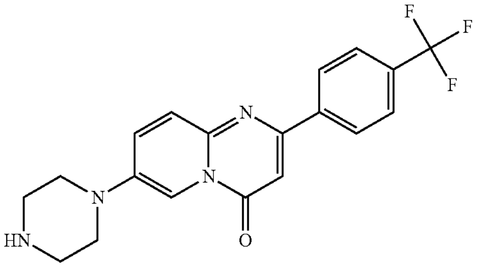
45
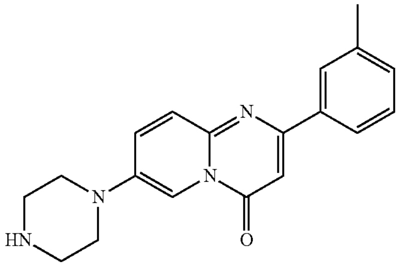
46
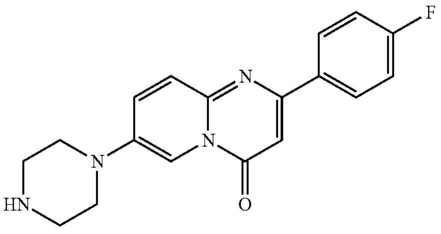
47
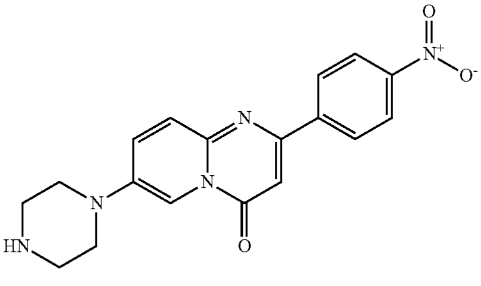
-continued
48
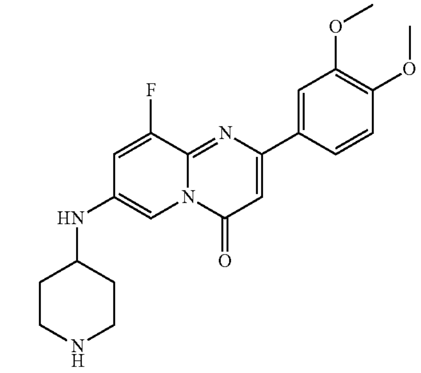
49
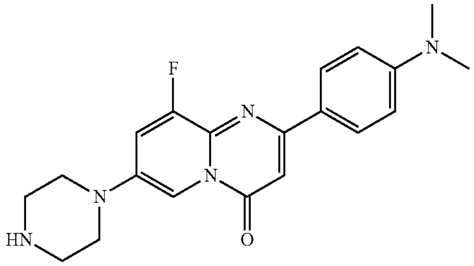
50
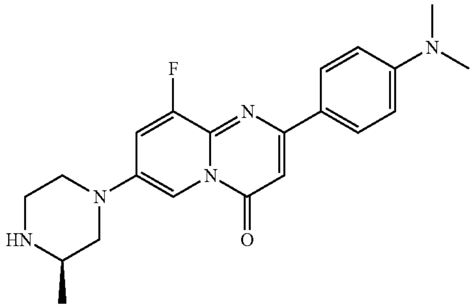
51
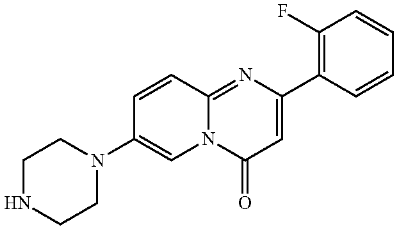
52
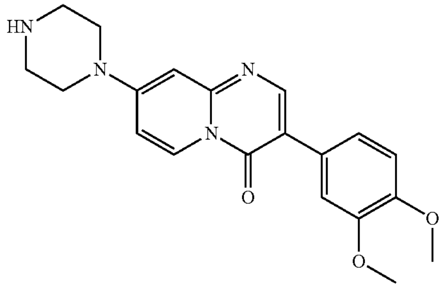

-continued
53
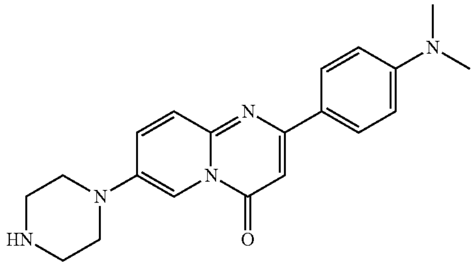
54
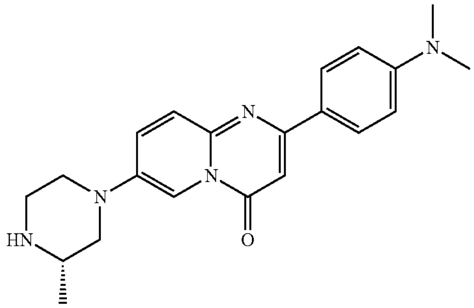
55
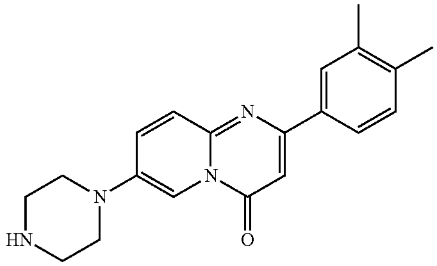
56
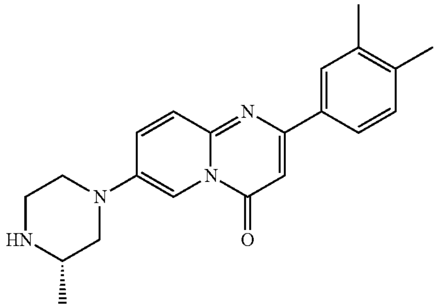
57
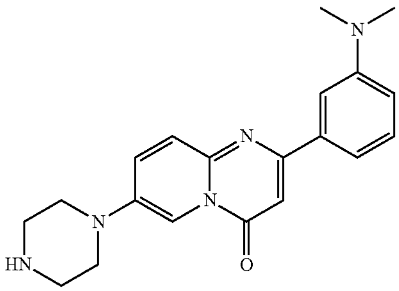
-continued
58
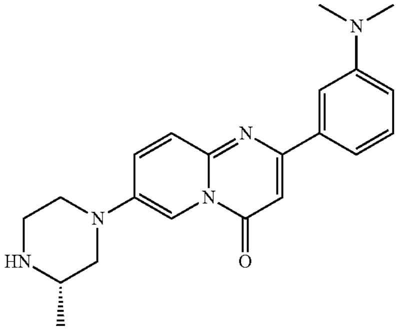
59
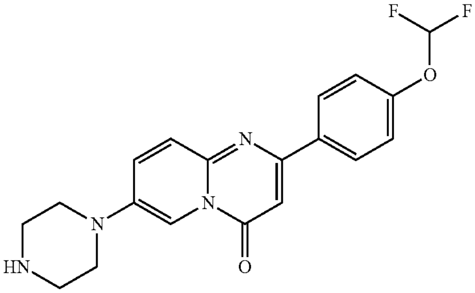
60
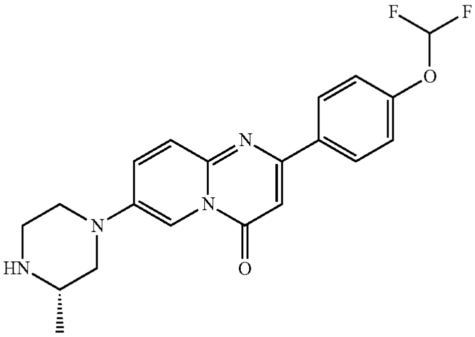
61
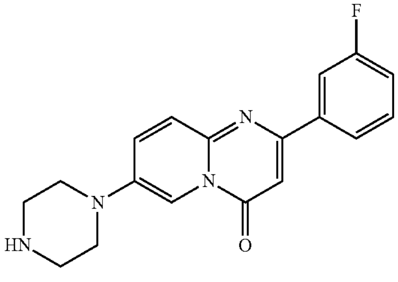
62
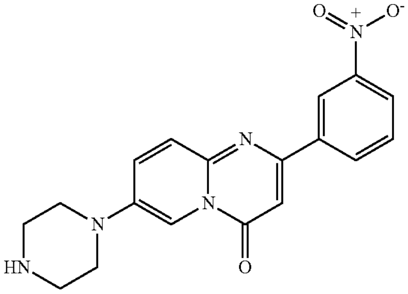

-continued
63
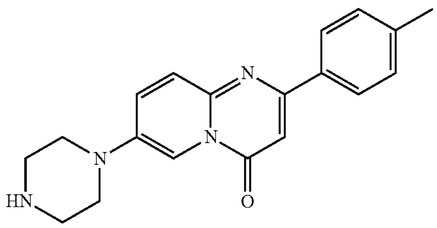
64
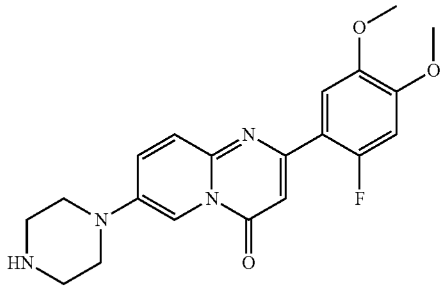
65
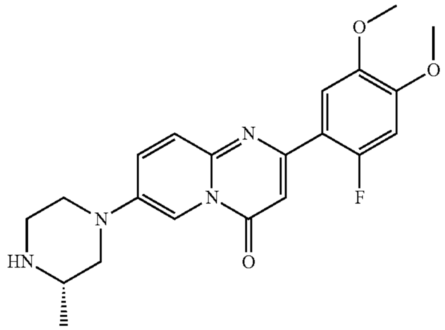
66
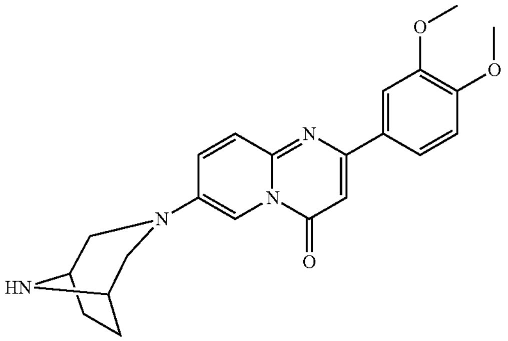
67
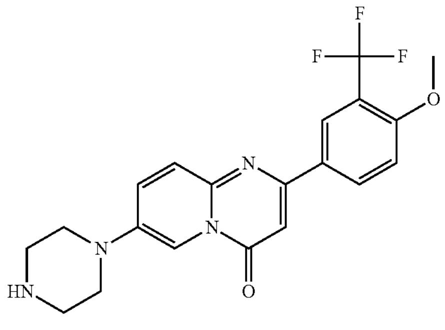
-continued
68
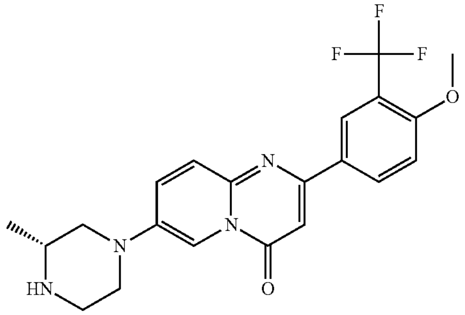
69
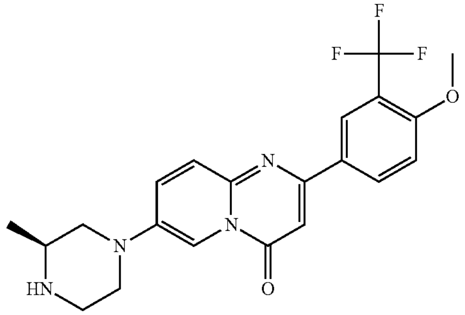
70
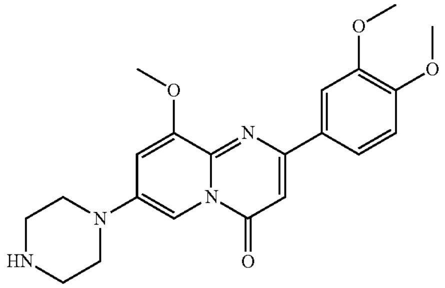
71
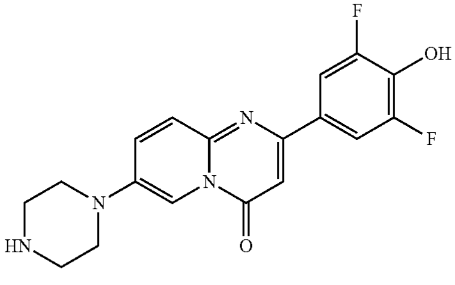
72
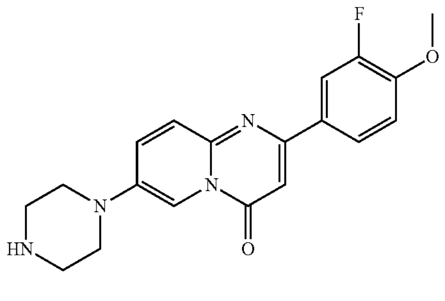

-continued
73
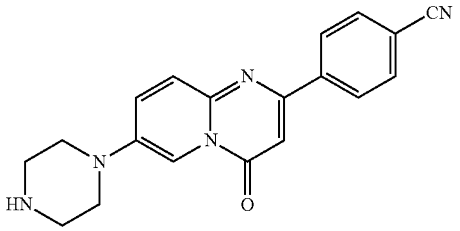
74
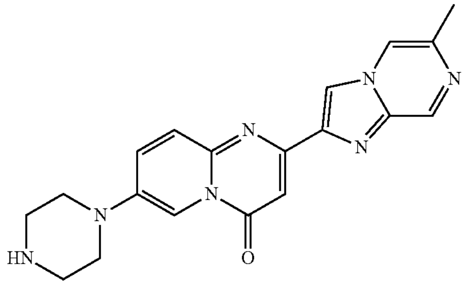
75
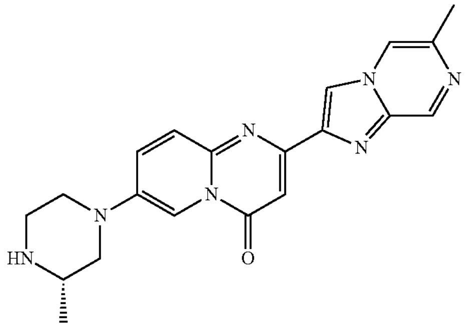
76
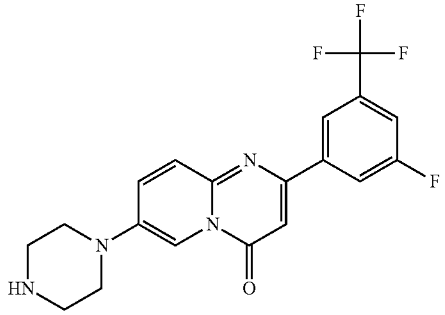
77
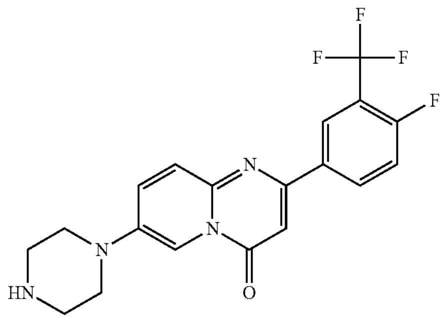
-continued
78
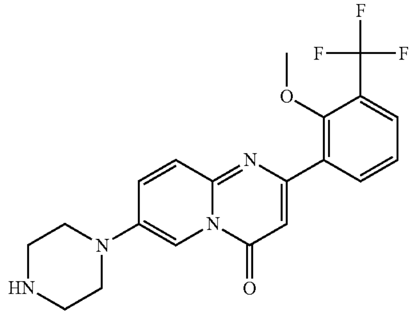
79
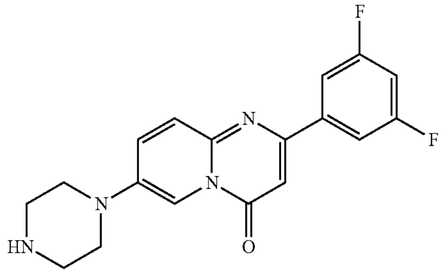
80
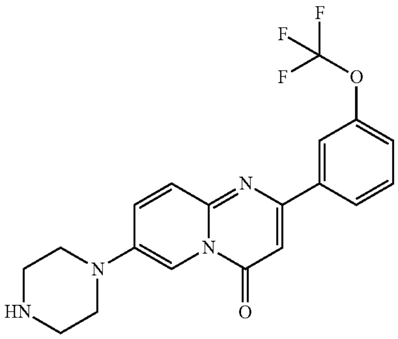
81
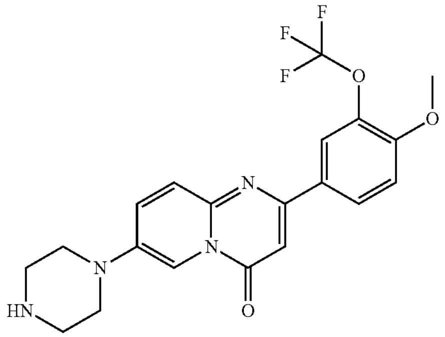
82
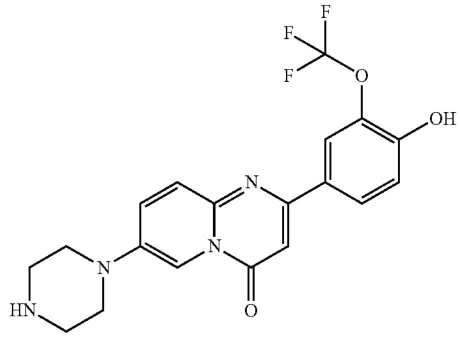

-continued
83
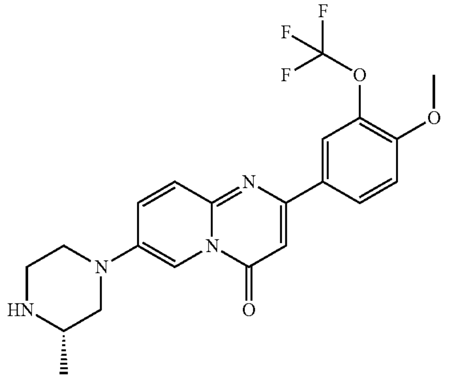
84
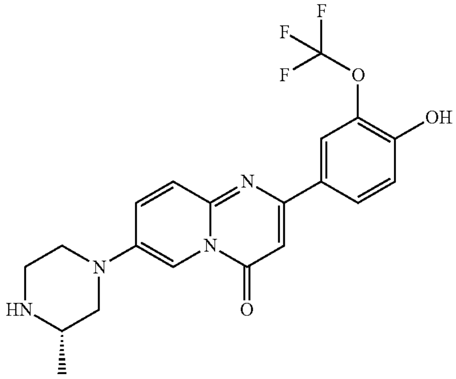
85
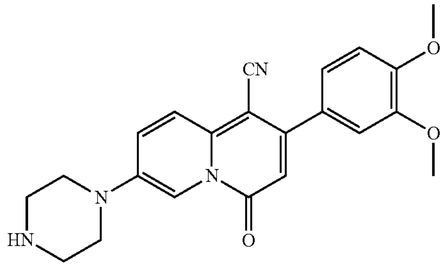
86
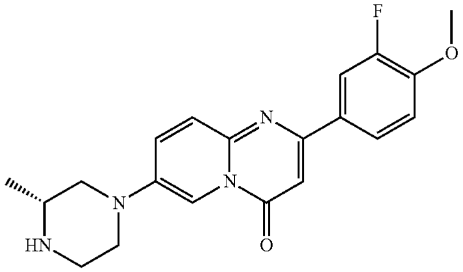
87
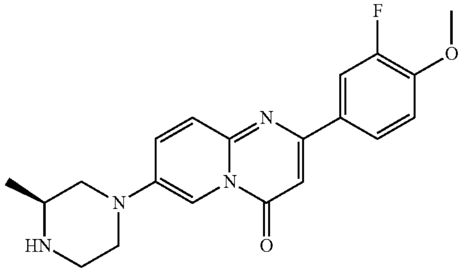
-continued
88
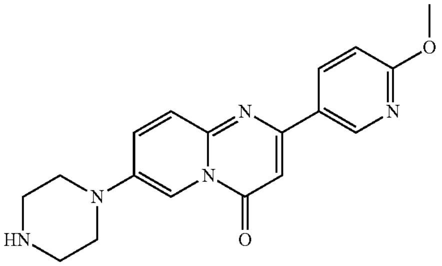
89
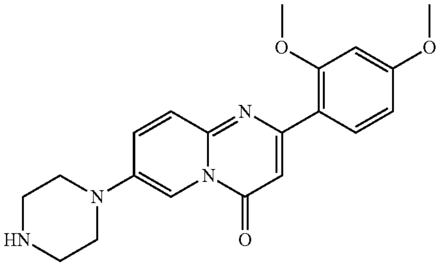
90
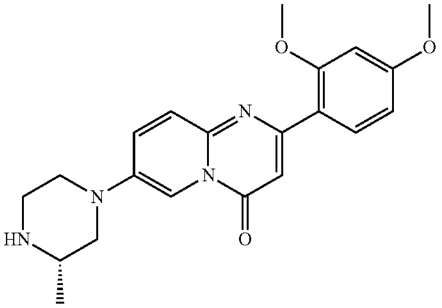
91
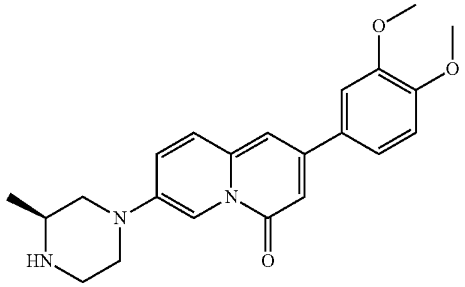
92
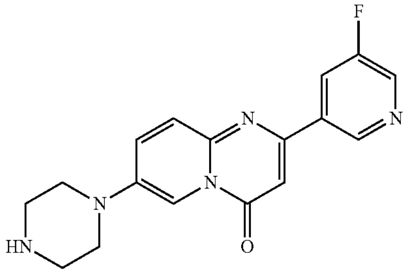

-continued
93
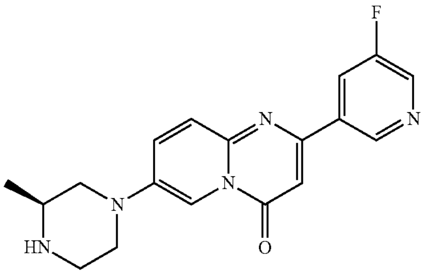
94
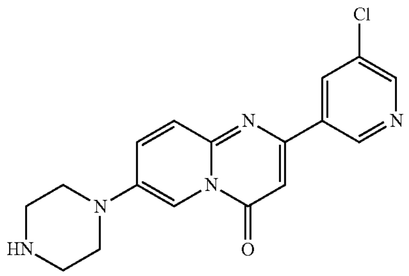
95
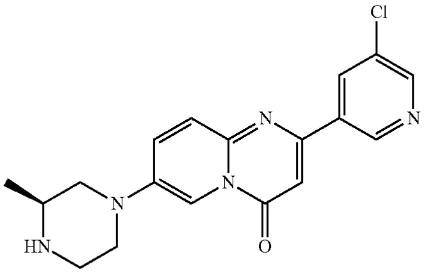
96
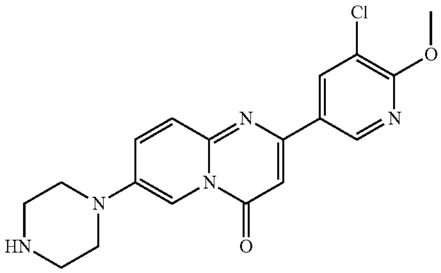
97
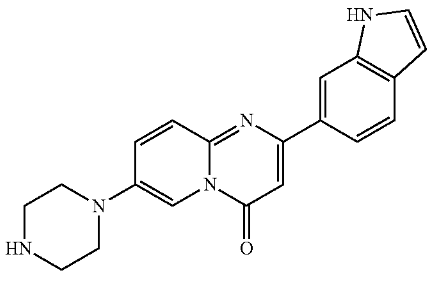
-continued
98
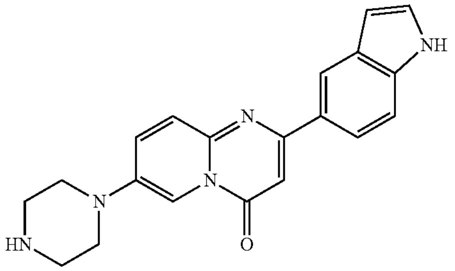
99
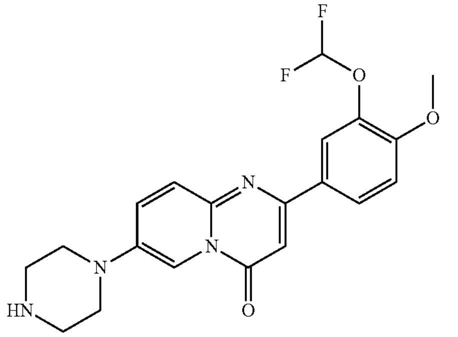
100
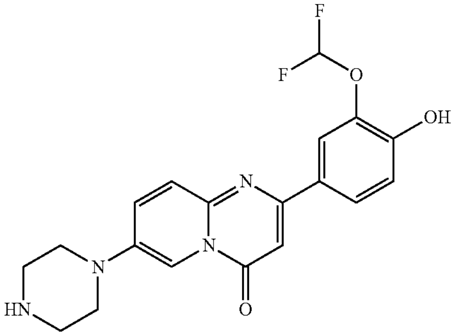
101
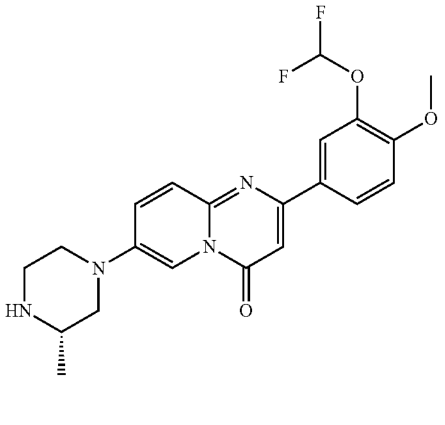

-continued
102
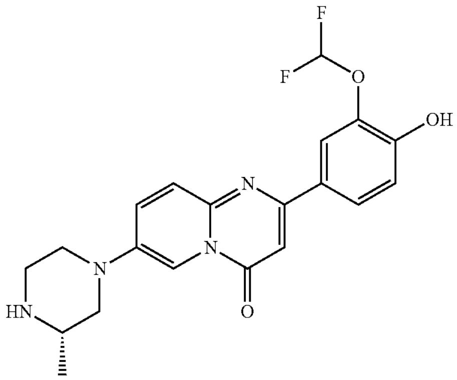
103
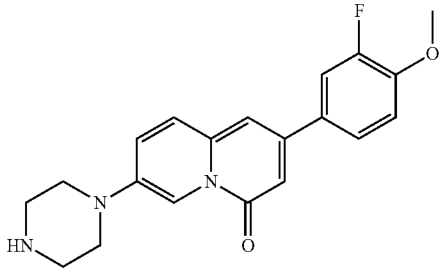
104
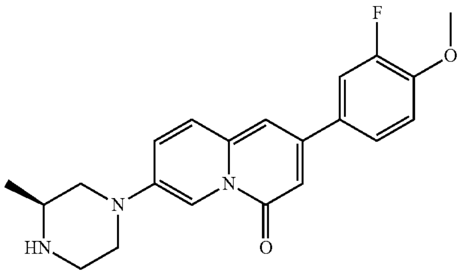
105
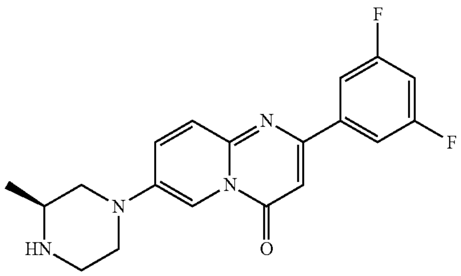
106
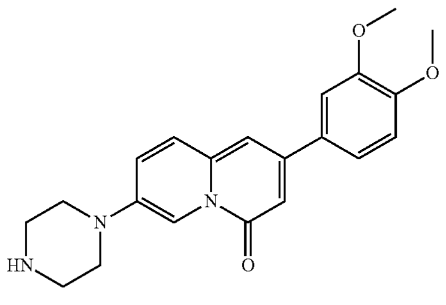
-continued
107
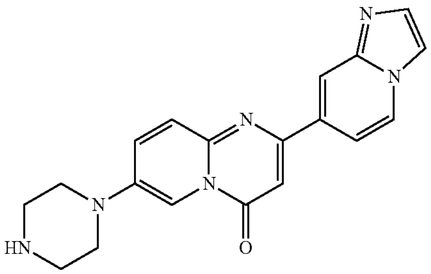
108
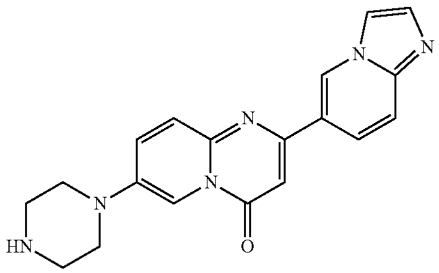
109
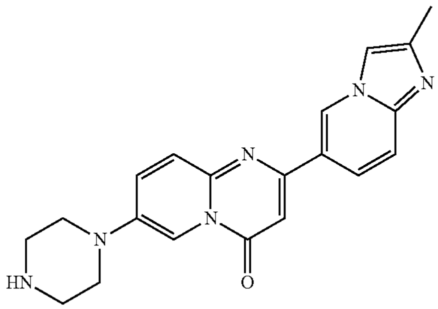
110
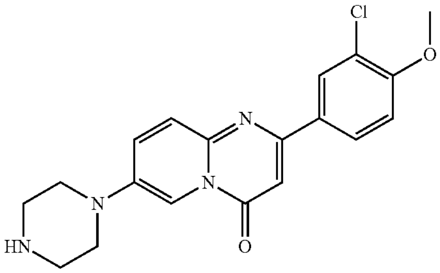
111
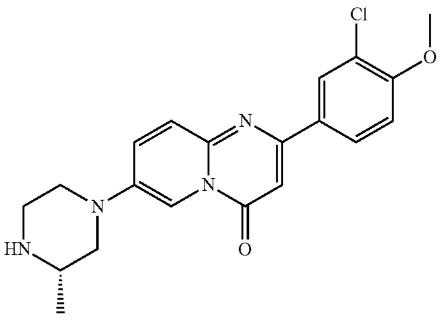

-continued
112
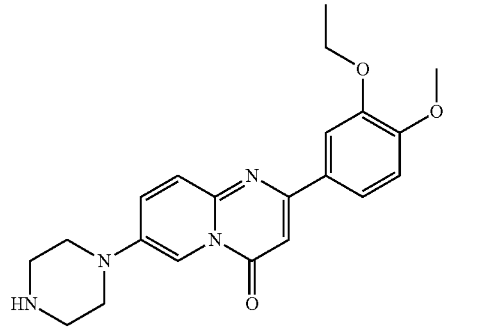
113
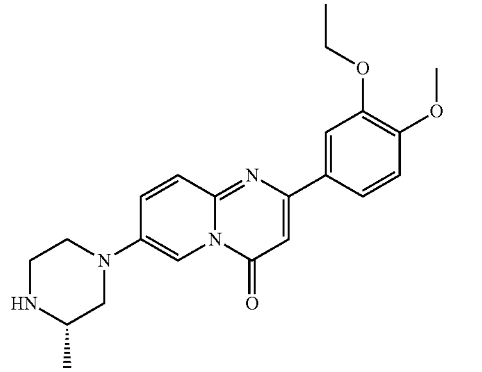
114
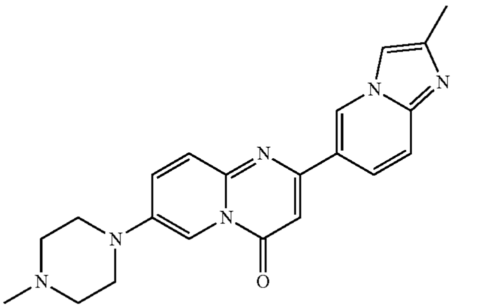
115
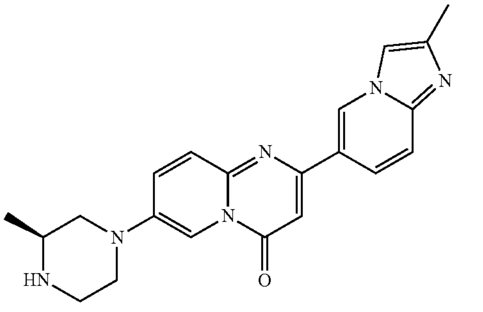
116
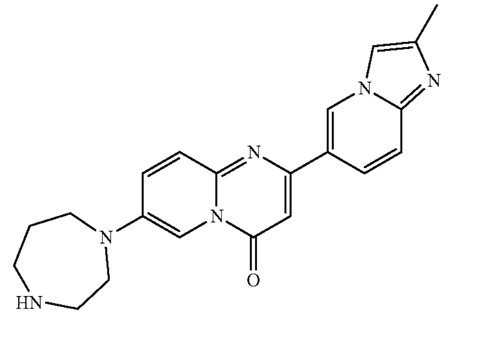
-continued
117
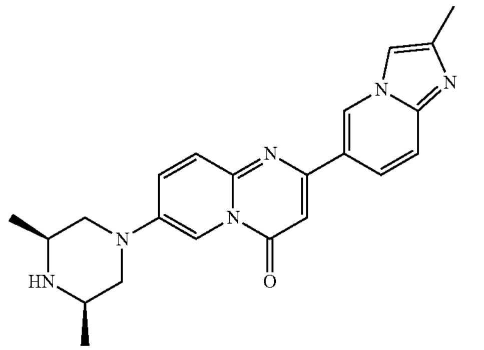
118
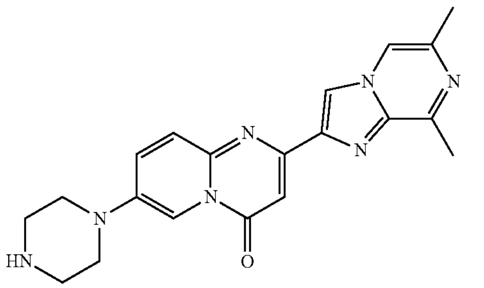
119
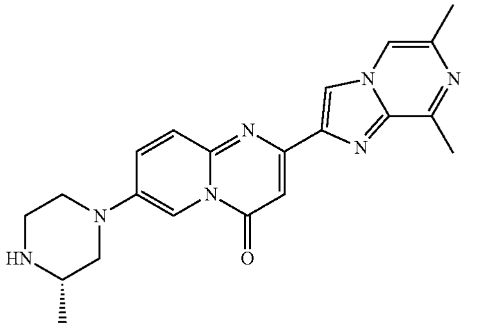
120
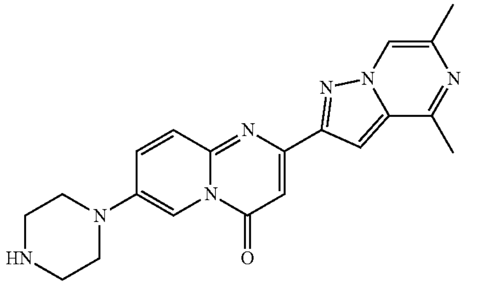
121
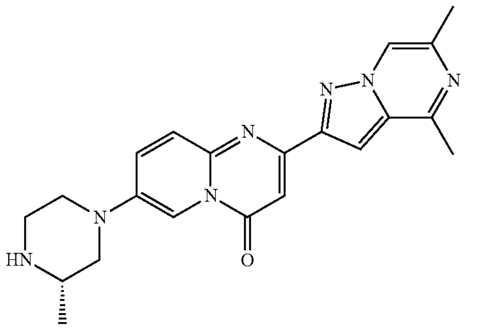

-continued
122
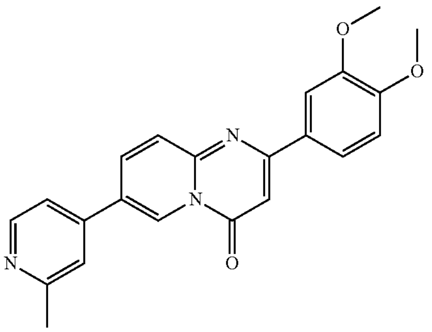
123
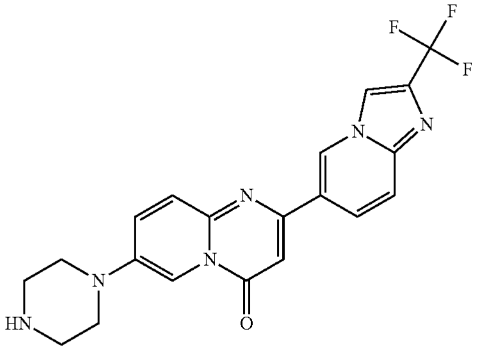
124
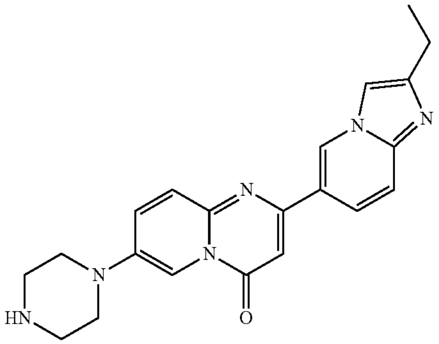
125
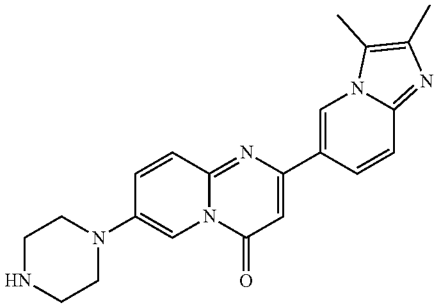
-continued
126
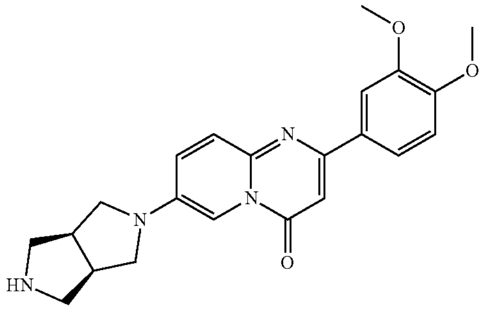
127
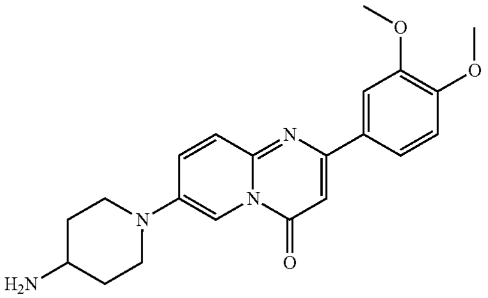
128
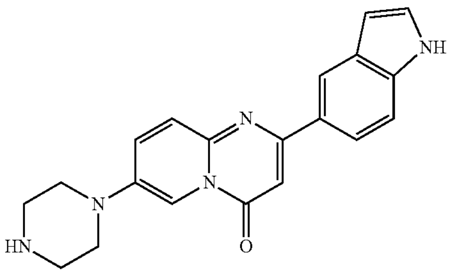
129
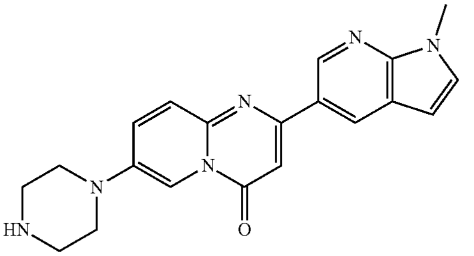
130
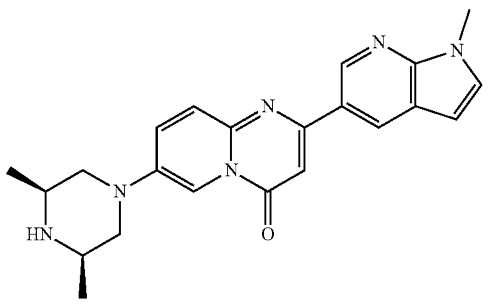

-continued
131
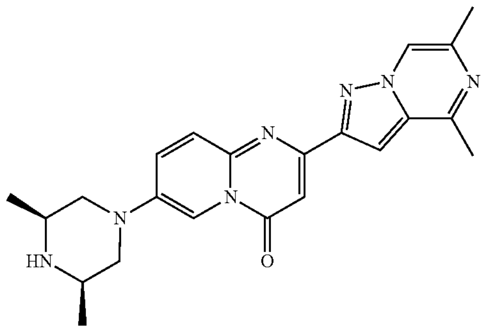
132
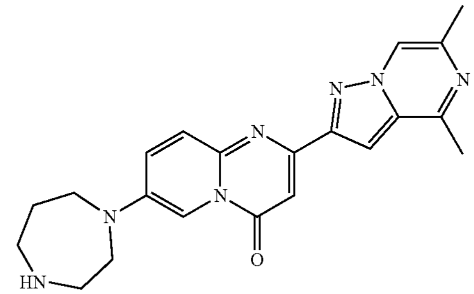
133
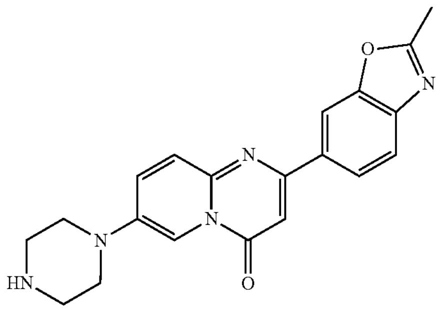
134
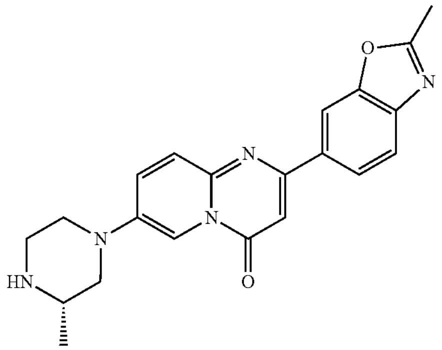
-continued
135
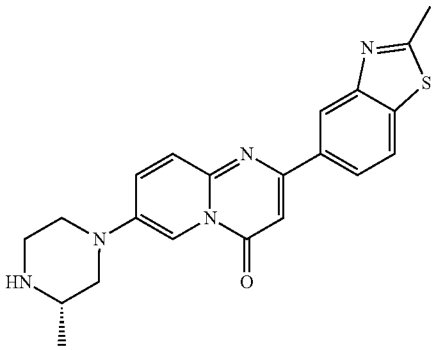
136
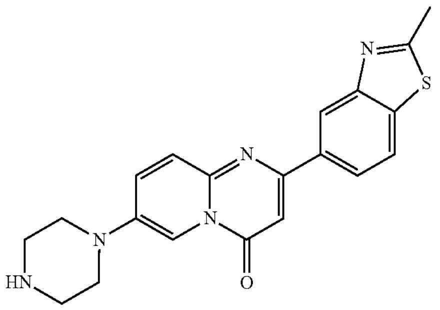
137
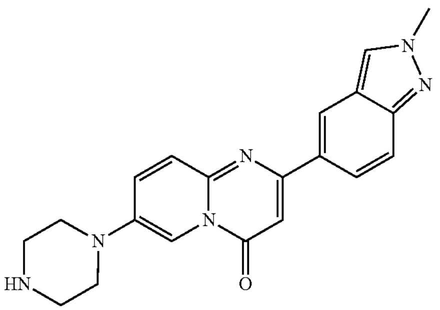
138
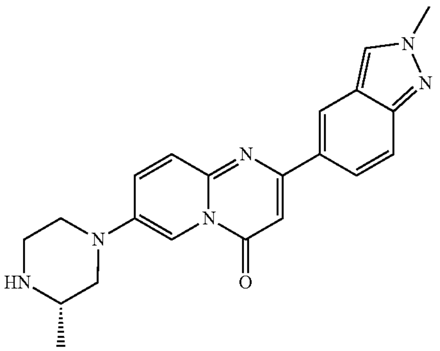
139
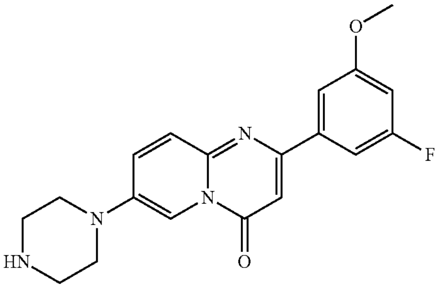

-continued
140
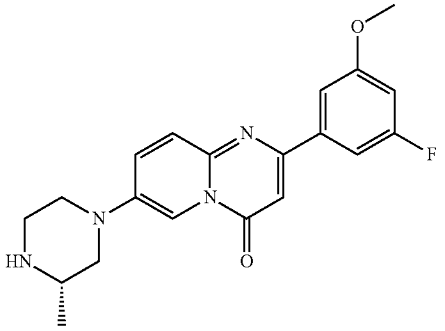
141
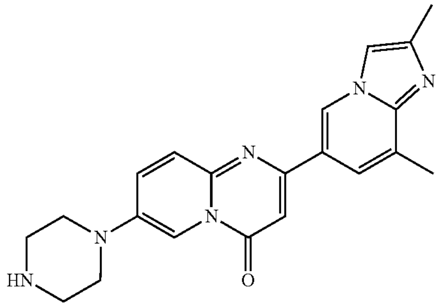
142
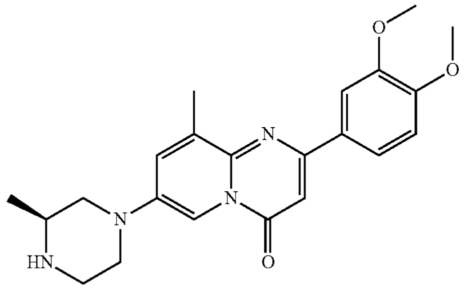
143
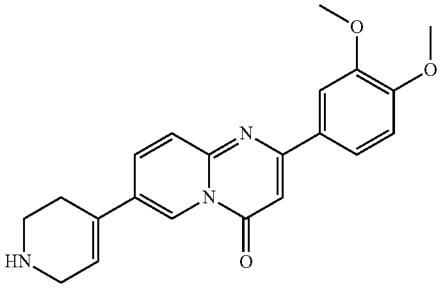
144
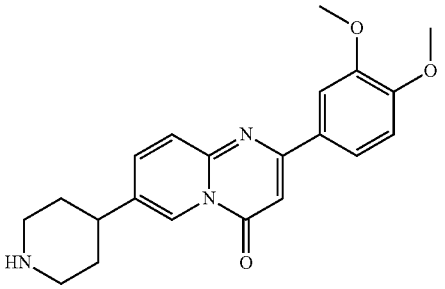
-continued
145
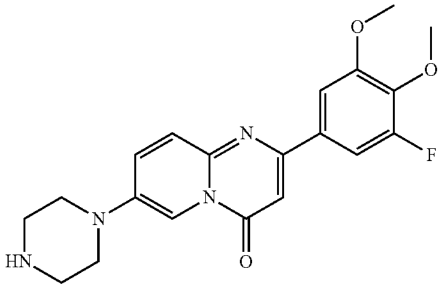
146
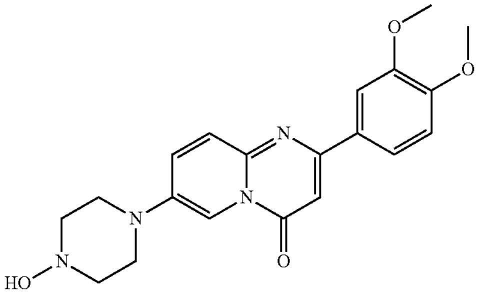
147
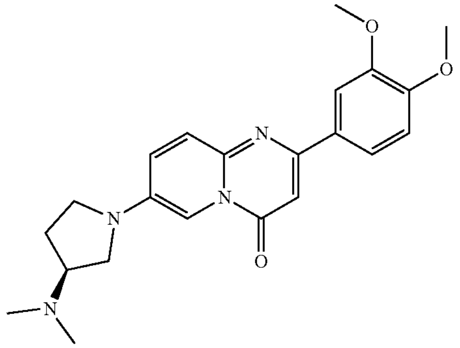
148
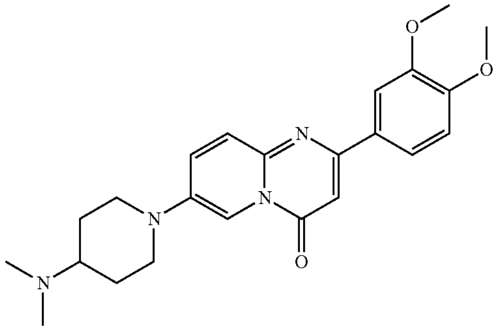
149
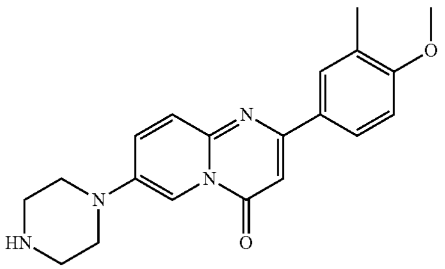

-continued
150
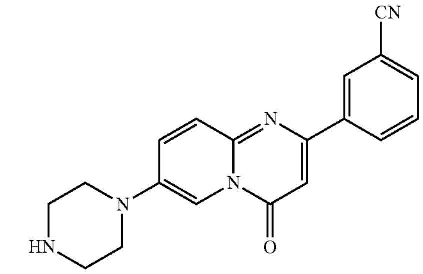
151
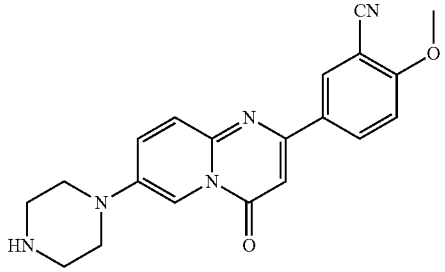
152
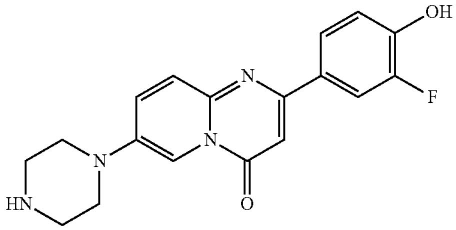
153
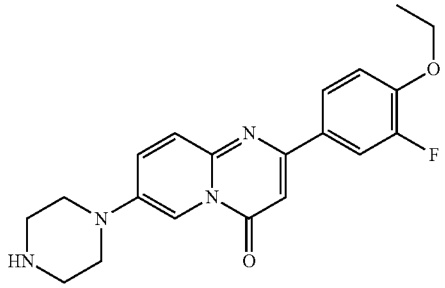
154
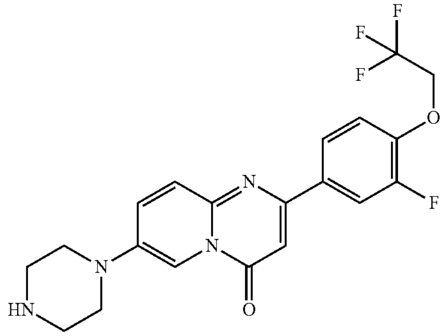
-continued
155
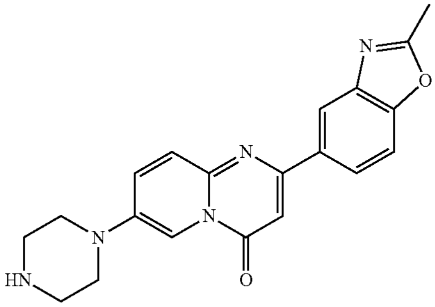
156
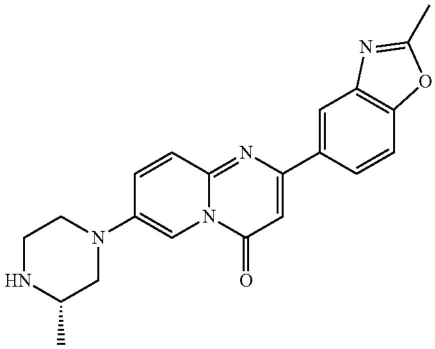
157
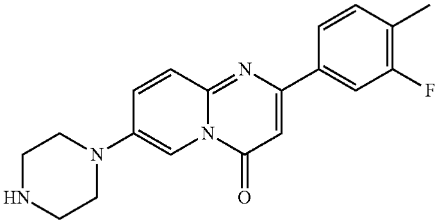
158
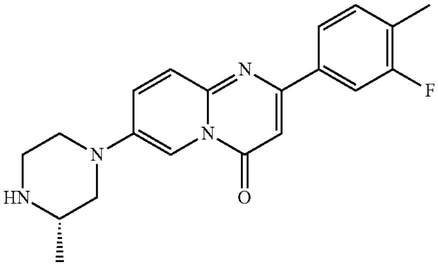
159
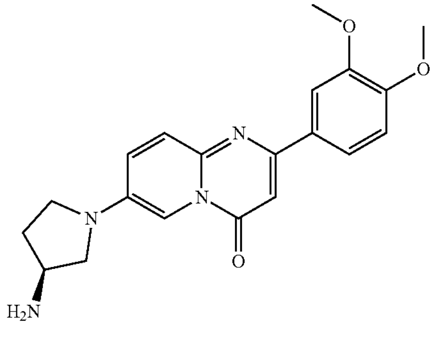

-continued
160
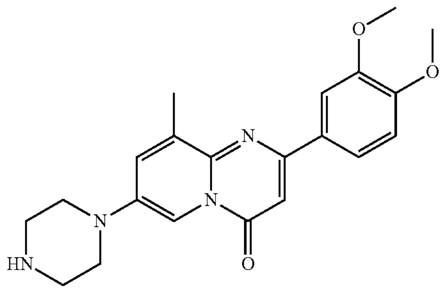
161
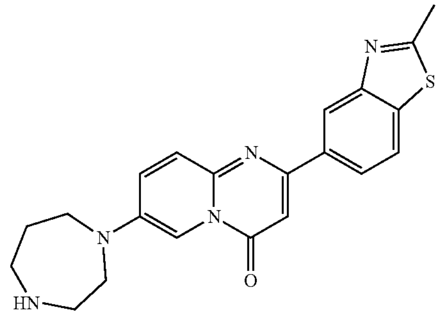
162
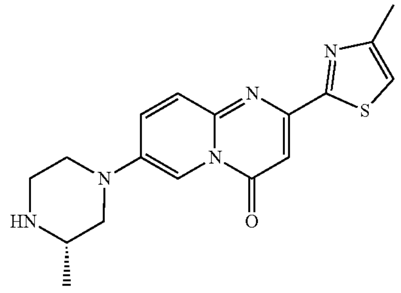
163
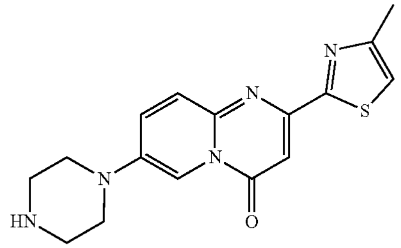
164
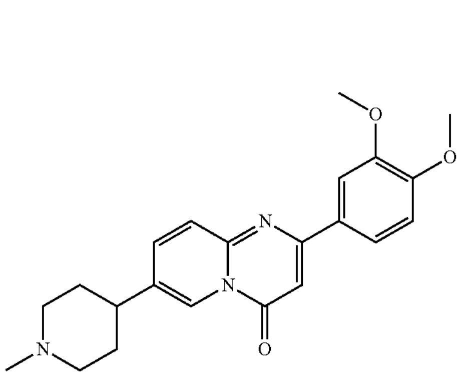
-continued
165
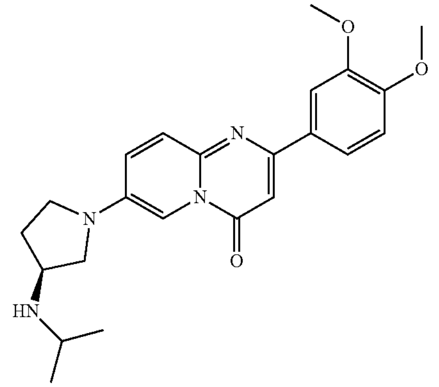
166
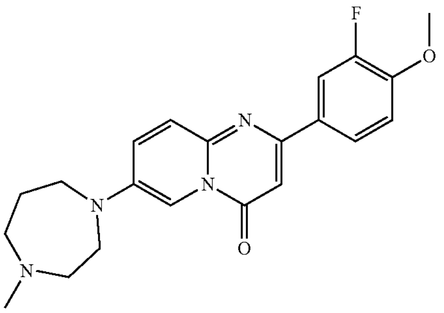
167
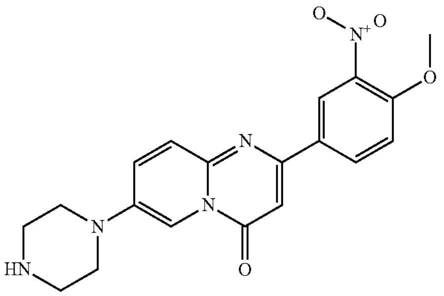
168
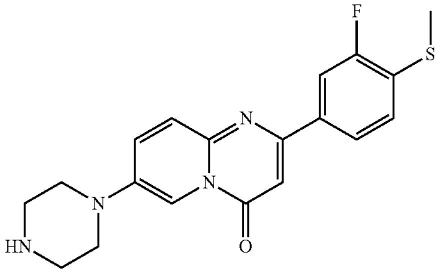
169
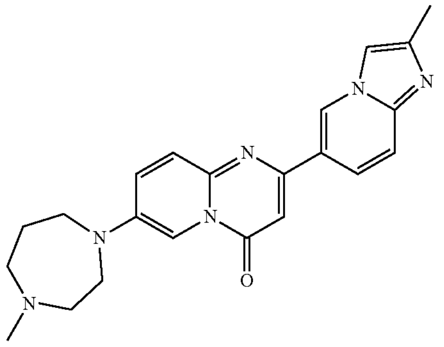

-continued
170
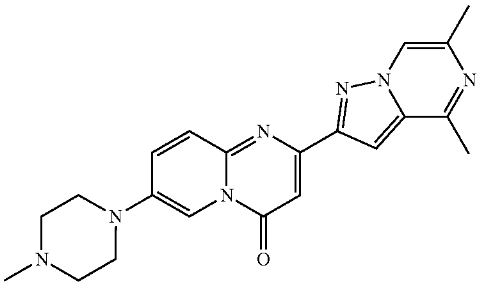
171
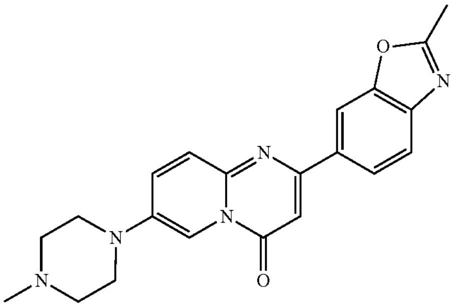
172
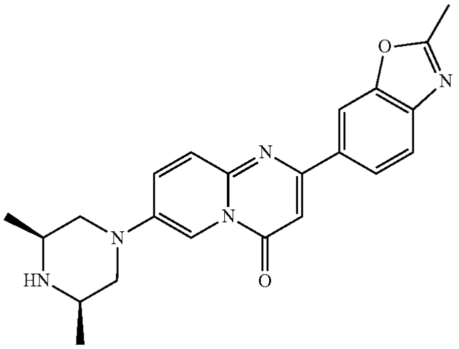
173
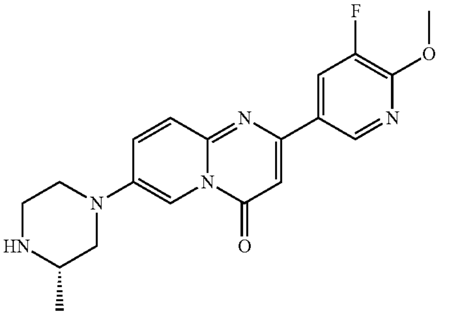
174
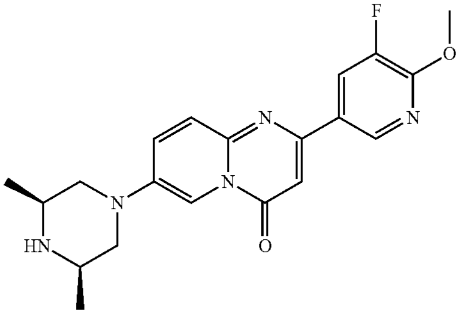
-continued
175
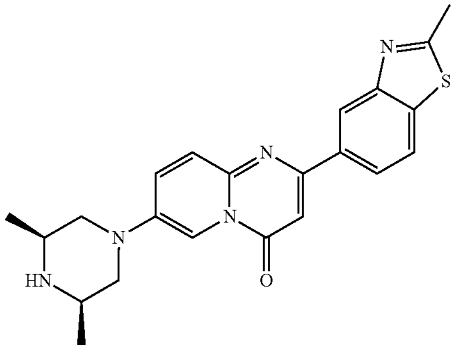
176
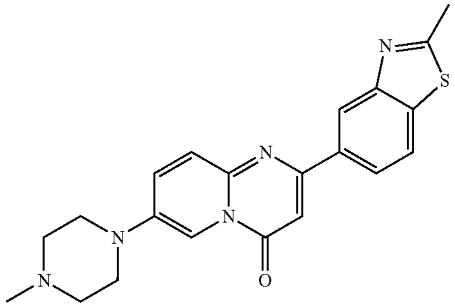
177
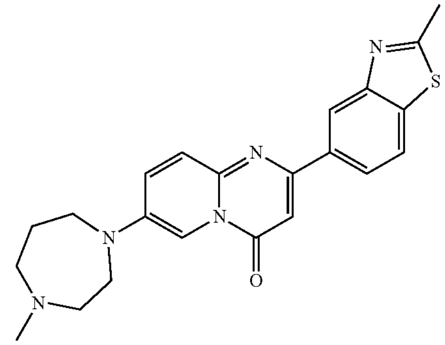
178
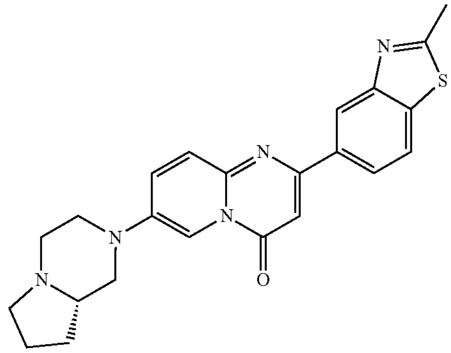
179
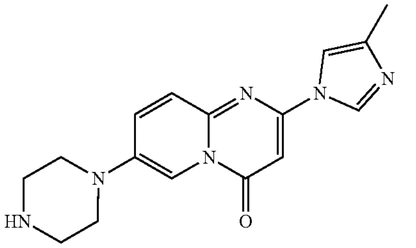

-continued
180
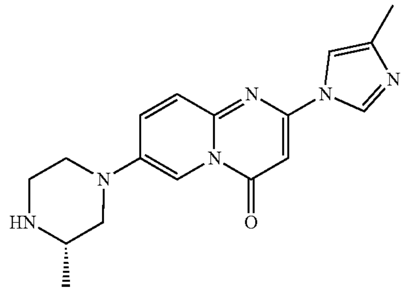
181
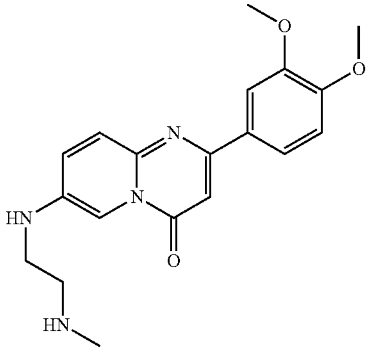
182
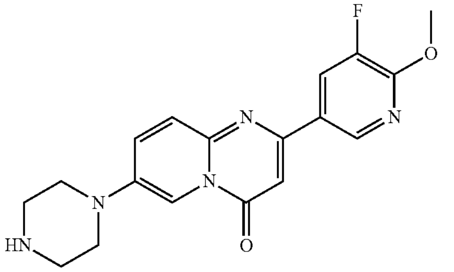
183
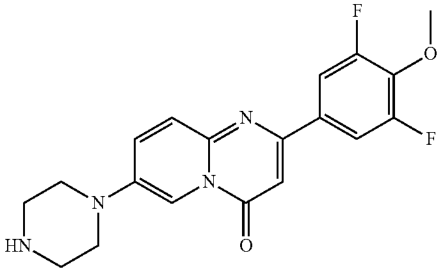
184
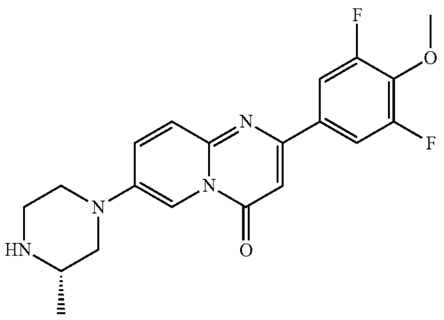
-continued
185
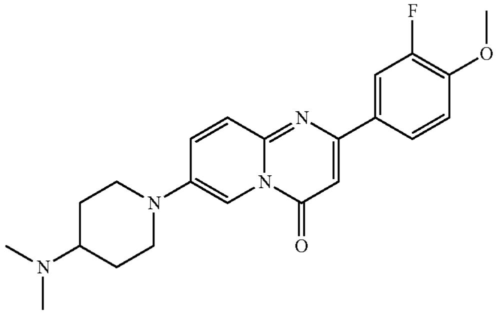
186
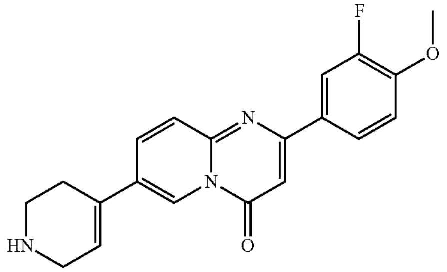
187
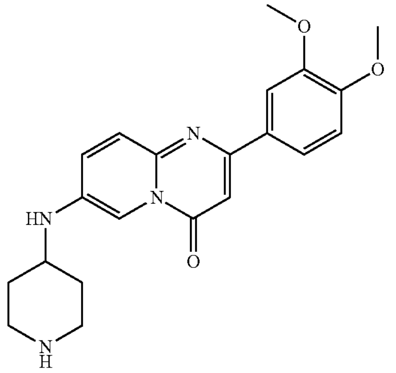
188
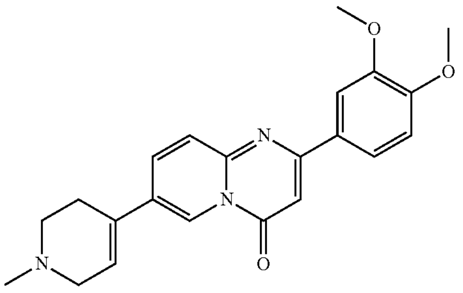
189
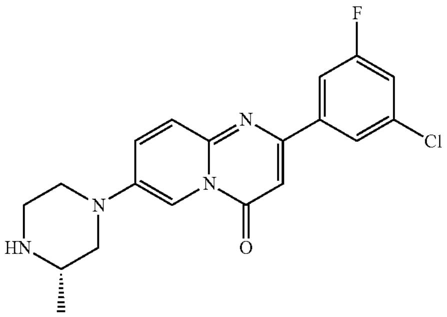

-continued
190
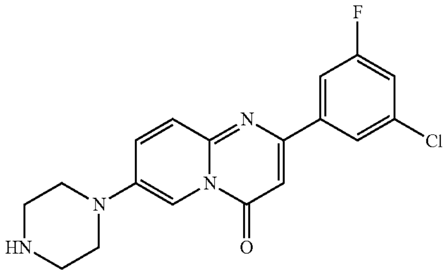
191
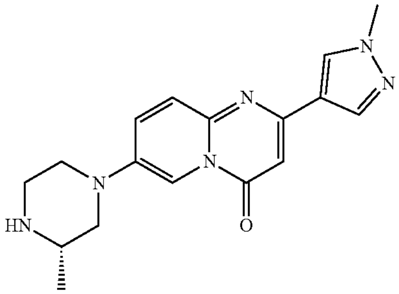
192
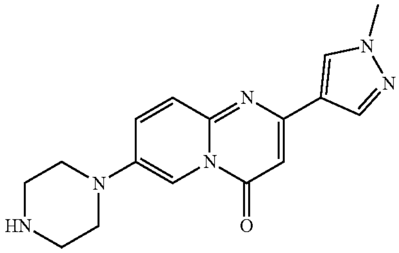
193
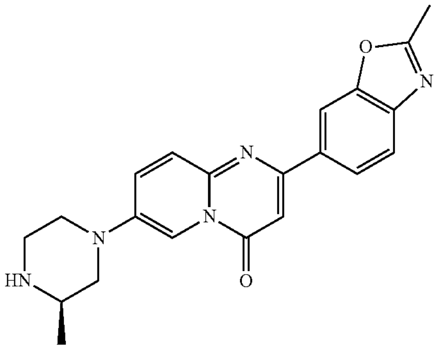
194
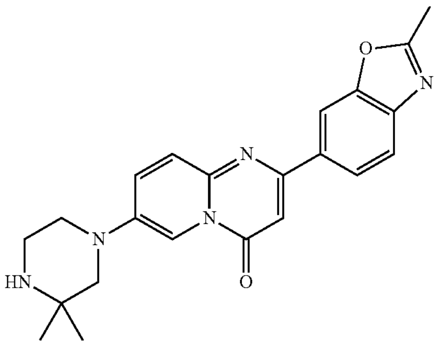
-continued
195
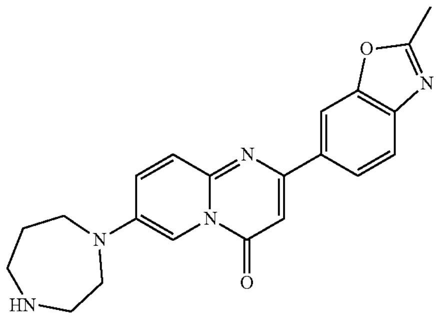
196
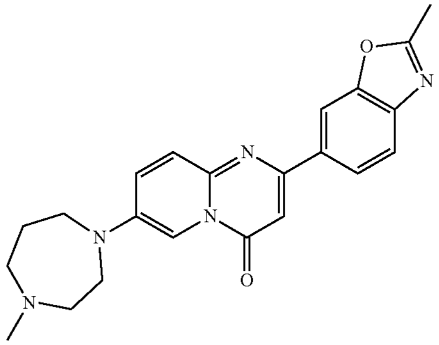
197
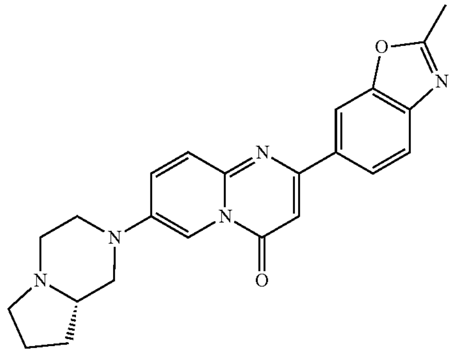
198
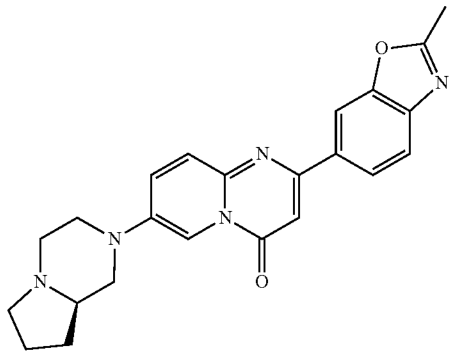

-continued
199
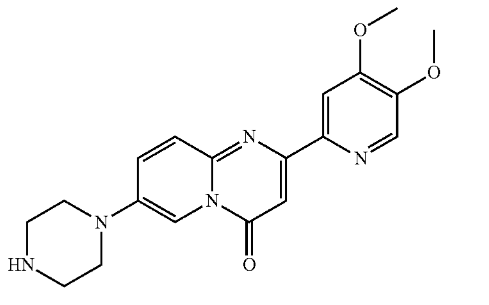
200
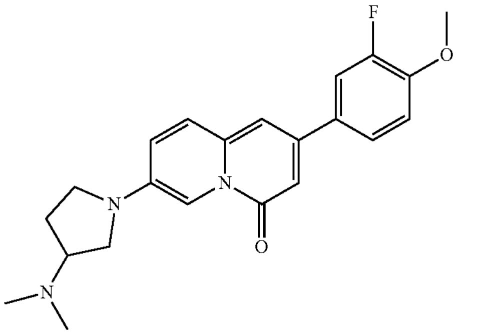
201
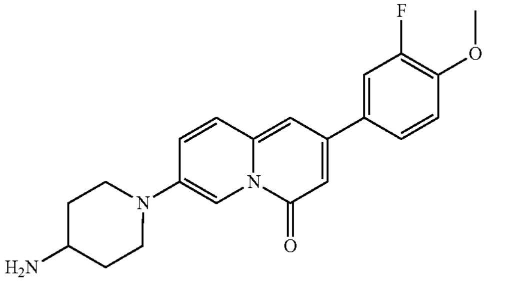
202
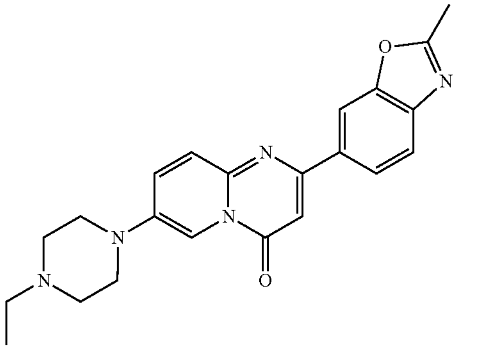
203
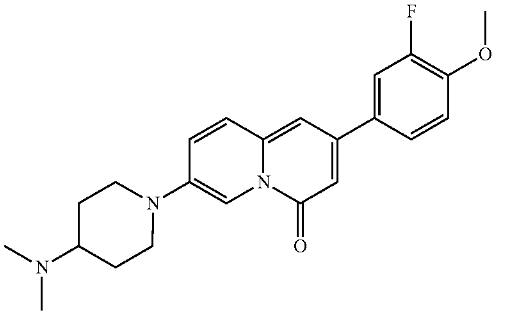
-continued
204
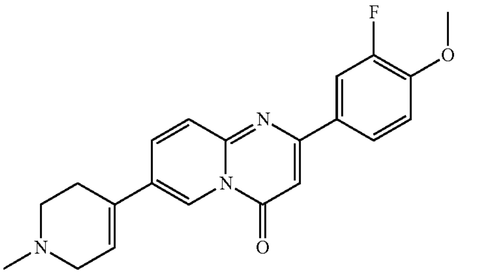
205
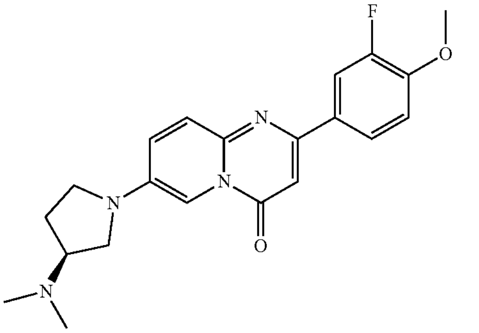
206
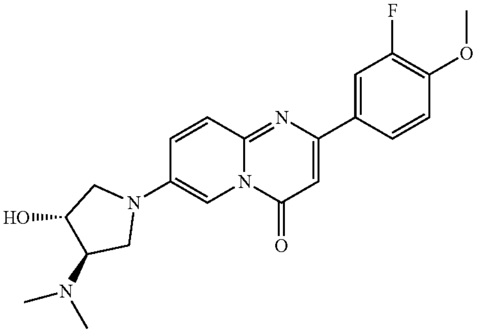
207
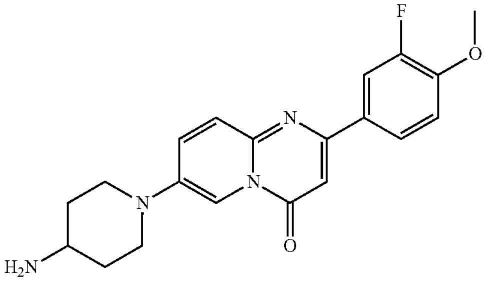
208
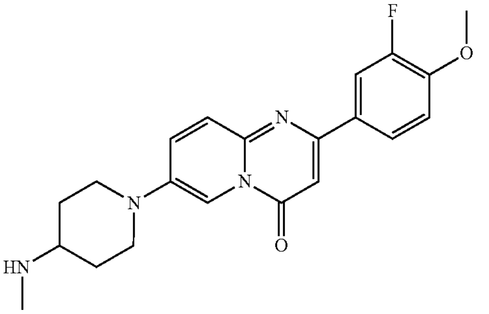

-continued
209
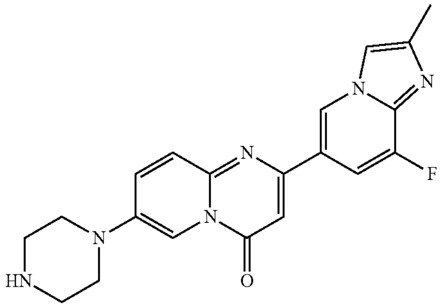
210
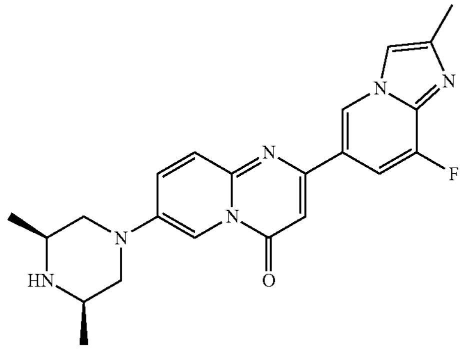
211
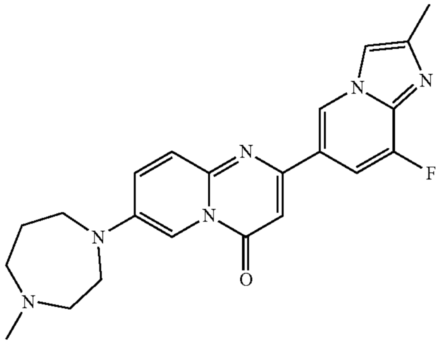
212
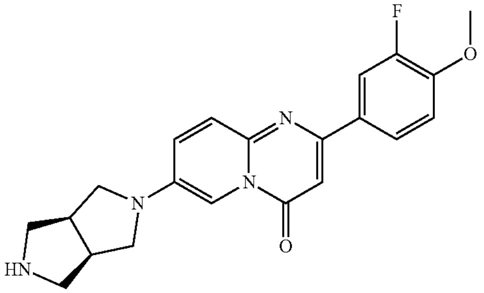
213
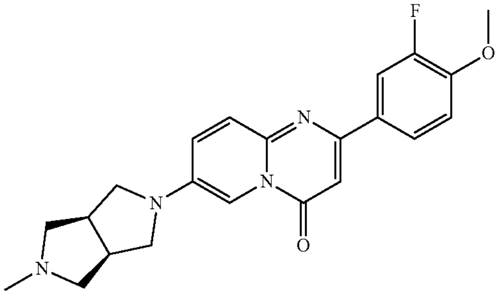
-continued
214
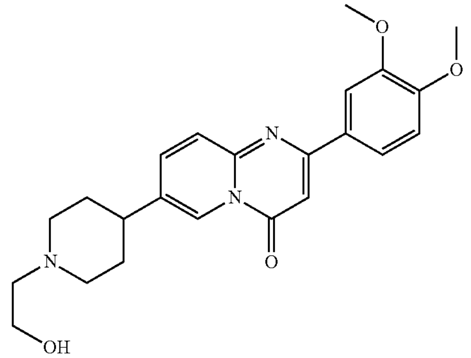
215
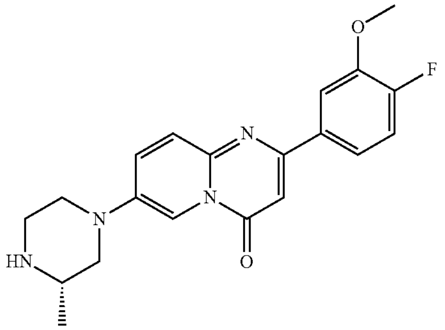
216
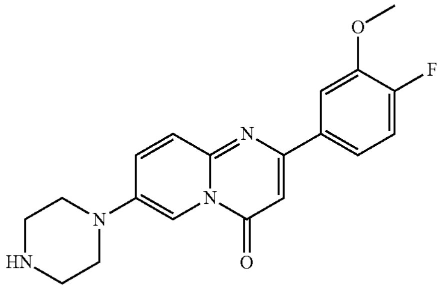
217
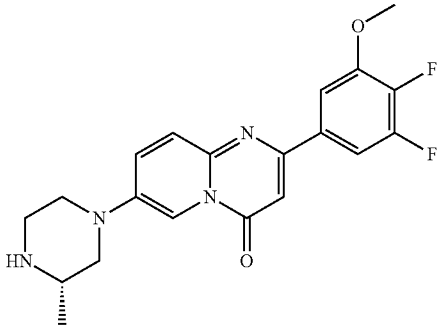
218
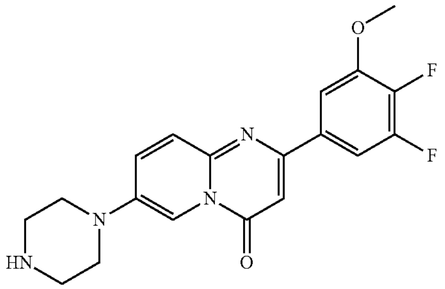

-continued
219
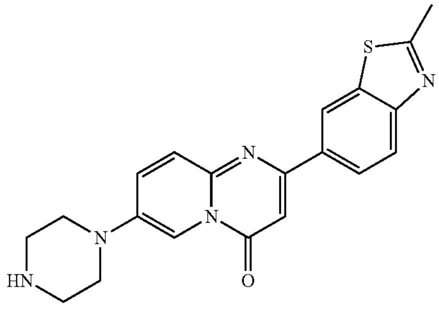
220
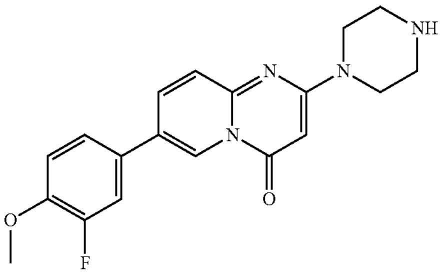
221
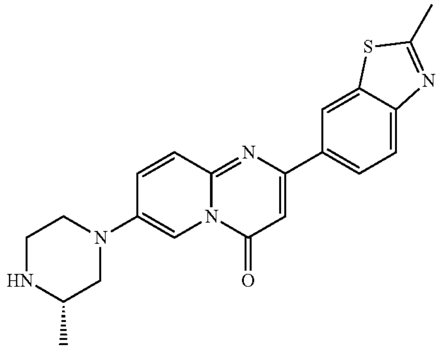
222
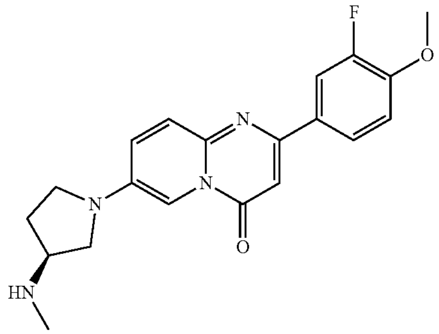
223
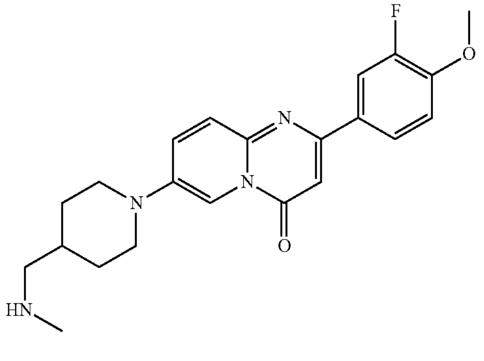
-continued
224
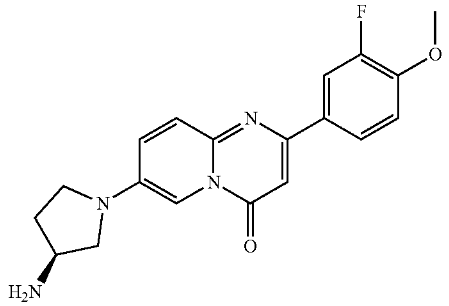
225
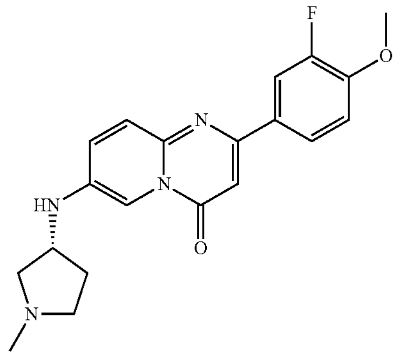
226
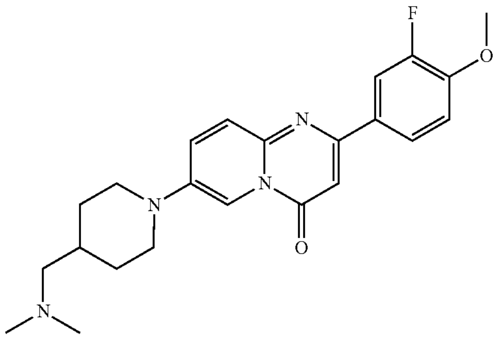
227
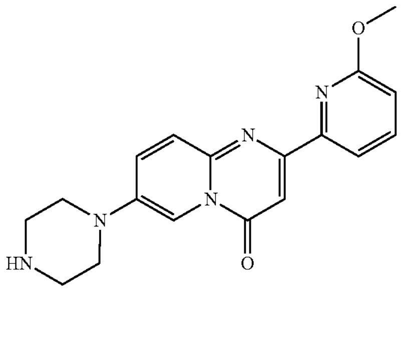
228
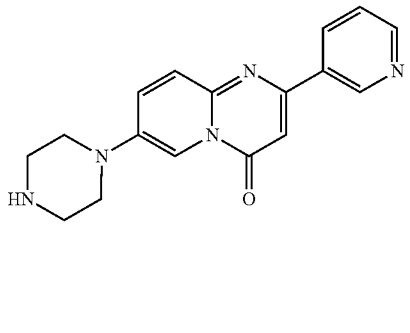

-continued
229
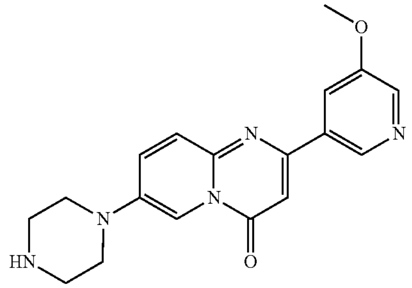
230
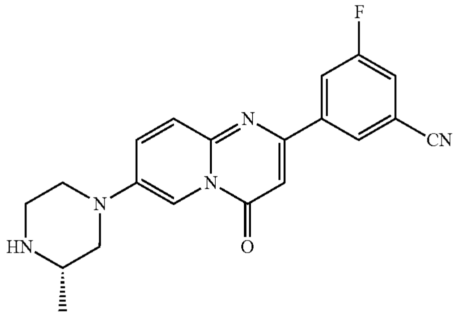
231
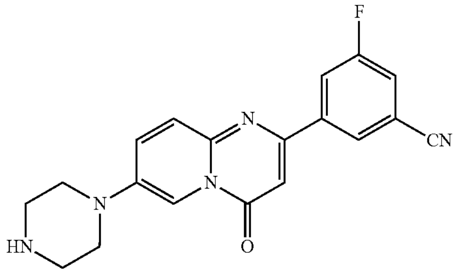
232
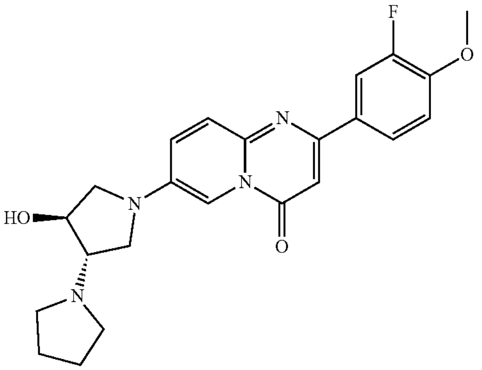
233
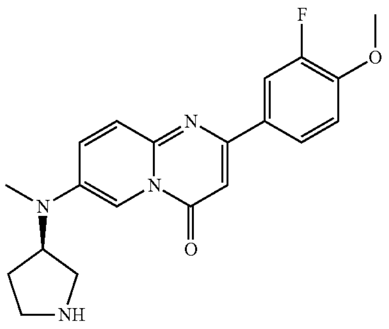
-continued
234
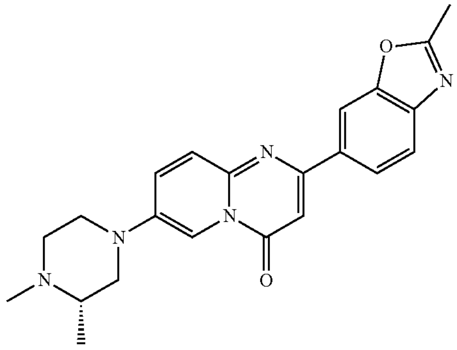
235
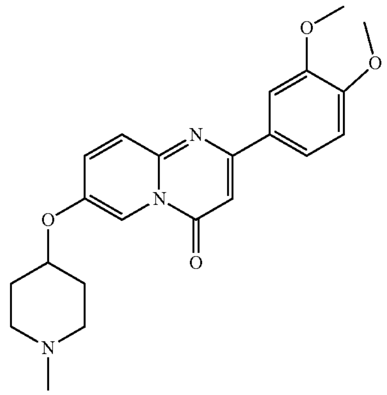
236
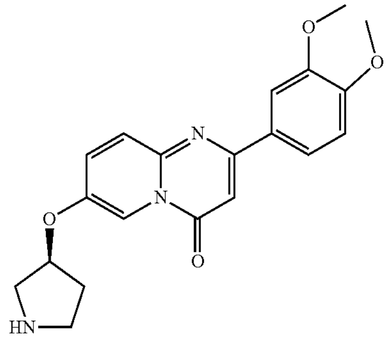
237
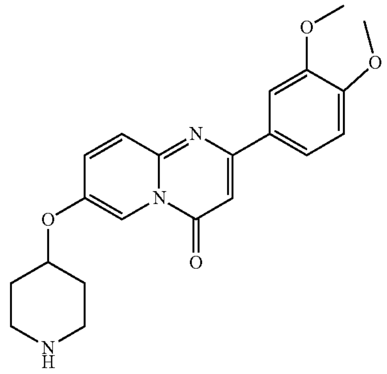

-continued
238
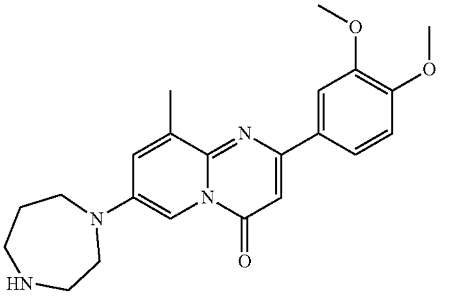
239
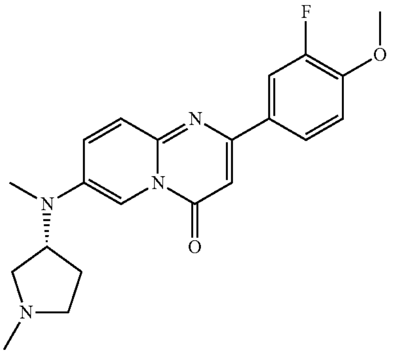
240
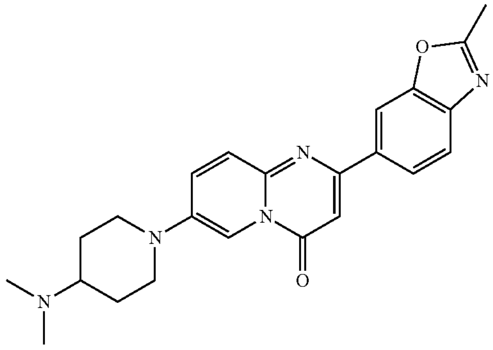
241
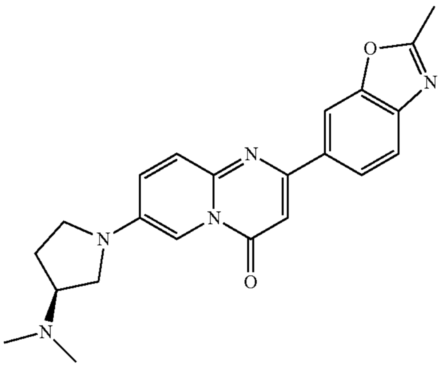
-continued
242
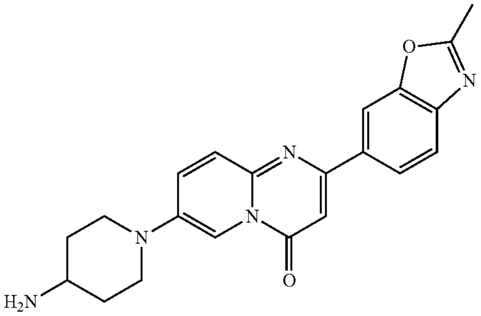
243
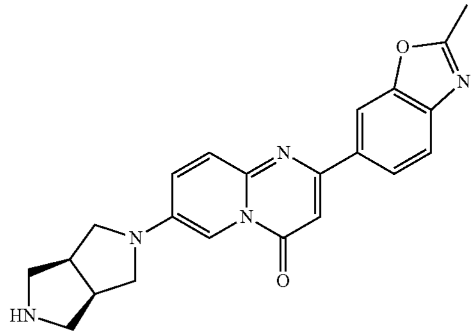
244
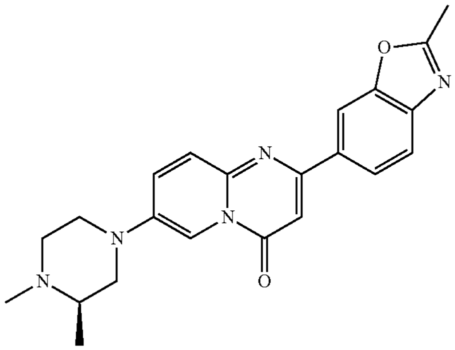
245
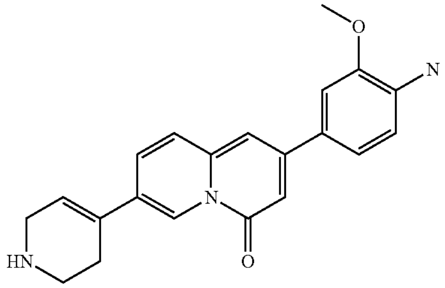
246
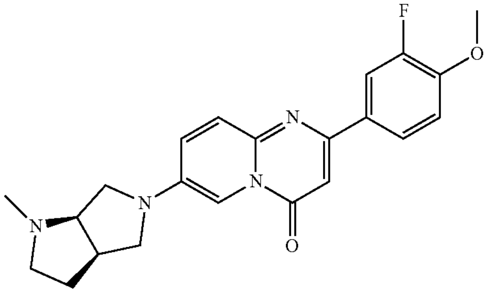

-continued
247
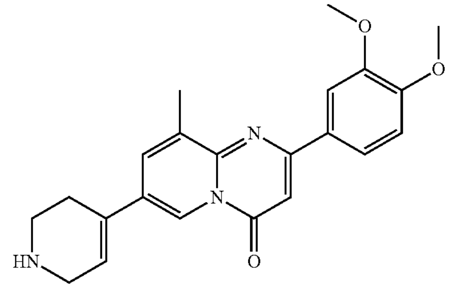
248
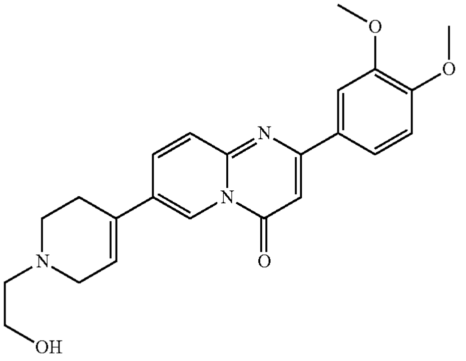
249
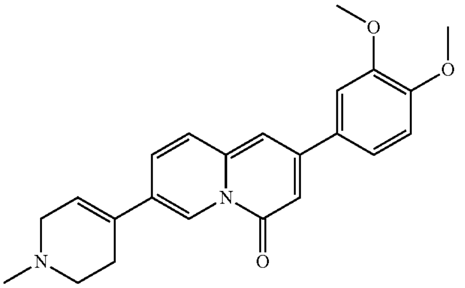
250
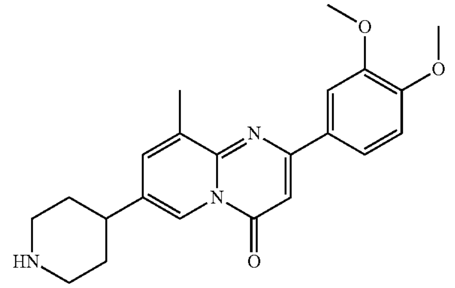
251
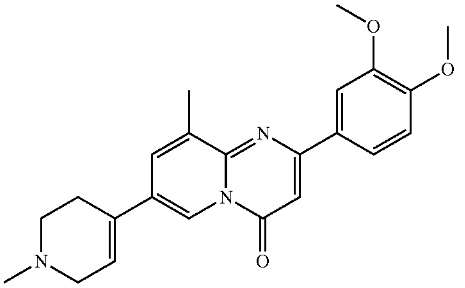
-continued
252
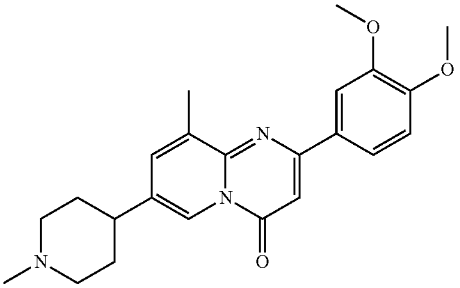
253
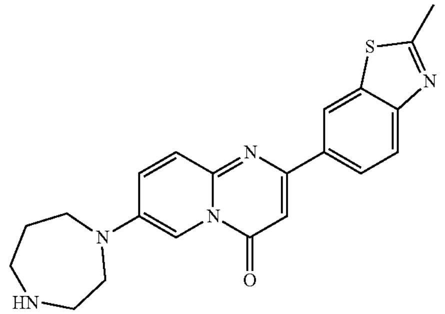
254
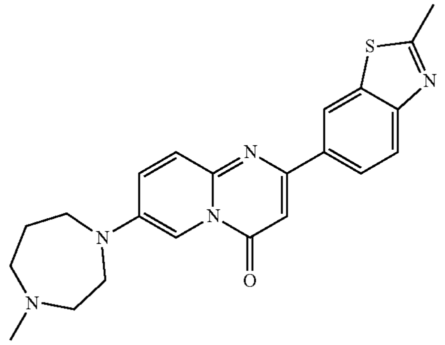
255
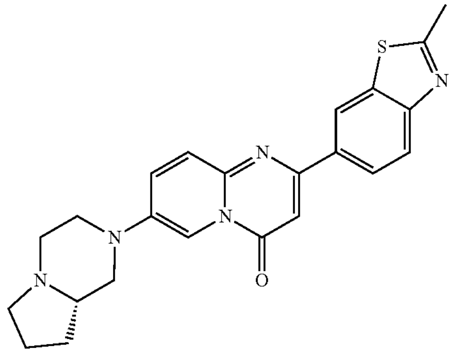
256
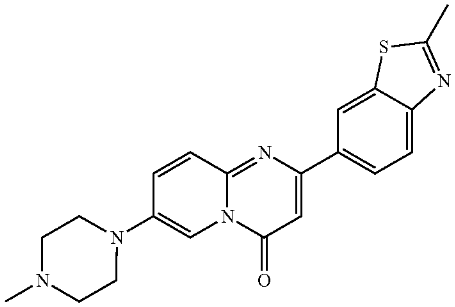

-continued
257
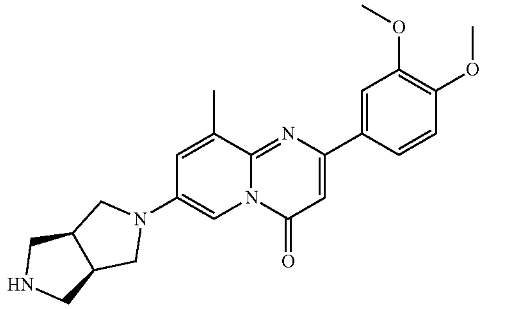
258
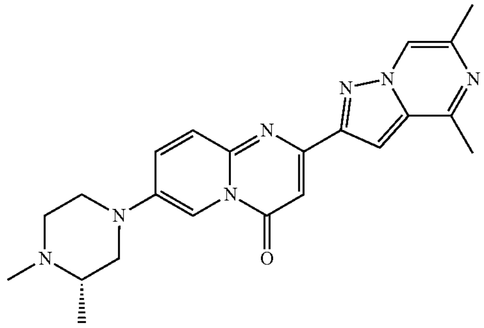
259
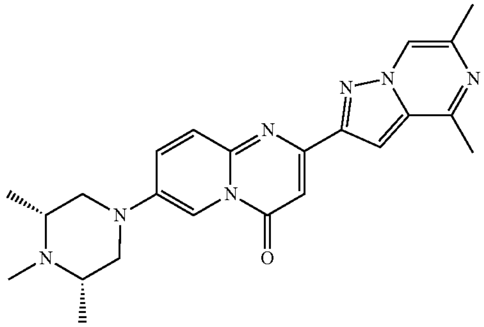
260
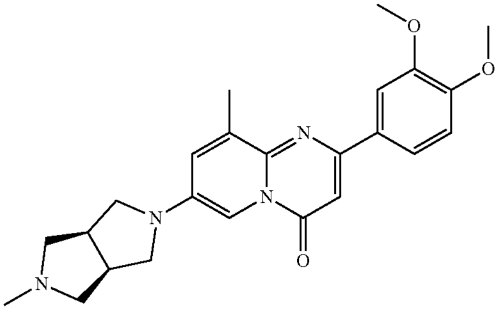
261
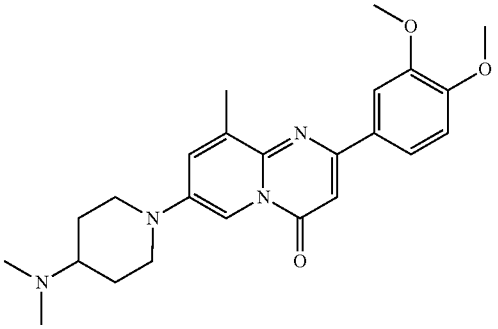
-continued
262
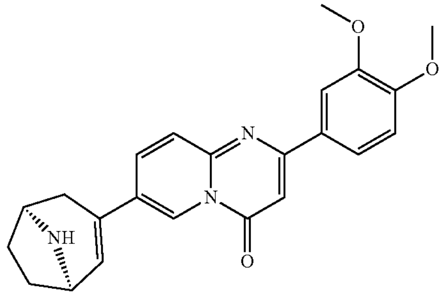
263
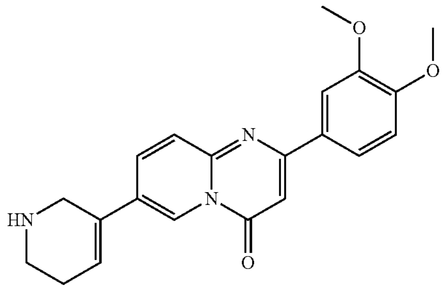
264
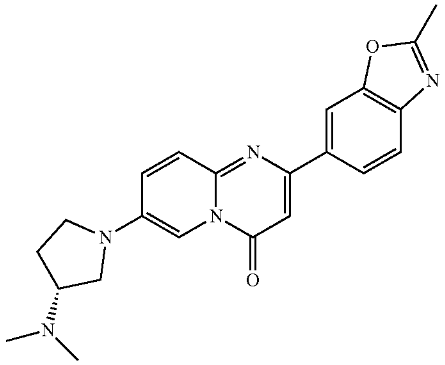
265
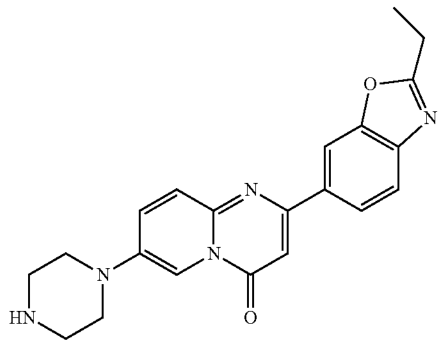

-continued
266
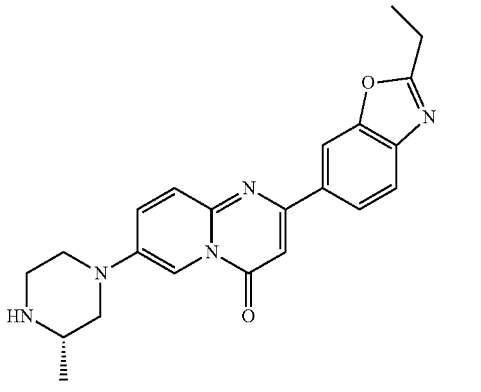
267
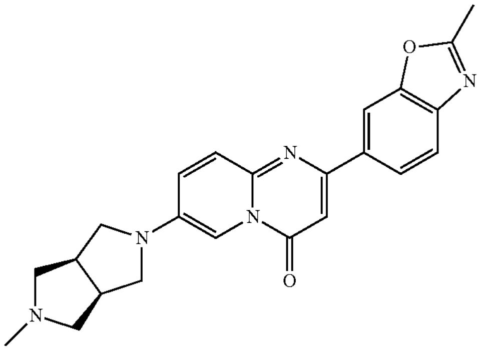
268
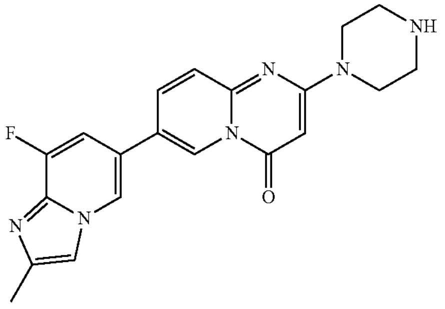
269
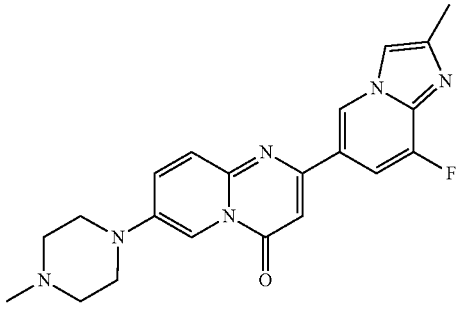
-continued
270
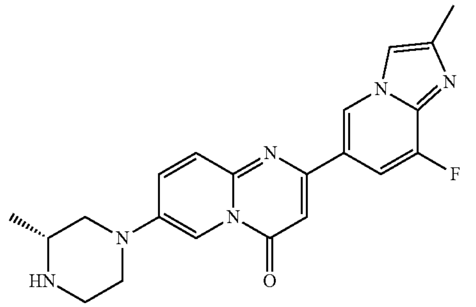
271
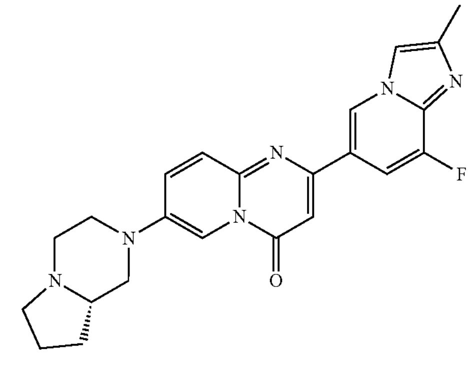
272
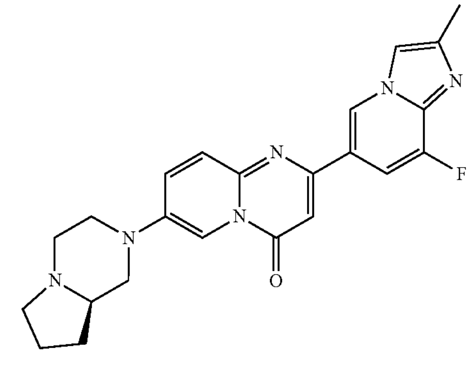
273
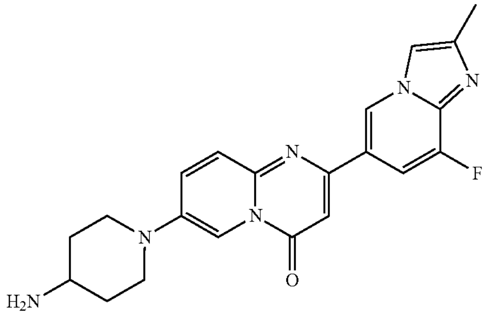

-continued
274
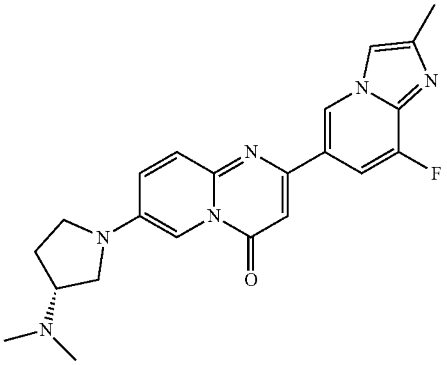
275
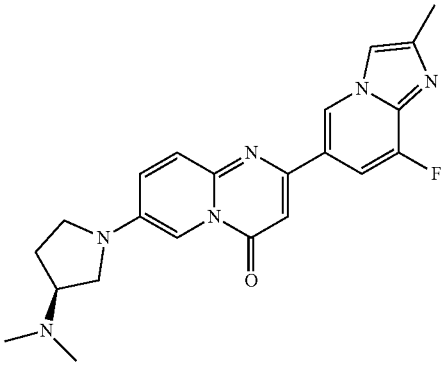
276
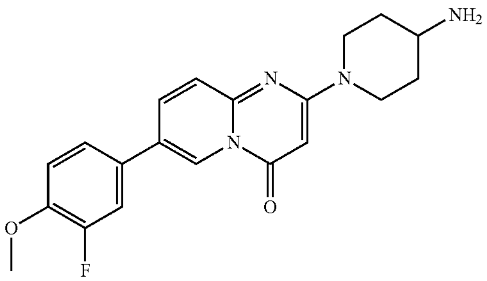
277
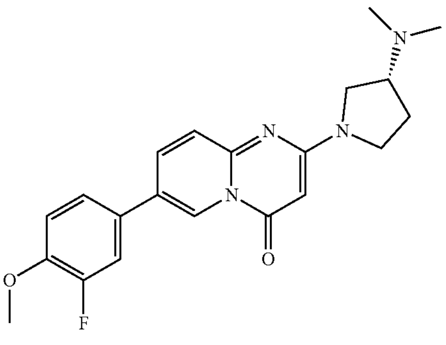
-continued
278
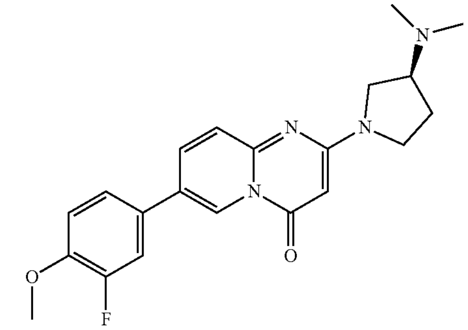
279
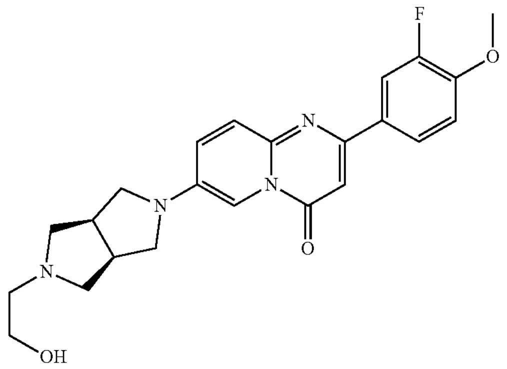
280
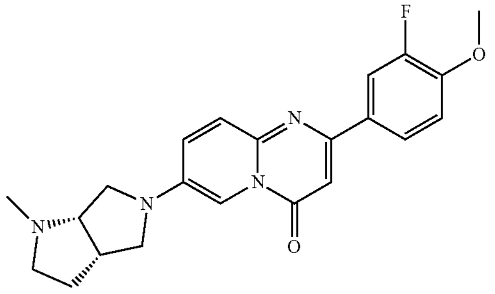
281
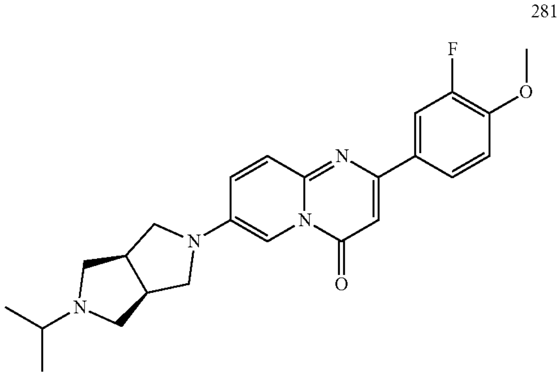

-continued
282
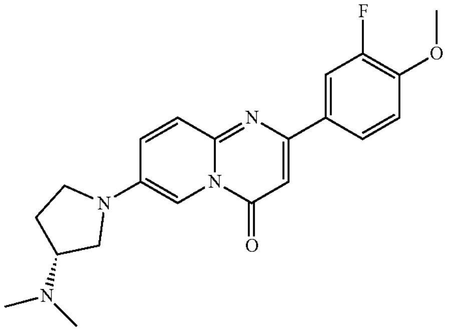
283
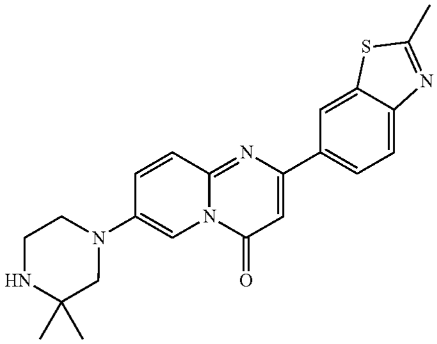
284
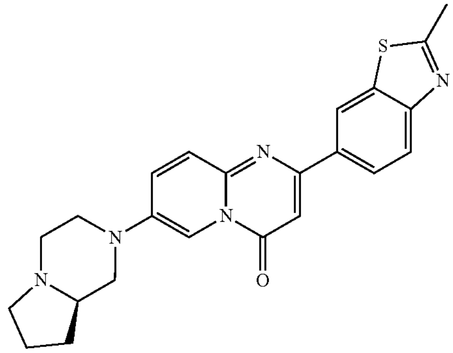
285
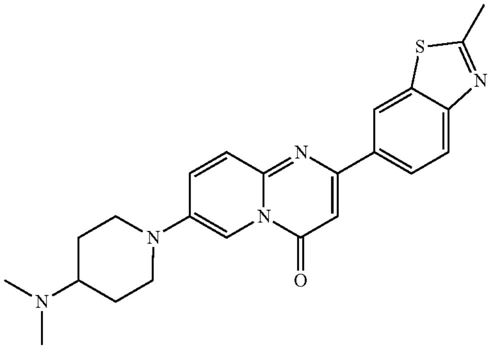
-continued
286
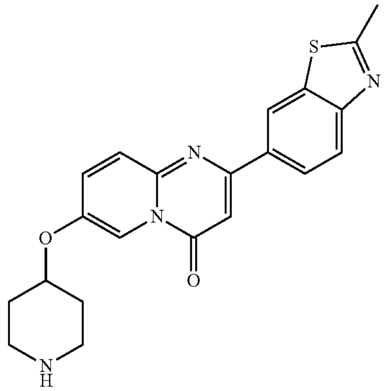
287
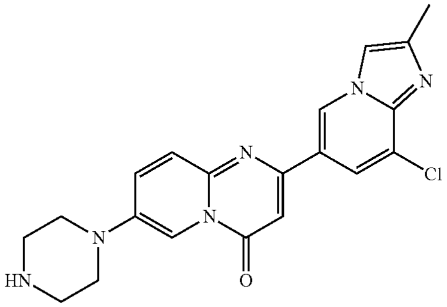
288
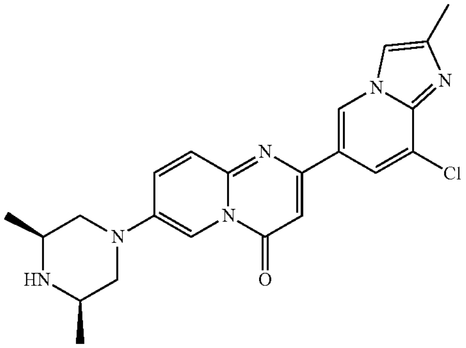
289
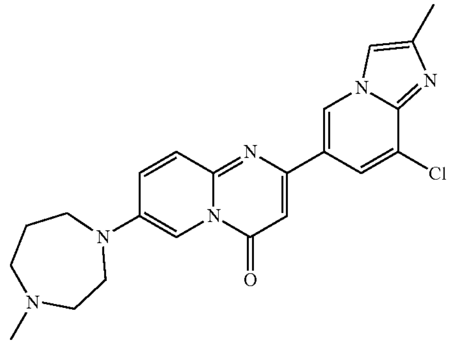

-continued
290
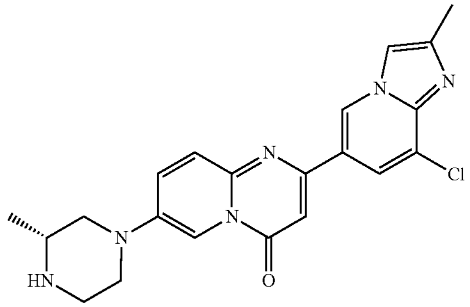
291
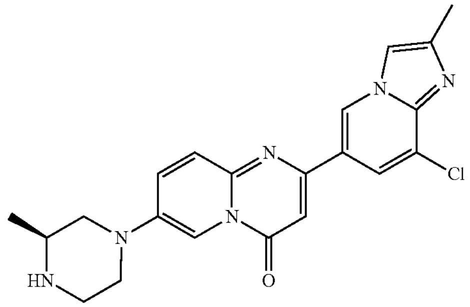
292
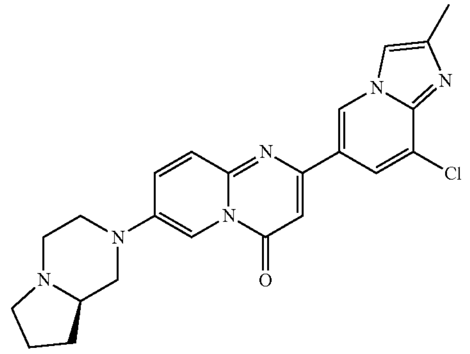
293
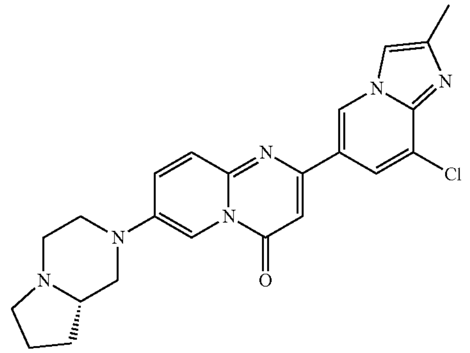
-continued
294
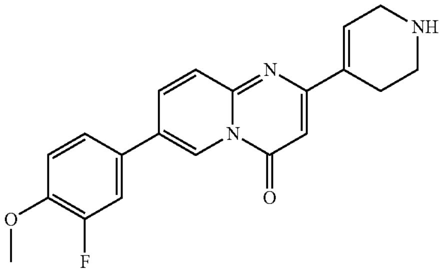
295
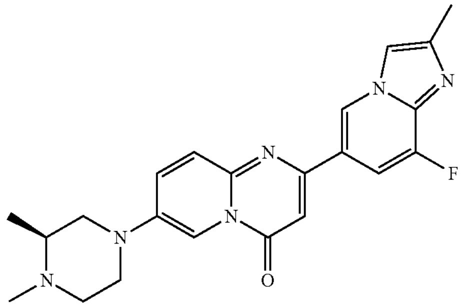
296
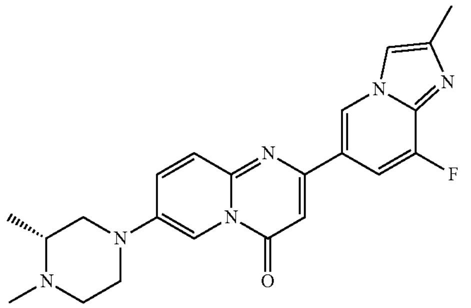
297
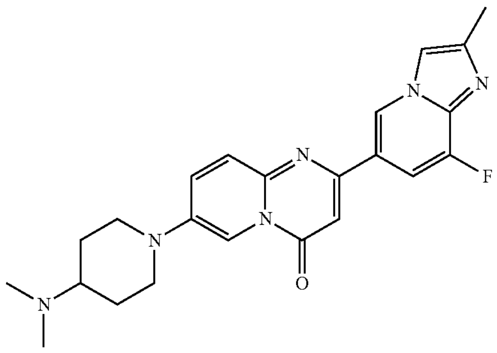
298
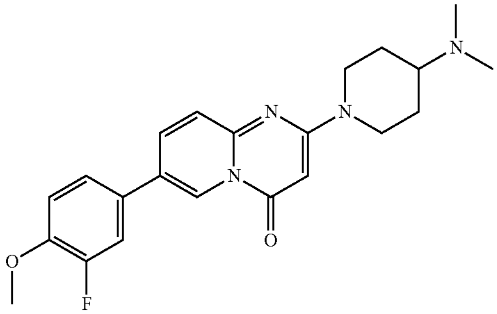

-continued
299
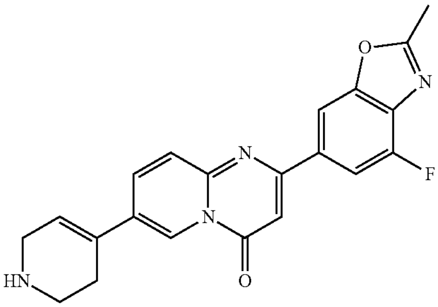
300
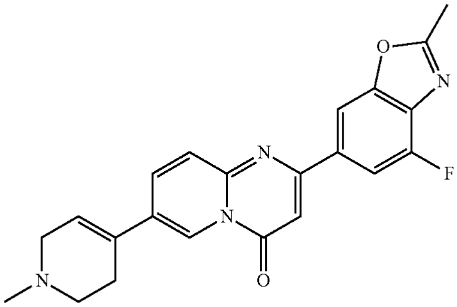
301
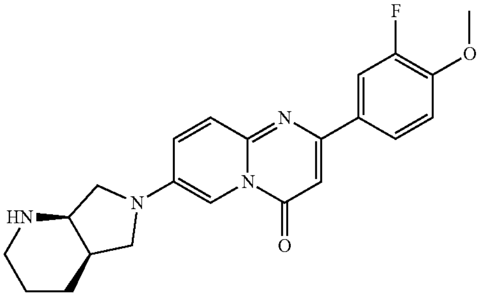
302
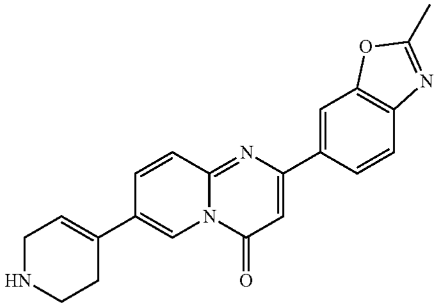
303
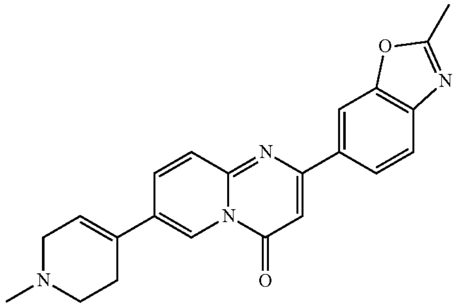
-continued
304
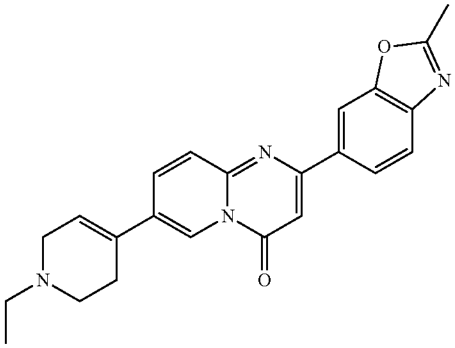
305
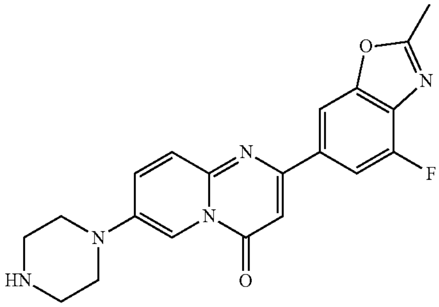
306
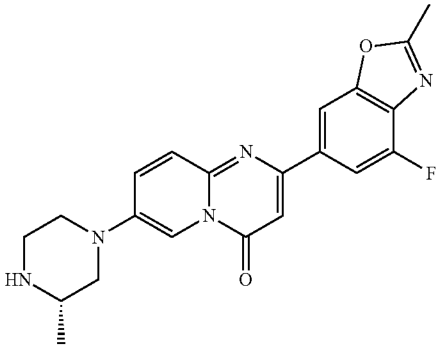
307
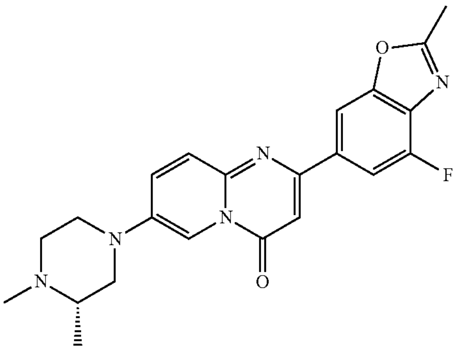

-continued
308
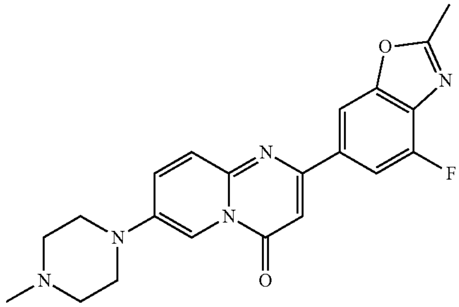
309
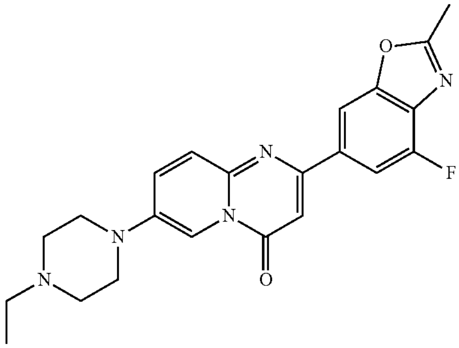
310
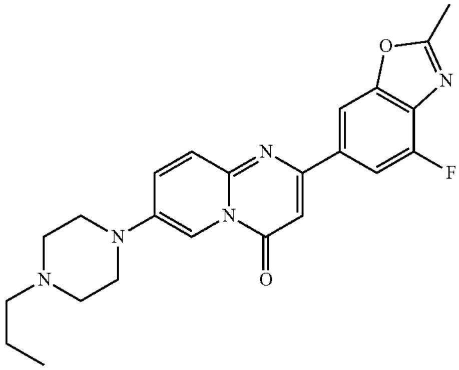
311
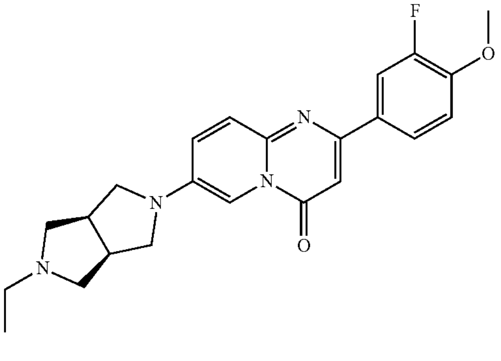
312
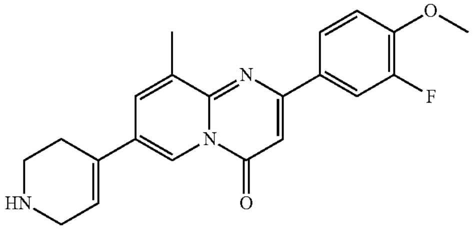
-continued
313
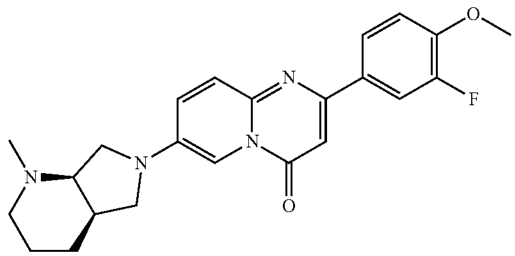
314
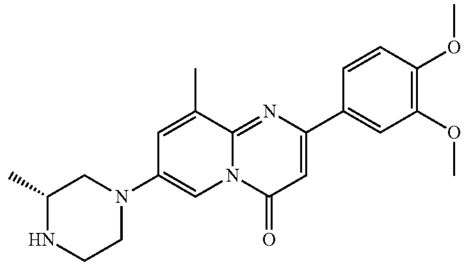
315
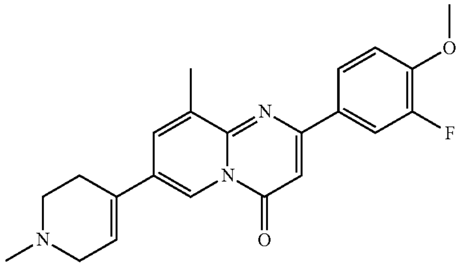
316
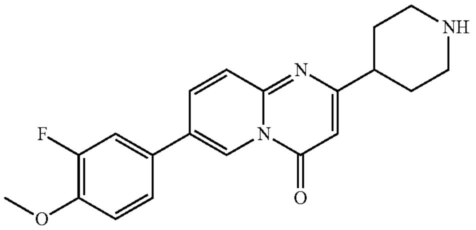
317
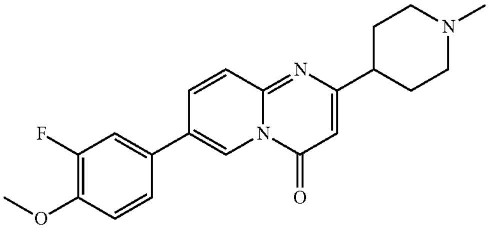
318
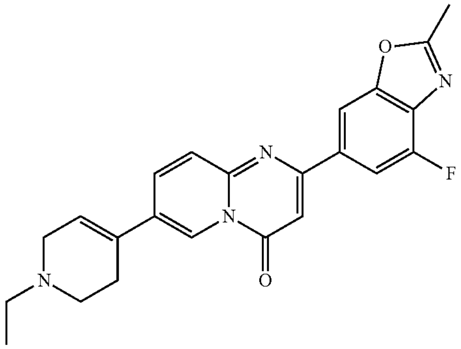

-continued
319
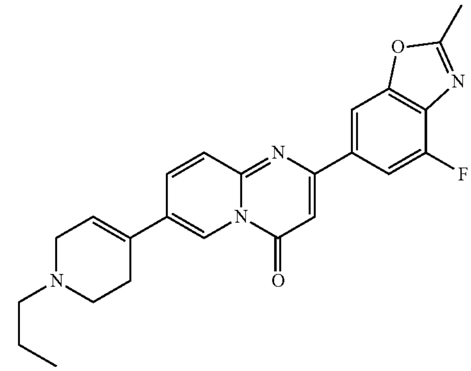
320
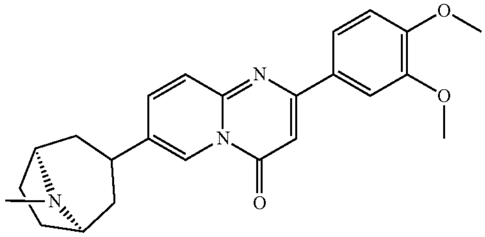
321
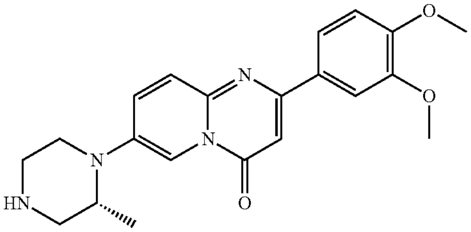
322
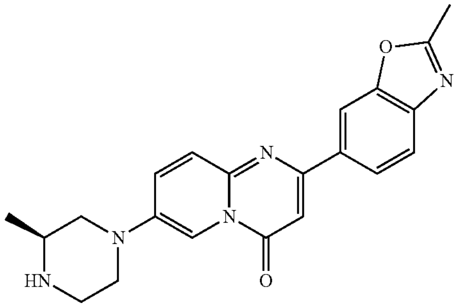
323
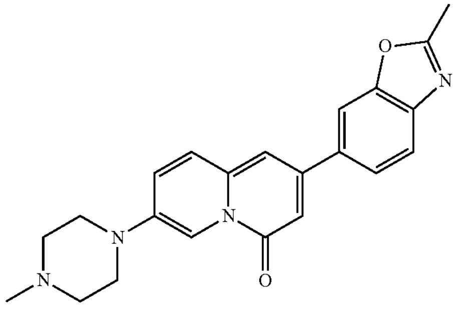
-continued
324
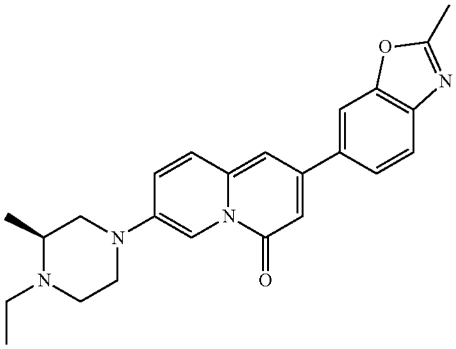
325
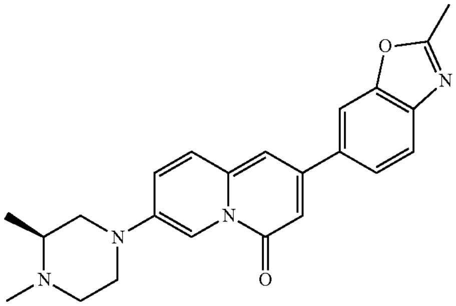
326
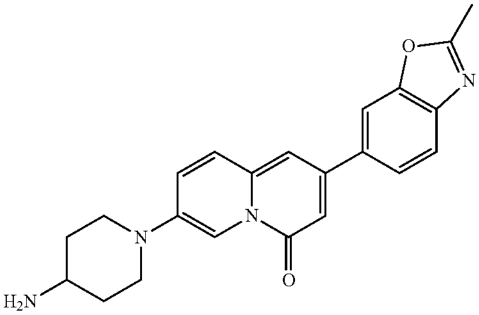
327
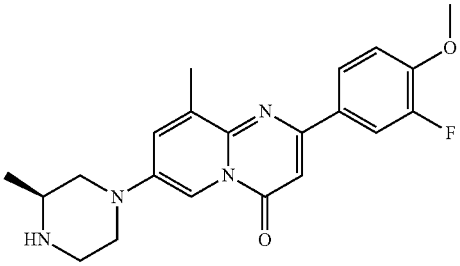
328
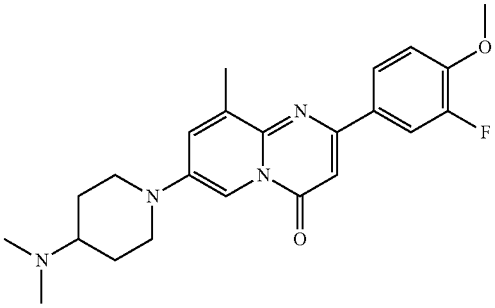

329
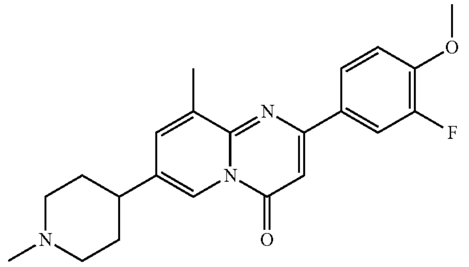
330
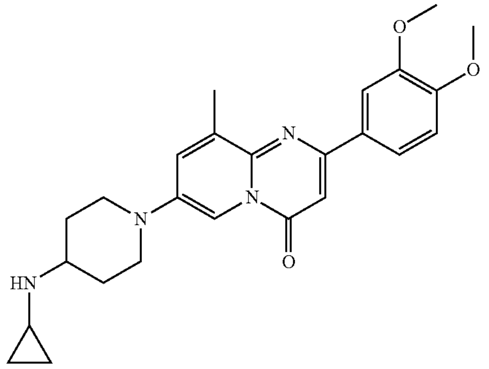
331
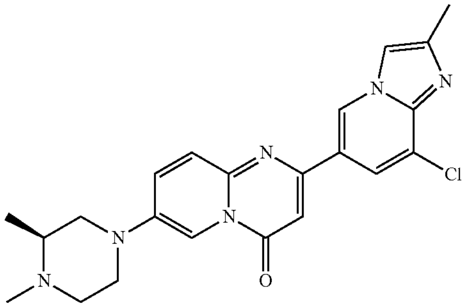
332
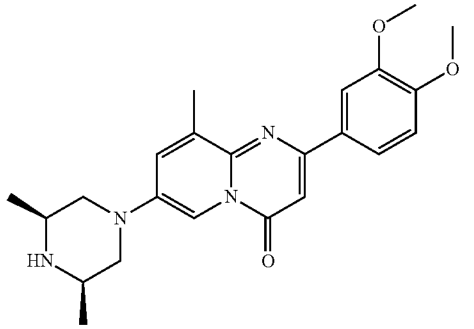
333
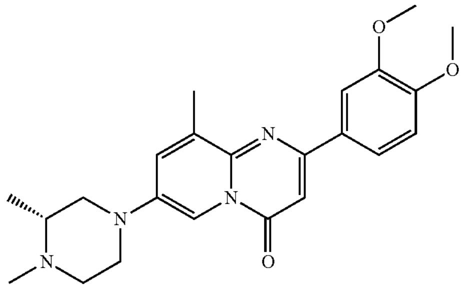
334
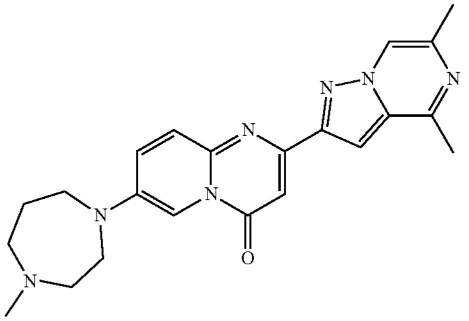
335
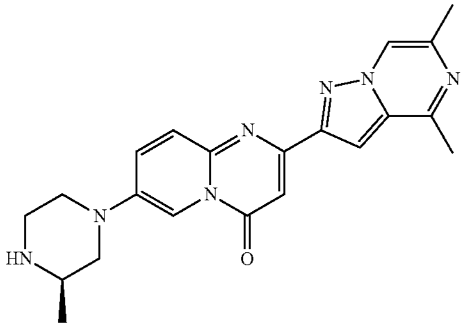
336
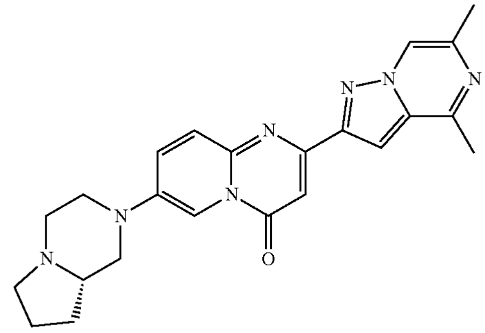
337
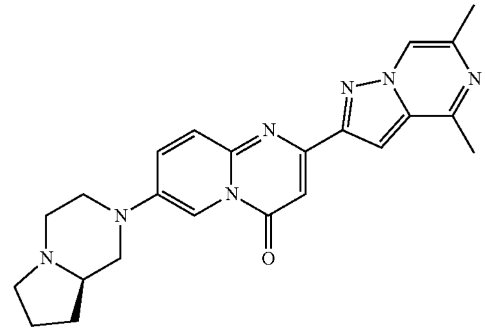

-continued
338
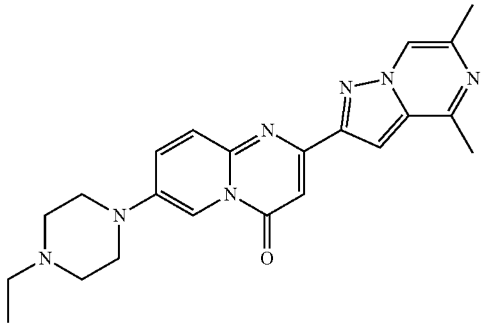
339
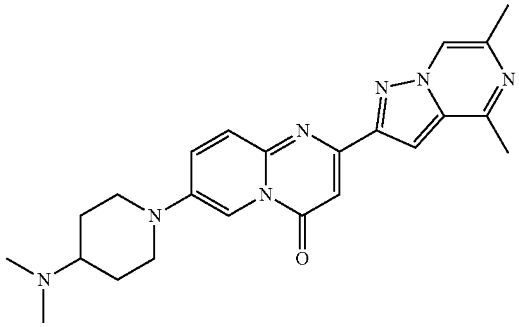
340
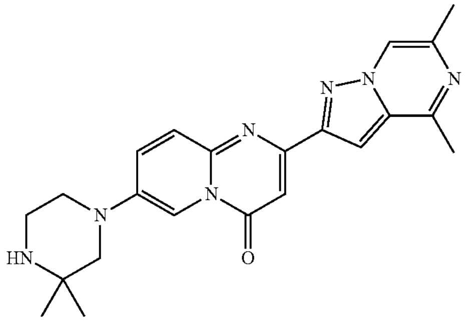
341
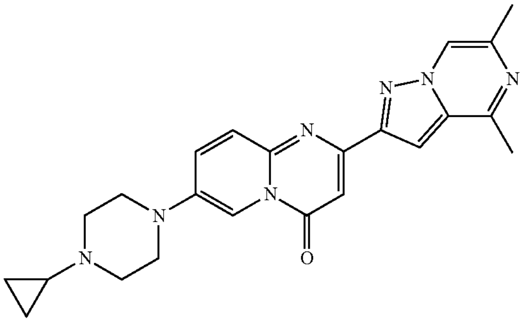
342
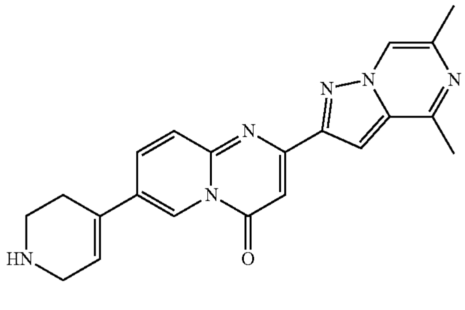
-continued
343
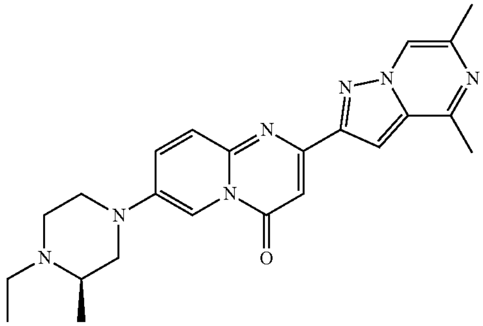
344
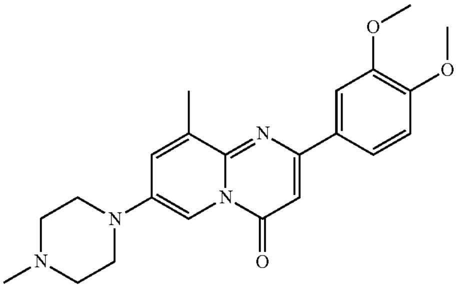
345
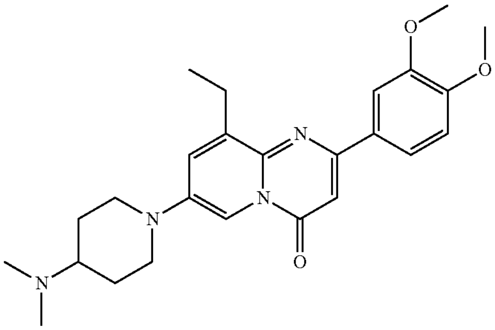
346
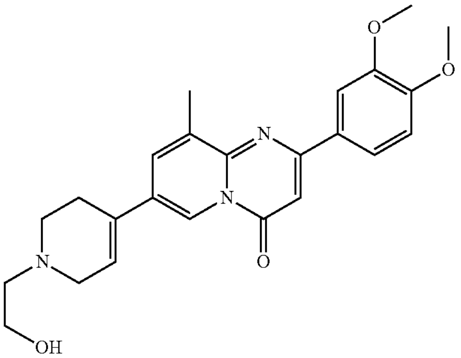

-continued
347
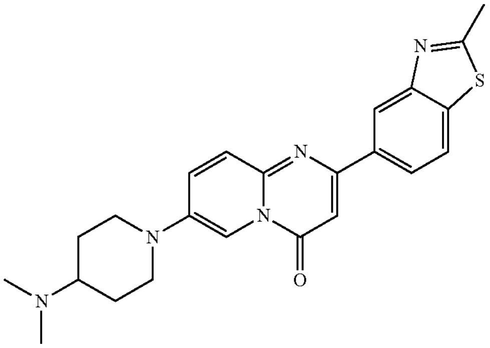
348
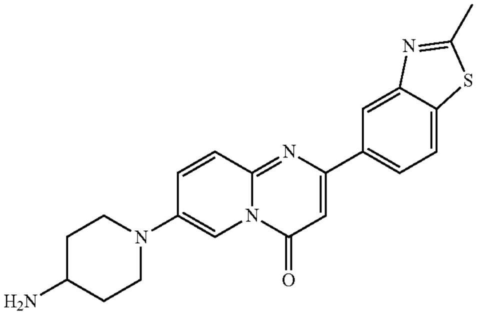
349
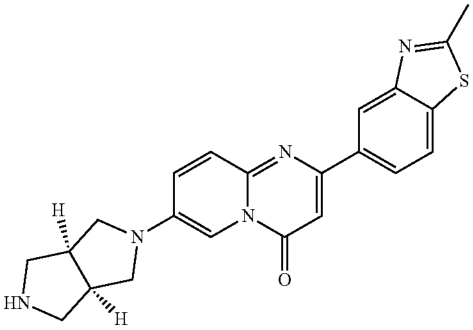
350
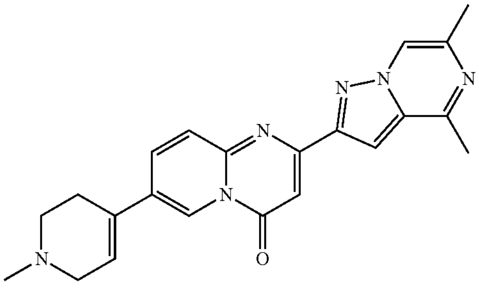
351
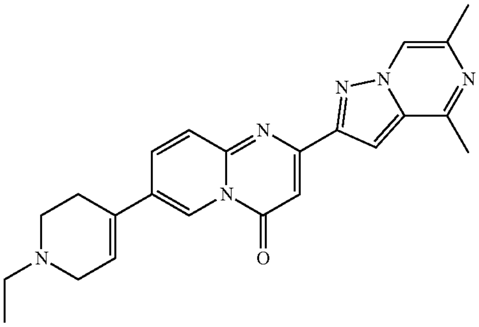
-continued
352
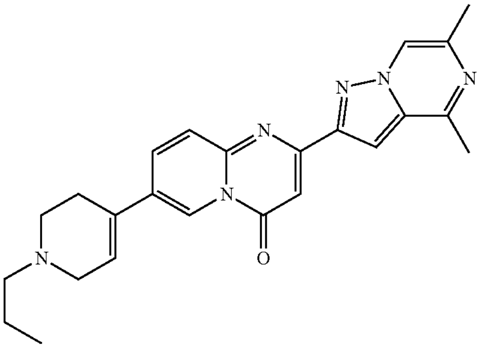
353
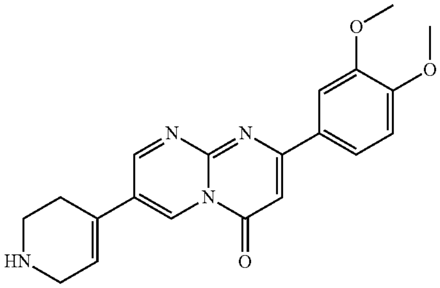
354
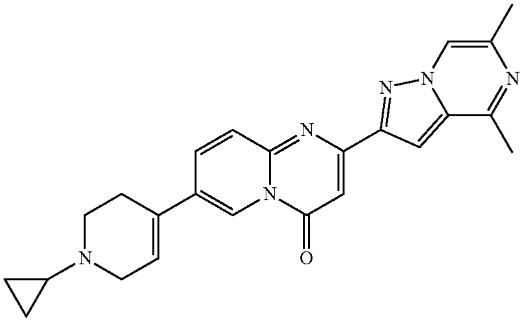
355
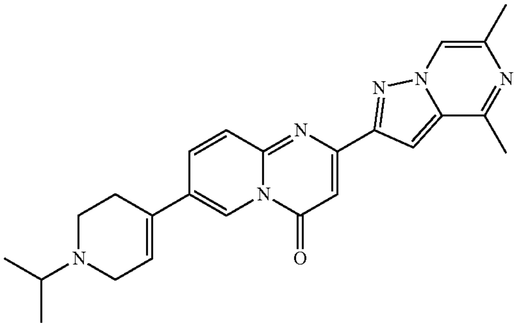

-continued
356
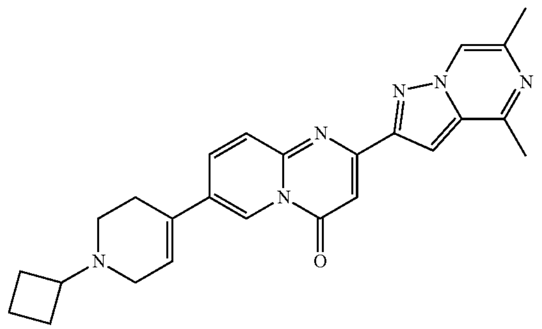
357
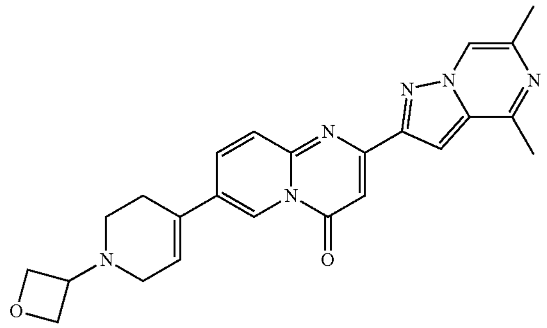
358
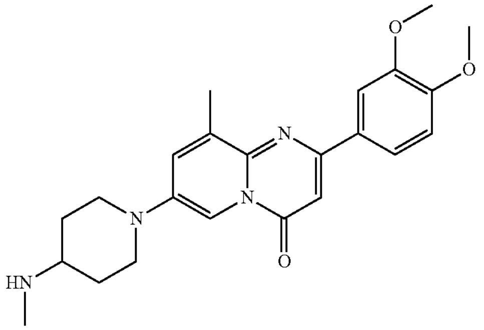
359
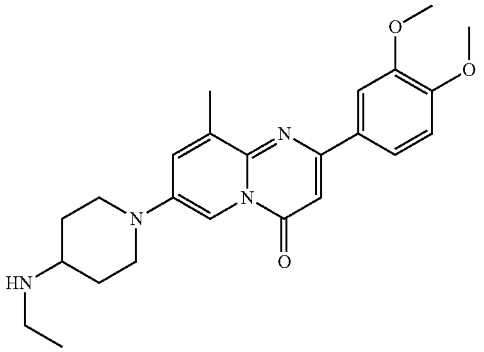
-continued
360
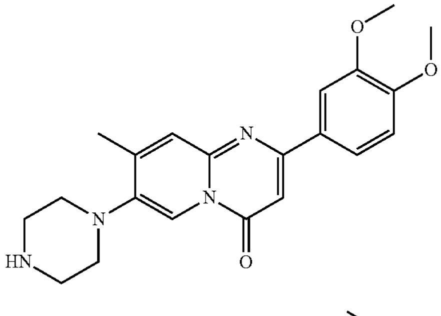
361
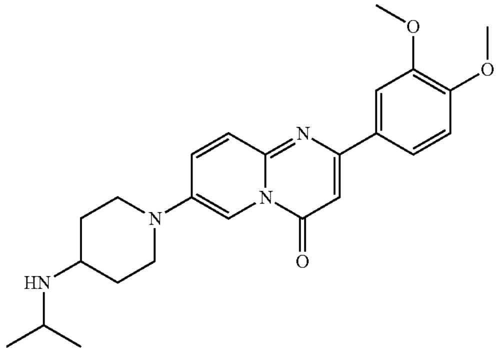
362
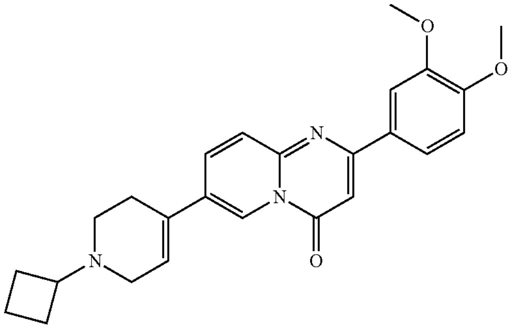
363
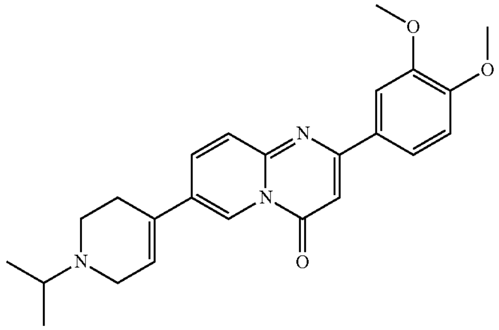
364
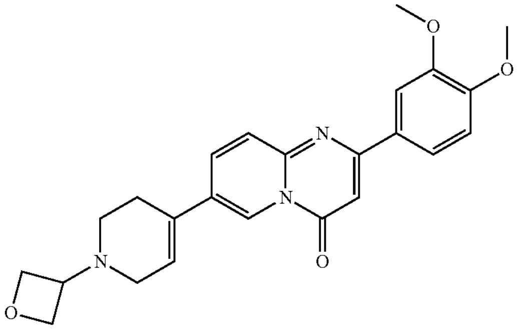

-continued
365
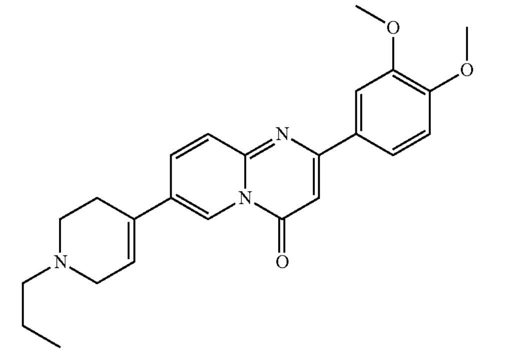
366
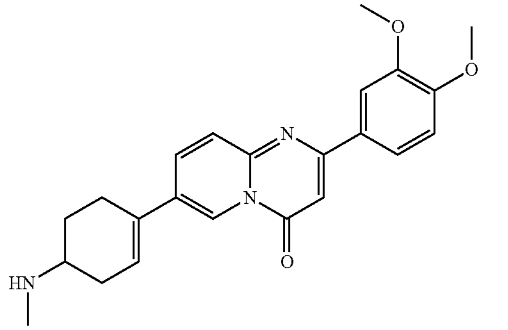
367
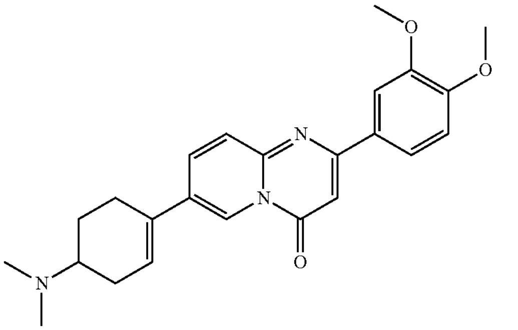
368
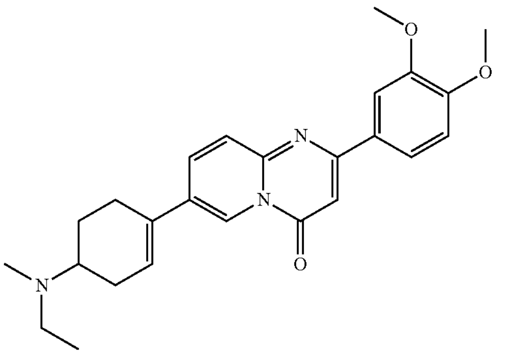
-continued
369
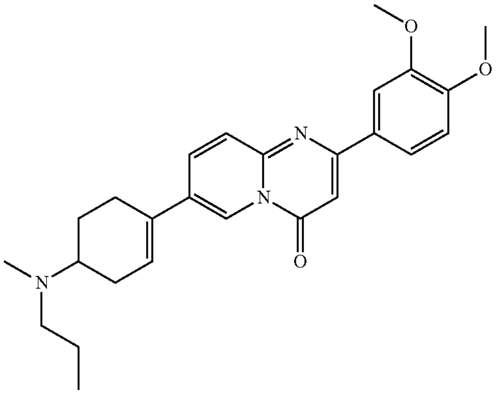
370
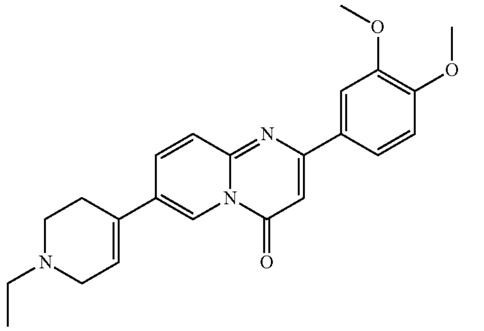
371
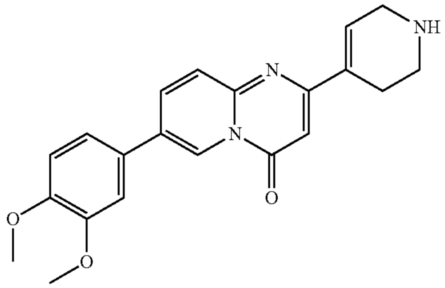
372
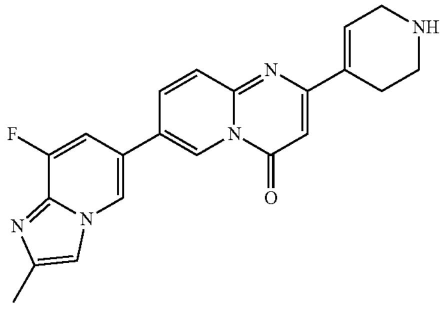

-continued
373
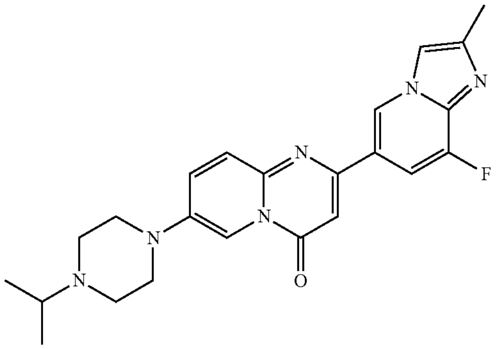
374
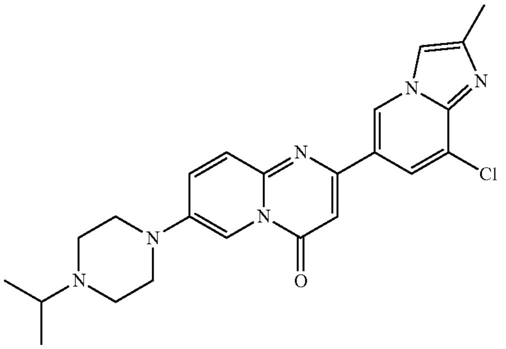
375
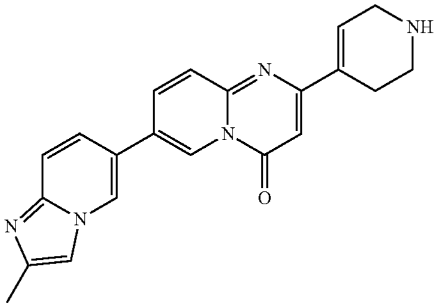
376
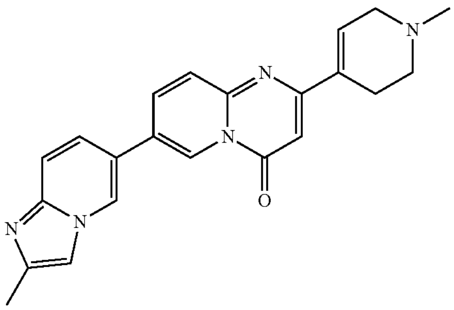
377
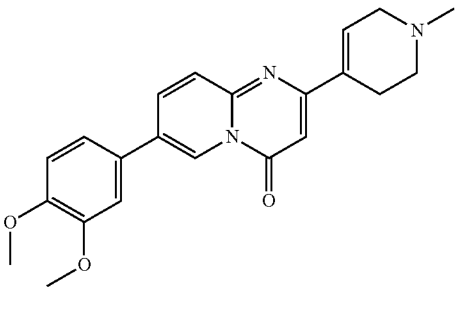
-continued
378
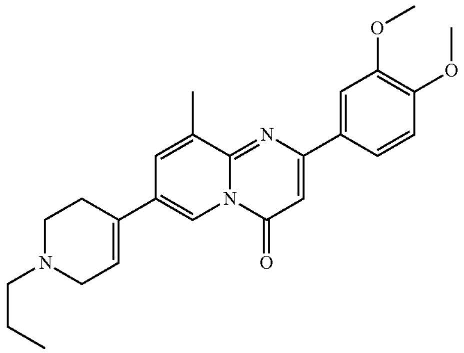
379
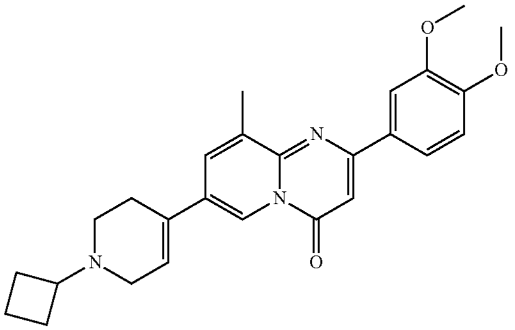
380
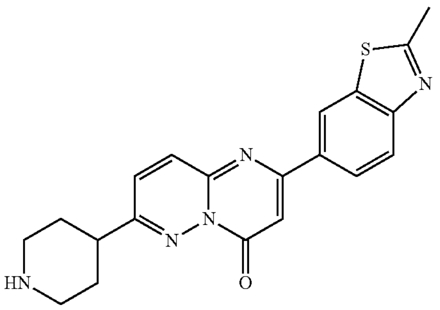
381
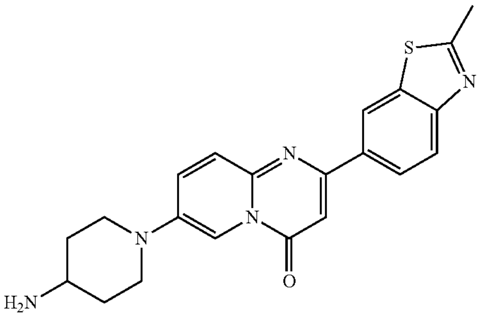

-continued
382
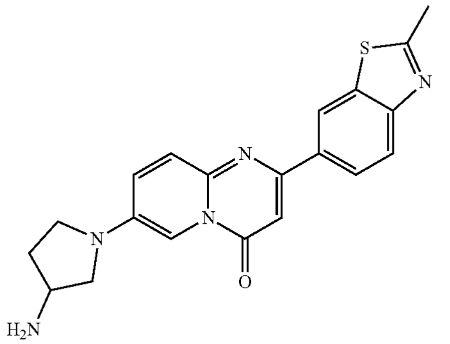
383
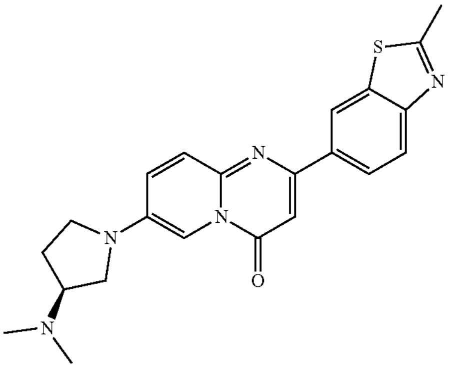
384
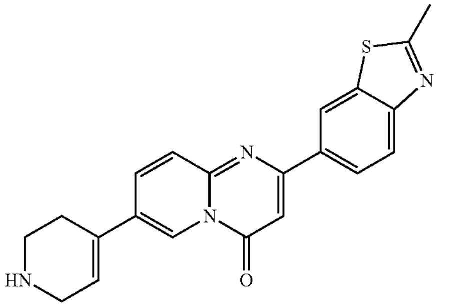
385
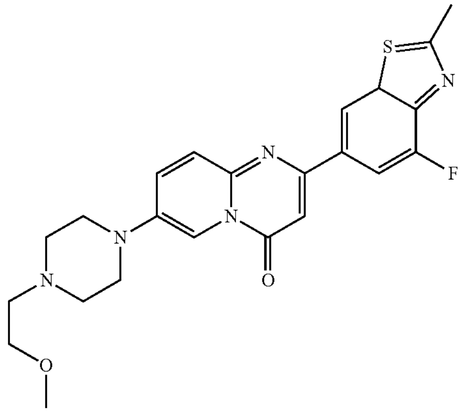
-continued
386
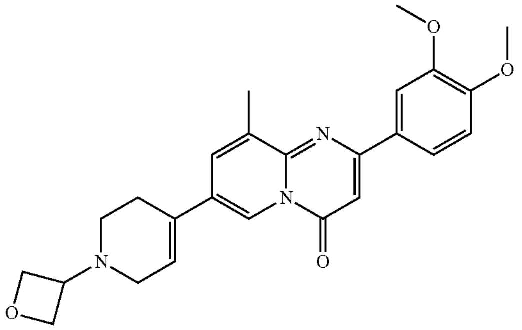
387
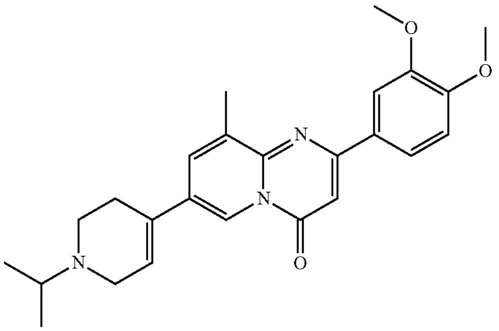
388
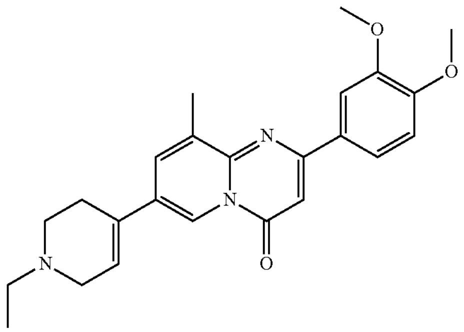
389
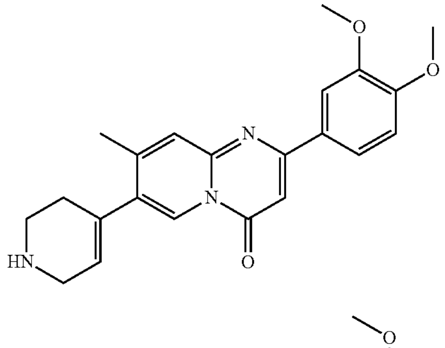
390
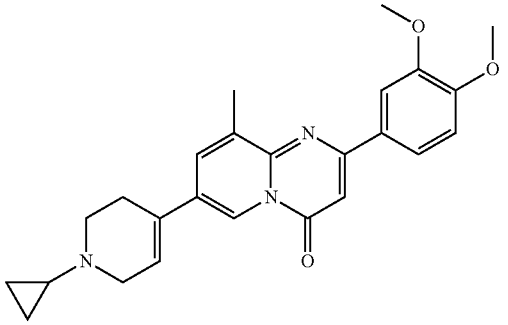

-continued
391
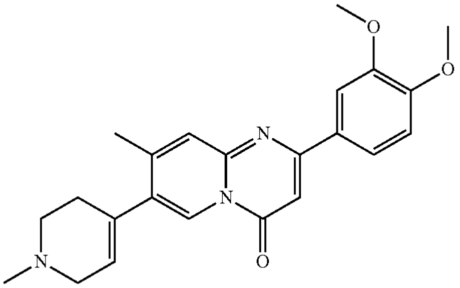
392
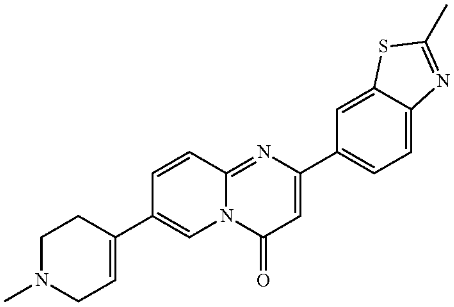
393
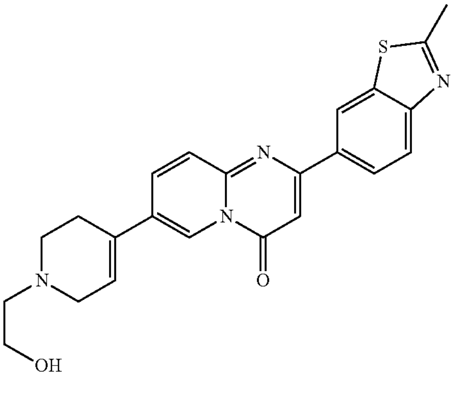
394
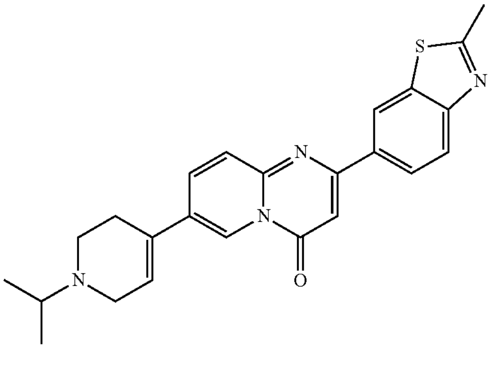
-continued
395
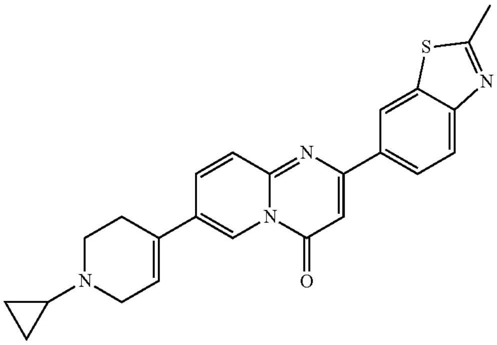
396
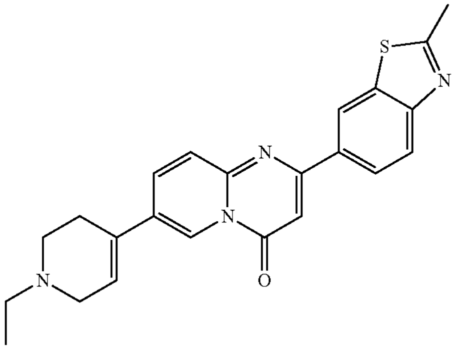
397
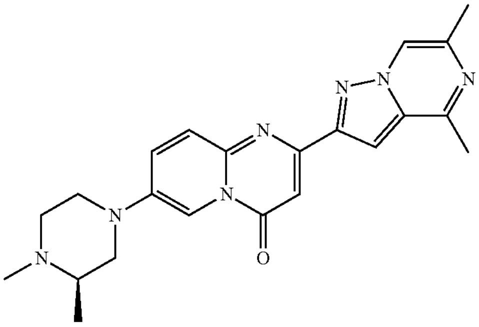
398
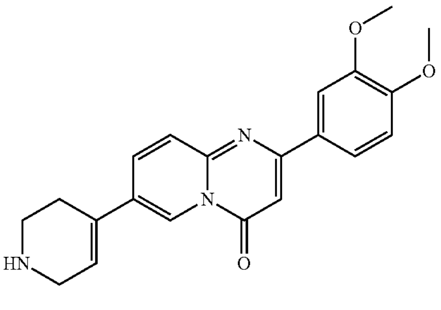
399
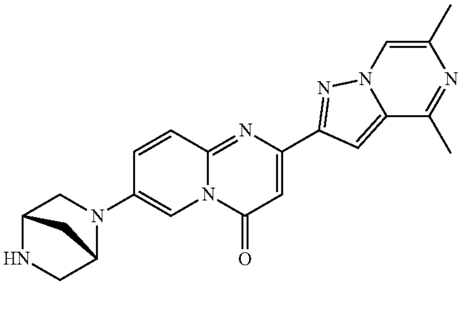

-continued
400
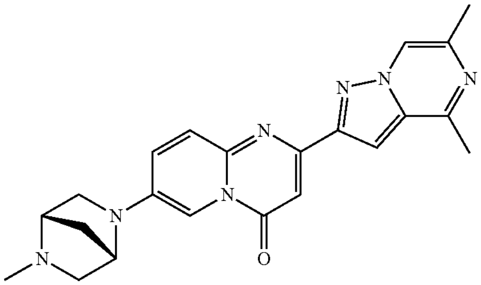
401
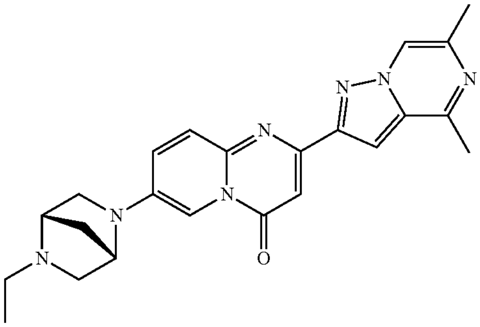
402
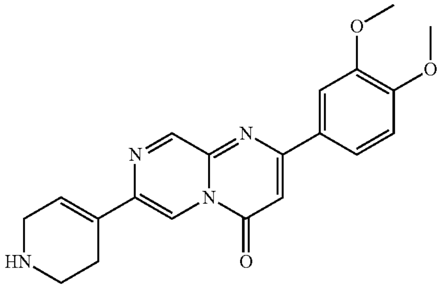
403
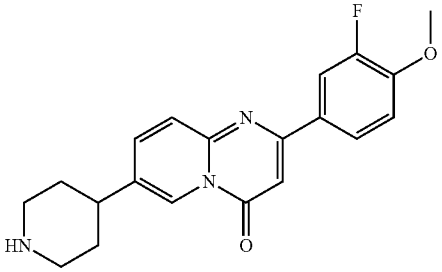
404
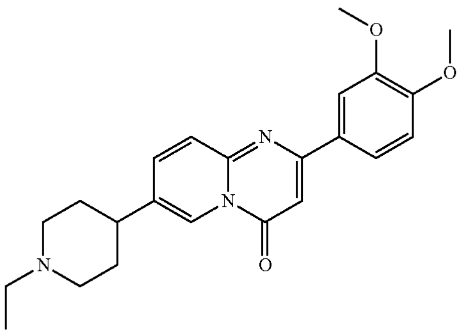
-continued
405
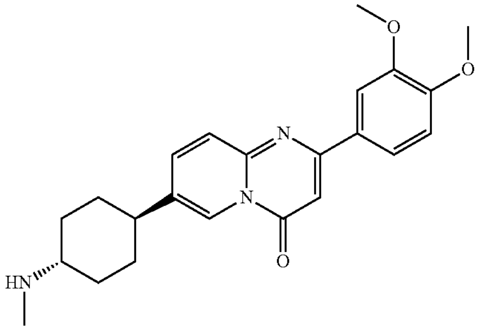
406
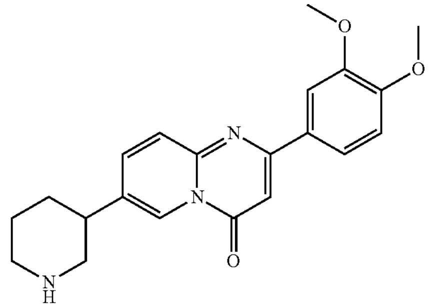
407
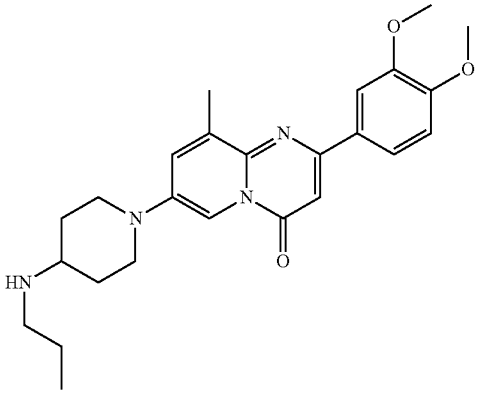
408
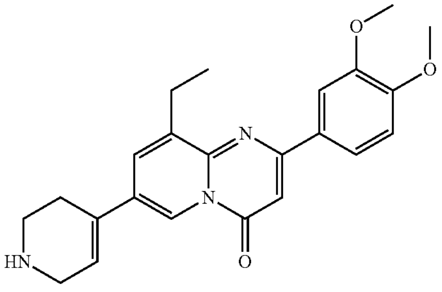
409
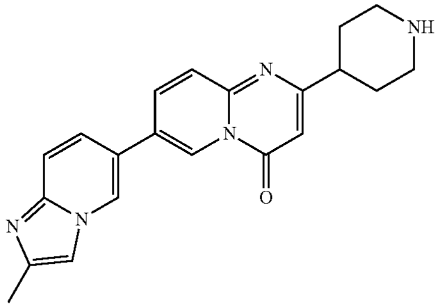

-continued
410
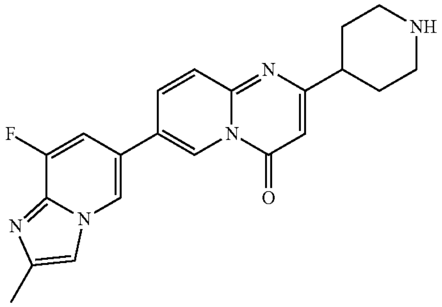
411
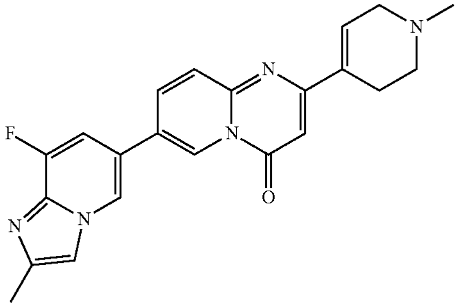
412
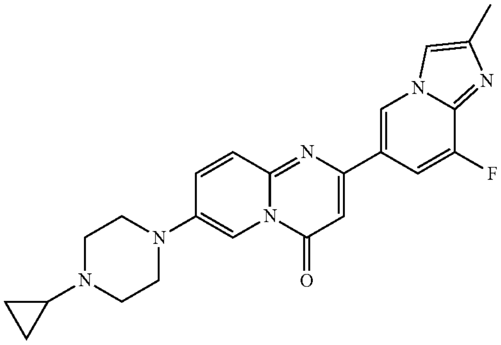
413
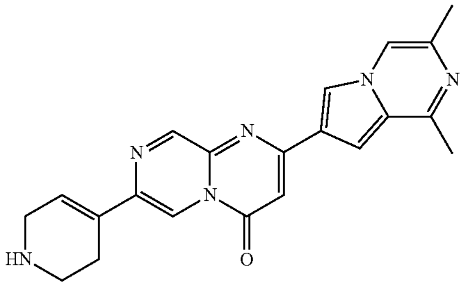
414
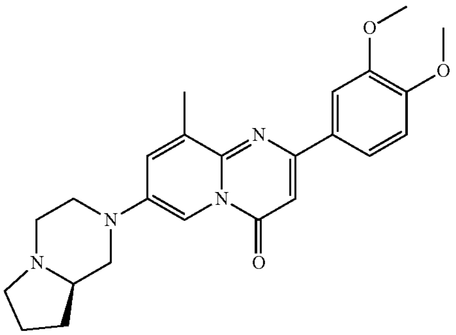
-continued
415
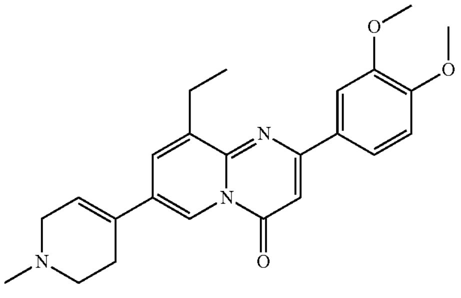
416
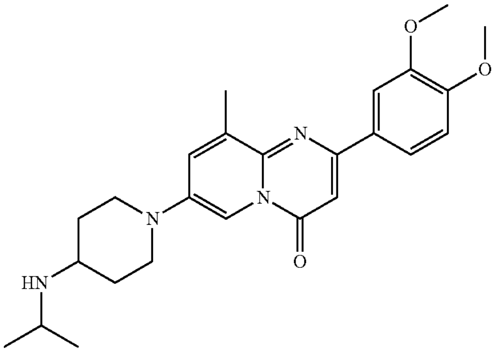
417
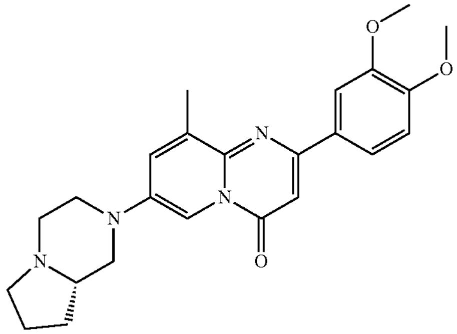
418
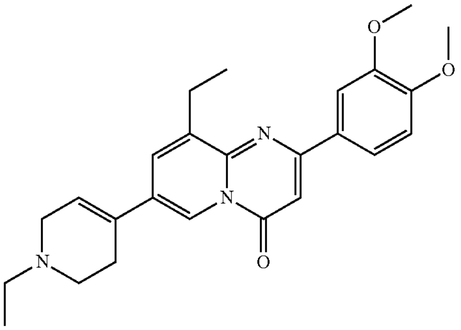

-continued
419
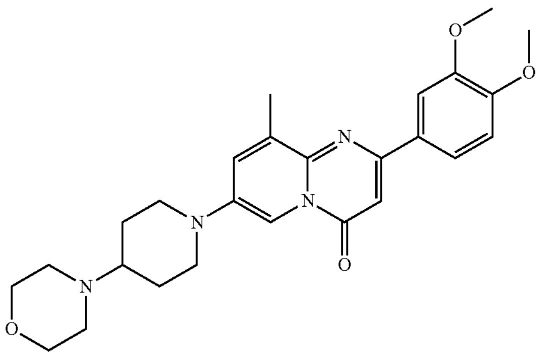
420
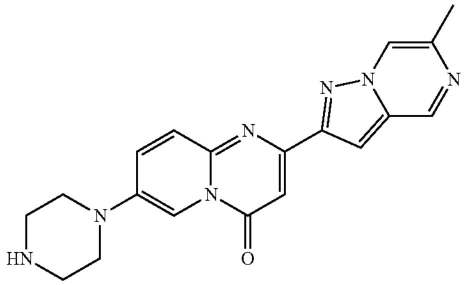
421
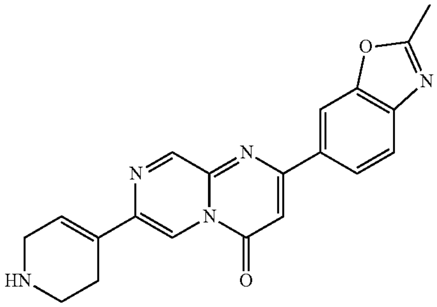
422
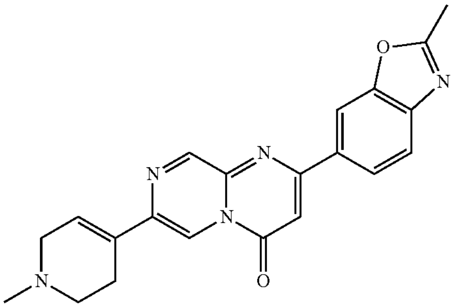
423
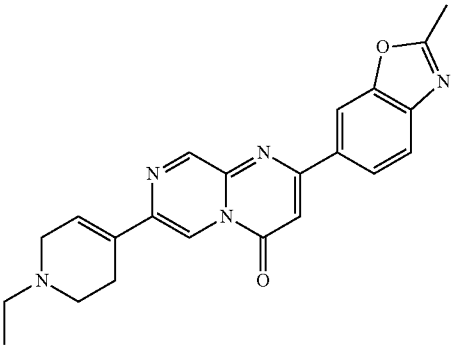
-continued
424
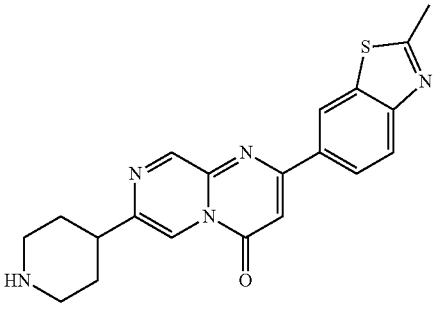
425
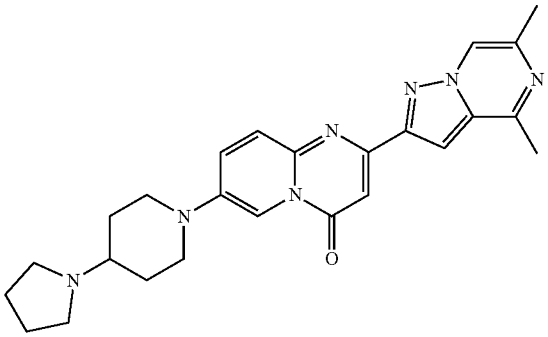
426
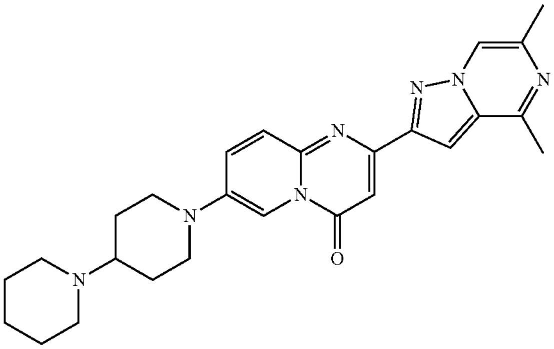
427
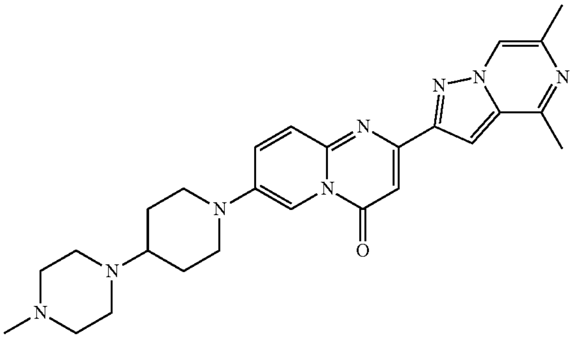

-continued
428
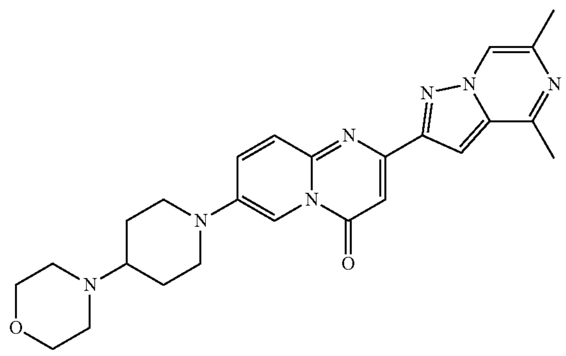
429
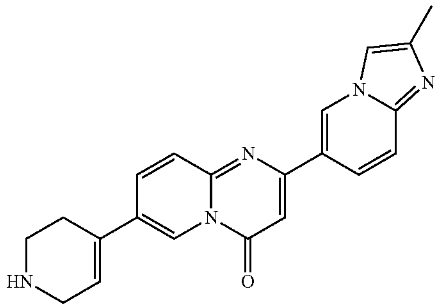
430
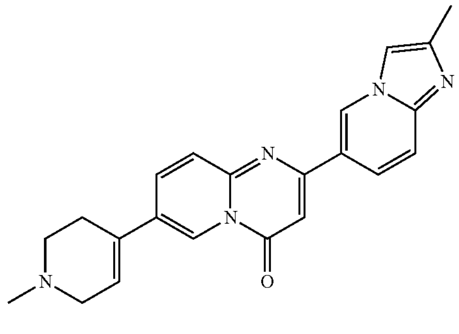
431
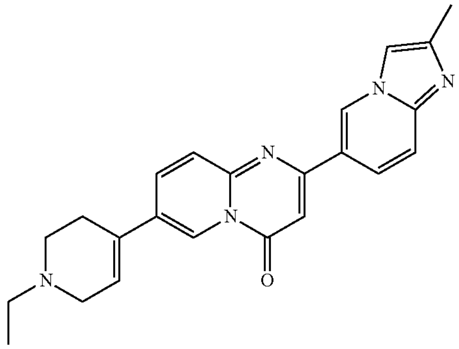
-continued
432
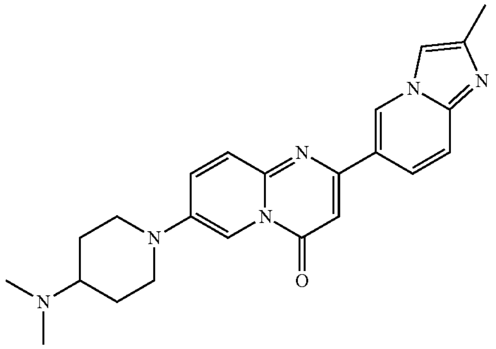
433
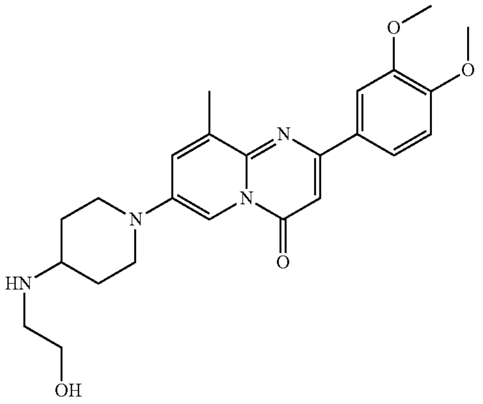
434
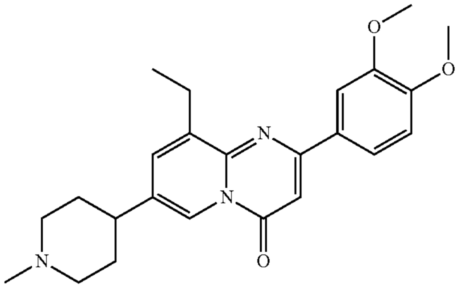
435
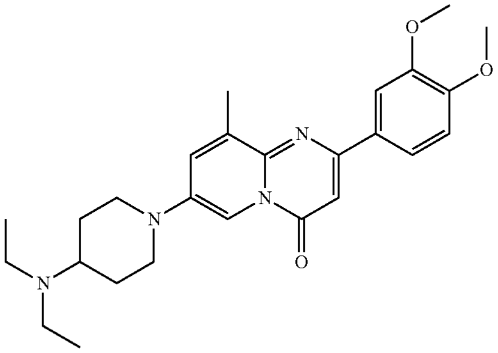

-continued
436
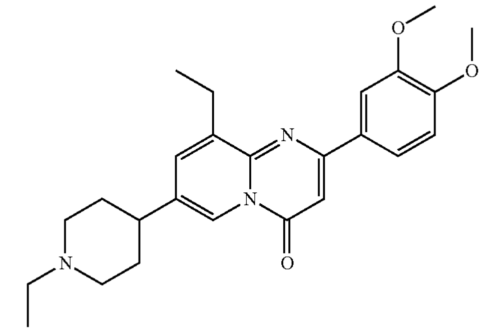
437
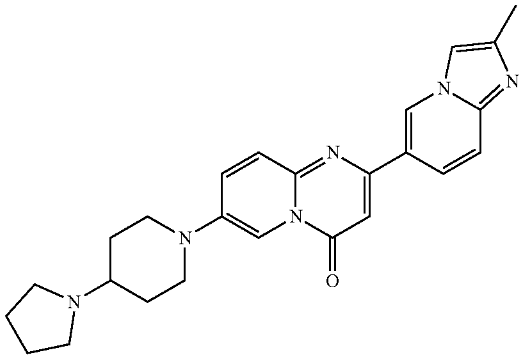
438
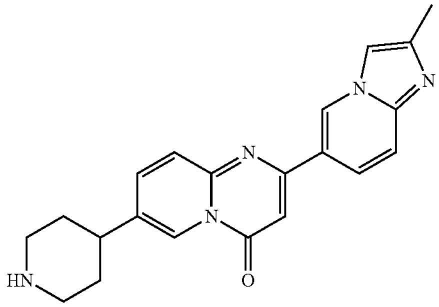
439
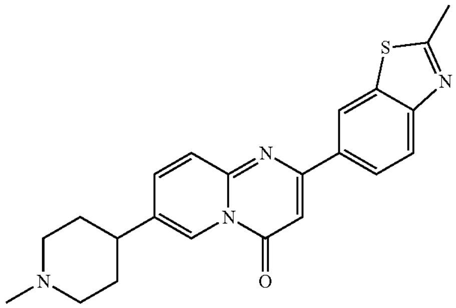
440
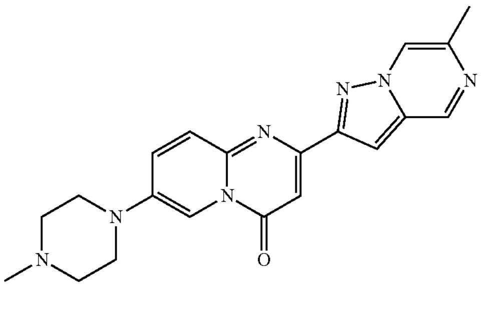
-continued
441
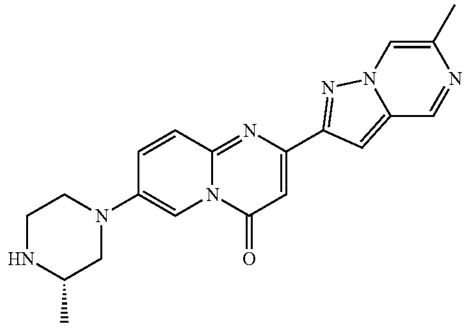
442
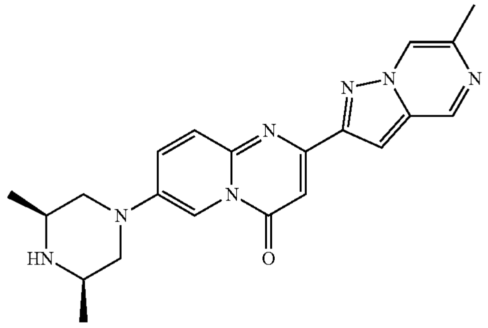
443
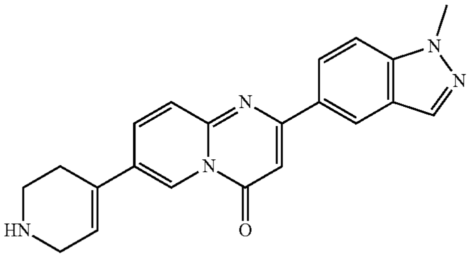
444
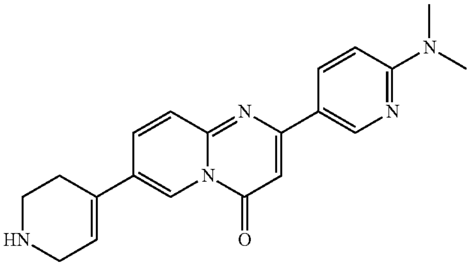
445
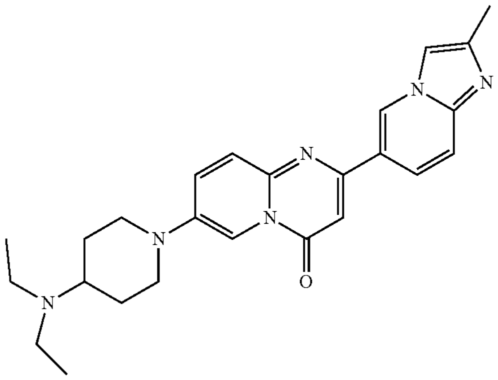

-continued
446
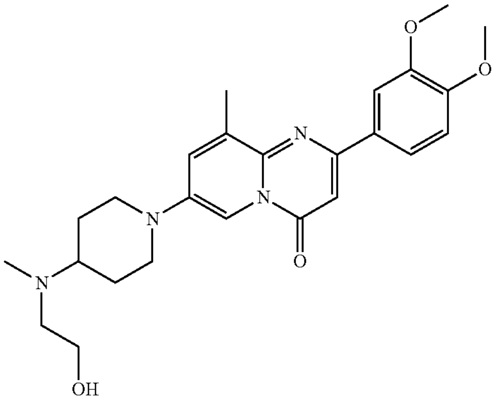
447
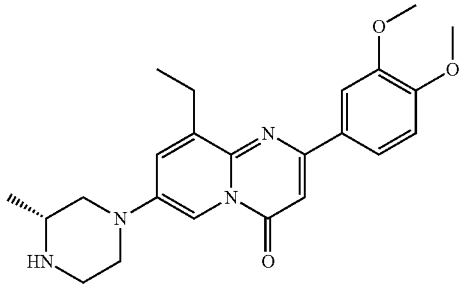
448
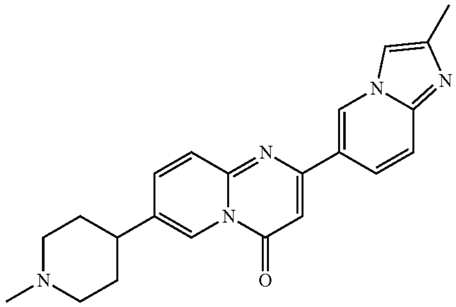
449
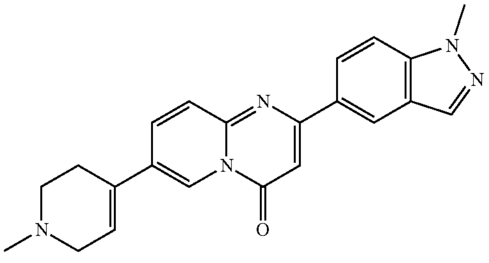
450
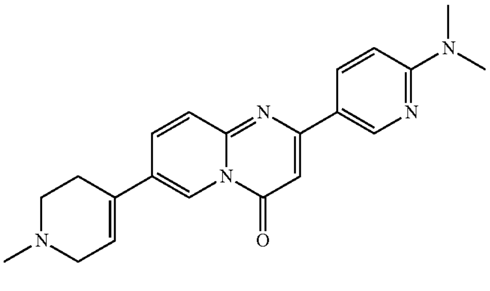
-continued
451
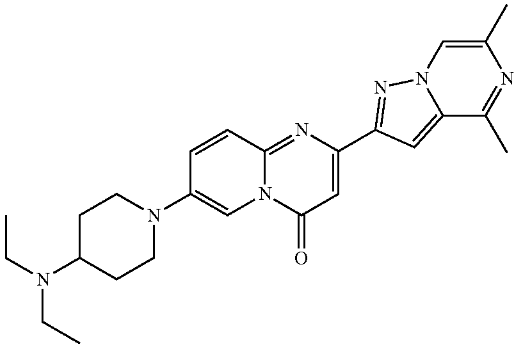
452
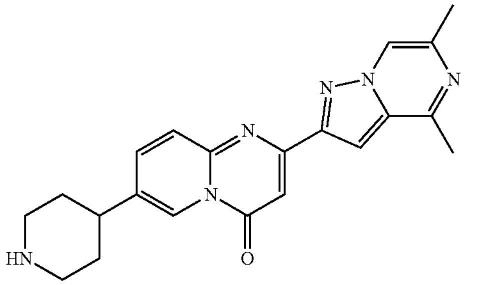
453
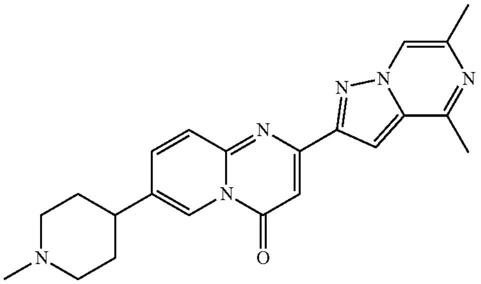
454
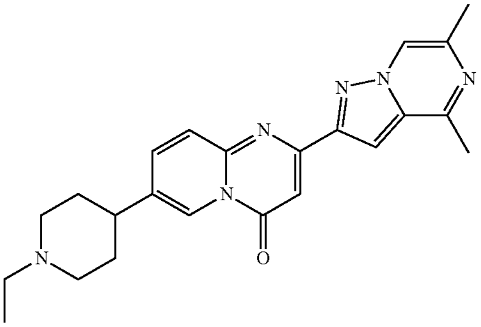
455
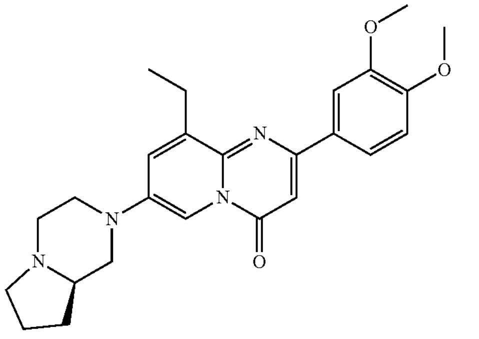

-continued
456
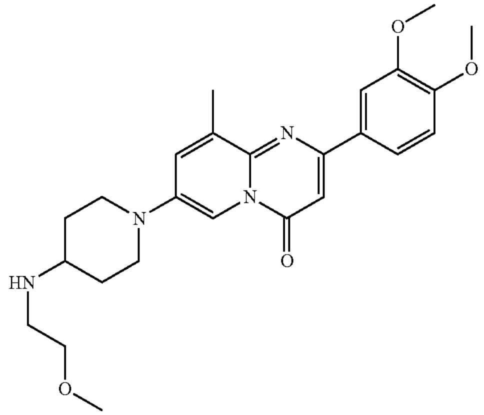
457
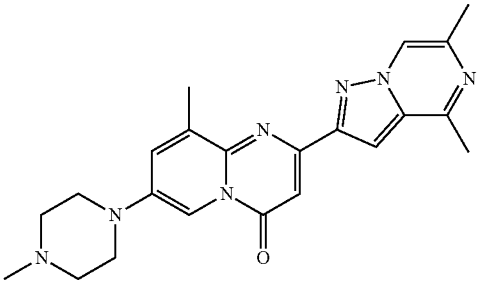
458
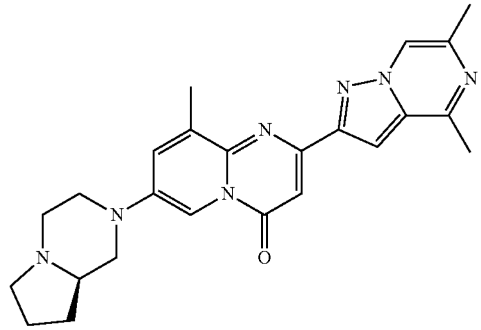
459
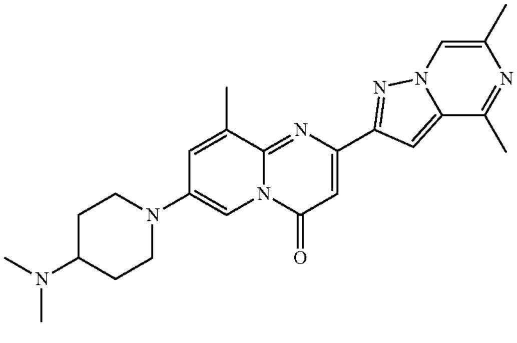
-continued
460
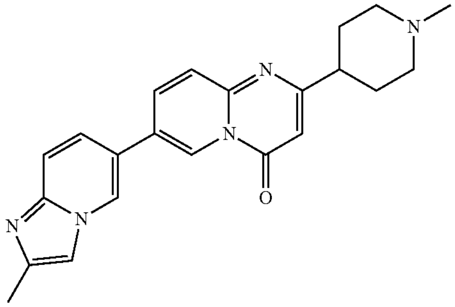
461
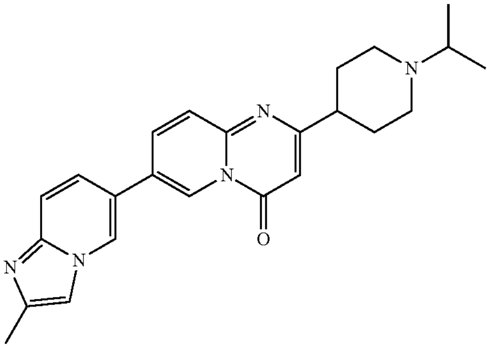
462
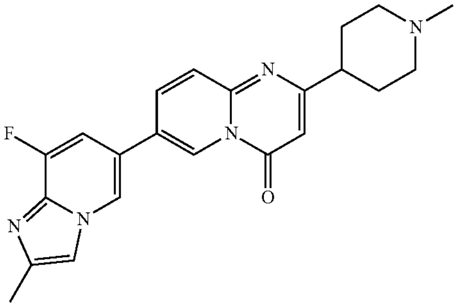
463
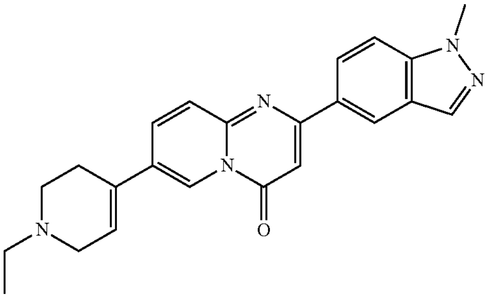
464
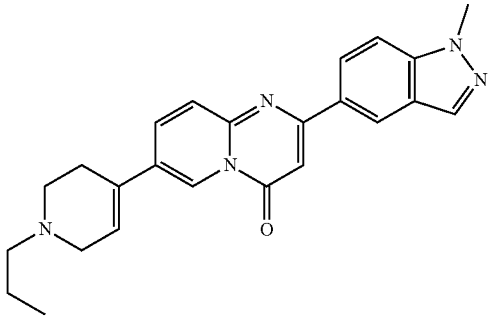

-continued
465
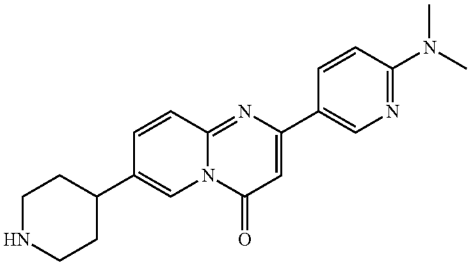
466
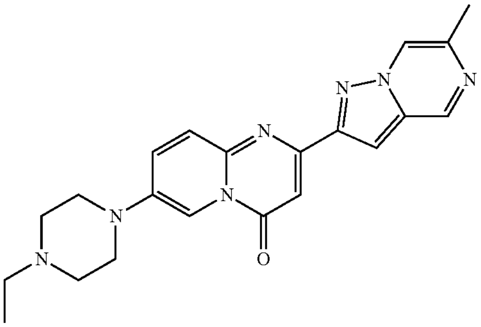
467
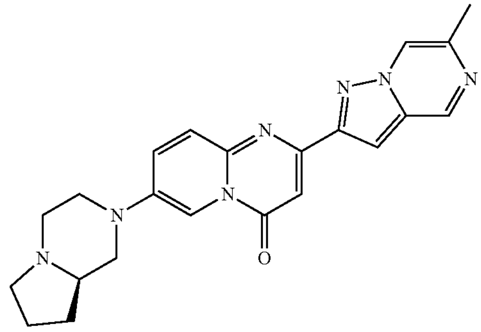
468
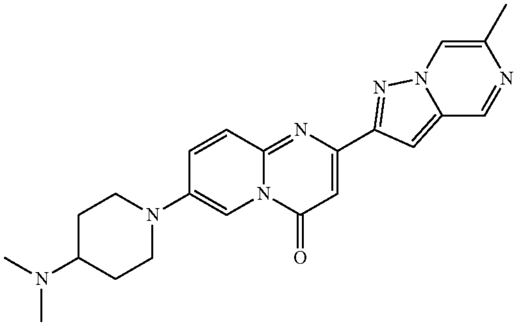
469
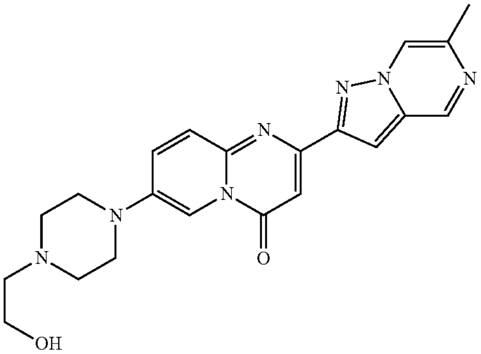
-continued
470
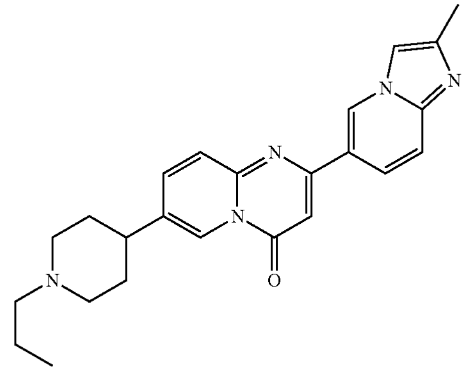
471
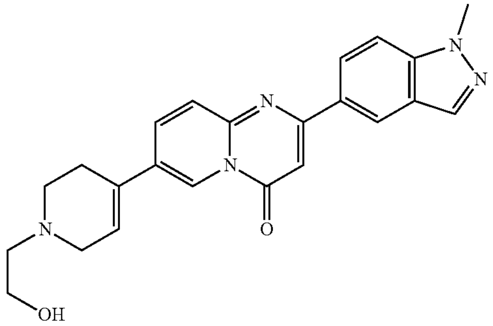
472
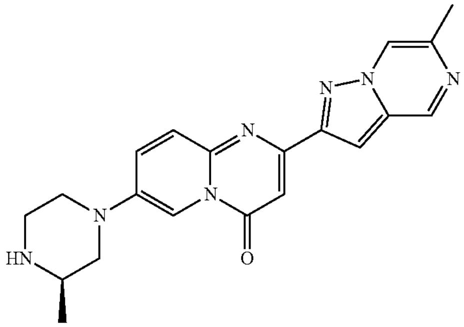
473
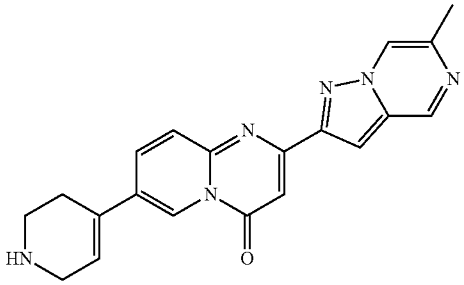
474
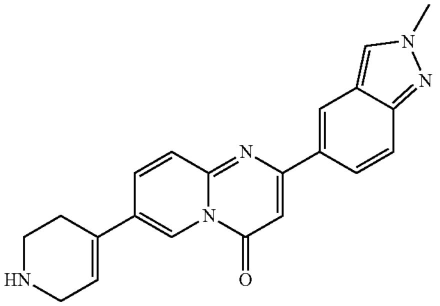

-continued
475
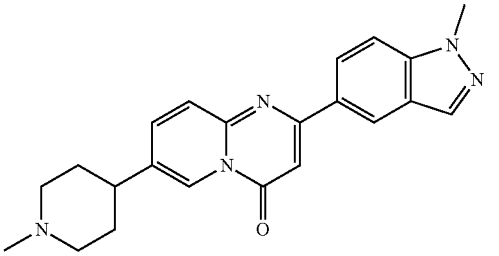
476
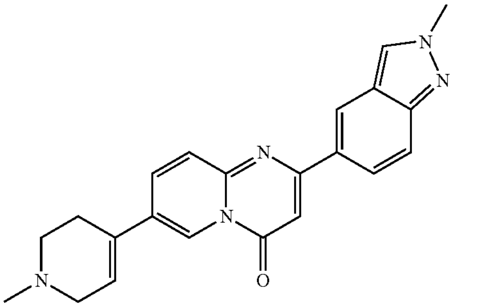
477
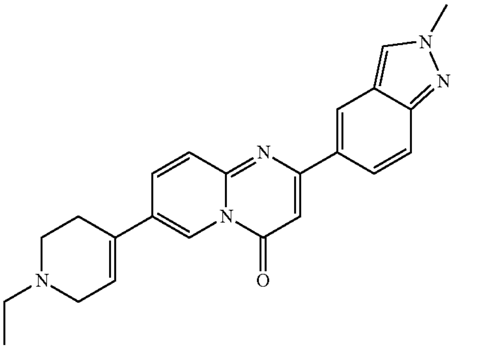
478
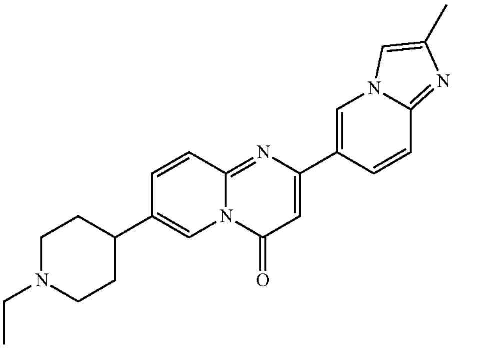
479
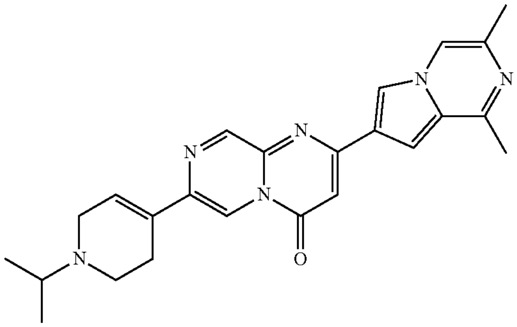
-continued
480
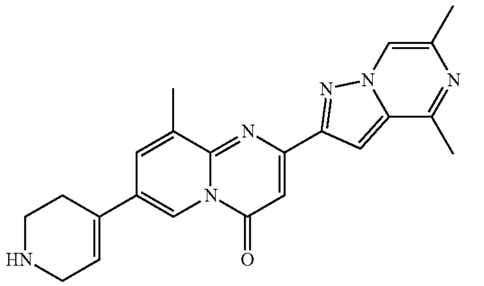
481
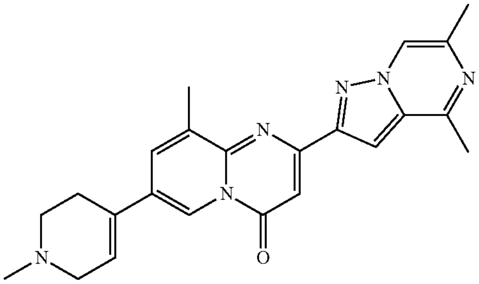
482
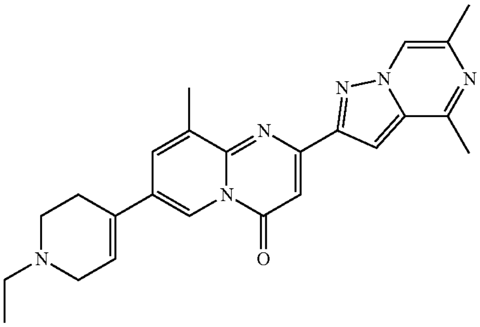
483
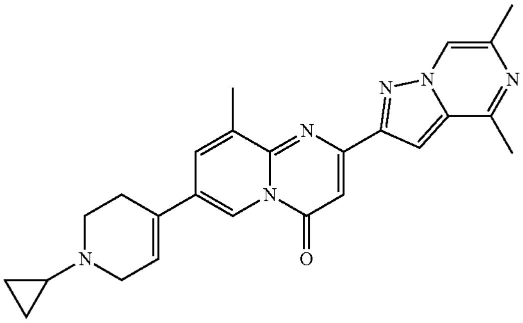
484
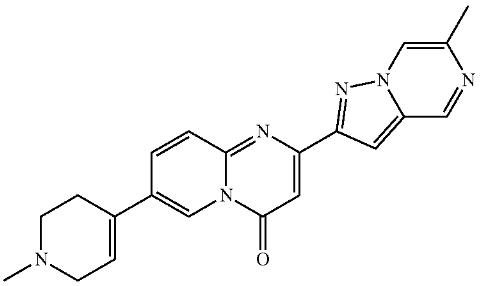

-continued
485
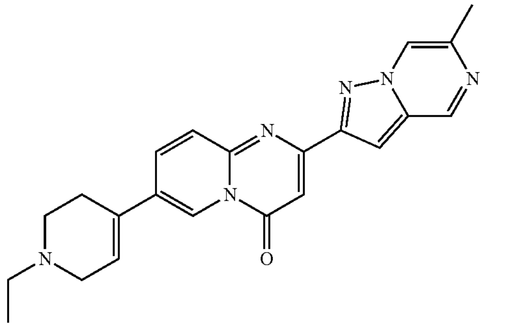
486
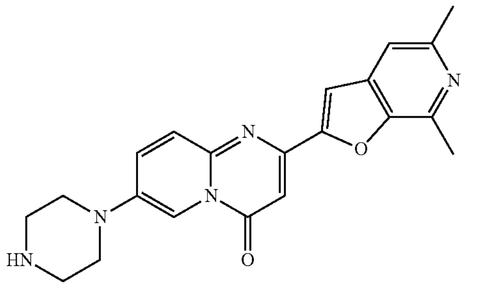
487
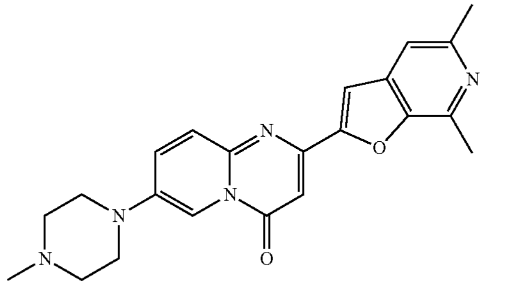
488
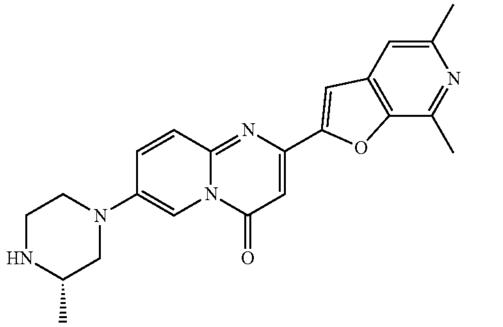
489
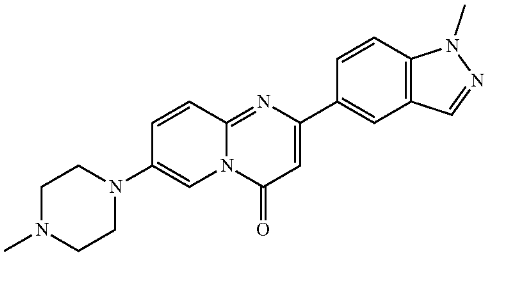
-continued
490
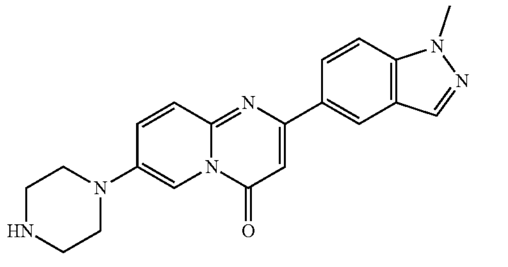
491
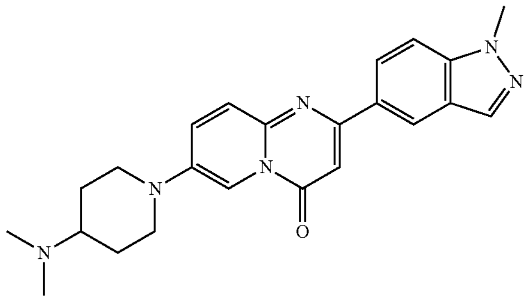
492
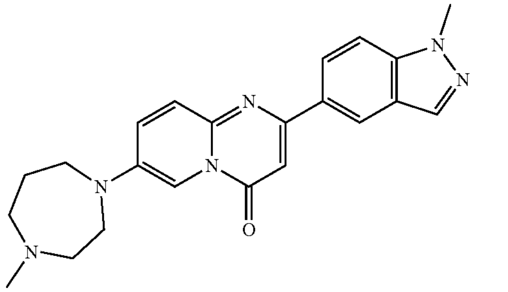
493
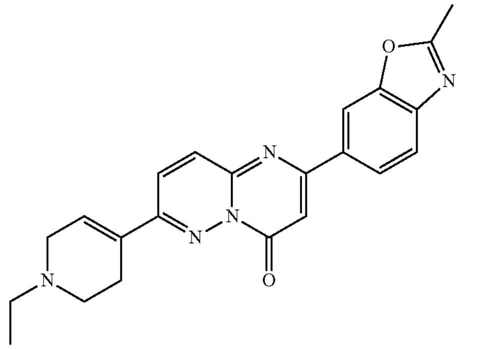
494
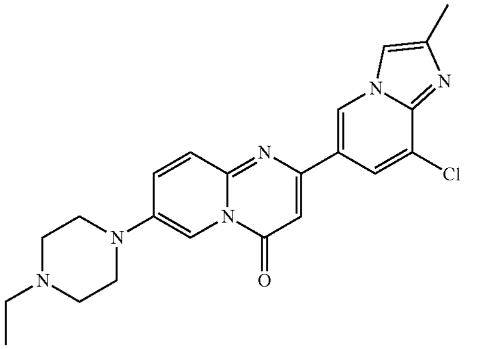

-continued
495
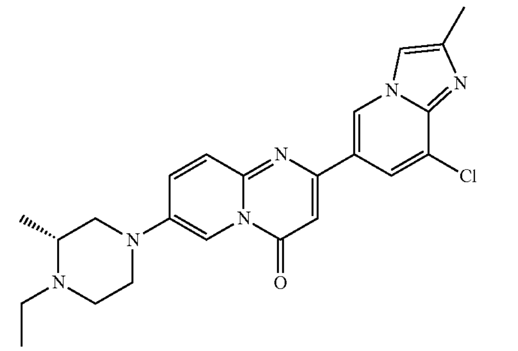
496
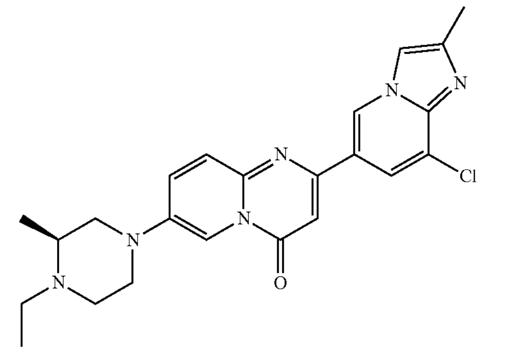
497
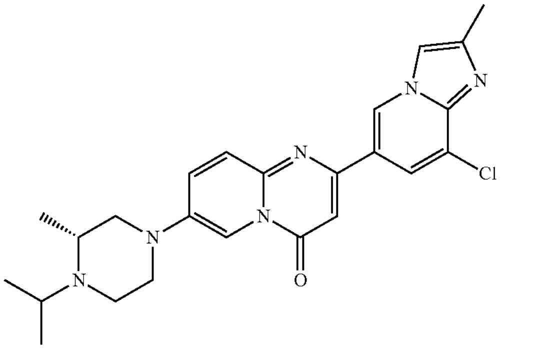
498
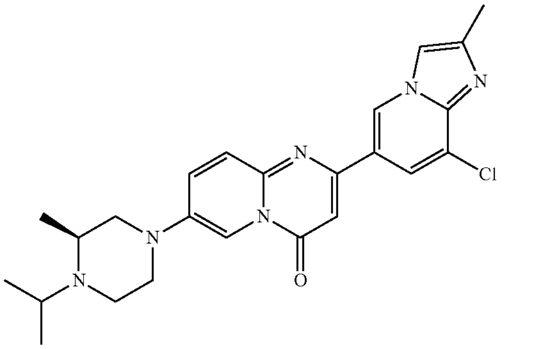
-continued
499
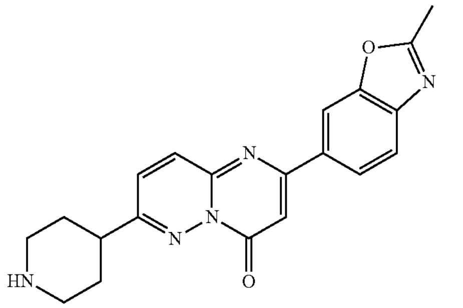
500
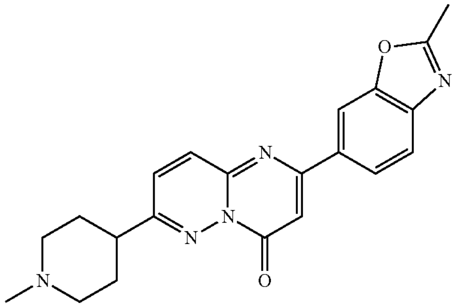
501
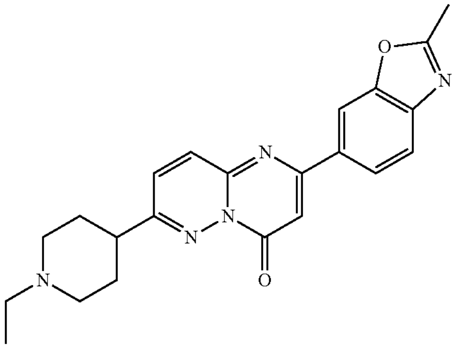
502
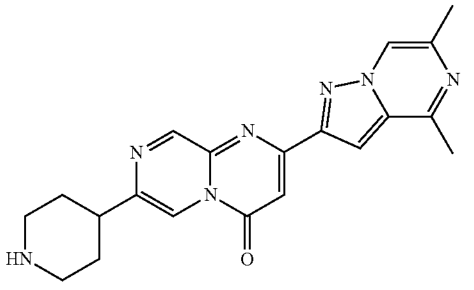
503
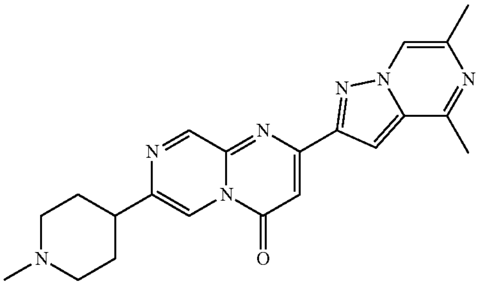

-continued
504
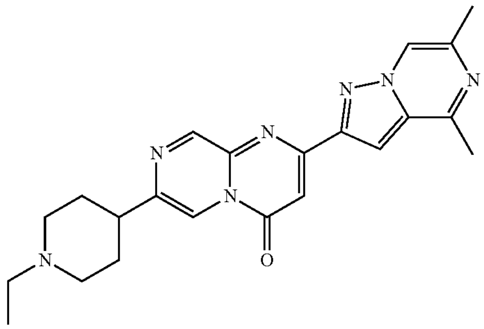
505
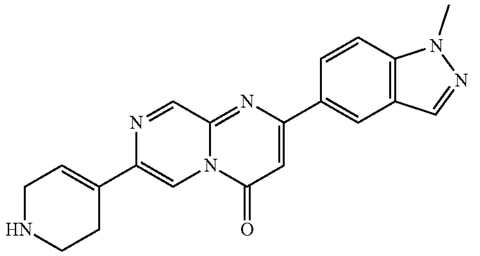
506
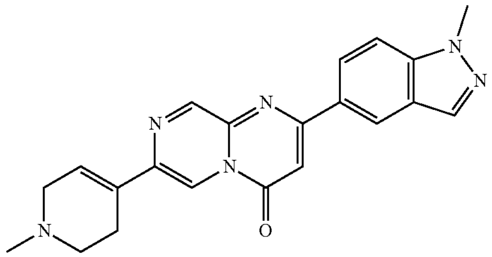
507
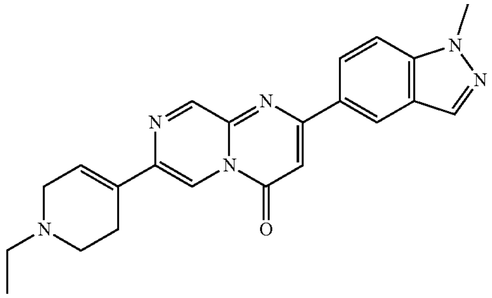
508
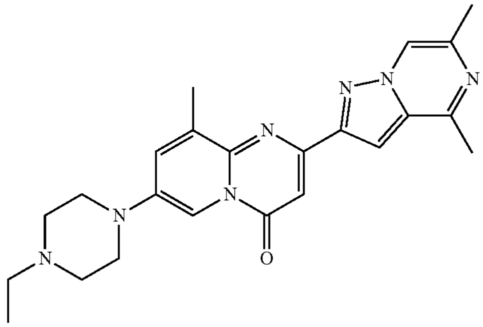
-continued
509
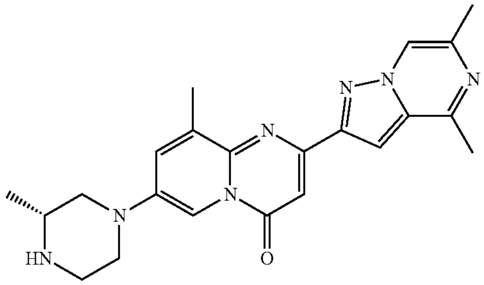
510
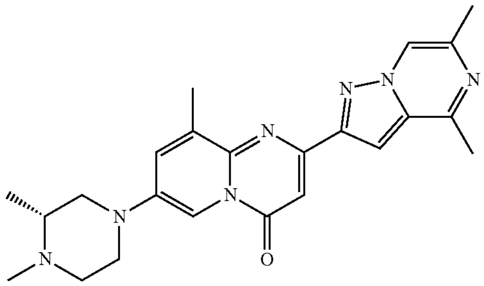
511
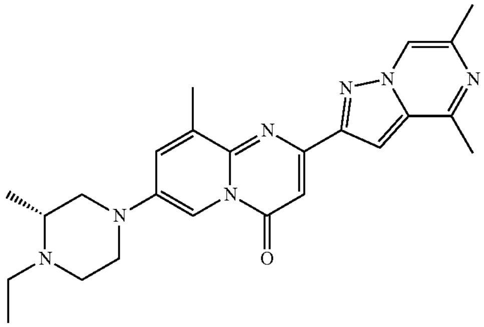
512
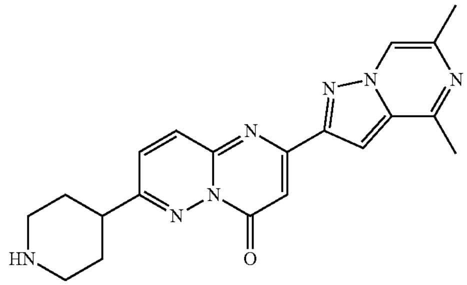
513
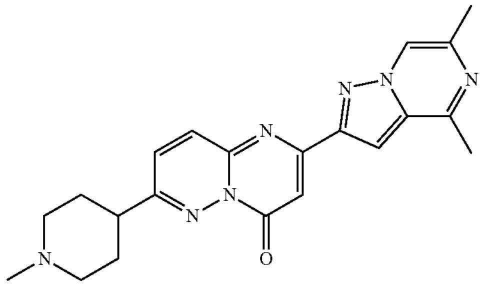

-continued
514
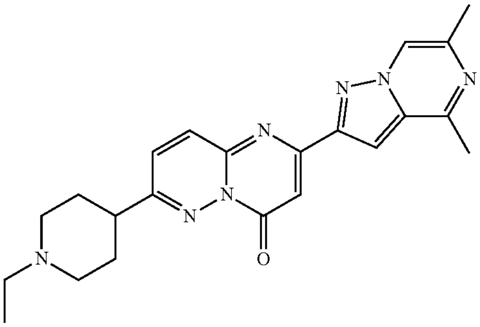
515
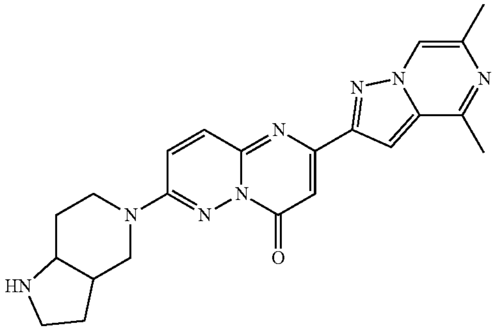
516
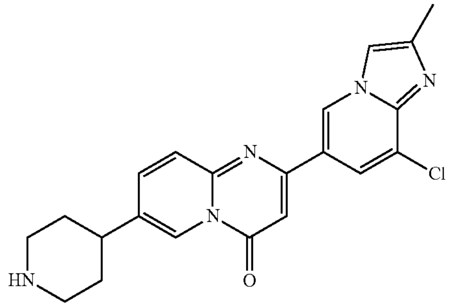
517
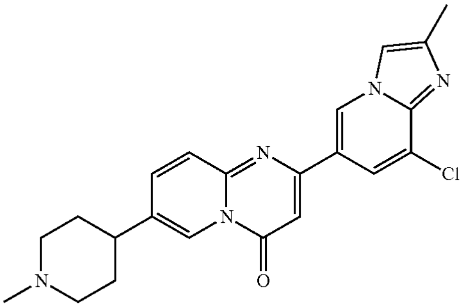
518
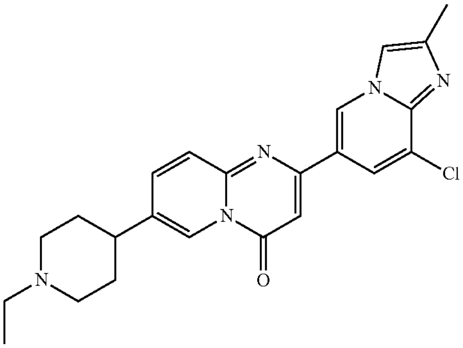
-continued
519
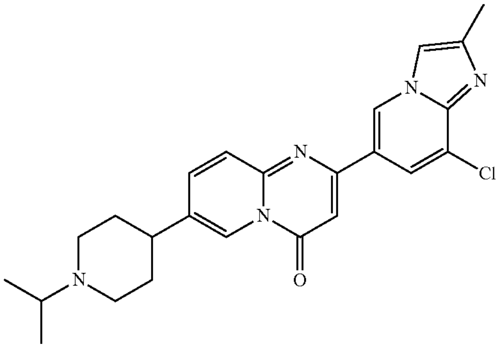
520
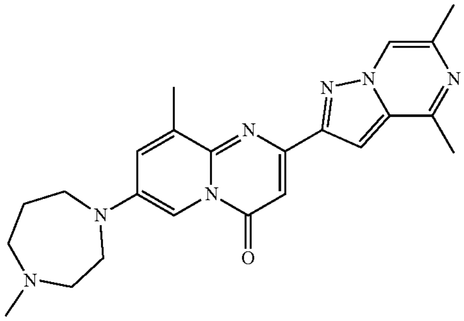
521
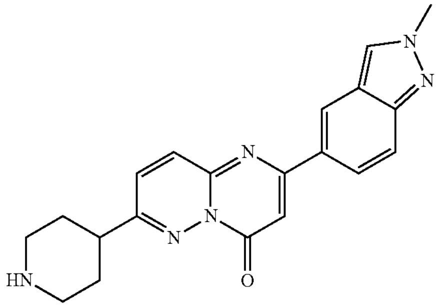
522
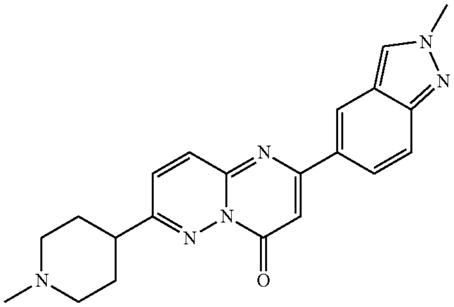

-continued
523
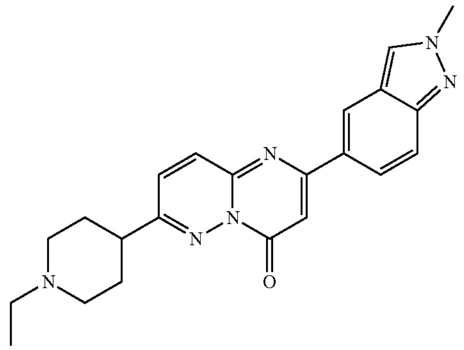
524
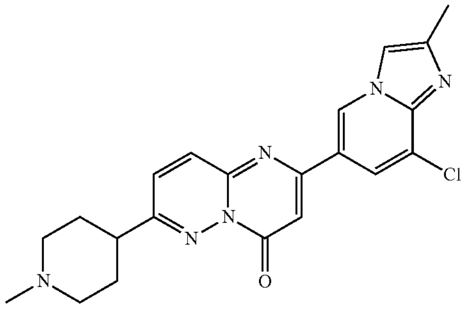
525
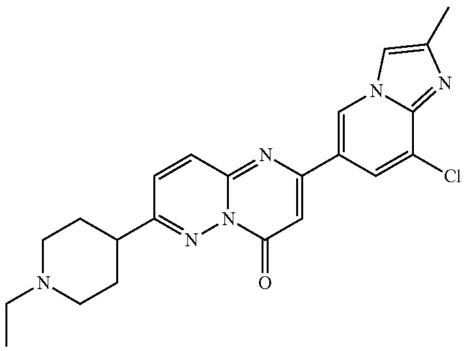
526
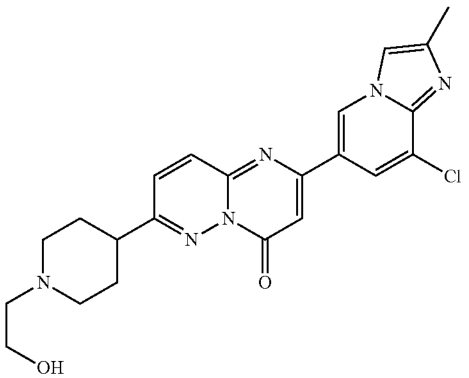
-continued
527
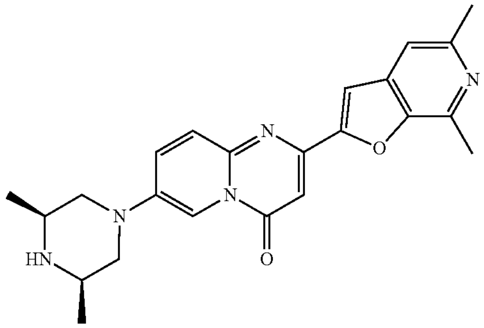
528
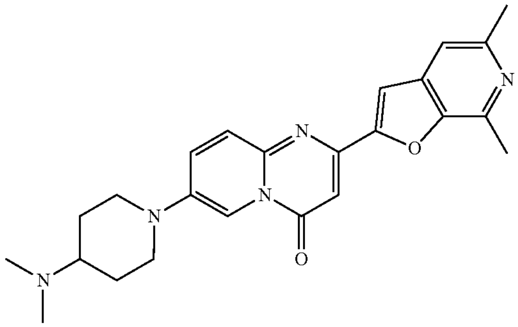
529
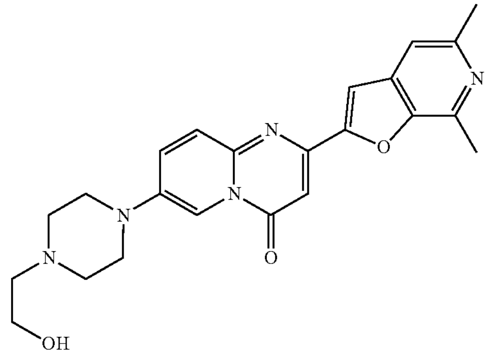
530
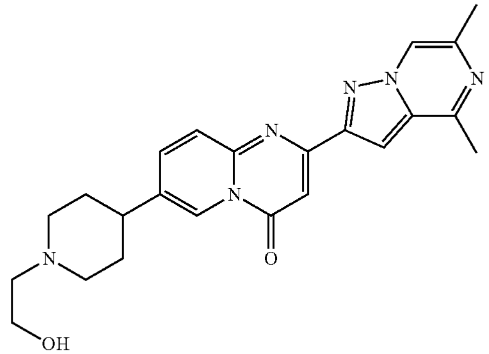

-continued
531
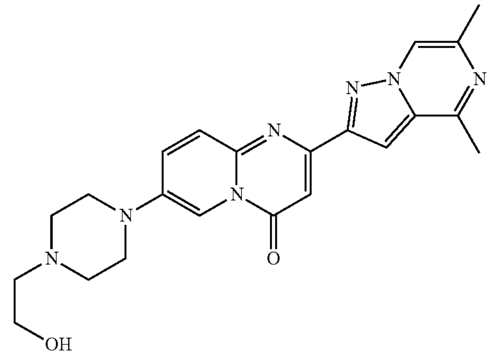
532
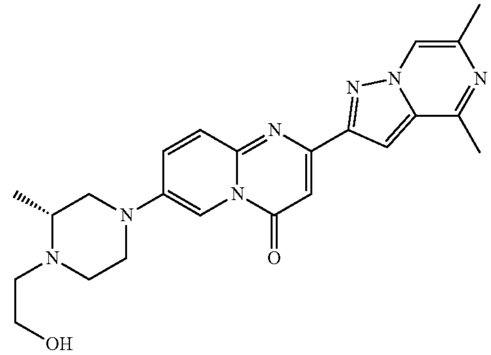
533
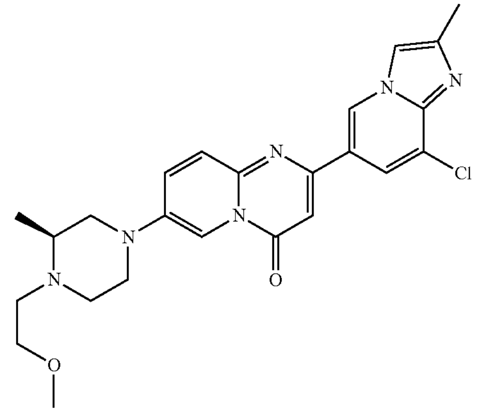
534
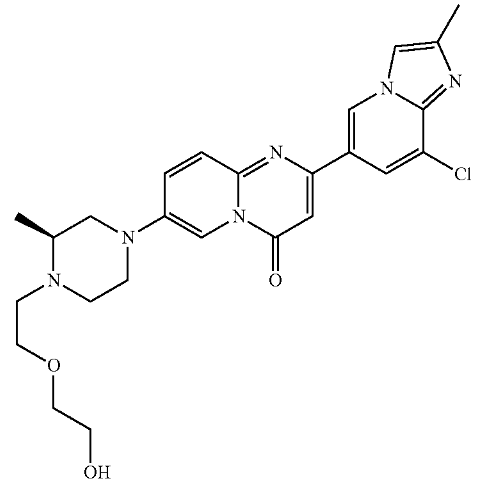
-continued
535
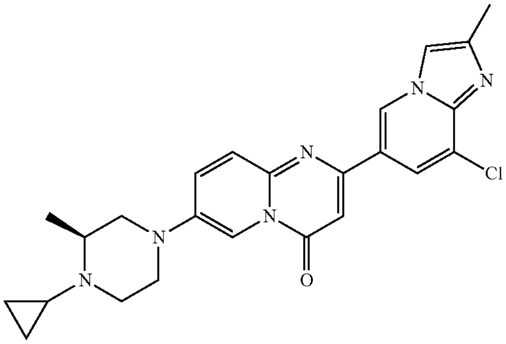
536
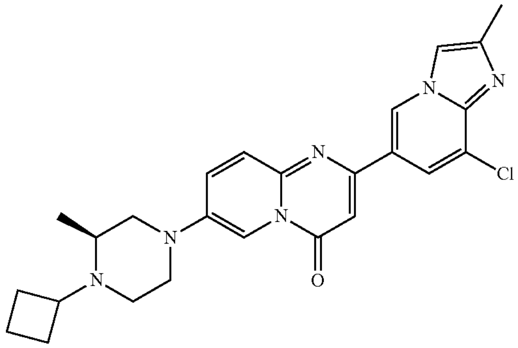
537
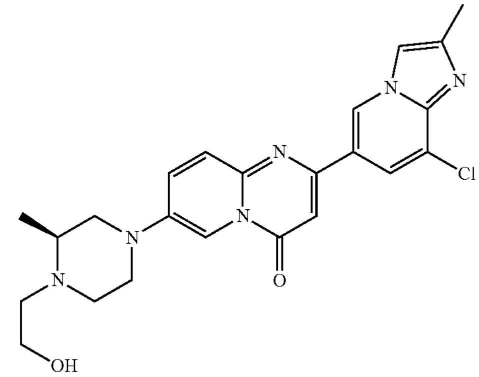
538
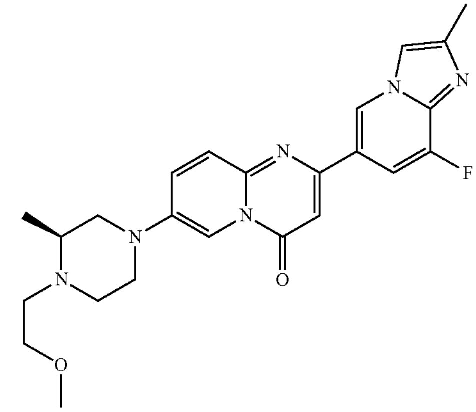

539
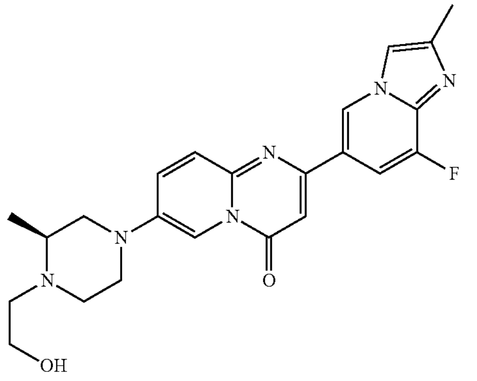
540
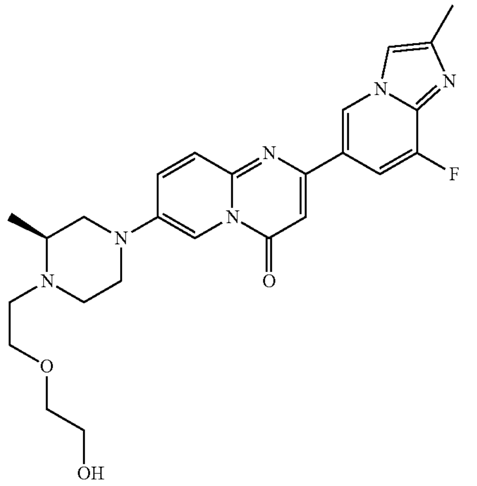
541
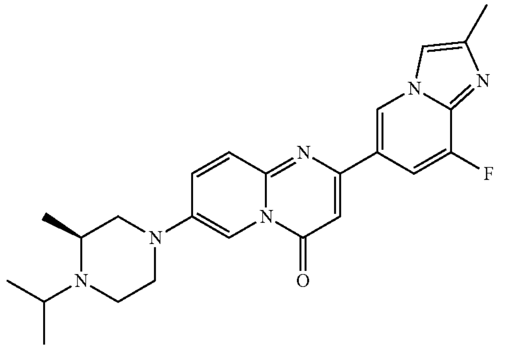
542
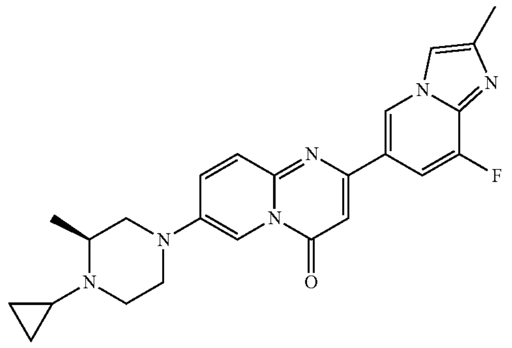
543
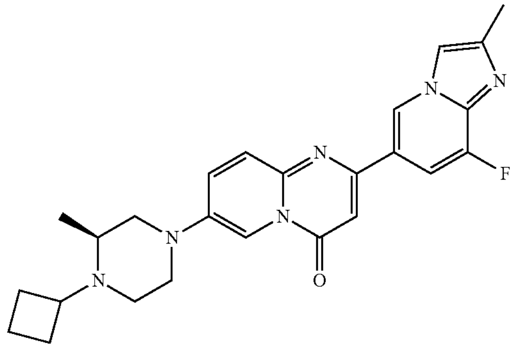
544
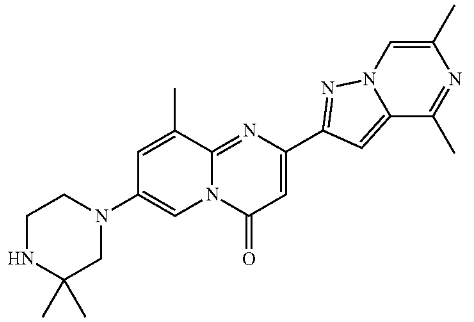
545
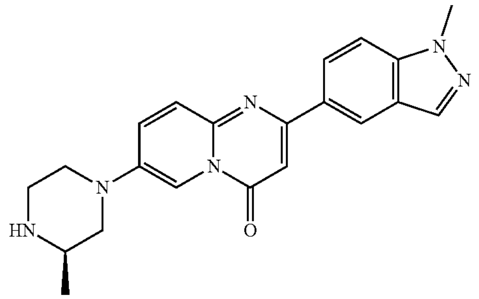
546
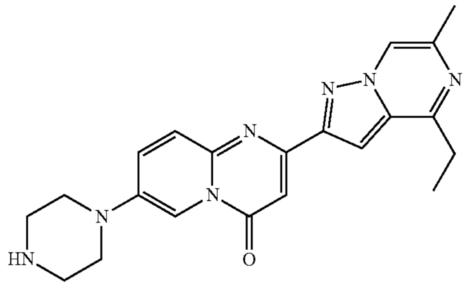
547
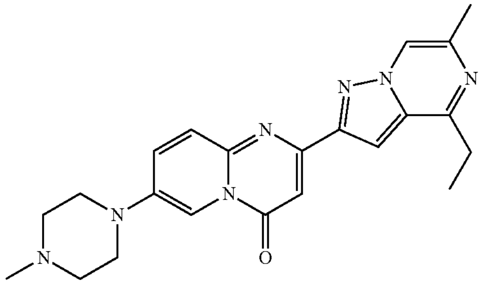

-continued
548
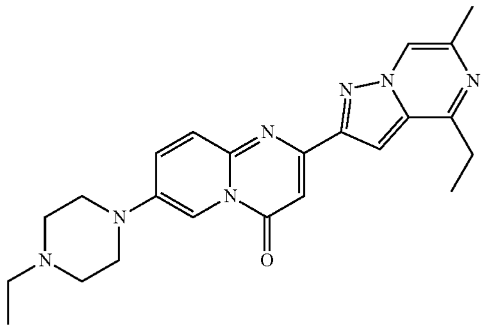
549
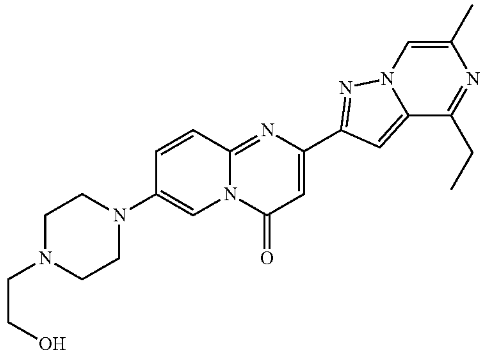
550
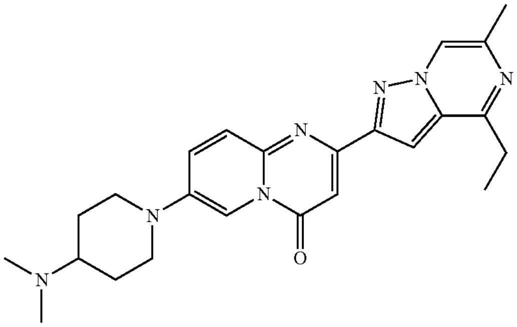
551
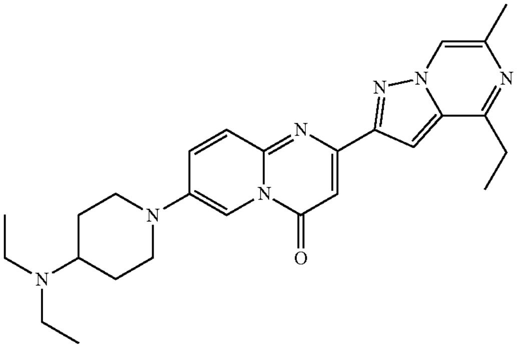
-continued
552
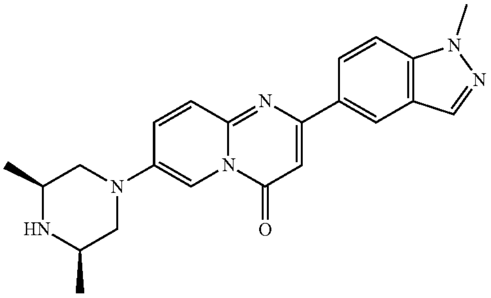
553
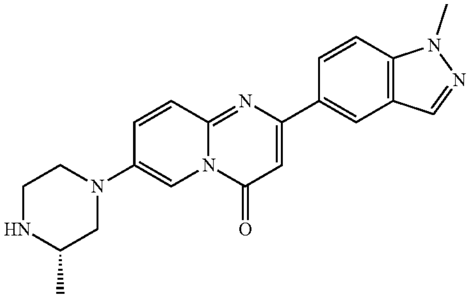
554
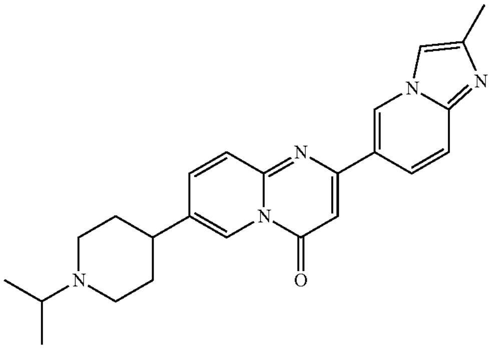
555
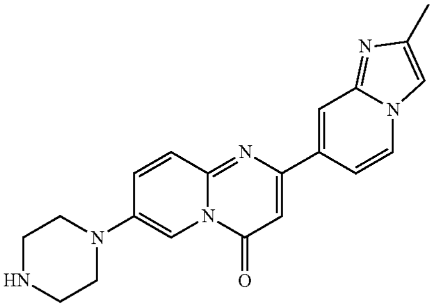
556
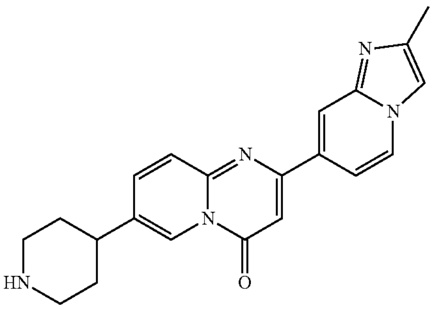

-continued
557
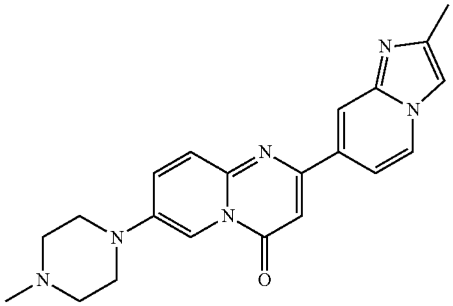
558
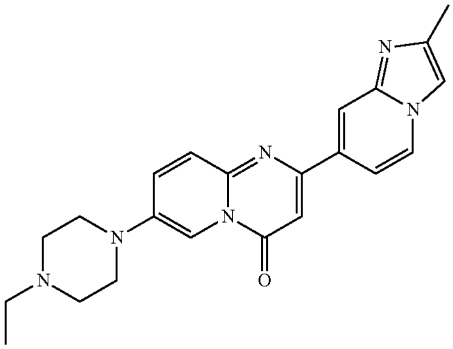
559
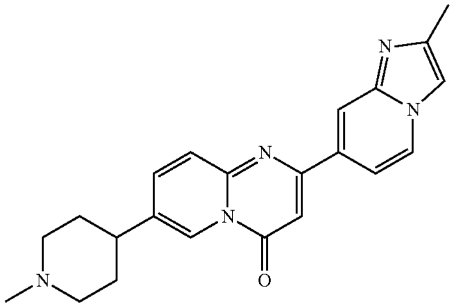
560
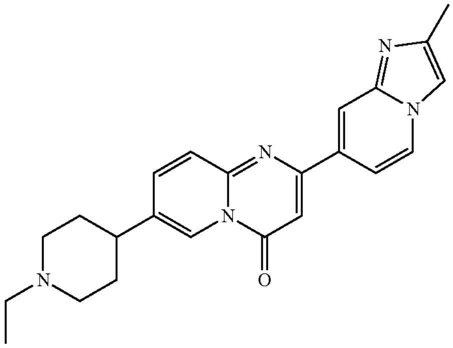
561
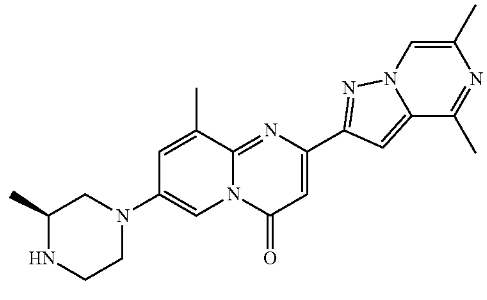
-continued
562
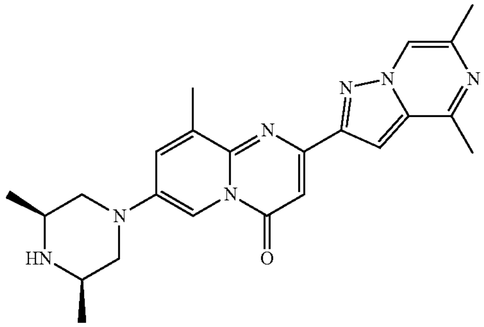
563
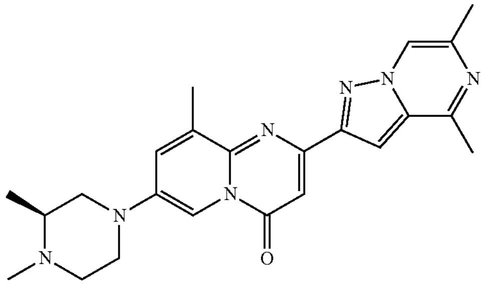
564
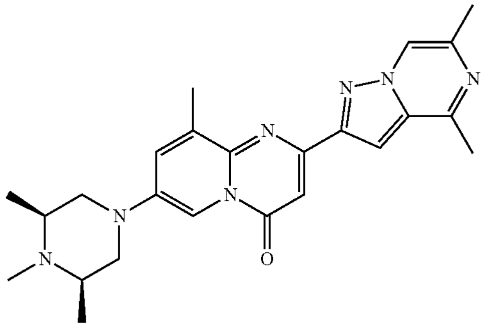
565
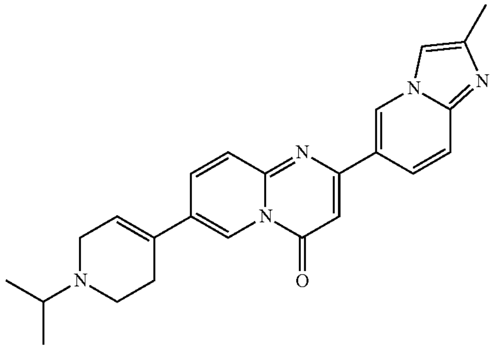
566
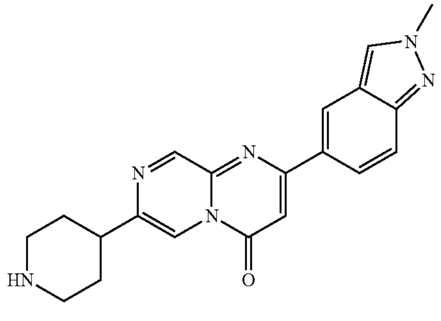

-continued
567
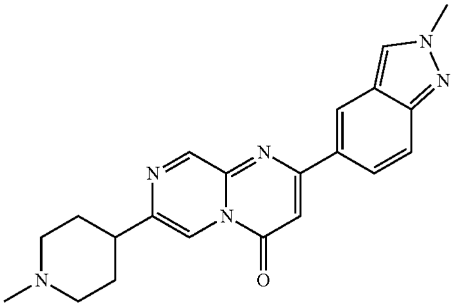
568
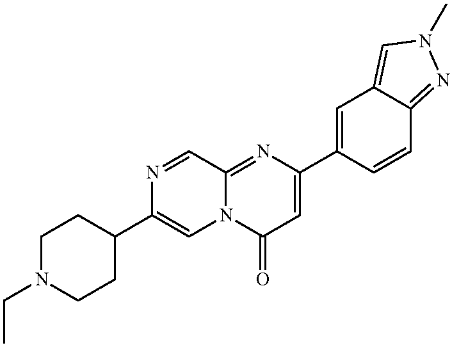
569
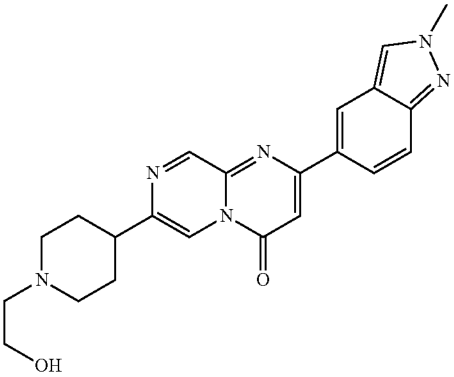
570
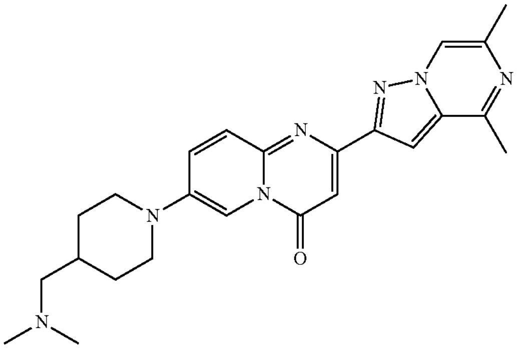
571
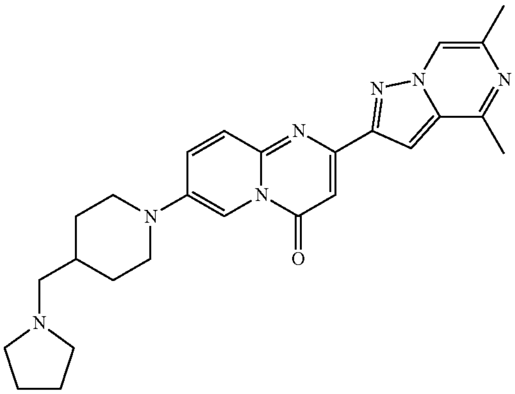
572
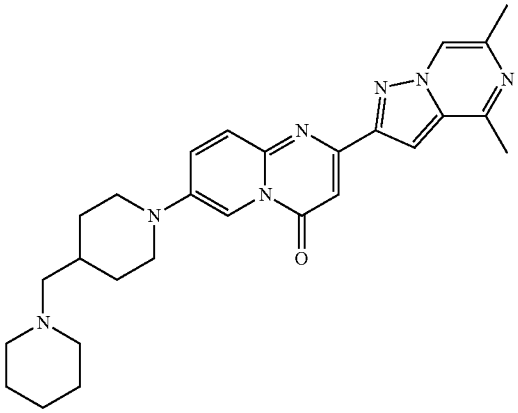
573
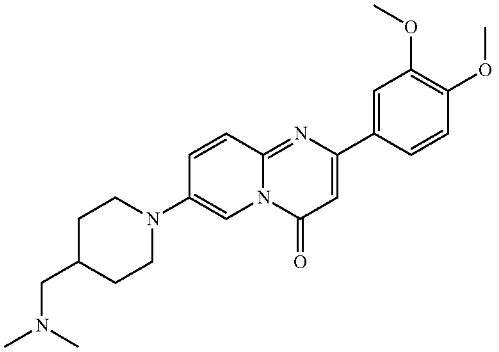
574
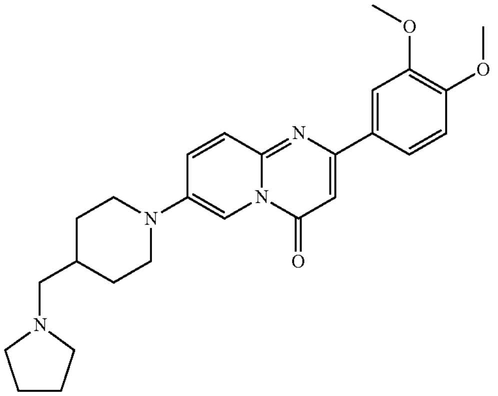

-continued
575
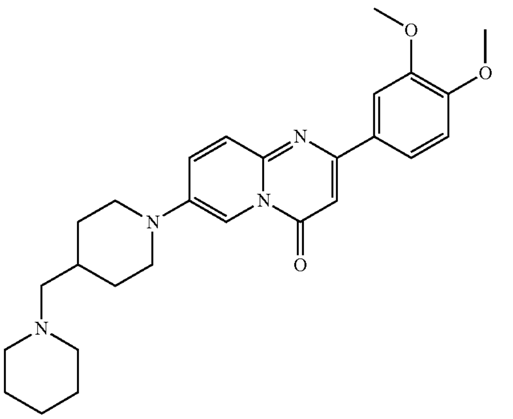
576
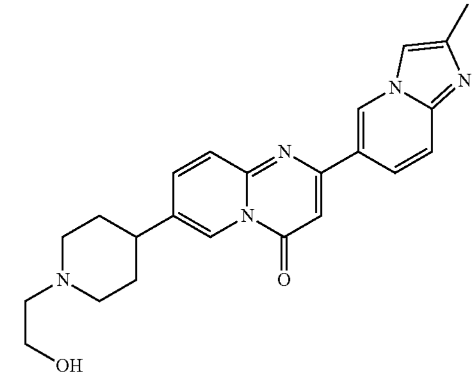
577
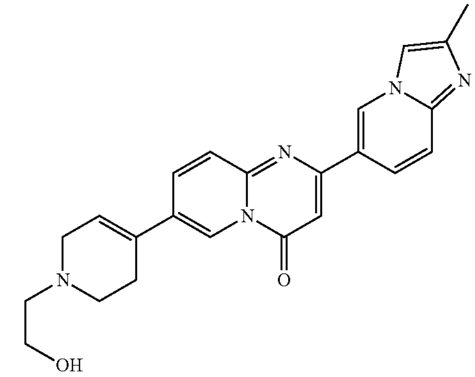
578
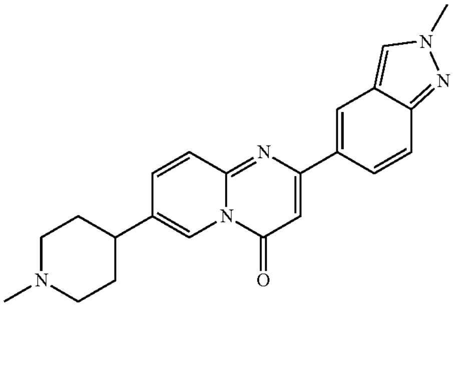
-continued
579
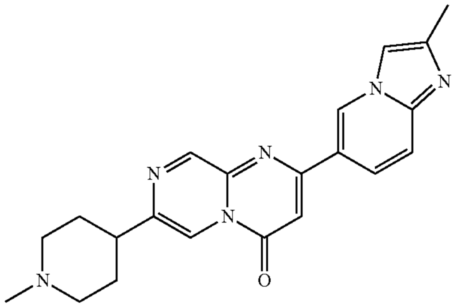
580
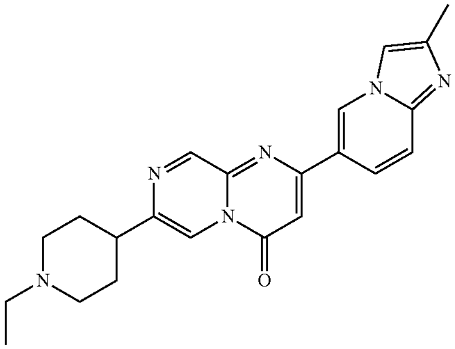
581
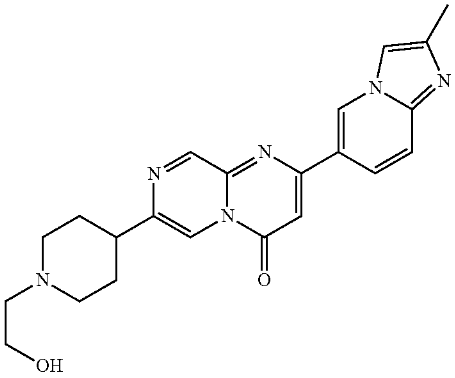
582
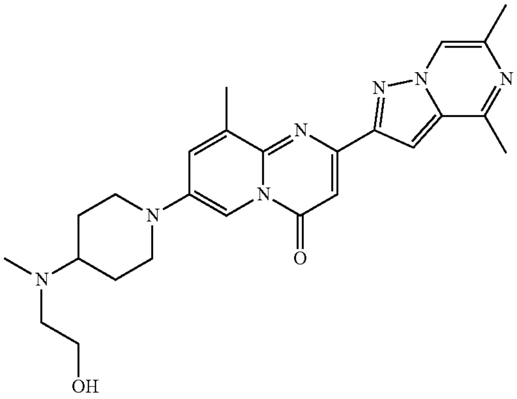

-continued
583
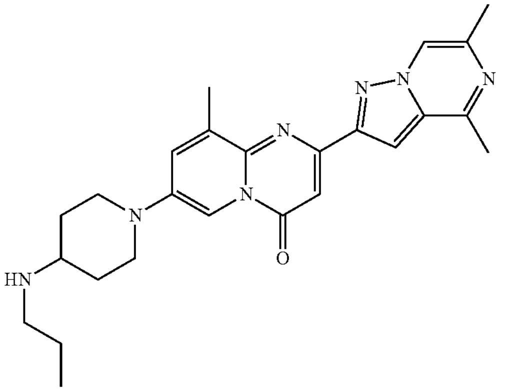
584
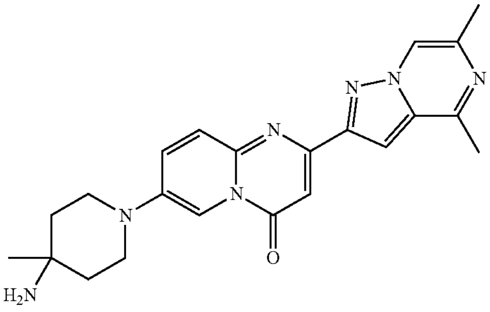
585
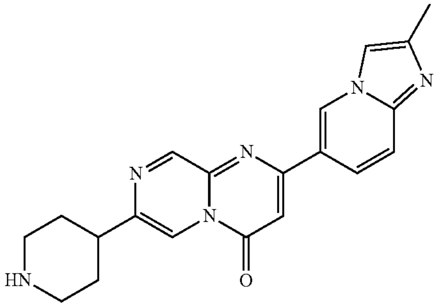
586
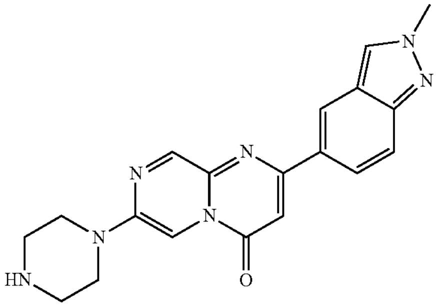
-continued
587
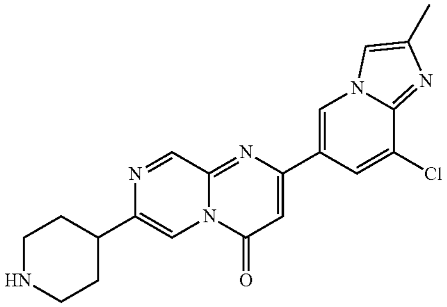
588
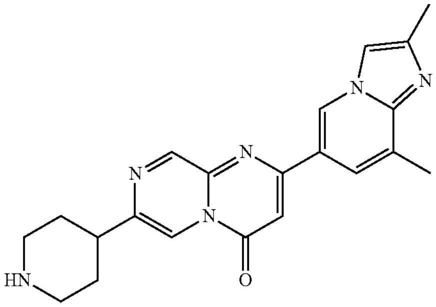
589
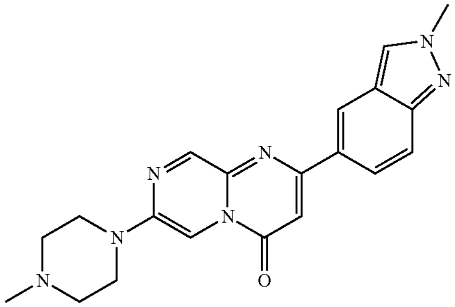
590
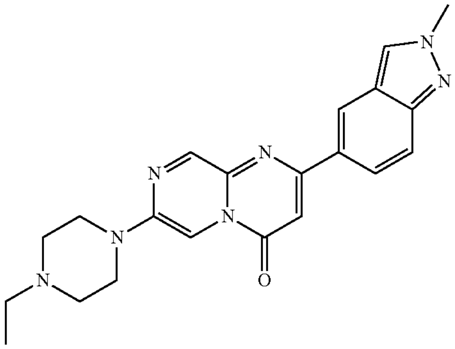

-continued
591
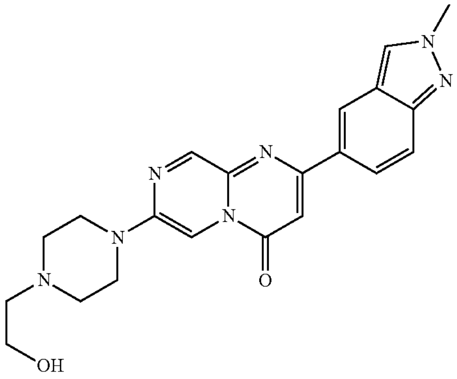
592
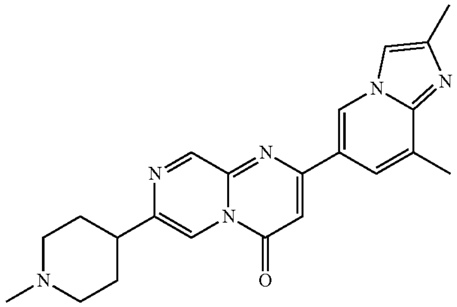
593
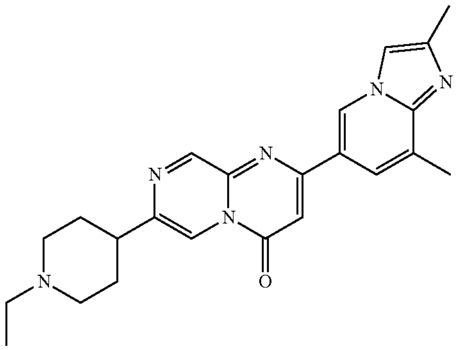
594
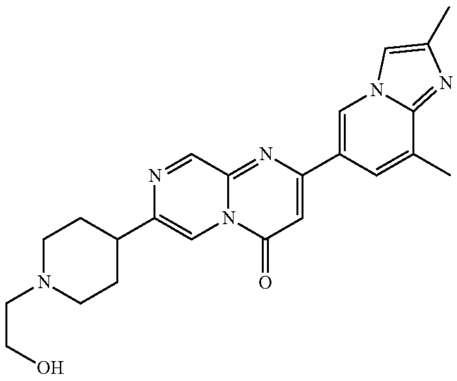
-continued
595
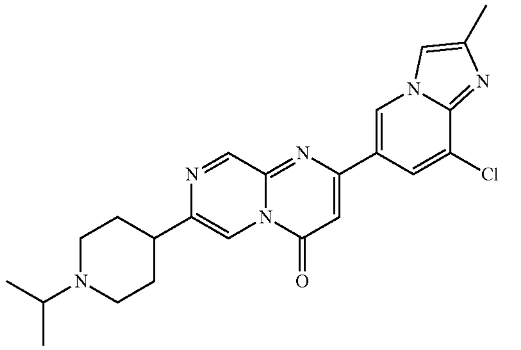
596
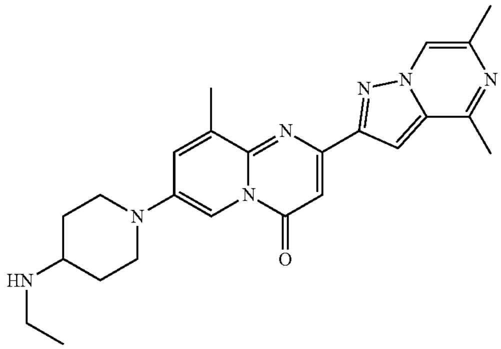
597
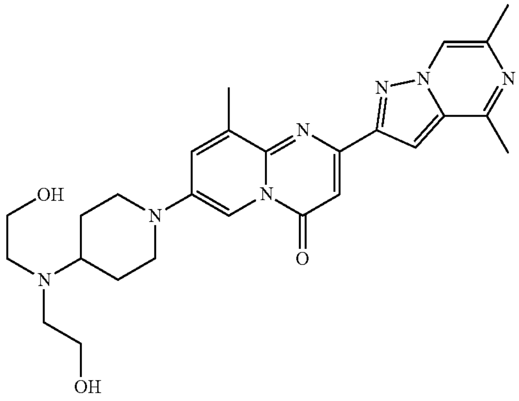
598
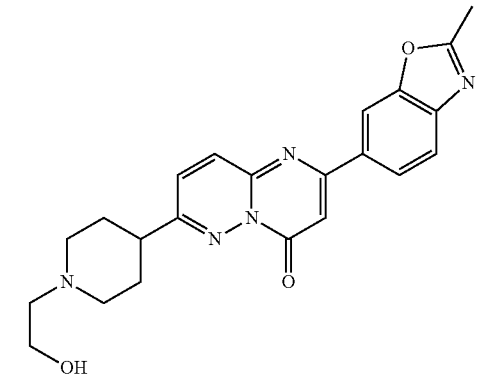

-continued
599
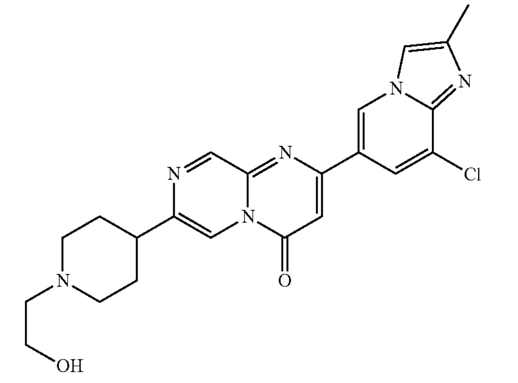
600
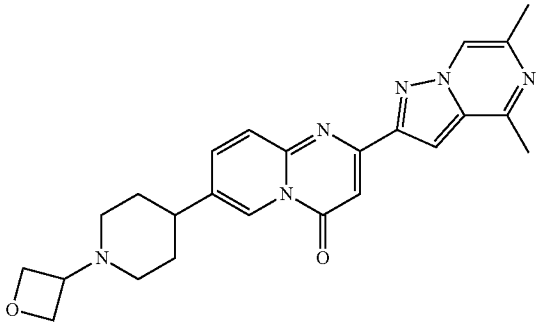
601
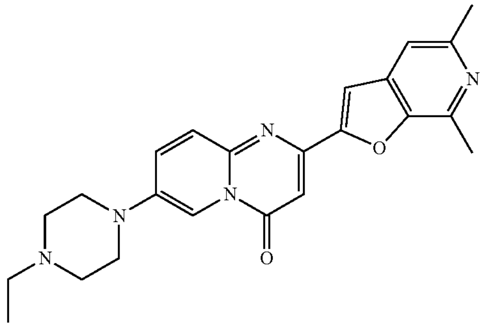
602
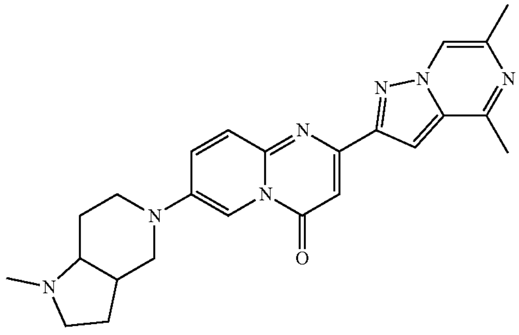
-continued
603
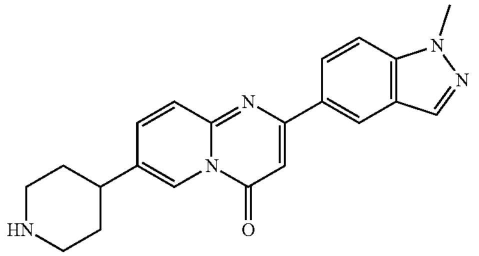
604
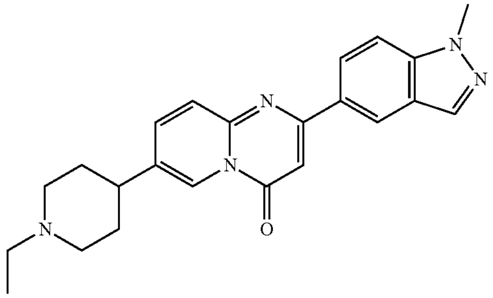
605
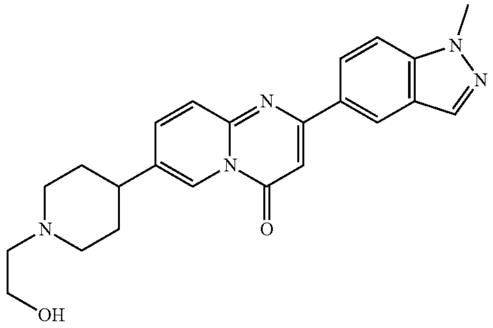
606
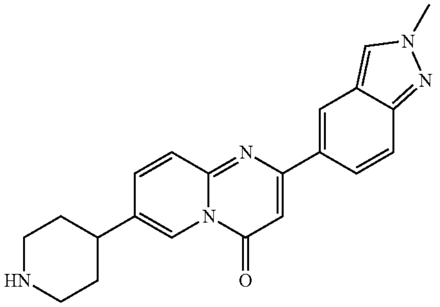
607
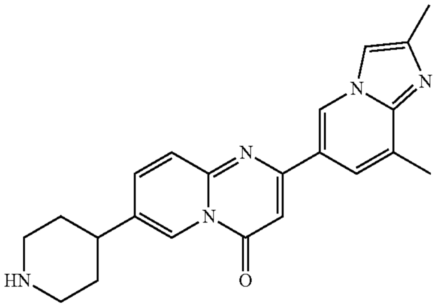

-continued
608
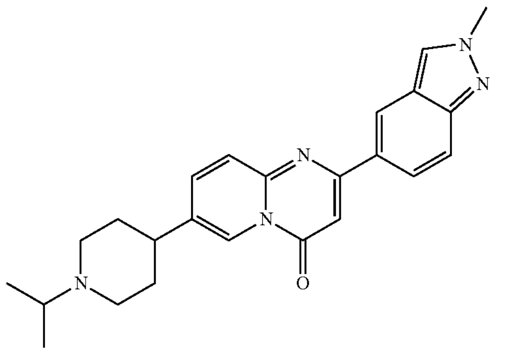
609
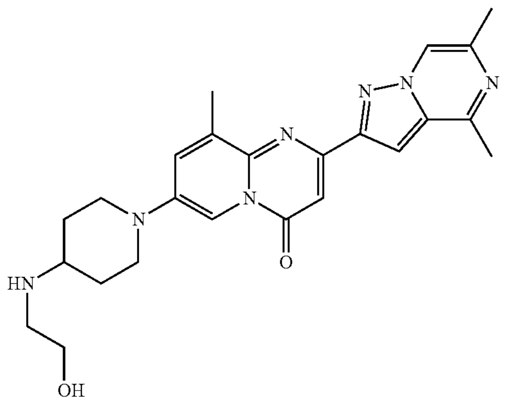
610
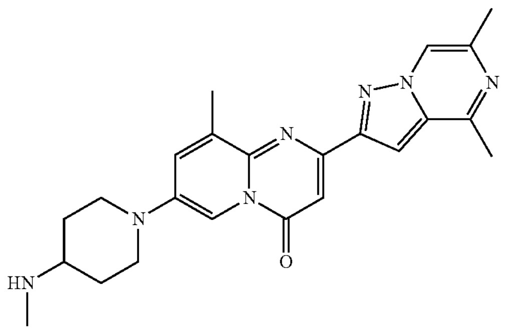
611
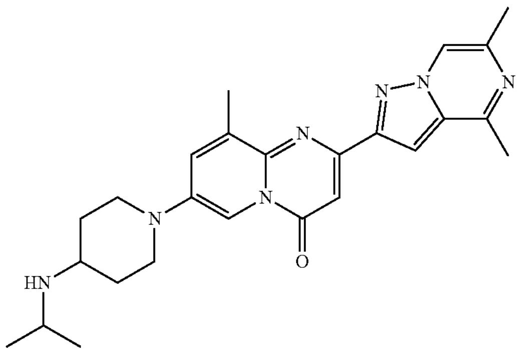
-continued
612
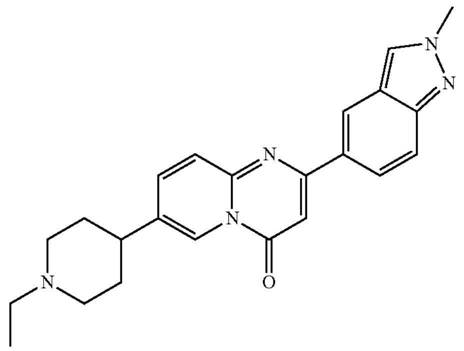
613
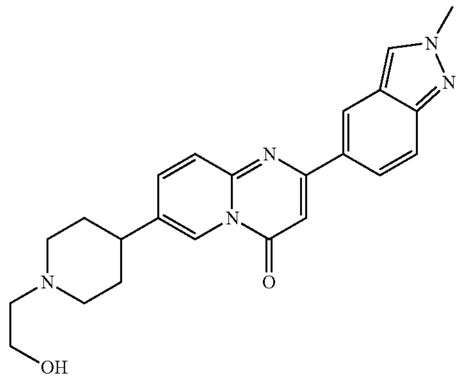
614
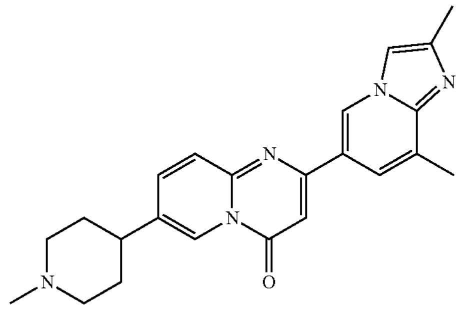
615
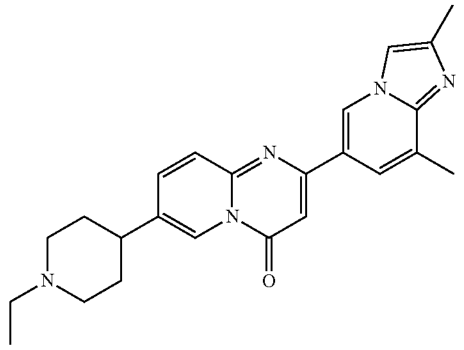

-continued
616
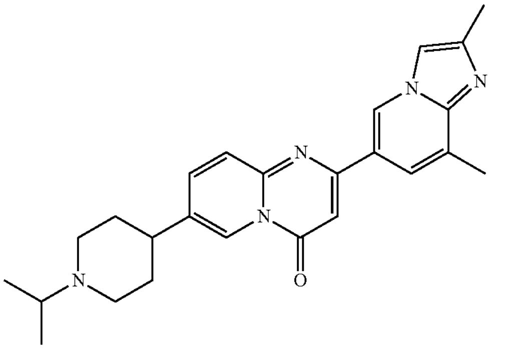
617
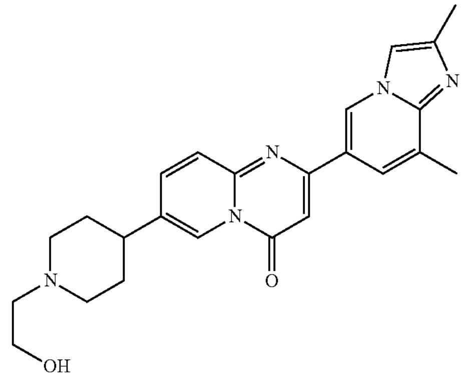
618
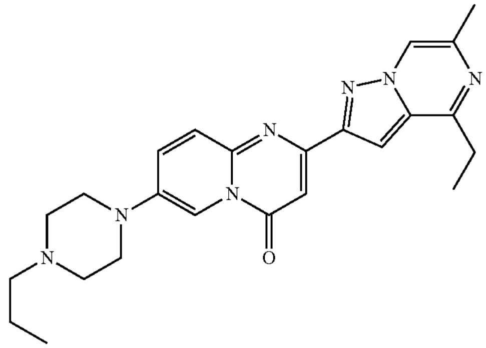
619
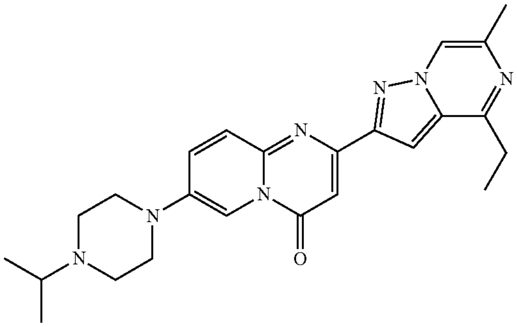
-continued
620
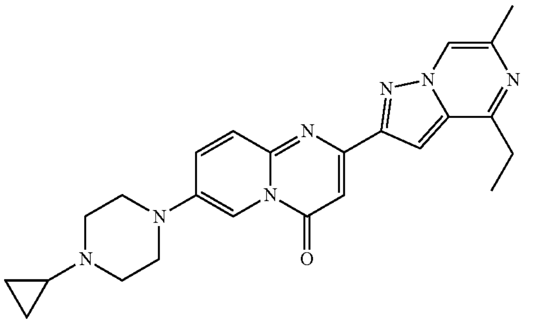
621
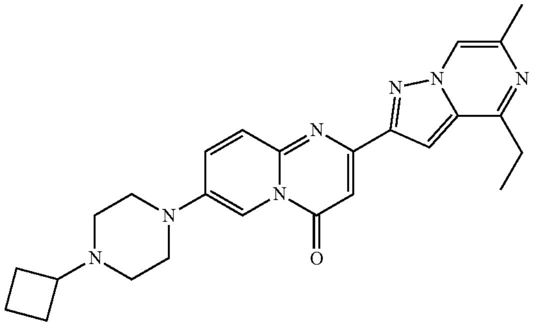
622
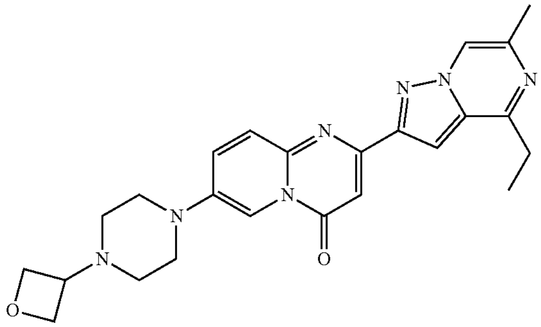
623
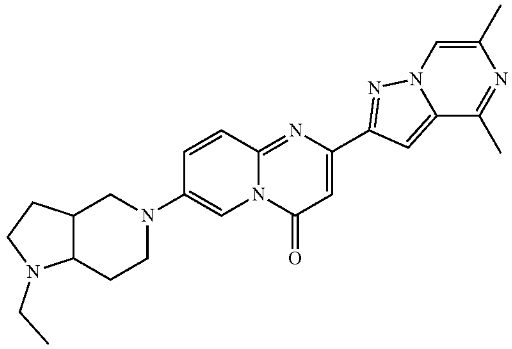

-continued
624
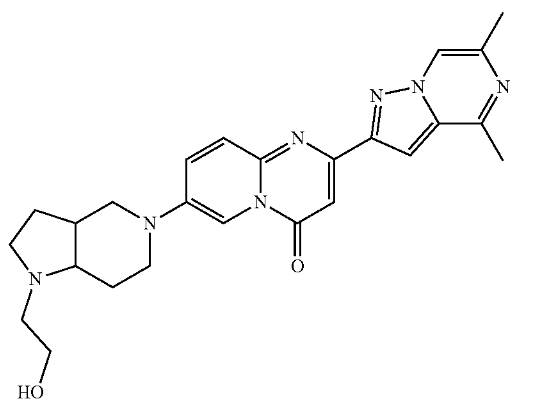
625
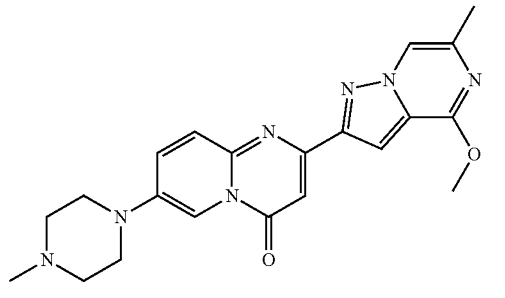
626
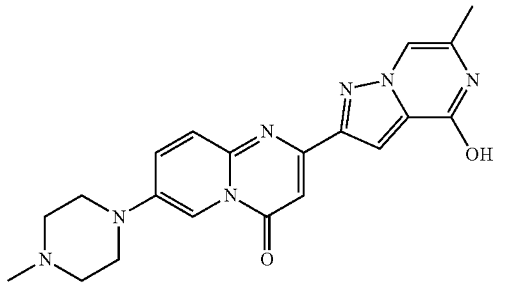
627
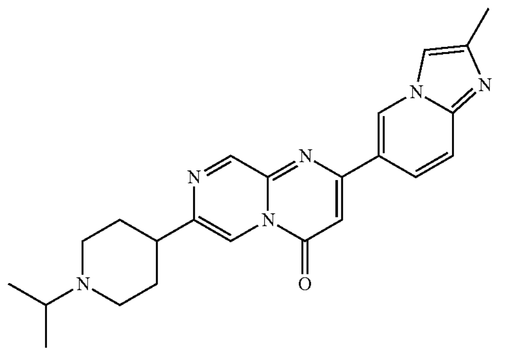
-continued
628
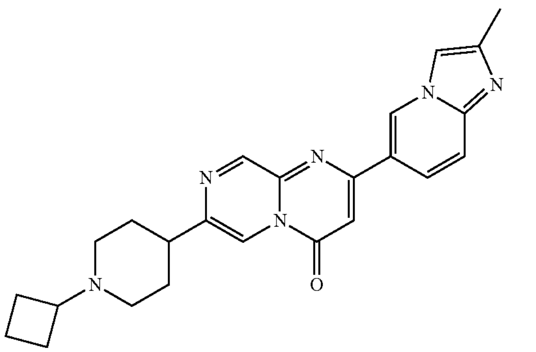
629
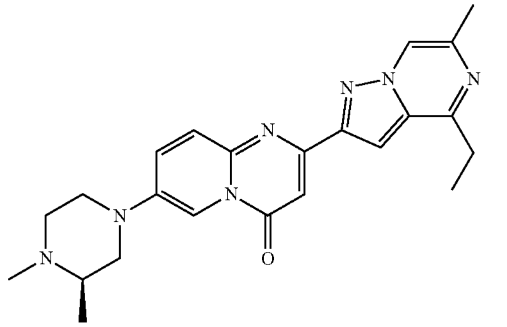
630
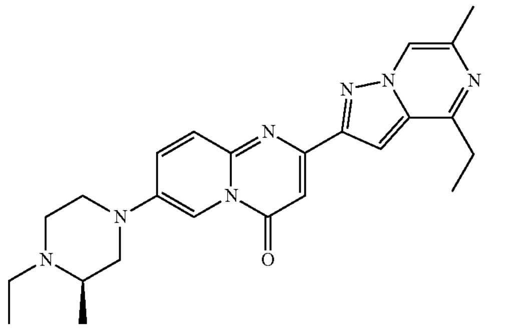
631
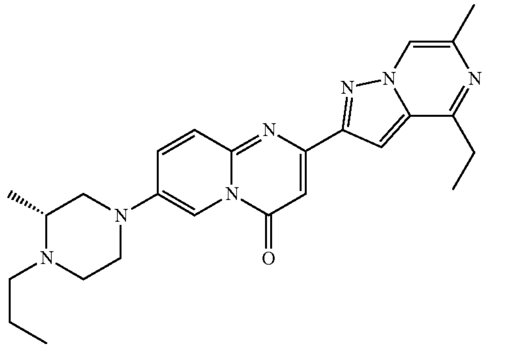

-continued
632
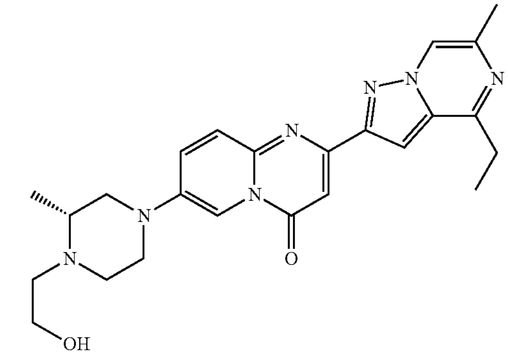
633
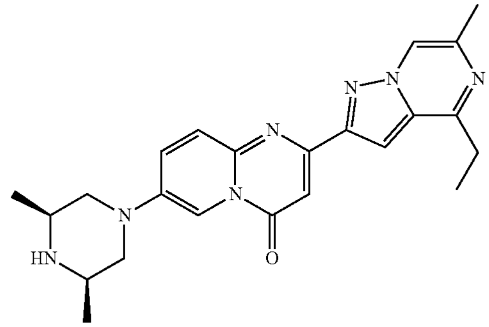
634
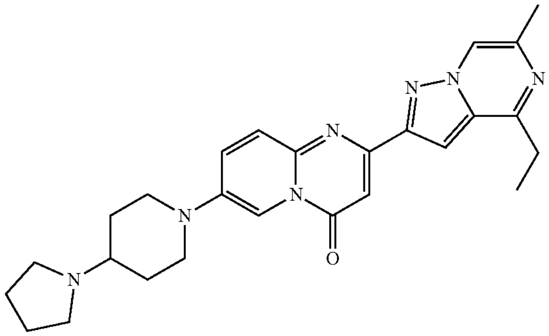
635
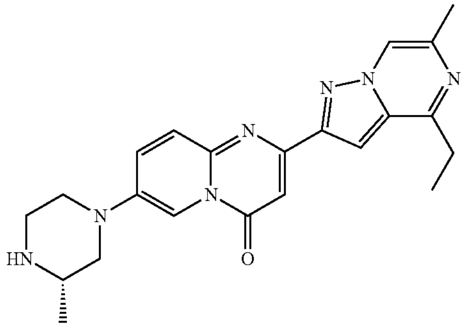
-continued
636
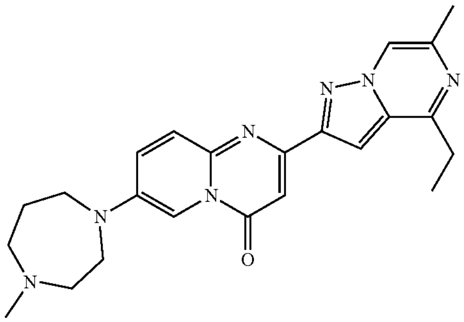
637
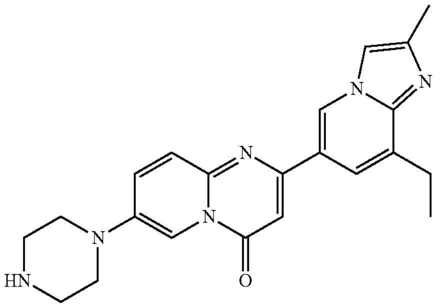
638
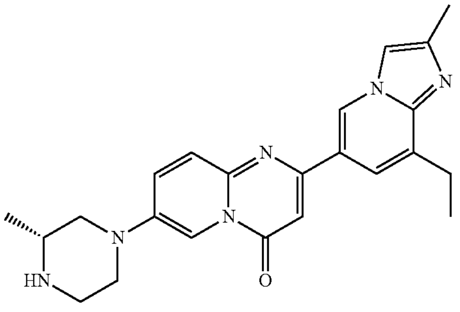
639
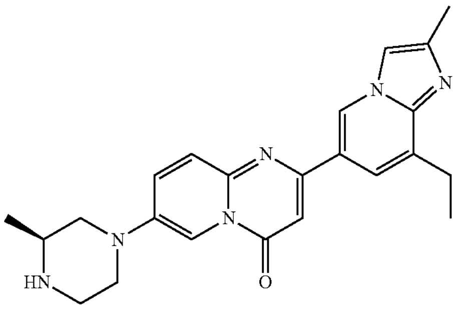
640
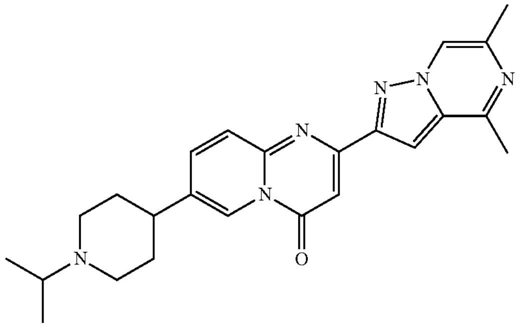

-continued
641
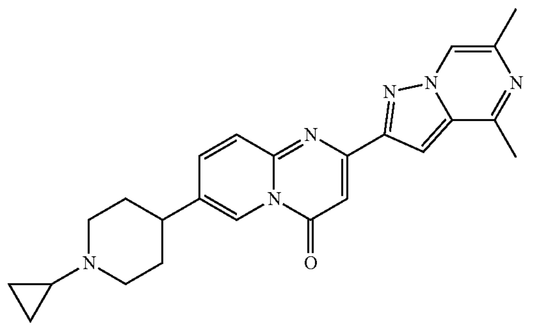
642
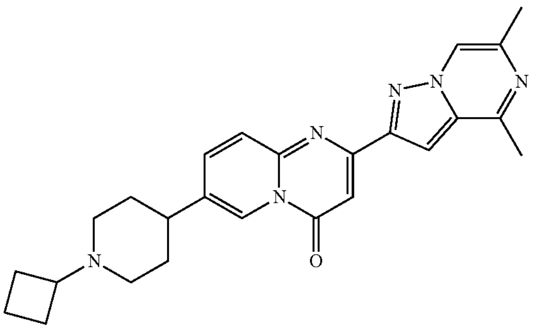
643
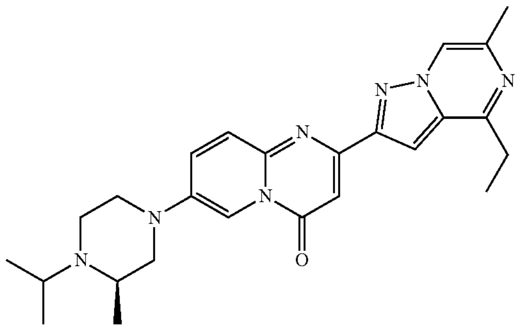
644
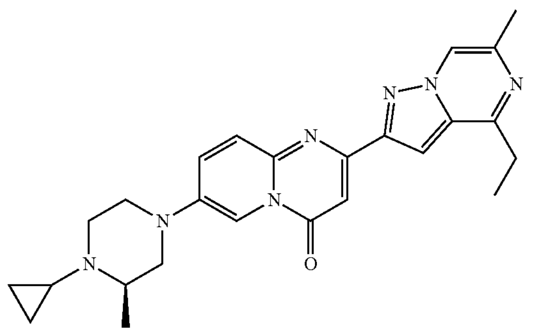
-continued
645
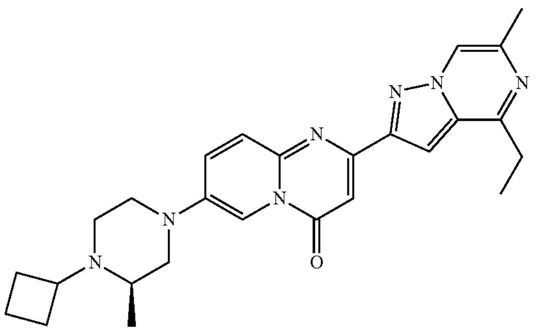
646
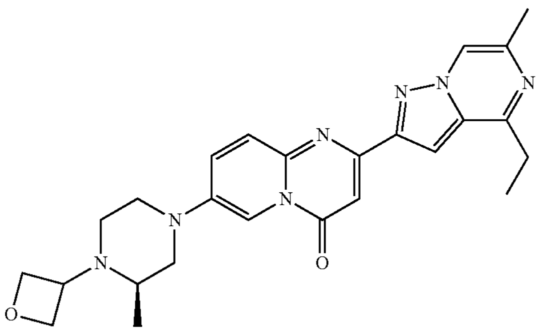
647
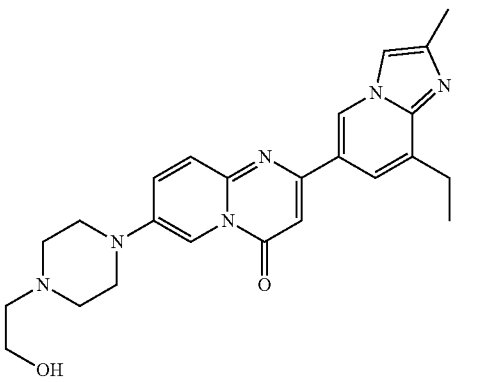
648
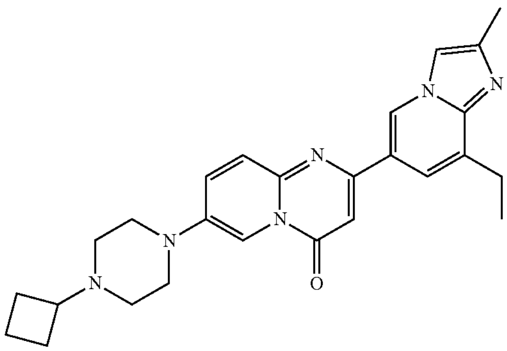

-continued
649
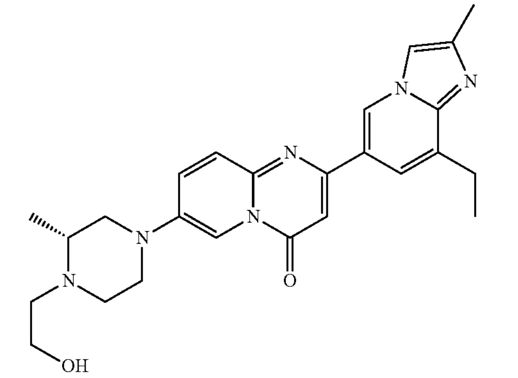
650
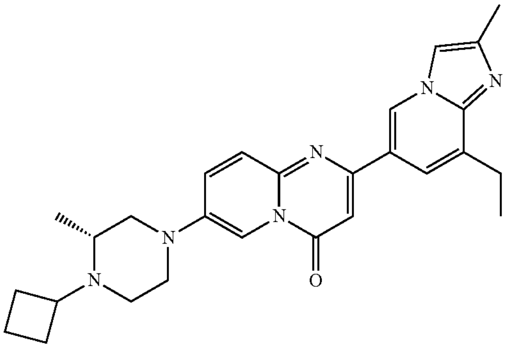
651
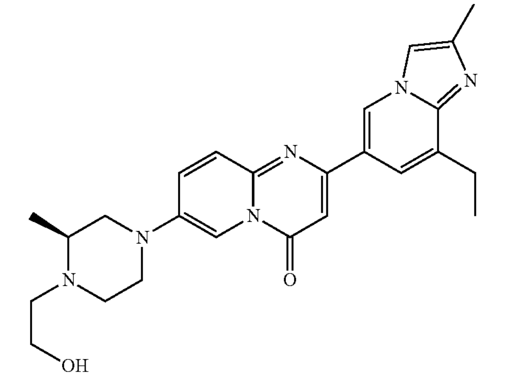
652
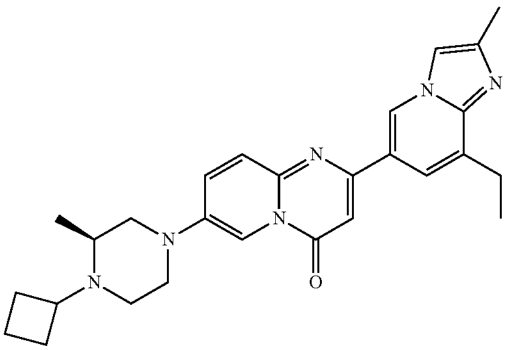
-continued
653
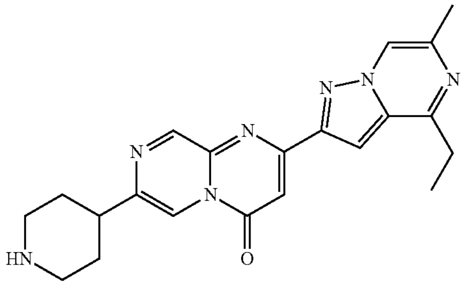
654
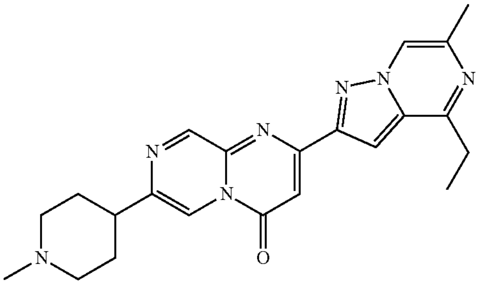
655
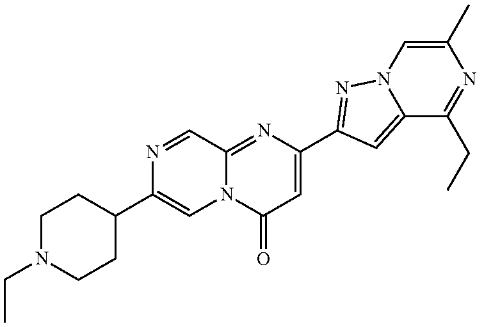
656
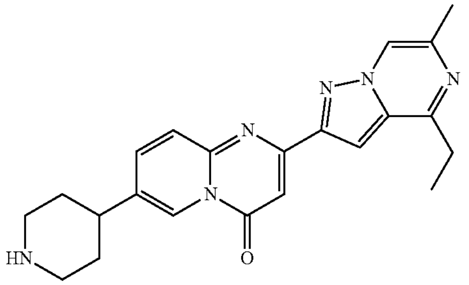
657
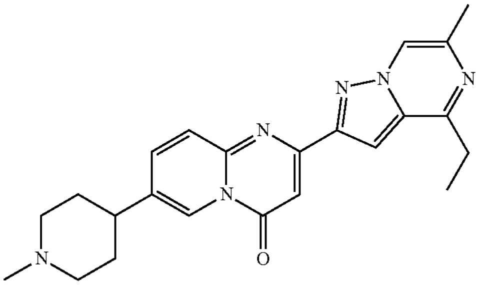

-continued
658
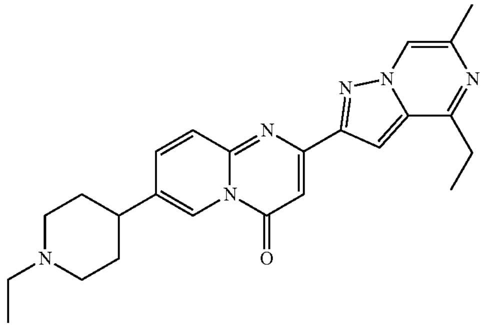
659
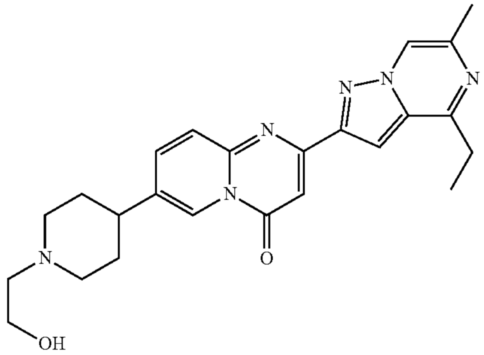
660
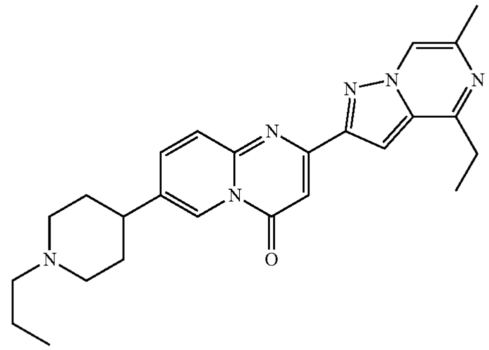
661
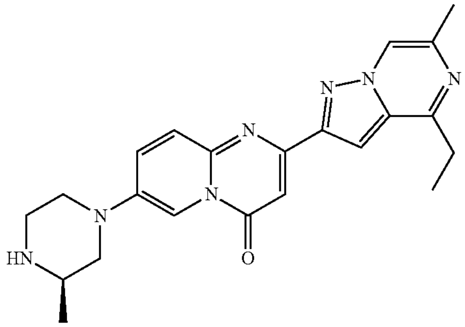
-continued
662
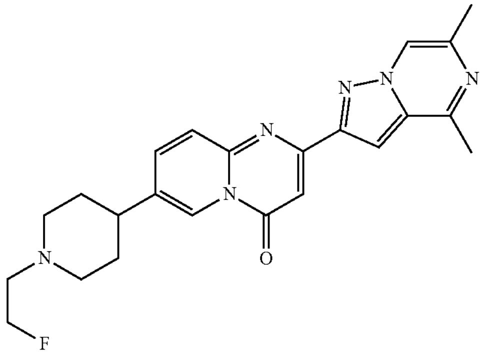
663
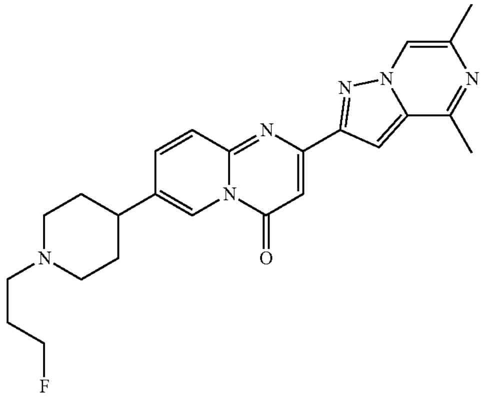
664
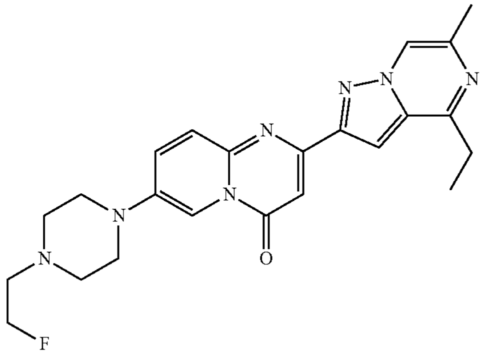
665
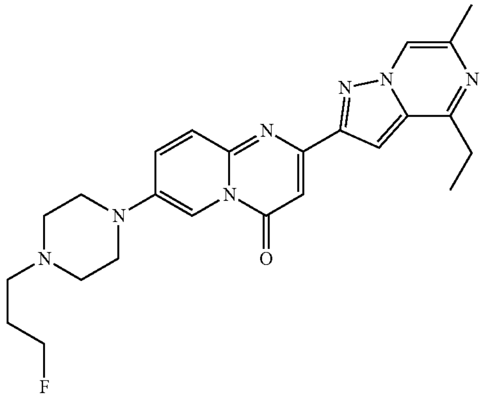

-continued
666
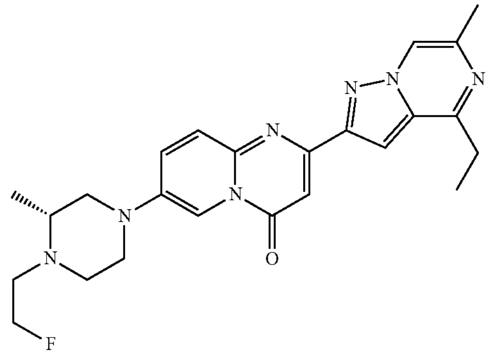
667
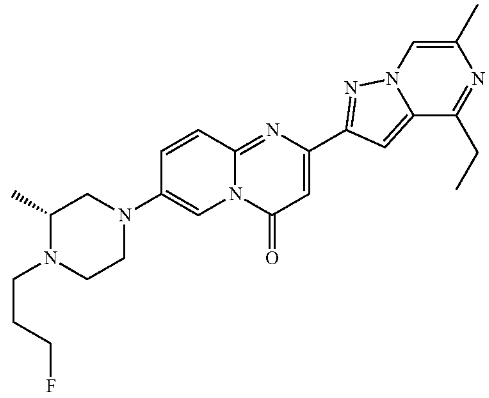
668
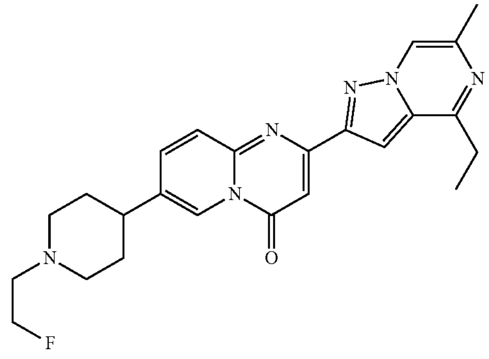
669
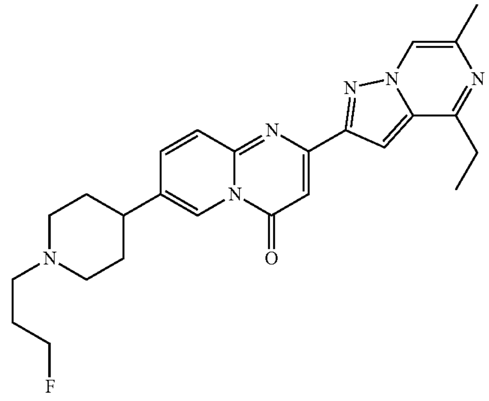
-continued
670
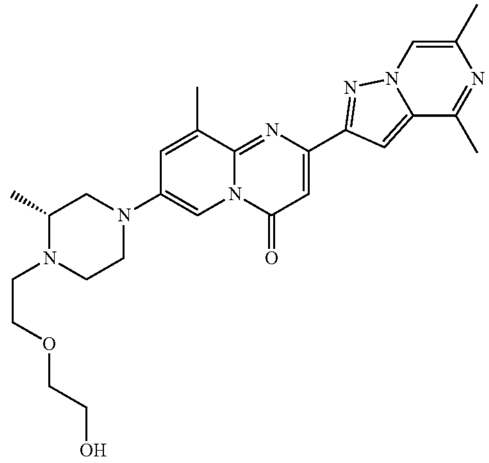
671
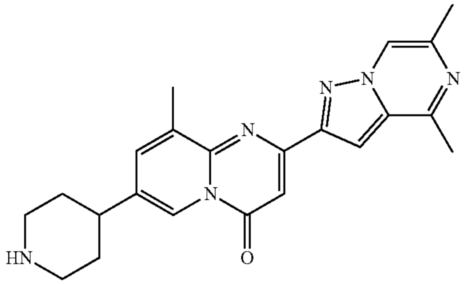
672
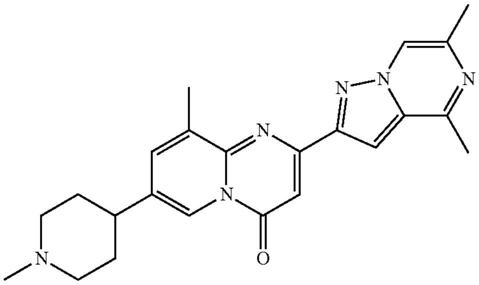
673
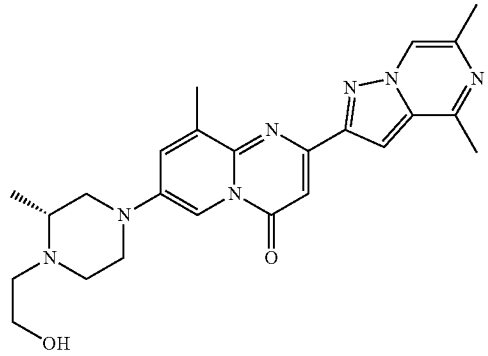

-continued
674
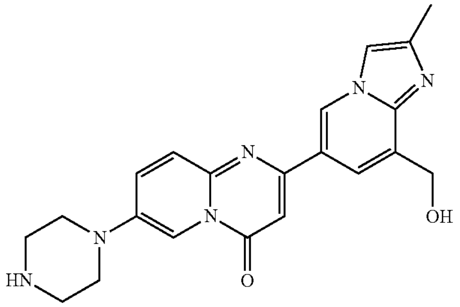
675
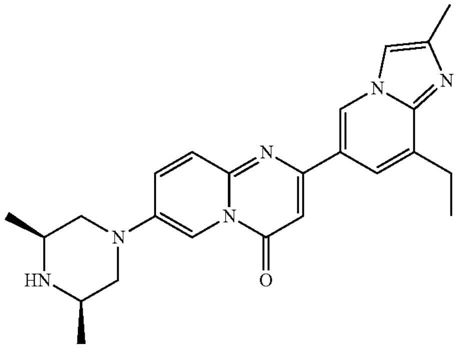
676
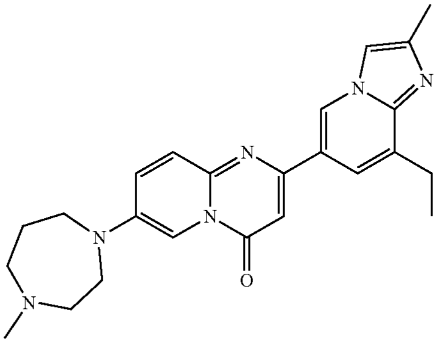
677
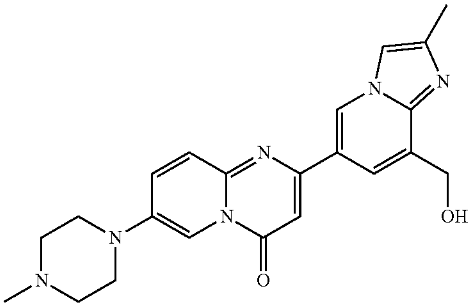
-continued
678
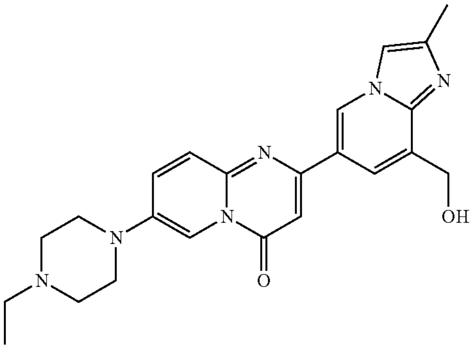
679
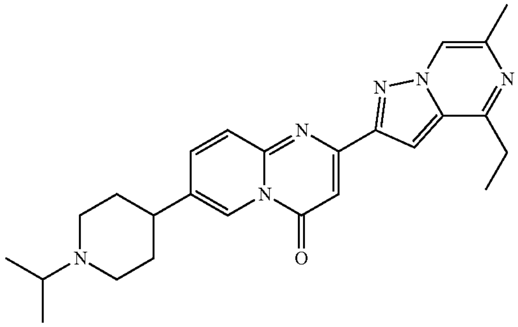
680
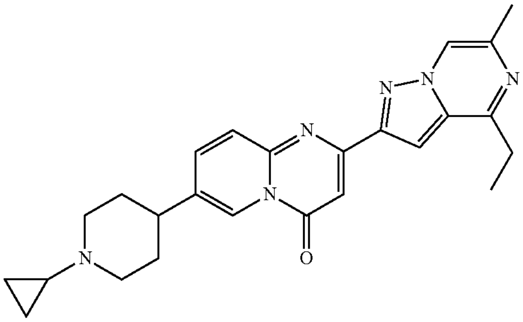
681
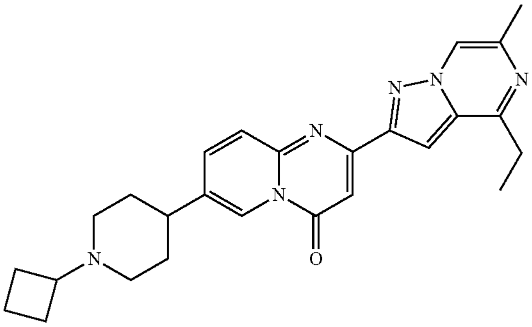

-continued
682
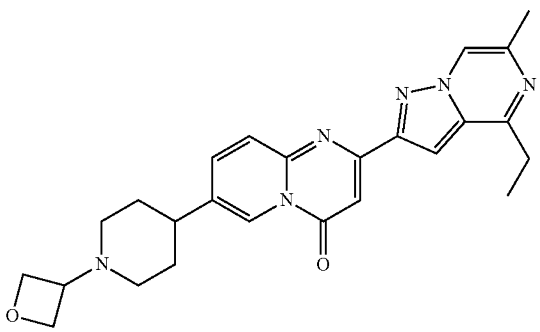
683
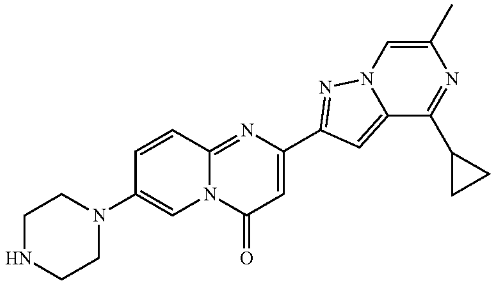
684
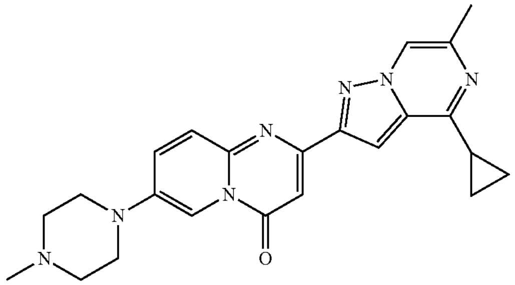
685
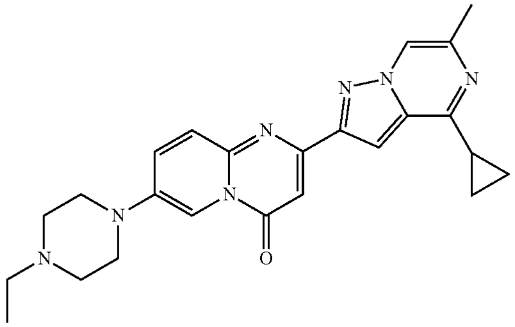
686
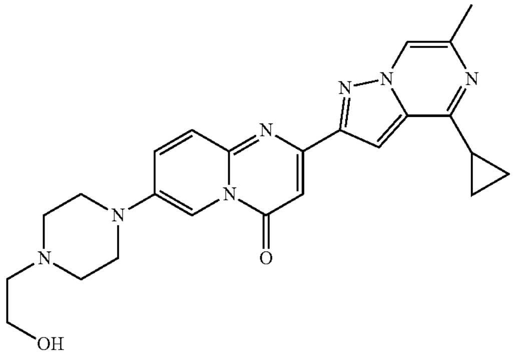
-continued
687
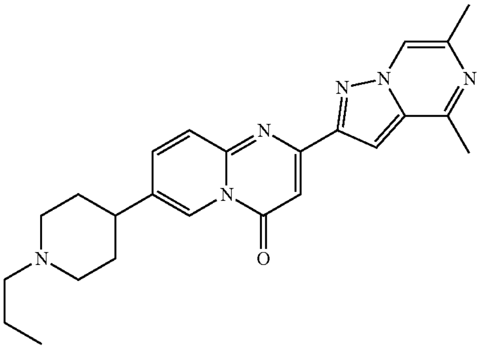
688
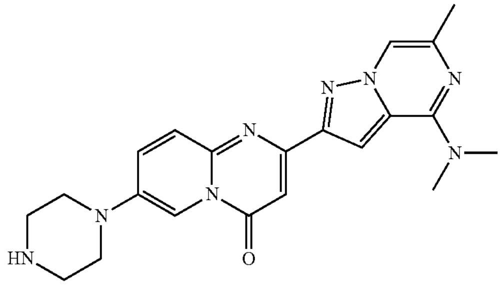
689
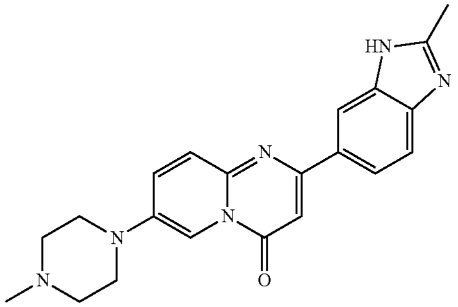
690
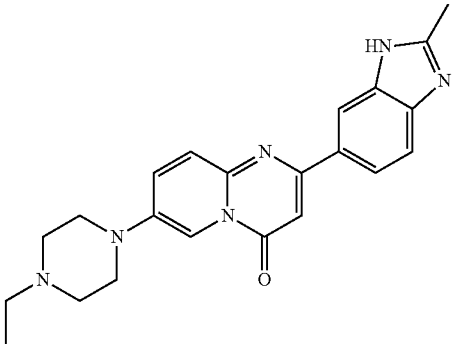
691
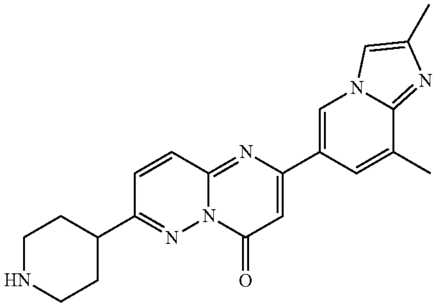

-continued
692
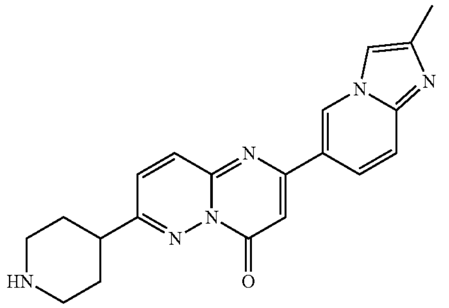
693
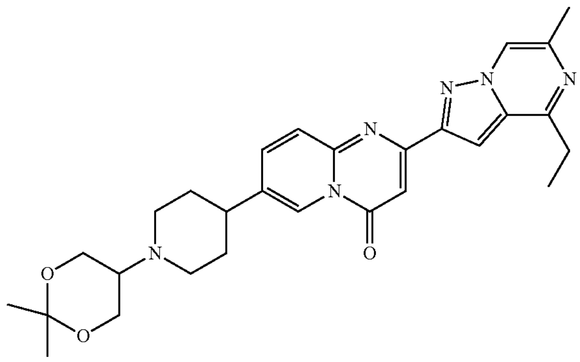
694
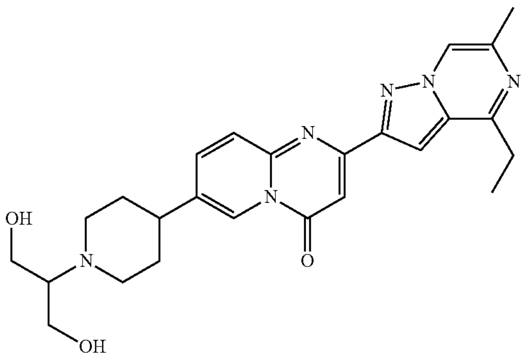
695
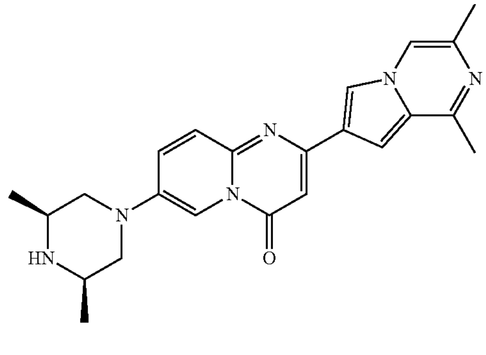
-continued
696
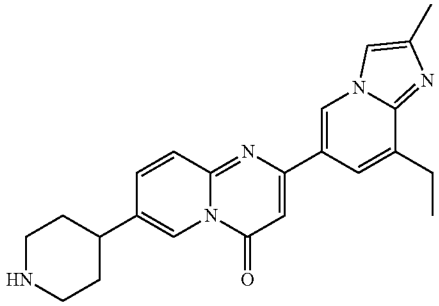
697
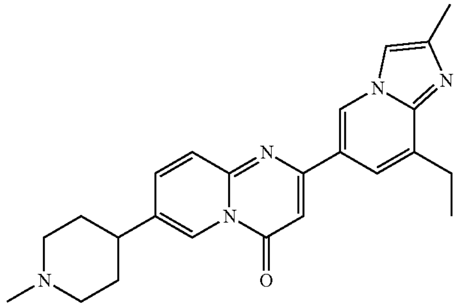
698
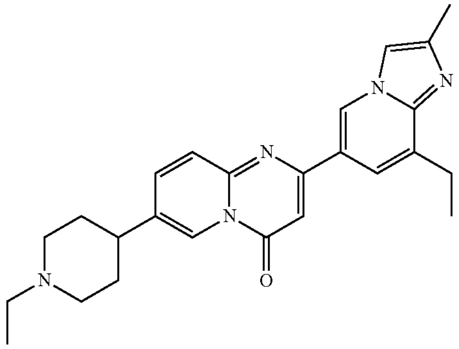
699
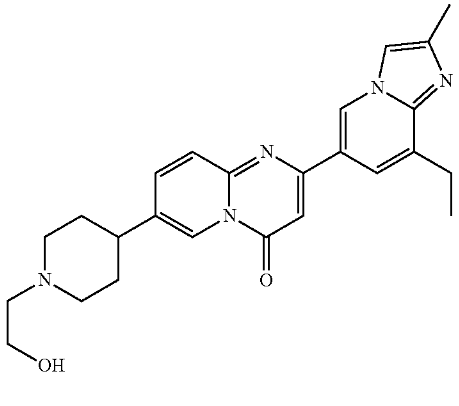

-continued
700
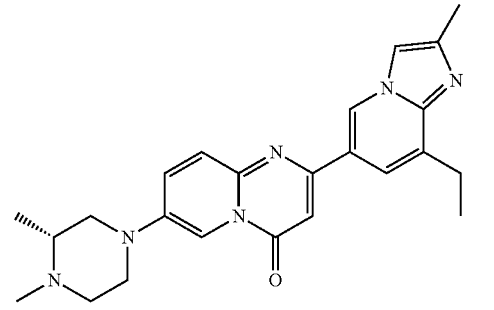
701
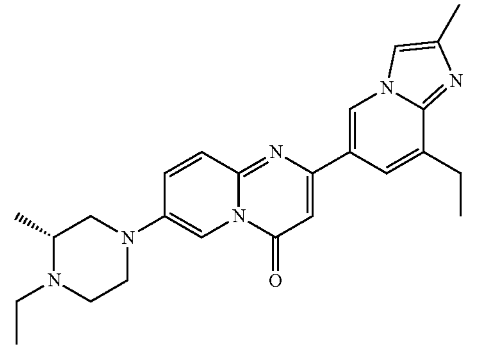
702
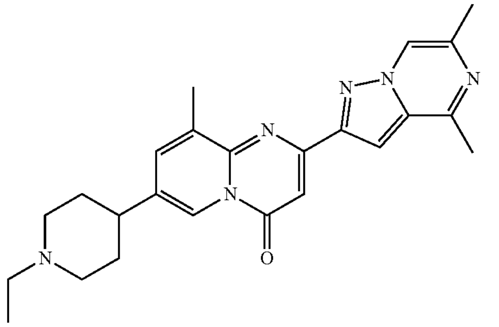
703
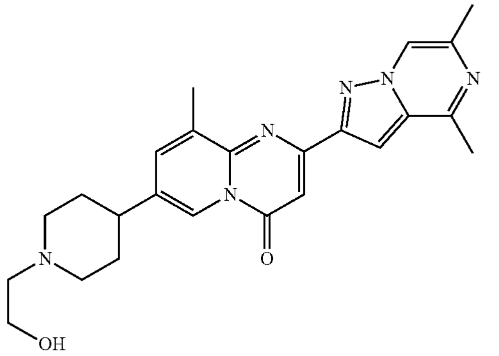
-continued
704
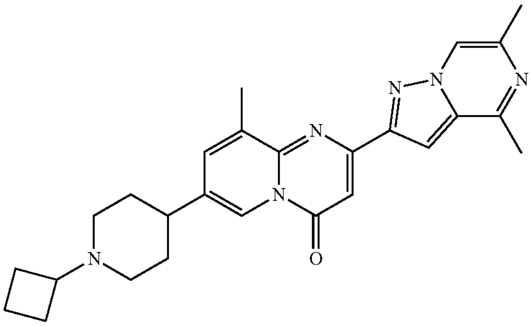
705
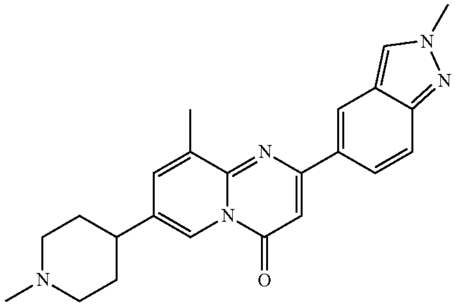
706
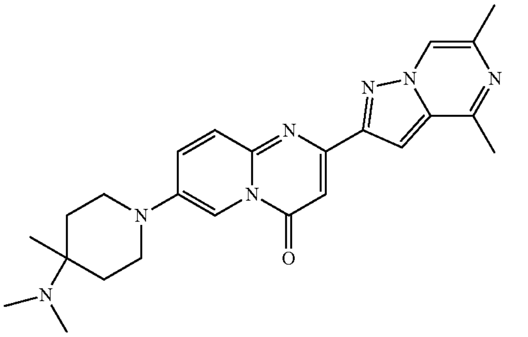
707
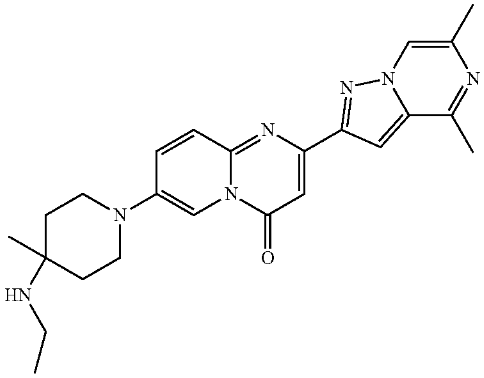

-continued
708
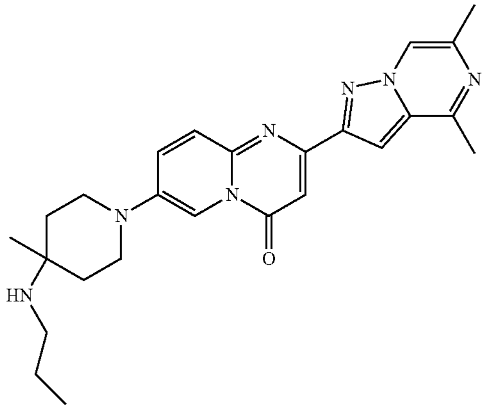
709
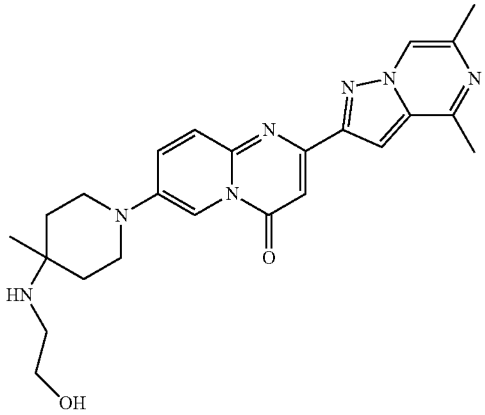
710
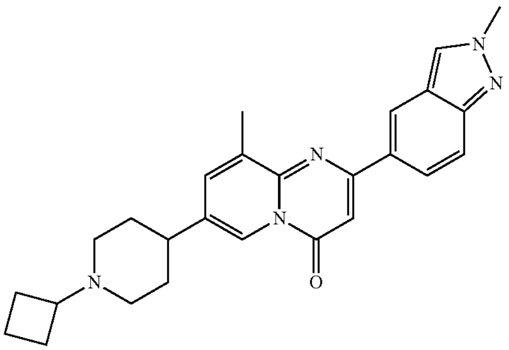
711
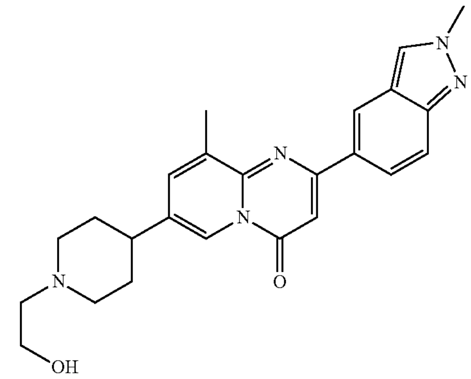
-continued
712
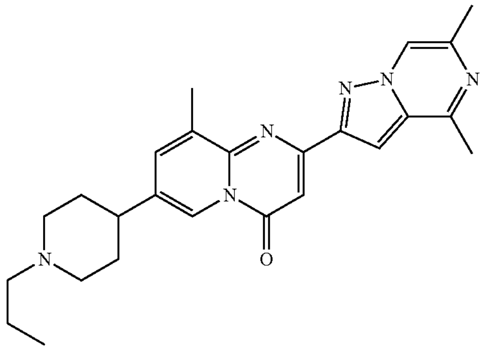
713
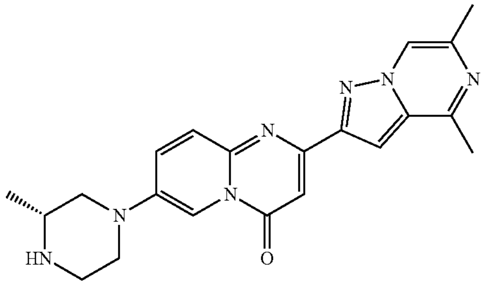
714
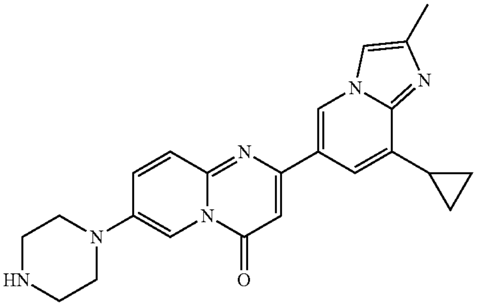
715
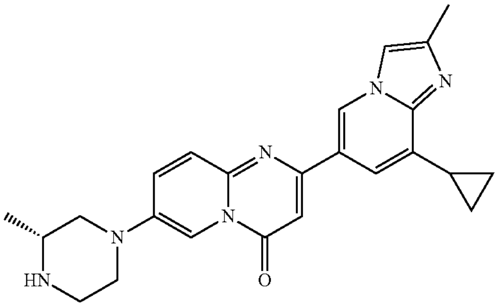
716
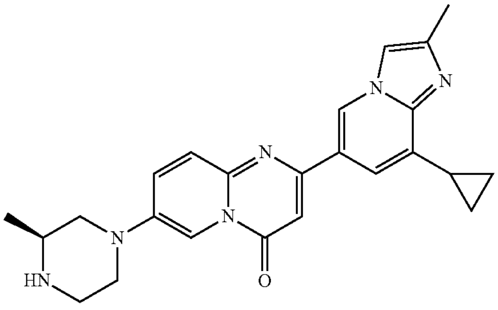

-continued
717
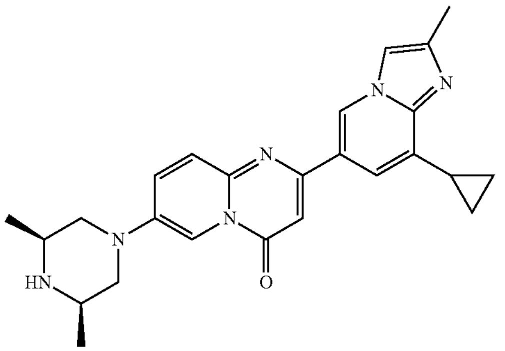
718
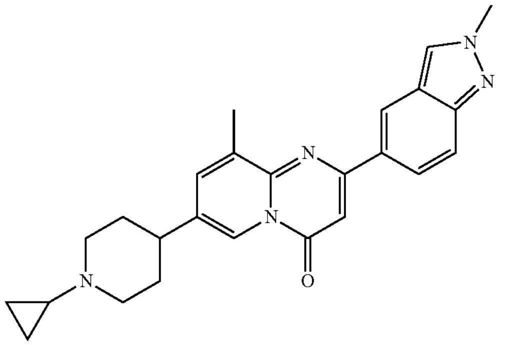
719
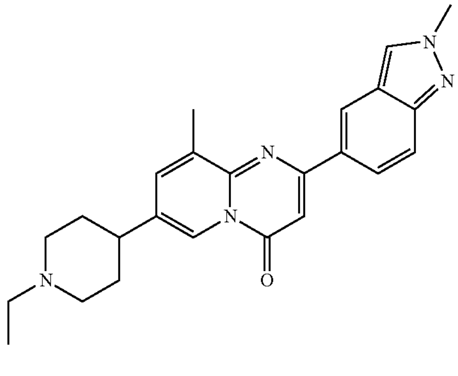
720
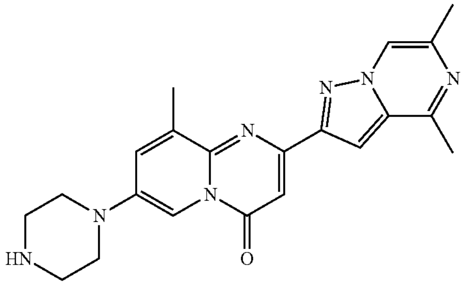
-continued
721
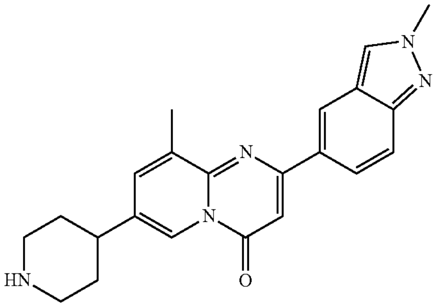
722
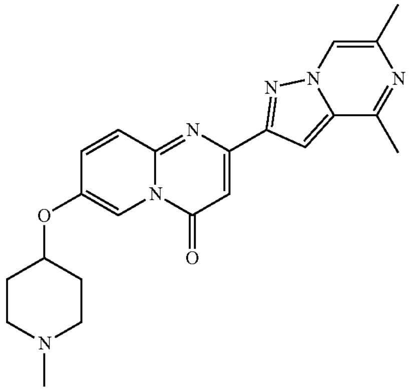
723
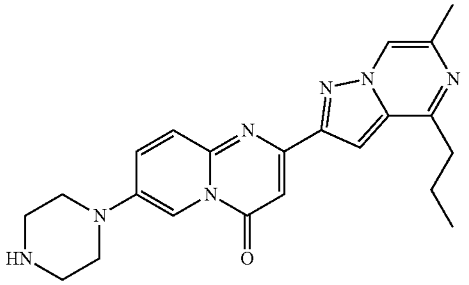
724
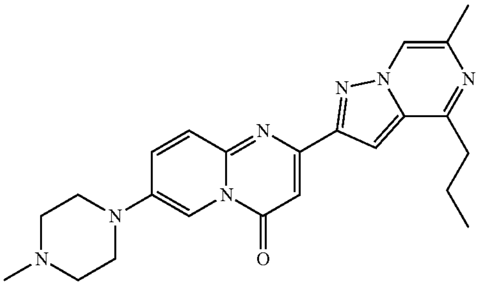
725
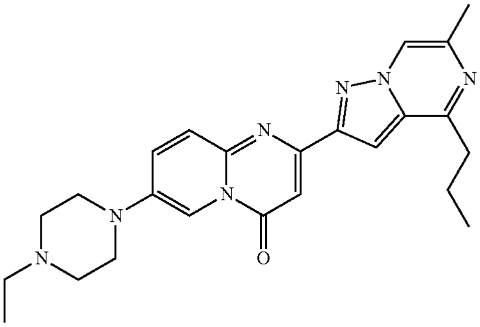

-continued
726
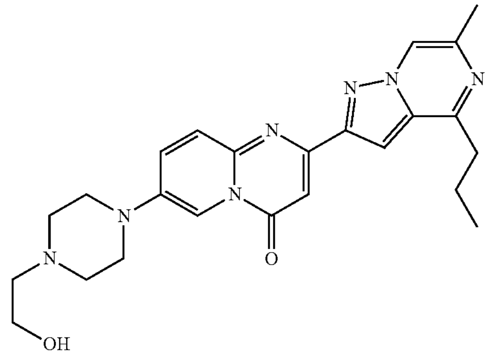
727
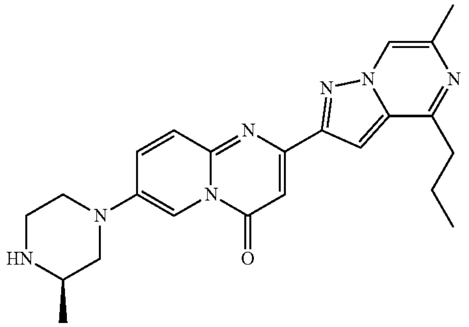
728
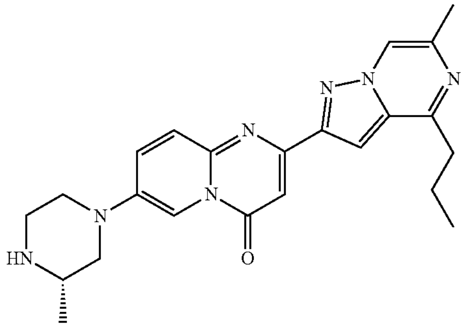
729
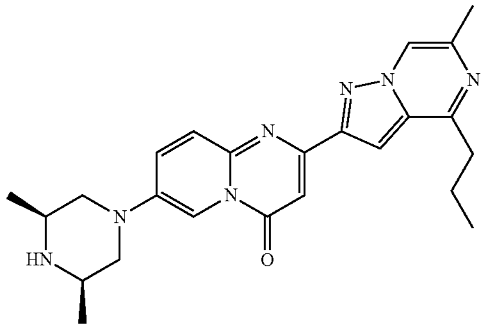
-continued
730
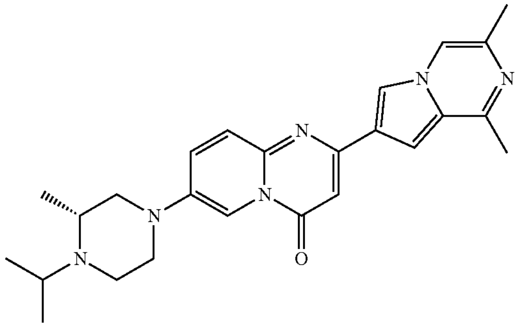
731
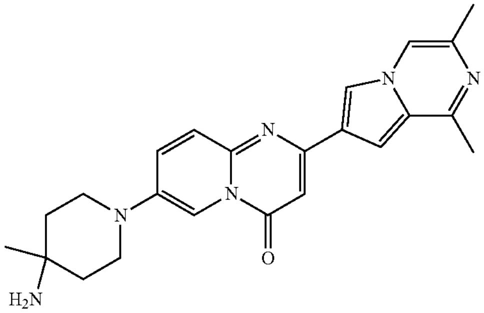
732
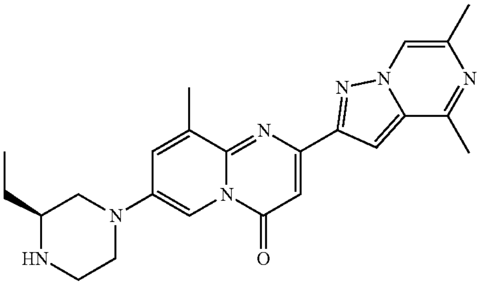
733
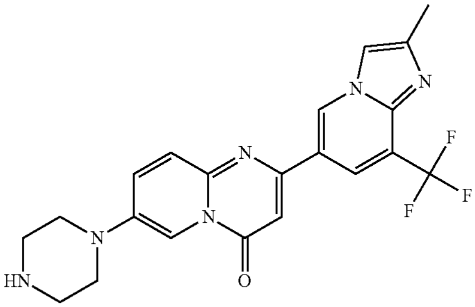
734
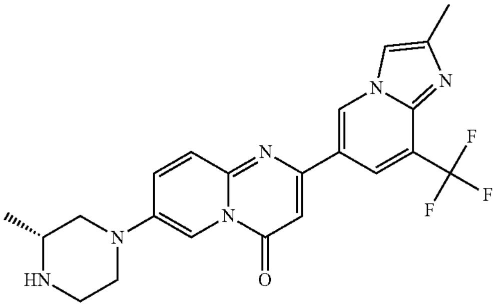

-continued
735
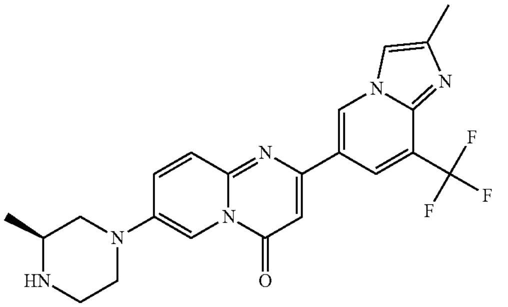
736
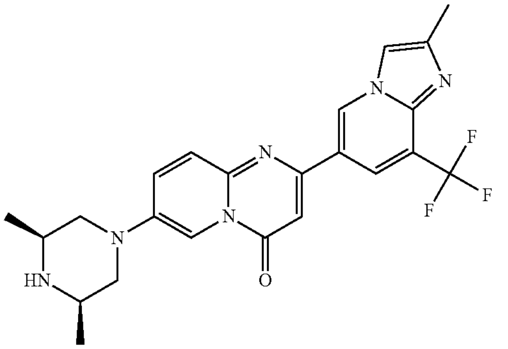
737
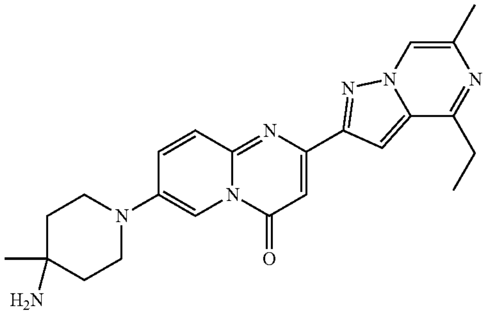
738
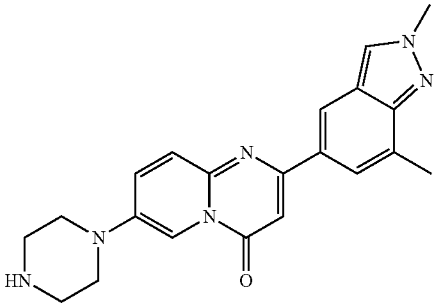
739
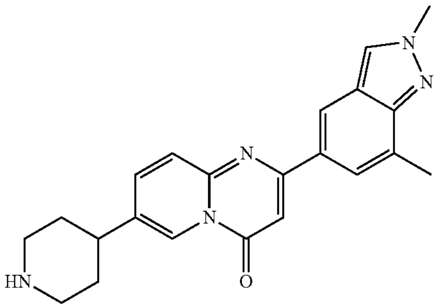
-continued
740
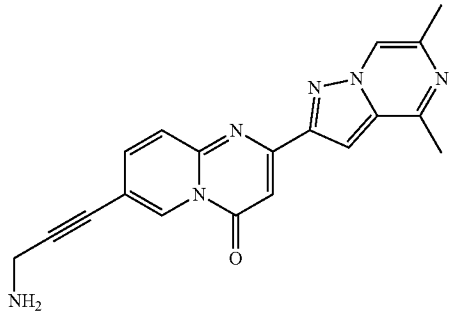
741
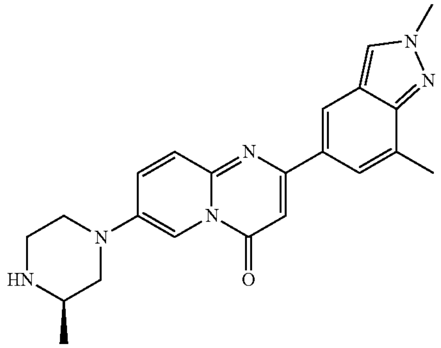
742
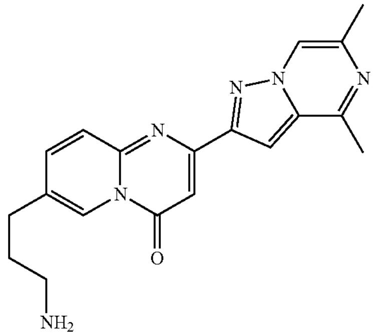
743
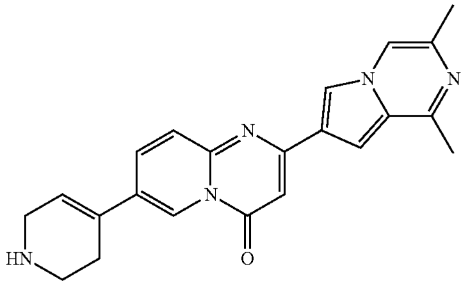
744
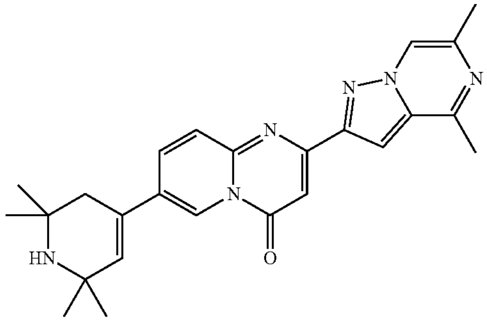

745
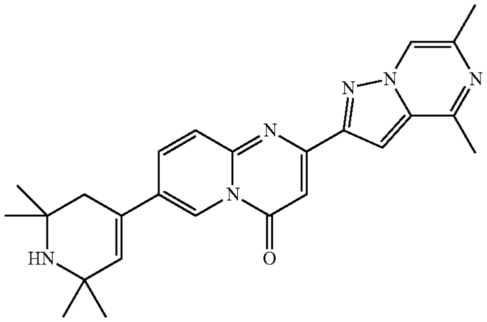
746
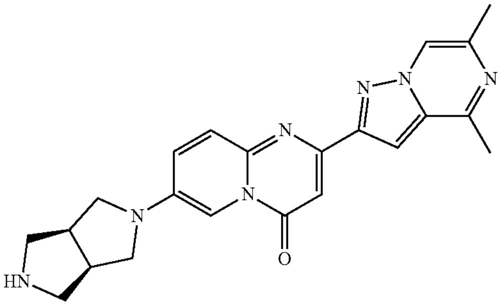
747
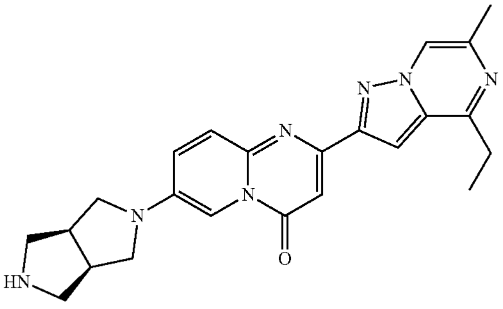
748
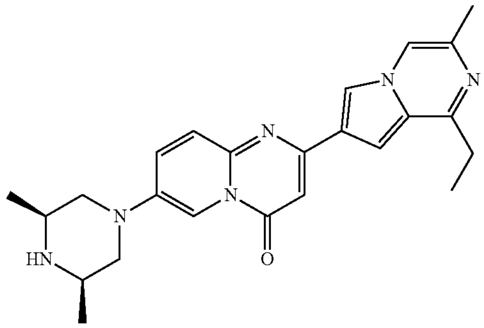
749
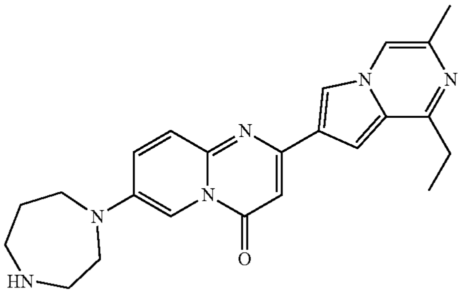
750
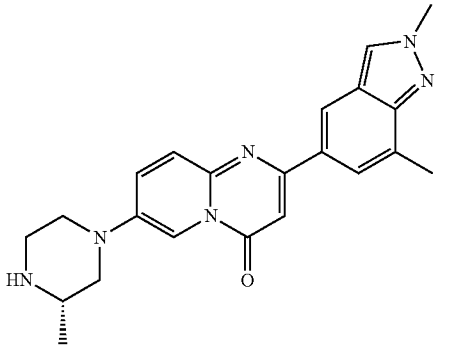
751
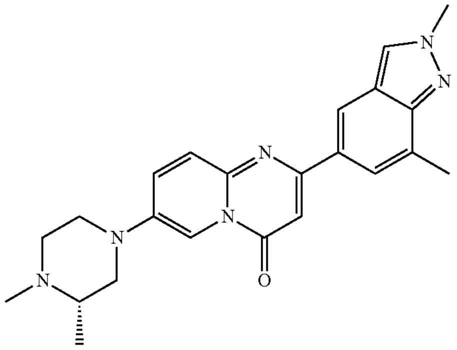
752
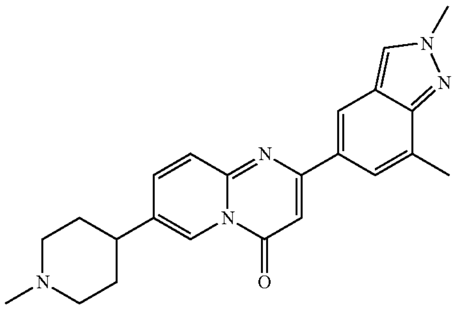
753
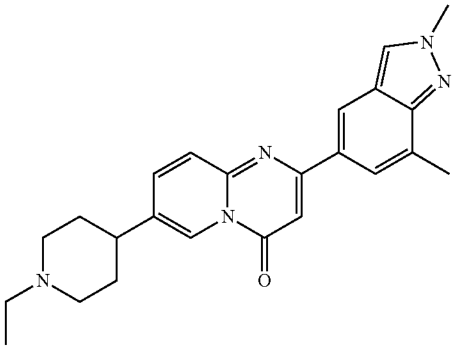

-continued
754
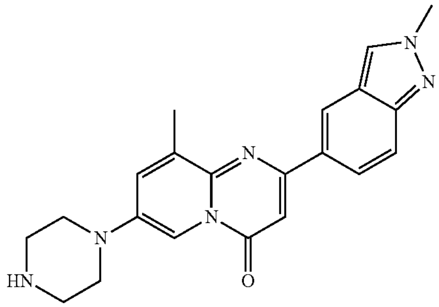
755
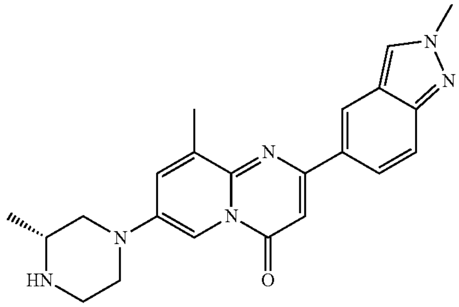
756
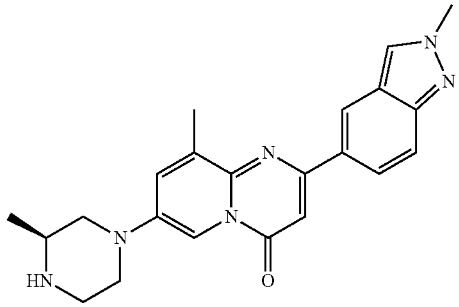
757
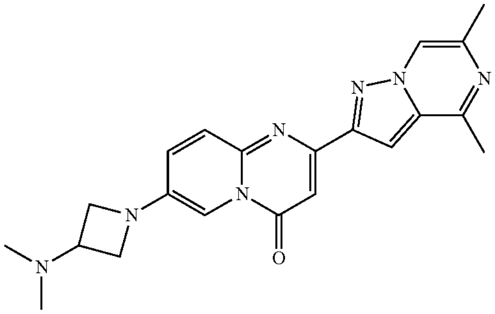
758
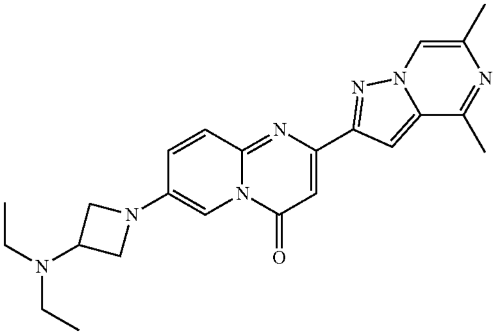
-continued
759
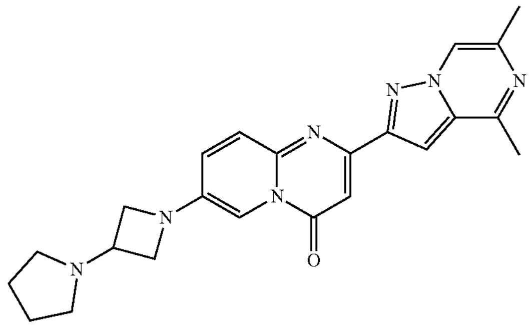
760
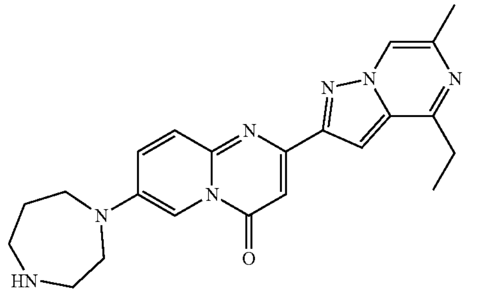
761
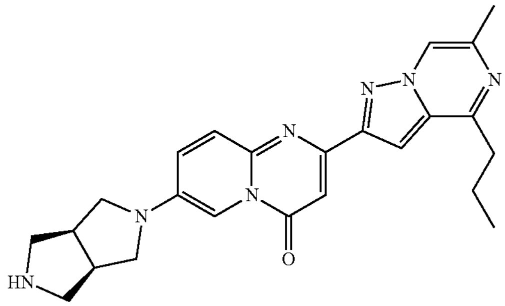
762
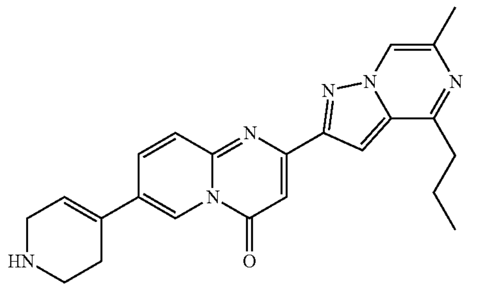
763
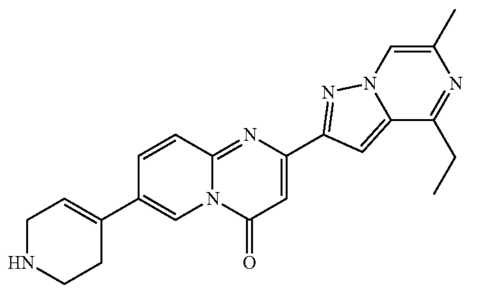

-continued
764
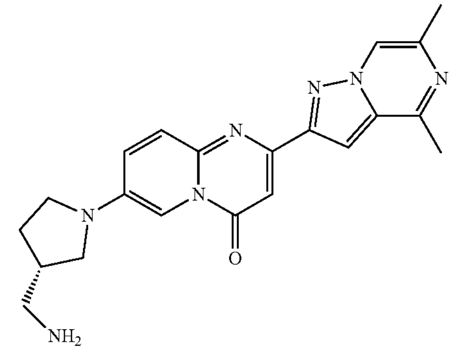
765
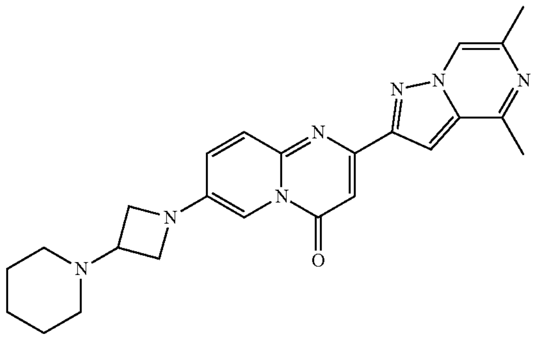
766
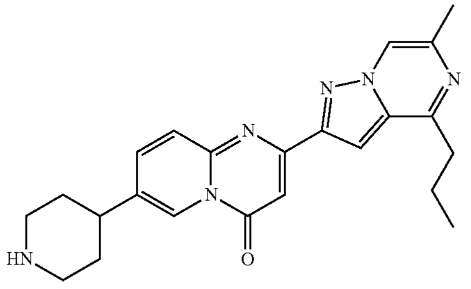
767
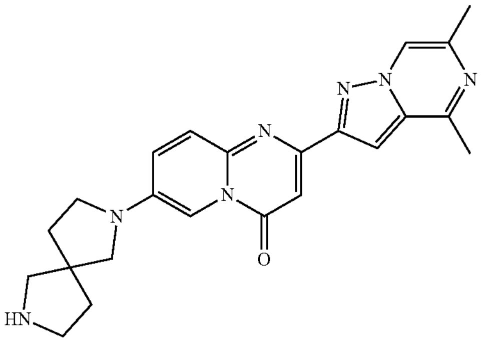
-continued
768
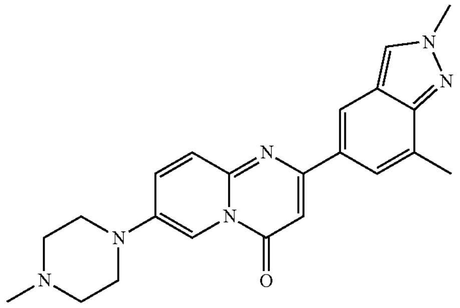
769
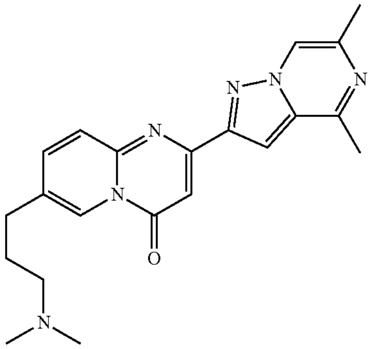
770
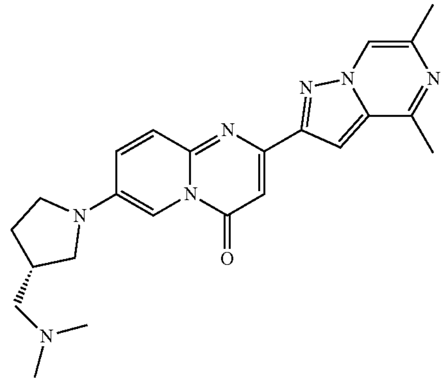
771
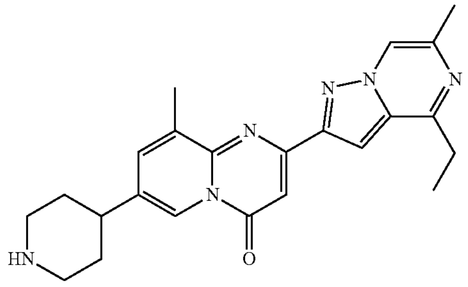
772
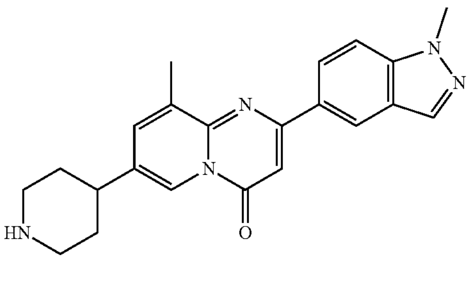

-continued
773
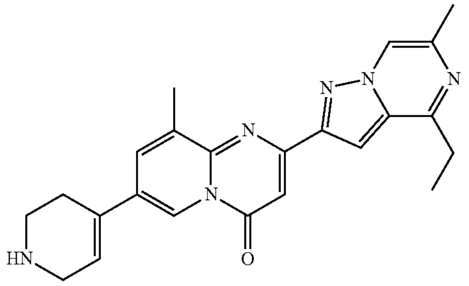
774
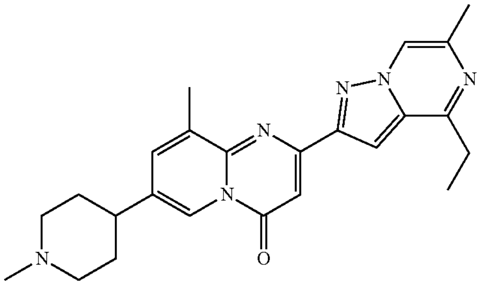
775
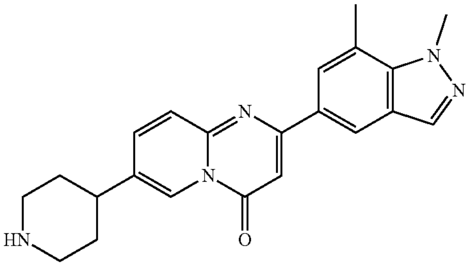
776
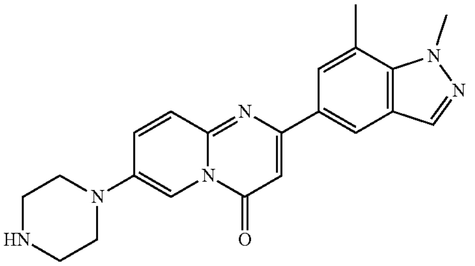
777
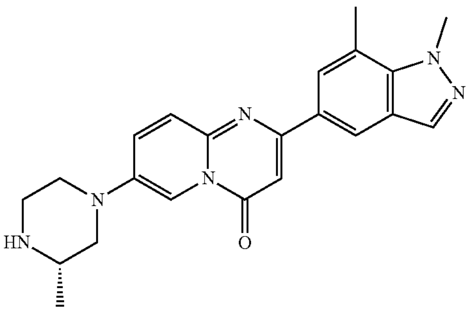
-continued
778
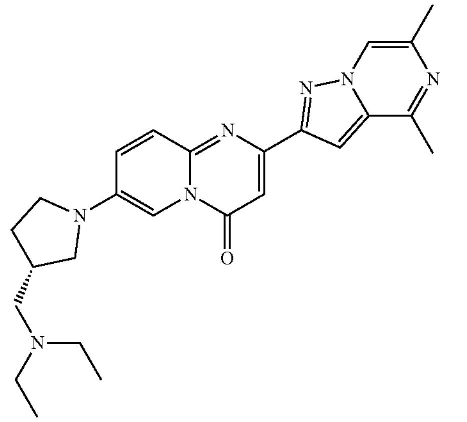
779
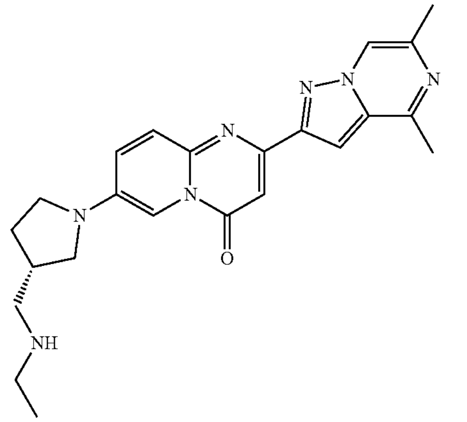
780
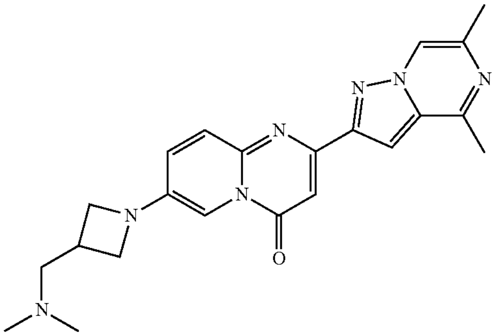
781
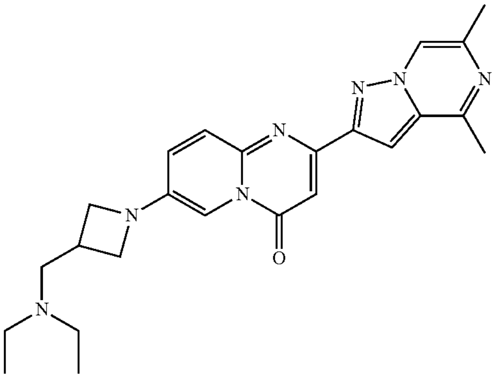

782
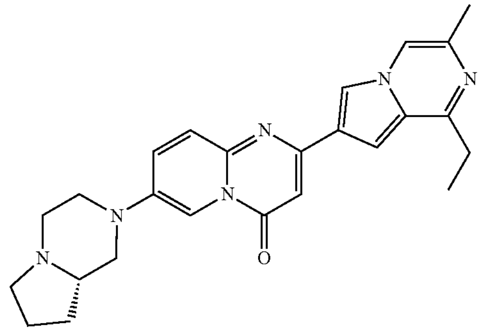
783
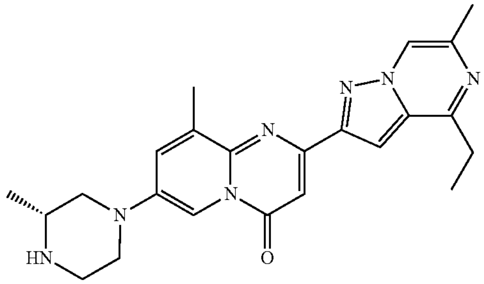
784
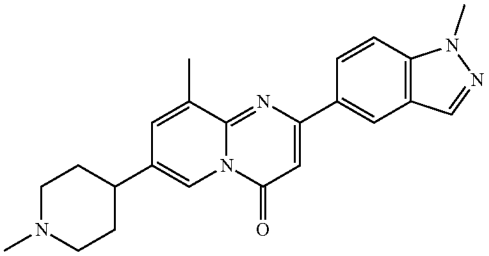
785
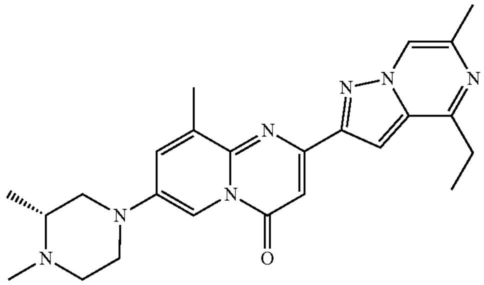
786
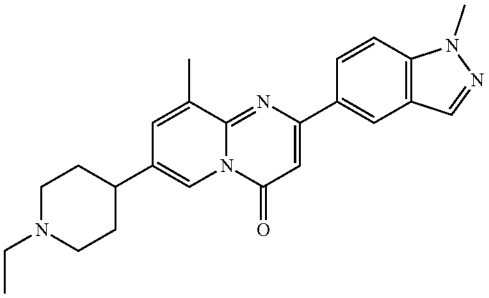
787
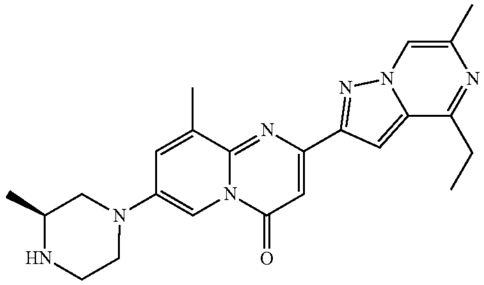
788
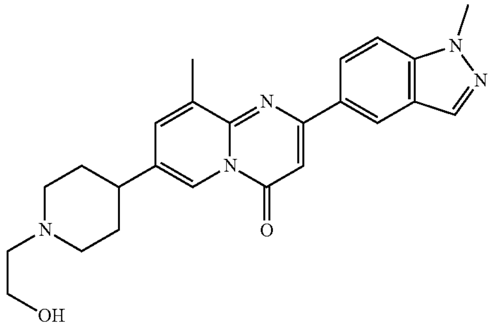
789
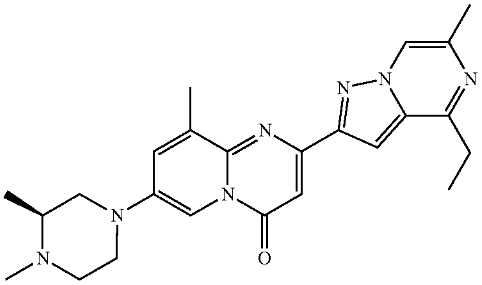
790
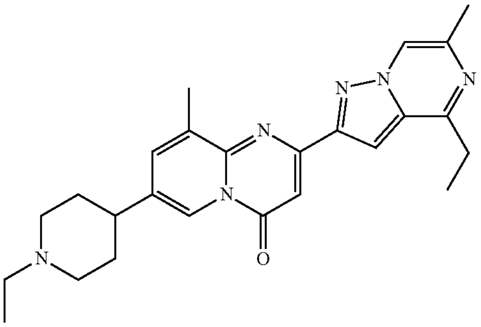
791
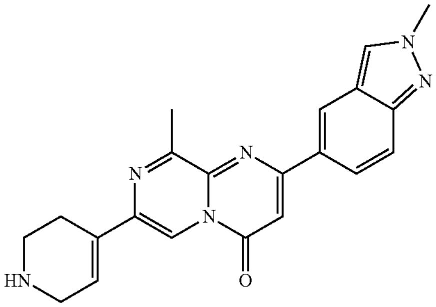

-continued
792
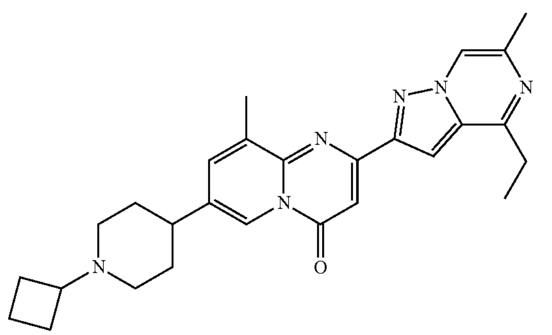
793
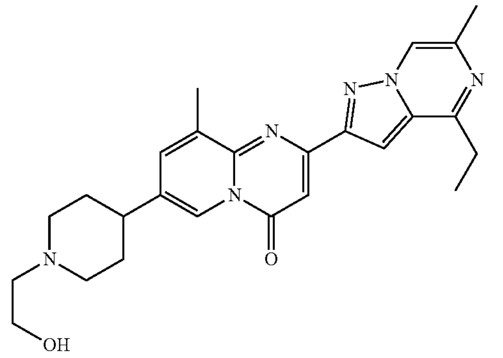
794
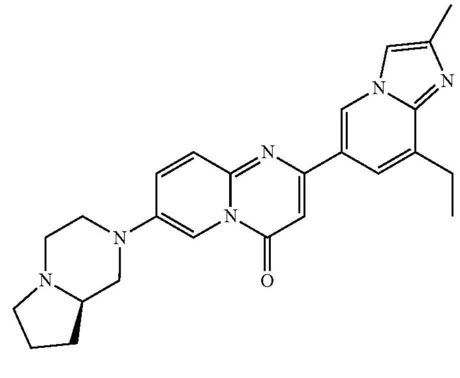
795
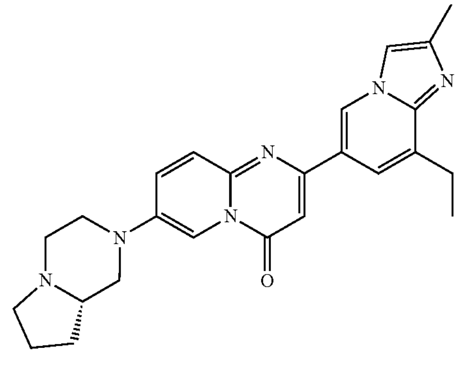
-continued
796
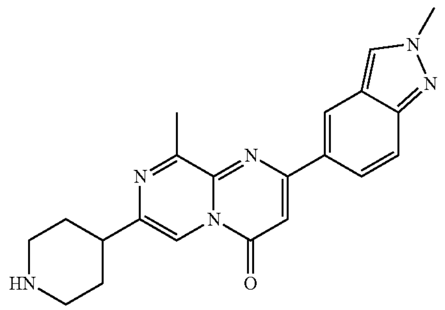
797
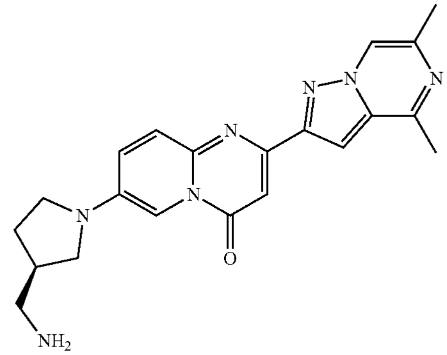
798
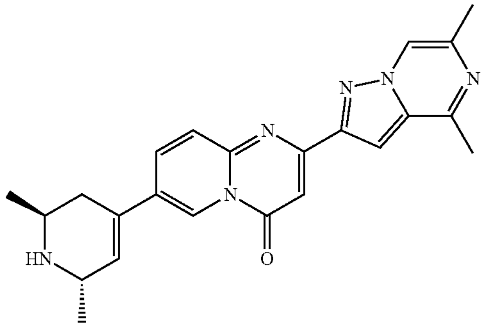
799
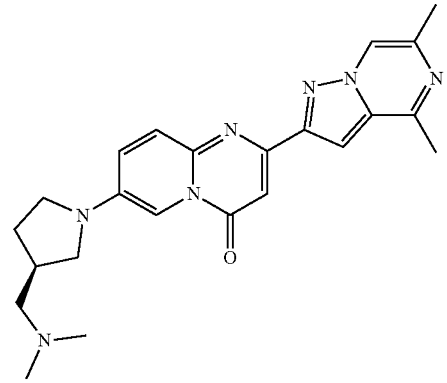

-continued
800
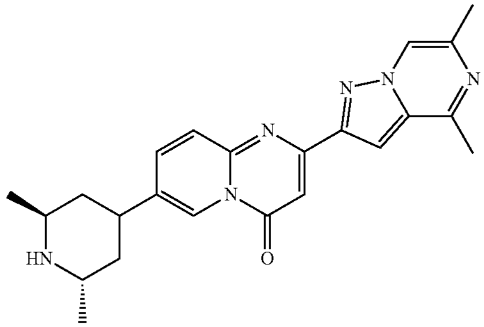
801
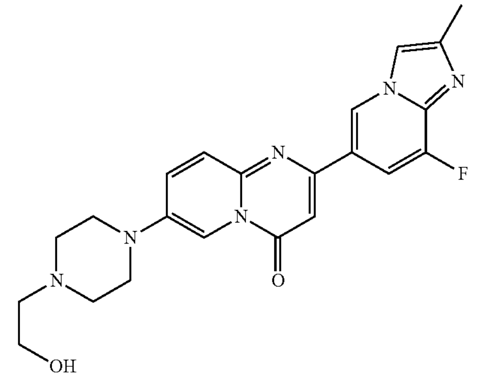
802
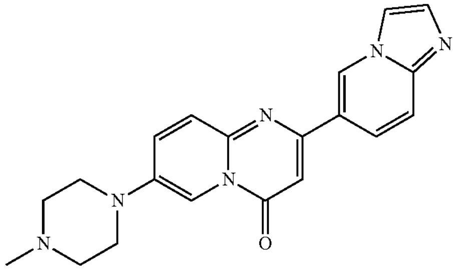
803
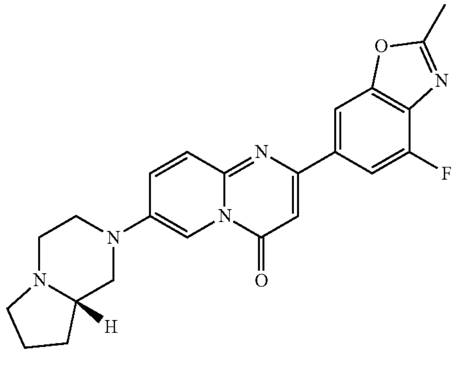
-continued
804
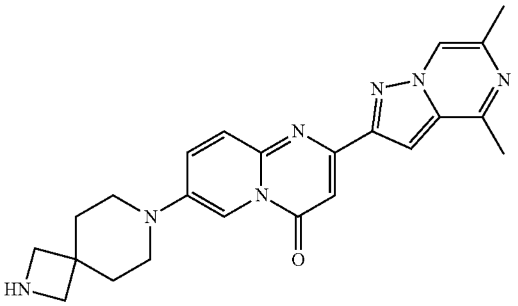
805
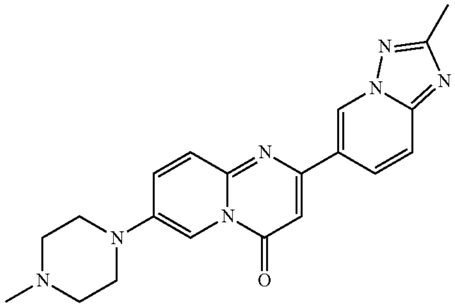
806
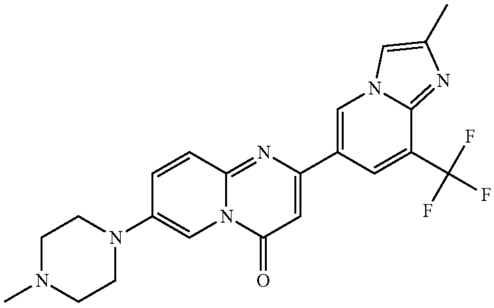
807
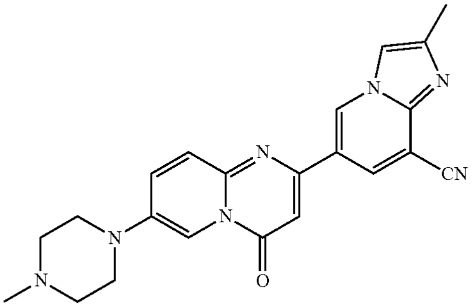
808
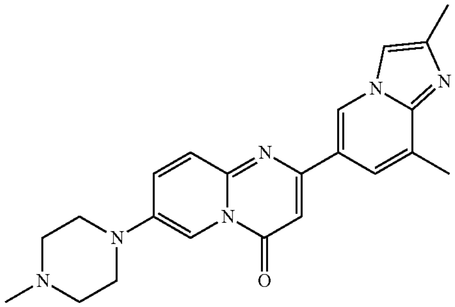

-continued
809
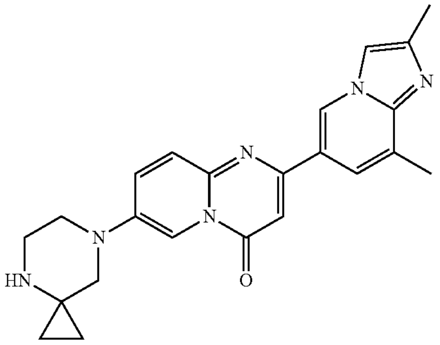
810
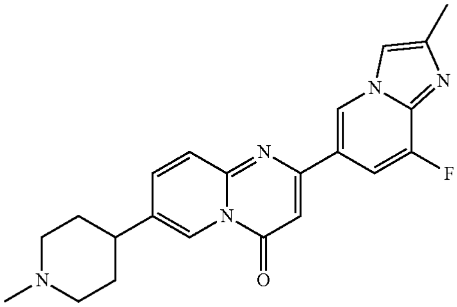
811
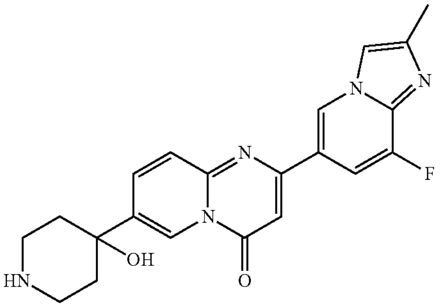
812
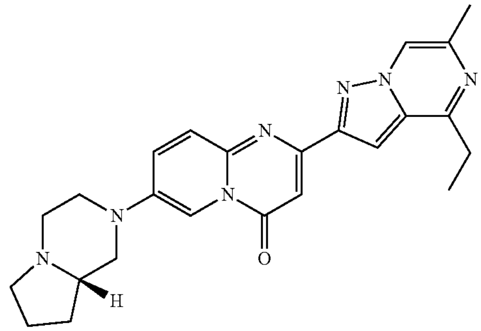
813
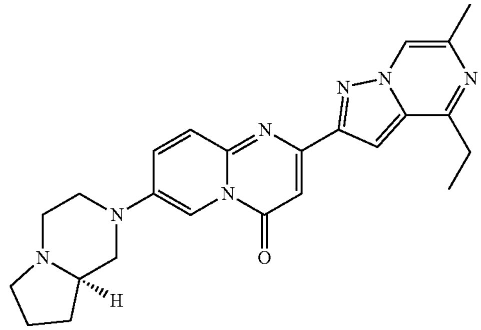
-continued
814
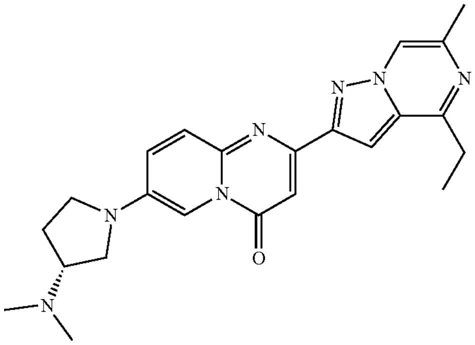
815
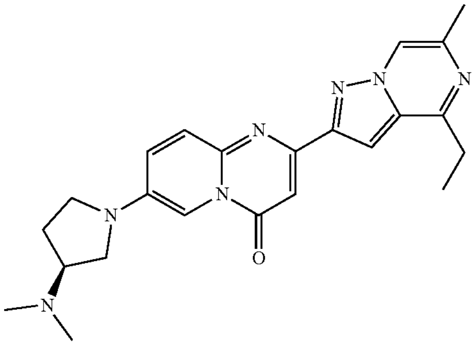
816
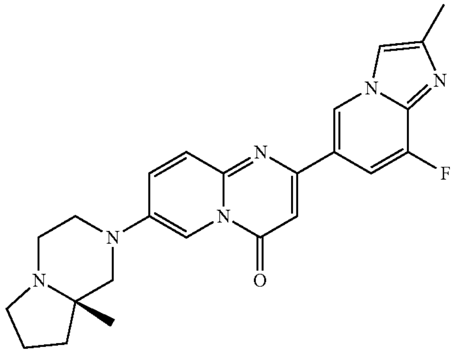
817
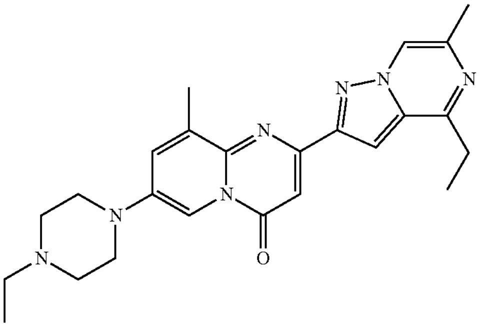

-continued
818
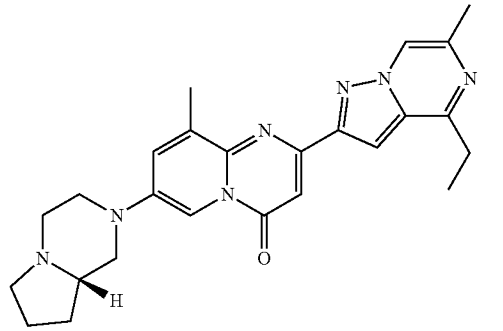
819
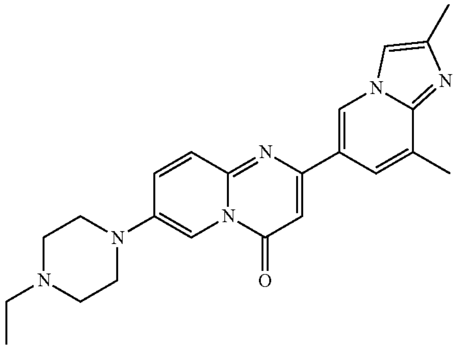
820
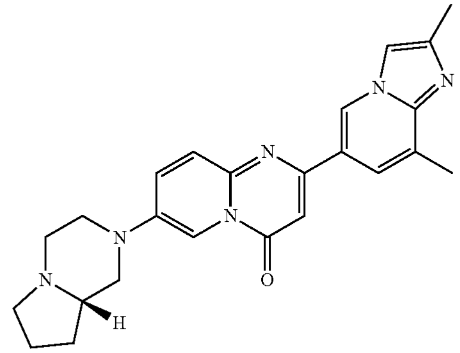
821
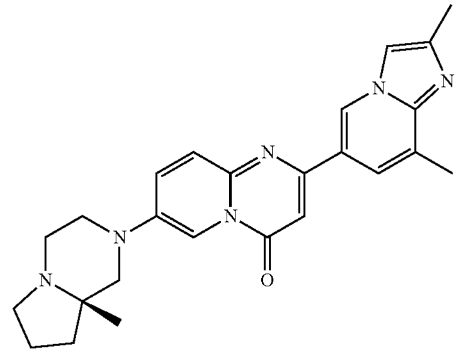
-continued
822
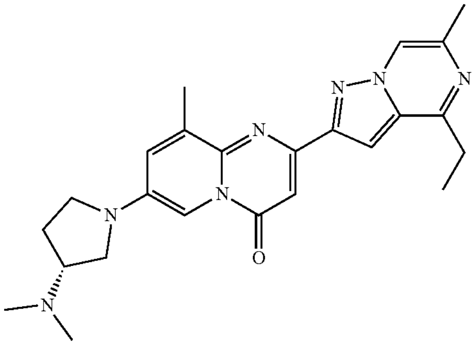
823
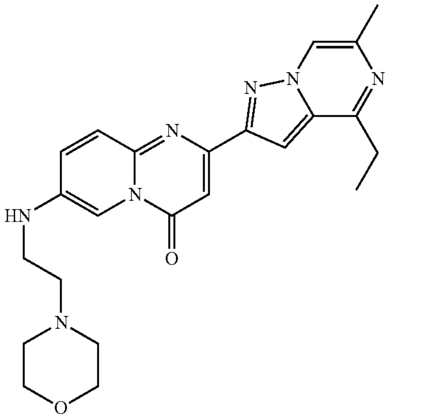
824
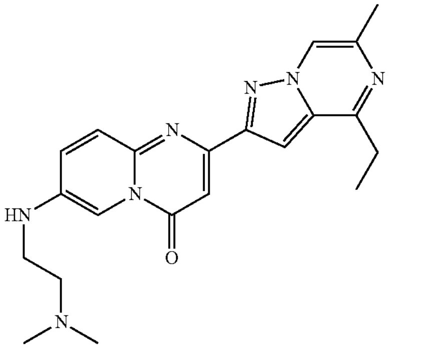
825
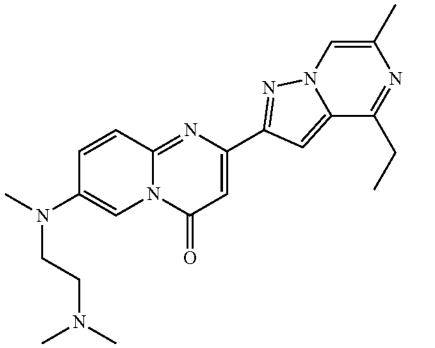

-continued
826
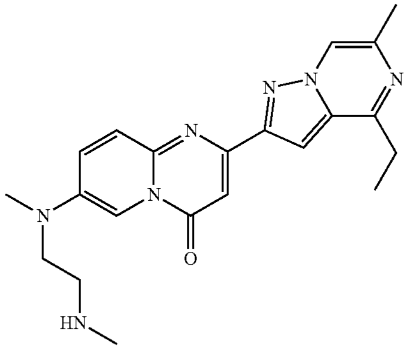
827
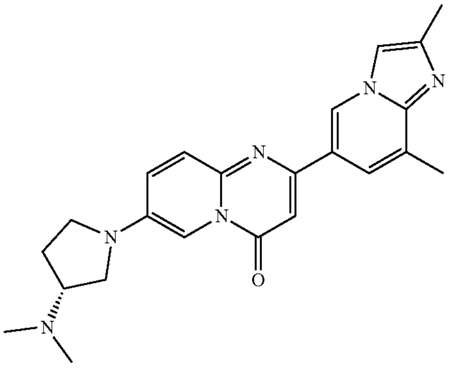
828
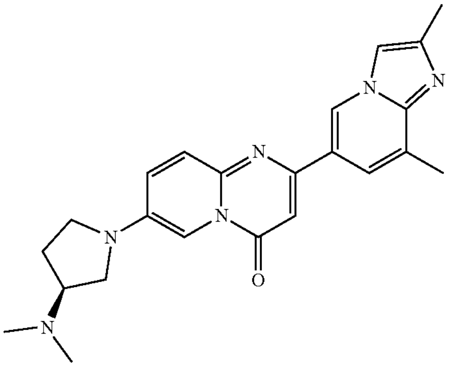
829
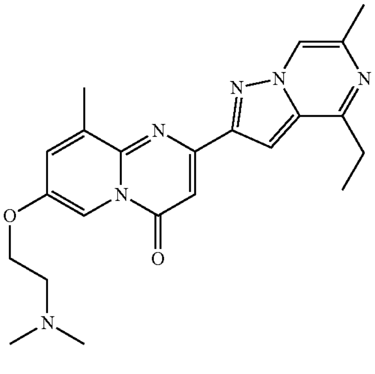
-continued
830
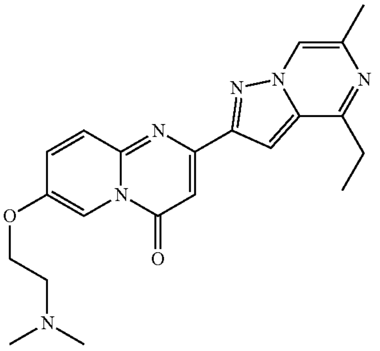
831
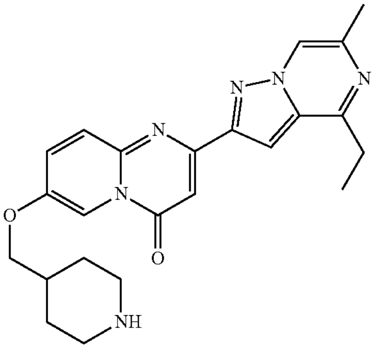
832
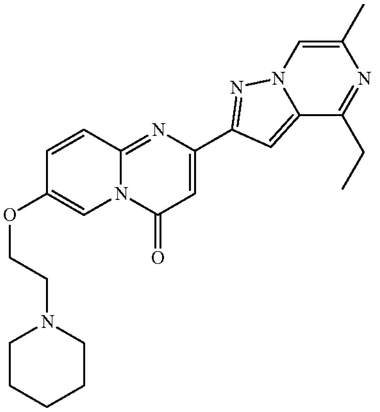
833
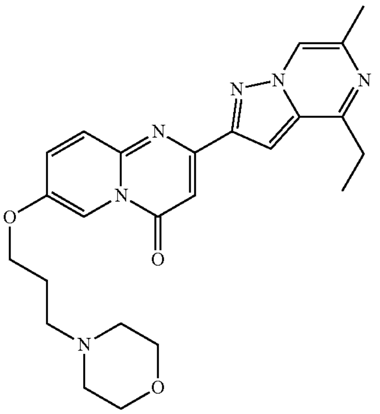

-continued

834

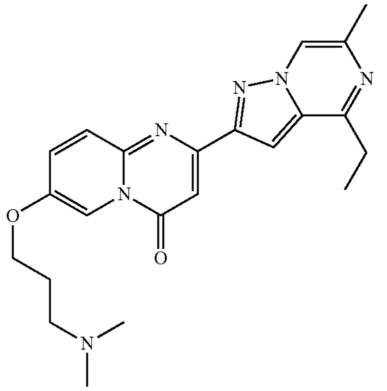

835

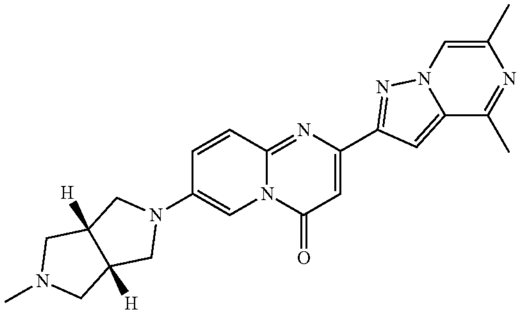

or a form thereof.

In another embodiment, the compound of Formula (I) used in a method disclosed herein is a compound selected from the group consisting of:

2-(4-methoxyphenyl)-7-(piperazin-1-yl)-4H-pyrido[1,2-a]pyrimidin-4-one
2-(4-methoxyphenyl)-7-(4-methylpiperazin-1-yl)-4H-pyrido[1,2-a]pyrimidin-4-one
2-(4-methoxyphenyl)-7-[(3R)-3-methylpiperazin-1-yl]-4H-pyrido[1,2-a]pyrimidin-4-one
7-[(3R,5S)-3,5-dimethylpiperazin-1-yl]-2-(4-methoxyphenyl)-4H-pyrido[1,2-a]pyrimidin-4-one
7-(1,4-diazepan-1-yl)-2-(4-methoxyphenyl)-4H-pyrido[1,2-a]pyrimidin-4-one
2-(3,4-dimethoxyphenyl)-7-(piperazin-1-yl)-4H-pyrido[1,2-a]pyrimidin-4-one
2-(3,4-dimethoxyphenyl)-7-(3,3-dimethylpiperazin-1-yl)-4H-pyrido[1,2-a]pyrimidin-4-one
2-(3,4-dimethoxyphenyl)-7-[(3R)-3-methylpiperazin-1-yl]-4H-pyrido[1,2-a]pyrimidin-4-one
2-(3,4-dimethoxyphenyl)-7-(4-ethylpiperazin-1-yl)-4H-pyrido[1,2-a]pyrimidin-4-one
7-(1,4-diazepan-1-yl)-2-(3,4-dimethoxyphenyl)-4H-pyrido[1,2-a]pyrimidin-4-one
2-(3,4-dimethoxyphenyl)-7-(4-methyl-1,4-diazepan-1-yl)-4H-pyrido[1,2-a]pyrimidin-4-one
2-(4-methoxyphenyl)-7-[(3S)-3-methylpiperazin-1-yl]-4H-pyrido[1,2-a]pyrimidin-4-one
2-(3,4-dimethoxyphenyl)-7-(4-methylpiperazin-1-yl)-4H-pyrido[1,2-a]pyrimidin-4-one
2-(3,4-dimethoxyphenyl)-7-[(3R,5S)-3,5-dimethylpiperazin-1-yl]-4H-pyrido[1,2-a]pyrimidin-4-one
2-(3,4-dimethoxyphenyl)-7-(4-propylpiperazin-1-yl)-4H-pyrido[1,2-a]pyrimidin-4-one
2-(4-methoxyphenyl)-7-(4-methyl-1,4-diazepan-1-yl)-4H-pyrido[1,2-a]pyrimidin-4-one
7-(3,3-dimethylpiperazin-1-yl)-2-(4-methoxyphenyl)-4H-pyrido[1,2-a]pyrimidin-4-one
2-(1,3-benzodioxol-5-yl)-7-(piperazin-1-yl)-4H-pyrido[1,2-a]pyrimidin-4-one
2-(1,3-benzodioxol-5-yl)-7-(4-methylpiperazin-1-yl)-4H-pyrido[1,2-a]pyrimidin-4-one
2-(1,3-benzodioxol-5-yl)-7-[(3R)-3-methylpiperazin-1-yl]-4H-pyrido[1,2-a]pyrimidin-4-one
2-(1,3-benzodioxol-5-yl)-7-[(3R,5S)-3,5-dimethylpiperazin-1-yl]-4H-pyrido[1,2-a]pyrimidin-4-one
2-(3-methoxyphenyl)-7-(piperazin-1-yl)-4H-pyrido[1,2-a]pyrimidin-4-one
2-(3-methoxyphenyl)-7-(4-methylpiperazin-1-yl)-4H-pyrido[1,2-a]pyrimidin-4-one
2-(3-methoxyphenyl)-7-[(3R)-3-methylpiperazin-1-yl]-4H-pyrido[1,2-a]pyrimidin-4-one
7-[(3R,5S)-3,5-dimethylpiperazin-1-yl]-2-(3-methoxyphenyl)-4H-pyrido[1,2-a]pyrimidin-4-one
7-(4-ethylpiperazin-1-yl)-2-(3-methoxyphenyl)-4H-pyrido[1,2-a]pyrimidin-4-one
7-(1,4-diazepan-1-yl)-2-(3-methoxyphenyl)-4H-pyrido[1,2-a]pyrimidin-4-one
2-(3-methoxyphenyl)-7-(4-methyl-1,4-diazepan-1-yl)-4H-pyrido[1,2-a]pyrimidin-4-one
2-(6-methylimidazo[1,2-a]pyridin-2-yl)-7-(piperazin-1-yl)-4H-pyrido[1,2-a]pyrimidin-4-one
2-(3,4-dimethoxyphenyl)-7-[(3S)-3-methylpiperazin-1-yl]-4H-pyrido[1,2-a]pyrimidin-4-one
2-(2,3-dihydro-1,4-benzodioxin-6-yl)-7-(piperazin-1-yl)-4H-pyrido[1,2-a]pyrimidin-4-one
2-(2,3-dihydro-1,4-benzodioxin-6-yl)-7-[(3S)-3-methylpiperazin-1-yl]-4H-pyrido[1,2-a]pyrimidin-4-one
2-phenyl-7-(piperazin-1-yl)-4H-pyrido[1,2-a]pyrimidin-4-one
7-[(3S)-3-methylpiperazin-1-yl]-2-phenyl-4H-pyrido[1,2-a]pyrimidin-4-one
2-(2,3-dihydro-1,4-benzodioxin-6-yl)-7-[(3R)-3-methylpiperazin-1-yl]-4H-pyrido[1,2-a]pyrimidin-4-one
2-(2,3-dihydro-1,4-benzodioxin-6-yl)-7-(3,3-dimethylpiperazin-1-yl)-4H-pyrido[1,2-a]pyrimidin-4-one
2-(2,3-dihydro-1,4-benzodioxin-6-yl)-7-[(3R,5S)-3,5-dimethylpiperazin-1-yl]-4H-pyrido[1,2-a]pyrimidin-4-one
7-(1,4-diazepan-1-yl)-2-(2,3-dihydro-1,4-benzodioxin-6-yl)-4H-pyrido[1,2-a]pyrimidin-4-one
2-(2,3-dihydro-1,4-benzodioxin-6-yl)-7-(4-methyl-1,4-diazepan-1-yl)-4H-pyrido[1,2-a]pyrimidin-4-one
2-(3,4-dimethoxyphenyl)-9-fluoro-7-(4-methylpiperazin-1-yl)-4H-pyrido[1,2-a]pyrimidin-4-one
2-(3-chlorophenyl)-7-(piperazin-1-yl)-4H-pyrido[1,2-a]pyrimidin-4-one
2-(4-chlorophenyl)-7-(piperazin-1-yl)-4H-pyrido[1,2-a]pyrimidin-4-one
7-(piperazin-1-yl)-2-[3-(trifluoromethyl)phenyl]-4H-pyrido[1,2-a]pyrimidin-4-one
7-(piperazin-1-yl)-2-[4-(trifluoromethyl)phenyl]-4H-pyrido[1,2-a]pyrimidin-4-one
2-(3-methylphenyl)-7-(piperazin-1-yl)-4H-pyrido[1,2-a]pyrimidin-4-one
2-(4-fluorophenyl)-7-(piperazin-1-yl)-4H-pyrido[1,2-a]pyrimidin-4-one
2-(4-nitrophenyl)-7-(piperazin-1-yl)-4H-pyrido[1,2-a]pyrimidin-4-one
2-(3,4-dimethoxyphenyl)-9-fluoro-7-(piperidin-4-ylamino)-4H-pyrido[1,2-a]pyrimidin-4-one 2-[4-(dimethylamino)phenyl]-9-fluoro-7-(piperazin-1-yl)-4H-pyrido[1,2-a]pyrimidin-4-one 2-[4-(dimethylamino)phenyl]-9-fluoro-7-[(3R)-3-methylpiperazin-1-yl]-4H-pyrido[1,2-a]pyrimidin-4-one 2-(2-fluorophenyl)-7-(piperazin-1-yl)-4H-pyrido[1,2-a]pyrimidin-4-one 3-(3,4-dimethoxyphenyl)-8-(piperazin-1-yl)-4H-pyrido[1,2-a]pyrimidin-4-one 2-[4-(dimethylamino)phenyl]-7-(piperazin-1-yl)-4H-pyrido[1,2-a]pyrimidin-4-one 2-[4-(dimethylamino)phenyl]-7-[(3S)-3-methylpiperazin-1-yl]-4H-pyrido[1,2-a]pyrimidin-4-one 2-(3,4-dimethylphenyl)-7-(piperazin-1-yl)-4H-pyrido[1,2-a]pyrimidin-4-one 2-(3,4-dimethylphenyl)-7-[(3S)-3-methylpiperazin-1-yl]-4H-pyrido[1,2-a]pyrimidin-4-one 2-[3-(dimethylamino)phenyl]-7-(piperazin-1-yl)-4H-pyrido[1,2-a]pyrimidin-4-one 2-[3-(dimethylamino)phenyl]-7-[(3S)-3-methylpiperazin-1-yl]-4H-pyrido[1,2-a]pyrimidin-4-one 2-[4-(difluoromethoxy)phenyl]-7-(piperazin-1-yl)-4H-pyrido[1,2-a]pyrimidin-4-one 2-[4-(difluoromethoxy)phenyl]-7-[(3S)-3-methylpiperazin-1-yl]-4H-pyrido[1,2-a]pyrimidin-4-one 2-(3-fluorophenyl)-7-(piperazin-1-yl)-4H-pyrido[1,2-a]pyrimidin-4-one 2-(3-nitrophenyl)-7-(piperazin-1-yl)-4H-pyrido[1,2-a]pyrimidin-4-one 2-(4-methylphenyl)-7-(piperazin-1-yl)-4H-pyrido[1,2-a]pyrimidin-4-one 2-(2-fluoro-4,5-dimethoxyphenyl)-7-(piperazin-1-yl)-4H-pyrido[1,2-a]pyrimidin-4-one 2-(2-fluoro-4,5-dimethoxyphenyl)-7-[(3S)-3-methylpiperazin-1-yl]-4H-pyrido[1,2-a]pyrimidin-4-one 7-(3,8-diazabicyclo[3.2.1]oct-3-yl)-2-(3,4-dimethoxyphenyl)-4H-pyrido[1,2-a]pyrimidin-4-one 2-[4-methoxy-3-(trifluoromethyl)phenyl]-7-(piperazin-1-yl)-4H-pyrido[1,2-a]pyrimidin-4-one 2-[4-methoxy-3-(trifluoromethyl)phenyl]-7-[(3R)-3-methylpiperazin-1-yl]-4H-pyrido[1,2-a]pyrimidin-4-one 2-[4-methoxy-3-(trifluoromethyl)phenyl]-7-[(3S)-3-methylpiperazin-1-yl]-4H-pyrido[1,2-a]pyrimidin-4-one 2-(3,4-dimethoxyphenyl)-9-methoxy-7-(piperazin-1-yl)-4H-pyrido[1,2-a]pyrimidin-4-one 2-(3,5-difluoro-4-hydroxyphenyl)-7-(piperazin-1-yl)-4H-pyrido[1,2-a]pyrimidin-4-one 2-(3-fluoro-4-methoxyphenyl)-7-(piperazin-1-yl)-4H-pyrido[1,2-a]pyrimidin-4-one 4-[4-oxo-7-(piperazin-1-yl)-4H-pyrido[1,2-a]pyrimidin-2-yl]benzonitrile 2-(6-methylimidazo[1,2-a]pyrazin-2-yl)-7-(piperazin-1-yl)-4H-pyrido[1,2-a]pyrimidin-4-one 2-(6-methylimidazo[1,2-a]pyrazin-2-yl)-7-[(3S)-3-methylpiperazin-1-yl]-4H-pyrido[1,2-a]pyrimidin-4-one 2-[3-fluoro-5-(trifluoromethyl)phenyl]-7-(piperazin-1-yl)-4H-pyrido[1,2-a]pyrimidin-4-one 2-[4-fluoro-3-(trifluoromethyl)phenyl]-7-(piperazin-1-yl)-4H-pyrido[1,2-a]pyrimidin-4-one 2-[2-methoxy-3-(trifluoromethyl)phenyl]-7-(piperazin-1-yl)-4H-pyrido[1,2-a]pyrimidin-4-one 2-(3,5-difluorophenyl)-7-(piperazin-1-yl)-4H-pyrido[1,2-a]pyrimidin-4-one 7-(piperazin-1-yl)-2-[3-(trifluoromethoxy)phenyl]-4H-pyrido[1,2-a]pyrimidin-4-one 2-[4-methoxy-3-(trifluoromethoxy)phenyl]-7-(piperazin-1-yl)-4H-pyrido[1,2-a]pyrimidin-4-one 2-[4-hydroxy-3-(trifluoromethoxy)phenyl]-7-(piperazin-1-yl)-4H-pyrido[1,2-a]pyrimidin-4-one 2-[4-methoxy-3-(trifluoromethoxy)phenyl]-7-[(3S)-3-methylpiperazin-1-yl]-4H-pyrido[1,2-a]pyrimidin-4-one 2-[4-hydroxy-3-(trifluoromethoxy)phenyl]-7-[(3S)-3-methylpiperazin-1-yl]-4H-pyrido[1,2-a]pyrimidin-4-one 2-(3,4-dimethoxyphenyl)-4-oxo-7-(piperazin-1-yl)-4H-quinolizine-1-carbonitrile 2-(3-fluoro-4-methoxyphenyl)-7-[(3R)-3-methylpiperazin-1-yl]-4H-pyrido[1,2-a]pyrimidin-4-one 2-(3-fluoro-4-methoxyphenyl)-7-[(3S)-3-methylpiperazin-1-yl]-4H-pyrido[1,2-a]pyrimidin-4-one 2-(6-methoxypyridin-3-yl)-7-(piperazin-1-yl)-4H-pyrido[1,2-a]pyrimidin-4-one 2-(2,4-dimethoxyphenyl)-7-(piperazin-1-yl)-4H-pyrido[1,2-a]pyrimidin-4-one 2-(2,4-dimethoxyphenyl)-7-[(3S)-3-methylpiperazin-1-yl]-4H-pyrido[1,2-a]pyrimidin-4-one 2-(3,4-dimethoxyphenyl)-7-[(3S)-3-methylpiperazin-1-yl]-4H-quinolizin-4-one 2-(5-fluoropyridin-3-yl)-7-(piperazin-1-yl)-4H-pyrido[1,2-a]pyrimidin-4-one 2-(5-fluoropyridin-3-yl)-7-[(3S)-3-methylpiperazin-1-yl]-4H-pyrido[1,2-a]pyrimidin-4-one 2-(5-chloropyridin-3-yl)-7-(piperazin-1-yl)-4H-pyrido[1,2-a]pyrimidin-4-one 2-(5-chloropyridin-3-yl)-7-[(3S)-3-methylpiperazin-1-yl]-4H-pyrido[1,2-a]pyrimidin-4-one 2-(5-chloro-6-methoxypyridin-3-yl)-7-(piperazin-1-yl)-4H-pyrido[1,2-a]pyrimidin-4-one 2-(1H-indol-6-yl)-7-(piperazin-1-yl)-4H-pyrido[1,2-a]pyrimidin-4-one 2-(1H-indol-5-yl)-7-(piperazin-1-yl)-4H-pyrido[1,2-a]pyrimidin-4-one 2-[3-(difluoromethoxy)-4-methoxyphenyl]-7-(piperazin-1-yl)-4H-pyrido[1,2-a]pyrimidin-4-one 2-[3-(difluoromethoxy)-4-hydroxyphenyl]-7-(piperazin-1-yl)-4H-pyrido[1,2-a]pyrimidin-4-one 2-[3-(difluoromethoxy)-4-methoxyphenyl]-7-[(3S)-3-methylpiperazin-1-yl]-4H-pyrido[1,2-a]pyrimidin-4-one 2-[3-(difluoromethoxy)-4-hydroxyphenyl]-7-[(3S)-3-methylpiperazin-1-yl]-4H-pyrido[1,2-a]pyrimidin-4-one 2-(3-fluoro-4-methoxyphenyl)-7-(piperazin-1-yl)-4H-quinolizin-4-one 2-(3-fluoro-4-methoxyphenyl)-7-[(3S)-3-methylpiperazin-1-yl]-4H-quinolizin-4-one 2-(3,5-difluorophenyl)-7-[(3S)-3-methylpiperazin-1-yl]-4H-pyrido[1,2-a]pyrimidin-4-one 2-(3,4-dimethoxyphenyl)-7-(piperazin-1-yl)-4H-quinolizin-4-one 2-(imidazo[1,2-a]pyridin-7-yl)-7-(piperazin-1-yl)-4H-pyrido[1,2-a]pyrimidin-4-one 2-(imidazo[1,2-a]pyridin-6-yl)-7-(piperazin-1-yl)-4H-pyrido[1,2-a]pyrimidin-4-one 2-(2-methylimidazo[1,2-a]pyridin-6-yl)-7-(piperazin-1-yl)-4H-pyrido[1,2-a]pyrimidin-4-one 2-(3-chloro-4-methoxyphenyl)-7-(piperazin-1-yl)-4H-pyrido[1,2-a]pyrimidin-4-one 2-(3-chloro-4-methoxyphenyl)-7-[(3S)-3-methylpiperazin-1-yl]-4H-pyrido[1,2-a]pyrimidin-4-one 2-(3-ethoxy-4-methoxyphenyl)-7-(piperazin-1-yl)-4H-pyrido[1,2-a]pyrimidin-4-one 2-(3-ethoxy-4-methoxyphenyl)-7-[(3S)-3-methylpiperazin-1-yl]-4H-pyrido[1,2-a]pyrimidin-4-one 2-(2-methylimidazo[1,2-a]pyridin-6-yl)-7-(4-methylpiperazin-1-yl)-4H-pyrido[1,2-a]pyrimidin-4-one 2-(2-methylimidazo[1,2-a]pyridin-6-yl)-7-[(3S)-3-methylpiperazin-1-yl]-4H-pyrido[1,2-a]pyrimidin-4-one
7-(1,4-diazepan-1-yl)-2-(2-methylimidazo[1,2-a]pyridin-6-yl)-4H-pyrido[1,2-a]pyrimidin-4-one
7-[(3R,5S)-3,5-dimethylpiperazin-1-yl]-2-(2-methylimidazo[1,2-a]pyridin-6-yl)-4H-pyrido[1,2-a]pyrimidin-4-one
2-(6,8-dimethylimidazo[1,2-a]pyrazin-2-yl)-7-(piperazin-1-yl)-4H-pyrido[1,2-a]pyrimidin-4-one
2-(6,8-dimethylimidazo[1,2-a]pyrazin-2-yl)-7-[(3S)-3-methylpiperazin-1-yl]-4H-pyrido[1,2-a]pyrimidin-4-one
2-(4,6-dimethylpyrazolo[1,5-a]pyrazin-2-yl)-7-(piperazin-1-yl)-4H-pyrido[1,2-a]pyrimidin-4-one
2-(4,6-dimethylpyrazolo[1,5-a]pyrazin-2-yl)-7-[(3S)-3-methylpiperazin-1-yl]-4H-pyrido[1,2-a]pyrimidin-4-one
2-(3,4-dimethoxyphenyl)-7-(2-methylpyridin-4-yl)-4H-pyrido[1,2-a]pyrimidin-4-one
7-(piperazin-1-yl)-2-[2-(trifluoromethyl)imidazo[1,2-a]pyridin-6-yl]-4H-pyrido[1,2-a]pyrimidin-4-one
2-(2-ethylimidazo[1,2-a]pyridin-6-yl)-7-(piperazin-1-yl)-4H-pyrido[1,2-a]pyrimidin-4-one
2-(2,3-dimethylimidazo[1,2-a]pyridin-6-yl)-7-(piperazin-1-yl)-4H-pyrido[1,2-a]pyrimidin-4-one
2-(3,4-dimethoxyphenyl)-7-[(3aR,6aS)-hexahydropyrrolo[3,4-c]pyrrol-2(1H)-yl]-4H-pyrido[1,2-a]pyrimidin-4-one
7-(4-aminopiperidin-1-yl)-2-(3,4-dimethoxyphenyl)-4H-pyrido[1,2-a]pyrimidin-4-one
7-(piperazin-1-yl)-2-(1H-pyrrolo[2,3-b]pyridin-5-yl)-4H-pyrido[1,2-a]pyrimidin-4-one
2-(1-methyl-1H-pyrrolo[2,3-b]pyridin-5-yl)-7-(piperazin-1-yl)-4H-pyrido[1,2-a]pyrimidin-4-one
7-[(3R,5S)-3,5-dimethylpiperazin-1-yl]-2-(1-methyl-1H-pyrrolo[2,3-b]pyridin-5-yl)-4H-pyrido[1,2-a]pyrimidin-4-one
7-[(3R,5S)-3,5-dimethylpiperazin-1-yl]-2-(4,6-dimethylpyrazolo[1,5-a]pyrazin-2-yl)-4H-pyrido[1,2-a]pyrimidin-4-one
7-(1,4-diazepan-1-yl)-2-(4,6-dimethylpyrazolo[1,5-a]pyrazin-2-yl)-4H-pyrido[1,2-a]pyrimidin-4-one
2-(2-methyl-1,3-benzoxazol-6-yl)-7-(piperazin-1-yl)-4H-pyrido[1,2-a]pyrimidin-4-one
2-(2-methyl-1,3-benzoxazol-6-yl)-7-[(3S)-3-methylpiperazin-1-yl]-4H-pyrido[1,2-a]pyrimidin-4-one
2-(2-methyl-1,3-benzothiazol-5-yl)-7-[(3S)-3-methylpiperazin-1-yl]-4H-pyrido[1,2-a]pyrimidin-4-one
2-(2-methyl-1,3-benzothiazol-5-yl)-7-(piperazin-1-yl)-4H-pyrido[1,2-a]pyrimidin-4-one
2-(2-methyl-2H-indazol-5-yl)-7-(piperazin-1-yl)-4H-pyrido[1,2-a]pyrimidin-4-one
2-(2-methyl-2H-indazol-5-yl)-7-[(3S)-3-methylpiperazin-1-yl]-4H-pyrido[1,2-a]pyrimidin-4-one
2-(3-fluoro-5-methoxyphenyl)-7-(piperazin-1-yl)-4H-pyrido[1,2-a]pyrimidin-4-one
2-(3-fluoro-5-methoxyphenyl)-7-[(3S)-3-methylpiperazin-1-yl]-4H-pyrido[1,2-a]pyrimidin-4-one
2-(2,8-dimethylimidazo[1,2-a]pyridin-6-yl)-7-(piperazin-1-yl)-4H-pyrido[1,2-a]pyrimidin-4-one
2-(3,4-dimethoxyphenyl)-9-methyl-7-[(3S)-3-methylpiperazin-1-yl]-4H-pyrido[1,2-a]pyrimidin-4-one
2-(3,4-dimethoxyphenyl)-7-(1,2,3,6-tetrahydropyridin-4-yl)-4H-pyrido[1,2-a]pyrimidin-4-one
2-(3,4-dimethoxyphenyl)-7-(piperidin-4-yl)-4H-pyrido[1,2-a]pyrimidin-4-one
2-(3-fluoro-4,5-dimethoxyphenyl)-7-(piperazin-1-yl)-4H-pyrido[1,2-a]pyrimidin-4-one
2-(3,4-dimethoxyphenyl)-7-(4-hydroxypiperazin-1-yl)-4H-pyrido[1,2-a]pyrimidin-4-one
2-(3,4-dimethoxyphenyl)-7-[(3S)-3-(dimethylamino)pyrrolidin-1-yl]-4H-pyrido[1,2-a]pyrimidin-4-one
2-(3,4-dimethoxyphenyl)-7-[4-(dimethylamino)piperidin-1-yl]-4H-pyrido[1,2-a]pyrimidin-4-one
2-(4-methoxy-3-methylphenyl)-7-(piperazin-1-yl)-4H-pyrido[1,2-a]pyrimidin-4-one
3-[4-oxo-7-(piperazin-1-yl)-4H-pyrido[1,2-a]pyrimidin-2-yl]benzonitrile
2-methoxy-5-[4-oxo-7-(piperazin-1-yl)-4H-pyrido[1,2-a]pyrimidin-2-yl]benzonitrile
2-(3-fluoro-4-hydroxyphenyl)-7-(piperazin-1-yl)-4H-pyrido[1,2-a]pyrimidin-4-one
2-(4-ethoxy-3-fluorophenyl)-7-(piperazin-1-yl)-4H-pyrido[1,2-a]pyrimidin-4-one
2-[3-fluoro-4-(2,2,2-trifluoroethoxy)phenyl]-7-(piperazin-1-yl)-4H-pyrido[1,2-a]pyrimidin-4-one
2-(2-methyl-1,3-benzoxazol-5-yl)-7-(piperazin-1-yl)-4H-pyrido[1,2-a]pyrimidin-4-one
2-(2-methyl-1,3-benzoxazol-5-yl)-7-[(3S)-3-methylpiperazin-1-yl]-4H-pyrido[1,2-a]pyrimidin-4-one
2-(3-fluoro-4-methylphenyl)-7-(piperazin-1-yl)-4H-pyrido[1,2-a]pyrimidin-4-one
2-(3-fluoro-4-methylphenyl)-7-[(3S)-3-methylpiperazin-1-yl]-4H-pyrido[1,2-a]pyrimidin-4-one
7-[(3S)-3-aminopyrrolidin-1-yl]-2-(3,4-dimethoxyphenyl)-4H-pyrido[1,2-a]pyrimidin-4-one
2-(3,4-dimethoxyphenyl)-9-methyl-7-(piperazin-1-yl)-4H-pyrido[1,2-a]pyrimidin-4-one
7-(1,4-diazepan-1-yl)-2-(2-methyl-1,3-benzothiazol-5-yl)-4H-pyrido[1,2-a]pyrimidin-4-one
7-[(3S)-3-methylpiperazin-1-yl]-2-(4-methyl-1,3-thiazol-2-yl)-4H-pyrido[1,2-a]pyrimidin-4-one
2-(4-methyl-1,3-thiazol-2-yl)-7-(piperazin-1-yl)-4H-pyrido[1,2-a]pyrimidin-4-one
2-(3,4-dimethoxyphenyl)-7-(1-methylpiperidin-4-yl)-4H-pyrido[1,2-a]pyrimidin-4-one
2-(3,4-dimethoxyphenyl)-7-[(3S)-3-(propan-2-ylamino)pyrrolidin-1-yl]-4H-pyrido[1,2-a]pyrimidin-4-one
2-(3-fluoro-4-methoxyphenyl)-7-(4-methyl-1,4-diazepan-1-yl)-4H-pyrido[1,2-a]pyrimidin-4-one
2-(4-methoxy-3-nitrophenyl)-7-(piperazin-1-yl)-4H-pyrido[1,2-a]pyrimidin-4-one
2-[3-fluoro-4-(methylsulfanyl)phenyl]-7-(piperazin-1-yl)-4H-pyrido[1,2-a]pyrimidin-4-one
7-(4-methyl-1,4-diazepan-1-yl)-2-(2-methylimidazo[1,2-a]pyridin-6-yl)-4H-pyrido[1,2-a]pyrimidin-4-one
2-(4,6-dimethylpyrazolo[1,5-a]pyrazin-2-yl)-7-(4-methylpiperazin-1-yl)-4H-pyrido[1,2-a]pyrimidin-4-one
2-(2-methyl-1,3-benzoxazol-6-yl)-7-(4-methylpiperazin-1-yl)-4H-pyrido[1,2-a]pyrimidin-4-one
7-[(3R,5S)-3,5-dimethylpiperazin-1-yl]-2-(2-methyl-1,3-benzoxazol-6-yl)-4H-pyrido[1,2-a]pyrimidin-4-one
2-(5-fluoro-6-methoxypyridin-3-yl)-7-[(3S)-3-methylpiperazin-1-yl]-4H-pyrido[1,2-a]pyrimidin-4-one
7-[(3R,5S)-3,5-dimethylpiperazin-1-yl]-2-(5-fluoro-6-methoxypyridin-3-yl)-4H-pyrido[1,2-a]pyrimidin-4-one
7-[(3R,5S)-3,5-dimethylpiperazin-1-yl]-2-(2-methyl-1,3-benzothiazol-5-yl)-4H-pyrido[1,2-a]pyrimidin-4-one
2-(2-methyl-1,3-benzothiazol-5-yl)-7-(4-methylpiperazin-1-yl)-4H-pyrido[1,2-a]pyrimidin-4-one
2-(2-methyl-1,3-benzothiazol-5-yl)-7-(4-methyl-1,4-diazepan-1-yl)-4H-pyrido[1,2-a]pyrimidin-4-one
7-[(8aS)-hexahydropyrrolo[1,2-a]pyrazin-2(1H)-yl]-2-(2-methyl-1,3-benzothiazol-5-yl)-4H-pyrido[1,2-a]pyrimidin-4-one 2-(4-methyl-1H-imidazol-1-yl)-7-(piperazin-1-yl)-4H-pyrido[1,2-a]pyrimidin-4-one 2-(4-methyl-1H-imidazol-1-yl)-7-[(3S)-3-methylpiperazin-1-yl]-4H-pyrido[1,2-a]pyrimidin-4-one 2-(3,4-dimethoxyphenyl)-7-{[2-(methylamino)ethyl]amino}-4H-pyrido[1,2-a]pyrimidin-4-one 2-(5-fluoro-6-methoxypyridin-3-yl)-7-(piperazin-1-yl)-4H-pyrido[1,2-a]pyrimidin-4-one 2-(3,5-difluoro-4-methoxyphenyl)-7-(piperazin-1-yl)-4H-pyrido[1,2-a]pyrimidin-4-one 2-(3,5-difluoro-4-methoxyphenyl)-7-[(3S)-3-methylpiperazin-1-yl]-4H-pyrido[1,2-a]pyrimidin-4-one 7-[4-(dimethylamino)piperidin-1-yl]-2-(3-fluoro-4-methoxyphenyl)-4H-pyrido[1,2-a]pyrimidin-4-one 2-(3-fluoro-4-methoxyphenyl)-7-(1,2,3,6-tetrahydropyridin-4-yl)-4H-pyrido[1,2-a]pyrimidin-4-one 2-(3,4-dimethoxyphenyl)-7-(piperidin-4-ylamino)-4H-pyrido[1,2-a]pyrimidin-4-one 2-(3,4-dimethoxyphenyl)-7-(1-methyl-1,2,3,6-tetrahydropyridin-4-yl)-4H-pyrido[1,2-a]pyrimidin-4-one 2-(3-chloro-5-fluorophenyl)-7-[(3S)-3-methylpiperazin-1-yl]-4H-pyrido[1,2-a]pyrimidin-4-one 2-(3-chloro-5-fluorophenyl)-7-(piperazin-1-yl)-4H-pyrido[1,2-a]pyrimidin-4-one 7-[(3S)-3-methylpiperazin-1-yl]-2-(1-methyl-1H-pyrazol-4-yl)-4H-pyrido[1,2-a]pyrimidin-4-one 2-(1-methyl-1H-pyrazol-4-yl)-7-(piperazin-1-yl)-4H-pyrido[1,2-a]pyrimidin-4-one 2-(2-methyl-1,3-benzoxazol-6-yl)-7-[(3R)-3-methylpiperazin-1-yl]-4H-pyrido[1,2-a]pyrimidin-4-one 7-(3,3-dimethylpiperazin-1-yl)-2-(2-methyl-1,3-benzoxazol-6-yl)-4H-pyrido[1,2-a]pyrimidin-4-one 7-(1,4-diazepan-1-yl)-2-(2-methyl-1,3-benzoxazol-6-yl)-4H-pyrido[1,2-a]pyrimidin-4-one 2-(2-methyl-1,3-benzoxazol-6-yl)-7-(4-methyl-1,4-diazepan-1-yl)-4H-pyrido[1,2-a]pyrimidin-4-one 7-[(8aS)-hexahydropyrrolo[1,2-a]pyrazin-2(1H)-yl]-2-(2-methyl-1,3-benzoxazol-6-yl)-4H-pyrido[1,2-a]pyrimidin-4-one 7-[(8aR)-hexahydropyrrolo[1,2-a]pyrazin-2(1H)-yl]-2-(2-methyl-1,3-benzoxazol-6-yl)-4H-pyrido[1,2-a]pyrimidin-4-one 2-(4,5-dimethoxypyridin-2-yl)-7-(piperazin-1-yl)-4H-pyrido[1,2-a]pyrimidin-4-one 7-[3-(dimethylamino)pyrrolidin-1-yl]-2-(3-fluoro-4-methoxyphenyl)-4H-quinolizin-4-one 7-(4-aminopiperidin-1-yl)-2-(3-fluoro-4-methoxyphenyl)-4H-quinolizin-4-one 7-(4-ethylpiperazin-1-yl)-2-(2-methyl-1,3-benzoxazol-6-yl)-4H-pyrido[1,2-a]pyrimidin-4-one 7-[4-(dimethylamino)piperidin-1-yl]-2-(3-fluoro-4-methoxyphenyl)-4H-quinolizin-4-one 2-(3-fluoro-4-methoxyphenyl)-7-(1-methyl-1,2,3,6-tetrahydropyridin-4-yl)-4H-pyrido[1,2-a]pyrimidin-4-one 7-[(3S)-3-(dimethylamino)pyrrolidin-1-yl]-2-(3-fluoro-4-methoxyphenyl)-4H-pyrido[1,2-a]pyrimidin-4-one 7-[(3R,4R)-3-(dimethylamino)-4-hydroxypyrrolidin-1-yl]-2-(3-fluoro-4-methoxyphenyl)-4H-pyrido[1,2-a]pyrimidin-4-one 7-(4-aminopiperidin-1-yl)-2-(3-fluoro-4-methoxyphenyl)-4H-pyrido[1,2-a]pyrimidin-4-one 2-(3-fluoro-4-methoxyphenyl)-7-[4-(methylamino)piperidin-1-yl]-4H-pyrido[1,2-a]pyrimidin-4-one 2-(8-fluoro-2-methylimidazo[1,2-a]pyridin-6-yl)-7-(piperazin-1-yl)-4H-pyrido[1,2-a]pyrimidin-4-one 7-[(3R,5S)-3,5-dimethylpiperazin-1-yl]-2-(8-fluoro-2-methylimidazo[1,2-a]pyridin-6-yl)-4H-pyrido[1,2-a]pyrimidin-4-one 2-(8-fluoro-2-methylimidazo[1,2-a]pyridin-6-yl)-7-(4-methyl-1,4-diazepan-1-yl)-4H-pyrido[1,2-a]pyrimidin-4-one 2-(3-fluoro-4-methoxyphenyl)-7-[(3aR,6aS)-hexahydropyrrolo[3,4-c]pyrrol-2(1H)-yl]-4H-pyrido[1,2-a]pyrimidin-4-one 2-(3-fluoro-4-methoxyphenyl)-7-[(3aR,6aS)-5-methylhexahydropyrrolo[3,4-c]pyrrol-2(1H)-yl]-4H-pyrido[1,2-a]pyrimidin-4-one 2-(3,4-dimethoxyphenyl)-7-[1-(2-hydroxyethyl)piperidin-4-yl]-4H-pyrido[1,2-a]pyrimidin-4-one 2-(4-fluoro-3-methoxyphenyl)-7-[(3S)-3-methylpiperazin-1-yl]-4H-pyrido[1,2-a]pyrimidin-4-one 2-(4-fluoro-3-methoxyphenyl)-7-(piperazin-1-yl)-4H-pyrido[1,2-a]pyrimidin-4-one 2-(3,4-difluoro-5-methoxyphenyl)-7-[(3S)-3-methylpiperazin-1-yl]-4H-pyrido[1,2-a]pyrimidin-4-one 2-(3,4-difluoro-5-methoxyphenyl)-7-(piperazin-1-yl)-4H-pyrido[1,2-a]pyrimidin-4-one 2-(2-methyl-1,3-benzothiazol-6-yl)-7-(piperazin-1-yl)-4H-pyrido[1,2-a]pyrimidin-4-one 7-(3-fluoro-4-methoxyphenyl)-2-(piperazin-1-yl)-4H-pyrido[1,2-a]pyrimidin-4-one 2-(2-methyl-1,3-benzothiazol-6-yl)-7-[(3S)-3-methylpiperazin-1-yl]-4H-pyrido[1,2-a]pyrimidin-4-one 2-(3-fluoro-4-methoxyphenyl)-7-[(3S)-3-(methylamino)pyrrolidin-1-yl]-4H-pyrido[1,2-a]pyrimidin-4-one 2-(3-fluoro-4-methoxyphenyl)-7-{4-[(methylamino)methyl]piperidin-1-yl}-4H-pyrido[1,2-a]pyrimidin-4-one 7-[(3S)-3-aminopyrrolidin-1-yl]-2-(3-fluoro-4-methoxyphenyl)-4H-pyrido[1,2-a]pyrimidin-4-one 2-(3-fluoro-4-methoxyphenyl)-7-{[(3R)-1-methylpyrrolidin-3-yl]amino}-4H-pyrido[1,2-a]pyrimidin-4-one 7-{4-[(dimethylamino)methyl]piperidin-1-yl}-2-(3-fluoro-4-methoxyphenyl)-4H-pyrido[1,2-a]pyrimidin-4-one 2-(6-methoxypyridin-2-yl)-7-(piperazin-1-yl)-4H-pyrido[1,2-a]pyrimidin-4-one 7-(piperazin-1-yl)-2-(pyridin-3-yl)-4H-pyrido[1,2-a]pyrimidin-4-one 2-(5-methoxypyridin-3-yl)-7-(piperazin-1-yl)-4H-pyrido[1,2-a]pyrimidin-4-one 3-fluoro-5-{7-[(3S)-3-methylpiperazin-1-yl]-4-oxo-4H-pyrido[1,2-a]pyrimidin-2-yl}benzonitrile 3-fluoro-5-[4-oxo-7-(piperazin-1-yl)-4H-pyrido[1,2-a]pyrimidin-2-yl]benzonitrile 2-(3-fluoro-4-methoxyphenyl)-7-[(3'S,4'S)-4'-hydroxy-1,3'-bipyrrolidin-1'-yl]-4H-pyrido[1,2-a]pyrimidin-4-one 2-(3-fluoro-4-methoxyphenyl)-7-{methyl[(3R)-pyrrolidin-3-yl]amino}-4H-pyrido[1,2-a]pyrimidin-4-one 7-[(3S)-3,4-dimethylpiperazin-1-yl]-2-(2-methyl-1,3-benzoxazol-6-yl)-4H-pyrido[1,2-a]pyrimidin-4-one 2-(3,4-dimethoxyphenyl)-7-[(1-methylpiperidin-4-yl)oxy]-4H-pyrido[1,2-a]pyrimidin-4-one 2-(3,4-dimethoxyphenyl)-7-[(3S)-pyrrolidin-3-yloxy]-4H-pyrido[1,2-a]pyrimidin-4-one 2-(3,4-dimethoxyphenyl)-7-(piperidin-4-yloxy)-4H-pyrido[1,2-a]pyrimidin-4-one 7-(1,4-diazepan-1-yl)-2-(3,4-dimethoxyphenyl)-9-methyl-4H-pyrido[1,2-a]pyrimidin-4-one 2-(3-fluoro-4-methoxyphenyl)-7-{methyl[(3R)-1-methylpyrrolidin-3-yl]amino}-4H-pyrido[1,2-a]pyrimidin-4-one 7-[4-(dimethylamino)piperidin-1-yl]-2-(2-methyl-1,3-benzoxazol-6-yl)-4H-pyrido[1,2-a]pyrimidin-4-one 7-[(3S)-3-(dimethylamino)pyrrolidin-1-yl]-2-(2-methyl-1,3-benzoxazol-6-yl)-4H-pyrido[1,2-a]pyrimidin-4-one
7-(4-aminopiperidin-1-yl)-2-(2-methyl-1,3-benzoxazol-6-yl)-4H-pyrido[1,2-a]pyrimidin-4-one
7-[(3aR,6aS)-hexahydropyrrolo[3,4-c]pyrrol-2(1H)-yl]-2-(2-methyl-1,3-benzoxazol-6-yl)-4H-pyrido[1,2-a]pyrimidin-4-one
7-[(3R)-3,4-dimethylpiperazin-1-yl]-2-(2-methyl-1,3-benzoxazol-6-yl)-4H-pyrido[1,2-a]pyrimidin-4-one
2-(3,4-dimethoxyphenyl)-7-(1,2,3,6-tetrahydropyridin-4-yl)-4H-quinolizin-4-one
2-(3-fluoro-4-methoxyphenyl)-7-[(3aR,6aR)-1-methylhexahydropyrrolo[3,4-b]pyrrol-5(1H)-yl]-4H-pyrido[1,2-a]pyrimidin-4-one
2-(3,4-dimethoxyphenyl)-9-methyl-7-(1,2,3,6-tetrahydropyridin-4-yl)-4H-pyrido[1,2-a]pyrimidin-4-one
2-(3,4-dimethoxyphenyl)-7-[1-(2-hydroxyethyl)-1,2,3,6-tetrahydropyridin-4-yl]-4H-pyrido[1,2-a]pyrimidin-4-one
2-(3,4-dimethoxyphenyl)-7-(1-methyl-1,2,3,6-tetrahydropyridin-4-yl)-4H-quinolizin-4-one
2-(3,4-dimethoxyphenyl)-9-methyl-7-(piperidin-4-yl)-4H-pyrido[1,2-a]pyrimidin-4-one
2-(3,4-dimethoxyphenyl)-9-methyl-7-(1-methyl-1,2,3,6-tetrahydropyridin-4-yl)-4H-pyrido[1,2-a]pyrimidin-4-one
2-(3,4-dimethoxyphenyl)-9-methyl-7-(1-methylpiperidin-4-yl)-4H-pyrido[1,2-a]pyrimidin-4-one
7-(1,4-diazepan-1-yl)-2-(2-methyl-1,3-benzothiazol-6-yl)-4H-pyrido[1,2-a]pyrimidin-4-one
2-(2-methyl-1,3-benzothiazol-6-yl)-7-(4-methyl-1,4-diazepan-1-yl)-4H-pyrido[1,2-a]pyrimidin-4-one
7-[(8aS)-hexahydropyrrolo[1,2-a]pyrazin-2(1H)-yl]-2-(2-methyl-1,3-benzothiazol-6-yl)-4H-pyrido[1,2-a]pyrimidin-4-one
2-(2-methyl-1,3-benzothiazol-6-yl)-7-(4-methylpiperazin-1-yl)-4H-pyrido[1,2-a]pyrimidin-4-one
2-(3,4-dimethoxyphenyl)-7-[(3aR,6aS)-hexahydropyrrolo[3,4-c]pyrrol-2(1H)-yl]-9-methyl-4H-pyrido[1,2-a]pyrimidin-4-one
7-[(3S)-3,4-dimethylpiperazin-1-yl]-2-(4,6-dimethylpyrazolo[1,5-a]pyrazin-2-yl)-4H-pyrido[1,2-a]pyrimidin-4-one
2-(4,6-dimethylpyrazolo[1,5-a]pyrazin-2-yl)-7-[(3R,5S)-3,4,5-trimethylpiperazin-1-yl]-4H-pyrido[1,2-a]pyrimidin-4-one
2-(3,4-dimethoxyphenyl)-9-methyl-7-[(3aR,6aS)-5-methylhexahydropyrrolo[3,4-c]pyrrol-2(1H)-yl]-4H-pyrido[1,2-a]pyrimidin-4-one
2-(3,4-dimethoxyphenyl)-7-[4-(dimethylamino)piperidin-1-yl]-9-methyl-4H-pyrido[1,2-a]pyrimidin-4-one
7-[(1R,5S)-8-azabicyclo[3.2.1]oct-2-en-3-yl]-2-(3,4-dimethoxyphenyl)-4H-pyrido[1,2-a]pyrimidin-4-one
2-(3,4-dimethoxyphenyl)-7-(1,2,5,6-tetrahydropyridin-3-yl)-4H-pyrido[1,2-a]pyrimidin-4-one
7-[(3R)-3-(dimethylamino)pyrrolidin-1-yl]-2-(2-methyl-1,3-benzoxazol-6-yl)-4H-pyrido[1,2-a]pyrimidin-4-one
2-(2-ethyl-1,3-benzoxazol-6-yl)-7-(piperazin-1-yl)-4H-pyrido[1,2-a]pyrimidin-4-one
2-(2-ethyl-1,3-benzoxazol-6-yl)-7-[(3S)-3-methylpiperazin-1-yl]-4H-pyrido[1,2-a]pyrimidin-4-one
2-(2-methyl-1,3-benzoxazol-6-yl)-7-[(3aR,6aS)-5-methylhexahydropyrrolo[3,4-c]pyrrol-2(1H)-yl]-4H-pyrido[1,2-a]pyrimidin-4-one
7-(8-fluoro-2-methylimidazo[1,2-a]pyridin-6-yl)-2-(piperazin-1-yl)-4H-pyrido[1,2-a]pyrimidin-4-one
2-(8-fluoro-2-methylimidazo[1,2-a]pyridin-6-yl)-7-(4-methylpiperazin-1-yl)-4H-pyrido[1,2-a]pyrimidin-4-one
2-(8-fluoro-2-methylimidazo[1,2-a]pyridin-6-yl)-7-[(3R)-3-methylpiperazin-1-yl]-4H-pyrido[1,2-a]pyrimidin-4-one
2-(8-fluoro-2-methylimidazo[1,2-a]pyridin-6-yl)-7-[(8aS)-hexahydropyrrolo[1,2-a]pyrazin-2(1H)-yl]-4H-pyrido[1,2-a]pyrimidin-4-one
2-(8-fluoro-2-methylimidazo[1,2-a]pyridin-6-yl)-7-[(8aR)-hexahydropyrrolo[1,2-a]pyrazin-2(1H)-yl]-4H-pyrido[1,2-a]pyrimidin-4-one
7-(4-aminopiperidin-1-yl)-2-(8-fluoro-2-methylimidazo[1,2-a]pyridin-6-yl)-4H-pyrido[1,2-a]pyrimidin-4-one
7-[(3R)-3-(dimethylamino)pyrrolidin-1-yl]-2-(8-fluoro-2-methylimidazo[1,2-a]pyridin-6-yl)-4H-pyrido[1,2-a]pyrimidin-4-one
7-[(3S)-3-(dimethylamino)pyrrolidin-1-yl]-2-(8-fluoro-2-methylimidazo[1,2-a]pyridin-6-yl)-4H-pyrido[1,2-a]pyrimidin-4-one
2-(4-aminopiperidin-1-yl)-7-(3-fluoro-4-methoxyphenyl)-4H-pyrido[1,2-a]pyrimidin-4-one
2-[(3R)-3-(dimethylamino)pyrrolidin-1-yl]-7-(3-fluoro-4-methoxyphenyl)-4H-pyrido[1,2-a]pyrimidin-4-one
2-[(3S)-3-(dimethylamino)pyrrolidin-1-yl]-7-(3-fluoro-4-methoxyphenyl)-4H-pyrido[1,2-a]pyrimidin-4-one
2-(3-fluoro-4-methoxyphenyl)-7-[(3aR,6aS)-5-(2-hydroxyethyl)hexahydropyrrolo[3,4-c]pyrrol-2(1H)-yl]-4H-pyrido[1,2-a]pyrimidin-4-one
2-(3-fluoro-4-methoxyphenyl)-7-[(3aS,6aS)-1-methylhexahydropyrrolo[3,4-b]pyrrol-5(1H)-yl]-4H-pyrido[1,2-a]pyrimidin-4-one
2-(3-fluoro-4-methoxyphenyl)-7-[(3aR,6aS)-5-(propan-2-yl)hexahydropyrrolo[3,4-c]pyrrol-2(1H)-yl]-4H-pyrido[1,2-a]pyrimidin-4-one
7-[(3R)-3-(dimethylamino)pyrrolidin-1-yl]-2-(3-fluoro-4-methoxyphenyl)-4H-pyrido[1,2-a]pyrimidin-4-one
7-(3,3-dimethylpiperazin-1-yl)-2-(2-methyl-1,3-benzothiazol-6-yl)-4H-pyrido[1,2-a]pyrimidin-4-one
7-[(8aR)-hexahydropyrrolo[1,2-a]pyrazin-2(1H)-yl]-2-(2-methyl-1,3-benzothiazol-6-yl)-4H-pyrido[1,2-a]pyrimidin-4-one
7-[4-(dimethylamino)piperidin-1-yl]-2-(2-methyl-1,3-benzothiazol-6-yl)-4H-pyrido[1,2-a]pyrimidin-4-one
2-(2-methyl-1,3-benzothiazol-6-yl)-7-(piperidin-4-yloxy)-4H-pyrido[1,2-a]pyrimidin-4-one
2-(8-chloro-2-methylimidazo[1,2-a]pyridin-6-yl)-7-(piperazin-1-yl)-4H-pyrido[1,2-a]pyrimidin-4-one
2-(8-chloro-2-methylimidazo[1,2-a]pyridin-6-yl)-7-[(3R,5S)-3,5-dimethylpiperazin-1-yl]-4H-pyrido[1,2-a]pyrimidin-4-one
2-(8-chloro-2-methylimidazo[1,2-a]pyridin-6-yl)-7-(4-methyl-1,4-diazepan-1-yl)-4H-pyrido[1,2-a]pyrimidin-4-one
2-(8-chloro-2-methylimidazo[1,2-a]pyridin-6-yl)-7-[(3R)-3-methylpiperazin-1-yl]-4H-pyrido[1,2-a]pyrimidin-4-one
2-(8-chloro-2-methylimidazo[1,2-a]pyridin-6-yl)-7-[(3S)-3-methylpiperazin-1-yl]-4H-pyrido[1,2-a]pyrimidin-4-one
2-(8-chloro-2-methylimidazo[1,2-a]pyridin-6-yl)-7-[(8aR)-hexahydropyrrolo[1,2-a]pyrazin-2(1H)-yl]-4H-pyrido[1,2-a]pyrimidin-4-one
2-(8-chloro-2-methylimidazo[1,2-a]pyridin-6-yl)-7-[(8aS)-hexahydropyrrolo[1,2-a]pyrazin-2(1H)-yl]-4H-pyrido[1,2-a]pyrimidin-4-one
7-(3-fluoro-4-methoxyphenyl)-2-(1,2,3,6-tetrahydropyridin-4-yl)-4H-pyrido[1,2-a]pyrimidin-4-one
7-[(3S)-3,4-dimethylpiperazin-1-yl]-2-(8-fluoro-2-methylimidazo[1,2-a]pyridin-6-yl)-4H-pyrido[1,2-a]pyrimidin-4-one 7-[(3R)-3,4-dimethylpiperazin-1-yl]-2-(8-fluoro-2-methylimidazo[1,2-a]pyridin-6-yl)-4H-pyrido[1,2-a]pyrimidin-4-one 7-[4-(dimethylamino)piperidin-1-yl]-2-(8-fluoro-2-methylimidazo[1,2-a]pyridin-6-yl)-4H-pyrido[1,2-a]pyrimidin-4-one 2-[4-(dimethylamino)piperidin-1-yl]-7-(3-fluoro-4-methoxyphenyl)-4H-pyrido[1,2-a]pyrimidin-4-one 2-(4-fluoro-2-methyl-1,3-benzoxazol-6-yl)-7-(1,2,3,6-tetrahydropyridin-4-yl)-4H-pyrido[1,2-a]pyrimidin-4-one 2-(4-fluoro-2-methyl-1,3-benzoxazol-6-yl)-7-(1-methyl-1,2,3,6-tetrahydropyridin-4-yl)-4H-pyrido[1,2-a]pyrimidin-4-one 2-(3-fluoro-4-methoxyphenyl)-7-[(4aR,7aR)-octahydro-6H-pyrrolo[3,4-b]pyridin-6-yl]-4H-pyrido[1,2-a]pyrimidin-4-one 2-(2-methyl-1,3-benzoxazol-6-yl)-7-(1,2,3,6-tetrahydropyridin-4-yl)-4H-pyrido[1,2-a]pyrimidin-4-one 2-(2-methyl-1,3-benzoxazol-6-yl)-7-(1-methyl-1,2,3,6-tetrahydropyridin-4-yl)-4H-pyrido[1,2-a]pyrimidin-4-one 7-(1-ethyl-1,2,3,6-tetrahydropyridin-4-yl)-2-(2-methyl-1,3-benzoxazol-6-yl)-4H-pyrido[1,2-a]pyrimidin-4-one 2-(4-fluoro-2-methyl-1,3-benzoxazol-6-yl)-7-(piperazin-1-yl)-4H-pyrido[1,2-a]pyrimidin-4-one 2-(4-fluoro-2-methyl-1,3-benzoxazol-6-yl)-7-[(3S)-3-methylpiperazin-1-yl]-4H-pyrido[1,2-a]pyrimidin-4-one 7-[(3S)-3,4-dimethylpiperazin-1-yl]-2-(4-fluoro-2-methyl-1,3-benzoxazol-6-yl)-4H-pyrido[1,2-a]pyrimidin-4-one 2-(4-fluoro-2-methyl-1,3-benzoxazol-6-yl)-7-(4-methylpiperazin-1-yl)-4H-pyrido[1,2-a]pyrimidin-4-one 7-(4-ethylpiperazin-1-yl)-2-(4-fluoro-2-methyl-1,3-benzoxazol-6-yl)-4H-pyrido[1,2-a]pyrimidin-4-one 2-(4-fluoro-2-methyl-1,3-benzoxazol-6-yl)-7-(4-propylpiperazin-1-yl)-4H-pyrido[1,2-a]pyrimidin-4-one 7-[(3aR,6aS)-5-ethylhexahydropyrrolo[3,4-c]pyrrol-2(1H)-yl]-2-(3-fluoro-4-methoxyphenyl)-4H-pyrido[1,2-a]pyrimidin-4-one 2-(3-fluoro-4-methoxyphenyl)-9-methyl-7-(1,2,3,6-tetrahydropyridin-4-yl)-4H-pyrido[1,2-a]pyrimidin-4-one 2-(3-fluoro-4-methoxyphenyl)-7-[(4aR,7aR)-1-methyloctahydro-6H-pyrrolo[3,4-b]pyridin-6-yl]-4H-pyrido[1,2-a]pyrimidin-4-one 2-(3,4-dimethoxyphenyl)-9-methyl-7-[(3R)-3-methylpiperazin-1-yl]-4H-pyrido[1,2-a]pyrimidin-4-one 2-(3-fluoro-4-methoxyphenyl)-9-methyl-7-(1-methyl-1,2,3,6-tetrahydropyridin-4-yl)-4H-pyrido[1,2-a]pyrimidin-4-one 7-(3-fluoro-4-methoxyphenyl)-2-(piperidin-4-yl)-4H-pyrido[1,2-a]pyrimidin-4-one 7-(3-fluoro-4-methoxyphenyl)-2-(1-methylpiperidin-4-yl)-4H-pyrido[1,2-a]pyrimidin-4-one 7-(1-ethyl-1,2,3,6-tetrahydropyridin-4-yl)-2-(4-fluoro-2-methyl-1,3-benzoxazol-6-yl)-4H-pyrido[1,2-a]pyrimidin-4-one 2-(4-fluoro-2-methyl-1,3-benzoxazol-6-yl)-7-(1-propyl-1,2,3,6-tetrahydropyridin-4-yl)-4H-pyrido[1,2-a]pyrimidin-4-one 2-(3,4-dimethoxyphenyl)-7-[(1R,5S)-8-methyl-8-azabicyclo[3.2.1]oct-3-yl]-4H-pyrido[1,2-a]pyrimidin-4-one 2-(3,4-dimethoxyphenyl)-7-[(2R)-2-methylpiperazin-1-yl]-4H-pyrido[1,2-a]pyrimidin-4-one 2-(2-methyl-1,3-benzoxazol-6-yl)-7-[(3S)-3-methylpiperazin-1-yl]-4H-quinolizin-4-one 2-(2-methyl-1,3-benzoxazol-6-yl)-7-(4-methylpiperazin-1-yl)-4H-quinolizin-4-one 7-[(3S)-4-ethyl-3-methylpiperazin-1-yl]-2-(2-methyl-1,3-benzoxazol-6-yl)-4H-quinolizin-4-one 7-[(3S)-3,4-dimethylpiperazin-1-yl]-2-(2-methyl-1,3-benzoxazol-6-yl)-4H-quinolizin-4-one 7-(4-aminopiperidin-1-yl)-2-(2-methyl-1,3-benzoxazol-6-yl)-4H-quinolizin-4-one 2-(3-fluoro-4-methoxyphenyl)-9-methyl-7-[(3S)-3-methylpiperazin-1-yl]-4H-pyrido[1,2-a]pyrimidin-4-one 7-[4-(dimethylamino)piperidin-1-yl]-2-(3-fluoro-4-methoxyphenyl)-9-methyl-4H-pyrido[1,2-a]pyrimidin-4-one 2-(3-fluoro-4-methoxyphenyl)-9-methyl-7-(1-methylpiperidin-4-yl)-4H-pyrido[1,2-a]pyrimidin-4-one 7-[4-(cyclopropylamino)piperidin-1-yl]-2-(3,4-dimethoxyphenyl)-9-methyl-4H-pyrido[1,2-a]pyrimidin-4-one 2-(8-chloro-2-methylimidazo[1,2-a]pyridin-6-yl)-7-[(3S)-3,4-dimethylpiperazin-1-yl]-4H-pyrido[1,2-a]pyrimidin-4-one 2-(3,4-dimethoxyphenyl)-7-[(3R,5S)-3,5-dimethylpiperazin-1-yl]-9-methyl-4H-pyrido[1,2-a]pyrimidin-4-one 2-(3,4-dimethoxyphenyl)-7-[(3R)-3,4-dimethylpiperazin-1-yl]-9-methyl-4H-pyrido[1,2-a]pyrimidin-4-one 2-(4,6-dimethylpyrazolo[1,5-a]pyrazin-2-yl)-7-(4-methyl-1,4-diazepan-1-yl)-4H-pyrido[1,2-a]pyrimidin-4-one 2-(4,6-dimethylpyrazolo[1,5-a]pyrazin-2-yl)-7-[(3R)-3-methylpiperazin-1-yl]-4H-pyrido[1,2-a]pyrimidin-4-one 2-(4,6-dimethylpyrazolo[1,5-a]pyrazin-2-yl)-7-[(8aS)-hexahydropyrrolo[1,2-a]pyrazin-2(1H)-yl]-4H-pyrido[1,2-a]pyrimidin-4-one 2-(4,6-dimethylpyrazolo[1,5-a]pyrazin-2-yl)-7-[(8aR)-hexahydropyrrolo[1,2-a]pyrazin-2(1H)-yl]-4H-pyrido[1,2-a]pyrimidin-4-one 2-(4,6-dimethylpyrazolo[1,5-a]pyrazin-2-yl)-7-(4-ethylpiperazin-1-yl)-4H-pyrido[1,2-a]pyrimidin-4-one 7-[4-(dimethylamino)piperidin-1-yl]-2-(4,6-dimethylpyrazolo[1,5-a]pyrazin-2-yl)-4H-pyrido[1,2-a]pyrimidin-4-one 7-(3,3-dimethylpiperazin-1-yl)-2-(4,6-dimethylpyrazolo[1,5-a]pyrazin-2-yl)-4H-pyrido[1,2-a]pyrimidin-4-one 7-(4-cyclopropylpiperazin-1-yl)-2-(4,6-dimethylpyrazolo[1,5-a]pyrazin-2-yl)-4H-pyrido[1,2-a]pyrimidin-4-one 2-(4,6-dimethylpyrazolo[1,5-a]pyrazin-2-yl)-7-(1,2,3,6-tetrahydropyridin-4-yl)-4H-pyrido[1,2-a]pyrimidin-4-one 2-(4,6-dimethylpyrazolo[1,5-a]pyrazin-2-yl)-7-[(3R)-4-ethyl-3-methylpiperazin-1-yl]-4H-pyrido[1,2-a]pyrimidin-4-one 2-(3,4-dimethoxyphenyl)-9-methyl-7-(4-methylpiperazin-1-yl)-4H-pyrido[1,2-a]pyrimidin-4-one 2-(3,4-dimethoxyphenyl)-7-[4-(dimethylamino)piperidin-1-yl]-9-ethyl-4H-pyrido[1,2-a]pyrimidin-4-one 2-(3,4-dimethoxyphenyl)-7-[1-(2-hydroxyethyl)-1,2,3,6-tetrahydropyridin-4-yl]-9-methyl-4H-pyrido[1,2-a]pyrimidin-4-one 7-[4-(dimethylamino)piperidin-1-yl]-2-(2-methyl-1,3-benzothiazol-5-yl)-4H-pyrido[1,2-a]pyrimidin-4-one 7-(4-aminopiperidin-1-yl)-2-(2-methyl-1,3-benzothiazol-5-yl)-4H-pyrido[1,2-a]pyrimidin-4-one 7-[(3aR,6aS)-hexahydropyrrolo[3,4-c]pyrrol-2(1H)-yl]-2-(2-methyl-1,3-benzothiazol-5-yl)-4H-pyrido[1,2-a]pyrimidin-4-one 2-(4,6-dimethylpyrazolo[1,5-a]pyrazin-2-yl)-7-(1-methyl-1,2,3,6-tetrahydropyridin-4-yl)-4H-pyrido[1,2-a]pyrimidin-4-one 2-(4,6-dimethylpyrazolo[1,5-a]pyrazin-2-yl)-7-(1-ethyl-1,2,3,6-tetrahydropyridin-4-yl)-4H-pyrido[1,2-a]pyrimidin-4-one 2-(4,6-dimethylpyrazolo[1,5-a]pyrazin-2-yl)-7-(1-propyl-1,2,3,6-tetrahydropyridin-4-yl)-4H-pyrido[1,2-a]pyrimidin-4-one 2-(3,4-dimethoxyphenyl)-7-(1,2,3,6-tetrahydropyridin-4-yl)-4H-pyrimido[1,2-a]pyrimidin-4-one
7-(1-cyclopropyl-1,2,3,6-tetrahydropyridin-4-yl)-2-(4,6-dimethylpyrazolo[1,5-a]pyrazin-2-yl)-4H-pyrido[1,2-a]pyrimidin-4-one
2-(4,6-dimethylpyrazolo[1,5-a]pyrazin-2-yl)-7-[1-(propan-2-yl)-1,2,3,6-tetrahydropyridin-4-yl]-4H-pyrido[1,2-a]pyrimidin-4-one
7-(1-cyclobutyl-1,2,3,6-tetrahydropyridin-4-yl)-2-(4,6-dimethylpyrazolo[1,5-a]pyrazin-2-yl)-4H-pyrido[1,2-a]pyrimidin-4-one
2-(4,6-dimethylpyrazolo[1,5-a]pyrazin-2-yl)-7-[1-(oxetan-3-yl)-1,2,3,6-tetrahydropyridin-4-yl]-4H-pyrido[1,2-a]pyrimidin-4-one
2-(3,4-dimethoxyphenyl)-9-methyl-7-[4-(methylamino)piperidin-1-yl]-4H-pyrido[1,2-a]pyrimidin-4-one
2-(3,4-dimethoxyphenyl)-7-[4-(ethylamino)piperidin-1-yl]-9-methyl-4H-pyrido[1,2-a]pyrimidin-4-one
2-(3,4-dimethoxyphenyl)-8-methyl-7-(piperazin-1-yl)-4H-pyrido[1,2-a]pyrimidin-4-one
2-(3,4-dimethoxyphenyl)-7-[4-(propan-2-ylamino)piperidin-1-yl]-4H-pyrido[1,2-a]pyrimidin-4-one
7-(1-cyclobutyl-1,2,3,6-tetrahydropyridin-4-yl)-2-(3,4-dimethoxyphenyl)-4H-pyrido[1,2-a]pyrimidin-4-one
2-(3,4-dimethoxyphenyl)-7-[1-(propan-2-yl)-1,2,3,6-tetrahydropyridin-4-yl]-4H-pyrido[1,2-a]pyrimidin-4-one
2-(3,4-dimethoxyphenyl)-7-[1-(oxetan-3-yl)-1,2,3,6-tetrahydropyridin-4-yl]-4H-pyrido[1,2-a]pyrimidin-4-one
2-(3,4-dimethoxyphenyl)-7-(1-propyl-1,2,3,6-tetrahydropyridin-4-yl)-4H-pyrido[1,2-a]pyrimidin-4-one
2-(3,4-dimethoxyphenyl)-7-[4-(methylamino)cyclohex-1-en-1-yl]-4H-pyrido[1,2-a]pyrimidin-4-one
2-(3,4-dimethoxyphenyl)-7-[4-(dimethylamino)cyclohex-1-en-1-yl]-4H-pyrido[1,2-a]pyrimidin-4-one
2-(3,4-dimethoxyphenyl)-7-{4-[ethyl(methyl)amino]cyclohex-1-en-1-yl}-4H-pyrido[1,2-a]pyrimidin-4-one
2-(3,4-dimethoxyphenyl)-7-{4-[methyl(propyl)amino]cyclohex-1-en-1-yl}-4H-pyrido[1,2-a]pyrimidin-4-one
2-(3,4-dimethoxyphenyl)-7-(1-ethyl-1,2,3,6-tetrahydropyridin-4-yl)-4H-pyrido[1,2-a]pyrimidin-4-one
7-(3,4-dimethoxyphenyl)-2-(1,2,3,6-tetrahydropyridin-4-yl)-4H-pyrido[1,2-a]pyrimidin-4-one
7-(8-fluoro-2-methylimidazo[1,2-a]pyridin-6-yl)-2-(1,2,3,6-tetrahydropyridin-4-yl)-4H-pyrido[1,2-a]pyrimidin-4-one
2-(8-fluoro-2-methylimidazo[1,2-a]pyridin-6-yl)-7-[4-(propan-2-yl)piperazin-1-yl]-4H-pyrido[1,2-a]pyrimidin-4-one
2-(8-chloro-2-methylimidazo[1,2-a]pyridin-6-yl)-7-[4-(propan-2-yl)piperazin-1-yl]-4H-pyrido[1,2-a]pyrimidin-4-one
7-(2-methylimidazo[1,2-a]pyridin-6-yl)-2-(1,2,3,6-tetrahydropyridin-4-yl)-4H-pyrido[1,2-a]pyrimidin-4-one
7-(2-methylimidazo[1,2-a]pyridin-6-yl)-2-(1-methyl-1,2,3,6-tetrahydropyridin-4-yl)-4H-pyrido[1,2-a]pyrimidin-4-one
7-(3,4-dimethoxyphenyl)-2-(1-methyl-1,2,3,6-tetrahydropyridin-4-yl)-4H-pyrido[1,2-a]pyrimidin-4-one
2-(3,4-dimethoxyphenyl)-9-methyl-7-(1-propyl-1,2,3,6-tetrahydropyridin-4-yl)-4H-pyrido[1,2-a]pyrimidin-4-one
7-(1-cyclobutyl-1,2,3,6-tetrahydropyridin-4-yl)-2-(3,4-dimethoxyphenyl)-9-methyl-4H-pyrido[1,2-a]pyrimidin-4-one
2-(2-methyl-1,3-benzothiazol-6-yl)-7-(piperidin-4-yl)-4H-pyrimido[1,2-b]pyridazin-4-one
7-(4-aminopiperidin-1-yl)-2-(2-methyl-1,3-benzothiazol-6-yl)-4H-pyrido[1,2-a]pyrimidin-4-one
7-(3-aminopyrrolidin-1-yl)-2-(2-methyl-1,3-benzothiazol-6-yl)-4H-pyrido[1,2-a]pyrimidin-4-one
7-[(3R)-3-(dimethylamino)pyrrolidin-1-yl]-2-(2-methyl-1,3-benzothiazol-6-yl)-4H-pyrido[1,2-a]pyrimidin-4-one
2-(2-methyl-1,3-benzothiazol-6-yl)-7-(1,2,3,6-tetrahydropyridin-4-yl)-4H-pyrido[1,2-a]pyrimidin-4-one
2-(8-fluoro-2-methylimidazo[1,2-a]pyridin-6-yl)-7-[4-(2-methoxyethyl)piperazin-1-yl]-4H-pyrido[1,2-a]pyrimidin-4-one
2-(3,4-dimethoxyphenyl)-9-methyl-7-[1-(oxetan-3-yl)-1,2,3,6-tetrahydropyridin-4-yl]-4H-pyrido[1,2-a]pyrimidin-4-one
2-(3,4-dimethoxyphenyl)-9-methyl-7-[1-(propan-2-yl)-1,2,3,6-tetrahydropyridin-4-yl]-4H-pyrido[1,2-a]pyrimidin-4-one
2-(3,4-dimethoxyphenyl)-7-(1-ethyl-1,2,3,6-tetrahydropyridin-4-yl)-9-methyl-4H-pyrido[1,2-a]pyrimidin-4-one
2-(3,4-dimethoxyphenyl)-8-methyl-7-(1,2,3,6-tetrahydropyridin-4-yl)-4H-pyrido[1,2-a]pyrimidin-4-one
7-(1-cyclopropyl-1,2,3,6-tetrahydropyridin-4-yl)-2-(3,4-dimethoxyphenyl)-9-methyl-4H-pyrido[1,2-a]pyrimidin-4-one
2-(3,4-dimethoxyphenyl)-8-methyl-7-(1-methyl-1,2,3,6-tetrahydropyridin-4-yl)-4H-pyrido[1,2-a]pyrimidin-4-one
2-(2-methyl-1,3-benzothiazol-6-yl)-7-(1-methyl-1,2,3,6-tetrahydropyridin-4-yl)-4H-pyrido[1,2-a]pyrimidin-4-one
7-[1-(2-hydroxyethyl)-1,2,3,6-tetrahydropyridin-4-yl]-2-(2-methyl-1,3-benzothiazol-6-yl)-4H-pyrido[1,2-a]pyrimidin-4-one
2-(2-methyl-1,3-benzothiazol-6-yl)-7-[1-(propan-2-yl)-1,2,3,6-tetrahydropyridin-4-yl]-4H-pyrido[1,2-a]pyrimidin-4-one
7-(1-cyclopropyl-1,2,3,6-tetrahydropyridin-4-yl)-2-(2-methyl-1,3-benzothiazol-6-yl)-4H-pyrido[1,2-a]pyrimidin-4-one
7-(1-ethyl-1,2,3,6-tetrahydropyridin-4-yl)-2-(2-methyl-1,3-benzothiazol-6-yl)-4H-pyrido[1,2-a]pyrimidin-4-one
7-[(3R)-3,4-dimethylpiperazin-1-yl]-2-(4,6-dimethylpyrazolo[1,5-a]pyrazin-2-yl)-4H-pyrido[1,2-a]pyrimidin-4-one
2-(3,4-dimethoxyphenyl)-7-(1,2,3,6-tetrahydropyridin-4-yl)-4H-pyrimido[1,2-b]pyridazin-4-one
7-[(1S,4S)-2,5-diazabicyclo[2.2.1]hept-2-yl]-2-(4,6-dimethylpyrazolo[1,5-a]pyrazin-2-yl)-4H-pyrido[1,2-a]pyrimidin-4-one
2-(4,6-dimethylpyrazolo[1,5-a]pyrazin-2-yl)-7-[(1S,4S)-5-methyl-2,5-diazabicyclo[2.2.1]hept-2-yl]-4H-pyrido[1,2-a]pyrimidin-4-one
2-(4,6-dimethylpyrazolo[1,5-a]pyrazin-2-yl)-7-[(1S,4S)-5-ethyl-2,5-diazabicyclo[2.2.1]hept-2-yl]-4H-pyrido[1,2-a]pyrimidin-4-one
2-(3,4-dimethoxyphenyl)-7-(1,2,3,6-tetrahydropyridin-4-yl)-4H-pyrazino[1,2-a]pyrimidin-4-one
2-(3-fluoro-4-methoxyphenyl)-7-(piperidin-4-yl)-4H-pyrido[1,2-a]pyrimidin-4-one
2-(3,4-dimethoxyphenyl)-7-(1-ethylpiperidin-4-yl)-4H-pyrido[1,2-a]pyrimidin-4-one
2-(3,4-dimethoxyphenyl)-7-[cis-4-(methylamino)cyclohexyl]-4H-pyrido[1,2-a]pyrimidin-4-one
2-(3,4-dimethoxyphenyl)-7-(piperidin-3-yl)-4H-pyrido[1,2-a]pyrimidin-4-one
2-(3,4-dimethoxyphenyl)-9-methyl-7-[4-(propylamino)piperidin-1-yl]-4H-pyrido[1,2-a]pyrimidin-4-one
2-(3,4-dimethoxyphenyl)-9-ethyl-7-(1,2,3,6-tetrahydropyridin-4-yl)-4H-pyrido[1,2-a]pyrimidin-4-one
7-(2-methylimidazo[1,2-a]pyridin-6-yl)-2-(piperidin-4-yl)-4H-pyrido[1,2-a]pyrimidin-4-one 7-(8-fluoro-2-methylimidazo[1,2-a]pyridin-6-yl)-2-(piperidin-4-yl)-4H-pyrido[1,2-a]pyrimidin-4-one 7-(8-fluoro-2-methylimidazo[1,2-a]pyridin-6-yl)-2-(1-methyl-1,2,3,6-tetrahydropyridin-4-yl)-4H-pyrido[1,2-a]pyrimidin-4-one 7-(4-cyclopropylpiperazin-1-yl)-2-(8-fluoro-2-methylimidazo[1,2-a]pyridin-6-yl)-4H-pyrido[1,2-a]pyrimidin-4-one 2-(1,3-dimethylpyrrolo[1,2-a]pyrazin-7-yl)-7-(1,2,3,6-tetrahydropyridin-4-yl)-4H-pyrazino[1,2-a]pyrimidin-4-one 2-(3,4-dimethoxyphenyl)-7-[(8aR)-hexahydropyrrolo[1,2-a]pyrazin-2(1H)-yl]-9-methyl-4H-pyrido[1,2-a]pyrimidin-4-one 2-(3,4-dimethoxyphenyl)-9-ethyl-7-(1-methyl-1,2,3,6-tetrahydropyridin-4-yl)-4H-pyrido[1,2-a]pyrimidin-4-one 2-(3,4-dimethoxyphenyl)-9-methyl-7-[4-(propan-2-ylamino)piperidin-1-yl]-4H-pyrido[1,2-a]pyrimidin-4-one 2-(3,4-dimethoxyphenyl)-7-[(8aS)-hexahydropyrrolo[1,2-a]pyrazin-2(1H)-yl]-9-methyl-4H-pyrido[1,2-a]pyrimidin-4-one 2-(3,4-dimethoxyphenyl)-9-ethyl-7-(1-ethyl-1,2,3,6-tetrahydropyridin-4-yl)-4H-pyrido[1,2-a]pyrimidin-4-one 2-(3,4-dimethoxyphenyl)-9-methyl-7-[4-(morpholin-4-yl)piperidin-1-yl]-4H-pyrido[1,2-a]pyrimidin-4-one 2-(6-methylpyrazolo[1,5-a]pyrazin-2-yl)-7-(piperazin-1-yl)-4H-pyrido[1,2-a]pyrimidin-4-one 2-(2-methyl-1,3-benzoxazol-6-yl)-7-(1,2,3,6-tetrahydropyridin-4-yl)-4H-pyrazino[1,2-a]pyrimidin-4-one hydrochloride (1:1)

2-(2-methyl-1,3-benzoxazol-6-yl)-7-(1-methyl-1,2,3,6-tetrahydropyridin-4-yl)-4H-pyrazino[1,2-a]pyrimidin-4-one 7-(1-ethyl-1,2,3,6-tetrahydropyridin-4-yl)-2-(2-methyl-1,3-benzoxazol-6-yl)-4H-pyrazino[1,2-a]pyrimidin-4-one 2-(2-methyl-1,3-benzothiazol-6-yl)-7-(piperidin-4-yl)-4H-pyrido[1,2-a]pyrimidin-4-one 2-(4,6-dimethylpyrazolo[1,5-a]pyrazin-2-yl)-7-[4-(pyrrolidin-1-yl)piperidin-1-yl]-4H-pyrido[1,2-a]pyrimidin-4-one 7-(1,4'-bipiperidin-1'-yl)-2-(4,6-dimethylpyrazolo[1,5-a]pyrazin-2-yl)-4H-pyrido[1,2-a]pyrimidin-4-one 2-(4,6-dimethylpyrazolo[1,5-a]pyrazin-2-yl)-7-[4-(4-methylpiperazin-1-yl)piperidin-1-yl]-4H-pyrido[1,2-a]pyrimidin-4-one 2-(4,6-dimethylpyrazolo[1,5-a]pyrazin-2-yl)-7-[4-(morpholin-4-yl)piperidin-1-yl]-4H-pyrido[1,2-a]pyrimidin-4-one 2-(2-methylimidazo[1,2-a]pyridin-6-yl)-7-(1,2,3,6-tetrahydropyridin-4-yl)-4H-pyrido[1,2-a]pyrimidin-4-one 2-(2-methylimidazo[1,2-a]pyridin-6-yl)-7-(1-methyl-1,2,3,6-tetrahydropyridin-4-yl)-4H-pyrido[1,2-a]pyrimidin-4-one 7-(1-ethyl-1,2,3,6-tetrahydropyridin-4-yl)-2-(2-methylimidazo[1,2-a]pyridin-6-yl)-4H-pyrido[1,2-a]pyrimidin-4-one 7-[4-(dimethylamino)piperidin-1-yl]-2-(2-methylimidazo[1,2-a]pyridin-6-yl)-4H-pyrido[1,2-a]pyrimidin-4-one 2-(3,4-dimethoxyphenyl)-7-{4-[(2-hydroxyethyl)amino]piperidin-1-yl}-9-methyl-4H-pyrido[1,2-a]pyrimidin-4-one 2-(3,4-dimethoxyphenyl)-9-ethyl-7-(1-methylpiperidin-4-yl)-4H-pyrido[1,2-a]pyrimidin-4-one 7-[4-(diethylamino)piperidin-1-yl]-2-(3,4-dimethoxyphenyl)-9-methyl-4H-pyrido[1,2-a]pyrimidin-4-one 2-(3,4-dimethoxyphenyl)-9-ethyl-7-(1-ethylpiperidin-4-yl)-4H-pyrido[1,2-a]pyrimidin-4-one 2-(2-methylimidazo[1,2-a]pyridin-6-yl)-7-[4-(pyrrolidin-1-yl)piperidin-1-yl]-4H-pyrido[1,2-a]pyrimidin-4-one 2-(2-methylimidazo[1,2-a]pyridin-6-yl)-7-(piperidin-4-yl)-4H-pyrido[1,2-a]pyrimidin-4-one 2-(2-methyl-1,3-benzothiazol-6-yl)-7-(1-methylpiperidin-4-yl)-4H-pyrido[1,2-a]pyrimidin-4-one 7-(4-methylpiperazin-1-yl)-2-(6-methylpyrazolo[1,5-a]pyrazin-2-yl)-4H-pyrido[1,2-a]pyrimidin-4-one 7-[(3S)-3-methylpiperazin-1-yl]-2-(6-methylpyrazolo[1,5-a]pyrazin-2-yl)-4H-pyrido[1,2-a]pyrimidin-4-one 7-[(3R,5S)-3,5-dimethylpiperazin-1-yl]-2-(6-methylpyrazolo[1,5-a]pyrazin-2-yl)-4H-pyrido[1,2-a]pyrimidin-4-one 2-(1-methyl-1H-indazol-5-yl)-7-(1,2,3,6-tetrahydropyridin-4-yl)-4H-pyrido[1,2-a]pyrimidin-4-one 2-[6-(dimethylamino)pyridin-3-yl]-7-(1,2,3,6-tetrahydropyridin-4-yl)-4H-pyrido[1,2-a]pyrimidin-4-one 7-[4-(diethylamino)piperidin-1-yl]-2-(2-methylimidazo[1,2-a]pyridin-6-yl)-4H-pyrido[1,2-a]pyrimidin-4-one 2-(3,4-dimethoxyphenyl)-7-{4-[(2-hydroxyethyl)(methyl)amino]piperidin-1-yl}-9-methyl-4H-pyrido[1,2-a]pyrimidin-4-one 2-(3,4-dimethoxyphenyl)-9-ethyl-7-[(3R)-3-methylpiperazin-1-yl]-4H-pyrido[1,2-a]pyrimidin-4-one 2-(2-methylimidazo[1,2-a]pyridin-6-yl)-7-(1-methylpiperidin-4-yl)-4H-pyrido[1,2-a]pyrimidin-4-one 2-(1-methyl-1H-indazol-5-yl)-7-(1-methyl-1,2,3,6-tetrahydropyridin-4-yl)-4H-pyrido[1,2-a]pyrimidin-4-one 2-[6-(dimethylamino)pyridin-3-yl]-7-(1-methyl-1,2,3,6-tetrahydropyridin-4-yl)-4H-pyrido[1,2-a]pyrimidin-4-one 7-[4-(diethylamino)piperidin-1-yl]-2-(4,6-dimethylpyrazolo[1,5-a]pyrazin-2-yl)-4H-pyrido[1,2-a]pyrimidin-4-one 2-(4,6-dimethylpyrazolo[1,5-a]pyrazin-2-yl)-7-(piperidin-4-yl)-4H-pyrido[1,2-a]pyrimidin-4-one 2-(4,6-dimethylpyrazolo[1,5-a]pyrazin-2-yl)-7-(1-methylpiperidin-4-yl)-4H-pyrido[1,2-a]pyrimidin-4-one 2-(4,6-dimethylpyrazolo[1,5-a]pyrazin-2-yl)-7-(1-ethylpiperidin-4-yl)-4H-pyrido[1,2-a]pyrimidin-4-one 2-(3,4-dimethoxyphenyl)-9-ethyl-7-[(8aR)-hexahydropyrrolo[1,2-a]pyrazin-2(1H)-yl]-4H-pyrido[1,2-a]pyrimidin-4-one 2-(3,4-dimethoxyphenyl)-7-{4-[(2-methoxyethyl)amino]piperidin-1-yl}-9-methyl-4H-pyrido[1,2-a]pyrimidin-4-one 2-(4,6-dimethylpyrazolo[1,5-a]pyrazin-2-yl)-9-methyl-7-(4-methylpiperazin-1-yl)-4H-pyrido[1,2-a]pyrimidin-4-one 2-(4,6-dimethylpyrazolo[1,5-a]pyrazin-2-yl)-7-[(8aR)-hexahydropyrrolo[1,2-a]pyrazin-2(1H)-yl]-9-methyl-4H-pyrido[1,2-a]pyrimidin-4-one 7-[4-(dimethylamino)piperidin-1-yl]-2-(4,6-dimethylpyrazolo[1,5-a]pyrazin-2-yl)-9-methyl-4H-pyrido[1,2-a]pyrimidin-4-one 7-(2-methylimidazo[1,2-a]pyridin-6-yl)-2-(1-methylpiperidin-4-yl)-4H-pyrido[1,2-a]pyrimidin-4-one 7-(2-methylimidazo[1,2-a]pyridin-6-yl)-2-[1-(propan-2-yl)piperidin-4-yl]-4H-pyrido[1,2-a]pyrimidin-4-one 7-(8-fluoro-2-methylimidazo[1,2-a]pyridin-6-yl)-2-(1-methylpiperidin-4-yl)-4H-pyrido[1,2-a]pyrimidin-4-one 7-(1-ethyl-1,2,3,6-tetrahydropyridin-4-yl)-2-(1-methyl-1H-indazol-5-yl)-4H-pyrido[1,2-a]pyrimidin-4-one 2-(1-methyl-1H-indazol-5-yl)-7-(1-propyl-1,2,3,6-tetrahydropyridin-4-yl)-4H-pyrido[1,2-a]pyrimidin-4-one 2-[6-(dimethylamino)pyridin-3-yl]-7-(piperidin-4-yl)-4H-pyrido[1,2-a]pyrimidin-4-one 7-(4-ethylpiperazin-1-yl)-2-(6-methylpyrazolo[1,5-a]pyrazin-2-yl)-4H-pyrido[1,2-a]pyrimidin-4-one 7-[(8aR)-hexahydropyrrolo[1,2-a]pyrazin-2(1H)-yl]-2-(6-methylpyrazolo[1,5-a]pyrazin-2-yl)-4H-pyrido[1,2-a]pyrimidin-4-one 7-[4-(dimethylamino)piperidin-1-yl]-2-(6-methylpyrazolo[1,5-a]pyrazin-2-yl)-4H-pyrido[1,2-a]pyrimidin-4-one
7-[4-(2-hydroxyethyl)piperazin-1-yl]-2-(6-methylpyrazolo[1,5-a]pyrazin-2-yl)-4H-pyrido[1,2-a]pyrimidin-4-one
2-(2-methylimidazo[1,2-a]pyridin-6-yl)-7-(1-propylpiperidin-4-yl)-4H-pyrido[1,2-a]pyrimidin-4-one
7-[1-(2-hydroxyethyl)-1,2,3,6-tetrahydropyridin-4-yl]-2-(1-methyl-1H-indazol-5-yl)-4H-pyrido[1,2-a]pyrimidin-4-one
7-[(3R)-3-methylpiperazin-1-yl]-2-(6-methylpyrazolo[1,5-a]pyrazin-2-yl)-4H-pyrido[1,2-a]pyrimidin-4-one
2-(6-methylpyrazolo[1,5-a]pyrazin-2-yl)-7-(1,2,3,6-tetrahydropyridin-4-yl)-4H-pyrido[1,2-a]pyrimidin-4-one
2-(2-methyl-2H-indazol-5-yl)-7-(1,2,3,6-tetrahydropyridin-4-yl)-4H-pyrido[1,2-a]pyrimidin-4-one
2-(1-methyl-1H-indazol-5-yl)-7-(1-methylpiperidin-4-yl)-4H-pyrido[1,2-a]pyrimidin-4-one
2-(2-methyl-2H-indazol-5-yl)-7-(1-methyl-1,2,3,6-tetrahydropyridin-4-yl)-4H-pyrido[1,2-a]pyrimidin-4-one
7-(1-ethyl-1,2,3,6-tetrahydropyridin-4-yl)-2-(2-methyl-2H-indazol-5-yl)-4H-pyrido[1,2-a]pyrimidin-4-one
7-(1-ethylpiperidin-4-yl)-2-(2-methylimidazo[1,2-a]pyridin-6-yl)-4H-pyrido[1,2-a]pyrimidin-4-one
2-(1,3-dimethylpyrrolo[1,2-a]pyrazin-7-yl)-7-[1-(propan-2-yl)-1,2,3,6-tetrahydropyridin-4-yl]-4H-pyrazino[1,2-a]pyrimidin-4-one
2-(4,6-dimethylpyrazolo[1,5-a]pyrazin-2-yl)-9-methyl-7-(1,2,3,6-tetrahydropyridin-4-yl)-4H-pyrido[1,2-a]pyrimidin-4-one
2-(4,6-dimethylpyrazolo[1,5-a]pyrazin-2-yl)-9-methyl-7-(1-methyl-1,2,3,6-tetrahydropyridin-4-yl)-4H-pyrido[1,2-a]pyrimidin-4-one
2-(4,6-dimethylpyrazolo[1,5-a]pyrazin-2-yl)-7-(1-ethyl-1,2,3,6-tetrahydropyridin-4-yl)-9-methyl-4H-pyrido[1,2-a]pyrimidin-4-one
7-(1-cyclopropyl-1,2,3,6-tetrahydropyridin-4-yl)-2-(4,6-dimethylpyrazolo[1,5-a]pyrazin-2-yl)-9-methyl-4H-pyrido[1,2-a]pyrimidin-4-one
2-(6-methylpyrazolo[1,5-a]pyrazin-2-yl)-7-(1-methyl-1,2,3,6-tetrahydropyridin-4-yl)-4H-pyrido[1,2-a]pyrimidin-4-one
7-(1-ethyl-1,2,3,6-tetrahydropyridin-4-yl)-2-(6-methylpyrazolo[1,5-a]pyrazin-2-yl)-4H-pyrido[1,2-a]pyrimidin-4-one
2-(5,7-dimethylfuro[2,3-c]pyridin-2-yl)-7-(piperazin-1-yl)-4H-pyrido[1,2-a]pyrimidin-4-one
2-(5,7-dimethylfuro[2,3-c]pyridin-2-yl)-7-(4-methylpiperazin-1-yl)-4H-pyrido[1,2-a]pyrimidin-4-one
2-(5,7-dimethylfuro[2,3-c]pyridin-2-yl)-7-[(3S)-3-methylpiperazin-1-yl]-4H-pyrido[1,2-a]pyrimidin-4-one
2-(1-methyl-1H-indazol-5-yl)-7-(4-methylpiperazin-1-yl)-4H-pyrido[1,2-a]pyrimidin-4-one
2-(1-methyl-1H-indazol-5-yl)-7-(piperazin-1-yl)-4H-pyrido[1,2-a]pyrimidin-4-one
7-[4-(dimethylamino)piperidin-1-yl]-2-(1-methyl-1H-indazol-5-yl)-4H-pyrido[1,2-a]pyrimidin-4-one
7-(4-methyl-1,4-diazepan-1-yl)-2-(1-methyl-1H-indazol-5-yl)-4H-pyrido[1,2-a]pyrimidin-4-one
7-(1-ethyl-1,2,3,6-tetrahydropyridin-4-yl)-2-(2-methyl-1,3-benzoxazol-6-yl)-4H-pyrimido[1,2-b]pyridazin-4-one
2-(8-chloro-2-methylimidazo[1,2-a]pyridin-6-yl)-7-(4-ethylpiperazin-1-yl)-4H-pyrido[1,2-a]pyrimidin-4-one
2-(8-chloro-2-methylimidazo[1,2-a]pyridin-6-yl)-7-[(3R)-4-ethyl-3-methylpiperazin-1-yl]-4H-pyrido[1,2-a]pyrimidin-4-one
2-(8-chloro-2-methylimidazo[1,2-a]pyridin-6-yl)-7-[(3S)-4-ethyl-3-methylpiperazin-1-yl]-4H-pyrido[1,2-a]pyrimidin-4-one
2-(8-chloro-2-methylimidazo[1,2-a]pyridin-6-yl)-7-[(3R)-3-methyl-4-(propan-2-yl)piperazin-1-yl]-4H-pyrido[1,2-a]pyrimidin-4-one
2-(8-chloro-2-methylimidazo[1,2-a]pyridin-6-yl)-7-[(3S)-3-methyl-4-(propan-2-yl)piperazin-1-yl]-4H-pyrido[1,2-a]pyrimidin-4-one
2-(2-methyl-1,3-benzoxazol-6-yl)-7-(piperidin-4-yl)-4H-pyrimido[1,2-b]pyridazin-4-one
2-(2-methyl-1,3-benzoxazol-6-yl)-7-(1-methylpiperidin-4-yl)-4H-pyrimido[1,2-b]pyridazin-4-one
7-(1-ethylpiperidin-4-yl)-2-(2-methyl-1,3-benzoxazol-6-yl)-4H-pyrimido[1,2-b]pyridazin-4-one
2-(4,6-dimethylpyrazolo[1,5-a]pyrazin-2-yl)-7-(piperidin-4-yl)-4H-pyrazino[1,2-a]pyrimidin-4-one
2-(4,6-dimethylpyrazolo[1,5-a]pyrazin-2-yl)-7-(1-methylpiperidin-4-yl)-4H-pyrazino[1,2-a]pyrimidin-4-one
2-(4,6-dimethylpyrazolo[1,5-a]pyrazin-2-yl)-7-(1-ethylpiperidin-4-yl)-4H-pyrazino[1,2-a]pyrimidin-4-one
2-(1-methyl-1H-indazol-5-yl)-7-(1,2,3,6-tetrahydropyridin-4-yl)-4H-pyrazino[1,2-a]pyrimidin-4-one
2-(1-methyl-1H-indazol-5-yl)-7-(1-methyl-1,2,3,6-tetrahydropyridin-4-yl)-4H-pyrazino[1,2-a]pyrimidin-4-one
7-(1-ethyl-1,2,3,6-tetrahydropyridin-4-yl)-2-(1-methyl-1H-indazol-5-yl)-4H-pyrazino[1,2-a]pyrimidin-4-one
2-(4,6-dimethylpyrazolo[1,5-a]pyrazin-2-yl)-7-(4-ethylpiperazin-1-yl)-9-methyl-4H-pyrido[1,2-a]pyrimidin-4-one
2-(4,6-dimethylpyrazolo[1,5-a]pyrazin-2-yl)-9-methyl-7-[(3R)-3-methylpiperazin-1-yl]-4H-pyrido[1,2-a]pyrimidin-4-one
7-[(3R)-3,4-dimethylpiperazin-1-yl]-2-(4,6-dimethylpyrazolo[1,5-a]pyrazin-2-yl)-9-methyl-4H-pyrido[1,2-a]pyrimidin-4-one
2-(4,6-dimethylpyrazolo[1,5-a]pyrazin-2-yl)-7-[(3R)-4-ethyl-3-methylpiperazin-1-yl]-9-methyl-4H-pyrido[1,2-a]pyrimidin-4-one
2-(4,6-dimethylpyrazolo[1,5-a]pyrazin-2-yl)-7-(piperidin-4-yl)-4H-pyrimido[1,2-b]pyridazin-4-one
2-(4,6-dimethylpyrazolo[1,5-a]pyrazin-2-yl)-7-(1-methylpiperidin-4-yl)-4H-pyrimido[1,2-b]pyridazin-4-one
2-(4,6-dimethylpyrazolo[1,5-a]pyrazin-2-yl)-7-(1-ethylpiperidin-4-yl)-4H-pyrimido[1,2-b]pyridazin-4-one
2-(4,6-dimethylpyrazolo[1,5-a]pyrazin-2-yl)-7-(octahydro-5H-pyrrolo[3,2-c]pyridin-5-yl)-4H-pyrido[1,2-a]pyrimidin-4-one
2-(8-chloro-2-methylimidazo[1,2-a]pyridin-6-yl)-7-(piperidin-4-yl)-4H-pyrido[1,2-a]pyrimidin-4-one
2-(8-chloro-2-methylimidazo[1,2-a]pyridin-6-yl)-7-(1-methylpiperidin-4-yl)-4H-pyrido[1,2-a]pyrimidin-4-one
2-(8-chloro-2-methylimidazo[1,2-a]pyridin-6-yl)-7-(1-ethylpiperidin-4-yl)-4H-pyrido[1,2-a]pyrimidin-4-one
2-(8-chloro-2-methylimidazo[1,2-a]pyridin-6-yl)-7-[1-(propan-2-yl)piperidin-4-yl]-4H-pyrido[1,2-a]pyrimidin-4-one
2-(4,6-dimethylpyrazolo[1,5-a]pyrazin-2-yl)-9-methyl-7-(4-methyl-1,4-diazepan-1-yl)-4H-pyrido[1,2-a]pyrimidin-4-one
2-(2-methyl-2H-indazol-5-yl)-7-(piperidin-4-yl)-4H-pyrimido[1,2-b]pyridazin-4-one
2-(2-methyl-2H-indazol-5-yl)-7-(1-methylpiperidin-4-yl)-4H-pyrimido[1,2-b]pyridazin-4-one
7-(1-ethylpiperidin-4-yl)-2-(2-methyl-2H-indazol-5-yl)-4H-pyrimido[1,2-b]pyridazin-4-one 2-(8-chloro-2-methylimidazo[1,2-a]pyridin-6-yl)-7-(1-methylpiperidin-4-yl)-4H-pyrimido[1,2-b]pyridazin-4-one
2-(8-chloro-2-methylimidazo[1,2-a]pyridin-6-yl)-7-(1-ethylpiperidin-4-yl)-4H-pyrimido[1,2-b]pyridazin-4-one
2-(8-chloro-2-methylimidazo[1,2-a]pyridin-6-yl)-7-[1-(2-hydroxyethyl)piperidin-4-yl]-4H-pyrimido[1,2-b]pyridazin-4-one
2-(5,7-dimethylfuro[2,3-c]pyridin-2-yl)-7-[(3R,5S)-3,5-dimethylpiperazin-1-yl]-4H-pyrido[1,2-a]pyrimidin-4-one
7-[4-(dimethylamino)piperidin-1-yl]-2-(5,7-dimethylfuro[2,3-c]pyridin-2-yl)-4H-pyrido[1,2-a]pyrimidin-4-one
2-(5,7-dimethylfuro[2,3-c]pyridin-2-yl)-7-[4-(2-hydroxyethyl)piperazin-1-yl]-4H-pyrido[1,2-a]pyrimidin-4-one
2-(4,6-dimethylpyrazolo[1,5-a]pyrazin-2-yl)-7-[1-(2-hydroxyethyl)piperidin-4-yl]-4H-pyrido[1,2-a]pyrimidin-4-one
2-(4,6-dimethylpyrazolo[1,5-a]pyrazin-2-yl)-7-[4-(2-hydroxyethyl)piperazin-1-yl]-4H-pyrido[1,2-a]pyrimidin-4-one
2-(4,6-dimethylpyrazolo[1,5-a]pyrazin-2-yl)-7-[(3R)-4-(2-hydroxyethyl)-3-methylpiperazin-1-yl]-4H-pyrido[1,2-a]pyrimidin-4-one
2-(8-chloro-2-methylimidazo[1,2-a]pyridin-6-yl)-7-[(3S)-4-(2-methoxyethyl)-3-methylpiperazin-1-yl]-4H-pyrido[1,2-a]pyrimidin-4-one
2-(8-chloro-2-methylimidazo[1,2-a]pyridin-6-yl)-7-{(3S)-4-[2-(2-hydroxyethoxy)ethyl]-3-methylpiperazin-1-yl}-4H-pyrido[1,2-a]pyrimidin-4-one
2-(8-chloro-2-methylimidazo[1,2-a]pyridin-6-yl)-7-[(3S)-4-cyclopropyl-3-methylpiperazin-1-yl]-4H-pyrido[1,2-a]pyrimidin-4-one
2-(8-chloro-2-methylimidazo[1,2-a]pyridin-6-yl)-7-[(3S)-4-cyclobutyl-3-methylpiperazin-1-yl]-4H-pyrido[1,2-a]pyrimidin-4-one
2-(8-chloro-2-methylimidazo[1,2-a]pyridin-6-yl)-7-[(3S)-4-(2-hydroxyethyl)-3-methylpiperazin-1-yl]-4H-pyrido[1,2-a]pyrimidin-4-one
2-(8-fluoro-2-methylimidazo[1,2-a]pyridin-6-yl)-7-[(3S)-4-(2-methoxyethyl)-3-methylpiperazin-1-yl]-4H-pyrido[1,2-a]pyrimidin-4-one
2-(8-fluoro-2-methylimidazo[1,2-a]pyridin-6-yl)-7-[(3S)-4-(2-hydroxyethyl)-3-methylpiperazin-1-yl]-4H-pyrido[1,2-a]pyrimidin-4-one
2-(8-fluoro-2-methylimidazo[1,2-a]pyridin-6-yl)-7-{(3S)-4-[2-(2-hydroxyethoxy)ethyl]-3-methylpiperazin-1-yl}-4H-pyrido[1,2-a]pyrimidin-4-one
2-(8-fluoro-2-methylimidazo[1,2-a]pyridin-6-yl)-7-[(3S)-3-methyl-4-(propan-2-yl)piperazin-1-yl]-4H-pyrido[1,2-a]pyrimidin-4-one
7-[(3S)-4-cyclopropyl-3-methylpiperazin-1-yl]-2-(8-fluoro-2-methylimidazo[1,2-a]pyridin-6-yl)-4H-pyrido[1,2-a]pyrimidin-4-one
7-[(3S)-4-cyclobutyl-3-methylpiperazin-1-yl]-2-(8-fluoro-2-methylimidazo[1,2-a]pyridin-6-yl)-4H-pyrido[1,2-a]pyrimidin-4-one
7-(3,3-dimethylpiperazin-1-yl)-2-(4,6-dimethylpyrazolo[1,5-a]pyrazin-2-yl)-9-methyl-4H-pyrido[1,2-a]pyrimidin-4-one
2-(1-methyl-1H-indazol-5-yl)-7-[(3R)-3-methylpiperazin-1-yl]-4H-pyrido[1,2-a]pyrimidin-4-one
2-(4-ethyl-6-methylpyrazolo[1,5-a]pyrazin-2-yl)-7-(piperazin-1-yl)-4H-pyrido[1,2-a]pyrimidin-4-one
2-(4-ethyl-6-methylpyrazolo[1,5-a]pyrazin-2-yl)-7-(4-methylpiperazin-1-yl)-4H-pyrido[1,2-a]pyrimidin-4-one
2-(4-ethyl-6-methylpyrazolo[1,5-a]pyrazin-2-yl)-7-(4-ethylpiperazin-1-yl)-4H-pyrido[1,2-a]pyrimidin-4-one
2-(4-ethyl-6-methylpyrazolo[1,5-a]pyrazin-2-yl)-7-[4-(2-hydroxyethyl)piperazin-1-yl]-4H-pyrido[1,2-a]pyrimidin-4-one
7-[4-(dimethylamino)piperidin-1-yl]-2-(4-ethyl-6-methylpyrazolo[1,5-a]pyrazin-2-yl)-4H-pyrido[1,2-a]pyrimidin-4-one
7-[4-(diethylamino)piperidin-1-yl]-2-(4-ethyl-6-methylpyrazolo[1,5-a]pyrazin-2-yl)-4H-pyrido[1,2-a]pyrimidin-4-one
7-[(3R,5S)-3,5-dimethylpiperazin-1-yl]-2-(1-methyl-1H-indazol-5-yl)-4H-pyrido[1,2-a]pyrimidin-4-one
2-(1-methyl-1H-indazol-5-yl)-7-[(3S)-3-methylpiperazin-1-yl]-4H-pyrido[1,2-a]pyrimidin-4-one
2-(2-methylimidazo[1,2-a]pyridin-6-yl)-7-[1-(propan-2-yl)piperidin-4-yl]-4H-pyrido[1,2-a]pyrimidin-4-one
2-(2-methylimidazo[1,2-a]pyridin-7-yl)-7-(piperazin-1-yl)-4H-pyrido[1,2-a]pyrimidin-4-one
2-(2-methylimidazo[1,2-a]pyridin-7-yl)-7-(piperidin-4-yl)-4H-pyrido[1,2-a]pyrimidin-4-one
2-(2-methylimidazo[1,2-a]pyridin-7-yl)-7-(4-methylpiperazin-1-yl)-4H-pyrido[1,2-a]pyrimidin-4-one
7-(4-ethylpiperazin-1-yl)-2-(2-methylimidazo[1,2-a]pyridin-7-yl)-4H-pyrido[1,2-a]pyrimidin-4-one
2-(2-methylimidazo[1,2-a]pyridin-7-yl)-7-(1-methylpiperidin-4-yl)-4H-pyrido[1,2-a]pyrimidin-4-one
7-(1-ethylpiperidin-4-yl)-2-(2-methylimidazo[1,2-a]pyridin-7-yl)-4H-pyrido[1,2-a]pyrimidin-4-one
2-(4,6-dimethylpyrazolo[1,5-a]pyrazin-2-yl)-9-methyl-7-[(3S)-3-methylpiperazin-1-yl]-4H-pyrido[1,2-a]pyrimidin-4-one
7-[(3R,5S)-3,5-dimethylpiperazin-1-yl]-2-(4,6-dimethylpyrazolo[1,5-a]pyrazin-2-yl)-9-methyl-4H-pyrido[1,2-a]pyrimidin-4-one
7-[(3S)-3,4-dimethylpiperazin-1-yl]-2-(4,6-dimethylpyrazolo[1,5-a]pyrazin-2-yl)-9-methyl-4H-pyrido[1,2-a]pyrimidin-4-one
2-(4,6-dimethylpyrazolo[1,5-a]pyrazin-2-yl)-9-methyl-7-[(3R,5S)-3,4,5-trimethylpiperazin-1-yl]-4H-pyrido[1,2-a]pyrimidin-4-one
2-(2-methylimidazo[1,2-a]pyridin-6-yl)-7-[1-(propan-2-yl)-1,2,3,6-tetrahydropyridin-4-yl]-4H-pyrido[1,2-a]pyrimidin-4-one
2-(2-methyl-2H-indazol-5-yl)-7-(piperidin-4-yl)-4H-pyrazino[1,2-a]pyrimidin-4-one
2-(2-methyl-2H-indazol-5-yl)-7-(1-methylpiperidin-4-yl)-4H-pyrazino[1,2-a]pyrimidin-4-one
7-(1-ethylpiperidin-4-yl)-2-(2-methyl-2H-indazol-5-yl)-4H-pyrazino[1,2-a]pyrimidin-4-one
7-[1-(2-hydroxyethyl)piperidin-4-yl]-2-(2-methyl-2H-indazol-5-yl)-4H-pyrazino[1,2-a]pyrimidin-4-one
7-{4-[(dimethylamino)methyl]piperidin-1-yl}-2-(4,6-dimethylpyrazolo[1,5-a]pyrazin-2-yl)-4H-pyrido[1,2-a]pyrimidin-4-one
2-(4,6-dimethylpyrazolo[1,5-a]pyrazin-2-yl)-7-[4-(pyrrolidin-1-ylmethyl)piperidin-1-yl]-4H-pyrido[1,2-a]pyrimidin-4-one
2-(4,6-dimethylpyrazolo[1,5-a]pyrazin-2-yl)-7-[4-(piperidin-1-ylmethyl)piperidin-1-yl]-4H-pyrido[1,2-a]pyrimidin-4-one
2-(3,4-dimethoxyphenyl)-7-{4-[(dimethylamino)methyl]piperidin-1-yl}-4H-pyrido[1,2-a]pyrimidin-4-one
2-(3,4-dimethoxyphenyl)-7-[4-(pyrrolidin-1-ylmethyl)piperidin-1-yl]-4H-pyrido[1,2-a]pyrimidin-4-one
2-(3,4-dimethoxyphenyl)-7-[4-(piperidin-1-ylmethyl)piperidin-1-yl]-4H-pyrido[1,2-a]pyrimidin-4-one
7-[1-(2-hydroxyethyl)piperidin-4-yl]-2-(2-methylimidazo[1,2-a]pyridin-6-yl)-4H-pyrido[1,2-a]pyrimidin-4-one 7-[1-(2-hydroxyethyl)-1,2,3,6-tetrahydropyridin-4-yl]-2-(2-methylimidazo[1,2-a]pyridin-6-yl)-4H-pyrido[1,2-a]pyrimidin-4-one
2-(2-methyl-2H-indazol-5-yl)-7-(1-methylpiperidin-4-yl)-4H-pyrido[1,2-a]pyrimidin-4-one
2-(2-methylimidazo[1,2-a]pyridin-6-yl)-7-(1-methylpiperidin-4-yl)-4H-pyrazino[1,2-a]pyrimidin-4-one
7-(1-ethylpiperidin-4-yl)-2-(2-methylimidazo[1,2-a]pyridin-6-yl)-4H-pyrazino[1,2-a]pyrimidin-4-one
7-[1-(2-hydroxyethyl)piperidin-4-yl]-2-(2-methylimidazo[1,2-a]pyridin-6-yl)-4H-pyrazino[1,2-a]pyrimidin-4-one
2-(4,6-dimethylpyrazolo[1,5-a]pyrazin-2-yl)-7-{4-[(2-hydroxyethyl)(methyl)amino]piperidin-1-yl}-9-methyl-4H-pyrido[1,2-a]pyrimidin-4-one
2-(4,6-dimethylpyrazolo[1,5-a]pyrazin-2-yl)-9-methyl-7-[4-(propylamino)piperidin-1-yl]-4H-pyrido[1,2-a]pyrimidin-4-one
7-(4-amino-4-methylpiperidin-1-yl)-2-(4,6-dimethylpyrazolo[1,5-a]pyrazin-2-yl)-4H-pyrido[1,2-a]pyrimidin-4-one
2-(2-methylimidazo[1,2-a]pyridin-6-yl)-7-(piperidin-4-yl)-4H-pyrazino[1,2-a]pyrimidin-4-one
2-(2-methyl-2H-indazol-5-yl)-7-(piperazin-1-yl)-4H-pyrazino[1,2-a]pyrimidin-4-one
2-(8-chloro-2-methylimidazo[1,2-a]pyridin-6-yl)-7-(piperidin-4-yl)-4H-pyrazino[1,2-a]pyrimidin-4-one
2-(2,8-dimethylimidazo[1,2-a]pyridin-6-yl)-7-(piperidin-4-yl)-4H-pyrazino[1,2-a]pyrimidin-4-one
2-(2-methyl-2H-indazol-5-yl)-7-(4-methylpiperazin-1-yl)-4H-pyrazino[1,2-a]pyrimidin-4-one
7-(4-ethylpiperazin-1-yl)-2-(2-methyl-2H-indazol-5-yl)-4H-pyrazino[1,2-a]pyrimidin-4-one
7-[4-(2-hydroxyethyl)piperazin-1-yl]-2-(2-methyl-2H-indazol-5-yl)-4H-pyrazino[1,2-a]pyrimidin-4-one
2-(2,8-dimethylimidazo[1,2-a]pyridin-6-yl)-7-(1-methylpiperidin-4-yl)-4H-pyrazino[1,2-a]pyrimidin-4-one
2-(2,8-dimethylimidazo[1,2-a]pyridin-6-yl)-7-(1-ethylpiperidin-4-yl)-4H-pyrazino[1,2-a]pyrimidin-4-one
2-(2,8-dimethylimidazo[1,2-a]pyridin-6-yl)-7-[1-(2-hydroxyethyl)piperidin-4-yl]-4H-pyrazino[1,2-a]pyrimidin-4-one
2-(8-chloro-2-methylimidazo[1,2-a]pyridin-6-yl)-7-[1-(propan-2-yl)piperidin-4-yl]-4H-pyrazino[1,2-a]pyrimidin-4-one
2-(4,6-dimethylpyrazolo[1,5-a]pyrazin-2-yl)-7-[4-(ethylamino)piperidin-1-yl]-9-methyl-4H-pyrido[1,2-a]pyrimidin-4-one
7-{4-[bis(2-hydroxyethyl)amino]piperidin-1-yl}-2-(4,6-dimethylpyrazolo[1,5-a]pyrazin-2-yl)-9-methyl-4H-pyrido[1,2-a]pyrimidin-4-one
7-[1-(2-hydroxyethyl)piperidin-4-yl]-2-(2-methyl-1,3-benzoxazol-6-yl)-4H-pyrimido[1,2-b]pyridazin-4-one
2-(8-chloro-2-methylimidazo[1,2-a]pyridin-6-yl)-7-[1-(2-hydroxyethyl)piperidin-4-yl]-4H-pyrazino[1,2-a]pyrimidin-4-one
2-(4,6-dimethylpyrazolo[1,5-a]pyrazin-2-yl)-7-[1-(oxetan-3-yl)piperidin-4-yl]-4H-pyrido[1,2-a]pyrimidin-4-one
2-(5,7-dimethylfuro[2,3-c]pyridin-2-yl)-7-(4-ethylpiperazin-1-yl)-4H-pyrido[1,2-a]pyrimidin-4-one
2-(4,6-dimethylpyrazolo[1,5-a]pyrazin-2-yl)-7-(1-methyloctahydro-5H-pyrrolo[3,2-c]pyridin-5-yl)-4H-pyrido[1,2-a]pyrimidin-4-one
2-(1-methyl-1H-indazol-5-yl)-7-(piperidin-4-yl)-4H-pyrido[1,2-a]pyrimidin-4-one
7-(1-ethylpiperidin-4-yl)-2-(1-methyl-1H-indazol-5-yl)-4H-pyrido[1,2-a]pyrimidin-4-one
7-[1-(2-hydroxyethyl)piperidin-4-yl]-2-(1-methyl-1H-indazol-5-yl)-4H-pyrido[1,2-a]pyrimidin-4-one
2-(2-methyl-2H-indazol-5-yl)-7-(piperidin-4-yl)-4H-pyrido[1,2-a]pyrimidin-4-one
2-(2,8-dimethylimidazo[1,2-a]pyridin-6-yl)-7-(piperidin-4-yl)-4H-pyrido[1,2-a]pyrimidin-4-one
2-(2-methyl-2H-indazol-5-yl)-7-[1-(propan-2-yl)piperidin-4-yl]-4H-pyrido[1,2-a]pyrimidin-4-one
2-(4,6-dimethylpyrazolo[1,5-a]pyrazin-2-yl)-7-{4-[(2-hydroxyethyl)amino]piperidin-1-yl}-9-methyl-4H-pyrido[1,2-a]pyrimidin-4-one
2-(4,6-dimethylpyrazolo[1,5-a]pyrazin-2-yl)-9-methyl-7-[4-(methylamino)piperidin-1-yl]-4H-pyrido[1,2-a]pyrimidin-4-one
2-(4,6-dimethylpyrazolo[1,5-a]pyrazin-2-yl)-9-methyl-7-[4-(propan-2-ylamino)piperidin-1-yl]-4H-pyrido[1,2-a]pyrimidin-4-one
7-(1-ethylpiperidin-4-yl)-2-(2-methyl-2H-indazol-5-yl)-4H-pyrido[1,2-a]pyrimidin-4-one
7-[1-(2-hydroxyethyl)piperidin-4-yl]-2-(2-methyl-2H-indazol-5-yl)-4H-pyrido[1,2-a]pyrimidin-4-one
2-(2,8-dimethylimidazo[1,2-a]pyridin-6-yl)-7-(1-methylpiperidin-4-yl)-4H-pyrido[1,2-a]pyrimidin-4-one
2-(2,8-dimethylimidazo[1,2-a]pyridin-6-yl)-7-(1-ethylpiperidin-4-yl)-4H-pyrido[1,2-a]pyrimidin-4-one
2-(2,8-dimethylimidazo[1,2-a]pyridin-6-yl)-7-[1-(propan-2-yl)piperidin-4-yl]-4H-pyrido[1,2-a]pyrimidin-4-one
2-(2,8-dimethylimidazo[1,2-a]pyridin-6-yl)-7-[1-(2-hydroxyethyl)piperidin-4-yl]-4H-pyrido[1,2-a]pyrimidin-4-one
2-(4-ethyl-6-methylpyrazolo[1,5-a]pyrazin-2-yl)-7-(4-propylpiperazin-1-yl)-4H-pyrido[1,2-a]pyrimidin-4-one
2-(4-ethyl-6-methylpyrazolo[1,5-a]pyrazin-2-yl)-7-[4-(propan-2-yl)piperazin-1-yl]-4H-pyrido[1,2-a]pyrimidin-4-one
7-(4-cyclopropylpiperazin-1-yl)-2-(4-ethyl-6-methylpyrazolo[1,5-a]pyrazin-2-yl)-4H-pyrido[1,2-a]pyrimidin-4-one
7-(4-cyclobutylpiperazin-1-yl)-2-(4-ethyl-6-methylpyrazolo[1,5-a]pyrazin-2-yl)-4H-pyrido[1,2-a]pyrimidin-4-one
2-(4-ethyl-6-methylpyrazolo[1,5-a]pyrazin-2-yl)-7-[4-(oxetan-3-yl)piperazin-1-yl]-4H-pyrido[1,2-a]pyrimidin-4-one
2-(4,6-dimethylpyrazolo[1,5-a]pyrazin-2-yl)-7-(1-ethyloctahydro-5H-pyrrolo[3,2-c]pyridin-5-yl)-4H-pyrido[1,2-a]pyrimidin-4-one
2-(4,6-dimethylpyrazolo[1,5-a]pyrazin-2-yl)-7-[1-(2-hydroxyethyl)octahydro-5H-pyrrolo[3,2-c]pyridin-5-yl]-4H-pyrido[1,2-a]pyrimidin-4-one
2-(4-methoxy-6-methylpyrazolo[1,5-a]pyrazin-2-yl)-7-(4-methylpiperazin-1-yl)-4H-pyrido[1,2-a]pyrimidin-4-one
2-(4-hydroxy-6-methylpyrazolo[1,5-a]pyrazin-2-yl)-7-(4-methylpiperazin-1-yl)-4H-pyrido[1,2-a]pyrimidin-4-one
2-(2-methylimidazo[1,2-a]pyridin-6-yl)-7-[1-(propan-2-yl)piperidin-4-yl]-4H-pyrazino[1,2-a]pyrimidin-4-one
7-(1-cyclobutylpiperidin-4-yl)-2-(2-methylimidazo[1,2-a]pyridin-6-yl)-4H-pyrazino[1,2-a]pyrimidin-4-one
7-[(3R)-3,4-dimethylpiperazin-1-yl]-2-(4-ethyl-6-methylpyrazolo[1,5-a]pyrazin-2-yl)-4H-pyrido[1,2-a]pyrimidin-4-one
7-[(3R)-4-ethyl-3-methylpiperazin-1-yl]-2-(4-ethyl-6-methylpyrazolo[1,5-a]pyrazin-2-yl)-4H-pyrido[1,2-a]pyrimidin-4-one
2-(4-ethyl-6-methylpyrazolo[1,5-a]pyrazin-2-yl)-7-[(3R)-3-methyl-4-propylpiperazin-1-yl]-4H-pyrido[1,2-a]pyrimidin-4-one 2-(4-ethyl-6-methylpyrazolo[1,5-a]pyrazin-2-yl)-7-[(3R)-4-(2-hydroxyethyl)-3-methylpiperazin-1-yl]-4H-pyrido[1,2-a]pyrimidin-4-one
7-[(3R,5S)-3,5-dimethylpiperazin-1-yl]-2-(4-ethyl-6-methylpyrazolo[1,5-a]pyrazin-2-yl)-4H-pyrido[1,2-a]pyrimidin-4-one
2-(4-ethyl-6-methylpyrazolo[1,5-a]pyrazin-2-yl)-7-[4-(pyrrolidin-1-yl)piperidin-1-yl]-4H-pyrido[1,2-a]pyrimidin-4-one
2-(4-ethyl-6-methylpyrazolo[1,5-a]pyrazin-2-yl)-7-[(3S)-3-methylpiperazin-1-yl]-4H-pyrido[1,2-a]pyrimidin-4-one
2-(4-ethyl-6-methylpyrazolo[1,5-a]pyrazin-2-yl)-7-(4-methyl-1,4-diazepan-1-yl)-4H-pyrido[1,2-a]pyrimidin-4-one
2-(8-ethyl-2-methylimidazo[1,2-a]pyridin-6-yl)-7-(piperazin-1-yl)-4H-pyrido[1,2-a]pyrimidin-4-one
2-(8-ethyl-2-methylimidazo[1,2-a]pyridin-6-yl)-7-[(3R)-3-methylpiperazin-1-yl]-4H-pyrido[1,2-a]pyrimidin-4-one
2-(8-ethyl-2-methylimidazo[1,2-a]pyridin-6-yl)-7-[(3S)-3-methylpiperazin-1-yl]-4H-pyrido[1,2-a]pyrimidin-4-one
2-(4,6-dimethylpyrazolo[1,5-a]pyrazin-2-yl)-7-[1-(propan-2-yl)piperidin-4-yl]-4H-pyrido[1,2-a]pyrimidin-4-one
7-(1-cyclopropylpiperidin-4-yl)-2-(4,6-dimethylpyrazolo[1,5-a]pyrazin-2-yl)-4H-pyrido[1,2-a]pyrimidin-4-one
7-(1-cyclobutylpiperidin-4-yl)-2-(4,6-dimethylpyrazolo[1,5-a]pyrazin-2-yl)-4H-pyrido[1,2-a]pyrimidin-4-one
2-(4-ethyl-6-methylpyrazolo[1,5-a]pyrazin-2-yl)-7-[(3R)-3-methyl-4-(propan-2-yl)piperazin-1-yl]-4H-pyrido[1,2-a]pyrimidin-4-one
7-[(3R)-4-cyclopropyl-3-methylpiperazin-1-yl]-2-(4-ethyl-6-methylpyrazolo[1,5-a]pyrazin-2-yl)-4H-pyrido[1,2-a]pyrimidin-4-one
7-[(3R)-4-cyclobutyl-3-methylpiperazin-1-yl]-2-(4-ethyl-6-methylpyrazolo[1,5-a]pyrazin-2-yl)-4H-pyrido[1,2-a]pyrimidin-4-one
2-(4-ethyl-6-methylpyrazolo[1,5-a]pyrazin-2-yl)-7-[(3R)-3-methyl-4-(oxetan-3-yl)piperazin-1-yl]-4H-pyrido[1,2-a]pyrimidin-4-one
2-(8-ethyl-2-methylimidazo[1,2-a]pyridin-6-yl)-7-[4-(2-hydroxyethyl)piperazin-1-yl]-4H-pyrido[1,2-a]pyrimidin-4-one
7-(4-cyclobutylpiperazin-1-yl)-2-(8-ethyl-2-methylimidazo[1,2-a]pyridin-6-yl)-4H-pyrido[1,2-a]pyrimidin-4-one
2-(8-ethyl-2-methylimidazo[1,2-a]pyridin-6-yl)-7-[(3R)-4-(2-hydroxyethyl)-3-methylpiperazin-1-yl]-4H-pyrido[1,2-a]pyrimidin-4-one
7-[(3R)-4-cyclobutyl-3-methylpiperazin-1-yl]-2-(8-ethyl-2-methylimidazo[1,2-a]pyridin-6-yl)-4H-pyrido[1,2-a]pyrimidin-4-one
2-(8-ethyl-2-methylimidazo[1,2-a]pyridin-6-yl)-7-[(3S)-4-(2-hydroxyethyl)-3-methylpiperazin-1-yl]-4H-pyrido[1,2-a]pyrimidin-4-one
7-[(3S)-4-cyclobutyl-3-methylpiperazin-1-yl]-2-(8-ethyl-2-methylimidazo[1,2-a]pyridin-6-yl)-4H-pyrido[1,2-a]pyrimidin-4-one
2-(4-ethyl-6-methylpyrazolo[1,5-a]pyrazin-2-yl)-7-(piperidin-4-yl)-4H-pyrazino[1,2-a]pyrimidin-4-one
2-(4-ethyl-6-methylpyrazolo[1,5-a]pyrazin-2-yl)-7-(1-methylpiperidin-4-yl)-4H-pyrazino[1,2-a]pyrimidin-4-one
2-(4-ethyl-6-methylpyrazolo[1,5-a]pyrazin-2-yl)-7-(1-ethylpiperidin-4-yl)-4H-pyrazino[1,2-a]pyrimidin-4-one
2-(4-ethyl-6-methylpyrazolo[1,5-a]pyrazin-2-yl)-7-(piperidin-4-yl)-4H-pyrido[1,2-a]pyrimidin-4-one
2-(4-ethyl-6-methylpyrazolo[1,5-a]pyrazin-2-yl)-7-(1-methylpiperidin-4-yl)-4H-pyrido[1,2-a]pyrimidin-4-one
2-(4-ethyl-6-methylpyrazolo[1,5-a]pyrazin-2-yl)-7-(1-ethylpiperidin-4-yl)-4H-pyrido[1,2-a]pyrimidin-4-one
2-(4-ethyl-6-methylpyrazolo[1,5-a]pyrazin-2-yl)-7-[1-(2-hydroxyethyl)piperidin-4-yl]-4H-pyrido[1,2-a]pyrimidin-4-one
2-(4-ethyl-6-methylpyrazolo[1,5-a]pyrazin-2-yl)-7-(1-propylpiperidin-4-yl)-4H-pyrido[1,2-a]pyrimidin-4-one
2-(4-ethyl-6-methylpyrazolo[1,5-a]pyrazin-2-yl)-7-[(3R)-3-methylpiperazin-1-yl]-4H-pyrido[1,2-a]pyrimidin-4-one
2-(4,6-dimethylpyrazolo[1,5-a]pyrazin-2-yl)-7-[1-(2-fluoroethyl)piperidin-4-yl]-4H-pyrido[1,2-a]pyrimidin-4-one
2-(4,6-dimethylpyrazolo[1,5-a]pyrazin-2-yl)-7-[1-(3-fluoropropyl)piperidin-4-yl]-4H-pyrido[1,2-a]pyrimidin-4-one
2-(4-ethyl-6-methylpyrazolo[1,5-a]pyrazin-2-yl)-7-[4-(2-fluoroethyl)piperazin-1-yl]-4H-pyrido[1,2-a]pyrimidin-4-one
2-(4-ethyl-6-methylpyrazolo[1,5-a]pyrazin-2-yl)-7-[4-(3-fluoropropyl)piperazin-1-yl]-4H-pyrido[1,2-a]pyrimidin-4-one
2-(4-ethyl-6-methylpyrazolo[1,5-a]pyrazin-2-yl)-7-[(3R)-4-(2-fluoroethyl)-3-methylpiperazin-1-yl]-4H-pyrido[1,2-a]pyrimidin-4-one
2-(4-ethyl-6-methylpyrazolo[1,5-a]pyrazin-2-yl)-7-[(3R)-4-(3-fluoropropyl)-3-methylpiperazin-1-yl]-4H-pyrido[1,2-a]pyrimidin-4-one
2-(4-ethyl-6-methylpyrazolo[1,5-a]pyrazin-2-yl)-7-[1-(2-fluoroethyl)piperidin-4-yl]-4H-pyrido[1,2-a]pyrimidin-4-one
2-(4-ethyl-6-methylpyrazolo[1,5-a]pyrazin-2-yl)-7-[1-(3-fluoropropyl)piperidin-4-yl]-4H-pyrido[1,2-a]pyrimidin-4-one
2-(4,6-dimethylpyrazolo[1,5-a]pyrazin-2-yl)-7-{(3R)-4-[2-(2-hydroxyethoxy)ethyl]-3-methylpiperazin-1-yl}-9-methyl-4H-pyrido[1,2-a]pyrimidin-4-one
2-(4,6-dimethylpyrazolo[1,5-a]pyrazin-2-yl)-9-methyl-7-(piperidin-4-yl)-4H-pyrido[1,2-a]pyrimidin-4-one
2-(4,6-dimethylpyrazolo[1,5-a]pyrazin-2-yl)-9-methyl-7-(1-methylpiperidin-4-yl)-4H-pyrido[1,2-a]pyrimidin-4-one
2-(4,6-dimethylpyrazolo[1,5-a]pyrazin-2-yl)-7-[(3R)-4-(2-hydroxyethyl)-3-methylpiperazin-1-yl]-9-methyl-4H-pyrido[1,2-a]pyrimidin-4-one
2-[8-(hydroxymethyl)-2-methylimidazo[1,2-a]pyridin-6-yl]-7-(piperazin-1-yl)-4H-pyrido[1,2-a]pyrimidin-4-one
7-[(3R,5S)-3,5-dimethylpiperazin-1-yl]-2-(8-ethyl-2-methylimidazo[1,2-a]pyridin-6-yl)-4H-pyrido[1,2-a]pyrimidin-4-one
2-(8-ethyl-2-methylimidazo[1,2-a]pyridin-6-yl)-7-(4-methyl-1,4-diazepan-1-yl)-4H-pyrido[1,2-a]pyrimidin-4-one
2-[8-(hydroxymethyl)-2-methylimidazo[1,2-a]pyridin-6-yl]-7-(4-methylpiperazin-1-yl)-4H-pyrido[1,2-a]pyrimidin-4-one
7-(4-ethylpiperazin-1-yl)-2-[8-(hydroxymethyl)-2-methylimidazo[1,2-a]pyridin-6-yl]-4H-pyrido[1,2-a]pyrimidin-4-one
2-(4-ethyl-6-methylpyrazolo[1,5-a]pyrazin-2-yl)-7-[1-(propan-2-yl)piperidin-4-yl]-4H-pyrido[1,2-a]pyrimidin-4-one
7-(1-cyclopropylpiperidin-4-yl)-2-(4-ethyl-6-methylpyrazolo[1,5-a]pyrazin-2-yl)-4H-pyrido[1,2-a]pyrimidin-4-one
7-(1-cyclobutylpiperidin-4-yl)-2-(4-ethyl-6-methylpyrazolo[1,5-a]pyrazin-2-yl)-4H-pyrido[1,2-a]pyrimidin-4-one 2-(4-ethyl-6-methylpyrazolo[1,5-a]pyrazin-2-yl)-7-[1-(oxetan-3-yl)piperidin-4-yl]-4H-pyrido[1,2-a]pyrimidin-4-one 2-(4-cyclopropyl-6-methylpyrazolo[1,5-a]pyrazin-2-yl)-7-(piperazin-1-yl)-4H-pyrido[1,2-a]pyrimidin-4-one 2-(4-cyclopropyl-6-methylpyrazolo[1,5-a]pyrazin-2-yl)-7-(4-methylpiperazin-1-yl)-4H-pyrido[1,2-a]pyrimidin-4-one 2-(4-cyclopropyl-6-methylpyrazolo[1,5-a]pyrazin-2-yl)-7-(4-ethylpiperazin-1-yl)-4H-pyrido[1,2-a]pyrimidin-4-one 2-(4-cyclopropyl-6-methylpyrazolo[1,5-a]pyrazin-2-yl)-7-[4-(2-hydroxyethyl)piperazin-1-yl]-4H-pyrido[1,2-a]pyrimidin-4-one 2-(4,6-dimethylpyrazolo[1,5-a]pyrazin-2-yl)-7-(1-propylpiperidin-4-yl)-4H-pyrido[1,2-a]pyrimidin-4-one 2-[4-(dimethylamino)-6-methylpyrazolo[1,5-a]pyrazin-2-yl]-7-(piperazin-1-yl)-4H-pyrido[1,2-a]pyrimidin-4-one 2-(2-methyl-1H-benzimidazol-6-yl)-7-(4-methylpiperazin-1-yl)-4H-pyrido[1,2-a]pyrimidin-4-one 7-(4-ethylpiperazin-1-yl)-2-(2-methyl-1H-benzimidazol-6-yl)-4H-pyrido[1,2-a]pyrimidin-4-one 2-(2,8-dimethylimidazo[1,2-a]pyridin-6-yl)-7-(piperidin-4-yl)-4H-pyrimido[1,2-b]pyridazin-4-one 2-(2-methylimidazo[1,2-a]pyridin-6-yl)-7-(piperidin-4-yl)-4H-pyrimido[1,2-b]pyridazin-4-one 7-[1-(2,2-dimethyl-1,3-dioxan-5-yl)piperidin-4-yl]-2-(4-ethyl-6-methylpyrazolo[1,5-a]pyrazin-2-yl)-4H-pyrido[1,2-a]pyrimidin-4-one 7-[1-(1,3-dihydroxypropan-2-yl)piperidin-4-yl]-2-(4-ethyl-6-methylpyrazolo[1,5-a]pyrazin-2-yl)-4H-pyrido[1,2-a]pyrimidin-4-one 7-[(3R,5S)-3,5-dimethylpiperazin-1-yl]-2-(1,3-dimethylpyrrolo[1,2-a]pyrazin-7-yl)-4H-pyrido[1,2-a]pyrimidin-4-one 2-(8-ethyl-2-methylimidazo[1,2-a]pyridin-6-yl)-7-(piperidin-4-yl)-4H-pyrido[1,2-a]pyrimidin-4-one 2-(8-ethyl-2-methylimidazo[1,2-a]pyridin-6-yl)-7-(1-methylpiperidin-4-yl)-4H-pyrido[1,2-a]pyrimidin-4-one 2-(8-ethyl-2-methylimidazo[1,2-a]pyridin-6-yl)-7-(1-ethylpiperidin-4-yl)-4H-pyrido[1,2-a]pyrimidin-4-one 2-(8-ethyl-2-methylimidazo[1,2-a]pyridin-6-yl)-7-[1-(2-hydroxyethyl)piperidin-4-yl]-4H-pyrido[1,2-a]pyrimidin-4-one 7-[(3R)-3,4-dimethylpiperazin-1-yl]-2-(8-ethyl-2-methylimidazo[1,2-a]pyridin-6-yl)-4H-pyrido[1,2-a]pyrimidin-4-one 2-(8-ethyl-2-methylimidazo[1,2-a]pyridin-6-yl)-7-[(3R)-4-ethyl-3-methylpiperazin-1-yl]-4H-pyrido[1,2-a]pyrimidin-4-one 2-(4,6-dimethylpyrazolo[1,5-a]pyrazin-2-yl)-7-(1-ethylpiperidin-4-yl)-9-methyl-4H-pyrido[1,2-a]pyrimidin-4-one 2-(4,6-dimethylpyrazolo[1,5-a]pyrazin-2-yl)-7-[1-(2-hydroxyethyl)piperidin-4-yl]-9-methyl-4H-pyrido[1,2-a]pyrimidin-4-one 7-(1-cyclobutylpiperidin-4-yl)-2-(4,6-dimethylpyrazolo[1,5-a]pyrazin-2-yl)-9-methyl-4H-pyrido[1,2-a]pyrimidin-4-one 9-methyl-2-(2-methyl-2H-indazol-5-yl)-7-(1-methylpiperidin-4-yl)-4H-pyrido[1,2-a]pyrimidin-4-one 7-[4-(dimethylamino)-4-methylpiperidin-1-yl]-2-(4,6-dimethylpyrazolo[1,5-a]pyrazin-2-yl)-4H-pyrido[1,2-a]pyrimidin-4-one 2-(4,6-dimethylpyrazolo[1,5-a]pyrazin-2-yl)-7-[4-(ethylamino)-4-methylpiperidin-1-yl]-4H-pyrido[1,2-a]pyrimidin-4-one 2-(4,6-dimethylpyrazolo[1,5-a]pyrazin-2-yl)-7-[4-methyl-4-(propylamino)piperidin-1-yl]-4H-pyrido[1,2-a]pyrimidin-4-one 2-(4,6-dimethylpyrazolo[1,5-a]pyrazin-2-yl)-7-{4-[(2-hydroxyethyl)amino]-4-methylpiperidin-1-yl}-4H-pyrido[1,2-a]pyrimidin-4-one 7-(1-cyclobutylpiperidin-4-yl)-9-methyl-2-(2-methyl-2H-indazol-5-yl)-4H-pyrido[1,2-a]pyrimidin-4-one 7-[1-(2-hydroxyethyl)piperidin-4-yl]-9-methyl-2-(2-methyl-2H-indazol-5-yl)-4H-pyrido[1,2-a]pyrimidin-4-one 2-(4,6-dimethylpyrazolo[1,5-a]pyrazin-2-yl)-9-methyl-7-(1-propylpiperidin-4-yl)-4H-pyrido[1,2-a]pyrimidin-4-one 2-(1,3-dimethylpyrrolo[1,2-a]pyrazin-7-yl)-7-[(3R)-3-methylpiperazin-1-yl]-4H-pyrido[1,2-a]pyrimidin-4-one 2-(8-cyclopropyl-2-methylimidazo[1,2-a]pyridin-6-yl)-7-(piperazin-1-yl)-4H-pyrido[1,2-a]pyrimidin-4-one 2-(8-cyclopropyl-2-methylimidazo[1,2-a]pyridin-6-yl)-7-[(3R)-3-methylpiperazin-1-yl]-4H-pyrido[1,2-a]pyrimidin-4-one 2-(8-cyclopropyl-2-methylimidazo[1,2-a]pyridin-6-yl)-7-[(3S)-3-methylpiperazin-1-yl]-4H-pyrido[1,2-a]pyrimidin-4-one 2-(8-cyclopropyl-2-methylimidazo[1,2-a]pyridin-6-yl)-7-[(3R,5S)-3,5-dimethylpiperazin-1-yl]-4H-pyrido[1,2-a]pyrimidin-4-one 7-(1-cyclopropylpiperidin-4-yl)-9-methyl-2-(2-methyl-2H-indazol-5-yl)-4H-pyrido[1,2-a]pyrimidin-4-one 7-(1-ethylpiperidin-4-yl)-9-methyl-2-(2-methyl-2H-indazol-5-yl)-4H-pyrido[1,2-a]pyrimidin-4-one 2-(4,6-dimethylpyrazolo[1,5-a]pyrazin-2-yl)-9-methyl-7-(piperazin-1-yl)-4H-pyrido[1,2-a]pyrimidin-4-one 9-methyl-2-(2-methyl-2H-indazol-5-yl)-7-(piperidin-4-yl)-4H-pyrido[1,2-a]pyrimidin-4-one 2-(4,6-dimethylpyrazolo[1,5-a]pyrazin-2-yl)-7-[(1-methylpiperidin-4-yl)oxy]-4H-pyrido[1,2-a]pyrimidin-4-one 2-(6-methyl-4-propylpyrazolo[1,5-a]pyrazin-2-yl)-7-(piperazin-1-yl)-4H-pyrido[1,2-a]pyrimidin-4-one 7-(4-methylpiperazin-1-yl)-2-(6-methyl-4-propylpyrazolo[1,5-a]pyrazin-2-yl)-4H-pyrido[1,2-a]pyrimidin-4-one 7-(4-ethylpiperazin-1-yl)-2-(6-methyl-4-propylpyrazolo[1,5-a]pyrazin-2-yl)-4H-pyrido[1,2-a]pyrimidin-4-one 7-[4-(2-hydroxyethyl)piperazin-1-yl]-2-(6-methyl-4-propylpyrazolo[1,5-a]pyrazin-2-yl)-4H-pyrido[1,2-a]pyrimidin-4-one 7-[(3R)-3-methylpiperazin-1-yl]-2-(6-methyl-4-propylpyrazolo[1,5-a]pyrazin-2-yl)-4H-pyrido[1,2-a]pyrimidin-4-one 7-[(3S)-3-methylpiperazin-1-yl]-2-(6-methyl-4-propylpyrazolo[1,5-a]pyrazin-2-yl)-4H-pyrido[1,2-a]pyrimidin-4-one 7-[(3R,5S)-3,5-dimethylpiperazin-1-yl]-2-(6-methyl-4-propylpyrazolo[1,5-a]pyrazin-2-yl)-4H-pyrido[1,2-a]pyrimidin-4-one 2-(1,3-dimethylpyrrolo[1,2-a]pyrazin-7-yl)-7-[(3R)-3-methyl-4-(propan-2-yl)piperazin-1-yl]-4H-pyrido[1,2-a]pyrimidin-4-one 7-(4-amino-4-methylpiperidin-1-yl)-2-(1,3-dimethylpyrrolo[1,2-a]pyrazin-7-yl)-4H-pyrido[1,2-a]pyrimidin-4-one 2-(4,6-dimethylpyrazolo[1,5-a]pyrazin-2-yl)-7-[(3S)-3-ethylpiperazin-1-yl]-9-methyl-4H-pyrido[1,2-a]pyrimidin-4-one 2-[2-methyl-8-(trifluoromethyl)imidazo[1,2-a]pyridin-6-yl]-7-(piperazin-1-yl)-4H-pyrido[1,2-a]pyrimidin-4-one 7-[(3R)-3-methylpiperazin-1-yl]-2-[2-methyl-8-(trifluoromethyl)imidazo[1,2-a]pyridin-6-yl]-4H-pyrido[1,2-a]pyrimidin-4-one 7-[(3S)-3-methylpiperazin-1-yl]-2-[2-methyl-8-(trifluoromethyl)imidazo[1,2-a]pyridin-6-yl]-4H-pyrido[1,2-a]pyrimidin-4-one 7-[(3R,5S)-3,5-dimethylpiperazin-1-yl]-2-[2-methyl-8-(trifluoromethyl)imidazo[1,2-a]pyridin-6-yl]-4H-pyrido[1,2-a]pyrimidin-4-one 7-(4-amino-4-methylpiperidin-1-yl)-2-(4-ethyl-6-methylpyrazolo[1,5-a]pyrazin-2-yl)-4H-pyrido[1,2-a]pyrimidin-4-one 2-(2,7-dimethyl-2H-indazol-5-yl)-7-(piperazin-1-yl)-4H-pyrido[1,2-a]pyrimidin-4-one 2-(2,7-dimethyl-2H-indazol-5-yl)-7-(piperidin-4-yl)-4H-pyrido[1,2-a]pyrimidin-4-one 7-(3-aminoprop-1-yn-1-yl)-2-(4,6-dimethylpyrazolo[1,5-a]pyrazin-2-yl)-4H-pyrido[1,2-a]pyrimidin-4-one 2-(2,7-dimethyl-2H-indazol-5-yl)-7-[(3R)-3-methylpiperazin-1-yl]-4H-pyrido[1,2-a]pyrimidin-4-one 7-(3-aminopropyl)-2-(4,6-dimethylpyrazolo[1,5-a]pyrazin-2-yl)-4H-pyrido[1,2-a]pyrimidin-4-one 2-(1,3-dimethylpyrrolo[1,2-a]pyrazin-7-yl)-7-(1,2,3,6-tetrahydropyridin-4-yl)-4H-pyrido[1,2-a]pyrimidin-4-one 2-(4,6-dimethylpyrazolo[1,5-a]pyrazin-2-yl)-7-(2,2,6,6-tetramethyl-1,2,3,6-tetrahydropyridin-4-yl)-4H-pyrido[1,2-a]pyrimidin-4-one 2-(4-ethyl-6-methylpyrazolo[1,5-a]pyrazin-2-yl)-7-(2,2,6,6-tetramethyl-1,2,3,6-tetrahydropyridin-4-yl)-4H-pyrido[1,2-a]pyrimidin-4-one 2-(4,6-dimethylpyrazolo[1,5-a]pyrazin-2-yl)-7-[(3aR,6aS)-hexahydropyrrolo[3,4-c]pyrrol-2(1H)-yl]-4H-pyrido[1,2-a]pyrimidin-4-one 2-(4-ethyl-6-methylpyrazolo[1,5-a]pyrazin-2-yl)-7-[(3aR,6aS)-hexahydropyrrolo[3,4-c]pyrrol-2(1H)-yl]-4H-pyrido[1,2-a]pyrimidin-4-one 7-[(3R,5S)-3,5-dimethylpiperazin-1-yl]-2-(1-ethyl-3-methylpyrrolo[1,2-a]pyrazin-7-yl)-4H-pyrido[1,2-a]pyrimidin-4-one 7-(1,4-diazepan-1-yl)-2-(1-ethyl-3-methylpyrrolo[1,2-a]pyrazin-7-yl)-4H-pyrido[1,2-a]pyrimidin-4-one 2-(2,7-dimethyl-2H-indazol-5-yl)-7-[(3S)-3-methylpiperazin-1-yl]-4H-pyrido[1,2-a]pyrimidin-4-one 2-(2,7-dimethyl-2H-indazol-5-yl)-7-[(3S)-3,4-dimethylpiperazin-1-yl]-4H-pyrido[1,2-a]pyrimidin-4-one 2-(2,7-dimethyl-2H-indazol-5-yl)-7-(1-methylpiperidin-4-yl)-4H-pyrido[1,2-a]pyrimidin-4-one 2-(2,7-dimethyl-2H-indazol-5-yl)-7-(1-ethylpiperidin-4-yl)-4H-pyrido[1,2-a]pyrimidin-4-one 9-methyl-2-(2-methyl-2H-indazol-5-yl)-7-(piperazin-1-yl)-4H-pyrido[1,2-a]pyrimidin-4-one 9-methyl-2-(2-methyl-2H-indazol-5-yl)-7-[(3R)-3-methylpiperazin-1-yl]-4H-pyrido[1,2-a]pyrimidin-4-one 9-methyl-2-(2-methyl-2H-indazol-5-yl)-7-[(3S)-3-methylpiperazin-1-yl]-4H-pyrido[1,2-a]pyrimidin-4-one 7-[3-(dimethylamino)azetidin-1-yl]-2-(4,6-dimethylpyrazolo[1,5-a]pyrazin-2-yl)-4H-pyrido[1,2-a]pyrimidin-4-one 7-[3-(diethylamino)azetidin-1-yl]-2-(4,6-dimethylpyrazolo[1,5-a]pyrazin-2-yl)-4H-pyrido[1,2-a]pyrimidin-4-one 2-(4,6-dimethylpyrazolo[1,5-a]pyrazin-2-yl)-7-[3-(pyrrolidin-1-yl)azetidin-1-yl]-4H-pyrido[1,2-a]pyrimidin-4-one 7-(1,4-diazepan-1-yl)-2-(4-ethyl-6-methylpyrazolo[1,5-a]pyrazin-2-yl)-4H-pyrido[1,2-a]pyrimidin-4-one 7-[(3aR,6aS)-hexahydropyrrolo[3,4-c]pyrrol-2(1H)-yl]-2-(6-methyl-4-propylpyrazolo[1,5-a]pyrazin-2-yl)-4H-pyrido[1,2-a]pyrimidin-4-one 2-(6-methyl-4-propylpyrazolo[1,5-a]pyrazin-2-yl)-7-(1,2,3,6-tetrahydropyridin-4-yl)-4H-pyrido[1,2-a]pyrimidin-4-one 2-(4-ethyl-6-methylpyrazolo[1,5-a]pyrazin-2-yl)-7-(1,2,3,6-tetrahydropyridin-4-yl)-4H-pyrido[1,2-a]pyrimidin-4-one 7-[(3S)-3-(aminomethyl)pyrrolidin-1-yl]-2-(4,6-dimethylpyrazolo[1,5-a]pyrazin-2-yl)-4H-pyrido[1,2-a]pyrimidin-4-one 2-(4,6-dimethylpyrazolo[1,5-a]pyrazin-2-yl)-7-[3-(piperidin-1-yl)azetidin-1-yl]-4H-pyrido[1,2-a]pyrimidin-4-one 2-(6-methyl-4-propylpyrazolo[1,5-a]pyrazin-2-yl)-7-(piperidin-4-yl)-4H-pyrido[1,2-a]pyrimidin-4-one 7-(2,7-diazaspiro[4.4]non-2-yl)-2-(4,6-dimethylpyrazolo[1,5-a]pyrazin-2-yl)-4H-pyrido[1,2-a]pyrimidin-4-one 2-(2,7-dimethyl-2H-indazol-5-yl)-7-(4-methylpiperazin-1-yl)-4H-pyrido[1,2-a]pyrimidin-4-one 7-[3-(dimethylamino)propyl]-2-(4,6-dimethylpyrazolo[1,5-a]pyrazin-2-yl)-4H-pyrido[1,2-a]pyrimidin-4-one 7-{(3S)-3-[(dimethylamino)methyl]pyrrolidin-1-yl}-2-(4,6-dimethylpyrazolo[1,5-a]pyrazin-2-yl)-4H-pyrido[1,2-a]pyrimidin-4-one 2-(4-ethyl-6-methylpyrazolo[1,5-a]pyrazin-2-yl)-9-methyl-7-(piperidin-4-yl)-4H-pyrido[1,2-a]pyrimidin-4-one 9-methyl-2-(1-methyl-1H-indazol-5-yl)-7-(piperidin-4-yl)-4H-pyrido[1,2-a]pyrimidin-4-one 2-(4-ethyl-6-methylpyrazolo[1,5-a]pyrazin-2-yl)-9-methyl-7-(1,2,3,6-tetrahydropyridin-4-yl)-4H-pyrido[1,2-a]pyrimidin-4-one 2-(4-ethyl-6-methylpyrazolo[1,5-a]pyrazin-2-yl)-9-methyl-7-(1-methylpiperidin-4-yl)-4H-pyrido[1,2-a]pyrimidin-4-one 2-(1,7-dimethyl-1H-indazol-5-yl)-7-(piperidin-4-yl)-4H-pyrido[1,2-a]pyrimidin-4-one 2-(1,7-dimethyl-1H-indazol-5-yl)-7-(piperazin-1-yl)-4H-pyrido[1,2-a]pyrimidin-4-one 2-(1,7-dimethyl-1H-indazol-5-yl)-7-[(3S)-3-methylpiperazin-1-yl]-4H-pyrido[1,2-a]pyrimidin-4-one 7-{(3S)-3-[(diethylamino)methyl]pyrrolidin-1-yl}-2-(4,6-dimethylpyrazolo[1,5-a]pyrazin-2-yl)-4H-pyrido[1,2-a]pyrimidin-4-one 2-(4,6-dimethylpyrazolo[1,5-a]pyrazin-2-yl)-7-{(3S)-3-[(ethylamino)methyl]pyrrolidin-1-yl}-4H-pyrido[1,2-a]pyrimidin-4-one 7-{3-[(dimethylamino)methyl]azetidin-1-yl}-2-(4,6-dimethylpyrazolo[1,5-a]pyrazin-2-yl)-4H-pyrido[1,2-a]pyrimidin-4-one 7-{3-[(diethylamino)methyl]azetidin-1-yl}-2-(4,6-dimethylpyrazolo[1,5-a]pyrazin-2-yl)-4H-pyrido[1,2-a]pyrimidin-4-one 2-(1-ethyl-3-methylpyrrolo[1,2-a]pyrazin-7-yl)-7-[(8aS)-hexahydropyrrolo[1,2-a]pyrazin-2(1H)-yl]-4H-pyrido[1,2-a]pyrimidin-4-one 2-(4-ethyl-6-methylpyrazolo[1,5-a]pyrazin-2-yl)-9-methyl-7-[(3R)-3-methylpiperazin-1-yl]-4H-pyrido[1,2-a]pyrimidin-4-one 9-methyl-2-(1-methyl-1H-indazol-5-yl)-7-(1-methylpiperidin-4-yl)-4H-pyrido[1,2-a]pyrimidin-4-one 7-[(3R)-3,4-dimethylpiperazin-1-yl]-2-(4-ethyl-6-methylpyrazolo[1,5-a]pyrazin-2-yl)-9-methyl-4H-pyrido[1,2-a]pyrimidin-4-one 7-(1-ethylpiperidin-4-yl)-9-methyl-2-(1-methyl-1H-indazol-5-yl)-4H-pyrido[1,2-a]pyrimidin-4-one 2-(4-ethyl-6-methylpyrazolo[1,5-a]pyrazin-2-yl)-9-methyl-7-[(3S)-3-methylpiperazin-1-yl]-4H-pyrido[1,2-a]pyrimidin-4-one 7-[1-(2-hydroxyethyl)piperidin-4-yl]-9-methyl-2-(1-methyl-1H-indazol-5-yl)-4H-pyrido[1,2-a]pyrimidin-4-one 7-[(3S)-3,4-dimethylpiperazin-1-yl]-2-(4-ethyl-6-methylpyrazolo[1,5-a]pyrazin-2-yl)-9-methyl-4H-pyrido[1,2-a]pyrimidin-4-one 2-(4-ethyl-6-methylpyrazolo[1,5-a]pyrazin-2-yl)-7-(1-ethylpiperidin-4-yl)-9-methyl-4H-pyrido[1,2-a]pyrimidin-4-one 9-methyl-2-(2-methyl-2H-indazol-5-yl)-7-(1,2,3,6-tetrahydropyridin-4-yl)-4H-pyrazino[1,2-a]pyrimidin-4-one 7-(1-cyclobutylpiperidin-4-yl)-2-(4-ethyl-6-methylpyrazolo[1,5-a]pyrazin-2-yl)-9-methyl-4H-pyrido[1,2-a]pyrimidin-4-one 2-(4-ethyl-6-methylpyrazolo[1,5-a]pyrazin-2-yl)-7-[1-(2-hydroxyethyl)piperidin-4-yl]-9-methyl-4H-pyrido[1,2-a]pyrimidin-4-one 2-(8-ethyl-2-methylimidazo[1,2-a]pyridin-6-yl)-7-[(8aR)-hexahydropyrrolo[1,2-a]pyrazin-2(1H)-yl]-4H-pyrido[1,2-a]pyrimidin-4-one 2-(8-ethyl-2-methylimidazo[1,2-a]pyridin-6-yl)-7-[(8aS)-hexahydropyrrolo[1,2-a]pyrazin-2(1H)-yl]-4H-pyrido[1,2-a]pyrimidin-4-one 9-methyl-2-(2-methyl-2H-indazol-5-yl)-7-(piperidin-4-yl)-4H-pyrazino[1,2-a]pyrimidin-4-one 7-[(3R)-3-(aminomethyl)pyrrolidin-1-yl]-2-(4,6-dimethylpyrazolo[1,5-a]pyrazin-2-yl)-4H-pyrido[1,2-a]pyrimidin-4-one 2-(4,6-dimethylpyrazolo[1,5-a]pyrazin-2-yl)-7-[(2S,6S)-2,6-dimethyl-1,2,3,6-tetrahydropyridin-4-yl]-4H-pyrido[1,2-a]pyrimidin-4-one 7-{(3R)-3-[(dimethylamino)methyl]pyrrolidin-1-yl}-2-(4,6-dimethylpyrazolo[1,5-a]pyrazin-2-yl)-4H-pyrido[1,2-a]pyrimidin-4-one 7-[(2S,6S)-2,6-dimethylpiperidin-4-yl]-2-(4,6-dimethylpyrazolo[1,5-a]pyrazin-2-yl)-4H-pyrido[1,2-a]pyrimidin-4-one 2-(8-fluoro-2-methylimidazo[1,2-a]pyridin-6-yl)-7-[4-(2-hydroxyethyl)piperazin-1-yl]-4H-pyrido[1,2-a]pyrimidin-4-one 2-(imidazo[1,2-a]pyridin-6-yl)-7-(4-methylpiperazin-1-yl)-4H-pyrido[1,2-a]pyrimidin-4-one 2-(4-fluoro-2-methyl-1,3-benzoxazol-6-yl)-7-[(8aS)-hexahydropyrrolo[1,2-a]pyrazin-2(1H)-yl]-4H-pyrido[1,2-a]pyrimidin-4-one 7-(2,7-diazaspiro[3.5]non-7-yl)-2-(4,6-dimethylpyrazolo[1,5-a]pyrazin-2-yl)-4H-pyrido[1,2-a]pyrimidin-4-one 7-(4-methylpiperazin-1-yl)-2-(2-methyl[1,2,4]triazolo[1,5-a]pyridin-6-yl)-4H-pyrido[1,2-a]pyrimidin-4-one 7-(4-methylpiperazin-1-yl)-2-[2-methyl-8-(trifluoromethyl)imidazo[1,2-a]pyridin-6-yl]-4H-pyrido[1,2-a]pyrimidin-4-one 2-methyl-6-[7-(4-methylpiperazin-1-yl)-4-oxo-4H-pyrido[1,2-a]pyrimidin-2-yl]imidazo[1,2-a]pyridine-8-carbonitrile 2-(2,8-dimethylimidazo[1,2-a]pyridin-6-yl)-7-(4-methylpiperazin-1-yl)-4H-pyrido[1,2-a]pyrimidin-4-one 7-(4,7-diazaspiro[2.5]oct-7-yl)-2-(2,8-dimethylimidazo[1,2-a]pyridin-6-yl)-4H-pyrido[1,2-a]pyrimidin-4-one 2-(8-fluoro-2-methylimidazo[1,2-a]pyridin-6-yl)-7-(1-methylpiperidin-4-yl)-4H-pyrido[1,2-a]pyrimidin-4-one 2-(8-fluoro-2-methylimidazo[1,2-a]pyridin-6-yl)-7-(4-hydroxypiperidin-4-yl)-4H-pyrido[1,2-a]pyrimidin-4-one 2-(4-ethyl-6-methylpyrazolo[1,5-a]pyrazin-2-yl)-7-[(8aS)-hexahydropyrrolo[1,2-a]pyrazin-2(1H)-yl]-4H-pyrido[1,2-a]pyrimidin-4-one 2-(4-ethyl-6-methylpyrazolo[1,5-a]pyrazin-2-yl)-7-[(8aR)-hexahydropyrrolo[1,2-a]pyrazin-2(1H)-yl]-4H-pyrido[1,2-a]pyrimidin-4-one 7-[(3R)-3-(dimethylamino)pyrrolidin-1-yl]-2-(4-ethyl-6-methylpyrazolo[1,5-a]pyrazin-2-yl)-4H-pyrido[1,2-a]pyrimidin-4-one 7-[(3S)-3-(dimethylamino)pyrrolidin-1-yl]-2-(4-ethyl-6-methylpyrazolo[1,5-a]pyrazin-2-yl)-4H-pyrido[1,2-a]pyrimidin-4-one 2-(8-fluoro-2-methylimidazo[1,2-a]pyridin-6-yl)-7-[(8aS)-8a-methylhexahydropyrrolo[1,2-a]pyrazin-2(1H)-yl]-4H-pyrido[1,2-a]pyrimidin-4-one 2-(4-ethyl-6-methylpyrazolo[1,5-a]pyrazin-2-yl)-7-(4-ethylpiperazin-1-yl)-9-methyl-4H-pyrido[1,2-a]pyrimidin-4-one 2-(4-ethyl-6-methylpyrazolo[1,5-a]pyrazin-2-yl)-7-[(8aS)-hexahydropyrrolo[1,2-a]pyrazin-2(1H)-yl]-9-methyl-4H-pyrido[1,2-a]pyrimidin-4-one 2-(2,8-dimethylimidazo[1,2-a]pyridin-6-yl)-7-(4-ethylpiperazin-1-yl)-4H-pyrido[1,2-a]pyrimidin-4-one 2-(2,8-dimethylimidazo[1,2-a]pyridin-6-yl)-7-[(8aS)-hexahydropyrrolo[1,2-a]pyrazin-2(1H)-yl]-4H-pyrido[1,2-a]pyrimidin-4-one 2-(2,8-dimethylimidazo[1,2-a]pyridin-6-yl)-7-(8a-methylhexahydropyrrolo[1,2-a]pyrazin-2(1H)-yl)-4H-pyrido[1,2-a]pyrimidin-4-one 7-[(3R)-3-(dimethylamino)pyrrolidin-1-yl]-2-(4-ethyl-6-methylpyrazolo[1,5-a]pyrazin-2-yl)-9-methyl-4H-pyrido[1,2-a]pyrimidin-4-one 2-(4-ethyl-6-methylpyrazolo[1,5-a]pyrazin-2-yl)-7-{[2-(morpholin-4-yl)ethyl]amino}-4H-pyrido[1,2-a]pyrimidin-4-one 7-{[2-(dimethylamino)ethyl]amino}-2-(4-ethyl-6-methylpyrazolo[1,5-a]pyrazin-2-yl)-4H-pyrido[1,2-a]pyrimidin-4-one 7-{[2-(dimethylamino)ethyl](methyl)amino}-2-(4-ethyl-6-methylpyrazolo[1,5-a]pyrazin-2-yl)-4H-pyrido[1,2-a]pyrimidin-4-one 2-(4-ethyl-6-methylpyrazolo[1,5-a]pyrazin-2-yl)-7-{methyl[2-(methylamino)ethyl]amino}-4H-pyrido[1,2-a]pyrimidin-4-one 7-[(3R)-3-(dimethylamino)pyrrolidin-1-yl]-2-(2,8-dimethylimidazo[1,2-a]pyridin-6-yl)-4H-pyrido[1,2-a]pyrimidin-4-one 7-[(3S)-3-(dimethylamino)pyrrolidin-1-yl]-2-(2,8-dimethylimidazo[1,2-a]pyridin-6-yl)-4H-pyrido[1,2-a]pyrimidin-4-one 7-[2-(dimethylamino)ethoxy]-2-(4-ethyl-6-methylpyrazolo[1,5-a]pyrazin-2-yl)-9-methyl-4H-pyrido[1,2-a]pyrimidin-4-one 7-[2-(dimethylamino)ethoxy]-2-(4-ethyl-6-methylpyrazolo[1,5-a]pyrazin-2-yl)-4H-pyrido[1,2-a]pyrimidin-4-one 2-(4-ethyl-6-methylpyrazolo[1,5-a]pyrazin-2-yl)-7-(piperidin-4-ylmethoxy)-4H-pyrido[1,2-a]pyrimidin-4-one 2-(4-ethyl-6-methylpyrazolo[1,5-a]pyrazin-2-yl)-7-[2-(piperidin-1-yl)ethoxy]-4H-pyrido[1,2-a]pyrimidin-4-one 2-(4-ethyl-6-methylpyrazolo[1,5-a]pyrazin-2-yl)-7-[3-(morpholin-4-yl)propoxy]-4H-pyrido[1,2-a]pyrimidin-4-one 7-[3-(dimethylamino)propoxy]-2-(4-ethyl-6-methylpyrazolo[1,5-a]pyrazin-2-yl)-4H-pyrido[1,2-a]pyrimidin-4-one, or 2-(4,6-dimethylpyrazolo[1,5-a]pyrazin-2-yl)-7-[(3aR,6aS)-5-methylhexahydropyrrolo[3,4-c]pyrrol-2(1H)-yl]-4H-pyrido[1,2-a]pyrimidin-4-one or a salt, isotopologue, stereoisomer, racemate, enantiomer, diastereomer or tautomer thereof.

In another embodiment, the compound of Formula (I) used in a method disclosed herein is a compound selected from the group consisting of:

2-(3,5-difluoro-4-hydroxyphenyl)-7-(piperazin-1-yl)-4H-pyrido[1,2-a]pyrimidin-4-one hydrochloride 7-[4-(dimethylamino)piperidin-1-yl]-2-(3-fluoro-4-methoxyphenyl)-4H-quinolizin-4-one acetate 2-(2-methyl-1,3-benzothiazol-6-yl)-7-(piperidin-4-yl)-4H-pyrimido[1,2-b]pyridazin-4-one trifluoroacetate (1:1), or 2-(1,3-dimethylpyrrolo[1,2-a]pyrazin-7-yl)-7-(1,2,3,6-tetrahydropyridin-4-yl)-4H-pyrazino[1,2-a]pyrimidin-4-one hydrochloride (1:2)

or a free base, isotopologue, stereoisomer, racemate, enantiomer, diastereomer or tautomer thereof.

Compounds of Formula (I) can be prepared using reagents and methods known in the art, including the methods provided in International Application No. PCT/US2013/025292, filed on Feb. 8, 2013, and published as International Publication No. WO 2013/119916 on Aug. 15, 2013, the entire contents which are incorporated herein by reference (see in particular, General Synthetic Methods, Schemes A-J, at paragraphs [001126] to [001159]; and Specific Synthetic Examples, at paragraphs [001160] to [001573] and Table 1).

Terminology

The chemical terms used above and throughout the description herein, unless specifically defined otherwise, shall be understood by one of ordinary skill in the art to have the following indicated meanings.

As used herein, the term "$C_{1-8}$alkyl" generally refers to saturated hydrocarbon radicals having from one to eight carbon atoms in a straight or branched chain configuration, including, but not limited to, methyl, ethyl, n-propyl (also referred to as propyl or propanyl), isopropyl, n-butyl (also referred to as butyl or butanyl), isobutyl, sec-butyl, tert-butyl, n-pentyl (also referred to as pentyl or pentanyl), n-hexyl (also referred to as hexyl or hexanyl), n-heptyl (also referred to as heptyl or heptanyl), n-octyl and the like. In some embodiments, $C_{1-8}$alkyl includes, but is not limited to, $C_{1-6}$alkyl, $C_{1-4}$alkyl and the like. A $C_{1-8}$alkyl radical is optionally substituted with substituent species as described herein where allowed by available valences.

As used herein, the term "$C_{2-8}$alkenyl" generally refers to partially unsaturated hydrocarbon radicals having from two to eight carbon atoms in a straight or branched chain configuration and one or more carbon-carbon double bonds therein, including, but not limited to, ethenyl (also referred to as vinyl), allyl, propenyl and the like. In some embodiments, $C_{2-8}$alkenyl includes, but is not limited to, $C_{2-6}$alkenyl, $C_{2-4}$alkenyl and the like. A $C_{2-8}$alkenyl radical is optionally substituted with substituent species as described herein where allowed by available valences.

As used herein, the term "$C_{2-8}$alkynyl" generally refers to partially unsaturated hydrocarbon radicals having from two to eight carbon atoms in a straight or branched chain configuration and one or more carbon-carbon triple bonds therein, including, but not limited to, ethynyl, propynyl, butynyl and the like. In some embodiments, $C_{2-8}$alkynyl includes, but is not limited to, $C_{2-6}$alkynyl, $C_{2-4}$alkynyl and the like. A $C_{2-8}$alkynyl radical is optionally substituted with substituent species as described herein where allowed by available valences.

As used herein, the term "$C_{1-8}$alkoxy" generally refers to saturated hydrocarbon radicals having from one to eight carbon atoms in a straight or branched chain configuration of the formula: —O—$C_{1-8}$alkyl, including, but not limited to, methoxy, ethoxy, n-propoxy, isopropoxy, n-butoxy, isobutoxy, sec-butoxy, tert-butoxy, n-pentoxy, n-hexoxy and the like. In some embodiments, $C_{1-8}$alkoxy includes, but is not limited to, $C_{1-6}$alkoxy, $C_{1-4}$alkoxy and the like. A $C_{1-8}$alkoxy radical is optionally substituted with substituent species as described herein where allowed by available valences.

As used herein, the term "$C_{3-14}$cycloalkyl" generally refers to a saturated or partially unsaturated monocyclic, bicyclic or polycyclic hydrocarbon radical, including, but not limited to, cyclopropyl, cyclobutyl, cyclopentyl, cyclohexyl, cyclohexenyl, cycloheptyl, cyclooctyl, 1H-indanyl, indenyl, tetrahydro-naphthalenyl and the like. In some embodiments, $C_{3-14}$cycloalkyl includes, but is not limited to, $C_{3-8}$cycloalkyl, $C_{5-8}$cycloalkyl, $C_{3-10}$cycloalkyl and the like. A $C_{3-14}$cycloalkyl radical is optionally substituted with substituent species as described herein where allowed by available valences.

As used herein, the term "aryl" generally refers to a monocyclic, bicyclic or polycyclic aromatic carbon atom ring structure radical, including, but not limited to, phenyl, naphthyl, anthracenyl, fluorenyl, azulenyl, phenanthrenyl and the like. An aryl radical is optionally substituted with substituent species as described herein where allowed by available valences.

As used herein, the term "heteroaryl" generally refers to a monocyclic, bicyclic or polycyclic aromatic carbon atom ring structure radical in which one or more carbon atom ring members have been replaced, where allowed by structural stability, with one or more heteroatoms, such as an O, S or N atom, including, but not limited to, furanyl (also referred to as furyl), thienyl (also referred to as thiophenyl), pyrrolyl, 2H-pyrrolyl, 3H-pyrrolyl, pyrazolyl, 1H-pyrazolyl, imidazolyl, 1H-imidazolyl, isoxazolyl, isothiazolyl, oxazolyl, 1,3-thiazolyl, triazolyl (such as 1H-1,2,3-triazolyl and the like), oxadiazolyl (such as 1,2,4-oxadiazolyl, 1,3,4-oxadiazolyl and the like), thiadiazolyl, tetrazolyl (such as 1H-tetrazolyl, 2H-tetrazolyl and the like), pyridinyl (also referred to as pyridyl), pyrimidinyl, pyrazinyl, pyridazinyl, triazinyl, indolyl, 1H-indolyl, indazolyl, 1H-indazolyl, 2H-indazolyl, indolizinyl, isoindolyl, benzofuranyl, benzothienyl (also referred to as benzothiophenyl), benzoimidazolyl, 1H-benzoimidazolyl, 1,3-benzothiazolyl, 1,3-benzoxazolyl (also referred to as 1,3-benzooxazolyl), purinyl, 9H-purinyl, quinolinyl, isoquinolinyl, quinazolinyl, quinoxalinyl, 1,3-diazinyl, 1,2-diazinyl, 1,2-diazolyl, 1,4-diazanaphthalenyl, acridinyl, furo[3,2-b]pyridinyl, furo[3,2-c]pyridinyl, furo[2,3-c]pyridinyl, 6H-thieno[2,3-b]pyrrolyl, thieno[3,2-c]pyridinyl, thieno[2,3-d]pyrimidinyl, 1H-pyrrolo[2,3-b]pyridinyl, 1H-pyrrolo[2,3-c]pyridinyl, 1H-pyrrolo[3,2-b]pyridinyl, pyrrolo[1,2-a]pyrazinyl, pyrrolo[1,2-b]pyridazinyl, pyrazolo[1,5-a]pyridinyl, pyrazolo[1,5-a]pyrazinyl, imidazo[1,2-a]pyridinyl, 3H-imidazo[4,5-b]pyridinyl, imidazo[1,2-a]pyrimidinyl, imidazo[1,2-c]pyrimidinyl, imidazo[1,2-b]pyridazinyl, imidazo[1,2-a]pyrazinyl, imidazo[2,1-b][1,3]thiazolyl, imidazo[2,1-b][1,3,4]thiadiazolyl, [1,2,4]triazolo[1,5-a]pyridinyl, [1,2,4]triazolo[4,3-a]pyridinyl and the like. A heteroaryl radical is optionally substituted on a carbon or nitrogen atom ring member with substituent species as described herein where allowed by available valences.

As used herein, the term "heterocyclyl" generally refers to a saturated or partially unsaturated monocyclic, bicyclic or polycyclic carbon atom ring structure radical in which one or more carbon atom ring members have been replaced, where allowed by structural stability, with a heteroatom, such as an O, S or N atom, including, but not limited to, oxiranyl, oxetanyl, azetidinyl, tetrahydrofuranyl, pyrrolinyl, pyrrolidinyl, pyrazolinyl, pyrazolidinyl, imidazolinyl, imidazolidinyl, isoxazolinyl, isoxazolidinyl, isothiazolinyl, isothiazolidinyl, oxazolinyl, oxazolidinyl, thiazolinyl, thiazolidinyl, triazolinyl, triazolidinyl, oxadiazolinyl, oxadiazolidinyl, thiadiazolinyl, thiadiazolidinyl, tetrazolinyl, tetrazolidinyl, pyranyl, dihydro-2H-pyranyl, thiopyranyl, 1,3-dioxanyl, 1,2,5,6-tetrahydropyridinyl, 1,2,3,6-tetrahydropyridinyl, piperidinyl, piperazinyl, morpholinyl, thiomorpholinyl, 1,4-diazepanyl, 1,3-benzodioxolyl (also referred to as benzo[d][1,3]dioxolyl), 1,4-benzodioxanyl, 2,3-dihydro-1,4-benzodioxinyl (also referred to as 2,3-dihydrobenzo[b][1,4]dioxinyl), hexahydropyrrolo[3,4-b]pyrrol-(1H)-yl, (3aS,6aS)-hexahydropyrrolo[3,4-b]pyrrol-(1H)-yl, (3aR,6aR)-hexahydropyrrolo[3,4-b]pyrrol-(1H)-yl, hexahydropyrrolo[3,4-b]pyrrol-(2H)-yl, (3aS,6aS)-hexahydropyrrolo[3,4-b]pyrrol-(2H)-yl, (3aR,6aR)-hexahydropyrrolo[3,4-b]pyrrol-(2H)-yl, hexahydropyrrolo[3,4-c]pyrrol-(1H)-yl, (3aR,6aS)-hexahydropyrrolo[3,4-c]pyrrol-(1H)-yl, (3aR,6aR)-hexahydropyrrolo[3,4-c]pyrrol-(1H)-yl, octahydro-5H-pyrrolo[3,2-c]pyridinyl, octahydro-6H-pyrrolo[3,4-b]pyridinyl, (4aR,7aR)-octahydro-6H-pyrrolo[3,4-b]pyridinyl, (4aS,7aS)-octahydro-6H-pyrrolo[3,4-b]pyridinyl, hexahydropyrrolo[1,2-a]pyrazin-(1H)-yl, (7R,8aS)-hexahydropyrrolo[1,2-a]pyrazin-(1H)-yl, (8aS)-hexahydropyrrolo[1,2-a]pyrazin-(1H)-yl, (8aR)-hexahydropyrrolo[1,2-a]pyrazin-(1H)-yl, (8aS)-octahydropyrrolo[1,2-a]pyrazin-(1H)-yl, (8aR)-octahydropyrrolo[1,2-a]pyrazin-(1H)-yl, hexahydropyrrolo[1,2-a]pyrazin-(2H)-one, octahydro-2H-pyrido[1,2-a]pyrazinyl, 3-azabicyclo[3.1.0]hexyl, (1R,5S)-3-azabicyclo[3.1.0]hexyl, 8-azabicyclo[3.2.1]octyl, (1R,5S)-8-azabicyclo[3.2.1]octyl, 8-azabicyclo[3.2.1]oct-2-enyl, (1R,5S)-8-azabicyclo[3.2.1]oct-2-enyl, 9-azabicyclo[3.3.1]nonyl, (1R,5S)-9-azabicyclo[3.3.1]nonyl, 2,5-diazabicyclo[2.2.1]heptyl, (1S,4S)-2,5-diazabicyclo[2.2.1]heptyl, 2,5-diazabicyclo[2.2.2]octyl, 3,8-diazabicyclo[3.2.1]octyl, (1R,5S)-3,8-diazabicyclo[3.2.1]octyl, 1,4-diazabicyclo[3.2.2]nonyl, azaspiro[3.3]heptyl, 2,6-diazaspiro[3.3]heptyl, 2,7-diazaspiro[3.5]nonyl, 5,8-diazaspiro[3.5]nonyl, 2,7-diazaspiro[4.4]nonyl, 6,9-diazaspiro[4.5]decyl and the like. A heterocyclyl radical is optionally substituted on a carbon or nitrogen atom ring member with substituent species as described herein where allowed by available valences.

As used herein, the term "$C_{1-8}$alkoxy-$C_{1-8}$alkyl" refers to a radical of the formula: —$C_{1-8}$alkyl-O—$C_{1-8}$alkyl.

As used herein, the term "$C_{1-8}$alkoxy-$C_{1-8}$alkyl-amino" refers to a radical of the formula: —NH—$C_{1-8}$alkyl-O—$C_{1-8}$alkyl.

As used herein, the term "($C_{1-8}$alkoxy-$C_{1-8}$alkyl)$_2$-amino" refers to a radical of the formula: —N($C_{1-8}$alkyl-O—$C_{1-8}$alkyl)$_2$.

As used herein, the term "$C_{1-8}$alkoxy-$C_{1-8}$alkyl-amino-$C_{1-8}$alkoxy" refers to a radical of the formula: —O—$C_{1-8}$alkyl-NH—$C_{1-8}$alkyl-O—$C_{1-8}$alkyl.

As used herein, the term "($C_{1-8}$alkoxy-$C_{1-8}$alkyl)$_2$-amino-$C_{1-8}$alkoxy" refers to a radical of the formula: —$C_{1-8}$alkyl-N($C_{1-8}$alkyl-O—$C_{1-8}$alkyl)$_2$.

As used herein, the term "($C_{1-8}$alkoxy-$C_{1-8}$alkyl)($C_{1-8}$alkyl)amino-$C_{1-8}$alkoxy" refers to a radical of the formula: —$C_{1-8}$alkyl-N($C_{1-8}$alkyl)($C_{1-8}$alkyl-O—$C_{1-8}$alkyl).

As used herein, the term "$C_{1-8}$alkoxy-$C_{1-8}$alkyl-amino-$C_{1-8}$alkyl" refers to a radical of the formula: —$C_{1-8}$alkyl-NH—$C_{1-8}$alkyl-O—$C_{1-8}$alkyl.

As used herein, the term "($C_{1-8}$alkoxy-$C_{1-8}$alkyl)$_2$-amino-$C_{1-8}$alkyl" refers to a radical of the formula: —$C_{1-8}$alkyl-N($C_{1-8}$alkyl-O—$C_{1-8}$alkyl)$_2$.

As used herein, the term "($C_{1-8}$alkoxy-$C_{1-8}$alkyl)($C_{1-8}$alkyl)amino-$C_{1-8}$alkyl" refers to a radical of the formula: —$C_{1-8}$alkyl-N($C_{1-8}$alkyl)($C_{1-8}$alkyl-O—$C_{1-8}$alkyl).

As used herein, the term "$C_{1-8}$alkoxy-carbonyl" refers to a radical of the formula: —C(O)—O—$C_{1-8}$alkyl.

As used herein, the term "$C_{1-8}$alkoxy-carbonyl-$C_{2-8}$alkenyl" refers to a radical of the formula: —$C_{2-8}$alkenyl-C(O)—O—$C_{1-8}$alkyl.

As used herein, the term "$C_{1-8}$alkoxy-carbonyl-amino" refers to a radical of the formula: —NH—C(O)—O—$C_{1-8}$alkyl.

As used herein, the term "$C_{1-8}$alkyl-amino" refers to a radical of the formula: —NH—$C_{1-8}$alkyl.

As used herein, the term "($C_{1-8}$alkyl)$_2$-amino" refers to a radical of the formula: —N($C_{1-8}$alkyl)$_2$.

As used herein, the term "$C_{1-8}$alkyl-amino-$C_{2-8}$alkenyl" refers to a radical of the formula: —$C_{2-8}$alkenyl-NH—$C_{1-8}$alkyl.

As used herein, the term "($C_{1-8}$alkyl)$_2$-amino-$C_{2-8}$alkenyl" refers to a radical of the formula: —$C_{2-8}$alkenyl-N($C_{1-8}$alkyl)$_2$.

As used herein, the term "$C_{1-8}$alkyl-amino-$C_{1-8}$alkoxy" refers to a radical of the formula: —O—$C_{1-8}$alkyl-NH—$C_{1-8}$alkyl.

As used herein, the term "($C_{1-8}$alkyl)$_2$-amino-$C_{1-8}$alkoxy" refers to a radical of the formula: —O—$C_{1-8}$alkyl-N($C_{1-8}$alkyl)$_2$.

As used herein, the term "$C_{1-8}$alkyl-amino-$C_{1-8}$alkyl" refers to a radical of the formula: —$C_{1-8}$alkyl-NH—$C_{1-8}$alkyl.

As used herein, the term "($C_{1-8}$alkyl)$_2$-amino-$C_{1-8}$alkyl" refers to a radical of the formula: —$C_{1-8}$alkyl-N($C_{1-8}$alkyl)$_2$.

As used herein, the term "$C_{1-8}$alkyl-amino-$C_{1-8}$alkyl-amino" refers to a radical of the formula: —NH—$C_{1-8}$alkyl-NH—$C_{1-8}$alkyl.

As used herein, the term "($C_{1-8}$alkyl)$_2$-amino-$C_{1-8}$alkyl-amino" refers to a radical of the formula: —NH—$C_{1-8}$alkyl-N($C_{1-8}$alkyl)$_2$.

As used herein, the term "($C_{1-8}$alkyl-amino-$C_{1-8}$alkyl)$_2$-amino" refers to a radical of the formula: —N($C_{1-8}$alkyl-NH—$C_{1-8}$alkyl)$_2$.

As used herein, the term "[($C_{1-8}$alkyl)$_2$-amino-$C_{1-8}$alkyl]$_2$-amino" refers to a radical of the formula: —N[$C_{1-8}$alkyl-N($C_{1-8}$alkyl)$_2$]$_2$.

As used herein, the term "($C_{1-8}$alkyl-amino-$C_{1-8}$alkyl)($C_{1-8}$alkyl)amino" refers to a radical of the formula: —N($C_{1-8}$alkyl)($C_{1-8}$alkyl-NH—$C_{1-8}$alkyl).

As used herein, the term "[($C_{1-8}$alkyl)$_2$-amino-$C_{1-8}$alkyl]($C_{1-8}$alkyl)amino" refers to a radical of the formula: —N($C_{1-8}$alkyl)[$C_{1-8}$alkyl-N($C_{1-8}$alkyl)$_2$].

As used herein, the term "$C_{1-8}$alkyl-amino-$C_{2-8}$alkynyl" refers to a radical of the formula: —$C_{2-8}$alkynyl-NH—$C_{1-8}$alkyl.

As used herein, the term "($C_{1-8}$alkyl)$_2$-amino-$C_{2-8}$alkynyl" refers to a radical of the formula: —$C_{2-8}$alkynyl-N($C_{1-8}$alkyl)$_2$.

As used herein, the term "$C_{1-8}$alkyl-carbonyl" refers to a radical of the formula: —C(O)—$C_{1-8}$alkyl.

As used herein, the term "$C_{1-8}$alkyl-carbonyl-amino" refers to a radical of the formula: —NH—C(O)—$C_{1-8}$alkyl.

As used herein, the term "$C_{1-8}$alkyl-thio" refers to a radical of the formula: —S—$C_{1-8}$alkyl.

As used herein, the term "amino-$C_{2-8}$alkenyl" refers to a radical of the formula: —$C_{2-8}$alkenyl-$NH_2$.

As used herein, the term "amino-$C_{1-8}$alkoxy" refers to a radical of the formula: —O—$C_{1-8}$alkyl-$NH_2$.

As used herein, the term "amino-$C_{1-8}$alkyl" refers to a radical of the formula: —$C_{1-8}$alkyl-$NH_2$.

As used herein, the term "amino-$C_{1-8}$alkyl-amino" refers to a radical of the formula: —NH—$C_{1-8}$alkyl-$NH_2$.

As used herein, the term "(amino-$C_{1-8}$alkyl)$_2$-amino" refers to a radical of the formula: —N($C_{1-8}$alkyl-$NH_2$)$_2$.

As used herein, the term "(amino-$C_{1-8}$alkyl)($C_{1-8}$alkyl) amino" refers to a radical of the formula: —N($C_{1-8}$alkyl) ($C_{1-8}$alkyl-$NH_2$).

As used herein, the term "amino-$C_{2-8}$alkynyl" refers to a radical of the formula: —$C_{2-8}$alkynyl-$NH_2$.

As used herein, the term "aryl-$C_{1-8}$alkoxy-carbonyl" refers to a radical of the formula: —C(O)—O—$C_{1-8}$alkyl-aryl.

As used herein, the term "aryl-$C_{1-8}$alkyl" refers to a radical of the formula: —$C_{1-8}$alkyl-aryl.

As used herein, the term "aryl-$C_{1-8}$alkyl-amino" refers to a radical of the formula: —NH—$C_{1-8}$alkyl-aryl.

As used herein, the term "(aryl-$C_{1-8}$alkyl)$_2$-amino" refers to a radical of the formula: —N($C_{1-8}$alkyl-aryl)$_2$.

As used herein, the term "(aryl-$C_{1-8}$alkyl)($C_{1-8}$alkyl) amino" refers to a radical of the formula: —N($C_{1-8}$alkyl) ($C_{1-8}$alkyl-aryl).

As used herein, the term "aryl-$C_{1-8}$alkyl-amino-$C_{1-8}$alkyl" refers to a radical of the formula: —$C_{1-8}$alkyl-NH—$C_{1-8}$alkyl-aryl.

As used herein, the term "(aryl-$C_{1-8}$alkyl)$_2$-amino-$C_{1-8}$alkyl" refers to a radical of the formula: —$C_{1-8}$alkyl-N ($C_{1-8}$alkyl-aryl)$_2$.

As used herein, the term "(aryl-$C_{1-8}$alkyl)($C_{1-8}$alkyl) amino-$C_{1-8}$alkyl" refers to a radical of the formula: —$C_{1-8}$alkyl-N($C_{1-8}$alkyl)($C_{1-8}$alkyl-aryl).

As used herein, the term "aryl-amino" refers to a radical of the formula: —NH-aryl.

As used herein, the term "aryl-amino-carbonyl" refers to a radical of the formula: —C(O)—NH-aryl.

As used herein, the term "aryl-sulfonyloxy-$C_{1-8}$alkyl" refers to a radical of the formula: —$C_{1-8}$alkyl-O—$SO_2$-aryl.

As used herein, the term "benzoxy-carbonyl" refers to a radical of the formula: —C(O)O—$CH_2$-phenyl.

As used herein, the term "$C_{3-14}$cycloalkyl-$C_{1-8}$alkyl" refers to a radical of the formula: —$C_{1-8}$alkyl-$C_{3-14}$cycloalkyl.

As used herein, the term "$C_{3-14}$cycloalkyl-amino" refers to a radical of the formula: —NH—$C_{3-14}$cycloalkyl.

As used herein, the term "$C_{3-14}$cycloalkyl-oxy" refers to a radical of the formula: —O—$C_{3-14}$cycloalkyl.

As used herein, the term "halo" or "halogen" generally refers to a halogen atom radical, including fluoro, chloro, bromo and iodo.

As used herein, the term "halo-$C_{1-8}$alkoxy" refers to a radical of the formula: —O—$C_{1-8}$alkyl-halo, wherein $C_{1-8}$alkyl is partially or completely substituted with one or more halogen atoms where allowed by available valences.

As used herein, the term "halo-$C_{1-8}$alkyl" refers to a radical of the formula: —$C_{1-8}$alkyl-halo, wherein $C_{1-8}$alkyl is partially or completely substituted with one or more halogen atoms where allowed by available valences.

As used herein, the term "halo-$C_{1-8}$alkyl-amino" refers to a radical of the formula: —NH—$C_{1-8}$alkyl-halo.

As used herein, the term "(halo-$C_{1-8}$alkyl)($C_{1-8}$alkyl) amino" refers to a radical of the formula: —N($C_{1-8}$alkyl) ($C_{1-8}$alkyl-halo).

As used herein, the term "(halo-$C_{1-8}$alkyl)$_2$-amino" refers to a radical of the formula: —N($C_{1-8}$alkyl-halo)$_2$.

As used herein, the term "heteroaryl-$C_{1-8}$alkoxy" refers to a radical of the formula: —O—$C_{1-8}$alkyl-heteroaryl.

As used herein, the term "heteroaryl-$C_{1-8}$alkyl" refers to a radical of the formula: —$C_{1-8}$alkyl-heteroaryl.

As used herein, the term "heteroaryl-$C_{1-8}$alkyl-amino" refers to a radical of the formula: —NH—$C_{1-8}$alkyl-heteroaryl.

As used herein, the term "(heteroaryl-$C_{1-8}$alkyl)$_2$-amino" refers to a radical of the formula: —N($C_{1-8}$alkyl-heteroaryl)$_2$.

As used herein, the term "(heteroaryl-$C_{1-8}$alkyl)($C_{1-8}$alkyl)amino" refers to a radical of the formula: —N($C_{1-8}$alkyl) ($C_{1-8}$alkyl-heteroaryl).

As used herein, the term "heteroaryl-$C_{1-8}$alkyl-amino-$C_{1-8}$alkyl" refers to a radical of the formula: —$C_{1-8}$alkyl-NH—$C_{1-8}$alkyl-heteroaryl.

As used herein, the term "(heteroaryl-$C_{1-8}$alkyl)$_2$-amino-$C_{1-8}$alkyl" refers to a radical of the formula: —$C_{1-8}$alkyl-N ($C_{1-8}$alkyl-heteroaryl)$_2$.

As used herein, the term "(heteroaryl-$C_{1-8}$alkyl)($C_{1-8}$alkyl)amino-$C_{1-8}$alkyl" refers to a radical of the formula: —$C_{1-8}$alkyl-N($C_{1-8}$alkyl)($C_{1-8}$alkyl-heteroaryl).

As used herein, the term "heteroaryl-amino" refers to a radical of the formula: —NH-heteroaryl.

As used herein, the term "heterocyclyl-$C_{1-8}$alkoxy" refers to a radical of the formula: —O—$C_{1-8}$alkyl-heterocyclyl.

As used herein, the term "heterocyclyl-$C_{1-8}$alkyl" refers to a radical of the formula: —$C_{1-8}$alkyl-heterocyclyl.

As used herein, the term "heterocyclyl-$C_{1-8}$alkyl-amino" refers to a radical of the formula: —NH—$C_{1-8}$alkyl-heterocyclyl.

As used herein, the term "(heterocyclyl-$C_{1-8}$alkyl)$_2$-amino" refers to a radical of the formula: —N($C_{1-8}$alkyl-heterocyclyl)$_2$.

As used herein, the term "(heterocyclyl-$C_{1-8}$alkyl)($C_{1-8}$alkyl)amino" refers to a radical of the formula: —N ($C_{1-8}$alkyl)($C_{1-8}$alkyl-heterocyclyl).

As used herein, the term "heterocyclyl-$C_{1-8}$alkyl-amino-$C_{1-8}$alkyl" refers to a radical of the formula: —$C_{1-8}$alkyl-NH—$C_{1-8}$alkyl-heterocyclyl.

As used herein, the term "(heterocyclyl-$C_{1-8}$alkyl)$_2$-amino-$C_{1-8}$alkyl" refers to a radical of the formula: —$C_{1-8}$alkyl-N($C_{1-8}$alkyl-heterocyclyl)$_2$.

As used herein, the term "(heterocyclyl-$C_{1-8}$alkyl)($C_{1-8}$alkyl)amino-$C_{1-8}$alkyl" refers to a radical of the formula: —$C_{1-8}$alkyl-N($C_{1-8}$alkyl)($C_{1-8}$alkyl-heterocyclyl).

As used herein, the term "heterocyclyl-amino" refers to a radical of the formula: —NH-heterocyclyl.

As used herein, the term "(heterocyclyl)($C_{1-8}$alkyl) amino" refers to a radical of the formula: —N($C_{1-8}$alkyl) (heterocyclyl).

As used herein, the term "heterocyclyl-amino-$C_{1-8}$alkyl" refers to a radical of the formula: —$C_{1-8}$alkyl-NH-heterocyclyl.

As used herein, the term "heterocyclyl-carbonyl" refers to a radical of the formula: —C(O)-heterocyclyl.

As used herein, the term "heterocyclyl-carbonyl-oxy" refers to a radical of the formula: —O—C(O)-heterocyclyl.

As used herein, the term "heterocyclyl-oxy" refers to a radical of the formula: —O-heterocyclyl.

As used herein, the term "hydroxy" refers to a radical of the formula: —OH.

As used herein, the term "hydroxy-$C_{1-8}$alkoxy-$C_{1-8}$alkyl" refers to a radical of the formula: —$C_{1-8}$alkyl-O—$C_{1-8}$alkyl-OH.

As used herein, the term "hydroxy-$C_{1-8}$alkyl" refers to a radical of the formula: —$C_{1-8}$alkyl-OH, wherein $C_{1-8}$alkyl is partially or completely substituted with one or more hydroxy radicals where allowed by available valences.

As used herein, the term "hydroxy-$C_{1-8}$alkyl-amino" refers to a radical of the formula: —NH—$C_{1-8}$alkyl-OH.

As used herein, the term "(hydroxy-$C_{1-8}$alkyl)$_2$-amino" refers to a radical of the formula: —N($C_{1-8}$alkyl-OH)$_2$.

As used herein, the term "(hydroxy-$C_{1-8}$alkyl)($C_{1-8}$alkyl) amino" refers to a radical of the formula: —N($C_{1-8}$alkyl) ($C_{1-8}$alkyl-OH).

As used herein, the term "hydroxy-$C_{1-8}$alkyl-amino-$C_{1-8}$alkyl" refers to a radical of the formula: —$C_{1-8}$alkyl-NH—$C_{1-8}$alkyl-OH.

As used herein, the term "(hydroxy-$C_{1-8}$alkyl)$_2$-amino-$C_{1-8}$alkyl" refers to a radical of the formula: —$C_{1-8}$alkyl-N ($C_{1-8}$alkyl-OH)$_2$.

As used herein, the term "(hydroxy-$C_{1-8}$alkyl) ($C_{1-8}$alkyl)amino-$C_{1-8}$alkyl" refers to a radical of the formula: —$C_{1-8}$alkyl-N($C_{1-8}$alkyl)($C_{1-8}$alkyl-OH).

As used herein, the term "hydroxy-$C_{1-8}$alkyl-amino-$C_{1-8}$alkoxy" refers to a radical of the formula: —O—$C_{1-8}$alkyl-NH—$C_{1-8}$alkyl-OH.

As used herein, the term "(hydroxy-$C_{1-8}$alkyl)$_2$-amino-$C_{1-8}$alkoxy" refers to a radical of the formula: —$C_{1-8}$alkyl-N($C_{1-8}$alkyl-OH)$_2$.

As used herein, the term "(hydroxy-$C_{1-8}$alkyl)($C_{1-8}$alkyl) amino-$C_{1-8}$alkoxy" refers to a radical of the formula: —O—$C_{1-8}$alkyl-N($C_{1-8}$alkyl)($C_{1-8}$alkyl-OH).

As used herein, the term "hydroxy-$C_{1-8}$alkyl-amino-$C_{1-8}$alkyl-amino" refers to a radical of the formula: —NH—$C_{1-8}$alkyl-NH—$C_{1-8}$alkyl-OH.

As used herein, the term "(hydroxy-$C_{1-8}$alkyl-amino-$C_{1-8}$alkyl)$_2$-amino" refers to a radical of the formula: —N($C_{1-8}$alkyl-NH—$C_{1-8}$alkyl-OH)$_2$.

As used herein, the term "(hydroxy-$C_{1-8}$alkyl)$_2$-amino-$C_{1-8}$alkyl-amino" refers to a radical of the formula: —NH—$C_{1-8}$alkyl-N($C_{1-8}$alkyl-OH)$_2$.

As used herein, the term "(hydroxy-$C_{1-8}$alkyl-amino-$C_{1-8}$alkyl)($C_{1-8}$alkyl)amino" refers to a radical of the formula: —N($C_{1-8}$alkyl)($C_{1-8}$alkyl-NH—$C_{1-8}$alkyl-OH).

As used herein, the term "[(hydroxy-$C_{1-8}$alkyl)$_2$-amino-$C_{1-8}$alkyl]($C_{1-8}$alkyl)amino" refers to a radical of the formula: —N($C_{1-8}$alkyl)[$C_{1-8}$alkyl-N($C_{1-8}$alkyl-OH)$_2$].

As used herein, the term "(hydroxy-$C_{1-8}$alkyl)($C_{1-8}$alkyl) amino-$C_{1-8}$alkyl-amino" refers to a radical of the formula: —NH—$C_{1-8}$alkyl-N($C_{1-8}$alkyl, $C_{1-8}$alkyl-OH).

As used herein, the term "[(hydroxy-$C_{1-8}$alkyl)($C_{1-8}$alkyl) amino-$C_{1-8}$alkyl]($C_{1-8}$alkyl)amino" refers to a radical of the formula: —N($C_{1-8}$alkyl)[$C_{1-8}$alkyl —N($C_{1-8}$alkyl)($C_{1-8}$alkyl —OH)].

As used herein, the term "substituent" means positional variables on the atoms of a core molecule that are attached at a designated atom position, replacing one or more hydrogen atoms on the designated atom, provided that the atom of attachment does not exceed the available valence or shared valences, such that the substitution results in a stable compound. Accordingly, combinations of substituents and/or variables are permissible only if such combinations result in stable compounds. It should also be noted that any carbon as well as heteroatom with a valence level that appears to be unsatisfied as described or shown herein is assumed to have a sufficient number of hydrogen atom(s) to satisfy the valences described or shown.

For the purposes of this description, where one or more substituent variables for a compound of Formula (I) encompass functionalities incorporated into a compound of Formula (I), each functionality appearing at any location within the disclosed compound may be independently selected, and as appropriate, independently and/or optionally substituted.

As used herein, the terms "independently selected," or "each selected" refer to functional variables in a substituent list that may be attached more than once on the structure of a core molecule, where the pattern of substitution at each occurrence is independent of the pattern at any other occurrence. Further, the use of a generic substituent on a core structure for a compound provided herein is understood to include the replacement of the generic substituent with specie substituents that are included within the particular genus, e.g., aryl may be independently replaced with phenyl or naphthalenyl (also referred to as naphthyl) and the like, such that the resulting compound is intended to be included within the scope of the compounds described herein.

As used herein, the term "each instance of" when used in a phrase such as" . . . aryl, aryl-$C_{1-8}$alkyl, heterocyclyl and heterocyclyl-$C_{1-8}$alkyl, wherein each instance of aryl and heterocyclyl is optionally substituted with one or two substituents . . . " is intended to include optional, independent substitution on each of the aryl and heterocyclyl rings and on the aryl and heterocyclyl portions of aryl-$C_{1-8}$alkyl and heterocyclyl-$C_{1-8}$alkyl.

As used herein, the term "optionally substituted" means that the specified substituent variables, groups, radicals or moieties represent the scope of the genus and may be independently chosen as needed to replace one or more hydrogen atoms on the designated atom of attachment of a core molecule.

As used herein, the terms "stable compound" or "stable structure" mean a compound that is sufficiently robust to be isolated to a useful degree of purity from a reaction mixture and formulations thereof into an efficacious therapeutic agent.

Compound names provided herein were obtained using ACD Labs Index Name software provided by ACD Labs and/or ChemDraw Ultra software provided by CambridgeSoft®. When the compound name disclosed herein conflicts with the structure depicted, the structure shown will supercede the use of the name to define the compound intended. Nomenclature for substituent radicals defined herein may differ slightly from the chemical name from which they are derived; one skilled in the art will recognize that the definition of the substituent radical is intended to include the radical as found in the chemical name.

As used herein the term "aberrant" refers to a deviation from the norm of, e.g., the average healthy subject or a cell(s) or tissue sample from a healthy subject. The term "aberrant expression," as used herein, refers to abnormal expression (up-regulated or down-regulated resulting in an excessive or deficient amount thereof) of a gene product (e.g., RNA transcript or protein) by a cell, tissue sample, or subject relative to a corresponding normal, healthy cell, tissue sample or subject. In a specific embodiment, the "aberrant expression" refers to an altered level of a gene product (e.g., RNA transcript or protein) in a cell, tissue sample, or subject relative to a corresponding normal, healthy cell, tissue sample or subject. The term "aberrant amount" as used herein refers to an altered level of a gene product (e.g., RNA, protein, polypeptide, or peptide) in a cell, tissue sample, or subject relative to a corresponding normal, healthy cell, tissue sample or subject. In specific embodiments, the amount of a gene product (e.g., RNA, protein, polypeptide, or peptide) in a cell, tissue sample, or subject relative to a corresponding cell or tissue sample from a healthy subject or a healthy subject, is considered aberrant if it is 1, 1.5, 2, 2.5, 3, 3.5, 4, 4.5, 5, 5.5, 6-fold or more above or below the amount of the gene product in the corresponding cell or tissue sample from a healthy subject or healthy subject.

As used herein, the phrase "non-endogenous REMS" refers to a REMS not naturally found to be part of an RNA sequence or naturally encoded by a DNA sequence. In other words, the hand of man is required to manipulate the RNA or DNA sequence to introduce the REMS or the nucleotide sequence encoding the REMS.

As used herein, the term "substantial change" in the context of the amount of one or more RNA transcripts (e.g., rRNA, tRNA, miRNA, siRNA, lncRNA, pre-mRNA or mRNA transcripts), an alternative splice variant thereof or an isoform thereof, or one or more proteins thereof, each expressed as the product of one or more of genes, means that the amount of such products changes by a statistically significant amount such as, in a nonlimiting example, a p value less than a value selected from 0.1, 0.01, 0.001, or 0.0001.

As used herein, the terms "subject" and "patient" are used interchangeably to refer to an animal or any living organism having sensation and the power of voluntary movement, and which requires for its existence oxygen and organic food. Non-limiting examples include members of the human, equine, porcine, bovine, rattus, murine, canine and feline species. In some embodiments, the subject is a mammal or a warm-blooded vertebrate animal. In certain embodiments, the subject is a non-human animal. In specific embodiments, the subject is a human.

As used herein, the term "functional protein" refers to a form of a protein that retains a certain biological function or the functions of a full length protein or protein isoform encoding by a gene.

As used herein, in the context of a functional protein produced from an artificial construct, the term "produce substantially less" means that the amount of functional protein in the absence of a compound described herein is at least 20%, 25%, 30%, 35%, 40%, 45%, 50%, 55%, 60%, 70%, 75%, 80%, 85%, 90%, 95%, 98%, or 100% less than the amount of functional protein produced in the presence of the compound.

Compound Forms

As used herein, the terms "a compound of Formula (Ia)," "a compound of Formula (Ia1)," "a compound of Formula (Ia2)," "a compound of Formula (Ia3)," "a compound of Formula (Ia4)," "a compound of Formula (II)," "a compound of Formula (IIa)," "a compound of Formula (IIa1)," "a compound of Formula (IIa2)," "a compound of Formula (IIa3)," "a compound of Formula (IIa4)," "a compound of Formula (III)," "a compound of Formula (IIIa)," "a compound of Formula (IIIa1)," "a compound of Formula (IIIa2)," "a compound of Formula (IIIa3)," "a compound of Formula (IIIa4)," "a compound of Formula (IV)," "a compound of Formula (IVa)," "a compound of Formula (IVa1)," "a compound of Formula (IVa2)," "a compound of Formula (V)," "a compound of Formula (Va)," "a compound of Formula (Val)," "a compound of Formula (Va2)," "a compound of Formula (VI)," "a compound of Formula (VIa)," "a compound of Formula (VIa1)," "a compound of Formula (VIa2)," "a compound of Formula (VIa3)," "a compound of Formula (VIa4)," "a compound of Formula (VII)," "a compound of Formula (VIIa)," "a compound of Formula (VIIa1)," "a compound of Formula (VIIa2)," "a compound of Formula (VIII)," "a compound of Formula (VIIIa)," "a compound of Formula (VIIIa1)," "a compound of Formula (VIIIa2)," "a compound of Formula (IX)," "a compound of Formula (IXa)," "a compound of Formula (IXa1)," "a compound of Formula (IXa2)," "a compound of Formula (IXa3)," "a compound of Formula (IXa4)," "a compound of Formula (X)," "a compound of Formula (Xa)," "a compound of Formula (Xa1)," "a compound of Formula (Xa2)," "a compound of Formula (XI)," "a compound of Formula (XIa)," "a compound of Formula (XIa1)," "a compound of Formula (XIa2)," "a compound of Formula (XII)," "a compound of Formula (XIIa)," "a compound of Formula (XIIa1)," "a compound of Formula (XIIa2)," "a compound of Formula (XIIa3)," "a compound of Formula (XIIa4)," "a compound of Formula (XIII)," "a compound of Formula (XIIIa)," "a compound of Formula (XIIIa1)," "a compound of Formula (XIIIa2)," "a compound of Formula (XIV)," "a compound of Formula (XIVa)," "a compound of Formula (XIVa1)," and "a compound of Formula (XIVa2)," each refer to subgenera of the compound of Formula (I) or a form thereof.

Rather than repeat embodiments for the various subgenera of the compound of Formula (I), in certain embodiments, the term "a compound of Formula (I) or a form thereof" is used to inclusively to refer to a compound of Formula (Ia) or a form thereof, a compound of Formula (Ia1) or a form thereof, a compound of Formula (Ia2) or a form thereof, a compound of Formula (Ia3) or a form thereof, a compound of Formula (Ia4) or a form thereof, a compound of Formula (II) or a form thereof, a compound of Formula (IIa) or a form thereof, a compound of Formula (IIa1) or a form thereof, a compound of Formula (IIa2) or a form thereof, a compound of Formula (IIa3) or a form thereof, a compound of Formula (IIa4) or a form thereof, a compound of Formula (III) or a form thereof, a compound of Formula (IIIa) or a form thereof, a compound of Formula (IIIa1) or a form thereof, a compound of Formula (IIIa2) or a form thereof, a compound of Formula (IIIa3) or a form thereof, a compound of Formula (IIIa4) or a form thereof, a compound of Formula (IV) or a form thereof, a compound of Formula (IVa) or a form thereof, a compound of Formula (IVa1) or a form thereof, a compound of Formula (IVa2) or a form thereof, a compound of Formula (V) or a form thereof, a compound of Formula (Va) or a form thereof, a compound of Formula (Va1) or a form thereof, a compound of Formula (Va2) or a form thereof, a compound of Formula (VI) or a form thereof, a compound of Formula (VIa) or a form thereof, a compound of Formula (VIa1) or a form thereof, a compound of Formula (VIa2) or a form thereof, a compound of Formula (VIa3) or a form thereof, a compound of Formula (VIa4) or a form thereof, a compound of Formula (VII) or a form thereof, a compound of Formula (VIIa) or a form thereof, a compound of Formula (VIIa1) or a form thereof, a compound of Formula (VIIa2) or a form thereof, a compound of Formula (VIII) or a form thereof, a compound of Formula (VIIIa) or a form thereof, a compound of Formula (VIIIa1) or a form thereof, a compound of Formula (VIIIa2) or a form thereof, a compound of Formula (IX) or a form thereof, a compound of Formula (IXa) or a form thereof, a compound of Formula (IXa1) or a form thereof, a compound of Formula (IXa2) or a form thereof, a compound of Formula (IXa3) or a form thereof, a compound of Formula (IXa4) or a form thereof, a compound of Formula (X) or a form thereof, a compound of Formula (Xa) or a form thereof, a compound of Formula (Xa1) or a form thereof, a compound of Formula (Xa2) or a form thereof, a compound of Formula (XI) or a form thereof, a compound of Formula (XIa) or a form thereof, a compound of Formula (XIa1) or a form thereof, a compound of Formula (XIa2) or a form thereof, a compound of Formula (XII) or a form thereof, a compound of Formula (XIIa) or a form thereof, a compound of Formula (XIIa1) or a form thereof, a compound of Formula (XIIa2) or a form thereof, a compound of Formula (XIIa3) or a form thereof, a compound of Formula (XIIa4) or a form thereof, a compound of Formula (XIII) or a form thereof, a compound of Formula (XIIIa) or a form thereof, a compound of Formula (XIIIa1) or a form thereof, a compound of Formula (XIIIa2) or a form thereof, a compound of Formula (XIV) or a form thereof, a compound of Formula (XIVa) or a form thereof, a compound of Formula (XIVa1) or a form thereof or a compound of Formula (XIVa2) or a form thereof, either separately or together.

Thus, embodiments and references to "a compound of Formula (I)" are intended to be inclusive of compounds of Formula (Ia), Formula (Ia1), Formula (Ia2), Formula (Ia3), Formula (Ia4), Formula (II), Formula (IIa), Formula (IIa1), Formula (IIa2), Formula (IIa3), Formula (IIa4), Formula (III), Formula (IIIa), Formula (IIIa1), Formula (IIIa2), Formula (IIIa3), Formula (IIIa4), Formula (IV), Formula (IVa), Formula (IVa1), Formula (IVa2), Formula (V), Formula (Va), Formula (Va1), Formula (Va2), Formula (VI), Formula (VIa), Formula (VIa1), Formula (VIa2), Formula (VIa3), Formula (VIa4), Formula (VII), Formula (VIIa), Formula (VIIa1), Formula (VIIa2), Formula (VIII), Formula (VIIIa), Formula (VIIIa1), Formula (VIIIa2), Formula (IX), Formula (IXa), Formula (IXa1), Formula (IXa2), Formula (IXa3), Formula (IXa4), Formula (X), Formula (Xa), Formula (Xa1), Formula (Xa2), Formula (XI), Formula (XIa), Formula (XIa1), Formula (XIa2), Formula (XII), Formula (XIIa), Formula (XIIa1), Formula (XIIa2), Formula (XIIa3), Formula (XIIa4), Formula (XIII), Formula (XIIIa), Formula (XIIIa1), Formula (XIIIa2), Formula (XIV), Formula (XIVa), Formula (XIVa1) and Formula (XIVa2).

As used herein, the term "form" means a compound of Formula (I) selected from a free acid, free base, salt, isotopologue, stereoisomer, racemate, enantiomer, diastereomer, or tautomer thereof.

In certain embodiments described herein, the form of the compound of Formula (I) is a selected from a salt, isotopologue, stereoisomer, racemate, enantiomer, diastereomer or tautomer thereof.

In certain embodiments described herein, the form of the compound of Formula (I) is a selected from a free acid, isotopologue, stereoisomer, racemate, enantiomer, diastereomer or tautomer thereof.

In certain embodiments described herein, the form of the compound of Formula (I) is a selected from a free base, isotopologue, stereoisomer, racemate, enantiomer, diastereomer or tautomer thereof.

In certain embodiments described herein, the form of the compound of Formula (I) is a free acid, free base or salt thereof.

In certain embodiments described herein, the form of the compound of Formula (I) is an isotopologue thereof.

In certain embodiments described herein, the form of the compound of Formula (I) is a stereoisomer, racemate, enantiomer or diastereomer thereof.

In certain embodiments described herein, the form of the compound of Formula (I) is a tautomer thereof.

In certain embodiments described herein, the form of the compound of Formula (I) is a pharmaceutically acceptable form.

In certain embodiments described herein, the compound of Formula (I) or a form thereof is isolated for use.

As used herein, the term "isolated" means the physical state of a compound of Formula (I) or a form thereof after being isolated and/or purified from a synthetic process (e.g., from a reaction mixture) or natural source or combination thereof according to an isolation or purification process or processes described herein or which are well known to the skilled artisan (e.g., chromatography, recrystallization and the like) in sufficient purity to be characterizable by standard analytical techniques described herein or well known to the skilled artisan.

As used herein, the term "protected" means that a functional group on a compound of Formula (I) is in a form modified to preclude undesired side reactions at the protected site when the compound is subjected to a reaction. Suitable protecting groups will be recognized by those with ordinary skill in the art as well as by reference to standard textbooks such as, for example, T. W. Greene et al, Protective Groups in Organic Synthesis (1991), Wiley, New York.

Prodrugs of a compound of Formula (I) or a form thereof are also contemplated herein.

As used herein, the term "prodrug" means that a functional group on a compound of Formula (I) is in a form (e.g., acting as an active or inactive drug precursor) that is transformed in vivo to yield an active or more active compound of Formula (I) or a form thereof. The transformation may occur by various mechanisms (e.g., by metabolic and/or non-metabolic chemical processes), such as, for example, by hydrolysis and/or metabolism in blood, liver and/or other organs and tissues. A discussion of the use of prodrugs is provided by V. J. Stella, et. al., "Biotechnology: Pharmaceutical Aspects, Prodrugs: Challenges and Rewards," American Association of Pharmaceutical Scientists and Springer Press, 2007.

In one example, when a compound of Formula (I) or a form thereof contains a carboxylic acid functional group, a prodrug can comprise an ester formed by the replacement of the hydrogen atom of the acid group with a functional group such as alkyl and the like. In another example, when a compound of Formula (I) or a form thereof contains an alcohol functional group, a prodrug can be formed by the replacement of the hydrogen atom of the alcohol group with a functional group such as alkyl or substituted carbonyl and the like. In another example, when a compound of Formula (I) or a form thereof contains an amine functional group, a prodrug can be formed by the replacement of one or more amine hydrogen atoms with a functional group such as alkyl or substituted carbonyl. In another example, when a compound of Formula (I) or a form thereof contains a hydrogen substituent, a prodrug can be formed by the replacement of one or more hydrogen atoms with an alkyl substituent.

Pharmaceutically acceptable prodrugs of compounds of Formula (I) or a form thereof include those compounds substituted with one or more of the following groups: carboxylic acid esters, sulfonate esters, amino acid esters phosphonate esters, mono-, di- or triphosphate esters or alkyl substituents where appropriate. As described herein, it is understood by a person of ordinary skill in the art that one or more of such substituents may be used to provide a compound of Formula (I) or a form thereof for use as a prodrug.

The compounds of Formula (I) can form salts which are intended to be included within the scope of this description. Reference to a compound of Formula (I) herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of Formula (I) contains both a basic moiety, such as, but not limited to a pyridine or imidazole, and an acidic moiety, such as, but not limited to a carboxylic acid, zwitterions ("inner salts") may be formed and are included within the term "salt(s)" as used herein.

The term "pharmaceutically acceptable salt(s)", as used herein, means those salts of compounds described herein that are safe and effective (i.e., non-toxic, physiologically acceptable) for use in mammals and that possess biological activity, although other salts are also useful. Salts of the compounds of Formula (I) may be formed, for example, by reacting a compound of Formula (I) with an amount of acid or base, such as an equivalent or stoichiometric amount, in a medium such as one in which the salt precipitates or in an aqueous medium followed by lyophilization.

Pharmaceutically acceptable salts include one or more salts of acidic or basic groups present in compounds described herein. Embodiments of acid addition salts include, and are not limited to, acetate, acid phosphate, ascorbate, benzoate, benzenesulfonate, bisulfate, bitartrate, borate, butyrate, chloride, citrate, camphorate, camphorsulfonate, ethanesulfonate, formate, fumarate, gentisinate, gluconate, glucaronate, glutamate, hydrobromide, hydrochloride, dihydrochloride, hydroiodide, isonicotinate, lactate, maleate, methanesulfonate, naphthalenesulfonate, nitrate, oxalate, pamoate, pantothenate, phosphate, propionate, saccharate, salicylate, succinate, sulfate, tartrate, thiocyanate, toluenesulfonate (also known as tosylate), trifluoroacetate salts and the like. One or more embodiments of acid addition salts include a chloride, hydrochloride, dihydrochloride, trihydrochloride, hydrobromide, acetate, diacetate or trifluoroacetate salt. More particular embodiments include a chloride, hydrochloride, dihydrochloride, hydrobromide or trifluoroacetate salt.

Additionally, acids which are generally considered suitable for the formation of pharmaceutically useful salts from basic pharmaceutical compounds are discussed, for example, by P. Stahl et al, Camille G. (eds.) Handbook of Pharmaceutical Salts. Properties, Selection and Use. (2002) Zurich: Wiley-VCH; S. Berge et al, Journal of Pharmaceutical Sciences (1977) 66(1) 1-19; P. Gould, International J. of Pharmaceutics (1986) 33, 201-217; Anderson et al, The Practice of Medicinal Chemistry (1996), Academic Press, New York; and in The Orange Book (see, website for Food & Drug Administration, Washington, D.C.). These disclosures are incorporated herein by reference thereto.

Suitable basic salts include, but are not limited to, aluminum, ammonium, calcium, lithium, magnesium, potassium, sodium, zinc, and diethanolamine salts. Certain compounds described herein can also form pharmaceutically acceptable salts with organic bases (for example, organic amines) such as, but not limited to, dicyclohexylamines, tert-butyl amines and the like, and with various amino acids such as, but not limited to, arginine, lysine and the like. Basic nitrogen-containing groups may be quarternized with agents such as lower alkyl halides (e.g., methyl, ethyl, and butyl chlorides, bromides and iodides), dialkyl sulfates (e.g., dimethyl, diethyl, and dibutyl sulfates), long chain halides (e.g., decyl, lauryl, and stearyl chlorides, bromides and iodides), aralkyl halides (e.g., benzyl and phenethyl bromides), and others.

All such acid salts and base salts are intended to be pharmaceutically acceptable salts within the scope of the description herein and all such acid and base salts are considered equivalent to the free forms of the corresponding compounds for the purposes described herein.

Compounds of Formula I and forms thereof may further exist in a tautomeric form. All such tautomeric forms are contemplated herein as part of the present description.

The compounds of Formula (I) may contain asymmetric or chiral centers, and, therefore, may exist in different stereoisomeric forms. The present description is intended to include all stereoisomeric forms of the compounds of Formula (I) as well as mixtures thereof, including racemic mixtures.

The compounds of Formula (I) described herein may include one or more chiral centers, and as such may exist as racemic mixtures (R/S) or as substantially pure enantiomers and diastereomers. The compounds may also exist as substantially pure (R) or (S) enantiomers (when one chiral center is present). In one embodiment, the compounds of Formula (I) described herein are (S) isomers and may exist as enantiomerically pure compositions substantially comprising only the (S) isomer. In another embodiment, the compounds of Formula (I) described herein are (R) isomers and may exist as enantiomerically pure compositions substantially comprising only the (R) isomer. As one of skill in the art will recognize, when more than one chiral center is present, the compounds of Formula (I) described herein may also include portions described as an (R,R), (R,S), (S,R) or (S,S) isomer, as defined by IUPAC Nomenclature Recommendations.

As used herein, the term "substantially pure" refers to compounds consisting substantially of a single isomer in an amount greater than or equal to 90%, in an amount greater than or equal to 92%, in an amount greater than or equal to 95%, in an amount greater than or equal to 98%, in an amount greater than or equal to 99%, or in an amount equal to 100% of the single isomer.

In one aspect, a compound of Formula (I) is a substantially pure (S) enantiomer present in an amount greater than or equal to 90%, in an amount greater than or equal to 92%, in an amount greater than or equal to 95%, in an amount greater than or equal to 98%, in an amount greater than or equal to 99%, or in an amount equal to 100%.

In one aspect, a compound of Formula (I) is a substantially pure (R) enantiomer present in an amount greater than or equal to 90%, in an amount greater than or equal to 92%, in an amount greater than or equal to 95%, in an amount greater than or equal to 98%, in an amount greater than or equal to 99%, or in an amount equal to 100%.

As used herein, a "racemate" is any mixture of isometric forms that are not "enantiomerically pure", including mixtures such as, without limitation, in a ratio of about 50/50, about 60/40, about 70/30, about 80/20, about 85/15 or about 90/10.

In addition, the present description embraces all geometric and positional isomers. For example, if a compound of Formula (I) incorporates a double bond or a fused ring, both the cis- and trans-forms, as well as mixtures, are embraced within the scope of the description herein.

Diastereomeric mixtures can be separated into their individual diastereomers on the basis of their physical chemical differences by methods well known to those skilled in the art, such as, for example, by chromatography and/or fractional crystallization. Enantiomers can be separated by use of chiral HPLC column or other chromatographic methods known to those skilled in the art.

Enantiomers can also be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of Formula (I) may be atropisomers (e.g., substituted biaryls) and are considered part of this description.

All stereoisomer forms (for example, geometric isomers, optical isomers, positional isomers and the like) of the present compounds (including salts, solvates, esters and prodrugs and transformed prodrugs thereof) which may exist due to asymmetric carbons on various substituents, including enantiomeric forms (which may exist even in the absence of asymmetric carbons), rotameric forms, atropisomers, diastereomeric forms and regioisomeric forms are contemplated within the scope of the description herein. For example, if a compound of Formula (I) incorporates a double bond or a fused ring, both the cis- and trans-forms, as well as mixtures thereof, are embraced within the scope of the description herein. Also, for example, all keto-enol and imine-enamine tautomeric forms of the compounds are included in the description herein. Individual stereoisomers of the compounds of Formula (I) described herein may, for example, be substantially free of other isomers, or may be present in a racemic mixture, as described supra.

The use of the terms "salt," "prodrug" and "transformed prodrug" are intended to equally apply to the salts, prodrugs and transformed prodrugs of all contemplated isotopologues, stereoisomers, racemates or tautomers of the instant compounds.

The term "isotopologue" refers to isotopically-enriched compounds which are identical to those recited herein, but for the fact that one or more atoms are replaced by an atom having an atomic mass or mass number different from the atomic mass or mass number usually found in nature. Examples of isotopes that can be incorporated into compounds described herein include isotopes of hydrogen, carbon, nitrogen, oxygen, phosphorus, fluorine and chlorine, such as $H^2$, $H^3$, $C^{13}$, $C^{14}$, $N^{15}$, $O^{18}$, $O^{17}$, $P^{31}$, $P^{32}$, $S^{35}$, $F^{18}$, $Cl^{35}$ and $Cl^{36}$, respectively, each of which is also within the scope of this description.

Certain isotopically-enriched compounds described herein (e.g., those labeled with $H^3$ and $C^{14}$) are useful in compound and/or substrate tissue distribution assays. Tritiated (i.e., $H^3$) and carbon-14 (i.e., $C^{14}$) isotopes are particularly preferred for their ease of preparation and detectability. Further, substitution with heavier isotopes such as deuterium (i.e., "deuterium enriched") may afford certain therapeutic advantages resulting from greater metabolic stability (e.g., increased in vivo half-life or reduced dosage requirements) and hence may be preferred in some circumstances. Isotopically-enriched compounds of Formula (I) can generally be prepared using procedures known to persons of ordinary skill in the art by substituting an appropriate isotopically-enriched reagent for a non-isotopically-enriched reagent.

When the compounds are enriched with deuterium, the deuterium-to-hydrogen ratio on the deuterated atoms of the molecule substantially exceeds the naturally occurring deuterium-to-hydrogen ratio.

An embodiment described herein may include an isotopologue form of the compound of Formula (I), wherein the isotopologue is substituted on one or more atom members of the compound of Formula (I) with one or more deuterium atoms in place of one or more hydrogen atoms.

An embodiment described herein may include a compound of Formula (I) and forms thereof, wherein a carbon atom may have from 1 to 3 hydrogen atoms optionally replaced with deuterium.

One or more compounds described herein may exist in unsolvated as well as solvated forms with pharmaceutically acceptable solvents such as water, ethanol, and the like, and the description herein is intended to embrace both solvated and unsolvated forms.

As used herein, the term "solvate" means a physical association of a compound described herein with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. As used herein, "solvate" encompasses both solution-phase and isolatable solvates. Non-limiting examples of suitable solvates include ethanolates, methanolates, and the like.

One or more compounds described herein may optionally be converted to a solvate. Preparation of solvates is generally known. A typical, non-limiting process involves dissolving a compound in a desired amount of the desired solvent (organic or water or mixtures thereof) at a higher than ambient temperature, and cooling the solution at a rate sufficient to form crystals which are then isolated by standard methods. Analytical techniques such as, for example infrared spectroscopy, show the presence of the solvent (or water) in the crystals as a solvate (or hydrate).

As used herein, the term "hydrate" means a solvate wherein the solvent molecule is water.

Polymorphic crystalline and amorphous forms of the compounds of Formula (I), and of the salts, solvates, esters and prodrugs of the compounds of Formula (I), are further intended to be included in the scope of the compounds described herein Methods for Determining which Genes May be Modulated by the Compounds In another aspect, provided herein are methods for determining whether the splicing of the precursor RNA of a gene is likely to be modulated by a compound of Formula (I) or a form thereof, comprising searching for the presence of a REMS in the gene sequence, wherein the presence of a REMS upstream of a 3' splice site and a branch point in the gene sequence indicates that the splicing of the precursor RNA of the gene is likely to be modulated by the compound of Formula (I) or a form thereof, and the absence of a REMS upstream of a 3' splice site and a branch point in the gene sequence indicates that the splicing of the precursor RNA of the gene is unlikely to be modulated by the compound of Formula (I) or a form thereof. In certain embodiments, a compound of Formula (I) is a compound of Formula (II), Formula (III), Formula (IV), Formula (V), Formula (VI), Formula (VII), Formula (VIII), Formula (IX), Formula (X), Formula (XI), Formula (XII), Formula (XIII), or Formula (XIV) described herein. In specific embodiments, the methods further comprise searching for the presence of a 3' splice site and/or a branch point in the gene sequence downstream of the REMS.

In another aspect, provided herein are methods for determining whether the amount of a product (e.g., an mRNA transcript or protein) of a gene is likely to be modulated by a compound of Formula (I) or a form thereof, comprising searching for the presence of a REMS in the gene sequence, wherein the presence of a REMS upstream of a 3' splice site and a branch point in the gene sequence indicates that the amount of a product (e.g., an mRNA transcript or protein) of the gene is likely to be modulated by the compound of Formula (I) or a form thereof, and the absence of a REMS upstream of a 3' splice site and a branch point in the gene sequence indicates that the amount of a product (e.g., an mRNA transcript or protein) of the gene is unlikely to be modulated by the compound of Formula (I) or a form thereof. In certain embodiments, a compound of Formula (I) is a compound of Formula (II), Formula (III), Formula (IV), Formula (V), Formula (VI), Formula (VII), Formula (VIII), Formula (IX), Formula (X), Formula (XI), Formula (XII), Formula (XIII), or Formula (XIV) described herein. In specific embodiments, the methods further comprise searching for the presence of a 3' splice site and/or a branch point in the gene sequence downstream of the REMS.

The step of searching for the presence of a REMS, a 3' splice site, and/or a branch point in the gene sequence described herein can be performed by a computer system comprising a memory storing instructions for searching the presence of the REMS, the 3' splice site, and/or the branch point in the gene sequence, or can be performed manually.

In certain embodiments, the splicing of a precursor RNA containing a REMS is assessed by contacting a compound described herein with the precursor RNA in cell cultured in tissue culture. In some embodiments, the splicing of a precursor RNA containing a REMS is assessed by contacting a compound described herein with the precursor RNA in a cell-free extract. In a specific embodiment, the compound is one known to modulate the splicing of a precursor RNA containing a REMS. See, e.g., the section below relating to methods for determining whether a compound modulates the expression of certain genes, and the example below for techniques that could be used in these assessments.

Methods for Determining which Compounds of Formula (I) Modulate the Expression of Certain Genes Provided herein are methods for determining whether a compound of Formula (I) or a form thereof modulates the amount of one, two, three or more RNA transcripts (e.g., pre-mRNA or mRNA transcripts or isoforms thereof) of one, two, three or more genes. In some embodiments, the gene is any one of the genes disclosed in Tables 1-4 or any one of the genes disclosed in Table 6. In certain embodiments, the gene is not a gene disclosed in Tables 1-4. In some embodiments, the gene is not a gene disclosed in Table 6. In other embodiments, the gene is a gene disclosed in Table 6. In a specific embodiment, the gene is ERGIC3.

In one embodiment, provided herein is a method for determining whether a compound of Formula (I) or a form thereof modulates the amount of an RNA transcript, comprising: (a) contacting a cell(s) with a compound of Formula (I) or a form thereof, and (b) determining the amount of the RNA transcript produced by the cell(s), wherein an alteration in the amount of the RNA transcript in the presence of the compound relative to the amount of the RNA transcript in the absence of the compound or the presence of a negative control (e.g., a vehicle control such as PBS or DMSO) indicates that the compound of Formula (I) or a form thereof modulates the amount of the RNA transcript. In another embodiment, provided herein is a method for determining whether a compound of Formula (I) or a form thereof modulates the amount of an RNA transcript (e.g., an mRNA transcript), comprising: (a) contacting a first cell(s) with a compound of Formula (I) or a form thereof, (b) contacting a second cell(s) with a negative control (e.g., a vehicle control, such as PBS or DMSO); and (c) determining the amount of the RNA transcript produced by the first cell(s) and the second cell(s); and (d) comparing the amount of the RNA transcript produced by the first cell(s) to the amount of the RNA transcript expressed by the second cell(s), wherein an alteration in the amount of the RNA transcript produced by the first cell(s) relative to the amount of the RNA transcript produced by the second cell(s) indicates that the compound of Formula (I) or a form thereof modulates the amount of the RNA transcript. In certain embodiments, the contacting of the cell(s) with the compound occurs in cell culture. In other embodiments, the contacting of the cell(s) with the compound occurs in a subject, such as a non-human animal subject.

In another embodiment, provided herein is a method for determining whether a compound of Formula (I) or a form thereof modulates the splicing of an RNA transcript (e.g., an mRNA transcript), comprising: (a) culturing a cell(s) in the presence of a compound of Formula (I) or a form thereof; and (b) determining the amount of the two or more RNA transcript splice variants produced by the cell(s), wherein an alteration in the amount of the two or more RNA transcript in the presence of the compound relative to the amount of the two or more RNA transcript splice variants in the absence of the compound or the presence of a negative control (e.g., a vehicle control such as PBS or DMSO) indicates that the compound of Formula (I) or a form thereof modulates the splicing of the RNA transcript.

In another embodiment, provided herein is a method for determining whether a compound of Formula (I) or a form thereof modulates the splicing of an RNA transcript (e.g., an mRNA transcript), comprising: (a) culturing a cell(s) in the presence of a compound of Formula (I) or a form thereof; (b) isolating two or more RNA transcript splice variants from the cell(s) after a certain period of time; and (c) determining the amount of the two or more RNA transcript splice variants produced by the cell(s), wherein an alteration in the amount of the two or more RNA transcript in the presence of the compound relative to the amount of the two or more RNA transcript splice variants in the absence of the compound or the presence of a negative control (e.g., a vehicle control such as PBS or DMSO) indicates that the compound of Formula (I) or a form thereof modulates the splicing of the RNA transcript. In another embodiment, provided herein is a method for determining whether a compound of Formula (I) or a form thereof modulates the splicing of an RNA transcript (e.g., an mRNA transcript), comprising (a) culturing a first cell(s) in the presence of a compound of Formula (I) or a form thereof, (b) culturing a second cell(s) in the presence of a negative control (e.g., a vehicle control, such as PBS or DMSO); (c) isolating two or more RNA transcript splice variants produced by the first cell(s) and isolating two or more RNA transcript splice variants produced by the second cell(s); (d) determining the amount of the two or more RNA transcript splice variants produced by the first cell(s) and the second cell(s); and (e) comparing the amount of the two or more RNA transcript splice variants produced by the first cell(s) to the amount of the two or more RNA transcript splice variants produced by the second cell(s), wherein an alteration in the amount of the two or more RNA transcript splice variants produced by the first cell(s) relative to the amount of the two or more RNA transcript splice variants produced by the second cell(s) indicates that the compound of Formula (I) or a form thereof modulates the splicing of the RNA transcript.

In another embodiment, provided herein is a method for determining whether a compound of Formula (I) or a form thereof modulates the amount of an RNA transcript (e.g., an mRNA transcript), comprising: (a) contacting a cell-free system with a compound of Formula (I) or a form thereof, and (b) determining the amount of the RNA transcript produced by the cell-free system, wherein an alteration in the amount of the RNA transcript in the presence of the compound relative to the amount of the RNA transcript in the absence of the compound or the presence of a negative control (e.g., a vehicle control such as PBS or DMSO) indicates that the compound of Formula (I) or a form thereof modulates the amount of the RNA transcript. In another embodiment, provided herein is a method for determining whether a compound of Formula (I) or a form thereof modulates the amount of an RNA transcript (e.g., an mRNA transcript), comprising: (a) contacting a first cell-free system with a compound of Formula (I) or a form thereof, (b) contacting a second cell-free system with a negative control (e.g., a vehicle control, such as PBS or DMSO); and (c) determining the amount of the RNA transcript produced by the first cell-free system and the second cell-free system; and (d) comparing the amount of the RNA transcript produced by the first cell-free system to the amount of the RNA transcript expressed by the second cell-free system, wherein an alteration in the amount of the RNA transcript produced by the first cell-free system relative to the amount of the RNA transcript produced by the second cell-free system indicates that the compound of Formula (I) or a form thereof modulates the amount of the RNA transcript. In certain embodiments, the cell-free system comprises purely synthetic RNA, synthetic or recombinant (purified) enzymes, and protein factors. In other embodiments, the cell-free system comprises RNA transcribed from a synthetic DNA template, synthetic or recombinant (purified) enzymes, and protein factors. In other embodiments, the cell-free system comprises purely synthetic RNA and nuclear extract. In other embodiments, the cell-free system comprises RNA transcribed from a synthetic DNA template and nuclear extract. In other embodiments, the cell-free system comprises purely synthetic RNA and whole cell extract. In other embodiments, the cell-free system comprises RNA transcribed from a synthetic DNA template and whole cell extract. In certain embodiments, the cell-free system additionally comprises regulatory RNAs (e.g., microRNAs).

In another embodiment, provided herein is a method for determining whether a compound of Formula (I) or a form thereof modulates the splicing of an RNA transcript (e.g., an mRNA transcript), comprising: (a) contacting a cell-free system with a compound of Formula (I) or a form thereof, and (b) determining the amount of two or more RNA transcript splice variants produced by the cell-free system, wherein an alteration in the amount of the two or more RNA transcript splice variants in the presence of the compound relative to the amount of the two or more RNA transcript splice variants in the absence of the compound or the presence of a negative control (e.g., a vehicle control such as PBS or DMSO) indicates that the compound of Formula (I) or a form thereof modulates the splicing of the RNA transcript. In another embodiment, provided herein is a method for determining whether a compound of Formula (I) or a form thereof modulates the splicing of an RNA transcript (e.g., an mRNA transcript), comprising: (a) contacting a first cell-free system with a compound of Formula (I) or a form thereof, (b) contacting a second cell-free system with a negative control (e.g., a vehicle control, such as PBS or DMSO); and (c) determining the amount of two or more RNA transcript splice variants produced by the first cell-free system and the second cell-free system; and (d) comparing the amount of the two or more RNA transcript splice variants produced by the first cell-free system to the amount of the RNA transcript expressed by the second cell-free system, wherein an alteration in the amount of the two or more RNA transcript splice variants produced by the first cell-free system relative to the amount of the two or more RNA transcript splice variants produced by the second cell-free system indicates that the compound of Formula (I) or a form thereof modulates the splicing of the RNA transcript. In certain embodiments, the cell-free system comprises purely synthetic RNA, synthetic or recombinant (purified) enzymes, and protein factors. In other embodiments, the cell-free system comprises RNA transcribed from a synthetic DNA template, synthetic or recombinant (purified) enzymes, and protein factors. In other embodiments, the cell-free system comprises purely synthetic RNA and nuclear extract. In other embodiments, the cell-free system comprises RNA transcribed from a synthetic DNA template and nuclear extract. In other embodiments, the cell-free system comprises purely synthetic RNA and whole cell extract. In other embodiments, the cell-free system comprises RNA transcribed from a synthetic DNA template and whole cell extract. In certain embodiments, the cell-free system additionally comprises regulatory RNAs (e.g., microRNAs).

In another embodiment, provided herein is a method for determining whether a compound of Formula (I) or a form thereof modulates the amount of an RNA transcript (e.g., an mRNA transcript), comprising: (a) culturing a cell(s) in the presence of a compound of Formula (I) or a form thereof, (b) isolating the RNA transcript from the cell(s) after a certain period of time; and (c) determining the amount of the RNA transcript produced by the cell(s), wherein an alteration in the amount of the RNA transcript in the presence of the compound relative to the amount of the RNA transcript in the absence of the compound or the presence of a negative control (e.g., a vehicle control such as PBS or DMSO) indicates that the compound of Formula (I) or a form thereof modulates the amount of the RNA transcript. In another embodiment, provided herein is a method for determining whether a compound of Formula (I) or a form thereof modulates the amount of an RNA transcript (e.g., an mRNA transcript), comprising (a) culturing a first cell(s) in the presence of a compound of Formula (I) or a form thereof, (b) culturing a second cell(s) in the presence of a negative control (e.g., a vehicle control, such as PBS or DMSO); (c) isolating the RNA transcript produced by the first cell(s) and isolating the RNA transcript produced by the second cell(s); (d) determining the amount of the RNA transcript produced by the first cell(s) and the second cell(s); and (e) comparing the amount of the RNA transcript produced by the first cell(s) to the amount of the RNA transcript produced by the second cell(s), wherein an alteration in the amount of the RNA transcript produced by the first cell(s) relative to the amount of the RNA transcript produced by the second cell(s) indicates that the compound of Formula (I) or a form thereof modulates the amount of the RNA transcript.

In certain embodiments, the cell(s) contacted or cultured with a compound of Formula (I) or a form thereof is a primary cell(s) from a subject. In some embodiments, the cell(s) contacted or cultured with a compound of Formula (I) or a form thereof is a primary cell(s) from a subject with a disease. In specific embodiments, the cell(s) contacted or cultured with a compound of Formula (I) or a form thereof is a primary cell(s) from a subject with a disease associated with an aberrant amount of an RNA transcript(s) for a particular gene(s). In some specific embodiments, the cell(s) contacted or cultured with a compound of Formula (I) or a form thereof is a primary cell(s) from a subject with a disease associated with an aberrant amount of an isoform(s) of a particular gene(s). In some embodiments, the cell(s) contacted or cultured with a compound of Formula (I) or a form thereof is a fibroblast (e.g., GM03813 or PNN 1-46 fibroblasts), an immune cell (e.g., a T cell, B cell, natural killer cell, macrophage), or a muscle cell. In certain embodiments, the cell(s) contacted or cultured with a compound of Formula (I) or a form thereof is a cancer cell.

In certain embodiments, the cell(s) contacted or cultured with a compound of Formula (I) or a form thereof is from a cell line. In some embodiments, the cell(s) contacted or cultured with a compound of Formula (I) or a form thereof is a cell line derived from a subject with a disease. In certain embodiments, the cell(s) contacted or cultured with a compound of Formula (I) or a form thereof is from a cell line known to have aberrant RNA transcript levels for a particular gene(s). In specific embodiments, the cell(s) contacted or cultured with a compound of Formula (I) or a form thereof is from a cell line derived from a subject with a disease known to have aberrant RNA transcript levels for a particular gene(s). In certain embodiments, the cell(s) contacted or cultured with a compound of Formula (I) or a form thereof is a cancer cell line. In some specific embodiments, the cell(s) contacted or cultured with the compound of Formula (I) or a form thereof is from a cell line derived from a subject with a disease known to have an aberrant amount of an RNA isoform(s) and/or protein isoform(s) of a particular gene(s). Non-limiting examples of cell lines include 293, 3T3, 4T1, 721, 9L, A2780, A172, A20, A253, A431, A-549, ALC, B16, B35, BCP-1, BEAS-2B, bEnd.3, BHK, BR 293, BT2O, BT483, BxPC3, C2C12, C3H-10T1/2, C6/36, C6, Cal-27, CHO, COR-L23, COS, COV-434, CML T1, CMT, CRL7O3O, CT26, D17, DH82, DU145, DuCaP, EL4, EM2, EM3, EMT6, FM3, H1299, H69, HB54, HB55, HCA2, HEK-293, HeLa, Hepa1c1c7, HL-60, HMEC, Hs578T, HsS78Bst, HT-29, HTB2, HUVEC, Jurkat, J558L, JY, K562, Ku812, KCL22, KG1, KYO1, LNCap, Ma-Mel, MC-38, MCF-7, MCF-10A, MDA-MB-231, MDA-MB-468, MDA-MB-435, MDCK, MG63, MOR/0.2R, MONO-MAC 6, MRC5, MTD-1A, NCI-H69, NIH-3T3, NALM-1, NS0, NW-145, OPCN, OPCT, PNT-1A, PNT-2, Raji, RBL, RenCa, RIN-5F, RMA, Saos-2, Sf21, Sf9, SiHa, SKBR3, SKOV-3, T2, T-47D, T84, THP1, U373, U87, U937, VCaP, Vero, VERY, W138, WM39, WT-49, X63, YAC-1, and YAR cells. In one embodiment, the cells are from a patient.

In another embodiment, provided herein is a method for determining whether a compound of Formula (I) or a form thereof modulates the amount of an RNA transcript (e.g., an mRNA transcript), comprising: (a) contacting a tissue sample with a compound of Formula (I) or a form thereof, and (b) determining the amount of the RNA transcript produced by the tissue sample, wherein an alteration in the amount of the RNA transcript in the presence of the compound relative to the amount of the RNA transcript in the absence of the compound or the presence of a negative control (e.g., a vehicle control such as PBS or DMSO) indicates that the compound of Formula (I) or a form thereof modulates the amount of the RNA transcript. In another embodiment, provided herein is a method for determining whether a compound of Formula (I) or a form thereof modulates the amount of an RNA transcript (e.g., an mRNA transcript), comprising: (a) contacting a first tissue sample with a compound of Formula (I) or a form thereof, (b) contacting a second tissue sample with a negative control (e.g., a vehicle control, such as PBS or DMSO); and (c) determining the amount of the RNA transcript produced by the first tissue sample and the second tissue sample; and (d) comparing the amount of the RNA transcript produced by the first tissue sample to the amount of the RNA transcript produced by the second tissue sample, wherein an alteration in the amount of the RNA transcript produced by the first tissue sample relative to the amount of the RNA transcript produced by the second tissue sample indicates that the compound of Formula (I) or a form thereof modulates the amount of the RNA transcript. Any tissue sample containing cells may be used in the accordance with these methods. In certain embodiments, the tissue sample is a blood sample, a skin sample, a muscle sample, or a tumor sample. Techniques known to one skilled in the art may be used to obtain a tissue sample from a subject.

In some embodiments, a dose-response assay is performed. In one embodiment, the dose response assay comprises: (a) contacting a cell(s) with a concentration of a compound of Formula (I) or a form thereof, (b) determining the amount of the RNA transcript produced by the cell(s), wherein an alteration in the amount of the RNA transcript in the presence of the compound relative to the amount of the RNA transcript in the absence of the compound or the presence of a negative control (e.g., a vehicle control such as PBS or DMSO) indicates that the compound of Formula (I) or a form thereof modulates the amount of the RNA transcript; (c) repeating steps (a) and (b), wherein the only experimental variable changed is the concentration of the compound or a form thereof, and (d) comparing the amount of the RNA transcript produced at the different concentrations of the compound or a form thereof. In another embodiment, the dose response assay comprises: (a) culturing a cell(s) in the presence of a compound of Formula (I) or a form thereof, (b) isolating the RNA transcript from the cell(s) after a certain period of time; (c) determining the amount of the RNA transcript produced by the cell(s), wherein an alteration in the amount of the RNA transcript in the presence of the compound relative to the amount of the RNA transcript in the absence of the compound or the presence of a negative control (e.g., a vehicle control such as PBS or DMSO) indicates that the compound of Formula (I) or a form thereof modulates the amount of the RNA transcript; (d) repeating steps (a), (b), and (c), wherein the only experimental variable changed is the concentration of the compound or a form thereof, and (e) comparing the amount of the RNA transcript produced at the different concentrations of the compound or a form thereof. In another embodiments, the dose-response assay comprises: (a) contacting each well of a microtiter plate containing cells with a different concentration of a compound of Formula (I) or a form thereof, (b) determining the amount of an RNA transcript produced by cells in each well; and (c) assessing the change of the amount of the RNA transcript at the different concentrations of the compound or form thereof.

In one embodiment, the dose response assay comprises: (a) contacting a cell(s) with a concentration of a compound of Formula (I) or a form thereof, wherein the cells are within the wells of a tissue culture container (e.g., a 96-well plate) at about the same density within each well, and wherein the cells are contacted with different concentrations of compound in different wells; (b) isolating the RNA from said cells in each well; (c) determining the amount of the RNA transcript produced by the cell(s) in each well; and (d) assessing change in the amount of the RNA transcript in the presence of one or more concentrations of compound relative to the amount of the RNA transcript in the presence of a different concentration of the compound or the absence of the compound or the presence of a negative control (e.g., a vehicle control such as PBS or DMSO).

In certain embodiments, the contacting of the cell(s) with the compound occurs in cell culture. In other embodiments, the contacting of the cell(s) with the compound occurs in a subject, such as a non-human animal subject.

In certain embodiments described herein, the cell(s) is contacted or cultured with a compound of Formula (I) or a form thereof, or a tissue sample is contacted with a compound of Formula (I) or a form thereof, or a negative control for a period of 15 minutes, 30 minutes, 45 minutes, 1 hour, 2 hours, 3 hours, 4 hours, 5 hours, 6 hours, 8 hours, 12 hours, 18 hours, 24 hours, 48 hours, 72 hours or more. In other embodiments described herein, the cell(s) is contacted or cultured with a compound of Formula (I) or a form thereof, or a tissue sample is contacted with a compound of Formula (I) or a form thereof, or a negative control for a period of 15 minutes to 1 hour, 1 to 2 hours, 2 to 4 hours, 6 to 12 hours, 12 to 18 hours, 12 to 24 hours, 28 to 24 hours, 24 to 48 hours, 48 to 72 hours.

In certain embodiments described herein, the cell(s) is contacted or cultured with a certain concentration of a compound of Formula (I) or a form thereof, or a tissue sample is contacted with a certain concentration of a compound of Formula (I) or a form thereof, wherein the certain concentration is 0.01 μM, 0.05 μM, 1 μM, 2 μM, 5 μM, 10 μM, 15 μM, 20 μM, 25 μM, 50 μM, 75 μM, 100 μM, or 150 μM. In other embodiments described herein, the cell(s) is contacted or cultured with certain concentration of a compound of Formula (I) or a form thereof, or a tissue sample is contacted with a certain concentration of a compound of Formula (I) or a form thereof, wherein the certain concentration is 175 μM, 200 μM, 250 μM, 275 μM, 300 μM, 350 μM, 400 μM, 450 μM, 500 μM, 550 μM 600 μM, 650 μM, 700 μM, 750 μM, 800 μM, 850 μM, 900 μM, 950 μM or 1 mM. In some embodiments described herein, the cell(s) is contacted or cultured with certain concentration of a compound of Formula (I) or a form thereof, or a tissue sample is contacted with a certain concentration of a compound of Formula (I) or a form thereof, wherein the certain concentration is 5 nM, 10 nM, 20 nM, 30 nM, 40 nM, 50 nM, 60 nM, 70 nM, 80 nM, 90 nM, 100 nM, 150 nM, 200 nM, 250 nM, 300 nM, 350 nM, 400 nM, 450 nM, 500 nM, 550 nM, 600 nM, 650 nM, 700 nM, 750 nM, 800 nM, 850 nM, 900 nM, or 950 nM. In certain embodiments described herein, the cell(s) is contacted or cultured with certain concentration of a compound of Formula (I) or a form thereof, or a tissue sample is contacted with a certain concentration of a compound of Formula (I) or a form thereof, wherein the certain concentration is between 0.01 μM to 0.1 μM, 0.1 μM to 1 μM, 1 μM to 50 μM, 50 μM to 100 μM, 100 μM to 500 μM, 500 μM to 1 nM, 1 nM to 10 nM, 10 nM to 50 nM, 50 nM to 100 nM, 100 nM to 500 nM, 500 nM to 1000 nM.

In another embodiment, provided herein is a method for determining whether a compound of Formula (I) or a form thereof modulates the amount of an RNA transcript (e.g., an mRNA transcript), comprising: (a) administering a compound of Formula (I) or a form thereof to a subject (in certain embodiments, a non-human animal); and (b) determining the amount of the RNA transcript in a sample obtained from the subject, wherein an alteration in the amount of the RNA transcript measured in the sample from the subject administered the compound or form thereof relative to the amount of the RNA transcript in a sample from the subject prior to administration of the compound or form thereof or a sample from a different subject from the same species not administered the compound or form thereof indicates that the compound of Formula (I) or a form thereof modulates the amount of the RNA transcript. In another embodiment, provided herein is a method for determining whether a compound of Formula (I) or a form thereof modulates the amount of an RNA transcript (e.g., an mRNA transcript), comprising: (a) administering a compound of Formula (I) or a form thereof to a first subject (in certain embodiments, a non-human animal); (b) administering a negative control (e.g., a pharmaceutical carrier) to a second subject (in certain embodiments, a non-human animal) of the same species as the first subject; and (c) determining the amount of the RNA transcript in a first tissue sample from the first subject and the amount of the RNA transcript in the second tissue sample from the second subject; and (d) comparing the amount of the RNA transcript in the first tissue sample to the amount of the RNA transcript in the second tissue sample, wherein an alteration in the amount of the RNA transcript in the first tissue sample relative to the amount of the RNA transcript in the second tissue sample indicates that the compound of Formula (I) or a form thereof modulates the amount of the RNA transcript. In certain embodiments, a compound of Formula (I) or form thereof is administered to a subject at a dose of about 0.001 mg/kg/day to about 500 mg/kg/day. In some embodiments, a single dose of a compound of Formula (I) or a form thereof is administered to a subject in accordance with the methods described herein. In other embodiments, 2, 3, 4, 5 or more doses of a compound of Formula (I) is administered to a subject in accordance with the methods described herein. In specific embodiments, the compound of Formula (I) or a form thereof is administered in a subject in a pharmaceutically acceptable carrier, excipient or diluent.

In another embodiment, provided herein is a method for determining whether a compound of Formula (I) or a form thereof modulates the splicing of an RNA transcript (e.g., an mRNA transcript), comprising: (a) administering a compound of Formula (I) or a form thereof to a subject (in certain embodiments, a non-human animal); and (b) determining the amount of two or more RNA transcript splice variants in a sample obtained from the subject, wherein an alteration in the amount of the two or more RNA transcript splice variants measured in the sample from the subject administered the compound or form thereof relative to the amount of the two or more RNA transcript splice variants in a sample from the subject prior to administration of the compound or form thereof or a sample from a different subject from the same species not administered the compound or form thereof indicates that the compound of Formula (I) or a form thereof modulates the splicing of the RNA transcript. In another embodiment, provided herein is a method for determining whether a compound of Formula (I) or a form thereof modulates the splicing of an RNA transcript (e.g., an mRNA transcript), comprising: (a) administering a compound of Formula (I) or a form thereof to a first subject (in certain embodiments, a non-human animal); (b) administering a negative control (e.g., a pharmaceutical carrier) to a second subject (in certain embodiments, a non-human animal) of the same species as the first subject; and (c) determining the amount of two or more RNA transcript splice variants in a first tissue sample from the first subject and the amount of two or more RNA transcript splice variants in the second tissue sample from the second subject; and (d) comparing the amount of the two or more RNA transcript splice variants in the first tissue sample to the amount of the two or more RNA transcript splice variants in the second tissue sample, wherein an alteration in the amount of the two or more RNA transcript splice variants in the first tissue sample relative to the amount of the two or more RNA transcript splice variants in the second tissue sample indicates that the compound of Formula (I) or a form thereof modulates the splicing of the RNA transcript. In certain embodiments, a compound of Formula (I) or form thereof is administered to a subject at a dose of about 0.001 mg/kg/day to about 500 mg/kg/day. In some embodiments, a single dose of a compound of Formula (I) or a form thereof is administered to a subject in accordance with the methods described herein. In other embodiments, 2, 3, 4, 5 or more doses of a compound of Formula (I) is administered to a subject in accordance with the methods described herein. In specific embodiments, the compound of Formula (I) or a form thereof is administered in a subject in a pharmaceutically acceptable carrier, excipient or diluent.

In some embodiments, the compound of Formula (I) or a form thereof that is contacted or cultured with a cell(s) or a tissue sample, or administered to a subject is a compound of Formula (II), Formula (III), Formula (IV), Formula (V), Formula (VI), Formula (VII), Formula (VIII), Formula (IX), Formula (X), Formula (XI), Formula (XII), Formula (XIII), or Formula (XIV). In some embodiments, the compound of Formula (I) or a form thereof that is contacted or cultured with a cell(s) or a tissue sample, or administered to a subject is a compound described herein.

Techniques known to one skilled in the art may be used to determine the amount of an RNA transcript(s). In some embodiments, the amount of one, two, three or more RNA transcripts is measured using deep sequencing, such as ILLUMINA® RNASeq, ILLUMINA® next generation sequencing (NGS), ION TORRENT™ RNA next generation sequencing, 454™ pyrosequencing, or Sequencing by Oligo Ligation Detection (SOLID™). In other embodiments, the amount of multiple RNA transcripts is measured using an exon array, such as the GENECHIP® human exon array. In certain embodiments, the amount of one, two, three or more RNA transcripts is determined by RT-PCR. In other embodiments, the amount of one, two, three or more RNA transcripts is measured by RT-qPCR. Techniques for conducting these assays are known to one skilled in the art.

In some embodiments, a statistical analysis or other analysis is performed on data from the assay utilized to measure an RNA transcript. In certain embodiments, a student t-test statistical analysis is performed on data from the assay utilized to measure an RNA transcript to determined those RNA transcripts that have an alternation in amount in the presence of the compound relative to the amount in the absence of the compound or presence of a negative control. In specific embodiments, the student t-test value of those RNA transcripts with the alternation is 10%, 5%, 4%, 3%, 2%, 1%, 0.5% or 0.1%. In some specific embodiments, p value of those RNA transcripts with the alternation is 10%, 5%, 4%, 3%, 2%, 1%, 0.5% or 0.1%. In certain specific embodiments, the student t-test and p values of those RNA transcripts with the alteration are 10%, 5%, 4%, 3%, 2%, 1%, 0.5% or 0.1% and 10%, 5%, 4%, 3%, 2%, 1%, 0.5% or 0.1%, respectively.

In certain embodiments, a further analysis is performed to determine how the compound of Formula (I) or a form thereof is changing the amount of an RNA transcript(s). In specific embodiments, a further analysis is performed to determine if an alternation in the amount of an RNA transcript(s) in the presence of a compound of Formula (I) or a form thereof relative the amount of the RNA transcript(s) in the absence of the compound or a form thereof, or the presence of a negative control is due to changes in transcription, splicing, and/or stability of the RNA transcript(s). Techniques known to one skilled in the art may be used to determine whether a compound of Formula (I) or a form thereof changes, e.g., the transcription, splicing and/or stability of an RNA transcript(s).

In certain embodiments, the stability of one or more RNA transcripts is determined by serial analysis of gene expression (SAGE), differential display analysis (DD), RNA arbitrarily primer (RAP)-PCR, restriction endonuclease-lytic analysis of differentially expressed sequences (READS), amplified restriction fragment-length polymorphism (ALFP), total gene expression analysis (TOGA), RT-PCR, RT-qPCR, high-density cDNA filter hybridization analysis (HDFCA), suppression subtractive hybridization (SSH), differential screening (DS), cDNA arrays, oligonucleotide chips, or tissue microarrays. In other embodiments, the stability of one or more RNA transcripts is determined by Northern blots, RNase protection, or slot blots.

In some embodiments, the transcription in a cell(s) or tissue sample is inhibited before (e.g., 5 minutes, 10 minutes, 30 minutes, 1 hour, 2 hours, 4 hours, 6 hours, 8 hours, 12 hours, 18 hours, 24 hours, 36 hours, 48 hours, or 72 hours before) or after (e.g., 5 minutes, 10 minutes, 30 minutes, 1 hour, 2 hours, 4 hours, 6 hours, 8 hours, 12 hours, 18 hours, 24 hours, 36 hours, 48 hours, or 72 hours after) the cell or the tissue sample is contacted or cultured with an inhibitor of transcription, such as α-amanitin, DRB, flavopiridol, triptolide, or actinomycin-D. In other embodiments, the transcription in a cell(s) or tissue sample is inhibited with an inhibitor of transcription, such as α-amanitin, DRB, flavopiridol, triptolide, or actinomycin-D, while the cell(s) or tissue sample is contacted or cultured with a compound of Formula (I) or a form thereof.

In certain embodiments, the level of transcription of one or more RNA transcripts is determined by nuclear run-on assay or an in vitro transcription initiation and elongation assay. In some embodiments, the detection of transcription is based on measuring radioactivity or fluorescence. In some embodiments, a PCR-based amplification step is used.

In specific embodiments, the amount of alternatively spliced forms of the RNA transcripts of a particular gene are measured to see if there is an alteration in the amount of one, two or more alternatively spliced forms of the RNA transcripts of the gene. In some embodiments, the amount of an isoform(s) encoded by a particular gene is measured to see if there is an alteration in the amount of the isoform(s). In certain embodiments, the levels of spliced forms of RNA are quantified by RT-PCR, RT-qPCR, or northern blotting. In other embodiments, sequence-specific techniques may be used to detect the levels of an individual spliceoform. In certain embodiments, splicing is measured in vitro using nuclear extracts. In some embodiments, detection is based on measuring radioactivity or fluorescence. Techniques known to one skilled in the art may be used to measure alterations in the amount of alternatively spliced forms of an RNA transcript of a gene and alterations in the amount of an isoform encoded by a gene.

Pharmaceutical Compositions and Modes of Administration

When administered to a patient, a compound of Formula (I) or a form thereof is preferably administered as a component of a composition that optionally comprises a pharmaceutically acceptable carrier, excipient or diluent. The composition can be administered orally, or by any other convenient route, for example, by infusion or bolus injection, by absorption through epithelial or mucocutaneous linings (e.g., oral mucosa, rectal, and intestinal mucosa) and may be administered together with another biologically active agent. Administration can be systemic or local. Various delivery systems are known, e.g., encapsulation in liposomes, microparticles, microcapsules, capsules, and can be used to administer the compound.

Methods of administration include, but are not limited to, parenteral, intradermal, intramuscular, intraperitoneal, intravenous, subcutaneous, intranasal, epidural, oral, sublingual, intranasal, intraocular, intratumoral, intracerebral, intravaginal, transdermal, ocularly, rectally, by inhalation, or topically, particularly to the ears, nose, eyes, or skin. The mode of administration is left to the discretion of the practitioner. In most instances, administration will result in the release of a compound into the bloodstream, tissue or cell(s). In a specific embodiment, a compound is administered orally.

The amount of a compound of Formula (I) or a form thereof that will be effective in the treatment of a disease resulting from an aberrant amount of mRNA transcripts depends, e.g., on the route of administration, the disease being treated, the general health of the subject, ethnicity, age, weight, and gender of the subject, diet, time, and the severity of disease progress, and should be decided according to the judgment of the practitioner and each patient's or subject's circumstances.

In specific embodiments, an "effective amount" in the context of the administration of a compound of Formula (I) or a form thereof, or composition or medicament thereof refers to an amount of a compound of Formula (I) or a form thereof to a patient which has a therapeutic effect and/or beneficial effect. In certain specific embodiments, an "effective amount" in the context of the administration of a compound of Formula (I) or a form thereof, or composition or medicament thereof to a patient results in one, two or more of the following effects: (i) reduces or ameliorates the severity of a disease; (ii) delays onset of a disease; (iii) inhibits the progression of a disease; (iv) reduces hospitalization of a subject; (v) reduces hospitalization length for a subject; (vi) increases the survival of a subject; (vii) improves the quality of life of a subject; (viii) reduces the number of symptoms associated with a disease; (ix) reduces or ameliorates the severity of a symptom(s) associated with a disease; (x) reduces the duration of a symptom associated with a disease associated; (xi) prevents the recurrence of a symptom associated with a disease; (xii) inhibits the development or onset of a symptom of a disease; and/or (xiii) inhibits of the progression of a symptom associated with a disease. In certain embodiments, an effective amount of a compound of Formula (I) or a form thereof is an amount effective to restore the amount of a RNA transcript of a gene to the amount of the RNA transcript detectable in healthy patients or cells from healthy patients. In other embodiments, an effective amount of a compound of Formula (I) or a form thereof is an amount effective to restore the amount an RNA isoform and/or protein isoform of gene to the amount of the RNA isoform and/or protein isoform detectable in healthy patients or cells from healthy patients.

In certain embodiments, an effective amount of a compound of Formula (I) or a form thereof is an amount effective to decrease the aberrant amount of an RNA transcript of a gene which associated with a disease. In certain embodiments, an effective amount of a compound of Formula (I) or a form thereof is an amount effective to decrease the amount of the aberrant expression of an isoform of a gene. In some embodiments, an effective amount of a compound of Formula (I) or a form thereof is an amount effective to result in a substantial change in the amount of an RNA transcript (e.g., mRNA transcript), alternative splice variant or isoform.

In certain embodiments, an effective amount of a compound of Formula (I) or a form thereof is an amount effective to increase or decrease the amount of an RNA transcript (e.g., an mRNA transcript) of gene which is beneficial for the prevention and/or treatment of a disease. In certain embodiments, an effective amount of a compound of Formula (I) or a form thereof is an amount effective to increase or decrease the amount of an alternative splice variant of an RNA transcript of gene which is beneficial for the prevention and/or treatment of a disease. In certain embodiments, an effective amount of a compound of Formula (I) or a form thereof is an amount effective to increase or decrease the amount of an isoform of gene which is beneficial for the prevention and/or treatment of a disease. Non-limiting examples of effective amounts of a compound of Formula (I) or a form thereof are described herein.

For example, the effective amount may be the amount required to prevent and/or treat a disease associated with the aberrant amount of an mRNA transcript of gene in a human subject.

In general, the effective amount will be in a range of from about 0.001 mg/kg/day to about 500 mg/kg/day for a patient having a weight in a range of between about 1 kg to about 200 kg. The typical adult subject is expected to have a median weight in a range of between about 70 and about 100 kg.

Within the scope of the present description, the "effective amount" of a compound of Formula (I) or a form thereof for use in the manufacture of a medicament, the preparation of a pharmaceutical kit or in a method for preventing and/or treating a disease in a human subject in need thereof, is intended to include an amount in a range of from about 0.001 mg to about 35,000 mg.

The compositions described herein are formulated for administration to the subject via any drug delivery route known in the art. Non-limiting examples include oral, ocular, rectal, buccal, topical, nasal, ophthalmic, subcutaneous, intramuscular, intraveneous (bolus and infusion), intracerebral, transdermal, and pulmonary routes of administration.

Embodiments described herein include the use of a compound of Formula (I) or a form thereof in a pharmaceutical composition. In a specific embodiment, described herein is the use of a compound of Formula (I) or a form thereof in a pharmaceutical composition for preventing and/or treating a disease in a human subject in need thereof comprising administering an effective amount of a compound of Formula (I) or a form thereof in admixture with a pharmaceutically acceptable carrier, excipient or diluent. In a specific embodiment, the human subject is a patient with a disease associated with the aberrant amount of an mRNA transcript(s).

A compound of Formula (I) or a form thereof may optionally be in the form of a composition comprising the compound or a form thereof and an optional carrier, excipient or diluent. Other embodiments provided herein include pharmaceutical compositions comprising an effective amount of a compound of Formula (I) or a form thereof and a pharmaceutically acceptable carrier, excipient, or diluent. In a specific embodiment, the pharmaceutical compositions are suitable for veterinary and/or human administration. The pharmaceutical compositions provided herein can be in any form that allows for the composition to be administered to a subject.

In a specific embodiment and in this context, the term "pharmaceutically acceptable carrier, excipient or diluent" means a carrier, excipient or diluent approved by a regulatory agency of the Federal or a state government or listed in the U.S. Pharmacopeia or other generally recognized pharmacopeia for use in animals, and more particularly in humans. The term "carrier" refers to a diluent, adjuvant (e.g., Freund's adjuvant (complete and incomplete)), excipient, or vehicle with which a therapeutic agent is administered. Such pharmaceutical carriers can be sterile liquids, such as water and oils, including those of petroleum, animal, vegetable or synthetic origin, such as peanut oil, soybean oil, mineral oil, sesame oil and the like. Water is a specific carrier for intravenously administered pharmaceutical compositions. Saline solutions and aqueous dextrose and glycerol solutions can also be employed as liquid carriers, particularly for injectable solutions.

Typical compositions and dosage forms comprise one or more excipients. Suitable excipients are well-known to those skilled in the art of pharmacy, and non limiting examples of suitable excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Whether a particular excipient is suitable for incorporation into a pharmaceutical composition or dosage form depends on a variety of factors well known in the art including, but not limited to, the way in which the dosage form will be administered to a patient and the specific active ingredients in the dosage form. Further provided herein are anhydrous pharmaceutical compositions and dosage forms comprising one or more compounds of Formula (I) or a form thereof as described herein. The compositions and single unit dosage forms can take the form of solutions or syrups (optionally with a flavoring agent), suspensions (optionally with a flavoring agent), emulsions, tablets (e.g., chewable tablets), pills, capsules, granules, powder (optionally for reconstitution), taste-masked or sustained-release formulations and the like.

Pharmaceutical compositions provided herein that are suitable for oral administration can be presented as discrete dosage forms, such as, but are not limited to, tablets, caplets, capsules, granules, powder, and liquids. Such dosage forms contain predetermined amounts of active ingredients, and may be prepared by methods of pharmacy well known to those skilled in the art.

Examples of excipients that can be used in oral dosage forms provided herein include, but are not limited to, binders, fillers, disintegrants, and lubricants.

Methods of Modulating the Amount of RNA Transcripts Encoded by Certain Genes

In one aspect, described herein are methods for modulating the amount of a product of a gene, wherein a precursor RNA transcript transcribed from the gene contains a REMS, and the methods utilize a compound described herein. In certain embodiments, the gene is any one of the genes disclosed in Tables 1-4 or 6. In certain embodiments, the gene contains a nucleotide sequence encoding a non-endogenous REMS. In one embodiment, provided herein are methods for modulating the amount of one, two, three or more RNA transcripts of a gene, by way of nonlimiting example, disclosed in Table 6, infra, the method comprising contacting a cell with a compound of Formula (I) or a form thereof.

In another embodiment, provided herein are methods for modulating the amount of one, two, three or more RNA transcripts of a gene, not disclosed in Tables 1-4, infra, wherein the precursor transcript transcribed from the gene comprises a REMS, the method comprising contacting a cell with a compound of Formula (I) or a form thereof.

In another embodiment, provided herein are methods for modulating the amount of one, two, three or more RNA transcripts of a gene, not disclosed in International Patent Application No. PCT/US2014/071252 (International Publication No. WO 2015/105657 A1), wherein the precursor transcript transcribed from the gene comprises a REMS, the method comprising contacting a cell with a compound of Formula (I) or a form thereof.

In another embodiment, provided herein are methods for modulating the amount of one, two, three or more RNA transcripts of a gene, not disclosed in Table 6, infra, wherein the precursor transcript transcribed from the gene comprises a REMS, the method comprising contacting a cell with a compound of Formula (I) or a form thereof.

In another embodiment, provided herein are methods for modulating the amount of one, two, three or more RNA transcripts of ERGIC3, comprising contacting a cell with a compound of Formula (I) or a form thereof. See the example section for additional information regarding the genes in Table 6. In certain embodiments, the cell is contacted with the compound of Formula (I) or a form thereof in a cell culture. In other embodiments, the cell is contacted with the compound of Formula (I) or a form thereof in a subject (e.g., a non-human animal subject or a human subject).

In certain embodiments, the cell(s) contacted or cultured with a compound of Formula (I) or a form thereof is primary cell(s) or cell(s) from a cell line. In some embodiments, the cell(s) contacted or cultured with a compound of Formula (I) or a form thereof is a fibroblast(s), an immune cell(s), or a muscle cell(s). In some embodiments, the cell(s) contacted or cultured with a compound of Formula (I) or a form thereof is a cancer cell. Non-limiting examples of cell lines include 293, 3T3, 4T1, 721, 9L, A2780, A172, A20, A253, A431, A-549, ALC, B16, B35, BCP-1, BEAS-2B, bEnd.3, BHK, BR 293, BT2O, BT483, BxPC3, C2C12, C3H-10T1/2, C6/36, C6, Cal-27, CHO, COR-L23, COS, COV-434, CML T1, CMT, CRL7O3O, CT26, D17, DH82, DU145, DuCaP, EL4, EM2, EM3, EMT6, FM3, H1299, H69, HB54, HB55, HCA2, HEK-293, HeLa, Hepa1c1c7, HL-60, HMEC, Hs578T, HsS78Bst, HT-29, HTB2, HUVEC, Jurkat, J558L, JY, K562, Ku812, KCL22, KG1, KYO1, LNCap, Ma-Mel, MC-38, MCF-7, MCF-10A, MDA-MB-231, MDA-MB-468, MDA-MB-435, MDCK, MG63, MOR/0.2R, MONO-MAC 6, MRC5, MTD-1A, NCI-H69, NIH-3T3, NALM-1, NS0, NW-145, OPCN, OPCT, PNT-1A, PNT-2, Raji, RBL, RenCa, RIN-5F, RMA, Saos-2, Sf21, Sf9, SiHa, SKBR3, SKOV-3, T2, T-47D, T84, THP1, U373, U87, U937, VCaP, Vero, VERY, W138, WM39, WT-49, X63, YAC-1, and YAR cells. In one embodiment, the cells are from a patient.

In certain embodiments described herein, the cell(s) is contacted or cultured with a compound of Formula (I) or a form thereof with a compound of Formula (I) or a form thereof for a period of 15 minutes, 30 minutes, 45 minutes, 1 hour, 2 hours, 3 hours, 4 hours, 5 hours, 6 hours, 8 hours, 12 hours, 18 hours, 24 hours, 48 hours, 72 hours or more. In other embodiments described herein, the cell(s) is contacted or cultured with a compound of Formula (I) or a form thereof with a compound of Formula (I) or a form thereof for a period of 15 minutes to 1 hour, 1 to 2 hours, 2 to 4 hours, 6 to 12 hours, 12 to 18 hours, 12 to 24 hours, 28 to 24 hours, 24 to 48 hours, 48 to 72 hours.

In certain embodiments described herein, the cell(s) is contacted or cultured with certain concentration of a compound of Formula (I) or a form thereof, wherein the certain concentration is 0.01 μM, 0.05 μM, 1 μM, 2 μM, 5 μM, 10 μM, 15 μM, 20 μM, 25 μM, 50 μM, 75 μM, 100 μM, or 150 μM. In other embodiments described herein, the cell(s) is contacted or cultured with certain concentration of a compound of Formula (I) or a form thereof, wherein the certain concentration is 175 μM, 200 μM, 250 μM, 275 μM, 300 μM, 350 μM, 400 μM, 450 μM, 500 μM, 550 μM 600 μM, 650 μM, 700 μM, 750 μM, 800 μM, 850 μM, 900 μM, 950 μM or 1 mM. In some embodiments described herein, the cell(s) is contacted or cultured with certain concentration of a compound of Formula (I) or a form thereof, wherein the certain concentration is 5 nM, 10 nM, 20 nM, 30 nM, 40 nM, 50 nM, 60 nM, 70 nM, 80 nM, 90 nM, 100 nM, 150 nM, 200 nM, 250 nM, 300 nM, 350 nM, 400 nM, 450 nM, 500 nM, 550 nM, 600 nM, 650 nM, 700 nM, 750 nM, 800 nM, 850 nM, 900 nM, or 950 nM. In certain embodiments described herein, the cell(s) is contacted or cultured with certain concentration of a compound of Formula (I) or a form thereof, wherein the certain concentration is between 0.01 μM to 0.1 μM, 0.1 μM to 1 μM, 1 μM to 50 μM, 50 μM to 100 μM, 100 μM to 500 μM, 500 μM to 1 nM, 1 nM to 10 nM, 10 nM to 50 nM, 50 nM to 100 nM, 100 nM to 500 nM, 500 nM to 1000 nM. In certain embodiments described herein, the cell(s) is contacted or cultured with certain concentration of a compound of Formula (I) or a form thereof that results in a substantial change in the amount of an RNA transcript (e.g., an mRNA transcript), an alternatively spliced variant, or an isoform of a gene (e.g., a gene in Table 6, infra).

In another aspect, provided herein are methods for modulating the amount of one, two, three or more RNA transcripts of a gene, wherein the precursor RNA transcript transcribed from the gene comprises a REMS, the methods comprising administering to a patient in need thereof a compound of Formula (I) or a form thereof, or a pharmaceutical composition comprising a compound of Formula (I) or a form thereof and a pharmaceutically acceptable carrier, excipient or diluent.

In one embodiment, provided herein are methods for modulating the amount of one, two, three or more RNA transcripts of a gene, by way of nonlimiting example, disclosed in Table 6, infra, the methods comprising administering to a patient in need thereof a compound of Formula (I) or a form thereof, or a pharmaceutical composition comprising a compound of Formula (I) or a form thereof and a pharmaceutically acceptable carrier, excipient or diluent.

In another embodiment, provided herein are methods for modulating the amount of one, two, three or more RNA transcripts of a gene, not disclosed in Tables 1-4, infra, wherein the precursor RNA transcript transcribed from the gene comprises a REMS, the methods comprising administering to a patient in need thereof a compound of Formula (I) or a form thereof, or a pharmaceutical composition comprising a compound of Formula (I) or a form thereof and a pharmaceutically acceptable carrier, excipient or diluent.

In another embodiment, provided herein are methods for modulating the amount of one, two, three or more RNA transcripts of a gene in a subject, not disclosed in International Patent Application No. PCT/US2014/071252 (International Publication No. WO 2015/105657 A1), wherein the precursor RNA transcript transcribed from the gene comprises a REMS, the methods comprising administering to the subject a compound of Formula (I) or a form thereof, or a pharmaceutical composition comprising a compound of Formula (I) or a form thereof and a pharmaceutically acceptable carrier, excipient or diluent.

In another embodiment, provided herein are methods for modulating the amount of one, two, three or more RNA transcripts of a gene, not disclosed in International Patent Application No. PCT/US2014/071252 (International Publication No. WO 2015/105657 A1), wherein the precursor RNA transcript transcribed from the gene comprises a REMS, the methods comprising administering a patient in need thereof a compound of Formula (I) or a form thereof, or a pharmaceutical composition comprising a compound of Formula (I) or a form thereof and a pharmaceutically acceptable carrier, excipient or diluent.

In a particular aspect, provided herein are methods for modulating the amount of one, two, three or more RNA transcripts of a gene in a subject, wherein the precursor RNA transcript transcribed from the gene comprises a REMS (for example, an endogenous REMS or a non-endogenous REMS), the methods comprising administering to the subject a compound of Formula (I) or a form thereof, or a pharmaceutical composition comprising a compound of Formula (I) or a form thereof and a pharmaceutically acceptable carrier, excipient or diluent, wherein the gene is: ABCA1, ABCB7, ABCC1, ABHD10, ABL2, ABLIM3, ACACA, ACADVL, ACAT2, ADAM12, ADAM15, ADAM17, ADAM33, AFF2, AGK, AGPAT3, AGPS, AHCYL2, AHDC1, AHRR, AJUBA, AK021888, AK310472, AKAP1, AKAP9, AKNA, ALCAM, ALDH4A1, AMPD2, ANK2, ANKFY1, ANKHD1-EIF4EBP3, ANKRD17, ANKS6, ANP32A, ANXA11, ANXA6, AP2B1, APAF1, APLP2, APP, APPL2, APTX, ARHGAP22, ARID1A, ARID2, ARMCX3, ASAP1, ASL, ASNS, ASPH, ATAD2B, ATF7IP, ATG9A, ATMIN, ATP2C1, ATXN3, AURKA, AXIN1, B4GALT2, BACE1, BAG2, BASP1, BC033281, BCAR3, BEND6, BICD1, BIN1, BNC1, BRD2, BRPF1, BSCL2, BTBD10, BZW1, C11orf30, C11orf73, C17orf76-AS1, C4orf27, C5orf24, C6orf48, C9orf69, CAB39, CALU, CAMKK1, CAPNS1, CASC3, CASP8AP2, CAV1, CCAR1, CCDC77, CCDC88A, CCDC92, CCT6A, CD276, CD46, CDC25B, CDC40, $CDC_{42}$BPA, CDCA7, CDH11, CDH13, CDK11B, CDK16, CDKAL1, CEP68, CFLAR, CHD8, CIZ1, CLIC1, CLK4, CNOT1, COG1, COL12A1, COL1A1, COL6A1, COPS7B, CPEB2, CREB5, CRLS1, CRTAP, CSDE1, CSNK1A1, CTDSP2, CTNND1, CUL2, CUL4A, CUX1, CYB5B, CYBRD1, CYP51A1, DAB2, DACT1, DARS, DAXX, DCAF10, DCAF11, DCBLD2, DCUN1D4, DDAH1, DDAH2, DDHD2, DDR1, DDX39B, DDX42, DENND1A, DENND1B, DENND5A, DGCR2, DGKA, DHCR24, DHCR7, DHFR, DHX9, DIAPH1, DIAPH3, DIS3L, DKFZp434M1735, DKK3, DLC1, DNM2, DOCK1, DPP8, DSEL, DST, DSTN, EBF1, EEA1, EEF1A1, EFCAB14, EGR1, EHMT2, EIF2B3, EIF4G1, EIF4G2, EIF4G3, ELF2, ENG, ENPP2, ENSA, EPN1, EPT1, ERC1, ERGIC3, ETV5, EXO1, EXTL2, EYA3, FADS1, FADS2, FAF1, FAM111A, FAM198B, FAM219A, FAM219B, FAM3C, FAM65A, FBXO10, FBXO18, FBXO31, FBXO34, FBXO9, FDFT1, FDPS, FER, FEZ1, FGD5-AS1, FGFRL1, FHOD3, FLII, FLNB, FN1, FNBP1, FOCAD, FOS, FOSB, FOSL1, FOXK1, FOXM1, FUS, FYN, GABPB1, GALC, GALNT1, GAS7, GBA2, GCFC2, GGCT, GHDC, GIGYF2, GJC1, GMIP, GNA13, GNAS, GNL3L, GOLGA2, GOLGA4, GOLGB1, GORASP1, GPR1, GPR89A, GPSM2, GREM1, GRK6, GSE1, GTF2H2B, HAS2, HAT1, HAUS3, HAUS6, HDAC7, HEG1, HLA-A, HLA-E, HLTF, HMGA1, HMGB1, HMGCR, HMGCS1, HMOX1, HNRNPR, HNRNPUL1, HP1BP3, HRH1, HSD17B12, HSD17B4, HTT, IARS, IDH1, IDI1, IGF2BP2, IL6ST, INHBA, INSIG1, IQCE, ITGAV, ITGB5, ITM2C, ITSN1, KANSL3, KCNK2, KIAA1033, KIAA1143, KIAA1199, KIAA1522, KIAA1524, KIAA1549, KIAA1715, KIF14, KIF2A, KIF3A, KLC1, KLC2, KLF6, KLHL7, KRT18, KRT19, KRT34, KRTAP2-3, LAMA2, LAMB1, LARP4, LARP7, LATS2, LDLR, LEMD3, LGALS8, LIMS1, LINC00341, LINC00657, LMAN2L, LMO7, LONP1, LOX, LRCH4, LRIG1, LRP8, LRRC8A, LSS, LTBR, LUC7L2, LZTS2, MADD, MAGED4, MAGED4B, MAN1A2, MAP4K4, MBD1, MBOAT7, MDM2, MED1, MEDAG, MEF2D, MEIS2, MEMO1, MEPCE, MFGE8, MICAL2, MINPP1, MKL1, MKLN1, MKNK2, MLLT4, MLST8, MMAB, MMS19, MMS22L, MPPE1, MPZL1, MRPL3, MSANTD3, MSC, MSH2, MSH6, MSL3, MSMO1, MSRB3, MTAP, MTERFD1, MTHFD1L, MTMR9, MTRR, MUM1, MVD, MVK, MYADM, MYLK, MYO1D, MYO9B, MYOF, NAA35, NADK, NASP, NAV1, NAV2, NCOA1, NCOA3, NCOA4, NCSTN, NELFA, NEO1, NEURL1B, NF2, NFE2L1, NFX1, NID1, NID2, NIPA1, NKX3-1, NOL10, NOMO3, NPEPPS, NRD1, NREP, NRG1, NSUN4, NT5C2, NT5E, NTNG1, NUDT4, NUP153, NUP35, NUP50, NUPL1, NUSAP1, ODF2, OS9, OSBPL6, OSMR, P4HA1, P4HB, PABPC1, PAK4, PAPD4, PARD3, PARN, PARP14, PARP4, PARVB, PCBP2, PCBP4, PCDHGB3, PCGF3, PCM1, PCMTD2, PCNXL2, PCSK9, PDE4A, PDE7A, PDLIM7, PDXDC1, PEPD, PEX5, PFKP, PHF19, PHF8, PHRF1, PHTF2, PI4K2A, PIEZO1, PIGU, PIK3C2B, PITPNA, PITPNB, PITPNM1, PLAU, PLEC, PLEKHB2, PLSCR3, PLXNB2, PLXNC1, PMS1, POLE3, POLR3D, POSTN, POU2F1, PPAPDC1A, PPARA, PPHLN1, PPIP5K1, PPP1R12A, PPP6R1, PPP6R2, PRKACB, PRKDC, PRMT1, PRNP, PRSS23, PSMA4, PSMC1, PSMD6, PTK2B, PTPN14, PUF60, PUS7, PVR, PXN, QKI, RAB23, RAB2B, RAB34, RAD1, RAD23B, RALB, RAP1A, RAP1GDS1, RARG, RASSF8, RBCK1, RBFOX2, RBM10, RCC1, RFTN1, RFWD2, RGS10, RGS3, RIF1, RNF14, RNF19A, RNF38, RNFT1, RPL10, RPS6KC1, RRBP1, RWDD4, SAMD9, SAMD9L, SAR1A, SART3, SCAF4, SCAF8, SCD, SCLT1, SCO1, SDCBP, SEC14L1, SEC22A, SEC24B, SEC61A1, SEPT9, SERPINE2, SF1, SGOL2, SH3RF1, SKIL, SLC25A17, SLC39A3, SLC41A1, SLC4A4, SLC7A6, SLC7A8, SMARCA4, SMARCC2, SMC4, SMC6, SMCHD1, SMG1, SMN2, SMPD4, SMYD3, SMYD5, SNAP23, SNHG16, SNX14, SOCS2, SON, SOS2, SPATA20, SPATS2, SPG20, SPRED2, SQLE, SQRDL, SQSTM1, SRCAP, SREBF1, SREK1, SRSF3, STARD4, STAT1, STAT3, STAU1, STC2, STEAP2, STRIP1, STRN3, STX16, SUPT20H, SYNE1, SYNE2, SYT15, SYTL2, TACC1, TAF2, TANC2, TARBP1, TARS, TBC1D15, TBL2, TCF7L2, TENC1, TENM2, TEP1, TET3, TFCP2, TGFBI, TGFBR1, TGFBRAP1, THADA, THAP4, THRB, TIMP2, TJP2, TLE3, TLK1, TMEM154, TMEM47, TMEM63A, TNC, TNFAIP3, TNFRSF12A, TNIP1, TNKS1BP1, TNPO3, TNS1, TNS3, TOE1, TOMM40, TOMM5, TOPORS, TP53INP1, TRAF3, TRAK1, TRAPPC12, TRIB1, TRIM2, TRIM23, TRIM26, TRIM28, TRIM65, TRMT1L, TRPS1, TSC2, TSHZ1, TSPAN2, TTC7A, TUBB2C, TUBB3, TXNL1, TXNRD1, U2SURP, UBAP2L, UBE2G2, UBE2V1, UBQLN4, UCHL5, UHMK1, UHRF1BPL, UNC5B, USP19, USP7, VANGL1, VARS2, VCL, VIPAS39, VPS13A, VPS29, VPS51, VWA8, WDR19, WDR37, WDR48, WIPF1, WNT5B, WSB1, WWTR1, XIAP, XRN2, YAP1, YES1, YPEL5, YTHDF3, Z24749, ZAK, ZBTB10, ZBTB24, ZBTB7A, ZC3H12C, ZC3H14, ZC3H18, ZCCHC11, ZEB1, ZEB2, ZFAND1, ZFAND5, ZHX3, ZMIZ1, ZMYM2, ZNF12, ZNF148, ZNF219, ZNF227, ZNF24, ZNF268, ZNF28, ZNF281, ZNF335, ZNF37A, ZNF37BP, ZNF395, ZNF583, ZNF621, ZNF652, ZNF655, ZNF674, ZNF74, ZNF764, ZNF778, ZNF780A, ZNF827, ZNF839 or ZNF91.

In another particular aspect, provided herein are methods for modulating the amount of one, two, three or more RNA transcripts of a gene in a subject, wherein the precursor RNA transcript transcribed from the gene comprises a REMS (for example, an endogenous REMS or a non-endogenous REMS), the methods comprising administering to the subject a compound of Formula (I) or a form thereof, or a pharmaceutical composition comprising a compound of Formula (I) or a form thereof and a pharmaceutically acceptable carrier, excipient or diluent, wherein the gene is: SMN2, FOXM1, APLP2, GGCT, ABHD10, STRN3, VPS29, ERGIC3, MADD, LARP 7, ARMCX6, GALC, LAMA2, PRKDC, RCC1, FADS2, DIAPH3, FN1, PARP1, COL1A1, COL1A2, COL3A1 or COL5A2.

In another particular aspect, provided herein are methods for modulating the amount of one, two, three or more RNA transcripts of a gene in a subject, wherein the precursor RNA transcript transcribed from the gene comprises a REMS (for example, an endogenous REMS or a non-endogenous REMS), the methods comprising administering to the subject a compound of Formula (I) or a form thereof, or a pharmaceutical composition comprising a compound of Formula (I) or a form thereof and a pharmaceutically acceptable carrier, excipient or diluent, wherein the gene is: SMN2, FOXM1, APLP2, GGCT, ABHD10, STRN3, VPS29, ERGIC3, MADD, LARP7 or COL1A1.

In another particular aspect, provided herein are methods for modulating the amount of one, two, three or more RNA transcripts of a gene in a subject, wherein the precursor RNA transcript transcribed from the gene comprises a REMS (for example, an endogenous REMS or a non-endogenous REMS), the methods comprising administering to the subject a compound of Formula (I) or a form thereof, or a pharmaceutical composition comprising a compound of Formula (I) or a form thereof and a pharmaceutically acceptable carrier, excipient or diluent, wherein the gene is ERGIC3.

In another particular aspect, provided herein are methods for modulating the amount of one, two, three or more RNA transcripts of a gene in a subject, wherein the precursor RNA transcript transcribed from the gene comprises a non-endogenous REMS, the methods comprising administering to the subject a compound of Formula (I) or a form thereof, or a pharmaceutical composition comprising a compound of Formula (I) or a form thereof and a pharmaceutically acceptable carrier, excipient or diluent.

In another embodiment, provided herein are methods for modulating the amount of one, two, three or more RNA transcripts of a gene, not disclosed in Table 6, infra, wherein the precursor RNA transcript transcribed from the gene comprises a REMS, the methods comprising administering to a patient in need thereof a compound of Formula (I) or a form thereof, or a pharmaceutical composition comprising a compound of Formula (I) or a form thereof and a pharmaceutically acceptable carrier, excipient or diluent.

In another embodiment, provided herein are methods for modulating the amount of one, two, three or more RNA transcripts of ERGIC3, comprising administering to a patient in need thereof a compound of Formula (I) or a form thereof, or a pharmaceutical composition comprising a compound of Formula (I) or a form thereof and a pharmaceutically acceptable carrier, excipient or diluent. See the example section for additional information regarding the genes in Table 6.

In certain embodiments, a compound of Formula (I) or a form thereof contacted or cultured with a cell(s), or administered to a subject is a compound of Formula (II), Formula (III), Formula (IV), Formula (V), Formula (VI), Formula (VII), Formula (VIII), Formula (IX), Formula (X), Formula (XI), Formula (XII), Formula (XIII), or Formula (XIV). In some embodiments, a compound of Formula (I) or a form thereof contacted or cultured with a cell(s), or administered to a subject is a compound described herein.

Table 1 shows 263 genes that, in the presence of Compound 774 (3 □M), demonstrate an effect on isoform fold increase having a statistically significant adjusted p value of at least 0.01.

TABLE 1

| |
|---|
| ABCA1, ABCC1, ABL2, ACACA, ACAT2, AFF2, AHRR, AK021888, AK310472, AKAP1, ANK2, ANKHD1-EIF4EBP3, AP2B1, APAF1, APLP2, ARID1A, ARMCX3, ASAP1, ASPH, ATAD2B, ATF7IP, ATG9A, AXIN1, BACE1, BIN1, BNC1, BRPF1, BZW1, C11orf30, C11orf73, C17orf76-AS1, C4orf27, C6orf48, CAB39, CAMKK1, CCDC88A, CCDC92, CDC25B, CDC42BPA, CDCA7, CDH11, CDH13, CEP68, CFLAR, COPS7B, CREB5, CUL2, CUL4A, CUX1, CYP51A1, DCUN1D4, DDR1, DDX39B, DDX42, DENND1A, DENND5A, DGKA, DHCR24, DHCR7, DIAPH1, DIAPH3, DNM2, DOCK1, EFCAB14, EIF2B3, EPN1, EPT1, ERC1, ETV5, FADS1, FADS2, FAF1, FAM198B, FAM219B, FBXO10, FBXO9, FDFT1, FDPS, FER, FEZ1, FHOD3, FLIT, FLNB, FNBP1, FOS, FOSB, FOXM1, FYN, GABPB1, GALC, GAS7, GGCT, GJC1, GPSM2, GRK6, HAS2, HAT1, HLTF, HMGA1, HMGB1, HMGCR, HMGCS1, HMOX1, HP1BP3, HSD17B12, HTT, IDI1, INHBA, INSIG1, KANSL3, KIAA1199, KIAA1524, KIAA1715, KIF3A, KLF6, KRT19, KRT34, KRTAP2-3, LAMA2, LARP7, LDLR, LEMD3, LMAN2L, LRCH4, LRP8, LSS, MAGED4, MAGED4B, MAN1A2, MEDAG, MEF2D, MEMO1, MFGE8, MICAL2, MMAB, MMS19, MMS22L, MSL3, MSMO1, MTAP, MTERFD1, MVD, MVK, NASP, NAV2, NEURL1B, NFE2L1, NID1, NPEPPS, NREP, NRG1, NSUN4, NT5C2, NUP153, P4HA1, PABPC1, PAPD4, PCBP2, PCM1, PCSK9, PDXDC1, PEPD, PHF19, PHF8, PHTF2, PIK3C2B, PITPNB, PLEC, PMS1, POU2F1, PPHLN1, PRKDC, PRSS23, PSMC1, PTPN14, PUF60, PVR, RAB23, RAD23B, RAP1A, RASSF8, RBM10, RCC1, RFWD2, RNFT1, RWDD4, SAMD9L, SART3, SCAF4, SCD, SEC22A, SEC61A1, SERPINE2, SF1, SLC25A17, SLC7A6, SLC7A8, SMN2, SMYD3, SMYD5, SNAP23, SNHG16, SQLE, SQRDL, SQSTM1, SRCAP, SREBF1, STARD4, STAT1, STAU1, STEAP2, STRN3, SYNE1, TACC1, TAF2, TANC2, TARBP1, TBC1D15, TEP1, TFCP2, TGFBRAP1, THADA, TIMP2, TLK1, TMEM154, TNS3, TOMM5, TRAF3, TRAK1, TRAPPC12, TRIM2, TRIM26, TRIM65, TSPAN2, U2SURP, UBAP2L, UBE2V1, UCHL5, UHRF1BP1L, VANGL1, VARS2, VPS13A, VP529, VWA8, WSB1, XIAP, XRN2, YPEL5, ZAK, ZC3H18, ZFAND5, ZMIZ1, ZMYM2, ZNF219, ZNF227, ZNF24, ZNF37A, ZNF37BP, ZNF395, ZNF652, ZNF674, ZNF74 or ZNF778. |

Table 2 shows 234 genes that, in the presence of Compound 774 (0.3 □M), demonstrate an effect on isoform fold increase having a statistically significant adjusted p value of at least 0.01.

TABLE 2

| |
|---|
| ABCC1, ACADVL, ADAM15, AGPAT3, AHRR, AJUBA, AKAP1, AKAP9, ALCAM, ALDH4A1, ANKFY1, AP2B1, APLP2, APP, ARID1A, ARID2, ASPH, ATMIN, BASP1, BC033281, BCAR3, C11orf73, C17orf76-AS1, C5orf24, C6orf48, CAB39, CASP8AP2, CAV1, CCAR1, CCT6A, CD276, CD46, CDC25B, CDK16, CEP68, CHD8, CLIC1, COL12A1, CPEB2, CREB5, CRLS1, CRTAP, CTNND1, CUX1, CYBRD1, DACT1, DCAF10, DCAF11, DDHD2, DDX39B, DIAPH3, DKK3, DLC1, DSTN, EBF1, EGR1, EIF4G1, EIF4G3, ENG, ERC1, ETV5, FAM198B, FAM219A, FAM3C, FEZ1, FGD5-AS1, FLII, FN1, FNBP1, FOS, FOSB, FOXKl, FOXM1, FYN, GABPB1, GALC, GALNT1, GBA2, GGCT, GHDC, GMIP, GNA13, GNAS, GNL3L, GOLGA2, GORASP1, GREM1, GSE1, HAUS6, HDAC7, HEG1, HLA-A, HLA-E, HMGA1, HP1BP3, IL6ST, ITGAV, KIAA1549, KIF14, KLC1, KLF6, KLHL7, KRT18, LAMA2, LAMB1, LARP7, LATS2, LGALS8, LIMS1, LINC00341, LONP1, LOX, MDM2, MEPCE, MINPP1, MLLT4, MPPE1, MRPL3, MSH2, MSH6, MSL3, MTMR9, MTRR, MUM1, MYADM, MYLK, NADK, NAV2, NCSTN, NFE2L1, NID1, NIPA1, NPEPPS, NRD1, NUDT4, NUSAP1, P4HB, PABPC1, PAK4, PAPD4, PCNXL2, PDE4A, PDXDC1, PHRF1, PHTF2, PI4K2A, PIK3C2B, PLAU, LEKHB2, PLSCR3, PLXNB2, POSTN, POU2F1, PPPARA, PPP1R12A, PRKACB, PSMD6, PTPN14, PUS7, QKI, RAB34, RAD1, RAD23B, RASSF8, RBCK1, RBFOX2, RFTN1, RNF19A, RNF38, RPS6KC1, RWDD4, SEC14L1, SEC24B, SERPINE2, SF1, SLC39A3, SLC41A1, SLC4A4, SLC7A6, SMARCA4, SMN2, SNHG16, SNX14, SON, SPRED2, STAU1, STEAP2, STRIP1, STRN3, TBL2, TGFBI, TGFBR1, THAP4, TLE3, TMEM47, TNKS1BP1, TOMM40, TOPORS, TRAK1, TRAPPC12, TRIB1, TRIM2, TRIM23, TRIM65, TRMT1L, TRPS1, TXNL1, TXNRD1, U2SURP, UBE2G2, UBE2V1, UHMK1, USP7, VPS29, VWA8, WDR19, WDR37, WIPF1, YPEL5, YTHDF3, Z24749, ZBTB10, ZBTB7A, ZFAND5, ZMIZ1, ZNF12, ZNF148, ZNF335, ZNF395, ZNF583, ZNF621, ZNF655, ZNF74 or ZNF780A. |

Table 3 shows 384 genes that, in the presence of Compound 808 (3 □M), demonstrate an effect on isoform fold increase having a statistically significant adjusted p value of at least 0.01.

TABLE 3

| |
|---|
| ABCB7, ABHD10, ABLIM3, ACACA, ADAM12, ADAM17, ADAM33, AGK, AGPS, AHCYL2, AHDC1, AHRR, AK021888, AK310472, AKAP1, AKAP9, AKNA, AMPD2, ANKRD17, ANKS6, ANP32A, ANXA11, ANXA6, APLP2, APP, APPL2, APTX, ARHGAP22, ARMCX3, ASAP1, ASNS, ASPH, ATG9A, ATP2C1, AURKA, AXIN1, B4GALT2, BACE1, BASP1, BEND6, BICD1, BIN1, BRD2, BRPF1, BTBD10, C11orf30, C11orf73, C17orf76-AS1, C4orf27, C6orf48, CAB39, CAPNS1, CASC3, CCDC77, CCDC88A, CD46, CDC40, CDC42BPA, CDCA7, CDH13, CDK11B, CEP68, CIZ1, CLK4, CNOT1, COG1, COL12A1, COL1A1, COL6A1, COPS7B, CSDE1, CSNK1A1, CUX1, CYB5B, CYBRD1, DAB2, DARS, DCBLD2, DCUN1D4, DDAH2, DDR1, DDX39B, DDX42, DENND1A, DENND1B, DENND5A, DGKA, DHFR, DHX9, DIAPH1, DIAPH3, DIS3L, DNM2, DOCK1, DPP8, DSEL, EEA1, EFCAB14, EIF2B3, EIF4G1, EIF4G3, ELF2, ENG, ENPP2, EPN1, EXTL2, EYA3, FAF1, FAM198B, FAM3C, FBXO10, FBXO18, FBXO31, FBXO9, FER, FEZ1, FHOD3, FLII, FN1, FNBP1, FOCAD, FOSL1, FOXM1, GABPB1, GALC, GALNT1, GCFC2, GGCT, GIGYF2, GMIP, GNAS, GNL3L, GOLGB1, GPR89A, GPSM2, GREM1, GRK6, GTF2H2B, HAT1, HAUS3, HEG1, HLA-A, HLTF, HP1BP3, HRH1, HSD17B12, HSD17B4, HTT, IARS, IDH1, IGF2BP2, ITM2C, KCNK2, KIAA1033, KIAA1143, KIAA1522, KIAA1524, KIAA1715, KIF3A, KLHL7, LAMA2, LARP4, LARP7, LATS2, LIMS1, LINC00341, LINC00657, LMAN2L, LMO7, LRCH4, LRIG1, LRRC8A, LTBR, LUC7L2, LZTS2, MADD, MAGED4B, MAN1A2, MAP4K4, MED1, MEDAG, MEF2D, MEIS2, MEMO1, MICAL2, MKLN1, MLLT4, MMS19, MPZL1, MSANTD3, MSC, MSL3, MTAP, MTERFD1, MTHFD1L, MYADM, MYLK, MYO9B, MYOF, NASP, NAV2, NCOA3, NCOA4, NELFA, NEO1, NEURL1B, NF2, NID2, NOL10, NPEPPS, NRG1, NSUN4, NT5C2, NT5E, NTNG1, NUP153, NUP35, NUP50, NUSAP1, ODF2, OS9, OSBPL6, P4HA1, P4HB, PABPC1, PAPD4, PARN, PARP4, PCBP2, PCBP4, PCDHGB3, PCGF3, PCM1, PCMTD2, PDE7A, PDXDC1, PEPD, PFKP, PHF19, PHRF1, PHTF2, PIEZO1, PIGU, PITPNA, PITPNB, PITPNM1, PLAU, PLSCR3, PLXNC1, PMS1, POU2F1, PPAPDC1A, PPHLN1, PPIP5K1, PPP1R12A, PRKDC, PRMT1, PRSS23, PSMA4, PTK2B, PUF60, PVR, RAB23, RAB2B, RAD1, RAD23B, RAP1A, RAP1GDS1, RARG, RASSF8, RBCK1, RCC1, RFWD2, RGS3, RNF14, RNFT1, RPL10, RRBP1, RWDD4, SAR1A, SCAF4, SCAF8, SCLT1, SCO1, SDCBP, SEC22A, SEPT9, SF1, SGOL2, SLC25A17, SLC4A4, SLC7A6, SMARCC2, SMC4, SMC6, SMCHD1, SMN2, SMPD4, SMYD3, SNAP23, SNHG16, SOCS2, SOS2, SPATA20, SPATS2, SPG20, SQRDL, SREBF1, SREK1, SRSF3, STAT1, STAU1, STEAP2, STRN3, STX16, SUPT20H, SYNE1, SYNE2, SYT15, SYTL2, TAF2, TARBP1, TARS, TBL2, TCF7L2, TENC1, TENM2, TEP1, TET3, TGFBR1, THADA, THRB, TJP2, TLE3, TMEM47, TMEM63A, TNFAIP3, TNIP1, TNPO3, TNS1, TNS3, TOE1, TOMM5, TP53INP1, TRAF3, TRAPPC12, TRIM2, TRIM23, TRIM65, TSC2, TSPAN2, TUBB2C, TXNRD1, UBAP2L, UBE2V1, UCHL5, U5P19, VANGL1, VIPAS39, VPS29, VPS51, VWA8, WDR48, WNT5B, WSB1, WWTR1, XRN2, YAP1, YES1, YPEL5, YTHDF3, Z24749, ZBTB24, ZC3H14, ZFAND1, ZFAND5, ZHX3, ZMIZ1, ZMYM2, ZNF219, ZNF268, ZNF395, ZNF827 or ZNF91. |

Table 4 shows 219 genes that, in the presence of Compound 808 (0.3 □M), demonstrate an effect on isoform fold increase having a statistically significant adjusted p value of at least 0.01.

TABLE 4

| |
|---|
| ACACA, ACADVL, AFF2, AHCYL2, AHRR, AKAP1, ALDH4A1, ANKRD17, AP2B1, APLP2, ASL, ASPH, ATG9A, ATMIN, ATXN3, BAG2, BASP1, BRPF1, BSCL2, C11orf30, C11orf73, C17orf76-AS1, C6orf48, C9orf69, CAB39, CALU, CDC25B, CDC42BPA, CDKAL1, CLIC1, COL12A1, COL1A1, COL6A1, CSNK1A1, CTDSP2, CUL2, CUL4A, DAXX, DCAF10, DDAH1, DDR1, DDX39B, DENND1A, DGCR2, DKFZp434M1735, DKK3, DNM2, DST, EEF1A1, EFCAB14, EHMT2, EIF4G1, EIF4G2, EIF4G3, ENSA, EXO1, FAM111A, FAM198B, FAM65A, FBXO34, FEZ1, FGD5-AS1, FGFRL1, FLII, FN1, FOXK1, FOXM1, FUS, GALC, GALNT1, GAS7, GCFC2, GGCT, |

TABLE 4-continued

| |
|---|
| GJC1, GNA13, GNL3L, GOLGA4, GPR1, GREM1, HEG1, HLA-A, HLA-E, HLTF, HNRNPR, HNRNPUL1, IQCE, ITGB5, ITSN1, KIAA1033, KIF2A, KIF3A, KLC2, LATS2, LIMS1, LINC00341, LINC00657, LONP1, LOX, LUC7L2, MBD1, MBOAT7, MEF2D, MEIS2, MICAL2, MKL1, MKNK2, MLST8, MPPE1, MSL3, MSRB3, MTRR, MYADM, MYLK, MYO1D, NAA35, NAV1, NAV2, NCOA1, NFX1, NKX3-1, NOMO3, NRG1, NUDT4, NUPL1, NUSAP1, OSMR, P4HA1, P4HB, PAPD4, PARD3, PARN, PARP14, PARVB, PCBP2, PCBP4, PCGF3, PDLIM7, PDXDC1, PEX5, PFKP, PHRF1, PI4K2A, POLE3, POLR3D, POSTN, PPARA, PPP6R1, PPP6R2, PRNP, PXN, RAB34, RAD23B, RALB, RAP1A, RASSF8, RBCK1, RBFOX2, RGS10, RIF1, RNF14, RNF19A, SAMD9, SCAF4, SDCBP, SERPINE2, SF1, SH3RF1, SKIL, SLC25A17, SLC4A4, SMG1, SMN2, SNHG16, SREBF1, STAT3, STC2, STEAP2, STRN3, SYNE1, SYNE2, TACC1, TARS, TGFBI, TMEM47, TNC, TNFRSF12A, TNS1, TRAF3, TRIM28, TSC2, TSHZ1, TTC7A, TUBB2C, TUBB3, TXNL1, TXNRD1, UBE2G2, UBE2V1, UBQLN4, UNC5B, USP19, VARS2, VCL, VPS29, WDR37, WIPF1, WWTR1, ZC3H12C, ZCCHC11, ZEB1, ZEB2, ZFAND1, ZFAND5, ZMIZ1, ZNF28, ZNF281, ZNF655, ZNF764 or ZNF839. |

Methods of Preventing and/or Treating Diseases

In another aspect, provided herein are methods for preventing and/or treating a disease associated with the aberrant expression of a product of a gene (e.g., an mRNA transcript or protein), wherein the precursor RNA transcript transcribed from the gene comprises a REMS, the methods comprising administering to a patient in need thereof a compound of Formula (I) or a form thereof, or a pharmaceutical composition comprising a compound of Formula (I) or a form thereof and a pharmaceutically acceptable carrier, excipient or diluent.

In certain embodiments, the gene is any one of the genes disclosed in Tables 1-4 or 6. In certain embodiments, the gene contains a nucleotide sequence encoding a non-endogenous REMS. In one embodiment, provided herein are methods for preventing and/or treating a disease associated with aberrant expression of a product of a gene (e.g., an mRNA, RNA transcript or protein), by way of nonlimiting example, disclosed in Table 6, infra, the methods comprising administering to a patient in need thereof a compound of Formula (I) or a form thereof, or a pharmaceutical composition comprising a compound of Formula (I) or a form thereof and a pharmaceutically acceptable carrier, excipient or diluent.

In another embodiment, provided herein are methods for preventing and/or treating a disease associated with aberrant expression of a product of a gene (e.g., an mRNA, RNA transcript or protein), not disclosed in Tables 1-4, infra, wherein the precursor RNA transcript transcribed from the gene comprises a REMS, the methods comprising administering to a patient in need thereof a compound of Formula (I) or a form thereof, or a pharmaceutical composition comprising a compound of Formula (I) or a form thereof and a pharmaceutically acceptable carrier, excipient or diluent.

In another embodiment, provided herein are methods for preventing and/or treating a disease associated with aberrant expression of a product of a gene (e.g., an mRNA, RNA transcript or protein), by way of nonlimiting example, not disclosed in International Patent Application No. PCT/US2014/071252 (International Publication No. WO 2015/105657 A1), wherein the precursor RNA transcript transcribed from the gene comprises a REMS, the methods comprising administering to a patient in need thereof a compound of Formula (I) or a form thereof, or a pharmaceutical composition comprising a compound of Formula (I) or a form thereof and a pharmaceutically acceptable carrier, excipient or diluent.

In another embodiment, provided herein are methods for preventing and/or treating a disease associated with aberrant expression of a product of a gene (e.g., an mRNA, RNA transcript or protein), not disclosed in Table 6, infra, wherein the precursor RNA transcript transcribed from the gene comprises a REMS, the methods comprising administering to a patient in need thereof a compound of Formula (I) or a form thereof, or a pharmaceutical composition comprising a compound of Formula (I) or a form thereof and a pharmaceutically acceptable carrier, excipient or diluent.

In another embodiment, provided herein are methods for preventing and/or treating a disease associated with aberrant expression of a product of ERGIC3 (e.g., an mRNA, RNA transcript or protein), comprising administering to a patient in need thereof a compound of Formula (I) or a form thereof, or a pharmaceutical composition comprising a compound of Formula (I) or a form thereof and a pharmaceutically acceptable carrier, excipient or diluent. See the example section for additional information regarding the genes in Table 6.

In another aspect, provided herein are methods for preventing and/or treating a disease in which a change in the level of expression of one, two, three or more RNA isoforms encoded by a gene is beneficial to the prevention and/or treatment of the disease, wherein the precursor RNA transcript transcribed from the gene comprises a REMS, the methods comprising administering to a patient in need thereof a compound of Formula (I) or a form thereof, or a pharmaceutical composition comprising a compound of Formula (I) or a form thereof and a pharmaceutically acceptable carrier, excipient or diluent.

In certain embodiments, the gene is any one of the genes disclosed in Tables 1-4 or 6. In certain embodiments, the gene contains a nucleotide sequence encoding the non-endogenous REMS. In one embodiment, provided herein are methods for preventing and/or treating a disease in which the alteration (e.g., increase or decrease) in the expression one, two, three or more RNA isoforms encoded by a gene, by way of nonlimiting example, disclosed in Table 6, infra, is beneficial to the prevention and/or treatment of the disease, the methods comprising administering to a patient in need thereof a compound of Formula (I) or a form thereof, or a pharmaceutical composition comprising a compound of Formula (I) or a form thereof and a pharmaceutically acceptable carrier, excipient or diluent. In another embodiment, provided herein are methods for preventing and/or treating a disease in which the alteration (e.g., increase or decrease) in the expression one, two, three or more RNA isoforms encoded by a gene, not disclosed in Tables 1-4, infra, is beneficial to the prevention and/or treatment of the disease, wherein the precursor RNA transcript transcribed from the gene comprises a REMS, the methods comprising administering to a patient in need thereof a compound of Formula (I) or a form thereof, or a pharmaceutical composition comprising a compound of Formula (I) or a form thereof and a pharmaceutically acceptable carrier, excipient or diluent. In another embodiment, provided herein are methods for preventing and/or treating a disease in which the alteration (e.g., increase or decrease) in the expression one, two, three or more RNA isoforms encoded by a gene, not disclosed in International Patent Application No. PCT/US2014/071252 (International Publication No. WO 2015/105657 A1), is beneficial to the prevention and/or treatment of the disease, wherein the precursor RNA transcript transcribed from the gene comprises a REMS, the methods comprising administering to a patient in need thereof a compound of Formula (I) or a form thereof, or a pharmaceutical composition comprising a compound of Formula (I) or a form thereof and a pharmaceutically acceptable carrier, excipient or diluent. In another embodiment, provided herein are methods for preventing and/or treating a disease in which the alteration (e.g., increase or decrease) in the expression one, two, three or more RNA isoforms encoded by a gene, not disclosed in Table 6, infra, is beneficial to the prevention and/or treatment of the disease, wherein the precursor RNA transcript transcribed from the gene comprises a REMS, the methods comprising administering to a patient in need thereof a compound of Formula (I) or a form thereof, or a pharmaceutical composition comprising a compound of Formula (I) or a form thereof and a pharmaceutically acceptable carrier, excipient or diluent. In another embodiment, provided herein are methods for preventing and/or treating a disease in which the alteration (e.g., increase or decrease) in the expression one, two, three or more RNA isoforms encoded by ERGIC3, is beneficial to the prevention and/or treatment of the disease, the methods comprising administering to a patient in need thereof a compound of Formula (I) or a form thereof, or a pharmaceutical composition comprising a compound of Formula (I) or a form thereof and a pharmaceutically acceptable carrier, excipient or diluent. In a specific embodiment, one, two, three or more RNA isoforms encoded by ERGIC3 are decreased following administration of a compound of Formula (I) or a form thereof and a pharmaceutically acceptable carrier, excipient or diluent. See the example section for additional information regarding the genes in Table 6.

In another aspect, provided herein are methods for preventing and/or treating a disease in which a change in the level of expression of one, two, three or more protein isoforms encoded by a gene is beneficial to the prevention and/or treatment of the disease, wherein the precursor RNA transcript transcribed from the gene comprises a REMS, the methods comprising administering to a patient in need thereof a compound of Formula (I) or a form thereof, or a pharmaceutical composition comprising a compound of Formula (I) or a form thereof and a pharmaceutically acceptable carrier, excipient or diluent.

In certain embodiments, the gene is any one of the genes disclosed in Tables 1-4 or 6. In certain embodiments, the gene contains a nucleotide sequence encoding a non-endogenous REMS. In one embodiment, provided herein are methods for preventing and/or treating a disease in which the alteration (e.g., increase or decrease) in the expression one, two, three or more protein isoforms encoded by a gene, by way of nonlimiting example, disclosed in Table 6, infra, is beneficial to the prevention and/or treatment of the disease, the methods comprising administering to a patient in need thereof a compound of Formula (I) or a form thereof, or a pharmaceutical composition comprising a compound of Formula (I) or a form thereof and a pharmaceutically acceptable carrier, excipient or diluent.

In another embodiment, provided herein are methods for preventing and/or treating a disease in which the alteration (e.g., increase or decrease) in the expression one, two, three or more protein isoforms encoded by a gene, not disclosed in Tables 1-4, infra, is beneficial to the prevention and/or treatment of the disease, wherein the precursor RNA transcript transcribed from the gene comprises a REMS, the methods comprising administering to a patient in need thereof a compound of Formula (I) or a form thereof, or a pharmaceutical composition comprising a compound of Formula (I) or a form thereof and a pharmaceutically acceptable carrier, excipient or diluent.

In another embodiment, provided herein are methods for preventing and/or treating a disease in which the alteration (e.g., increase or decrease) in the expression one, two, three or more protein isoforms encoded by a gene, not disclosed in International Patent Application No. PCT/US2014/071252 (International Publication No. WO 2015/105657 A1), is beneficial to the prevention and/or treatment of the disease, wherein the precursor RNA transcript transcribed from the gene comprises a REMS, the methods comprising administering to a patient in need thereof a compound of Formula (I) or a form thereof, or a pharmaceutical composition comprising a compound of Formula (I) or a form thereof and a pharmaceutically acceptable carrier, excipient or diluent.

In another embodiment, provided herein are methods for preventing and/or treating a disease in which the alteration (e.g., increase or decrease) in the expression one, two, three or more protein isoforms encoded by a gene, not disclosed in Table 6, infra, is beneficial to the prevention and/or treatment of the disease, wherein the precursor RNA transcript transcribed from the gene comprises a REMS, the methods comprising administering to a patient in need thereof a compound of Formula (I) or a form thereof, or a pharmaceutical composition comprising a compound of Formula (I) or a form thereof and a pharmaceutically acceptable carrier, excipient or diluent.

In another embodiment, provided herein are methods for preventing and/or treating a disease in which the alteration (e.g., increase or decrease) in the expression one, two, three or more protein isoforms encoded by ERGIC3, is beneficial to the prevention and/or treatment of the disease, the methods comprising administering to a patient in need thereof a compound of Formula (I) or a form thereof, or a pharmaceutical composition comprising a compound of Formula (I) or a form thereof and a pharmaceutically acceptable carrier, excipient or diluent. In a specific embodiment, one, two, three or more RNA isoforms encoded by ERGIC3 are decreased following administration of a compound of Formula (I) or a form thereof and a pharmaceutically acceptable carrier, excipient or diluent. See the example section for additional information regarding the genes in Table 6.

In some embodiments, the compound of Formula (I) or a form thereof that is administered to a subject is a compound of Formula (II), Formula (III), Formula (IV), Formula (V), Formula (VI), Formula (VII), Formula (VIII), Formula (IX), Formula (X), Formula (XI), Formula (XII), Formula (XIII), or Formula (XIV). In some embodiments, the compound of Formula (I) or a form thereof that is administered to a subject is a compound described herein.

In a specific embodiment, the methods for preventing a disease described herein prevent the onset or development of one or symptoms of the disease. In another embodiment, the methods for preventing a disease described herein prevent the recurrence of the disease or delays the recurrence of the disease. In another embodiment, the methods for treating a disease described herein has one, two or more of the effects: (i) reduce or ameliorate the severity of the disease; (ii) inhibit the progression of the disease; (iii) reduce hospitalization of a subject; (iv) reduce hospitalization length for a subject; (v) increase the survival of a subject; (vi) improve the quality of life of a subject; (vii) reduce the number of symptoms associated with the disease; (viii) reduce or ameliorates the severity of a symptom(s) associated with the disease; (ix) reduce the duration of a symptom(s) associated with the disease; (x) prevent the recurrence of a symptom associated with the disease; (xi) inhibit the development or onset of a symptom of the disease; and/or (xii) inhibit of the progression of a symptom associated with the disease.

In certain embodiments, the disease or disorder prevented and/or treated in accordance with a method described herein is a disease or disorder associated with a gene listed in Table 6. In specific embodiments, the disease or disorder prevented and/or treated in accordance with a method described herein is leukemia, acute myeloid leukemia, colon cancer, gastric cancer, macular degeneration, acute monocytic leukemia, breast cancer, combined methylmalonic aciduria and homocystinuria, cblC type, hepatocellular carcinoma, cone-rod dystrophy, alveolar soft part sarcoma, myeloma, skin melanoma, prostatitis, pancreatitis, pancreatic cancer, retinitis, adenocarcinoma, adenoiditis, adenoid cystic carcinoma, cataract, retinal degeneration, gastrointestinal stromal tumor, Wegener's granulomatosis, sarcoma, myopathy, prostate adenocarcinoma, Alzheimer's disease, hyperprolinemia, acne, tuberculosis, succinic semialdehyde dehydrogenase deficiency, esophagitis, mental retardation, esophageal adenocarcinoma, glycine encephalopathy, Crohn's disease, spina bifida, tuberculosis, autosomal recessive disease, schizophrenia, neural tube defects, lung cancer, myelodysplastic syndromes, amyotropic lateral sclerosis, neuronitis, germ cell tumors, Parkinson's disease, talipes equinovarus, dystrophinopathies, Hodgkin's lymphoma, ovarian cancer, non-Hodgkin's lymphoma, multiple myeloma, chronic myeloid leukemia, ischemia, acute lymphoblastic leukemia, renal cell carcinoma, transitional cell carcinoma, colorectal cancer, chronic lymphocytic leukemia, anaplastic large cell lymphoma, kidney cancer, cerebritis, bladder related disorders, breast cancer, cervical cancer, cleft lip, cleft palate, cervicitis, spasticity, lipoma, scleroderma, Gitelman syndrome, poliomyelitis, paralysis, Aagenaes syndrome, or oculomotor nerve paralysis. In specific embodiments, the disease or disorder prevented and/or treated in accordance with a method described herein is basal cell carcinoma, goblet cell metaplasia, or a malignant glioma. In other specific embodiments, the disease or disorder prevented and/or treated in accordance with a method described herein is a cancer of the liver, breast, lung, prostate, cervix, uterus, colon, pancreas, kidney, stomach, bladder, ovary, or brain.

In certain embodiments, the disease prevented and/or treated in accordance with a method described herein is cancer amenable to treatment by upregulation or downregulation of a gene or isoform thereof as described herein. In specific embodiments, cancers that can be prevented and/or treated in accordance with a method described herein include, but are not limited to, cancer of the head, neck, eye, mouth, throat, esophagus, esophagus, chest, bone, lung, kidney, colon, rectum or other gastrointestinal tract organs, stomach, spleen, skeletal muscle, subcutaneous tissue, prostate, breast, ovaries, testicles or other reproductive organs, skin, thyroid, blood, lymph nodes, kidney, liver, pancreas, brain or central nervous system.

Specific examples of cancers that can be prevented and/or treated in accordance with the methods provided herein include, but are not limited to, the following: renal cancer, kidney cancer, glioblastoma multiforme, metastatic breast cancer; breast carcinoma; breast sarcoma; neurofibroma; neurofibromatosis; pediatric tumors; neuroblastoma; malignant melanoma; carcinomas of the epidermis; leukemias such as but not limited to, acute leukemia, acute lymphocytic leukemia, acute myelocytic leukemias such as myeloblastic, promyelocytic, myelomonocytic, monocytic, erythroleukemia leukemias and myclodysplastic syndrome, chronic leukemias such as but not limited to, chronic myclocytic (granulocytic) leukemia, chronic lymphocytic leukemia, hairy cell leukemia; polycythemia vera; lymphomas such as but not limited to Hodgkin's disease, non-Hodgkin's disease; multiple myelomas such as but not limited to smoldering multiple mycloma, nonsecretory myeloma, osteosclerotic myeloma, plasma cell leukemia, solitary plasmacytoma and extramedullary plasmacytoma; Waldenstrom's macroglobulinemia; monoclonal gammopathy of undetermined significance; benign monoclonal gammopathy; heavy chain disease; bone cancer and connective tissue sarcomas such as but not limited to bone sarcoma, myeloma bone disease, multiple myeloma, cholesteatoma-induced bone osteosarcoma, Paget's disease of bone, osteosarcoma, chondrosarcoma, Ewing's sarcoma, malignant giant cell tumor, fibrosarcoma of bone, chordoma, periosteal sarcoma, soft-tissue sarcomas, angiosarcoma (hemangiosarcoma), fibrosarcoma, Kaposi's sarcoma, leiomyosarcoma, liposarcoma, lymphangiosarcoma, neurilemmoma, rhabdomyosarcoma, and synovial sarcoma; brain tumors such as but not limited to, glioma, astrocytoma, brain stem glioma, ependymoma, oligodendroglioma, nonglial tumor, acoustic neurinoma, craniopharyngioma, medulloblastoma, meningioma, pineocytoma, pineoblastoma, and primary brain lymphoma; breast cancer including but not limited to adenocarcinoma, lobular (small cell) carcinoma, intraductal carcinoma, medullary breast cancer, mucinous breast cancer, tubular breast cancer, papillary breast cancer, Paget's disease (including juvenile Paget's disease) and inflammatory breast cancer; adrenal cancer such as but not limited to pheochromocytom and adrenocortical carcinoma; thyroid cancer such as but not limited to papillary or follicular thyroid cancer, medullary thyroid cancer and anaplastic thyroid cancer; pancreatic cancer such as but not limited to, insulinoma, gastrinoma, glucagonoma, vipoma, somatostatin-secreting tumor, and carcinoid or islet cell tumor; pituitary cancers such as but limited to Cushing's disease, prolactin-secreting tumor, acromegaly, and diabetes insipius; eye cancers such as but not limited to ocular melanoma such as iris melanoma, choroidal melanoma, and cilliary body melanoma, and retinoblastoma; vaginal cancers such as squamous cell carcinoma, adenocarcinoma, and melanoma; vulvar cancer such as squamous cell carcinoma, melanoma, adenocarcinoma, basal cell carcinoma, sarcoma, and Paget's disease; cervical cancers such as but not limited to, squamous cell carcinoma, and adenocarcinoma; uterine cancers such as but not limited to endometrial carcinoma and uterine sarcoma; ovarian cancers such as but not limited to, ovarian epithelial carcinoma, borderline tumor, germ cell tumor, and stromal tumor; cervical carcinoma; esophageal cancers such as but not limited to, squamous cancer, adenocarcinoma, adenoid cyctic carcinoma, mucoepidermoid carcinoma, adenosquamous carcinoma, sarcoma, melanoma, plasmacytoma, verrucous carcinoma, and oat cell (small cell) carcinoma; stomach cancers such as but not limited to, adenocarcinoma, fungating (polypoid), ulcerating, superficial spreading, diffusely spreading, malignant lymphoma, liposarcoma, fibrosarcoma, and carcinosarcoma; colon cancers; KRAS-mutated colorectal cancer; colon carcinoma; rectal cancers; liver cancers such as but not limited to hepatocellular carcinoma and hepatoblastoma, gallbladder cancers such as adenocarcinoma; cholangiocarcinomas such as but not limited to papillary, nodular, and diffuse; lung cancers such as KRAS-mutated non-small cell lung cancer, non-small cell lung cancer, squamous cell carcinoma (epidermoid carcinoma), adenocarcinoma, large-cell carcinoma and small-cell lung cancer; lung carcinoma; testicular cancers such as but not limited to germinal tumor, seminoma, anaplastic, classic (typical), spermatocytic, nonseminoma, embryonal carcinoma, teratoma carcinoma, choriocarcinoma (yolk-sac tumor), prostate cancers such as but not limited to, androgen-independent prostate cancer, androgen-dependent prostate cancer, adenocarcinoma, leiomyosarcoma, and rhabdomyosarcoma; penal cancers; oral cancers such as but not limited to squamous cell carcinoma; basal cancers; salivary gland cancers such as but not limited to adenocarcinoma, mucoepidermoid carcinoma, and adenoidcystic carcinoma; pharynx cancers such as but not limited to squamous cell cancer, and verrucous; skin cancers such as but not limited to, basal cell carcinoma, squamous cell carcinoma and melanoma, superficial spreading melanoma, nodular melanoma, lentigo malignant melanoma, acral lentiginous melanoma; kidney cancers such as but not limited to renal cell cancer, adenocarcinoma, hypernephroma, fibrosarcoma, transitional cell cancer (renal pelvis and/or uterer); renal carcinoma; Wilms' tumor; bladder cancers such as but not limited to transitional cell carcinoma, squamous cell cancer, adenocarcinoma, carcinosarcoma. In addition, cancers include myxosarcoma, osteogenic sarcoma, endotheliosarcoma, lymphangioendotheliosarcoma, mesothelioma, synovioma, hemangioblastoma, epithelial carcinoma, cystadenocarcinoma, bronchogenic carcinoma, sweat gland carcinoma, sebaceous gland carcinoma, papillary carcinoma and papillary adenocarcinomas.

In certain embodiments cancers that can be prevented and/or treated in accordance with the methods provided herein include, the following: pediatric solid tumor, Ewing's sarcoma, Wilms tumor, neuroblastoma, neurofibroma, carcinoma of the epidermis, malignant melanoma, cervical carcinoma, colon carcinoma, lung carcinoma, renal carcinoma, breast carcinoma, breast sarcoma, metastatic breast cancer, HIV-related Kaposi's sarcoma, prostate cancer, androgen-independent prostate cancer, androgen-dependent prostate cancer, neurofibromatosis, lung cancer, non-small cell lung cancer, KRAS-mutated non-small cell lung cancer, malignant melanoma, melanoma, colon cancer, KRAS-mutated colorectal cancer, glioblastoma multiforme, renal cancer, kidney cancer, bladder cancer, ovarian cancer, hepatocellular carcinoma, thyroid carcinoma, rhabdomyosarcoma, acute myeloid leukemia, and multiple myeloma.

In certain embodiments, cancers and conditions associated therewith that are prevented and/or treated in accordance with the methods provided herein are breast carcinomas, lung carcinomas, gastric carcinomas, esophageal carcinomas, colorectal carcinomas, liver carcinomas, ovarian carcinomas, thecomas, arrhenoblastomas, cervical carcinomas, endometrial carcinoma, endometrial hyperplasia, endometriosis, fibrosarcomas, choriocarcinoma, head and neck cancer, nasopharyngeal carcinoma, laryngeal carcinomas, hepatoblastoma, Kaposi's sarcoma, melanoma, skin carcinomas, hemangioma, cavernous hemangioma, hemangioblastoma, pancreas carcinomas, retinoblastoma, astrocytoma, glioblastoma, Schwannoma, oligodendroglioma, medulloblastoma, neuroblastomas, rhabdomyosarcoma, osteogenic sarcoma, leiomyosarcomas, urinary tract carcinomas, thyroid carcinomas, Wilm's tumor, renal cell carcinoma, prostate carcinoma, abnormal vascular proliferation associated with phakomatoses, edema (such as that associated with brain tumors), or Meigs' syndrome. In specific embodiment, the cancer astrocytoma, an oligodendroglioma, a mixture of oligodendroglioma and an astrocytoma elements, an ependymoma, a meningioma, a pituitary adenoma, a primitive neuroectodermal tumor, a medullblastoma, a primary central nervous system (CNS) lymphoma, or a CNS germ cell tumor. In specific embodiments, the cancer treated in accordance with the methods provided herein is an acoustic neuroma, an anaplastic astrocytoma, a glioblastoma multiforme, or a meningioma. In other specific embodiments, the cancer treated in accordance with the methods provided herein is a brain stem glioma, a craniopharyngioma, an ependyoma, a juvenile pilocytic astrocytoma, a medulloblastoma, an optic nerve glioma, primitive neuroectodermal tumor, or a rhabdoid tumor.

Specific examples of conditions that can be prevented and/or treated in accordance with the methods described herein include cystic fibrosis, muscular dystrophy, polycystic autosomal-dominant kidney disease, cancer-induced cachexia, benign prostatic hyperplasia, rheumatoid arthritis, psoriasis, atherosclerosis, obesity, retinopathies (including diabetic retinopathy and retinopathy of prematurity), retrolental fibroplasia, neovascular glaucoma, age-related macular degeneration, exudative macular degeneration, thyroid hyperplasias (including Grave's disease), corneal and other tissue transplantation, epidemic keratoconjunctivitis, Vitamin A deficiency, contact lens overwear, atopic keratitis, superior limbic keratitis, and pterygium keratitis sicca, viral infections, inflammation associated with viral infections, chronic inflammation, lung inflammation, nephrotic syndrome, preeclampsia, ascites, pericardial effusion (such as that associated with pericarditis), pleural effusion, Sjogren's syndrome, acne rosacea, phylectenulosis, syphilis, lipid degeneration, chemical burns, bacterial ulcers, fungal ulcers, Herpes simplex infection, Herpes zoster infections, protozoan infections, Mooren's ulcer, Terrien's marginal degeneration, marginal keratolysis, systemic lupus, polyarteritis, trauma, Wegener's sarcoidosis, Paget's disease, scleritis, Stevens-Johnson's disease, pemphigoid, radial keratotomy, Eales' disease, Behcet's disease, sickle cell anemia, pseudoxanthoma elasticum, Stargardt's disease, pars planitis, chronic retinal detachment, vein occlusion, artery occlusion, carotid obstructive disease, chronic uveitis/vitritis, ocular histoplasmosis, Mycobacteria infections, Lyme's disease, Best's disease, myopia, optic pits, hyperviscosity syndromes, toxoplasmosis, sarcoidosis, trauma, post-laser complications, diseases associated with rubeosis (neovascularization of the iris and of the angle), and diseases caused by the abnormal proliferation of fibrovascular or fibrous tissue, including all forms of prolific vitreoretinopathy. Certain examples of non-neoplastic conditions that can be prevented and/or treated in accordance with the methods described herein include viral infections, including but not limited to, those associated with viruses belonging to Flaviviridae, flavivirus, pestivirus, hepacivirus, West Nile virus, hepatitis C virus (HCV) or human papilloma virus (HPV).

Artificial Gene Constructs

In one aspect, provided herein are artificial gene constructs comprising a REMS. In one embodiment, an artificial gene construct comprises genomic DNA or DNA encoding exons and one, two or more introns, wherein a nucleotide sequence encoding a 5' splice site, which is upstream of a nucleotide sequence a branch point and a nucleotide sequence encoding a 3' splice site, is modified to introduce a nucleotide sequence encoding a REMS. In another embodiment, an artificial gene construct comprises DNA encoding exons, a 5' splice site(s), a 3' splice site(s) and a branch point(s), wherein a nucleotide sequence encoding a 5' splice site, which is upstream of at least one nucleotide sequence encoding a branch point and at least one nucleotide sequence encoding a 3' splice site, is modified to introduce a nucleotide sequence encoding a REMS. In another embodiment, an artificial gene construct comprises DNA encoding exons, a 3' splice site(s) and a branch point(s), wherein a nucleotide sequence encoding an exon, which is upstream of a nucleotide sequence encoding a branch point and a 3' splice site, is modified to introduce a nucleotide sequence encoding a REMS. In some embodiments, an artificial gene construct comprises a DNA sequence that is modified to introduce a nucleotide sequence encoding a REMS, wherein the location of the REMS is as illustrated in any of FIGS. 1A-1D. In certain embodiments, the DNA sequence chosen to be used in the production of an artificial gene construct contains a nucleotide sequence encoding a REMS and an additional nucleotide sequence encoding a REMS is introduced. In specific embodiments, the nucleotide sequence encoding a REMS is a nucleotide sequence encoding a non-endogenous REMS, i.e., not naturally found in the DNA sequence of the artificial gene construct. In certain embodiments, the artificial gene construct comprises other elements, such as a promoter (e.g., a constitutive, inducible or tissue specific promoter), a Poly(A) site, a transcription termination site, and a transcription binding site(s). In certain embodiments, the artificial gene construct comprises at least the exons of a gene encoding a therapeutic protein. In some embodiments, the artificial gene construct comprises at least the exons of a gene listed in Table 1, 2, 3, 4 or 6. In certain embodiments, the artificial gene construct comprises at least the exons of one of the following genes: SMN2, RIG-I, MDA5, LGP2, TLR7, TLR9, interferon gamma, vascular endothelial growth factor (VEGF), HER2, PSK9, Insulin receptor, CHM, growth hormone, IGF1, utrophin (UTRN), or EPO. In other embodiments, the artificial gene construct comprises at least the exons of a detectable reporter gene, such as green fluorescent protein (GFP), yellow fluorescent protein (YFP), red fluorescent protein, beta galactosidase, renilla luciferase, firefly luciferase, etc.

In certain embodiments, an artificial gene construct is produced as follows: a nucleotide sequence encoding a REMS is introduced into a nucleotide sequence encoding an existing 5' splice site of genomic DNA or DNA, wherein the DNA encodes two or more exons and one or more introns, and wherein the nucleotide sequence encoding the existing 5' splice site is upstream of a nucleotide sequence encoding a 3' splice site. In some embodiments, an artificial gene construct is produced as follows: a nucleotide sequence encoding a REMS is introduced upstream of a nucleotide sequence encoding a branch point and a 3' splice site of genomic DNA or DNA, wherein the DNA encodes two or more exons and an intron(s). In a specific embodiment, the nucleotide sequence encoding the REMS is introduced internally within a nucleotide sequence encoding an exon. In certain embodiments, an artificial gene construct is produced as follows: a nucleotide sequence encoding a REMS, a nucleotide sequence encoding a branch point, and a nucleotide sequence encoding a 3' splice site are introduced into a cDNA, wherein the nucleotide sequence encoding the REMS is upstream of the branch point and 3' splice site. The nucleotide sequence encoding the REMS can function as a 5' splice site. In certain embodiments, the nucleotide sequence encoding the REMS is internally within an exon. In a specific embodiment, the genomic DNA or DNA chosen for use in the production of an artificial gene construct does not contain a nucleotide sequence encoding a REMS. In certain embodiments, the genomic DNA or DNA chosen for use in the production of an artificial gene construct contains a REMS and an additional REMS is introduced. In introducing a nucleotide sequence encoding a REMS into a DNA sequence, care should be taken so as not to disrupt an open reading frame or introduce a stop codon. The introduction of a nucleotide sequence encoding a REMS into a DNA sequence may or may not result in an amino acid change at the protein level. In certain embodiments, the introduction of a nucleotide sequence encoding a REMS into a DNA sequence results in an amino acid change at the protein level. In some embodiments, this amino acid change is a conservative amino acid substitution. In other embodiments, the introduction of a nucleotide sequence encoding a REMS into a DNA sequence does not result in an amino acid change at the protein level. Techniques known to one of skill in the art may be used to introduce a REMS and other elements, such as a branch point or 3' splice site into a DNA sequence, e.g., gene editing techniques such as the CRISPR-Cas approach, Transcription Activator-Like Effector Nucleases (TALENs), or Zinc finger nucleases (ZFNs) may be used.

In certain embodiments, an artificial gene construct comprises an RNA sequence comprising exons and one, two or more introns, wherein a 5' splice site, which is upstream of a 3' splice site, is modified to introduce a REMS. In another embodiment, an artificial gene construct comprises an RNA sequence comprising exons, a 5' splice site(s), a 3' splice site(s) and a branch point(s), wherein a 5' splice site, which is upstream of a 3' splice site, is modified to introduce a REMS. In another embodiment, an artificial gene construct comprises an RNA sequence comprising exons, a 3' splice site(s) and a branch point(s), wherein an exon, which is upstream of a 3' splice site, is modified to introduce a REMS. In specific embodiments, the REMS is non-endogenous, i.e., not naturally found in the RNA sequence of the artificial gene construct. In certain embodiments, the artificial gene construct comprises other elements, such as a promoter (e.g., a tissue-specific promoter or constitutively expressed promoter), 5' untranslated region, 3' untranslated region, a binding site(s) for RNA binding proteins, a small molecule RNA sensor(s), e.g., riboswitches, stem-loop structures, and/or internal ribosome entry sites (IRES), etc. In certain embodiments, the artificial gene construct comprises at least the exons of a gene encoding a therapeutic protein. In some embodiments, the artificial gene construct comprises at least the exons of a gene listed in Table 1, 2, 3, 4 or 6. In certain embodiments, the artificial gene construct comprises at least the exons of one of the following genes: SMN2, RIG-I, MDA5, LGP2, TLR7, TLR9, interferon gamma, vascular endothelial growth factor (VEGF), HER2, PSK9, Insulin receptor, CHM, growth hormone, IGF1, utrophin (UTRN), or EPO. In a specific embodiment, the RNA transcript chosen to be used in the production of an artificial gene construct does not contain a REMS. In certain embodiments, the RNA transcript chosen to use in the production of an artificial gene construct contains a REMS and an additional REMS is introduced. In other embodiments, the artificial gene construct comprises at least the exons of a detectable reporter gene, such as green fluorescent protein (GFP), yellow fluorescent protein (YFP), red fluorescent protein, beta galactosidase, renilla luciferase, firefly luciferase, etc.

In certain embodiments, an artificial gene construct is produced as follows: a REMS is introduced into an existing 5' splice site of precursor RNA, wherein the RNA comprises two or more exons and one or more introns, and wherein the existing 5' splice site is upstream of a 3' splice site. In some embodiments, an artificial gene construct is produced as follows: a REMS is introduced upstream of a 3' splice site of precursor RNA, wherein the RNA comprises two or more exons and an intron(s). In a specific embodiment, the REMS is introduced internally within an exon. In certain embodiments, an artificial gene construct is produced as follows: a REMS, branch point, and a 3' splice site are introduced into an mRNA, wherein the REMS is upstream of the branch point and 3' splice site. The REMS can be a 5' splice site. In certain embodiments, the REMS is internally with an exon.

In introducing a REMS into an RNA sequence, care should be taken so as not to disrupt an open reading frame or introduce a stop codon. The introduction of a REMS into an RNA transcript may or may not result in an amino acid change at the protein level. In certain embodiments, the introduction of a REMS into an RNA transcript results in an amino acid change at the protein level. In some embodiments, this amino acid change is a conservative amino acid substitution. In other embodiments, the introduction of a REMS into an RNA transcript does not result in an amino acid change at the protein level. Techniques known to one of skill in the art may be used to introduce a REMS and other elements, such as a branch point or 3' splice site into an RNA transcript.

In some embodiments, an artificial gene construct is present in a viral vector (e.g., an adeno-associated virus (AAV), self-complimentary adeno-associated virus, adenovirus, retrovirus, lentivirus (e.g., Simian immunodeficiency virus, human immunodeficiency virus, or modified human immunodeficiency virus), Newcastle disease virus (NDV), herpes virus (e.g., herpes simplex virus), alphavirus, vaccinia virus, etc.), a plasmid, or other vector (e.g., non-viral vectors, such as lipoplexes, liposomes, polymerosomes, or nanoparticles).

In some embodiments the artificial gene construct is an RNA molecule modified to enable cellular uptake. In certain embodiments, the artificial gene construct is an RNA molecule containing pseudouridine or other modified/artificial nucleotides for enhanced cellular uptake and gene expression.

The use of an artificial gene construct described herein in gene therapy allows one to regulate the amount of a functional protein produced from the construct depending on whether or not a compound described herein is present. The compound is essentially a tunable switch that, depending on the amount and duration of the dose of the compound, regulates the amount of functional protein produced.

In certain embodiments, an RNA transcript transcribed from an artificial gene construct that is DNA would not produce or produce substantially less functional protein in the absence of a compound described herein than the amount of functional protein produced in the presence of a compound described herein. For example, if the artificial gene construct comprises a nucleotide sequence encoding a REMS in a 5' splice site, which is upstream of a nucleotide sequence encoding a 3' splice site, then less splicing would occur in the absence of the compound and this would result in exon skipping which would ultimately result in less functional protein being produced. In a particular example, if there is an IGF1 precursor mRNA containing a REMS-controlled exon, then in the absence of a compound described herein an exon-skipped mRNA is produced which cannot be translated into full length, functional IGF1. However, in the presence of a compound described herein, a full length, functional IGF1 protein is produced. Alternatively, in certain embodiments, an RNA transcript transcribed from an artificial gene construct that is DNA would not produce or would produce substantially less functional protein in the presence of a compound described herein than the amount of functional protein produced in the absence of a compound described herein. For example, if the artificial gene construct comprises a nucleotide sequence encoding a REMS in the middle of an exon, then ectopic splicing would occur in the presence of a compound described herein and this would result in reduction in the production of the functional protein. However, in the absence of a compound described herein, the normal splicing would occur, and the production of the functional protein will not be reduced. Either way, the amount of the functional protein produced can be titrated based on amount of a compound used and duration of exposure to the compound.

In certain embodiments, an artificial gene construct or vector comprising an artificial gene construct is used in cell culture. For example, in a cell(s) transfected with an artificial gene construct or transduced with a vector comprising an artificial gene construct, the amount of a functional protein produced from the artificial gene construct can be altered depending upon whether or not a compound described herein is contacted with the transfected cell(s). For example, if the artificial gene construct comprises a nucleotide sequence encoding a REMS in a 5' splice site, which is upstream of a nucleotide sequence encoding a 3' splice site, then less splicing would occur in the absence of the compound and this would result in exon skipping which would ultimately result in less functional protein being produced. Thus, the use of an artificial gene construct described herein allows one to regulate the amount of a functional protein produced from the construct depending on whether or not a compound described herein is present. In other words, a compound described herein is essentially a switch that regulates the amount of functional protein produced. This regulation of the production of functional protein could be useful, e.g., when trying to assess the role of certain genes or the effects of certain agents on pathways. The amount of the functional protein produced can be modified based on the amount of a compound described herein that is contacted with the transfected cell and/or how long the compound is contacted with the transfected cell.

In certain embodiments, an animal (e.g., a non-human animal, such as a mouse, rat, fly, etc.) is engineered to contain an artificial gene construct or a vector comprising an artificial gene construct. Techniques known to one of skill in the art may be used to engineer such animals. The amount of functional protein produced by this engineered animal can be regulated by whether or not a compound described herein is administered to the animal. The amount of the functional protein produced can be titrated based on the dose and/or the duration of administration of a compound described herein to the engineered animal. In certain embodiments, the artificial gene construct encodes a detectable reporter gene, such as green fluorescent protein (GFP), yellow fluorescent protein (YFP), red fluorescent protein, beta galactosidase, renilla luciferase, firefly luciferase, etc. In accordance with this embodiment, the engineered animal may be used to monitor development at different stages, visualize tissue function, etc. In other embodiments, the artificial gene construct encodes a therapeutic gene product, such as described the gene product of a gene in Tables 1-4 and 6, or one of the following genes: SMN2, RIG-I, MDA5, LGP2, TLR7, TLR9, interferon gamma, vascular endothelial growth factor (VEGF), HER2, PSK9, Insulin receptor, CHM, growth hormone, IGF1, utrophin (UTRN), or EPO. In accordance with this embodiment, the engineered animal may be used to monitor development at different stages or in functional biological studies where a certain protein or protein isoform needs to be expressed only for a period of time and not constitutively, etc.

In certain embodiments, an artificial gene construct or a vector comprising an artificial gene construct are used in gene therapy.

Gene Therapy

In another aspect, provided herein are artificial gene constructs or vectors comprising an artificial gene construct for use in gene therapy. The use of an artificial gene construct described herein in gene therapy allows one to regulate the amount of a functional protein produced from the construct depending on whether or not a compound described herein is present. The compound is essentially a switch that regulates the amount of functional protein produced.

In certain embodiments, an RNA transcript transcribed from an artificial gene construct that is DNA would not produce or produce substantially less functional protein in the absence of a compound described herein than the amount of functional protein produced in the presence of a compound described herein. For example, if the artificial gene construct comprises a nucleotide sequence encoding a REMS in a 5' splice site, which is upstream of a nucleotide sequence encoding a 3' splice site, then less splicing would occur in the absence of the compound and this would result in exon skipping which would ultimately result in less functional protein being produced. In a particular example, if there is an IGF1 precursor mRNA containing a REMS-controlled exon, then in the absence of a compound described herein an exon-skipped mRNA is produced which cannot be translated into full length, functional IGF1. However, in the presence of a compound described herein, a full length, functional IGF1 protein is produced. The amount of the functional protein produced can be titrated based on dose and duration of dosing of the compound. In this example, the IGF1 protein is turned on and off depending upon whether the compound is present, which may be beneficial for a subject to maintain muscle health. Thus, the use of an artificial gene construct or a vector comprising an artificial gene construct is useful may be useful in treating and/or preventing certain conditions or diseases associated with genes, such as those genes described in Tables 1-4 and 5, or the one of the following genes: SMN2, RIG-I, TLR7, TLR9, interferon gamma, vascular endothelial growth factor (VEGF), CHM, growth hormone, IGF1, or EPO. The conditions or diseases may include those described herein. Alternatively, in certain embodiments, an RNA transcript transcribed from an artificial gene construct that is DNA would not produce or would produce substantially less functional protein in the presence of a compound described herein than the amount of functional protein produced in the absence of a compound described herein. For example, if the artificial gene construct comprises a nucleotide sequence encoding a REMS in the middle of an exon, then ectopic splicing would occur in the presence of a compound described herein and this would result in reduction in the production of the functional protein. However, in the absence of a compound described herein, the normal splicing would occur, and the production of the functional protein will not be reduced. The amount of the functional protein produced can be titrated based on dose and duration of dosing of the compound.

An artificial gene construct, a vector comprising the artificial gene construct, or an RNA molecule comprising an artificial gene construct modified to enable cellular uptake may be introduced into cells or administered directly to patients. In one embodiment, an artificial gene construct or a vector comprising the artificial gene construct is introduced into cells ex vivo or in vivo. In a specific embodiment, an artificial gene construct or vector is introduced into a cell(s) ex vivo and the cell(s) may be administered to a subject. Various techniques known to one of skill in the art may be used to introduce an artificial gene construct or vector comprising the artificial gene construct into a cell(s), such as electroporation, transfection, transformation, etc. In another embodiment, an artificial gene construct or vector comprising the artificial gene construct is administered to a subject. The artificial gene constructor vector comprising the artificial gene construct may be administered to a subject by any technique known to one skilled in the art, e.g., intramuscularly, intravenously, subcutaneously, intradermally, topically, intrathecally, intraperitoneally, intratumorally, etc. In some embodiments, the artificial gene construct or vector comprising the artificial gene construct is administered to a subject systemically. In other embodiments, the artificial gene construct or vector comprising the artificial gene construct is administered to a subject locally.

Altering Endogenous Genes

In another aspect, provided herein are method for altering an endogenous gene such that it contains a nucleotide sequence encoding a REMS, or contains an additional nucleotide sequence encoding a REMS (in other words, a REMS not naturally found in the endogenous gene, i.e., a non-endogenous REMS). Techniques known to one of skill in the art can be used to introduce a REMS into an endogenous gene, e.g., the CRISPR-Cas approach, TALEN, or ZFN may be used. In certain embodiments, a nucleotide sequence encoding an existing 5' splice site can be replaced with a REMS or a REMS may be inserted internally within an exon. In introducing a nucleotide sequence encoding a REMS into an endogenous gene, care should be taken so as not to disrupt an open reading frame or introduce a stop codon. The introduction of a nucleotide sequence encoding a REMS into an endogenous gene may or may not result in an amino acid change at the protein level. In certain embodiments, the introduction of a nucleotide sequence encoding a REMS into an endogenous gene results in an amino acid change at the protein level. In some embodiments, this amino acid change is a conservative amino acid substitution. In other embodiments, the introduction of a nucleotide sequence encoding a REMS into an endogenous gene does not result in an amino acid change at the protein level.

Kits

In one aspect, provided herein are kits comprising, in a container, an artificial gene construct or a vector comprising an artificial construct. In certain embodiments, the kits further comprise a compound described herein, in a separate container, and/or a negative control, such as phosphate buffered saline or a compound that does not recognize REMS, in a separate container. In some embodiments, the kits further comprise primers and/or antibodies, in one or more separate containers, for assessing the production of an mRNA transcript from an artificial gene construct and/or protein production therefrom.

In another aspect, provided herein are kits comprising, in one or more containers, the components and/or reagents necessary to produce an artificial gene construct and/or a vector comprising an artificial gene construct. In another aspect, provided herein are kits comprising, in one or more containers, the components and/or reagents necessary to alter an endogenous gene so that it contains a nucleotide sequence encoding a REMS or an additional nucleotide sequence encoding a REMS (in other words, a REMS not naturally found in the endogenous gene, i.e., a non-endogenous REMS). In some embodiments, the kits further comprise primers and/or antibodies, in one or more separate containers, for assessing the production of an mRNA transcript from altered endogenous gene and/or protein production therefrom.

In another aspect, provided herein are kits comprising, in a container, a compound described herein, and instructions for use. In some embodiments, the kits further comprise a negative control, such as phosphate buffered saline or a compound that does not recognize REMS, in a separate container.

EXAMPLES

To describe in more detail and assist in understanding the present description, the following non-limiting biological examples are offered to more fully illustrate the scope of the description and are not to be construed as specifically limiting the scope thereof. Such variations of the present description that may be now known or later developed, which would be within the purview of one skilled in the art to ascertain, are considered to fall within the scope of the present description and as hereinafter claimed. The example below illustrates the existence of a recognition element for splicing modifier (REMS) that is important for the recognition of a compound described herein, and the binding of such a compound to the REMS on a precursor RNA permits or enhances the splicing of the precursor RNA, and suggests the usefulness of the REMS in combination with a compound described herein for modulating RNA splicing, and for modulating the amount of a gene product.

Materials and Methods

Minigene Constructs, Mutagenesis, Transfection, and End-Point RT-PCR Analysis

The SMN2 minigene construct was prepared by PCR amplification of DNA corresponding to a region of the SMN2 gene starting from the 5' end of exon 6 and ending at nucleotide 23 of exon 8 using specific primers (Forward: 5'-CGCGGATCCATAATTCCCCCACCACCTC-3' (SEQ ID NO: 10), reverse 5'-CGCGGATCCGTGCTGCTCTATGCCAGCA-3' (SEQ ID NO: 11)). The PCR fragment was cloned into the BamHI site of a derivative of the original pcDNA 3.1/Hygro vector which was modified as disclosed in United States Patent Publication US2005/0048549. Nucleotide alterations were introduced by site-directed mutagenesis using the GeneArt site-directed mutagenesis system (Life Technologies, Inc.). All mutants of SMN1 and SMN2 in this Example were derived from the SMN2 minigene by a single nucleotide or double nucleotide substitution in exon 7 or intron 7. See Naryshkin et al., Science (2014) 345: 688-93, which is incorporated herein by reference, for a description of the SMN2 minigene.

For plasmid transfections, 15 ng of plasmid DNA were transfected in SMA type 1 patient fibroblasts GM03813 in 96-well plates. Transfections were carried out using Lipofectamine LTX (Life Technologies, Inc.) according to the manufacturer's instructions. To ensure uniform transfection efficiency in cells in the 96-well plate, transfection complex for each mutant was prepared in bulk quantities and incubated with the cells for 30 minutes (reverse transfection). The total mixture of cells and transfection complexes was then distributed into each well of the 96-well plate. The plates were incubated for 16 hours in a cell culture incubator (37° C., 5% $CO_2$, 100% relative humidity). Transfected cells were then treated with Compound 702 at different concentrations (0.5% DMSO) in duplicate for 7 hours. Cells were then lysed with 50 μl of iScript RT-qPCR Sample Preparation Reagent (Bio-Rad Laboratories, Inc). One step RT-PCR was performed using 2 μl of cell lysate and AGPATH-ID ONE-STEP RT-PCR (Life Technologies, Inc.) under the following PCR conditions: Step 1: 48° C. (15 min), Step 2: 95° C. (10 min), Step 3: 95° C. (30 sec), Step 4: 55° C. (30 sec), Step 5: 68° C. (1 min), then repeat Steps 3 to 5 for 35 cycles, then hold at 4° C. To amplify only transcripts derived from the transfected plasmids, PCR was performed with the SMN Forward A primer (GATGCTGATGCTTTGGGAAGT (SEQ ID NO: 12)) which hybridizes to exon 6 of both SMN1 and SMN2 and a reverse primer that hybridizes to plasmid specific sequences. Minigene PCR products were separated on 4% agarose E-gels, stained with ethidium bromide and visualized using a gel imager (UVP).

Endpoint RT-PCR Analysis of Alternatively Spliced mRNAs in Cultured Cells

GM03813 cells derived from a patient with SMA type I (Coriell Institute) were plated at 5,000 cells/well in 200 μl DMEM with 10% FBS in 96-well plates, and incubated for 6 hours in a cell culture incubator (37° C., 5% $CO_2$, 100% relative humidity). Cells were then treated with Compound 702 at different concentrations (in 0.5% DMSO) in duplicate for 24 hours. After removal of the supernatant, cells were lysed in Cells-To-Ct lysis buffer (Life Technologies, Inc.). Reverse transcription was performed using 5 μl of cell lysate and the iScript RT enzyme kit (Bio-Rad Laboratories, Inc). PCR was performed using 5 μl of cDNA and Platinum Taq HiFi DNA Polymerase (Life Technologies, Inc.) under the following PCR conditions: Step 1: 94° C. (2 min), Step 2: 94° C. (30 sec), Step 3: 55° C. (30 sec), Step 4: 68° C. (1 min), then repeat Steps 2 to 4 for 33 cycles, then hold at 4° C. Alternatively spliced mRNAs were identified using primers listed in table 5. PCR products were separated on 2% agarose E-gels, stained with ethidium bromide and visualized using a gel imager (UVP).

TABLE 5

| Primer Name | Sequence |
|---|---|
| APLP2e6F1 | ACGGCACCATGTCAGACAA (SEQ ID NO: 13) |
| APLP2e8R1 | CAACATCATTGGTTGGCAGA (SEQ ID NO: 14) |
| STRN3e7F1 | ACTGCTGAAGATGGTGAAGGA (SEQ ID NO: 15) |
| STRN3e9R1 | CCAGATCAGCTATCATGTCGTAG (SEQ ID NO: 16) |
| RCC1e3F1 | AGACGATCTGCACTTCGCA (SEQ ID NO: 17) |
| RCC1e5e6R1 | GTGAGACCTTCACCTTCTTGC (SEQ ID NO: 18) |
| ERGIC3e6F1 | TGTATGGCTTCTTGGAAGTCAAT (SEQ ID NO: 19) |
| ERGIC3e9e10R1 | GTAGTGGGTCATGTTGATGTTGTC (SEQ ID NO: 20) |
| SMN For | GATGCTGATGCTTTGGGAAGT (SEQ ID NO: 12) |

TABLE 5-continued

| Primer Name | Sequence |
|---|---|
| SMN Rev | CGCTTCACATTCCAGATCTGTC (SEQ ID NO: 21) |
| FOXM1 For | GTGTTGCAGCCCTCGGT (SEQ ID NO: 22) |
| FOXM1 Rev | TGAACTGGAAGCAAAGGAGAA (SEQ ID NO: 23) |
| VPS29e1F1 | CGGTGGTGGTGACTGAGC (SEQ ID NO: 24) |
| VPS29e3R1 | GGGATGTGCAGATCTCCTAAT (SEQ ID NO: 25) |
| GGCTe1F1 | AGATGAGGAGAGTTTTCTGTACTTTG (SEQ ID NO: 26) |
| GGCTe4R1 | TCTCTTGATACTCCAGCGGC (SEQ ID NO: 27) |
| PRKDC e9F1 | GATCTGAAGAGATATGCTGTGCC (SEQ ID NO: 28) |
| PRKDC e12R1 | ACGGTCGTCACCAGTGTCTG (SEQ ID NO: 29) |
| PRKDC e50F1 | GGGTCCCTAAAGATGAAGTGTTA (SEQ ID NO: 30) |
| PRKDC e52R1 | ATTCACCAAAGCCTGGAAGTAT (SEQ ID NO: 31) |
| MADD e20F1 | CAGAAAGTGTAAATACCCCAGTTG (SEQ ID NO: 32) |
| MADD e22R1 | GCTCACACCACTGTCTGCG (SEQ ID NO: 33) |
| LARP7 5'UTRF1 | CTTCCTTGGCTTCGAGTCTCTC (SEQ ID NO: 34) |
| LARP7 e2R1 | CCTGTGTCCTATCATTTGTTTTCTC (SEQ ID NO: 35) |
| LARP7 e1F1 | CGAAAGTAACCGAGACTATCAGG (SEQ ID NO: 36) |
| LARP7 e4R1 | TTCAGTGCTTTCTTCTTCCATT (SEQ ID NO: 37) |
| ARMCX6 e2F1 | CGGCACAAGTTTCAGCGAG (SEQ ID NO: 38) |
| ARMCX6 e4R1 | CAGGGTGAGTAAGGATGGAGGG (SEQ ID NO: 39) |
| GALC e4F1 | GGATACGAGTGGTGGTTGATG (SEQ ID NO: 40) |
| GALC e7R1 | CAGAGATGGACTCCCAGAGATTA (SEQ ID NO: 41) |
| LAMA2 e4F1 | GGATTTTGGAACGCTCTCTT (SEQ ID NO: 42) |
| LAMA2 e6R1 | GAAATATCCTTGACCGAGTAGTAATA (SEQ ID NO: 43) |
| ABHD10e4F1 | GAGAAGGTCGTGGCTCTTATTG (SEQ ID NO: 44) |
| ABHD10e6R1 | GGGCTATGTAACAAGCAGTGATG (SEQ ID NO: 45) |
| FADS2e5F1 | CTGCCAACTGGTGGAATCA (SEQ ID NO: 46) |
| FADS2e8R1 | GATGCCGTAGAAAGGGATGTAG (SEQ ID NO: 47) |
| DIAPH3e10F1 | TCAATGCCCTGGTTACATCTC (SEQ ID NO: 48) |
| DIAPH3e13R1 | ACAATCTGGGATACACACTCATCA (SEQ ID NO: 49) |
| PDIA3e3F1 | CTGCCAACACTAACACCTGTAATA (SEQ ID NO: 50) |
| PDIA3e7R1 | AGTCCTTGCCCTGTATCAAATC (SEQ ID NO: 51) |
| FN1e34F1 | GCTCATCCGTGGTTGTATCAG (SEQ ID NO: 52) |
| FN1e36R1 | GATCGTCTCAGTCTTGGTTCTCC (SEQ ID NO: 53) |
| PARP1e20F1 | AGTGCCAACTACTGCCATACG (SEQ ID NO: 54) |
| PARP1ee23R1 | AATCCTTTCTGAGGTGGTTTAGT (SEQ ID NO: 55) |
| COL1Ae2F1 | CAAGGTGTTGTGCGATGACG (SEQ ID NO: 56) |
| COL1Ae6R1 | GGTTGATTTCTCATCATAGCCATAAG (SEQ ID NO: 57) |
| COLA1e7F1 | CCTCTGGTCCTCGTGGTCTC (SEQ ID NO: 58) |
| COL1Ae12R1 | CCATCCAAACCACTGAAACC (SEQ ID NO: 59) |

TABLE 5-continued

| Primer Name | Sequence |
|---|---|
| COLA1e27F1 | GGTCCTGCTGGCAAAGATG (SEQ ID NO: 60) |
| COLA1e31R1 | GCTCGCCAGGGAAACCTC (SEQ ID NO: 61) |
| COLA1e31F1 | AGGCGAGAGAGGTTTCCCT (SEQ ID NO: 62) |
| COLA1e33e34R1 | GGACCACTTTCACCCTTGTCA (SEQ ID NO: 63) |
| COLA1e47F1 | GGGCGACAGAGGCATAAAG (SEQ ID NO: 64) |
| COLA1e48R1 | TCACGGTCACGAACCACATT (SEQ ID NO: 65) |
| COL1A2e20F1 | CAAAGGAGAGAGCGGTAACAAG (SEQ ID NO: 66) |
| COL1A2e22R1 | AAGACCACGAGAACCAGGACTA (SEQ ID NO: 67) |
| COL1A2e22F1 | CCTGGTTCTCGTGGTCTTC (SEQ ID NO: 68) |
| COL1A2e24e25R1 | GCCGACAGGACCTTCTTT (SEQ ID NO: 69) |
| COL1A2e29F1 | TGGCAAACCAGGAGAAAGG (SEQ ID NO: 70) |
| COL1A2e31R1 | AAGGACCTCGGCTTCCAATA (SEQ ID NO: 71) |
| COL3A1e7e8F1 | GGCAAGCTGGTCCTTCAG (SEQ ID NO: 72) |
| COL3A1e11R1 | GGAGCACCTGTTTCACCCT (SEQ ID NO: 73) |
| COL3A1e45F1 | TGACAAAGGTGAAACAGGTGAAC (SEQ ID NO: 74) |
| COL3A1e47R1 | GTCCACTGGGTCCAACAGGT (SEQ ID NO: 75) |
| COL5A2e10e11F1 | AATGGGTCCGATTGGTTCAC (SEQ ID NO: 76) |
| COL52Ae16R1 | CAAGTCTCCCTCTCTCTCCTGG (SEQ ID NO: 77) |
| COL52Ae30F1 | GGTGAAAGAGGAGAACAAGGA (SEQ ID NO: 78) |
| COL52Ae33R1 | TCACCAGGGAGTCCAGTTAT (SEQ ID NO: 79) |
| COL52Ae33F1 | AGAACCTGGGATAACTGGACTC (SEQ ID NO: 80) |
| COL5A2e35e36R1 | AGACCTCTTGCACCATCATTT (SEQ ID NO: 81) |
| COL5A2e33F1 | AGGGAATGGCTGGAGGA (SEQ ID NO: 82) |
| COL5A2e36R1 | CCCAAAGGACCTGGAAGAC (SEQ ID NO: 83) |
| COL5A2e48F1 | AGGACCTCGTGGTGACAAAG (SEQ ID NO: 84) |
| COL5A2e50R1 | GCCCAGGGTTTCCTTCTTTA (SEQ ID NO: 85) |
| SMNe4F1 | GATGAAAGTGAGAACTCCAGGTC (SEQ ID NO: 86) |
| SMNe6R1 | CAAAGCATCAGCATCATCAAG (SEQ ID NO: 87) |

Results

Figure 2A:
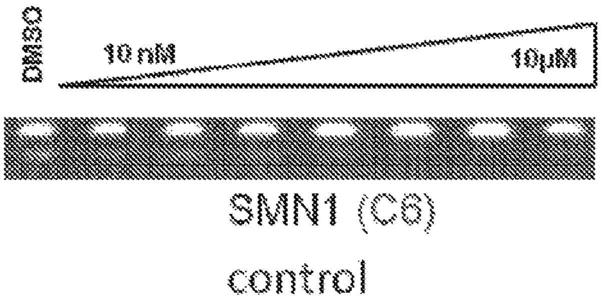
FIGS. 2A and 2B. SMN1 mutant C6 showed compound-dependent increased inclusion of exon 7 (FIG. 2A). The secondary structure of TSL2 (terminal stem loop 2) in SMN2. (Sequence shown is AUUCCUUAAAUUAAGGAguaagu (SEQ ID NO: 118) (FIG. 2B)).

SMN1 mutant C6 (i.e., single substitution of original nucleotide T6 of exon 7 to C6) showed compound-dependent increased inclusion of exon 7, demonstrating that the C6/T is not the working site of the compound (FIG. 2A).

Figure 2B:
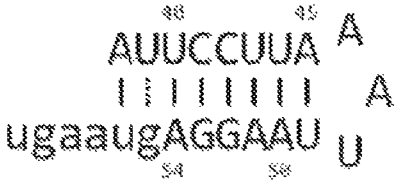
Figure 3A:
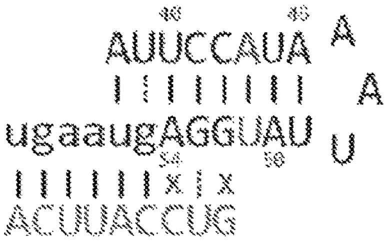
FIGS. 3A and 3B. Exemplary mutations introduced into TSL2 in SMN2. (Sequences shown are AUUCCAUAAAUUAUGGAguaagu (SEQ ID NO: 119) and ACUUACCUG (SEQ ID NO: 120) (FIG. 3A)). SMN2 T43A51T mutant was resistant to compound-dependent inclusion of exon 7 (FIG. 3B).
Figure 3B:
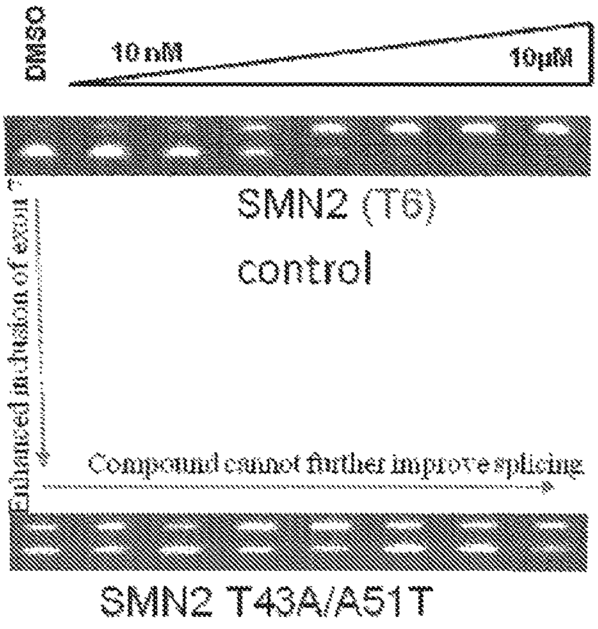
Figure 4A:
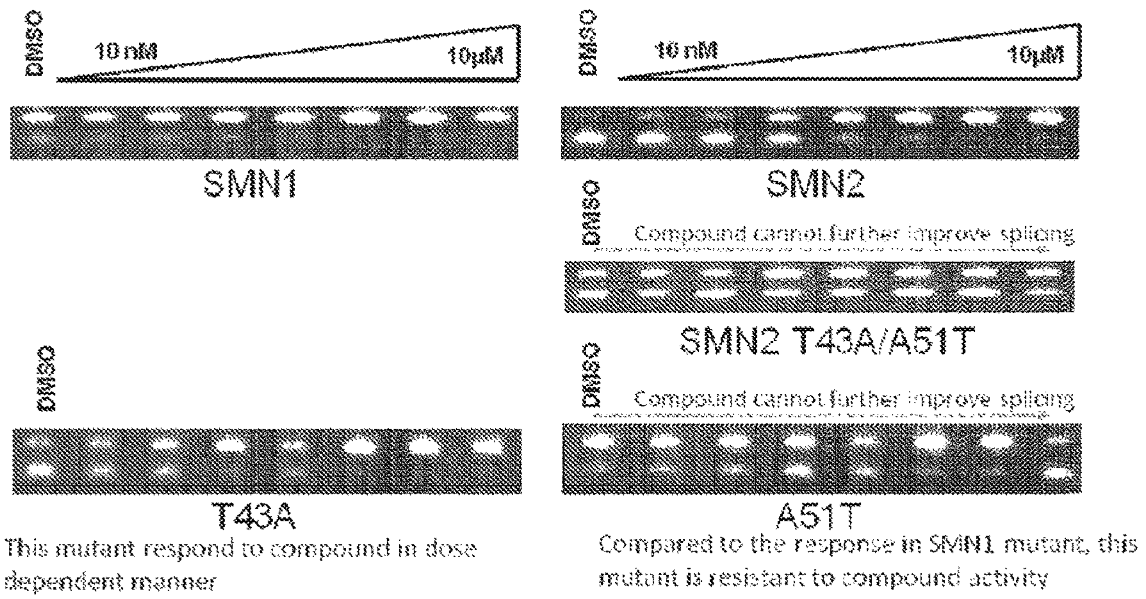
FIGS. 4A and 4B. The resistance of SMN2 T43A51T mutant to compound-dependent inclusion of exon 7 is driven by the A51 mutation.
Figure 4B:
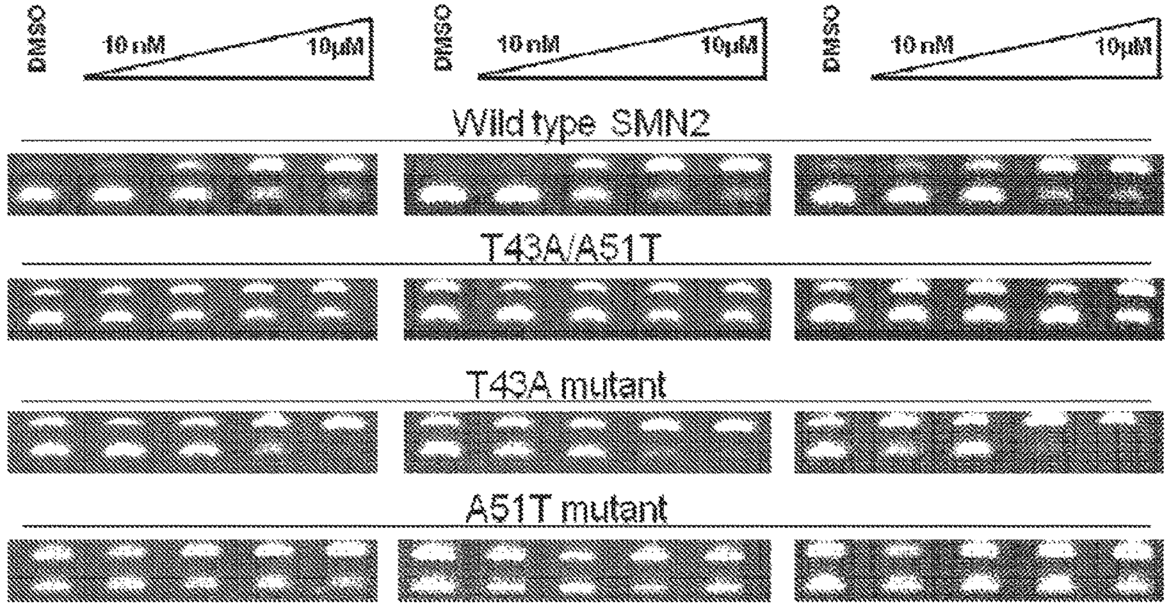

The initial work was focused on investigating the secondary structure of TSL2 (terminal stem loop 2, a predicted secondary structure in SMN2, not found in other responsive genes) as a potential working site of the compounds (FIG. 2B). Several mutations in that region were introduced to study the effect of the compounds on these mutants. One of the mutants particularly, SMN2 T43A, A51T (FIG. 3A), resulted in enhanced inclusion of exon 7 compare to wild-type SMN. However this mutant was resistant to compound-dependent inclusion of exon 7. No further enhancement of exon 7 inclusion could be achieved above baseline splicing in this mutant (FIGS. 3B, 4A, 4B), and the effect appeared to be driven by A51 mutant, since the effect was more pronounced with A51T single nucleotide change mutant (FIGS. 4A, 4B).

Figures 5A, 5B:
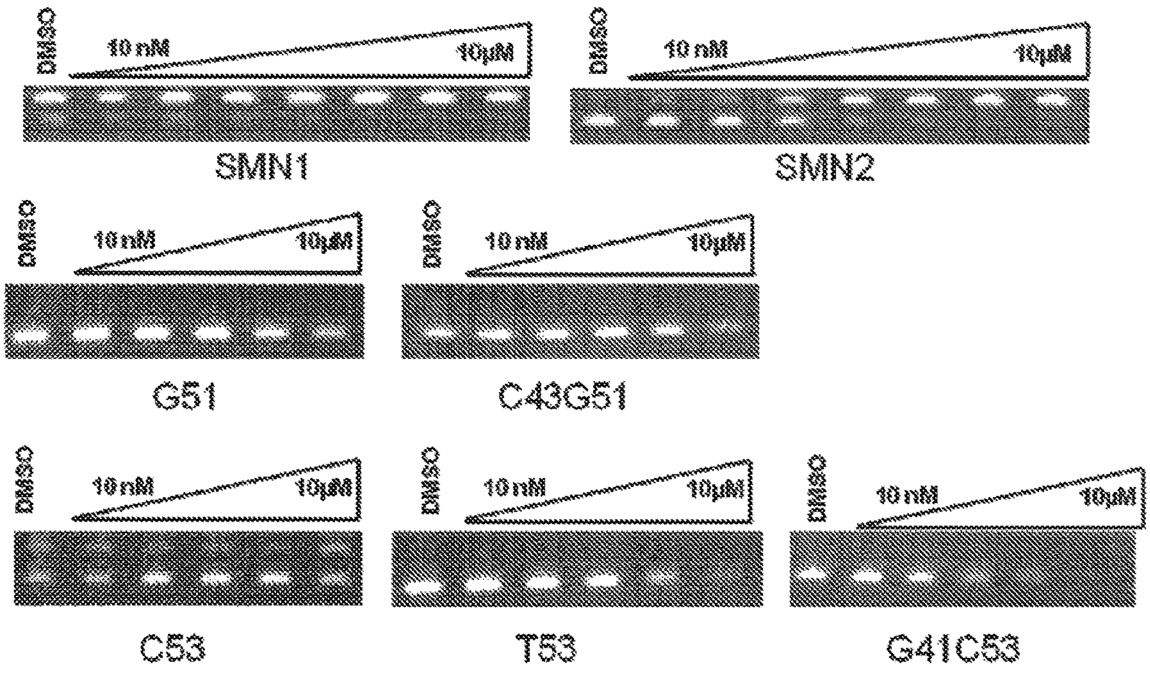
FIGS. 5A and 5B. REMS of SMN2 (sequence is AGGAguaagu (SEQ ID NO: 88) (FIG. 5A). Additional mutants confirmed the functional role of the REMS in SMN2 (FIG. 5B).

Additional mutants confirmed the functional role of a recognition element for splicing modifier (REMS) in SMN1 and SMN2 (FIG. 5A). The SMN2 G51, SMN2 C43G51 and SMN2 G43C51 mutants further demonstrated the functional role of A51, with decreased (G51, C43G51) inclusion of exon 7 compared to wild-type SMN2, (compare DMSO lanes), these mutants did not respond to compound (FIG. 5B). The SMN2 C53, SMN2 T53 and SMN2 G41C53 mutants further demonstrated the functional role of G53, with decreased (T53, G41C53) or increased (G41C53) inclusion of exon 7 compared to wild-type SMN2, (compare DMSO lanes), these mutants did not respond to compound FIG. 5B).

Figure 6:
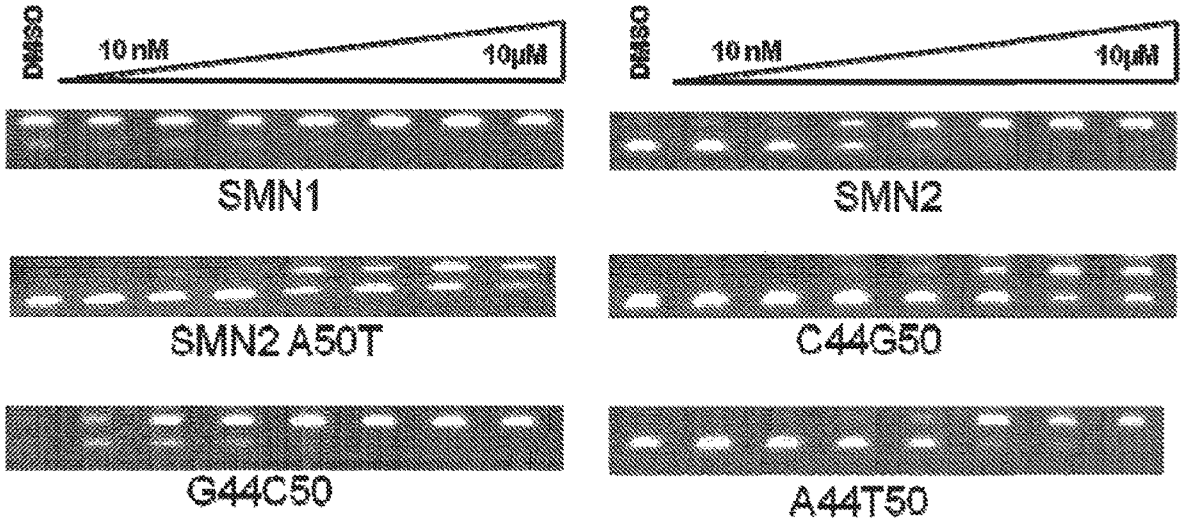
FIG. 6. Mutations outside of the REMS does not affect the activity of the compound on splicing.

In addition, the activity of the compound on splicing is maintained in mutations outside of the REMS (FIG. 6). The SMN2 A50T, SMN2 C44G50, SMN2 G44C50, SMN2 A44T50 mutants with either a decreased or an increased inclusion of exon 7 compared to wild-type SMN2, (compare DMSO lanes), showed compound-dependent increased inclusion of exon 7, demonstrating that position is not the interaction (direct or functional) site of the compound (FIG. 6).

Besides, testing the alternatively spliced mRNAs of additional genes also confirmed the existence of a consensus REMS. Testing results of alternatively spliced mRNAs are shown in Table 6 (affected genes), Table 7 (all genes tested) and FIGS. 7A-7L (correspond to Table 6), and are also summarized below:

For SMN2, the RT-PCR data showed that AGGAguaagu (SEQ ID NO: 88) sequence motif resulted in a compound-dependent increase in the inclusion of exon 7 of SMN2 (increase from 40% to 100%.

For FOXM1, ATCAgtaagt (SEQ ID NO: 89) sequence motif resulted in selectivity against the inclusion of exon 7A of FOXM1 in the presence of the compound. Only 10% increase in exon 7A inclusion was observed. However the upstream 5' alternative splicing site within exon 7A of FOXM1 with the sequence motif of ATGAgtaagt (SEQ ID NO: 90) (30 nucleotides downstream from the start of exon 7A) resulted in increased inclusion of exon 7A ΔC up to 90%.

For APLP2, ATGA (SEQ ID NO: 91) sequence motif resulted in a compound-dependent increase in the inclusion of exon 7 of APLP2 (increase from 10% to 30%).

For GGCT, ATGA (SEQ ID NO: 91) sequence motif resulted in a compound-dependent increase in the inclusion of exon 2 of GGCT (increase from 40% to 95%).

For ABHD10, ATGA (SEQ ID NO: 91) sequence motif resulted in a compound-dependent increase in the inclusion of exon 5 of ABHD10 (increase from 10% to 30%).

For STRN3, AAGA (SEQ ID NO: 92) sequence motif resulted in a compound-dependent increase in the inclusion of exon 8 of STRN3 (increase from 10% to 100%).

For VPS29, CAGA (SEQ ID NO: 93) sequence motif resulted in a compound-dependent increase in the inclusion of exon 2 of VPS29. Notably this exon consist of only 12 nucleotides.

For ERGIC3, GAGA (SEQ ID NO: 94) sequence motif resulted in a compound-dependent increase in the inclusion of exon 8 of ERGIC3 (increase from 0% to 10%).

For MADD, CAGA (SEQ ID NO: 93) sequence motif resulted in a compound-dependent increase in the inclusion of exon 21 of MADD (increase from 0% to 5%).

For LARP7, CGGA (SEQ ID NO: 95) sequence motif resulted in a compound-dependent increase in the inclusion of part of exon 1 of LARP7 (increase from 0% to 10%).

For LARP7, AAGA (SEQ ID NO: 92) sequence motif resulted in a compound-dependent increase in the inclusion of exon 2 of LARP7 (increase from 5% to 40%).

For COL1A1, AAGA (SEQ ID NO: 92) sequence motif result in a compound-dependent increase in the inclusion of exon 30 of COL1A1 (increase from 60% to 90%).

TABLE 6

Alternative splicing results of affected genes.

| Ser # | Gene | Exon | Sequence | Compound Tested | % Inclusion of Exon | % Inclusion of Exon with Compound |
|---|---|---|---|---|---|---|
| 1 | SMN2 | exon 7 | AGGAgtaagt (SEQ ID NO: 96) | Compound 702 | 40 | 100 |
| 2 | FOXM1 | exon 7A (114 nucleotides) | ATCAgtaagt (SEQ ID NO: 89) | Compound 702 | 0 | 10 |
| 3 | FOXM1 | exon 7A □C (34 nucleo-tides) | ATGAgtaagt (SEQ ID NO: 90) | Compound 702 | 0 | 90 |
| 4 | APLP2 | exon 7 | ATGAgtaagt (SEQ ID NO: 90) | Compound 702 | 10 | 30 |
| 5 | GGCT | exon 2 | ATGAgtaggt (SEQ ID NO: 97) | Compound 702 | 40 | 95 |
| 6 | ABHD10 | exon 5 | ATGAgtatgt (SEQ ID NO: 98) | Compound 702 | 10 | 30 |
| 7 | STRN3 | exon 8 | AAGAgtaagt (SEQ ID NO: 99) | Compound 702 | 10 | 100 |
| 8 | VPS29 | exon 2 | CAGAgtaagt (SEQ ID NO: 100) | Compound 702 | 40 | 100 |
| 9 | ERGIC3 | exon 8 | GAGAgtaagt (SEQ ID NO: 101) | Compound 702 | 0 | 10 |
| 10 | MADD | exon 21 | CAGAgtaagg (SEQ ID NO: 102) | Compound 702 | 0 | 5 |
| 11 | LARP7 | exon 1 | CGGAgtaagt (SEQ ID NO: 103) | Compound 702 | 0 | 10 |

TABLE 6-continued

| Alternative splicing results of affected genes. | | | | | | |
|---|---|---|---|---|---|---|
| Ser # | Gene | Exon | Sequence | Compound Tested | % Inclusion of Exon | % Inclusion of Exon with Compound |
| 12 | LARP7 | exon 2 | AAGAgtaaga (SEQ ID NO: 104) | Compound 702 | 10 | 40 |
| 13 | COL1A1 | exon 30 | AAGAgtaagt (SEQ ID NO: 99) | Compound 702 | 60 | 90 |

TABLE 7

| Alternative splicing of all genes tested. | | | | | | |
|---|---|---|---|---|---|---|
| Ser # | Gene | Exon | Sequence | Compound Tested | % Inclusion of Exon | % Inclusion of Exon with Compound |
| 1 | SMN2 | exon 7 | AGGAgtaagt (SEQ ID NO: 96) | Compound 702 | 40 | 100 |
| 2 | FOXM1 | exon 7A (114 nucleo-tides) | ATCAgtaagt (SEQ ID NO: 89) | Compound 702 | 0 | 10 |
| 3 | FOXM1 | exon 7A □C (34 nucleotides) | ATGAgtaagt (SEQ ID NO: 90) | Compound 702 | 0 | 90 |
| 5 | APLP2 | exon 7 | ATGAgtaagt (SEQ ID NO: 90) | Compound 702 | 10 | 30 |
| 8 | GGCT | exon 2 | ATGAgtaggt (SEQ ID NO: 97) | Compound 702 | 40 | 95 |
| 18 | ABHD10 | exon 5 | ATGAgtatgt (SEQ ID NO: 98) | Compound 702 | 20 | 80 |
| 4 | STRN3 | exon 8 | AAGAgtaagt (SEQ ID NO: 99) | Compound 702 | 10 | 100 |
| 6 | VP529 | exon 2 | CAGAgtaagt (SEQ ID NO: 100) | Compound 702 | 40 | 100 |
| 7 | ERGIC3 | exon 8 | GAGAgtaagt (SEQ ID NO: 101) | Compound 702 | 0 | 10 |
| 15 | MADD | exon 21 | CAGAgtaagg (SEQ ID NO: 102) | Compound 702 | 0 | 5 |
| 16 | LARP 7 | exon 1 | CGGAgtaagt (SEQ ID NO: 103) | Compound 702 | 0 | 10 |
| 17 | LARP 7 | exon 2 | AAGAgtaaga (SEQ ID NO: 104) | Compound 702 | 10 | 40 |
| 10 | ARMCX6 | exon 3 | TAGAgtatga (SEQ ID NO: 105) | Compound 702 | 0 | no change |
| 11 | GALC | exon 5 | TGGAgttagt (SEQ ID NO: 106) | Compound 702 | 90 | no change |
| 12 | LAMA2 | exon 5 | AAGAgtaagt (SEQ ID NO: 99) | Compound 702 | 100 | no change |
| 13 | PRKDC | exon 11 | AGGAgtatgt (SEQ ID NO: 107) | Compound 702 | 100 | no change |
| 14 | PRKDC | exon 51 | GCGAgtacgt (SEQ ID NO: 108) | Compound 702 | 100 | no change |
| 9 | RCC 1 | exon 4 | AGAGgtaaga (SEQ ID NO: 109) | Compound 702 | 90 | no change |

TABLE 7-continued

Alternative splicing of all genes tested.

| Ser # | Gene | Exon | Sequence | Compound Tested | % Inclusion of Exon | % Inclusion of Exon with Compound |
|---|---|---|---|---|---|---|
| 19 | FADS2 | exon 6 | CTGAgtaagt (SEQ ID NO: 110) | Compound 702 | 100 | no change |
| 20 | DIAPH3 | exon 11 | TTGAatatcc (SEQ ID NO: 111) | Compound 702 | 100 | no change |
| 21 | FN1 | exon 35 | GAGAgtaagt (SEQ ID NO: 101) | Compound 702 | 100 | no change |
| 22 | PARP1 | exon 22 | ACGAgtatcc (SEQ ID NO: 112) | Compound 702 | 100 | no change |
| 23 | COL1A1 | exon 5 | AGGAgtaagt (SEQ ID NO: 96) | Compound 702 | 0 | no change |
| 24 | COL1A1 | exon 11 | CAGAgtgagt (SEQ ID NO: 113) | Compound 702 | 100 | no change |
| 25 | COL1A1 | exon 30 | AAGAgtaagt (SEQ ID NO: 99) | Compound 702 | 60 | 90 |
| 26 | COL1A1 | exon 32 | CAGAgtaagt (SEQ ID NO: 100) | Compound 702 | 90 | no change |
| 27 | COL1A1 | exon 46 | CCGAgtaagt (SEQ ID NO: 114) | Compound 702 | 100 | no change |
| 28 | COL1A2 | exon 21 | GAGAgtaggt (SEQ ID NO: 115) | Compound 702 | 100 | no change |
| 29 | COL1A2 | exon 22 | CAGAgtaagt (SEQ ID NO: 100) | Compound 702 | 100 | no change |
| 30 | COL1A2 | exon 30 | AAGAgtaagt (SEQ ID NO: 99) | Compound 702 | 100 | no change |
| 31 | COL3A1 | exon 10 | CAGAgtaagt (SEQ ID NO: 100) | Compound 702 | 100 | no change |
| 32 | COL3A1 | exon 46 | CAGAgtaagt (SEQ ID NO: 100) | Compound 702 | 100 | no change |
| 33 | COL5A2 | exon 13 | CCGAgtaagt (SEQ ID NO: 114) | Compound 702 | 100 | no change |
| 34 | COL5A2 | exon 32 | TAGAgtaagt (SEQ ID NO: 116) | Compound 702 | 100 | no change |
| 35 | COL5A2 | exon 34 | CAGAgtaagt (SEQ ID NO: 100) | Compound 702 | 100 | no change |
| 36 | COL5A2 | exon 35 | AAGAgtaagt (SEQ ID NO: 99) | Compound 702 | 100 | no change |
| 37 | COL5A2 | exon 49 | AAGAgtaagt (SEQ ID NO: 99) | Compound 702 | 90 | no change |
| 38 | SMN2 | exon 5 | ACCAgtaagt (SEQ ID NO: 117) | Compound 702 | 50 | no change |

It will be appreciated that, although specific embodiments of the invention have been described herein for purposes of illustration, the invention described herein is not to be limited in scope by the specific embodiments herein disclosed. These embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description, which modification also intended to be within the scope of this invention.

All references cited herein are incorporated herein by reference in their entirety and for all purposes to the same extent as if each individual publication or patent or patent application was specifically and individually indicated to be incorporated by reference in its entirety for all purposes.

SEQUENCE LISTING

<160> NUMBER OF SEQ ID NOS: 120

<210> SEQ ID NO 1
<211> LENGTH: 8
<212> TYPE: RNA
<213> ORGANISM: Artificial Sequence
<220> FEATURE:
<223> OTHER INFORMATION: A variant of recognition element for splicing modifier(REMS)
<220> FEATURE:
<221> NAME/KEY: misc_feature
<222> LOCATION: 6, 8
<223> OTHER INFORMATION: n = A,U,C or G

<400> SEQUENCE: 1 gagurngn 8

<210> SEQ ID NO 2
<211> LENGTH: 8
<212> TYPE: RNA
<213> ORGANISM: Artificial Sequence
<220> FEATURE:
<223> OTHER INFORMATION: A variant of recognition element for splicing modifier(REMS)

<400> SEQUENCE: 2 gaguragu 8

<210> SEQ ID NO 3
<211> LENGTH: 10
<212> TYPE: RNA
<213> ORGANISM: Artificial Sequence
<220> FEATURE:
<223> OTHER INFORMATION: A variant of recognition element for splicing modifier(REMS)
<220> FEATURE:
<221> NAME/KEY: misc_feature
<222> LOCATION: 2, 8, 10
<223> OTHER INFORMATION: n = A,T,C or G

<400> SEQUENCE: 3 angagurngn 10

<210> SEQ ID NO 4
<211> LENGTH: 10
<212> TYPE: RNA
<213> ORGANISM: Artificial Sequence
<220> FEATURE:
<223> OTHER INFORMATION: A variant of recognition element for splicing modifier(REMS)
<220> FEATURE:
<221> NAME/KEY: misc_feature
<222> LOCATION: 2
<223> OTHER INFORMATION: n = A,T,C or G

<400> SEQUENCE: 4 angaguragu 10

<210> SEQ ID NO 5
<211> LENGTH: 8
<212> TYPE: DNA
<213> ORGANISM: Artificial Sequence
<220> FEATURE:
<223> OTHER INFORMATION: nucleotide sequence of a non-endogenous REMS introduced into the nucleotide sequence of the artificial gene construct
<220> FEATURE:
<221> NAME/KEY: misc_feature
<222> LOCATION: 6, 8
<223> OTHER INFORMATION: n = A,T,C or G

<400> SEQUENCE: 5 gagtrngn 8

<210> SEQ ID NO 6
<211> LENGTH: 8
<212> TYPE: DNA
<213> ORGANISM: Artificial Sequence
<220> FEATURE:
<223> OTHER INFORMATION: A variant of recognition element for splicing modifier(REMS)

<400> SEQUENCE: 6 gagtragt 8

<210> SEQ ID NO 7
<211> LENGTH: 10
<212> TYPE: DNA
<213> ORGANISM: Artificial Sequence
<220> FEATURE:
<223> OTHER INFORMATION: A variant of recognition element for splicing modifier(REMS)
<220> FEATURE:
<221> NAME/KEY: misc_feature
<222> LOCATION: 2, 8, 10
<223> OTHER INFORMATION: n = A,T,C or G

<400> SEQUENCE: 7 angagtrngn 10

<210> SEQ ID NO 8
<211> LENGTH: 10
<212> TYPE: DNA
<213> ORGANISM: Artificial Sequence
<220> FEATURE:
<223> OTHER INFORMATION: A variant of recognition element for splicing modifier(REMS)
<220> FEATURE:
<221> NAME/KEY: misc_feature
<222> LOCATION: 2
<223> OTHER INFORMATION: n = A,T,C or G

<400> SEQUENCE: 8 angagtragt 10

<210> SEQ ID NO 9
<211> LENGTH: 4
<212> TYPE: DNA
<213> ORGANISM: Artificial Sequence
<220> FEATURE:
<223> OTHER INFORMATION: A nucleotide sequence has affinity with U1 snRNP
<220> FEATURE:
<221> NAME/KEY: misc_feature
<222> LOCATION: 2
<223> OTHER INFORMATION: n = A,T,C or G

<400> SEQUENCE: 9 anga 4

<210> SEQ ID NO 10
<211> LENGTH: 28
<212> TYPE: DNA
<213> ORGANISM: Artificial Sequence
<220> FEATURE:
<223> OTHER INFORMATION: Forward primer used for preparing SNM2 minigene construct

<400> SEQUENCE: 10
cgcggatcca taattccccc accacctc 28

<210> SEQ ID NO 11
<211> LENGTH: 28
<212> TYPE: DNA
<213> ORGANISM: Artificial Sequence
<220> FEATURE:
<223> OTHER INFORMATION: Reverse primer used for preparing SNM2 minigene construct

<400> SEQUENCE: 11
cgcggatccg tgctgctcta tgccagca 28

<210> SEQ ID NO 12
<211> LENGTH: 21
<212> TYPE: DNA
<213> ORGANISM: Artificial Sequence
<220> FEATURE:
<223> OTHER INFORMATION: Forward primer used for amplifying only transcripts derived from the transfected plasmids

<400> SEQUENCE: 12
gatgctgatg ctttgggaag t 21

<210> SEQ ID NO 13
<211> LENGTH: 19
<212> TYPE: DNA
<213> ORGANISM: Artificial Sequence
<220> FEATURE:
<223> OTHER INFORMATION: primer used for identifying alternatively spliced mRNAs -APLP2e6F1

<400> SEQUENCE: 13
acggcaccat gtcagacaa 19

<210> SEQ ID NO 14
<211> LENGTH: 20
<212> TYPE: DNA
<213> ORGANISM: Artificial Sequence
<220> FEATURE:
<223> OTHER INFORMATION: Primer used for identifying alternatively spliced mRNAs - APLP2e8R1

<400> SEQUENCE: 14
caacatcatt ggttggcaga 20

<210> SEQ ID NO 15
<211> LENGTH: 21
<212> TYPE: DNA
<213> ORGANISM: Artificial Sequence
<220> FEATURE:
<223> OTHER INFORMATION: Primer used for identifying alternatively spliced mRNAs - STRN3e7F1

<400> SEQUENCE: 15
actgctgaag atggtgaagg a 21

<210> SEQ ID NO 16
<211> LENGTH: 23
<212> TYPE: DNA
<213> ORGANISM: Artificial Sequence
<220> FEATURE:
<223> OTHER INFORMATION: Primer used for identifying alternatively spliced mRNAs - STRN3e9R1

<400> SEQUENCE: 16

-continued ccagatcagc tatcatgtcg tag 23

<210> SEQ ID NO 17
<211> LENGTH: 19
<212> TYPE: DNA
<213> ORGANISM: Artificial Sequence
<220> FEATURE:
<223> OTHER INFORMATION: Primer used for identifying alternatively spliced mRNAs - RCC1e3F1

<400> SEQUENCE: 17
agacgatctg cacttcgca 19

<210> SEQ ID NO 18
<211> LENGTH: 21
<212> TYPE: DNA
<213> ORGANISM: Artificial Sequence
<220> FEATURE:
<223> OTHER INFORMATION: Primer used for identifying alternatively spliced mRNAs - RCC1e5e6R1

<400> SEQUENCE: 18
gtgagacctt caccttcttg c 21

<210> SEQ ID NO 19
<211> LENGTH: 23
<212> TYPE: DNA
<213> ORGANISM: Artificial Sequence
<220> FEATURE:
<223> OTHER INFORMATION: Primer used for identifying alternatively spliced mRNAs - ERGIC3e6F1

<400> SEQUENCE: 19
tgtatggctt cttggaagtc aat 23

<210> SEQ ID NO 20
<211> LENGTH: 24
<212> TYPE: DNA
<213> ORGANISM: Artificial Sequence
<220> FEATURE:
<223> OTHER INFORMATION: Primer used for identifying alternatively spliced mRNAs - ERGIC3e9e10R1

<400> SEQUENCE: 20
gtagtgggtc atgttgatgt tgtc 24

<210> SEQ ID NO 21
<211> LENGTH: 22
<212> TYPE: DNA
<213> ORGANISM: Artificial Sequence
<220> FEATURE:
<223> OTHER INFORMATION: Primer used for identifying alternatively spliced mRNAs - SMN Rev

<400> SEQUENCE: 21
cgcttcacat tccagatctg tc 22

<210> SEQ ID NO 22
<211> LENGTH: 17
<212> TYPE: DNA
<213> ORGANISM: Artificial Sequence
<220> FEATURE:
<223> OTHER INFORMATION: Primer used for identifying alternatively spliced mRNAs - FOXM1 For

<400> SEQUENCE: 22
gtgttgcagc cctcggt 17

<210> SEQ ID NO 23
<211> LENGTH: 21
<212> TYPE: DNA
<213> ORGANISM: Artificial Sequence
<220> FEATURE:
<223> OTHER INFORMATION: Primer used for identifying alternatively spliced mRNAs - FOXM1 Rev

<400> SEQUENCE: 23
tgaactggaa gcaaaggaga a 21

<210> SEQ ID NO 24
<211> LENGTH: 18
<212> TYPE: DNA
<213> ORGANISM: Artificial Sequence
<220> FEATURE:
<223> OTHER INFORMATION: Primer used for identifying alternatively spliced mRNAs - VPS29e1F1

<400> SEQUENCE: 24
cggtggtggt gactgagc 18

<210> SEQ ID NO 25
<211> LENGTH: 21
<212> TYPE: DNA
<213> ORGANISM: Artificial Sequence
<220> FEATURE:
<223> OTHER INFORMATION: Primer used for identifying alternatively spliced mRNAs - VPS29e3R1

<400> SEQUENCE: 25
gggatgtgca gatctcctaa t 21

<210> SEQ ID NO 26
<211> LENGTH: 26
<212> TYPE: DNA
<213> ORGANISM: Artificial Sequence
<220> FEATURE:
<223> OTHER INFORMATION: Primer used for identifying alternatively spliced mRNAs - GGCTe1F1

<400> SEQUENCE: 26
agatgaggag agttttctgt actttg 26

<210> SEQ ID NO 27
<211> LENGTH: 20
<212> TYPE: DNA
<213> ORGANISM: Artificial Sequence
<220> FEATURE:
<223> OTHER INFORMATION: Primer used for identifying alternatively spliced mRNAs - GGCTe4R1

<400> SEQUENCE: 27
tctcttgata ctccagcggc 20

<210> SEQ ID NO 28
<211> LENGTH: 23
<212> TYPE: DNA
<213> ORGANISM: Artificial Sequence
<220> FEATURE:
<223> OTHER INFORMATION: Primer used for identifying alternatively spliced mRNAs - PRKDC e9F1

<400> SEQUENCE: 28
gatctgaaga gatatgctgt gcc 23

-continued

<210> SEQ ID NO 29
<211> LENGTH: 20
<212> TYPE: DNA
<213> ORGANISM: Artificial Sequence
<220> FEATURE:
<223> OTHER INFORMATION: Primer used for identifying alternatively
spliced mRNAs - PRKDC e12R1

<400> SEQUENCE: 29
acggtcgtca ccagtgtctg 20

<210> SEQ ID NO 30
<211> LENGTH: 23
<212> TYPE: DNA
<213> ORGANISM: Artificial Sequence
<220> FEATURE:
<223> OTHER INFORMATION: Primer used for identifying alternatively
spliced mRNAs - PRKDC e50F1

<400> SEQUENCE: 30
gggtccctaa agatgaagtg tta 23

<210> SEQ ID NO 31
<211> LENGTH: 22
<212> TYPE: DNA
<213> ORGANISM: Artificial Sequence
<220> FEATURE:
<223> OTHER INFORMATION: Primer used for identifying alternatively
spliced mRNAs - PRKDC e52R1

<400> SEQUENCE: 31
attcaccaaa gcctggaagt at 22

<210> SEQ ID NO 32
<211> LENGTH: 24
<212> TYPE: DNA
<213> ORGANISM: Artificial Sequence
<220> FEATURE:
<223> OTHER INFORMATION: Primer used for identifying alternatively
spliced mRNAs - MADD e20F1

<400> SEQUENCE: 32
cagaaagtgt aaatacccca gttg 24

<210> SEQ ID NO 33
<211> LENGTH: 19
<212> TYPE: DNA
<213> ORGANISM: Artificial Sequence
<220> FEATURE:
<223> OTHER INFORMATION: Primer used for identifying alternatively
spliced mRNAs - MADD e22R1

<400> SEQUENCE: 33
gctcacacca ctgtctgcg 19

<210> SEQ ID NO 34
<211> LENGTH: 22
<212> TYPE: DNA
<213> ORGANISM: Artificial Sequence
<220> FEATURE:
<223> OTHER INFORMATION: Primer used for identifying alternatively
spliced mRNAs - LARP7 5'UTRF1

<400> SEQUENCE: 34
cttccttggc ttcgagtctc tc 22

<210> SEQ ID NO 35
<211> LENGTH: 25
<212> TYPE: DNA
<213> ORGANISM: Artificial Sequence
<220> FEATURE:
<223> OTHER INFORMATION: Primer used for identifying alternatively spliced mRNAs - LARP7 e2R1

<400> SEQUENCE: 35
cctgtgtcct atcatttgtt ttctc 25

<210> SEQ ID NO 36
<211> LENGTH: 23
<212> TYPE: DNA
<213> ORGANISM: Artificial Sequence
<220> FEATURE:
<223> OTHER INFORMATION: Primer used for identifying alternatively spliced mRNAs - LARP7 e1F1

<400> SEQUENCE: 36
cgaaagtaac cgagactatc agg 23

<210> SEQ ID NO 37
<211> LENGTH: 22
<212> TYPE: DNA
<213> ORGANISM: Artificial Sequence
<220> FEATURE:
<223> OTHER INFORMATION: Primer used for identifying alternatively spliced mRNAs - LARP7 e4R1

<400> SEQUENCE: 37
ttcagtgctt tcttcttcca tt 22

<210> SEQ ID NO 38
<211> LENGTH: 19
<212> TYPE: DNA
<213> ORGANISM: Artificial Sequence
<220> FEATURE:
<223> OTHER INFORMATION: Primer used for identifying alternatively spliced mRNAs - ARMCX6 e2F1

<400> SEQUENCE: 38
cggcacaagt ttcagcgag 19

<210> SEQ ID NO 39
<211> LENGTH: 22
<212> TYPE: DNA
<213> ORGANISM: Artificial Sequence
<220> FEATURE:
<223> OTHER INFORMATION: Primer used for identifying alternatively spliced mRNAs - ARMCX6 e4R1

<400> SEQUENCE: 39
cagggtgagt aaggatggag gg 22

<210> SEQ ID NO 40
<211> LENGTH: 21
<212> TYPE: DNA
<213> ORGANISM: Artificial Sequence
<220> FEATURE:
<223> OTHER INFORMATION: Primer used for identifying alternatively spliced mRNAs - GALC e4F1

<400> SEQUENCE: 40
ggatacgagt ggtggttgat g 21

<210> SEQ ID NO 41

<211> LENGTH: 23
<212> TYPE: DNA
<213> ORGANISM: Artificial Sequence
<220> FEATURE:
<223> OTHER INFORMATION: Primer used for identifying alternatively spliced mRNAs - GALC e7R1

<400> SEQUENCE: 41
cagagatgga ctcccagaga tta 23

<210> SEQ ID NO 42
<211> LENGTH: 20
<212> TYPE: DNA
<213> ORGANISM: Artificial Sequence
<220> FEATURE:
<223> OTHER INFORMATION: Primer used for identifying alternatively spliced mRNAs - LAMA2 e4F1

<400> SEQUENCE: 42
ggattttgga acgctctctt 20

<210> SEQ ID NO 43
<211> LENGTH: 26
<212> TYPE: DNA
<213> ORGANISM: Artificial Sequence
<220> FEATURE:
<223> OTHER INFORMATION: Primer used for identifying alternatively spliced mRNAs - LAMA2 e6R1

<400> SEQUENCE: 43
gaaatatcct tgaccgagta gtaata 26

<210> SEQ ID NO 44
<211> LENGTH: 22
<212> TYPE: DNA
<213> ORGANISM: Artificial Sequence
<220> FEATURE:
<223> OTHER INFORMATION: Primer used for identifying alternatively spliced mRNAs - ABHD10e4F1

<400> SEQUENCE: 44
gagaaggtcg tggctcttat tg 22

<210> SEQ ID NO 45
<211> LENGTH: 23
<212> TYPE: DNA
<213> ORGANISM: Artificial Sequence
<220> FEATURE:
<223> OTHER INFORMATION: Primer used for identifying alternatively spliced mRNAs - ABHD10e6R1

<400> SEQUENCE: 45
gggctatgta acaagcagtg atg 23

<210> SEQ ID NO 46
<211> LENGTH: 19
<212> TYPE: DNA
<213> ORGANISM: Artificial Sequence
<220> FEATURE:
<223> OTHER INFORMATION: Primer used for identifying alternatively spliced mRNAs - FADS2e5F1

<400> SEQUENCE: 46
ctgccaactg gtggaatca 19

<210> SEQ ID NO 47
<211> LENGTH: 22

-continued

<212> TYPE: DNA
<213> ORGANISM: Artificial Sequence
<220> FEATURE:
<223> OTHER INFORMATION: Primer used for identifying alternatively
      spliced mRNAs - FADS2e8R1

<400> SEQUENCE: 47
gatgccgtag aaagggatgt ag 22

<210> SEQ ID NO 48
<211> LENGTH: 21
<212> TYPE: DNA
<213> ORGANISM: Artificial Sequence
<220> FEATURE:
<223> OTHER INFORMATION: Primer used for identifying alternatively
      spliced mRNAs - DIAPH3e10F1

<400> SEQUENCE: 48
tcaatgccct ggttacatct c 21

<210> SEQ ID NO 49
<211> LENGTH: 24
<212> TYPE: DNA
<213> ORGANISM: Artificial Sequence
<220> FEATURE:
<223> OTHER INFORMATION: Primer used for identifying alternatively
      spliced mRNAs - DIAPH3e13R1

<400> SEQUENCE: 49
acaatctggg atacacactc atca 24

<210> SEQ ID NO 50
<211> LENGTH: 24
<212> TYPE: DNA
<213> ORGANISM: Artificial Sequence
<220> FEATURE:
<223> OTHER INFORMATION: Primer used for identifying alternatively
      spliced mRNAs - PDIA3e3F1

<400> SEQUENCE: 50
ctgccaacac taacacctgt aata 24

<210> SEQ ID NO 51
<211> LENGTH: 22
<212> TYPE: DNA
<213> ORGANISM: Artificial Sequence
<220> FEATURE:
<223> OTHER INFORMATION: Primer used for identifying alternatively
      spliced mRNAs - PDIA3e7R1

<400> SEQUENCE: 51
agtccttgcc ctgtatcaaa tc 22

<210> SEQ ID NO 52
<211> LENGTH: 21
<212> TYPE: DNA
<213> ORGANISM: Artificial Sequence
<220> FEATURE:
<223> OTHER INFORMATION: Primer used for identifying alternatively
      spliced mRNAs - FN1e34F1

<400> SEQUENCE: 52
gctcatccgt ggttgtatca g 21

<210> SEQ ID NO 53
<211> LENGTH: 23
<212> TYPE: DNA

<213> ORGANISM: Artificial Sequence
<220> FEATURE:
<223> OTHER INFORMATION: Primer used for identifying alternatively spliced mRNAs - FN1e36R1

<400> SEQUENCE: 53
gatcgtctca gtcttggttc tcc 23

<210> SEQ ID NO 54
<211> LENGTH: 21
<212> TYPE: DNA
<213> ORGANISM: Artificial Sequence
<220> FEATURE:
<223> OTHER INFORMATION: Primer used for identifying alternatively spliced mRNAs - PARP1e20F1

<400> SEQUENCE: 54
agtgccaact actgccatac g 21

<210> SEQ ID NO 55
<211> LENGTH: 23
<212> TYPE: DNA
<213> ORGANISM: Artificial Sequence
<220> FEATURE:
<223> OTHER INFORMATION: Primer used for identifying alternatively spliced mRNAs - PARP1ee23R1

<400> SEQUENCE: 55
aatcctttct gaggtggttt agt 23

<210> SEQ ID NO 56
<211> LENGTH: 20
<212> TYPE: DNA
<213> ORGANISM: Artificial Sequence
<220> FEATURE:
<223> OTHER INFORMATION: Primer used for identifying alternatively spliced mRNAs - COL1Ae2F1

<400> SEQUENCE: 56
caaggtgttg tgcgatgacg 20

<210> SEQ ID NO 57
<211> LENGTH: 26
<212> TYPE: DNA
<213> ORGANISM: Artificial Sequence
<220> FEATURE:
<223> OTHER INFORMATION: Primer used for identifying alternatively spliced mRNAs - COL1Ae6R1

<400> SEQUENCE: 57
ggttgatttc tcatcatagc cataag 26

<210> SEQ ID NO 58
<211> LENGTH: 20
<212> TYPE: DNA
<213> ORGANISM: Artificial Sequence
<220> FEATURE:
<223> OTHER INFORMATION: Primer used for identifying alternatively spliced mRNAs - COLA1e7F1

<400> SEQUENCE: 58
cctctggtcc tcgtggtctc 20

<210> SEQ ID NO 59
<211> LENGTH: 20
<212> TYPE: DNA
<213> ORGANISM: Artificial Sequence
<220> FEATURE:
<223> OTHER INFORMATION: Primer used for identifying alternatively
spliced mRNAs - COL1Ae12R1

<400> SEQUENCE: 59
ccatccaaac cactgaaacc 20

<210> SEQ ID NO 60
<211> LENGTH: 19
<212> TYPE: DNA
<213> ORGANISM: Artificial Sequence
<220> FEATURE:
<223> OTHER INFORMATION: Primer used for identifying alternatively
spliced mRNAs - COLA1e27F1

<400> SEQUENCE: 60
ggtcctgctg gcaaagatg 19

<210> SEQ ID NO 61
<211> LENGTH: 18
<212> TYPE: DNA
<213> ORGANISM: Artificial Sequence
<220> FEATURE:
<223> OTHER INFORMATION: Primer used for identifying alternatively
spliced mRNAs - COLA1e31R1

<400> SEQUENCE: 61
gctcgccagg gaaacctc 18

<210> SEQ ID NO 62
<211> LENGTH: 19
<212> TYPE: DNA
<213> ORGANISM: Artificial Sequence
<220> FEATURE:
<223> OTHER INFORMATION: Primer used for identifying alternatively
spliced mRNAs - COLA1e31F1

<400> SEQUENCE: 62
aggcgagaga ggtttccct 19

<210> SEQ ID NO 63
<211> LENGTH: 21
<212> TYPE: DNA
<213> ORGANISM: Artificial Sequence
<220> FEATURE:
<223> OTHER INFORMATION: Primer used for identifying alternatively
spliced mRNAs - COLA1e33e34R1

<400> SEQUENCE: 63
ggaccacttt cacccttgtc a 21

<210> SEQ ID NO 64
<211> LENGTH: 19
<212> TYPE: DNA
<213> ORGANISM: Artificial Sequence
<220> FEATURE:
<223> OTHER INFORMATION: Primer used for identifying alternatively
spliced mRNAs - COLA1e47F1

<400> SEQUENCE: 64
gggcgacaga ggcataaag 19

<210> SEQ ID NO 65
<211> LENGTH: 20
<212> TYPE: DNA
<213> ORGANISM: Artificial Sequence
<220> FEATURE:

<223> OTHER INFORMATION: Primer used for identifying alternatively
spliced mRNAs - COLA1e48R1

<400> SEQUENCE: 65
tcacggtcac gaaccacatt 20

<210> SEQ ID NO 66
<211> LENGTH: 22
<212> TYPE: DNA
<213> ORGANISM: Artificial Sequence
<220> FEATURE:
<223> OTHER INFORMATION: Primer used for identifying alternatively
spliced mRNAs - COL1A2e20F1

<400> SEQUENCE: 66
caaaggagag agcggtaaca ag 22

<210> SEQ ID NO 67
<211> LENGTH: 22
<212> TYPE: DNA
<213> ORGANISM: Artificial Sequence
<220> FEATURE:
<223> OTHER INFORMATION: Primer used for identifying alternatively
spliced mRNAs - COL1A2e22R1

<400> SEQUENCE: 67
aagaccacga gaaccaggac ta 22

<210> SEQ ID NO 68
<211> LENGTH: 19
<212> TYPE: DNA
<213> ORGANISM: Artificial Sequence
<220> FEATURE:
<223> OTHER INFORMATION: Primer used for identifying alternatively
spliced mRNAs - COL1A2e22F1

<400> SEQUENCE: 68
cctggttctc gtggtcttc 19

<210> SEQ ID NO 69
<211> LENGTH: 18
<212> TYPE: DNA
<213> ORGANISM: Artificial Sequence
<220> FEATURE:
<223> OTHER INFORMATION: Primer used for identifying alternatively
spliced mRNAs - COL1A2e24e25R1

<400> SEQUENCE: 69
gccgacagga ccttcttt 18

<210> SEQ ID NO 70
<211> LENGTH: 19
<212> TYPE: DNA
<213> ORGANISM: Artificial Sequence
<220> FEATURE:
<223> OTHER INFORMATION: Primer used for identifying alternatively
spliced mRNAs - COL1A2e29F1

<400> SEQUENCE: 70
tggcaaacca ggagaaagg 19

<210> SEQ ID NO 71
<211> LENGTH: 20
<212> TYPE: DNA
<213> ORGANISM: Artificial Sequence
<220> FEATURE:
<223> OTHER INFORMATION: Primer used for identifying alternatively spliced mRNAs - COL1A2e31R1

<400> SEQUENCE: 71
aaggacctcg gcttccaata 20

<210> SEQ ID NO 72
<211> LENGTH: 18
<212> TYPE: DNA
<213> ORGANISM: Artificial Sequence
<220> FEATURE:
<223> OTHER INFORMATION: Primer used for identifying alternatively spliced mRNAs - COL3A1e7e8F1

<400> SEQUENCE: 72
ggcaagctgg tccttcag 18

<210> SEQ ID NO 73
<211> LENGTH: 19
<212> TYPE: DNA
<213> ORGANISM: Artificial Sequence
<220> FEATURE:
<223> OTHER INFORMATION: Primer used for identifying alternatively spliced mRNAs - COL3A1e11R1

<400> SEQUENCE: 73
ggagcacctg tttcaccct 19

<210> SEQ ID NO 74
<211> LENGTH: 23
<212> TYPE: DNA
<213> ORGANISM: Artificial Sequence
<220> FEATURE:
<223> OTHER INFORMATION: Primer used for identifying alternatively spliced mRNAs - COL3A1e45F1

<400> SEQUENCE: 74
tgacaaaggt gaaacaggtg aac 23

<210> SEQ ID NO 75
<211> LENGTH: 20
<212> TYPE: DNA
<213> ORGANISM: Artificial Sequence
<220> FEATURE:
<223> OTHER INFORMATION: Primer used for identifying alternatively spliced mRNAs - COL3A1e47R1

<400> SEQUENCE: 75
gtccactggg tccaacaggt 20

<210> SEQ ID NO 76
<211> LENGTH: 20
<212> TYPE: DNA
<213> ORGANISM: Artificial Sequence
<220> FEATURE:
<223> OTHER INFORMATION: Primer used for identifying alternatively spliced mRNAs - COL5A2e10e11F1

<400> SEQUENCE: 76
aatgggtccg attggttcac 20

<210> SEQ ID NO 77
<211> LENGTH: 22
<212> TYPE: DNA
<213> ORGANISM: Artificial Sequence
<220> FEATURE:
<223> OTHER INFORMATION: Primer used for identifying alternatively spliced mRNAs - COL52Ae16R1

<400> SEQUENCE: 77
caagtctccc tctctctcct gg 22

<210> SEQ ID NO 78
<211> LENGTH: 21
<212> TYPE: DNA
<213> ORGANISM: Artificial Sequence
<220> FEATURE:
<223> OTHER INFORMATION: Primer used for identifying alternatively spliced mRNAs - COL52Ae30F1

<400> SEQUENCE: 78
ggtgaaagag gagaacaagg a 21

<210> SEQ ID NO 79
<211> LENGTH: 20
<212> TYPE: DNA
<213> ORGANISM: Artificial Sequence
<220> FEATURE:
<223> OTHER INFORMATION: Primer used for identifying alternatively spliced mRNAs - COL52Ae33R1

<400> SEQUENCE: 79
tcaccaggga gtccagttat 20

<210> SEQ ID NO 80
<211> LENGTH: 22
<212> TYPE: DNA
<213> ORGANISM: Artificial Sequence
<220> FEATURE:
<223> OTHER INFORMATION: Primer used for identifying alternatively spliced mRNAs - COL52Ae33F1

<400> SEQUENCE: 80
agaacctggg ataactggac tc 22

<210> SEQ ID NO 81
<211> LENGTH: 21
<212> TYPE: DNA
<213> ORGANISM: Artificial Sequence
<220> FEATURE:
<223> OTHER INFORMATION: Primer used for identifying alternatively spliced mRNAs - COL5A2e35e36R1

<400> SEQUENCE: 81
agacctcttg caccatcatt t 21

<210> SEQ ID NO 82
<211> LENGTH: 17
<212> TYPE: DNA
<213> ORGANISM: Artificial Sequence
<220> FEATURE:
<223> OTHER INFORMATION: Primer used for identifying alternatively spliced mRNAs - COL5A2e33F1

<400> SEQUENCE: 82
agggaatggc tggagga 17

<210> SEQ ID NO 83
<211> LENGTH: 19
<212> TYPE: DNA
<213> ORGANISM: Artificial Sequence
<220> FEATURE:
<223> OTHER INFORMATION: Primer used for identifying alternatively spliced mRNAs - COL5A2e36R1

<400> SEQUENCE: 83
cccaaaggac ctggaagac 19

<210> SEQ ID NO 84
<211> LENGTH: 20
<212> TYPE: DNA
<213> ORGANISM: Artificial Sequence
<220> FEATURE:
<223> OTHER INFORMATION: Primer used for identifying alternatively spliced mRNAs - COL5A2e48F1

<400> SEQUENCE: 84
aggacctcgt ggtgacaaag 20

<210> SEQ ID NO 85
<211> LENGTH: 20
<212> TYPE: DNA
<213> ORGANISM: Artificial Sequence
<220> FEATURE:
<223> OTHER INFORMATION: Primer used for identifying alternatively spliced mRNAs - COL5A2e50R1

<400> SEQUENCE: 85
gcccagggtt tccttcttta 20

<210> SEQ ID NO 86
<211> LENGTH: 23
<212> TYPE: DNA
<213> ORGANISM: Artificial Sequence
<220> FEATURE:
<223> OTHER INFORMATION: Primer used for identifying alternatively spliced mRNAs - SMNe4F1

<400> SEQUENCE: 86
gatgaaagtg agaactccag gtc 23

<210> SEQ ID NO 87
<211> LENGTH: 21
<212> TYPE: DNA
<213> ORGANISM: Artificial Sequence
<220> FEATURE:
<223> OTHER INFORMATION: Primer used for identifying alternatively spliced mRNAs - SMNe6R1

<400> SEQUENCE: 87
caaagcatca gcatcatcaa g 21

<210> SEQ ID NO 88
<211> LENGTH: 10
<212> TYPE: RNA
<213> ORGANISM: Artificial Sequence
<220> FEATURE:
<223> OTHER INFORMATION: sequence motif resulted in a compound-dependent increase in the inclusion of exon 7 of SMN2

<400> SEQUENCE: 88
aggaguaagu 10

<210> SEQ ID NO 89
<211> LENGTH: 10
<212> TYPE: DNA
<213> ORGANISM: Artificial Sequence
<220> FEATURE:
<223> OTHER INFORMATION: sequence motif resulted in selectivity against the inclusion of exon 7A of FOXM1

<400> SEQUENCE: 89
atcagtaagt 10

<210> SEQ ID NO 90
<211> LENGTH: 10
<212> TYPE: DNA
<213> ORGANISM: Artificial Sequence
<220> FEATURE:
<223> OTHER INFORMATION: Alternative splicing sequence motif which affected exon 7A Delta-C of gene FOXM1, or exon 7 of APLP2

<400> SEQUENCE: 90
atgagtaagt 10

<210> SEQ ID NO 91
<211> LENGTH: 4
<212> TYPE: DNA
<213> ORGANISM: Artificial Sequence
<220> FEATURE:
<223> OTHER INFORMATION: sequence motif resulted in a compound-dependent increase in the inclusion of exon 7 of APLP2, exon 2 of GGCT, or exon 5 of ABHD10

<400> SEQUENCE: 91 atga 4

<210> SEQ ID NO 92
<211> LENGTH: 4
<212> TYPE: DNA
<213> ORGANISM: Artificial Sequence
<220> FEATURE:
<223> OTHER INFORMATION: sequence motif resulted in a compound-dependent increase in the inclusion of exon 8 of STRN3, exon 2 of LARP7, or exon 30 of COL1A1

<400> SEQUENCE: 92 aaga 4

<210> SEQ ID NO 93
<211> LENGTH: 4
<212> TYPE: DNA
<213> ORGANISM: Artificial Sequence
<220> FEATURE:
<223> OTHER INFORMATION: sequence motif resulted in a compound-dependent increase in the inclusion of exon 2 of VPS29 or exon 21 of MADD

<400> SEQUENCE: 93 caga 4

<210> SEQ ID NO 94
<211> LENGTH: 4
<212> TYPE: DNA
<213> ORGANISM: Artificial Sequence
<220> FEATURE:
<223> OTHER INFORMATION: sequence motif resulted in a compound-dependent increase in the inclusion of exon 8 of ERGIC3

<400> SEQUENCE: 94 gaga 4

<210> SEQ ID NO 95
<211> LENGTH: 4
<212> TYPE: DNA
<213> ORGANISM: Artificial Sequence
<220> FEATURE:
<223> OTHER INFORMATION: sequence motif resulted in a compound-dependent increase in the inclusion of part of exon 1 of LARP7

<400> SEQUENCE: 95 cgga 4

<210> SEQ ID NO 96
<211> LENGTH: 10
<212> TYPE: DNA
<213> ORGANISM: Artificial Sequence
<220> FEATURE:
<223> OTHER INFORMATION: Alternative splicing sequence motif which affected exon 7 of gene SMN2, or exon 5 of COL1A1

<400> SEQUENCE: 96
aggagtaagt 10

<210> SEQ ID NO 97
<211> LENGTH: 10
<212> TYPE: DNA
<213> ORGANISM: Artificial Sequence
<220> FEATURE:
<223> OTHER INFORMATION: Alternative splicing sequence motif which affected exon 2 of gene GGCT

<400> SEQUENCE: 97
atgagtaggt 10

<210> SEQ ID NO 98
<211> LENGTH: 10
<212> TYPE: DNA
<213> ORGANISM: Artificial Sequence
<220> FEATURE:
<223> OTHER INFORMATION: Alternative splicing sequence motif which affected exon 5 of gene ABHD10

<400> SEQUENCE: 98
atgagtatgt 10

<210> SEQ ID NO 99
<211> LENGTH: 10
<212> TYPE: DNA
<213> ORGANISM: Artificial Sequence
<220> FEATURE:
<223> OTHER INFORMATION: Alternative splicing sequence motif which affected exon 8 of gene STRN3, exon 30 of COL1A1, exon 5 of LAMA2, exon 30 of COL1A2, exon 35 of COL5A2, or exon 49 of COL5A2

<400> SEQUENCE: 99
aagagtaagt 10

<210> SEQ ID NO 100
<211> LENGTH: 10
<212> TYPE: DNA
<213> ORGANISM: Artificial Sequence
<220> FEATURE:
<223> OTHER INFORMATION: Alternative splicing sequence motif which affected exon 2 of gene VPS29, exon 32 of COL1A1, exon 22 of COL1A2, exon 10 of COL3A1, exon 46 of COL3A1, or exon 34 of COL5A2

<400> SEQUENCE: 100
cagagtaagt 10

<210> SEQ ID NO 101
<211> LENGTH: 10
<212> TYPE: DNA
<213> ORGANISM: Artificial Sequence
<220> FEATURE:
<223> OTHER INFORMATION: Alternative splicing sequence motif which affected exon 8 of gene ERGIC3, or exon 35 of FN1

<400> SEQUENCE: 101
gagagtaagt 10

<210> SEQ ID NO 102
<211> LENGTH: 10
<212> TYPE: DNA
<213> ORGANISM: Artificial Sequence
<220> FEATURE:
<223> OTHER INFORMATION: Alternative splicing sequence motif which
affected exon 21 of gene MADD

<400> SEQUENCE: 102
cagagtaagg 10

<210> SEQ ID NO 103
<211> LENGTH: 10
<212> TYPE: DNA
<213> ORGANISM: Artificial Sequence
<220> FEATURE:
<223> OTHER INFORMATION: Alternative splicing sequence motif which
affected exon 1 of gene LARP7

<400> SEQUENCE: 103
cggagtaagt 10

<210> SEQ ID NO 104
<211> LENGTH: 10
<212> TYPE: DNA
<213> ORGANISM: Artificial Sequence
<220> FEATURE:
<223> OTHER INFORMATION: Alternative splicing sequence motif which
affected exon 2 of gene LARP7

<400> SEQUENCE: 104
aagagtaaga 10

<210> SEQ ID NO 105
<211> LENGTH: 10
<212> TYPE: DNA
<213> ORGANISM: Artificial Sequence
<220> FEATURE:
<223> OTHER INFORMATION: Alternative splicing sequence motif which
affected exon 3 of gene ARMCX6

<400> SEQUENCE: 105
tagagtatga 10

<210> SEQ ID NO 106
<211> LENGTH: 10
<212> TYPE: DNA
<213> ORGANISM: Artificial Sequence
<220> FEATURE:
<223> OTHER INFORMATION: Alternative splicing sequence motif which
affected exon 5 of gene GALC

<400> SEQUENCE: 106
tggagttagt 10

<210> SEQ ID NO 107
<211> LENGTH: 10
<212> TYPE: DNA
<213> ORGANISM: Artificial Sequence
<220> FEATURE:
<223> OTHER INFORMATION: Alternative splicing sequence motif which
affected exon 11 of gene PRKDC

<400> SEQUENCE: 107
aggagtatgt 10

<210> SEQ ID NO 108
<211> LENGTH: 10
<212> TYPE: DNA
<213> ORGANISM: Artificial Sequence
<220> FEATURE:
<223> OTHER INFORMATION: Alternative splicing sequence motif which affected exon 51 of gene PRKDC

<400> SEQUENCE: 108
gcgagtacgt 10

<210> SEQ ID NO 109
<211> LENGTH: 10
<212> TYPE: DNA
<213> ORGANISM: Artificial Sequence
<220> FEATURE:
<223> OTHER INFORMATION: Alternative splicing sequence motif which affected exon 4 of gene RCC1

<400> SEQUENCE: 109
agaggtaaga 10

<210> SEQ ID NO 110
<211> LENGTH: 10
<212> TYPE: DNA
<213> ORGANISM: Artificial Sequence
<220> FEATURE:
<223> OTHER INFORMATION: Alternative splicing sequence motif which affected exon 6 of gene FADS2

<400> SEQUENCE: 110
ctgagtaagt 10

<210> SEQ ID NO 111
<211> LENGTH: 10
<212> TYPE: DNA
<213> ORGANISM: Artificial Sequence
<220> FEATURE:
<223> OTHER INFORMATION: Alternative splicing sequence motif which affected exon 11 of gene DIAPH3

<400> SEQUENCE: 111
ttgaatatcc 10

<210> SEQ ID NO 112
<211> LENGTH: 10
<212> TYPE: DNA
<213> ORGANISM: Artificial Sequence
<220> FEATURE:
<223> OTHER INFORMATION: Alternative splicing sequence motif which affected exon 35 of gene PARP1

<400> SEQUENCE: 112
acgagtatcc 10

<210> SEQ ID NO 113
<211> LENGTH: 10
<212> TYPE: DNA
<213> ORGANISM: Artificial Sequence
<220> FEATURE:
<223> OTHER INFORMATION: Alternative splicing sequence motif which affected exon 11 of gene COL1A1

<400> SEQUENCE: 113
cagagtgagt 10

<210> SEQ ID NO 114
<211> LENGTH: 10
<212> TYPE: DNA
<213> ORGANISM: Artificial Sequence
<220> FEATURE:
<223> OTHER INFORMATION: Alternative splicing sequence motif which
affected exon 46 of gene COL1A1 or exon 13 of COL5A2

<400> SEQUENCE: 114
ccgagtaagt 10

<210> SEQ ID NO 115
<211> LENGTH: 10
<212> TYPE: DNA
<213> ORGANISM: Artificial Sequence
<220> FEATURE:
<223> OTHER INFORMATION: Alternative splicing sequence motif which
affected exon 21 of gene COL1A2

<400> SEQUENCE: 115
gagagtaggt 10

<210> SEQ ID NO 116
<211> LENGTH: 10
<212> TYPE: DNA
<213> ORGANISM: Artificial Sequence
<220> FEATURE:
<223> OTHER INFORMATION: Alternative splicing sequence motif which
affected exon 32 of gene COL5A2

<400> SEQUENCE: 116
tagagtaagt 10

<210> SEQ ID NO 117
<211> LENGTH: 10
<212> TYPE: DNA
<213> ORGANISM: Artificial Sequence
<220> FEATURE:
<223> OTHER INFORMATION: Alternative splicing sequence motif which
affected exon 5 of gene SMN2

<400> SEQUENCE: 117
accagtaagt 10

<210> SEQ ID NO 118
<211> LENGTH: 23
<212> TYPE: RNA
<213> ORGANISM: Artificial Sequence
<220> FEATURE:
<223> OTHER INFORMATION: TSL2 (terminal stem loop 2) in SMN2

<400> SEQUENCE: 118
auuccuuaaa uuaaggagua agu 23

<210> SEQ ID NO 119
<211> LENGTH: 23
<212> TYPE: RNA
<213> ORGANISM: Artificial Sequence
<220> FEATURE:
<223> OTHER INFORMATION: Sequence illustrating examplary mutations
introduced into TSL2 in SMN2

<400> SEQUENCE: 119
auuccauaaa uuauggagua agu 23

-continued

```
<210> SEQ ID NO 120
<211> LENGTH: 9
<212> TYPE: RNA
<213> ORGANISM: Artificial Sequence
<220> FEATURE:
<223> OTHER INFORMATION: Sequence illustrating examplary mutations
      introduced into TSL2 in SMN2

<400> SEQUENCE: 120

acuuaccug                                                        9
```

With:
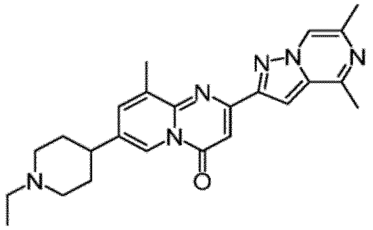
In Column 389, Claim 7, approximately Lines 10-21, replace the structure of:
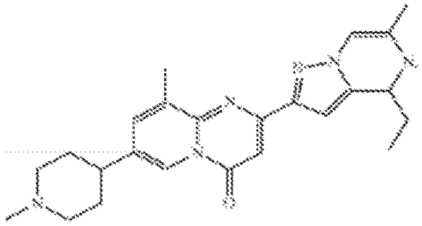
With:
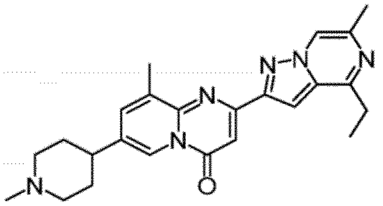
In Column 389, Claim 7, approximately Lines 26-39, replace the structure of:
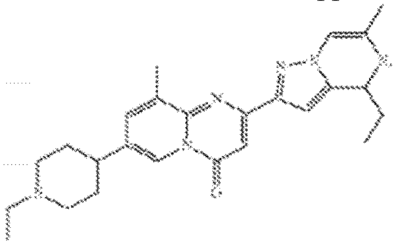
With:
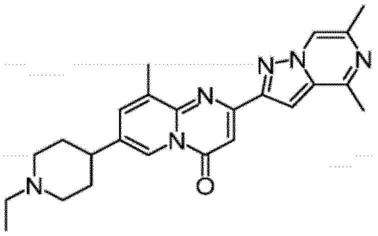

What is claimed is:

1. A method for regulating the amount of a functional protein produced from an artificial gene construct in a cell obtained from a human subject, the method comprising: (a) contacting the artificial gene construct or a vector comprising the artificial gene construct with the cell; and (b) contacting a compound or a form thereof with the cell, wherein the artificial gene construct comprises: (A) a DNA sequence encoding exons and one, two or more introns, wherein a nucleotide sequence encoding a 5' splice site, which is upstream of a nucleotide sequence encoding a branch point and a nucleotide sequence encoding a 3' splice site, contains a nucleotide sequence encoding a non-endogenous recognition element for splicing modifier (REMS), wherein the non-endogenous REMS in the DNA sequence comprises the sequence ANGAgtrngn (SEQ ID NO: 7), wherein r is A or G and N or n is any nucleotide; or (B) an RNA sequence comprising exons and one, two or more introns, wherein a 5' splice site, which is upstream of a branch point and a 3' splice site, contains a non-endogenous REMS, wherein the non-endogenous REMS in the RNA sequence comprises the sequence ANGAgurngn (SEQ ID NO: 3), wherein r is A or G and N or n is any nucleotide, and wherein the compound is:

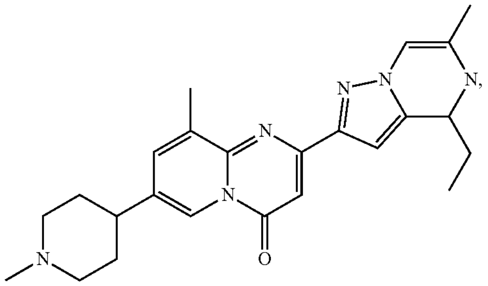

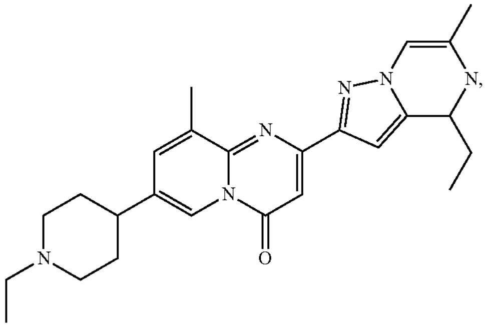

or

-continued

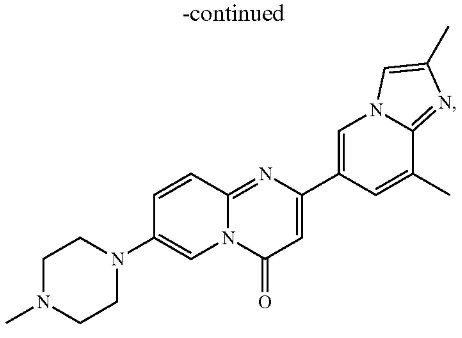

and wherein contacting the cell with the artificial gene construct or the vector and the compound or a form thereof occurs in cell culture.

2. The method of claim 1, wherein the vector is a viral vector.

3. The method of claim 2, wherein the viral vector is an adeno-associated virus, an adenovirus, a retrovirus, a lentivirus, a Newcastle disease virus, a herpes virus, an alphavirus, or a vaccinia virus.

4. The method of claim 1, wherein the artificial gene construct further comprises a promoter, a poly(A) site, a transcription termination site, and a transcription binding site.

5. The method of claim 1, wherein the non-endogenous REMS in the DNA sequence comprises the sequence ANGAgtragt (SEQ ID NO: 8), wherein r is A or G and N is any nucleotide.

6. The method of claim 1, wherein the non-endogenous REMS in the RNA sequence comprises the sequence ANGAguragu (SEQ ID NO: 4), wherein r is A or G and N is any nucleotide.

7. A method for regulating the amount of a functional protein produced from an artificial gene construct in a cell obtained from a human subject, the method comprising contacting a compound or a form thereof with the cell, wherein the cell was previously contacted with the artificial gene construct or a vector comprising the artificial gene construct, wherein the artificial gene construct comprises: (A) a DNA sequence encoding exons and one, two or more introns, wherein a nucleotide sequence encoding a 5' splice site, which is upstream of a nucleotide sequence encoding a branch point and a nucleotide sequence encoding a 3' splice site, contains a nucleotide sequence encoding a non-endogenous recognition element for splicing modifier (REMS), wherein the non-endogenous REMS in the DNA sequence comprises the sequence ANGAgtrngn (SEQ ID NO: 7), wherein r is A or G and N or n is any nucleotide; or (B) an RNA sequence comprising exons and one, two or more introns, wherein a 5' splice site, which is upstream of a branch point and a 3' splice site, contains a non-endogenous REMS, wherein the non-endogenous REMS in the RNA sequence comprises the sequence ANGAgurngn (SEQ ID NO: 3), wherein r is A or G and N or n is any nucleotide, and wherein the compound is:

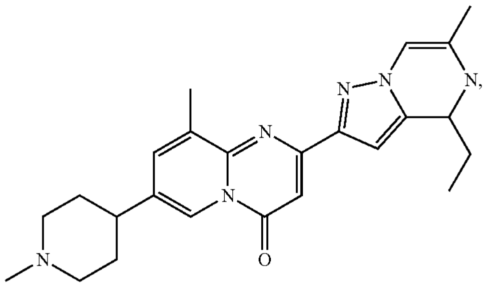

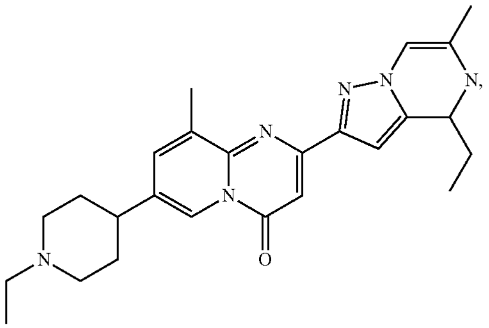

or

-continued

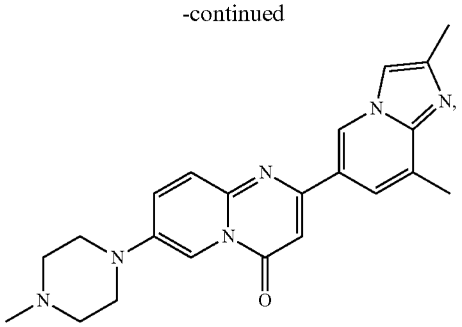

and wherein contacting the compound or a form thereof with the cell occurs in cell culture.

8. The method of claim 7, wherein the vector is a viral vector.

9. The method of claim 8, wherein the viral vector is an adeno-associated virus, an adenovirus, a retrovirus, a lentivirus, a Newcastle disease virus, a herpes virus, an alphavirus, or a vaccinia virus.

10. The method of claim 7, wherein the artificial gene construct further comprises a promoter, a poly(A) site, a transcription termination site, and a transcription binding site.

11. The method of claim 7, wherein the non-endogenous REMS in the DNA sequence comprises the sequence ANGAgtragt (SEQ ID NO: 8), wherein r is A or G and N is any nucleotide.

12. The method of claim 7, wherein the non-endogenous REMS in the RNA sequence comprises the sequence ANGAguragu (SEQ ID NO: 4), wherein r is A or G and N is any nucleotide.

13. The method of claim 1, wherein the functional protein is a therapeutic protein.

14. The method of claim 7, wherein the functional protein is a therapeutic protein.

* * * * *

UNITED STATES PATENT AND TRADEMARK OFFICE
CERTIFICATE OF CORRECTION

PATENT NO. : 11,602,567 B2
APPLICATION NO. : 16/847330
DATED : March 14, 2023
INVENTOR(S) : Nikolai Naryshkin et al.

It is certified that error appears in the above-identified patent and that said Letters Patent is hereby corrected as shown below:

In the Claims

In Column 387, Claim 1, approximately Lines 43-55, replace the structure of:

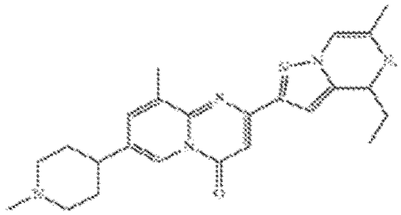

With:

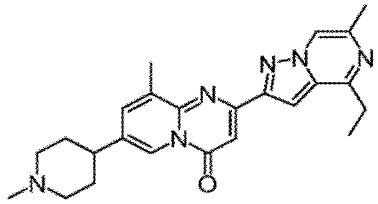

In Column 387, Claim 1, approximately Lines 55-67, replace the structure of:

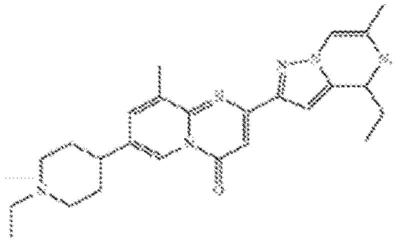

Signed and Sealed this
Sixteenth Day of May, 2023

Katherine Kelly Vidal
*Director of the United States Patent and Trademark Office*